United States Patent
Lu et al.

(10) Patent No.: US 11,040,031 B2
(45) Date of Patent: Jun. 22, 2021

(54) PYRAZOLE DERIVATIVES AS MALT1 INHIBITORS

(71) Applicant: Janssen Pharmaceutica NV, Beerse (BE)

(72) Inventors: Tianbao Lu, Churchville, PA (US); Peter J. Connolly, New Providence, NJ (US); Maxwell David Cummings, Ambler, PA (US); Joseph Kent Barbay, Flourtown, PA (US); Kevin D. Kreutter, Plainsboro, NJ (US); Tongfei Wu, Hever (BE); Gaston Stanislas Marcella Diels, Turnhout (BE); Jan Willem Thuring, Antwerp (BE); Ulrike Philippar, Antwerp (BE); James Patrick Edwards, Ambler, PA (US); Fang Shen, Fort Washington, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/440,302

(22) Filed: Jun. 13, 2019

(65) Prior Publication Data
US 2019/0381019 A1    Dec. 19, 2019

Related U.S. Application Data

(60) Provisional application No. 62/686,447, filed on Jun. 18, 2018.

(51) Int. Cl.
| | |
|---|---|
| *A61K 31/444* | (2006.01) |
| *A61P 35/00* | (2006.01) |
| *A61K 31/519* | (2006.01) |
| *A61K 31/5377* | (2006.01) |
| *A61K 39/395* | (2006.01) |
| *C07D 403/14* | (2006.01) |
| *C07D 407/14* | (2006.01) |
| *C07D 413/14* | (2006.01) |

(52) U.S. Cl.
CPC .......... *A61K 31/444* (2013.01); *A61K 31/519* (2013.01); *A61K 31/5377* (2013.01); *A61K 39/3955* (2013.01); *A61P 35/00* (2018.01); *C07D 403/14* (2013.01); *C07D 407/14* (2013.01); *C07D 413/14* (2013.01)

(58) Field of Classification Search
CPC ................ A61K 31/444; A61K 31/519; A61K 31/5377; A61K 39/3955; A61P 35/00; C07D 403/14; C07D 407/14; C07D 413/14
USPC ....................................................... 546/256
See application file for complete search history.

(56) References Cited

U.S. PATENT DOCUMENTS

| | | | |
|---|---|---|---|
| 6,339,099 B1 | 1/2002 | Lam et al. | |
| 7,015,218 B1* | 3/2006 | Ushio | A61K 31/00 514/227.8 |
| 7,151,113 B2 | 12/2006 | Dyckman et al. | |
| 7,223,782 B2 | 5/2007 | Atkinson et al. | |
| 7,253,170 B2 | 8/2007 | Dyckman et al. | |
| 7,390,810 B2 | 6/2008 | Dyckman et al. | |
| 7,396,935 B2 | 7/2008 | Dyckman et al. | |
| 7,414,056 B2 | 8/2008 | Dyckman et al. | |
| 7,592,338 B2 | 9/2009 | Dyckman et al. | |
| 7,605,273 B2 | 10/2009 | Dyckman et al. | |
| 9,375,008 B2 | 6/2016 | Gross et al. | |
| 10,888,550 B2* | 1/2021 | Lu | A61K 31/437 |
| 2012/0316172 A1* | 12/2012 | Galley | C07D 413/14 514/236.5 |
| 2013/0211075 A1* | 8/2013 | Ushio | C07D 401/12 540/597 |
| 2015/0065715 A1* | 3/2015 | Watanabe | C07D 401/14 546/19 |
| 2015/0191458 A1* | 7/2015 | Galley | C07D 403/12 514/236.2 |

(Continued)

FOREIGN PATENT DOCUMENTS

| | | |
|---|---|---|
| WO | WO 2001/002385 A1 | 1/2001 |
| WO | WO 2003/037274 A2 | 5/2003 |
| WO | WO 2003/037274 A3 | 5/2003 |

(Continued)

OTHER PUBLICATIONS

STN Registry Database, record for RN 1808788-01-3, entered into STN on Sep. 29, 2015. (Year: 2015).*

(Continued)

*Primary Examiner* — Daniel R Carcanague

(57) ABSTRACT

Disclosed are compounds, compositions and methods for treating of diseases, syndromes, conditions, and disorders that are affected by the modulation of MALT1. Such compounds are represented by Formula (I) as follows:

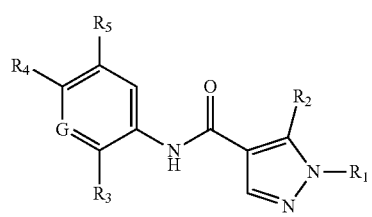

Formula (I)

wherein $R_1$, $R_2$, $R_3$, $R_4$, $R_5$, and G, are defined herein.

9 Claims, No Drawings

(56) References Cited

U.S. PATENT DOCUMENTS

| | | | |
|---|---|---|---|
| 2018/0170909 A1* | 6/2018 | Lu | C07D 401/12 |
| 2019/0381012 A1* | 12/2019 | Lu | C07K 16/2896 |

FOREIGN PATENT DOCUMENTS

| | | |
|---|---|---|
| WO | WO 2004/098518 A2 | 11/2004 |
| WO | WO 2004/098518 A3 | 11/2004 |
| WO | WO 2008/008286 A2 | 1/2008 |
| WO | WO 2008/008286 A3 | 1/2008 |
| WO | WO 2010/064875 A2 | 6/2010 |
| WO | WO 2012/063896 A1 | 5/2012 |
| WO | WO 2015/181747 A1 | 12/2015 |
| WO | 2016/090382 A1 | 6/2016 |
| WO | WO 2017/081641 A1 | 5/2017 |
| WO | WO 2018/114501 A1 | 6/2018 |
| WO | WO 2018/114503 A1 | 6/2018 |
| WO | WO 2018/115880 A1 | 6/2018 |
| WO | WO 2018/116201 A1 | 6/2018 |
| WO | WO 2018/116259 A1 | 6/2018 |
| WO | WO 2018/119036 A1 | 6/2018 |

OTHER PUBLICATIONS

International Preliminary Report on Patentability, International Application PCT/IB2019/054964, dated Dec. 22, 2020. 7 Pages. (Year: 2020).*
Bornancin, F., et al., "Deficiency of MALT1 Paracaspase Activity Results in Unbalanced Regulatory and Effector T and B Cell Responses Leading to Multiorgan Inflammation", J. Immunology, (2015), vol. 194, No. 8, pp. 3723-3734.
Demeyer, A., et al., "Targeting MALT1 Proteolytic Activity in Immunity, Inflammation and Disease: Good or Bad?", Trends Mol Med, (2016), vol. 22, No. 2, pp. 135-150.
Fontan, L., et al., "MALT1 Small Molecule Inhibitors Specifically Suppress ABC-DLBCL In Vitro and In Vivo", Cancer Cell, (2012), vol. 22, No. 6, pp. 812-824.
Gewies, A., et al., "Uncoupling Malt1 Threshold Function from Paracaspase Activity Results in Destructive Autoimmune Inflammation", Cell Reports, (2014), vol. 9, pp. 1292-1305.
Jabara, H.H., et al., "A homozygous mucosa-associated lymphoid tissue 1 (MALT1) mutation in a family with combined immunodeficiency", J. Allergy Clin. Immunol., (2013), vol. 132, pp. 151-158.
Jaworski, M., et al., "Malt1 protease inactivation efficiently dampens immune responses but causes spontaneous autoimmunity", The EMBO Journal, (2014), vol. 33, No. 23, pp. 2765-2781.
Jaworski, M., et al., "The paracaspase MALT1: biological function and potential for therapeutic inhibition", Cell. Mol. Life Sci., (2016), vol. 73, pp. 459-473.
Lim, K., et al., "Pathogentic importance and therapeutica implications of NF-κß in lymphoid malignancies", Immunological Reviews, (2012), vol. 246, pp. 359-378.
Mc Guire, C., et al., "Pharmacological inhibition of MALT1 protease activity protects mice in a mouse model of multiple sclerosis", Journal of Neuroinflammation, (2014), vol. 11, No. 124, pp. 1-12.
McKinnon et al., "Combined immunodeficiency associated with homozygous MALT1 mutations", J. Allergy Clin. Immunol. (2014), vol. 133, No. 5, pp. 1458-1462.e7.
Nagel, D., et al., "Pharmacologic Inhibition of MALT1 Protease by Phenothiazines as a Therapeutic Approach for the Treatment of Aggressive ABC-DLBCL", Cancer Cell, (2012), vol. 22, pp. 825-837.
Punwani, D., et al., "Combined Immunodeficiency Due to MALT1 Mutations, Treated by Hematopoietic Cell Transplantation", J Clin Immunol, (2015), vol. 35, pp. 135-146.
Rosebeck, S., et al., "Cleavage of NIK by the API2-MALT1 Fusion Oncoprotein Leads to Noncanonical NF-kB Activation", Science, (2011), vol. 331, pp. 468-472.
Rosebeck, S., et al., "API2-MALT1 oncoprotein promotes lymphomagenesis via unique program of substrate ubiquitination and proteolysis", World J Biol Chem, (2016), vol. 7, No. 1, pp. 128-137.
Yu, J.W., et al., "MALT1 Protease Activity is Required for Innate and Adaptive Immune Responses", PLOS One, (2015), pp. 1-20.
Bundgaard, H., "Design of Prodrugs", (1985), Table of Contents.
McOmie, J., "Protective Groups in Organic Chemistry", (1973), Title Page and Table of Contents.
T.W. Greene & P.G.M. Wutz (eds.), Protective Groups in Organic Synthesis, $2^{nd}$ edition, John Wiley & Sons, Inc., (1991), Table of Contents.
T.W. Greene & P.G.M. Wutz (eds.), Protective Groups in Organic Synthesis, $3^{rd}$ edition, John Wiley & Sons, Inc., (1999), Table of Contents.
Hughes, J.P., et al., "Principles of early drug discovery", British Journal of Pharmacology, (2011), vol. 162, pp. 1239-1249.
International Search Report from PCT/IB2019/054964 dated Oct. 18, 2019.
Bernstein, J., "Polymorphism in Molecular Crystals", (2002), Clarendon Press Oxford, pp. 115-118 & 272.
Braga, D., et al., "Making crystals from crystals: a green route to crystal engineering and polymorphism", (2005), J. Royal Soc. Chem. Commun., pp. 3635-3645.
Davidovich, M., et al., "Detection of Polymorphism by Powder X-Ray Diffraction: Interference by Preferred Orientation", (2004), Am. Pharm. Rev, vol. 7, No. 1, pp. 10, 12, 14, 16, 100.
Dean, "Analytical Chem . . ."(1995), pp. 10.24-10.26.
Guillory, J.K., "Polymorphism in Pharmaceutical Solids", (in Brittain ed.), (1999), NY: Mercel Dekker, Inc., 1-2, 125-181, 183-226.
Ivanisevic, I., et al., "Uses of X-Ray Powder Diffraction in the Pharmaceutical Industry", (2010), Pharm. Sci. Encycl., pp. 1-42.
Jain, N.K., et al., "Polymorphism in Pharmacy", (1986), Indian Drugs, vol. 23, No. 6, pp. 315-329.
Jordan, V.C., "Tamoxifen: A Most Unlikely Pioneering Medicine", (2003), Nature Reviews, vol. 2, pp. 205-213.
Kirk-Othmer, "Crystallization", (2002), Encyclopedia of Chemical, vol. 8, pp. 95-147.
Seddon, K.R., "Pseudopolymorph: A Polemic", (2004), Crystal Growth & Design, vol. 4, No. 6, p. 108 (two pages from internet).
Vippagunta, S.R., et al., "Crystalline solids", (2001), Advanced Drug Delivery Review, vol. 48, pp. 3-26.
Yu, L., et al., "Physical characterization of polymorphic drugs: an integrated characterization strategy", (1998), PSTT, vol. 1, No. 3, pp. 118-127.

\* cited by examiner

PYRAZOLE DERIVATIVES AS MALT1 INHIBITORS

CROSS-REFERENCE TO RELATED APPLICATIONS

This application claims priority from U.S. Application No. 62/686,447, filed on Jun. 18, 2018, which is incorporated herein by reference.

FIELD OF THE INVENTION

The present invention relates to novel compounds that are MALT1 (mucosa-associated lymphoid tissue lymphoma translocation protein 1) inhibitors. These compounds may be useful for the treatment of a disease, syndrome, condition, or disorder, particularly a MALT1-related disease, syndrome, condition, or disorder, including but not limited to, cancer and immunological diseases. The invention also relates to pharmaceutical compositions comprising one or more of such compounds, to processes to prepare such compounds and compositions, and to the use of such compounds or pharmaceutical compositions for the treatment of cancer and autoimmunological diseases, syndromes, disorders, or conditions associated with MALT1 inhibitors.

BACKGROUND OF THE INVENTION

MALT1 (mucosa-associated lymphoid tissue lymphoma translocation 1) is a key mediator of the classical $NF_KB$ signaling pathway. MALT1 is the only human paracaspase and transduces signals from the B cell receptor (BCR) and T cell receptor (TCR). MALT1 is the active subunit of the CBM complex which is formed upon receptor activation. The CBM complex consists of multiple subunits of three proteins: CARD11 (caspase recruitment domain family member 11), BCL10 (B-cell CLL/Lymphoma 10) and MALT1. MALT1 affects $NF_KB$ signaling by two mechanisms: firstly, MALT1 functions as a scaffolding protein and recruits $NF_KB$ signaling proteins such as TRAF6, TAB-TAK1 or NEMO-IKKα/β; and secondly, MALT1, as a cysteine protease, cleaves and thereby deactivates negative regulators of $NF_KB$ signaling, such as RelB, A20 or CYLD. The ultimate endpoint of MALT1 activity is the nuclear translocation of the $NF_KB$ transcription factor complex and activation of $NF_KB$ signaling (Jaworski et al., Cell Mol Life Science 2016. 73, 459-473).

Constitutive activation of $NF_KB$ signaling is the hallmark of ABC-DLBCL (Diffuse Large B cell Lymphoma of the Activated B Cell-like subtype), the more aggressive form of DLBCL. DLBCL is the most common form of non-Hodgkin's lymphoma (NHL), accounting for approximately 25% of lymphoma cases while ABC-DLBCL comprises approximately 40% of DLBCL. $NF_KB$ pathway activation is driven by mutations of signaling components, such as CD79A/B, CARD11, MYD88 or A20, in ABC-DLBCL patients (Staudt, Cold Spring Harb Perspect Biol 2010, 2; Lim et al, Immunol Rev 2012, 246, 359-378).

The use of BTK inhibitors, for example Ibrutinib, provides clinical proof-of-concept that inhibiting $NF_KB$ signaling in ABC-DLBCL is efficacious. MALT1 is downstream of BTK in the $NF_KB$ signaling pathway and a MALT1 inhibitor could target ABC-DLBCL patients not responding to Ibrutinib, mainly patients with CARD11 mutations, as well as treat patients that acquired resistance to Ibrutinib.

Small molecule tool compound inhibitors of MALT1 protease have demonstrated efficacy in preclinical models of ABC-DLBCL (Fontan et al., Cancer Cell 2012, 22, 812-824; Nagel et al., Cancer Cell 2012, 22, 825-837). Interestingly, covalent catalytic site and allosteric inhibitors of MALT1 protease function have been described, suggesting that inhibitors of this protease may be useful as pharmaceutical agents (Demeyer et al., Trends Mol Med 2016, 22, 135-150).

The chromosomal translocation creating the API2-MALT1 fusion oncoprotein is the most common mutation identified in MALT (mucosa-associated lymphoid tissue) lymphoma. API2-MALT1 is a potent activator of the $NF_KB$ pathway (Rosebeck et al., World J Biol Chem 2016, 7, 128-137). API2-MALT1 mimics ligand-bound TNF receptor, promotes TRAF2-dependent ubiquitination of RIP 1 which acts as a scaffold for activating canonical $NF_KB$ signaling. Furthermore, API2-MALT1 has been shown to cleave and generate a stable, constitutively active fragment of $NF_KB$-inducing kinase (NIK) thereby activating the non-canonical $NF_KB$ pathway (Rosebeck et al., Science, 2011, 331, 468-472).

In addition to lymphomas, MALT1 has been shown to play a critical role in innate and adaptive immunity (Jaworski M, et al., Cell Mol Life Sci. 2016). MALT1 protease inhibitor can attenuate disease onset and progression of mouse experimental allergic encephalomyelitis, a mouse model of multiple sclerosis (Mc Guire et al., J. Neuroinflammation 2014, 11, 124). Mice expressing catalytically inactive MALT1 mutant showed loss of marginal zone B cells and B 1 B cells and general immune deficiency characterized as decreased T and B cell activation and proliferation. However, those mice also developed spontaneous multi-organ autoimmune inflammation at the age of 9 to 10 weeks. It is still poorly understood why MALT1 protease dead knock-in mice show a break of tolerance while conventional MALT1 KO mice do not. One hypothesis suggests the unbalanced immune homeostasis in MALT1 protease dead knock-in mice may be caused by incomplete deficiency in T and B cell but severe deficiency of immunoregulatory cells (Jaworski et al., EMBO J. 2014; Gewies et al., Cell Reports 2014; Bornancin et al., J. Immunology 2015; Yu et al., PLOS One 2015). Similarly, MALT deficiency in humans has been associated with combined immunodeficiency disorder (McKinnon et al., J. Allergy Clin. Immunol. 2014, 133, 1458-1462; Jabara et al., J. Allergy Clin. Immunol. 2013, 132, 151-158; Punwani et al., J. Clin. Immunol. 2015, 35, 135-146). Given the difference between genetic mutation and pharmacological inhibition, a phenotype of MALT1 protease dead knock-in mice might not resemble that of patients treated with MALT1 protease inhibitors. A reduction of immunosuppressive T cells by MALT1 protease inhibition may be beneficial to cancer patients by potentially increasing antitumor immunity.

Thus, MALT1 inhibitors of the present invention may provide a therapeutic benefit to patients suffering from cancer and/or immunological diseases.

SUMMARY OF THE INVENTION

The present invention is directed to compounds of Formula (I)

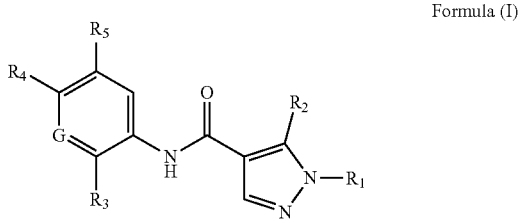

Formula (I)

wherein

R₁ is selected from the group consisting of
i) phenyl substituted with one to three substituents independently selected from the group consisting of 1-methoxyethyl, $C_{1-4}$alkyl, isopropyl, methoxy, chloro, fluoro, bromo, methanesulfonyl, cyclopropyl, methylthio, trifluoromethyl, amino, methylamino, and cyano;
ii) a heteroaryl of five to six members containing one to four heteroatoms selected from the group consisting of O, N, and S; such that no more than one heteroatom is O or S; wherein said heteroaryl of ii) is independently substituted with one to three substituents independently selected from $C_{1-4}$alkyl, methoxy, fluoro, chloro, bromo, cyano, amino, methylamino, methanesulfonyl, methylthio, tetrahydrofuran-2-yl, furan-2-yl, 5,6-dihydro-1,4-dioxin-2-yl, 1,4-dioxan-2-yl, trifluoromethyl, 3-hydroxyazetidin-1-yl, or N-oxido;
and
iii) a bicyclic ring system selected from the group consisting of 2,2-difluorobenzo[d][1,3]dioxol-4-yl, [1,3]dioxolo[4,5-b]pyridin-7-yl, 1-oxoisoindolin-4-yl, 1-methyl-1,2,3,4-tetrahydroquinolin-8-yl, indolin-4-yl, 1-methylindolin-4-yl, [1,3]dioxolo[4,5-b]pyridin-7-yl, 1-methyl-1,2,3,4-tetrahydroquinolin-5-yl, 4-methyl-3,4-dihydro-2H-benzo[b][1,4]oxazin-8-yl, benzo[d][1,3]dioxol-4-yl, and 2,3-dihydrobenzo[b][1,4]dioxin-5-yl;

R₂ is selected from the group consisting of $C_{1-4}$alkyl, 1-methoxy-ethyl, difluoromethyl, fluoro, chloro, bromo, cyano, methylthio, methylsulfonyl, and trifluoromethyl;

R₃ is hydrogen or methyl;

G is N or CH;

R₄ is a five-membered heteroaryl containing two to four heteroatoms selected from O and N or a six-membered heteroaryl containing one to two N; wherein said R₄ is optionally independently substituted with one to two substituents selected from the group consisting of amino, fluoro, chloro, bromo, cyano, $C_{1-4}$alkyl, and $R_a$—($C_{1-4}$)alkyl; wherein $R_a$ is independently selected from hydroxy, methoxy, dimethylamino, or amino;

R₅ is independently selected from the group consisting of hydrogen, chloro, fluoro, bromo, methoxy, methanesulfonyl, cyano, methyl, or trifluoromethyl;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, condition, or disorder in a subject, including a mammal and/or human in which the disease, syndrome, or condition is affected by the inhibition of MALT1, including but not limited to, cancer and/or immunological diseases, using a compound of Formula (I).

The present invention also is directed to the use of any of the compounds described herein in the preparation of a medicament wherein the medicament is prepared for treating a disease, syndrome, condition, or disorder that is affected by the inhibition of MALT1, such as cancer and/or immunological diseases.

The present invention is also directed to the preparation of substituted pyrazole derivatives that act as an inhibitor of MALT1.

Exemplifying the invention are methods of treating a disease, syndrome, condition, or disorder mediated by MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, ertholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor), comprising, consisting of, and/or consisting essentially of, administering to a subject in need thereof a therapeutically effective amount of any of the compounds or pharmaceutical compositions described in the present invention.

In another embodiment, the present invention is directed to a compound of Formula (I) for use in the treatment of a disease, syndrome, condition, or disorder affected by the inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising a compound of Formula (I) for the treatment of a disease, syndrome, condition, or disorder affected by inhibition of MALT1, selected from the group consisting of diffuse large B-cell lymphoma (DLBCL), mantle cell lymphoma (MCL), follicular lymphoma (FL), and mucosa-associated lymphoid tissue (MALT) lymphoma.

An embodiment of the present invention is directed to a composition comprising a compound of Formula (I) for the treatment of immunological diseases that are affected by the inhibition of MALT1, including but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephritis, rheumatic fever, gout, organ or transplact rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment, the present invention is directed to a composition comprising a compound of Formula (I) for the treatment of a disease, syndrome, condition, or disorder affected by inhibition of MALT1, selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Another embodiment of the present invention is directed to a pharmaceutical composition comprising a compound of Formula (I).

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2$ amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(═O)OH.
The term "formyl" refers to the group —C(═O)H.
The term "oxo" or "oxido" refers to the group (═O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

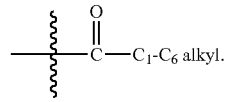

The label "R" at a stereocenter designates that the stereocenter is purely of the R-configuration as defined in the art; likewise, the label "S" means that the stereocenter is purely of the S-configuration. As used herein, the labels "*R" or "*S" at a stereocenter are used to designate that the stereocenter is of pure but unknown absolute configuration. As used herein, the label "RS" refers to a stereocenter that exists as a mixture of the R- and S-configurations.

A compound containing one stereocenter drawn without a stereo bond designation is a mixture of two enantiomers. A compound containing two stereocenters both drawn without stereo bond designations is a mixture of four diastereomers. A compound with two stereocenters both labeled "RS" and drawn with stereo bond designations is a mixture of two enantiomers with relative stereochemistry as drawn. A compound with two stereocenters both labeled "*RS" and drawn with stereo bond designations is a mixture of two enantiomers with a single, but unknown, relative stereochemistry.

Unlabeled stereocenters drawn without stereo bond designations are mixtures of the R- and S-configurations. For unlabeled stereocenters drawn with stereo bond designations, the relative and absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease.

In one embodiment, the term "therapeutically effective amount" refers to the amount of a compound of the present invention that, when administered to a subject, is effective to (1) at least partially alleviate, inhibit, prevent, and/or ameliorate a condition, or a disorder or a disease (i) mediated by MALT1; or (ii) associated with MALT1 activity; or (iii) characterized by activity (normal or abnormal) of MALT1; or (2) reduce or inhibit the activity of MALT1; or (3) reduce or inhibit the expression of MALT1; or (4) modify the protein levels of MALT1.

The term "composition" refers to a product that includes the specified ingredients in therapeutically effective amounts, as well as any product that results, directly, or indirectly, from combinations of the specified ingredients in the specified amounts.

The term "MALT1-mediated" refers to any disease, syndrome, condition, or disorder that might occur in the absence of MALT1 but can occur in the presence of MALT1. Suitable examples of a disease, syndrome, condition, or disorder mediated by MALT1 include, but are not limited to, lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), small lymphocytic lymphoma (SLL), Waldenström macroglobulinemia, lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erytholeukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

As used herein, the term "MALT1 inhibitor" refers to an agent that inhibits or reduces at least one condition, symptom, disorder, and/or disease of MALT1.

As used herein, unless otherwise noted, the term "affect" or "affected" (when referring to a disease, syndrome, condition or disorder that is affected by the inhibition of MALT1) includes a reduction in the frequency and/or severity of one or more symptoms or manifestations of said disease, syndrome, condition or disorder; and/or includes the prevention of the development of one or more symptoms or manifestations of said disease, syndrome, condition or disorder or the development of the disease, condition, syndrome or disorder.

As used herein, the term "treat", "treating", or "treatment" of any disease, condition, syndrome or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at lease one physical parameter including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

The compounds of the instant invention are useful in methods for treating or ameliorating a disease, a syndrome, a condition or a disorder that is affected by the inhibition of MALT1. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

One embodiment of the present invention is directed to a method of treating a MALT1-dependent or MALT1-mediated disease or condition in a subject in need thereof, including an animal, a mammal, and a human in need of such treatment, comprising administering to the subject a therapeutically effective amount of a compound of Formula (I).

In another embodiment, the MALT1-dependent or MALT1-mediated disease or condition is selected from cancers of hematopoietic origin or solid tumors such as chonic myelogenous leukemia, myeloid leukemia, non-Hodgkin lymphoma, and other B cell lymphomas.

In particular, the compounds of Formula (I), or an enantiomer, diastereomer, solvate or pharmaceutically acceptable salt form thereof are useful for treating or ameliorating diseases, syndromes, conditions, or disorders such as diffuse large B-cell lymphoma (DLBCL), mantle cell lymphoma (MCL), follicular lymphoma (FL), and mucosa-associated lymphoid tissue (MALT) lymphoma.

More particularly, the compounds of Formula (I), or an enantiomer, diastereomer, solvate or pharmaceutically acceptable salt form thereof, are useful for treating or ameliorating diffuse large B-cell lymphoma (DLBCL), mantle cell lymphoma (MCL), follicular lymphoma (FL), and mucosa-associated lymphoid tissue (MALT) lymphoma, comprising administering to a subject in need thereof a therapeutically effective amount of a compound of Formula (I), or an enantiomer, diastereomer, solvate or pharmaceutically acceptable salt form thereof as herein defined.

Further, the compounds of Formula (I), or an enantiomer, diastereomer, solvate or pharmaceutically acceptable salt form thereof, are useful for treating or ameliorating an immunological disease, syndrome, disorder, or condition selected from the group consisting of rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

Embodiments of the present invention include a compound of Formula (I)

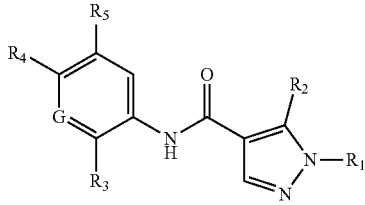

Formula (I)

wherein

A) $R_1$ is independently selected from the group consisting of
  i) phenyl substituted with one to three substituents independently selected from the group consisting of $C_{1-4}$alkyl, methoxy, chloro, fluoro, bromo, cyclopropyl, methylthio, amino, methylamino, and cyano;
  ii) a heteroaryl of five to six members containing one to four heteroatoms selected from the group consisting of O, N, and S; such that no more than one heteroatom is O or S; wherein said heteroaryl of ii) is independently substituted with one to three substituents independently selected from $C_{1-4}$alkyl, methoxy, fluoro, chloro, bromo, cyano, amino, methylamino, methanesulfonyl, methylthio, furan-2-yl, 5,6-dihydro-1,4-dioxin-2-yl, 1,4-dioxan-2-yl, trifluoromethyl, 3-hydroxyazetidin-1-yl, pyrimidin-2-yl, or tetrahydrofuran-2-yl;
  and
  a bicyclic ring system independently selected from the group consisting of 2,2-difluorobenzo[d][1,3]dioxol-4-yl, [1,3]dioxolo[4,5-b]pyridin-7-yl, 1-oxoisoindolin-4-yl, indolin-4-yl, 1-methylindolin-4-yl, [1,3]dioxolo[4,5-b]pyridin-7-yl, 4-methyl-3,4-dihydro-2H-benzo[b][1,4]oxazin-8-yl, benzo[d][1,3]dioxol-4-yl, and 2,3-dihydrobenzo[b][1,4]dioxin-5-yl;

B) $R_1$ is independently selected from the group consisting of
  i) phenyl substituted with one to three substituents independently selected from the group consisting of methyl, methoxy, chloro, fluoro, bromo, and cyano;
  ii) a heteroaryl of five to six members containing one to four heteroatoms selected from the group consisting of O, N, and S; such that no more than one heteroatom is O or S; wherein said heteroaryl of ii) is independently substituted with one to three substituents independently selected from $C_1$-4alkyl, fluoro, chloro, cyano, amino, or methylamino;
  and
  iii) a bicyclic ring system selected from the group consisting of [1,3]dioxolo[4,5-b]pyridin-7-yl, [1,3]dioxolo[4,5-b]pyridin-7-yl, and benzo[d][1,3]dioxol-4-yl;

C) $R_1$ is independently selected from the group consisting of
  i) phenyl substituted with one to three substituents independently selected from the group consisting of methyl, methoxy, chloro, fluoro, and cyano;
  ii) a heteroaryl of five to six members containing one to four heteroatoms selected from the group consisting of O, N, and S; such that no more than one heteroatom is O or S; wherein said heteroaryl of ii) is independently substituted with one to three substituents independently selected from $C_{1-4}$alkyl, fluoro, chloro, cyano, and amino;
  and
  iii) a bicyclic ring system selected from the group consisting of [1,3]dioxolo[4,5-b]pyridin-7-yl, and benzo[d][1,3]dioxol-4-yl;

D) $R^1$ is independently selected from the group consisting of 2-amino-5-methylpyridin-4-yl, 6-amino-5-fluoropyridin-2-yl, benzo[d][1,3]dioxol-4-yl, 6-amino-5-fluoro-3-methylpyridin-2-yl, 6-amino-5-chloropyridin-2-yl, 6-amino-5-cyanopyridin-2-yl, 2-amino-5-chloropyridin-4-yl, 4-cyano-2-methylphenyl, 4-chloro-2-methylphenyl, 3-chloropyridin-4-yl, 2-bromo-4-fluorophenyl, 2-chloro-4-fluorophenyl, [1,3]dioxolo[4,5-b]pyridin-7-yl, 4-fluoro-2-methoxyphenyl, 2-methylphenyl, 2-amino-3-chloropyridin-4-yl, 2-chloro-3,4-difluorophenyl, 2-chloro-3-fluorophenyl, 4-fluoro-2-methylphenyl, 6-amino-3-methylpyridin-2-yl, 5-fluoro-6-(methylamino)pyridin-2-yl, 3-fluoro-2-methylphenyl, 3,4-difluoro-2-methylphenyl, 4-cyanophenyl, 2-methoxypyridin-3-yl, 3-bromo-5-fluoropyridin-2-yl, 3,4-dichloropyridin-2-yl, 2,3-dimethylpyridin-4-yl, 3-chloro-2-methylpyridin-4-yl, 3,5-dichloropyridin-4-yl, 2,3-dihydrobenzo[b][1,4]dioxin-5-yl, 2,2-difluorobenzo[d][1,3]dioxol-4-yl, 5-chloro-2-methylpyridin-4-yl, 2-chloro-5-fluorophenyl, 2-chloro-4,6-difluorophenyl, 2-cyclopropylphenyl, 2-fluoro-6-methylphenyl, 2,6-dichloro-4-fluorophenyl, 5-fluoro-2-methylphenyl, 3-chloro-5-fluoropyridin-2-yl, 4-fluorophenyl, 2-chloro-4-cyanophenyl, 2,4-difluorophenyl, 5-fluoro-3-methylpyridin-2-yl, 2-chlorophenyl, 4-amino-3-chloropyridin-2-yl, 1-methylindolin-4-yl, indolin-4-yl, 4-methyl-3,4-dihydro-2H-benzo[b][1,4]oxazin-8-yl, 1-oxoisoindolin-4-yl, 2-(methylthio)phenyl, 2-amino-3-methylpyridin-4-yl, 3-methylpyridin-4-yl, 2,4,6-trifluorophenyl, 6-amino-3-chloropyridin-2-yl, 6-amino-4-methylpyridin-2-yl, 6-aminopyridin-2-yl, and 5-methyl-2(*R)-(tetrahydrofuran-2-yl)pyridin-4-yl;

E) $R^1$ is independently selected from the group consisting of 2-amino-5-methylpyridin-4-yl, 6-amino-5-fluoropyridin-2-yl, benzo[d][1,3]dioxol-4-yl, 6-amino-5-fluoro-3-methylpyridin-2-yl, 6-amino-5-chloropyridin-2-yl, 6-amino-5-cyanopyridin-2-yl, 2-amino-5-chloropyridin-4-yl, 4-cyano-2-methylphenyl, 4-chloro-2-methylphenyl, 3-chloropyridin-4-yl, 2-bromo-4-fluorophenyl, 2-chloro-4-fluorophenyl, [1,3]dioxolo[4,5-b]pyridin-7-yl, 4-fluoro-2-methoxyphenyl, 2-methylphenyl, 2-amino-3-chloropyridin-4-yl, 2-chloro-3,4-difluorophenyl, 2-chloro-3-fluorophenyl, 4-fluoro-2-methylphenyl, 6-amino-3-methylpyridin-2-yl, 5-fluoro-6-(methylamino)pyridin-2-yl, 3-fluoro-2-methylphenyl, 3,4-difluoro-2-methylphenyl, and 4-cyanophenyl;

F) $R^1$ is independently selected from the group consisting of 2-amino-5-methylpyridin-4-yl, 6-amino-5-fluoropyridin-2-yl, benzo[d][1,3]dioxol-4-yl, 6-amino-5-fluoro-3-methylpyridin-2-yl, 6-amino-5-chloropyridin-2-yl, 6-amino-5-cyanopyridin-2-yl, 2-amino-5-chloropyridin-4-yl, 4-cyano-2-methylphenyl, and 4-chloro-2-methylphenyl;

G) $R_2$ is independently selected from the group consisting of methyl, chloro, bromo, cyano, and trifluoromethyl;

H) $R_2$ is independently selected from the group consisting of methyl and trifluoromethyl;

I) $R_3$ is H;

J) G is N;

K) G is CH;

L) $R_4$ is a five-membered heteroaryl containing two to four heteroatoms selected from O and N, or a six-membered heteroaryl containing one to two N heteroatoms; wherein said $R_4$ is optionally independently substituted with one to two substituents selected from the group consisting of amino, fluoro, chloro, and methyl;

M) R₄ is a five or six-membered heteroaryl independently selected from the group consisting of triazolyl, oxazolyl, pyrazolyl, thiazolyl, tetrazolyl, oxadiazolyl, imidazolyl, and 2-amino-pyrimidin-4-yl;
N) R₄ is 2H-1,2,3-triazol-2-yl;
O) R₅ is independently selected from the group consisting of hydrogen, chloro, fluoro, bromo, cyano, methyl, and trifluoromethyl;
P) R₅ is independently selected from the group consisting of chloro, cyano, methyl, and trifluoromethyl;
Q) R₅ is independently selected from the group consisting of chloro and cyano;

and any combination of embodiments A) through Q) above, provided that it is understood that combinations in which different embodiments of the same substituent would be combined are excluded;

or an enantiomer, diastereomer, or pharmaceutically acceptable salt form thereof.

Embodiments of the present invention include a compound of Formula (I)

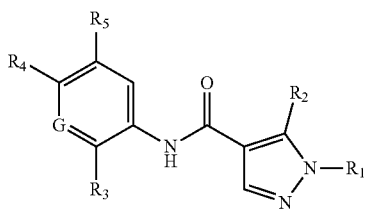

Formula (I)

wherein
R₁ is independently selected from the group consisting of
i) phenyl substituted with one to three substituents independently selected from the group consisting of C₁₋₄alkyl, methoxy, chloro, fluoro, bromo, cyclopropyl, methylthio, and cyano;
ii) a heteroaryl of five to six members containing one to four heteroatoms selected from the group consisting of O, N, and S; such that no more than one heteroatom is O or S; wherein said heteroaryl of ii) is independently substituted with one to three substituents independently selected from C₁₋₄alkyl, methoxy, fluoro, chloro, bromo, cyano, amino, methylamino, or tetrahydrofuran-2-yl; and
iii) a bicyclic ring system independently selected from the group consisting of 2,2-difluorobenzo[d][1,3]dioxol-4-yl, [1,3]dioxolo[4,5-b]pyridin-7-yl, 1-oxoisoindolin-4-yl, indolin-4-yl, 1-methylindolin-4-yl, [1,3]dioxolo[4,5-b]pyridin-7-yl, 4-methyl-3,4-dihydro-2H-benzo[b][1,4]oxazin-8-yl, benzo[d][1,3]dioxol-4-yl, and 2,3-dihydrobenzo[b][1,4]dioxin-5-yl;
R₂ is independently selected from the group consisting of methyl, chloro, bromo, cyano, and trifluoromethyl;
R₃ is hydrogen or methyl;
G is N or CH;
R₄ is a five-membered heteroaryl containing two to four heteroatoms selected from O and N, or a six-membered heteroaryl containing one to two N; wherein said R₄ is optionally independently substituted with one to two substituents selected from the group consisting of amino, fluoro, chloro, and methyl;
R₅ is independently selected from the group consisting of hydrogen, chloro, fluoro, bromo, cyano, methyl, and trifluoromethyl;

or an enantiomer, diastereomer, or pharmaceutically acceptable salt form thereof.

Embodiments of the present invention include a compound of Formula (I)

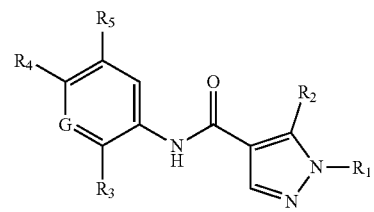

Formula (I)

wherein
R₁ is independently selected from the group consisting of
i) phenyl substituted with one to three substituents independently selected from the group consisting of methyl, methoxy, chloro, fluoro, bromo, and cyano;
ii) a heteroaryl of five to six members containing one to four heteroatoms selected from the group consisting of O, N, and S; such that no more than one heteroatom is O or S; wherein said heteroaryl of ii) is independently substituted with one to three substituents independently selected from C₁₋₄alkyl, fluoro, chloro, cyano, amino, and methylamino; and
iii) a bicyclic ring system selected from the group consisting of [1,3]dioxolo[4,5-b]pyridin-7-yl, [1,3]dioxolo[4,5-b]pyridin-7-yl, and benzo[d][1,3]dioxol-4-yl;
R₂ is independently selected from the group consisting of methyl, chloro, bromo, cyano, and trifluoromethyl;
R₃ is hydrogen;
G is N or CH;
R₄ is a five-membered heteroaryl containing two to four heteroatoms selected from O and N, or a six-membered heteroaryl containing one to two N; wherein said R₄ is optionally independently substituted with one to two substituents selected from the group consisting of amino, fluoro, chloro, and methyl;
R₅ is independently selected from the group consisting of hydrogen, chloro, fluoro, bromo, cyano, methyl, and trifluoromethyl;

or an enantiomer, diastereomer, or pharmaceutically acceptable salt form thereof.

Embodiments of the present invention include a compound of Formula (I)

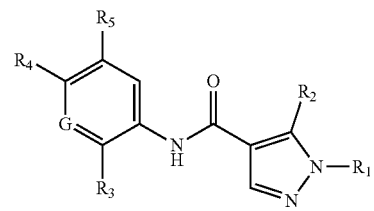

Formula (I)

wherein
R₁ is independently selected from the group consisting of
i) phenyl substituted with one to three substituents independently selected from the group consisting of methyl, methoxy, chloro, fluoro, and cyano;
ii) a heteroaryl of five to six members containing one to four heteroatoms selected from the group consisting of O, N, and S; such that no more than one heteroatom is O or S; wherein said heteroaryl of ii) is independently substituted with one or three substituents independently selected from $C_{1-4}$alkyl, fluoro, chloro, cyano, and amino; and iii) a bicyclic ring system independently selected from the group consisting of [1,3]dioxolo[4,5-b]pyridin-7-yl, and benzo[d][1,3]dioxol-4-yl;

$R_2$ is independently selected from the group consisting of methyl, chloro, bromo, cyano, and trifluoromethyl;

$R_3$ is hydrogen;

G is N or CH;

$R_4$ is a five or six-membered heteroaryl independently selected from the group consisting of triazolyl, oxazolyl, pyrazolyl, thiazolyl, tetrazolyl, oxadiazolyl, imidazolyl, and 2-amino-pyrimidin-4-yl;

$R_5$ is independently selected from the group consisting of chloro, cyano, methyl, and trifluoromethyl;

or an enantiomer, diastereomer, or pharmaceutically acceptable salt form thereof.

Embodiments of the present invention include a compound of Formula (I)

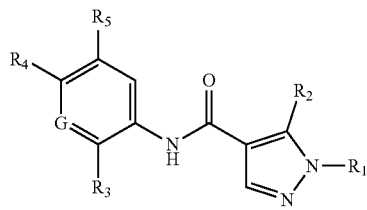

Formula (I)

wherein $R_1$ is independently selected from the group consisting of 2-amino-5-methylpyridin-4-yl, 6-amino-5-fluoropyridin-2-yl, benzo[d][1,3]dioxol-4-yl, 6-amino-5-fluoro-3-methylpyridin-2-yl, 6-amino-5-chloropyridin-2-yl, 6-amino-5-cyanopyridin-2-yl, 2-amino-5-chloropyridin-4-yl, 4-cyano-2-methylphenyl, 4-chloro-2-methylphenyl, 3-chloropyridin-4-yl, 2-bromo-4-fluorophenyl, 2-chloro-4-fluorophenyl, [1,3]dioxolo[4,5-b]pyridin-7-yl, 4-fluoro-2-methoxyphenyl, 2-methylphenyl, 2-amino-3-chloropyridin-4-yl, 2-chloro-3,4-difluorophenyl, 2-chloro-3-fluorophenyl, 4-fluoro-2-methylphenyl, 6-amino-3-methylpyridin-2-yl, 5-fluoro-6-(methylamino)pyridin-2-yl, 3-fluoro-2-methylphenyl, 3,4-difluoro-2-methylphenyl, 4-cyanophenyl, 2-methoxypyridin-3-yl, 3-bromo-5-fluoropyridin-2-yl, 3,4-dichloropyridin-2-yl, 2,3-dimethylpyridin-4-yl, 3-chloro-2-methylpyridin-4-yl, 3,5-dichloropyridin-4-yl, 2,3-dihydrobenzo[b][1,4]dioxin-5-yl, 2,2-difluorobenzo[d][1,3]dioxol-4-yl, 5-chloro-2-methylpyridin-4-yl, 2-chloro-5-fluorophenyl, 2-chloro-4,6-difluorophenyl, 2-cyclopropylphenyl, 2-fluoro-6-methylphenyl, 2,6-dichloro-4-fluorophenyl, 5-fluoro-2-methylphenyl, 3-chloro-5-fluoropyridin-2-yl, 4-fluorophenyl, 2-chloro-4-cyanophenyl, 2,4-difluorophenyl, 5-fluoro-3-methylpyridin-2-yl, 2-chlorophenyl, 4-amino-3-chloropyridin-2-yl, 1-methylindolin-4-yl, indolin-4-yl, 4-methyl-3,4-dihydro-2H-benzo[b][1,4]oxazin-8-yl, 1-oxoisoindolin-4-yl, 2-(methylthio)phenyl, 2-amino-3-methylpyridin-4-yl, 3-methylpyridin-4-yl, 2,4,6-trifluorophenyl, 6-amino-3-chloropyridin-2-yl, 6-amino-4-methylpyridin-2-yl, 6-aminopyridin-2-yl, and 5-methyl-2(*R)-(tetrahydrofuran-2-yl)pyridin-4-yl;

$R_2$ is independently selected from the group consisting of methyl, chloro, bromo, cyano, and trifluoromethyl;

$R_3$ is hydrogen;

G is N or CH;

$R_4$ is a five or six-membered heteroaryl independently selected from the group consisting of triazolyl, oxazolyl, pyrazolyl, thiazolyl, tetrazolyl, oxadiazolyl, imidazolyl, and 2-amino-pyrimidin-4-yl;

$R_5$ is independently selected from the group consisting of chloro, cyano, methyl, and trifluoromethyl;

or an enantiomer, diastereomer, or pharmaceutically acceptable salt form thereof.

Embodiments of the present invention include a compound of Formula (I)

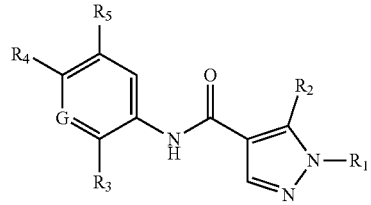

Formula (I)

wherein $R^1$ is selected from the group consisting of 2-amino-5-methylpyridin-4-yl, 6-amino-5-fluoropyridin-2-yl, benzo[d][1,3]dioxol-4-yl, 6-amino-5-fluoro-3-methylpyridin-2-yl, 6-amino-5-chloropyridin-2-yl, 6-amino-5-cyanopyridin-2-yl, 2-amino-5-chloropyridin-4-yl, 4-cyano-2-methylphenyl, 4-chloro-2-methylphenyl, 3-chloropyridin-4-yl, 2-bromo-4-fluorophenyl, 2-chloro-4-fluorophenyl, [1,3]dioxolo[4,5-b]pyridin-7-yl, 4-fluoro-2-methoxyphenyl, 2-methylphenyl, 2-amino-3-chloropyridin-4-yl, 2-chloro-3,4-difluorophenyl, 2-chloro-3-fluorophenyl, 4-fluoro-2-methylphenyl, 6-amino-3-methylpyridin-2-yl, 5-fluoro-6-(methylamino)pyridin-2-yl, 3-fluoro-2-methylphenyl, 3,4-difluoro-2-methylphenyl, and 4-cyanophenyl;

$R_2$ is independently selected from the group consisting of methyl, chloro, bromo, cyano, and trifluoromethyl;

$R_3$ is hydrogen;

G is N or CH;

$R_4$ is a five or six-membered heteroaryl independently selected from the group consisting of triazolyl, oxazolyl, pyrazolyl, thiazolyl, tetrazolyl, oxadiazolyl, imidazolyl, and 2-amino-pyrimidin-4-yl;

$R_5$ is independently selected from the group consisting of chloro and cyano; or an enantiomer, diastereomer, or pharmaceutically acceptable salt form thereof.

Embodiments of the present invention include a compound of Formula (I)

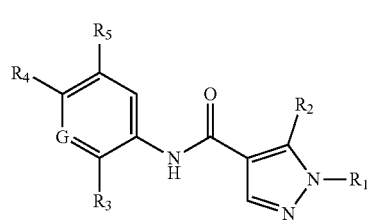

Formula (I)

wherein $R^1$ is independently selected from the group consisting of 2-amino-5-methylpyridin-4-yl, 6-amino-5-fluoropyridin-2-yl, benzo[d][1,3]dioxol-4-yl, 6-amino-5-fluoro-3-methylpyridin-2-yl, 6-amino-5-chloropyridin-2-yl, 6-amino-5-cyanopyridin-2-yl, 2-amino-5-chloropyridin-4-yl, 4-cyano-2-methylphenyl, and 4-chloro-2-methylphenyl;

$R_2$ is independently selected from the group consisting of methyl, chloro, bromo, cyano, and trifluoromethyl;

$R_3$ is hydrogen;

G is N or CH;

$R_4$ is a five or six-membered heteroaryl independently selected from the group consisting of triazolyl, oxazolyl, pyrazolyl, thiazolyl, tetrazolyl, oxadiazolyl, imidazolyl, and 2-amino-pyrimidin-4-yl;

$R_5$ is independently selected from the group consisting of chloro and cyano; or an enantiomer, diastereomer, or pharmaceutically acceptable salt form thereof.

Embodiments of the present invention include a compound of Formula (I)

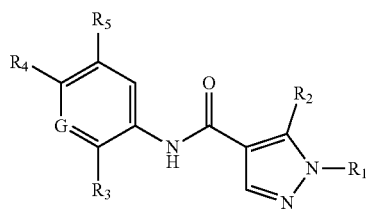

Formula (I)

wherein $R_1$ is independently selected from the group consisting of i) phenyl optionally substituted with one to three substituents independently selected from the group consisting of 1-methoxyethyl, $C_{(1-4)}$alkyl, methoxy, chloro, fluoro, bromo, methanesulfonyl, cyclopropyl, methylthio, trifluoromethyl, amino, and cyano;

ii) 4-methyl-pyridazin-3-yl, pyrimidinyl, pyrazinyl, or pyridinyl wherein said pyridinyl is optionally substituted with one to three substituents independently selected from the group consisting of $C_{(1-4)}$alkyl, methoxy, fluoro, chloro, bromo, cyano, amino, methylamino, tetrahydrofuran-2-yl, furan-2-yl, 5,6-dihydro-1,4-dioxin-2-yl, 1,4-dioxan-2-yl, trifluoromethyl, 3-hydroxyazetidin-1-yl, N-oxido, and aminocarbonyl; and iii) a bicyclic ring system independently selected from the group consisting of 2,2-difluorobenzo[d][1,3]dioxol-4-yl, [1,3]dioxolo[4,5-b]pyridin-7-yl, 1-oxoisoindolin-4-yl, 1-methyl-1,2,3,4-tetrahydroquinolin-8-yl, 1,2,3,4-tetrahydroisoquinolin-5-yl, indolin-4-yl, 1-methylindolin-4-yl, 1-methyl-1,2,3,4-tetrahydroquinolin-5-yl, 4-methyl-3,4-dihydro-2H-benzo[b][1,4]oxazin-8-yl, benzo[d][1,3]dioxol-4-yl, and 2,3-dihydrobenzo[b][1,4]dioxin-5-yl;

$R_2$ is independently selected from the group consisting of $C_{1-4}$alkyl, 1-methoxy-ethyl, difluoromethyl, fluoro, chloro, bromo, cyano, methylthio, methylsulfonyl, and trifluoromethyl;

$R_3$ is hydrogen or $C_{(1-4)}$alkyl;

G is N or CH;

$R_4$ is 2H-1,2,3-triazol-2-yl;

$R_5$ is independently selected from the group consisting of chloro, bromo, cyano, $C_{(1-4)}$alkyl or trifluoromethyl;

or an enantiomer, diastereomer, or pharmaceutically acceptable salt form thereof.

Embodiments of the present invention include a compound of Formula (I)

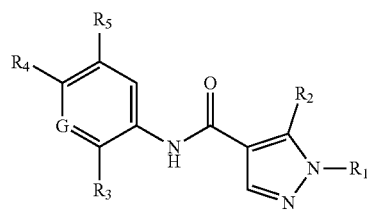

Formula (I)

wherein $R_1$ is independently selected from the group consisting of iv) phenyl optionally substituted with one to three substituents independently selected from the group consisting of 1-methoxyethyl, methyl, isopropyl, methoxy, chloro, fluoro, bromo, methanesulfonyl, cyclopropyl, methylthio, trifluoromethyl, amino, and cyano;

v) 4-methyl-pyridazin-3-yl, pyrimidinyl, pyrazinyl, or pyridinyl wherein said pyridinyl is optionally substituted with one to three substituents independently selected from the group consisting of methyl, methoxy, fluoro, chloro, bromo, cyano, amino, methylamino, tetrahydrofuran-2-yl, furan-2-yl, 5,6-dihydro-1,4-dioxin-2-yl, 1,4-dioxan-2-yl, trifluoromethyl, 3-hydroxyazetidin-1-yl, N-oxido, and aminocarbonyl; and vi) a bicyclic ring system independently selected from the group consisting of 2,2-difluorobenzo[d][1,3]dioxol-4-yl, [1,3]dioxolo[4,5-b]pyridin-7-yl, 1-oxoisoindolin-4-yl, 1-methyl-1,2,3,4-tetrahydroquinolin-8-yl, 1,2,3,4-tetrahydroisoquinolin-5-yl, indolin-4-yl, 1-methylindolin-4-yl, 1-methyl-1,2,3,4-tetrahydroquinolin-5-yl, 4-methyl-3,4-dihydro-2H-benzo[b][1,4]oxazin-8-yl, benzo[d][1,3]dioxol-4-yl, and 2,3-dihydrobenzo[b][1,4]dioxin-5-yl;

$R_2$ is independently selected from the group consisting of difluoromethyl, fluoro, and trifluoromethyl;

$R_3$ is hydrogen or methyl;

G is N or CH;

$R_4$ is 2H-1,2,3-triazol-2-yl;

$R_5$ is independently selected from the group consisting of chloro, bromo, cyano, or trifluoromethyl;

or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, as exemplified in the listing in Table 1, below.

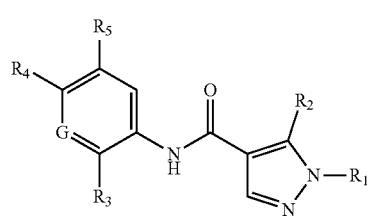

Formula (I)

TABLE 1

| Structure | Cpd no | Name |
|---|---|---|
| 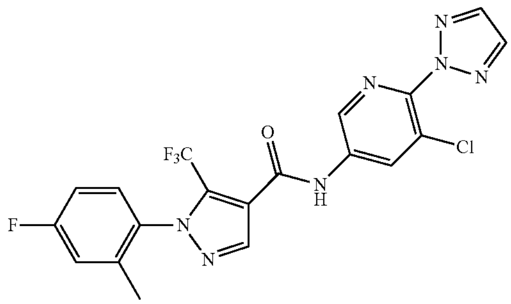 [SMILES: Cc1cc(F)ccc1-n1ncc(C(=O)Nc2cnc(-n3nccn3)c(Cl)c2)c1C(F)(F)F] | 1 | N-(5-Chloro-6-(2H-1,2,3-triazol-2-yl)pyridin-3-yl)-1-(4-fluoro-2-methylphenyl)-5-(trifluoromethyl)-1H-pyrazole-4-carboxamide |
| 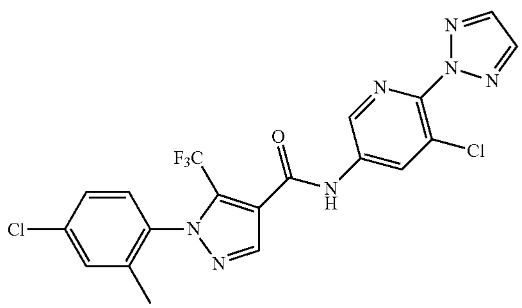 [SMILES: Cc1cc(Cl)ccc1-n1ncc(C(=O)Nc2cnc(-n3nccn3)c(Cl)c2)c1C(F)(F)F] | 2 | 1-(4-Chloro-2-methylphenyl)-N-(5-chloro-6-(2H-1,2,3-triazol-2-yl)pyridin-3-yl)-5-(trifluoromethyl)-1H-pyrazole-4-carboxamide |
| 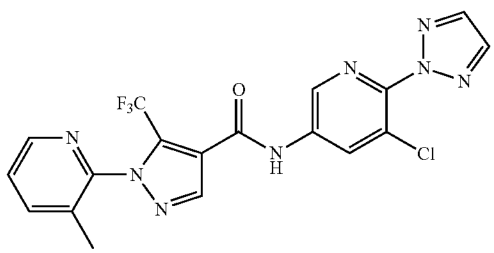 [SMILES: Cc1cccnc1-n1ncc(C(=O)Nc2cnc(-n3nccn3)c(Cl)c2)c1C(F)(F)F] | 3 | N-(5-Chloro-6-(2H-1,2,3-triazol-2-yl)pyridin-3-yl)-1-(3-methylpyridin-2-yl)-5-(trifluoromethyl)-1H-pyrazole-4-carboxamide |
| 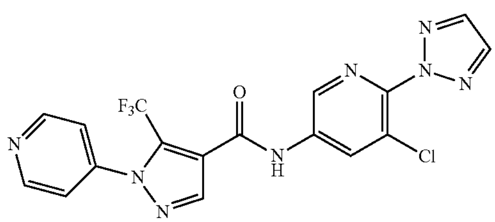 [SMILES: O=C(Nc1cnc(-n2nccn2)c(Cl)c1)c1cnn(-c2ccncc2)c1C(F)(F)F] | 4 | N-(5-Chloro-6-(2H-1,2,3-triazol-2-yl)pyridin-3-yl)-1-(pyridin-4-yl)-5-(trifluoromethyl)-1H-pyrazole-4-carboxamide |
| 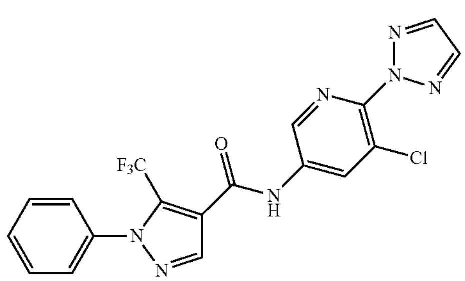 [SMILES: O=C(Nc1cnc(-n2nccn2)c(Cl)c1)c1cnn(-c2ccccc2)c1C(F)(F)F] | 5 | N-(5-Chloro-6-(2H-1,2,3-triazol-2-yl)pyridin-3-yl)-1-phenyl-5-(trifluoromethyl)-1H-pyrazole-4-carboxamide |

TABLE 1-continued

| Structure | Cpd no | Name |
|---|---|---|
| 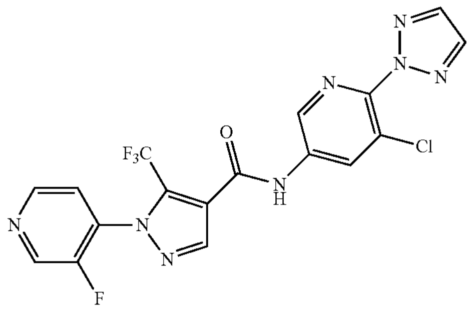 [SMILES: O=C(Nc1cnc(-n2nccn2)c(Cl)c1)c1cnn(-c2ccncc2F)c1C(F)(F)F] | 6 | N-(5-Chloro-6-(2H-1,2,3-triazol-2-yl)pyridin-3-yl)-1-(3-fluoropyridin-4-yl)-5-(trifluoromethyl)-1H-pyrazole-4-carboxamide |
| 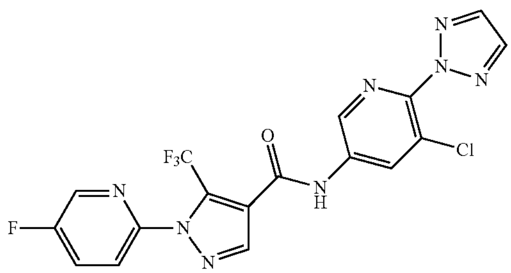 [SMILES: O=C(Nc1cnc(-n2nccn2)c(Cl)c1)c1cnn(-c2ccc(F)cn2)c1C(F)(F)F] | 7 | N-(5-Chloro-6-(2H-1,2,3-triazol-2-yl)pyridin-3-yl)-1-(5-fluoropyridin-2-yl)-5-(trifluoromethyl)-1H-pyrazole-4-carboxamide |
| 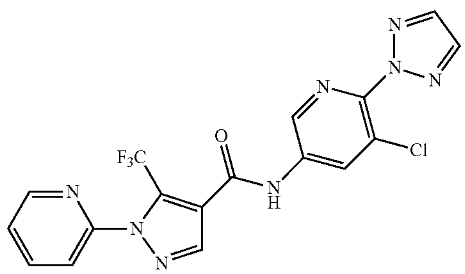 [SMILES: O=C(Nc1cnc(-n2nccn2)c(Cl)c1)c1cnn(-c2ccccn2)c1C(F)(F)F] | 8 | N-(5-Chloro-6-(2H-1,2,3-triazol-2-yl)pyridin-3-yl)-1-(pyridin-2-yl)-5-(trifluoromethyl)-1H-pyrazole-4-carboxamide |
| 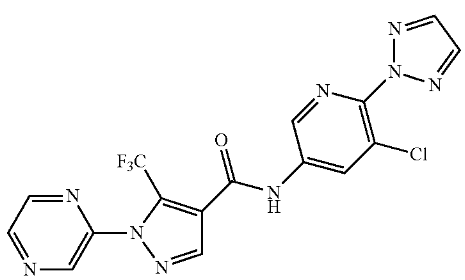 [SMILES: O=C(Nc1cnc(-n2nccn2)c(Cl)c1)c1cnn(-c2cnccn2)c1C(F)(F)F] | 9 | N-(5-Chloro-6-(2H-1,2,3-triazol-2-yl)pyridin-3-yl)-1-(pyrazin-2-yl)-5-(trifluoromethyl)-1H-pyrazole-4-carboxamide |
| 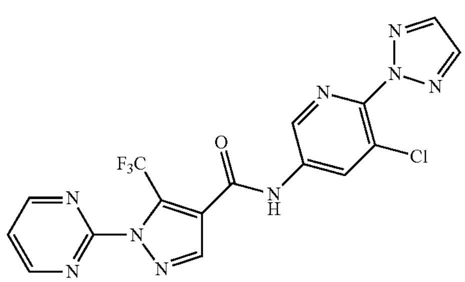 [SMILES: O=C(Nc1cnc(-n2nccn2)c(Cl)c1)c1cnn(-c2ncccn2)c1C(F)(F)F] | 10 | N-(5-Chloro-6-(2H-1,2,3-triazol-2-yl)pyridin-3-yl)-1-(pyrimidin-2-yl)-5-(trifluoromethyl)-1H-pyrazole-4-carboxamide |

TABLE 1-continued

| Structure | Cpd no | Name |
|---|---|---|
| 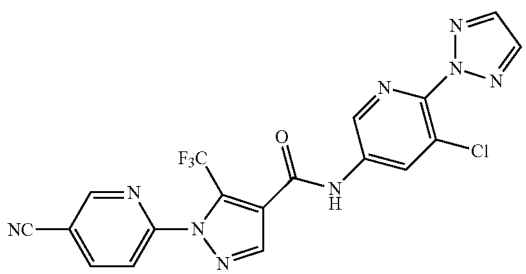 [SMILES: N#Cc1ccc(-n2ncc(C(=O)Nc3cnc(-n4nccn4)c(Cl)c3)c2C(F)(F)F)nc1] | 11 | N-(5-Chloro-6-(2H-1,2,3-triazol-2-yl)pyridin-3-yl)-1-(5-cyanopyridin-2-yl)-5-(trifluoromethyl)-1H-pyrazole-4-carboxamide |
| 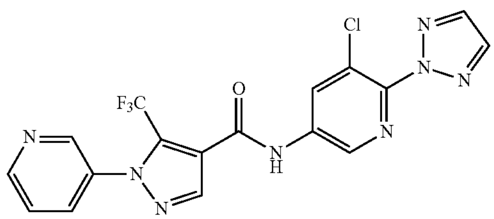 [SMILES: O=C(Nc1cnc(-n2nccn2)c(Cl)c1)c1cnn(-c2cccnc2)c1C(F)(F)F] | 12 | N-(5-Chloro-6-(2H-1,2,3-triazol-2-yl)pyridin-3-yl)-1-(pyridin-3-yl)-5-(trifluoromethyl)-1H-pyrazole-4-carboxamide |
| 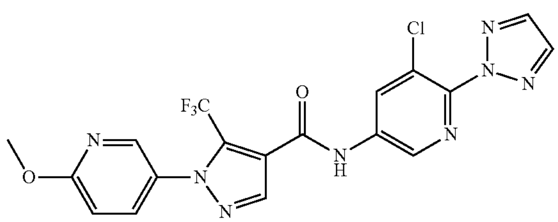 [SMILES: COc1ccc(-n2ncc(C(=O)Nc3cnc(-n4nccn4)c(Cl)c3)c2C(F)(F)F)cn1] | 13 | N-(5-Chloro-6-(2H-1,2,3-triazol-2-yl)pyridin-3-yl)-1-(6-methoxypyridin-3-yl)-5-(trifluoromethyl)-1H-pyrazole-4-carboxamide |
| 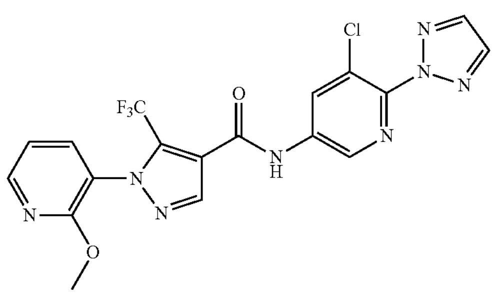 [SMILES: COc1ncccc1-n1ncc(C(=O)Nc2cnc(-n3nccn3)c(Cl)c2)c1C(F)(F)F] | 14 | N-(5-Chloro-6-(2H-1,2,3-triazol-2-yl)pyridin-3-yl)-1-(2-methoxypyridin-3-yl)-5-(trifluoromethyl)-1H-pyrazole-4-carboxamide |
| 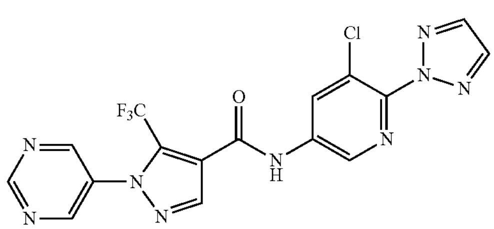 [SMILES: O=C(Nc1cnc(-n2nccn2)c(Cl)c1)c1cnn(-c2cncnc2)c1C(F)(F)F] | 15 | N-(5-Chloro-6-(2H-1,2,3-triazol-2-yl)pyridin-3-yl)-1-(pyrimidin-5-yl)-5-(trifluoromethyl)-1H-pyrazole-4-carboxamide |
| 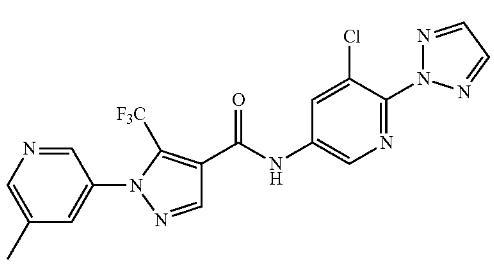 [SMILES: Cc1cncc(-n2ncc(C(=O)Nc3cnc(-n4nccn4)c(Cl)c3)c2C(F)(F)F)c1] | 16 | N-(5-Chloro-6-(2H-1,2,3-triazol-2-yl)pyridin-3-yl)-1-(5-methylpyridin-3-yl)-5-(trifluoromethyl)-1H-pyrazole-4-carboxamide |

TABLE 1-continued

| Structure | Cpd no | Name |
|---|---|---|
| 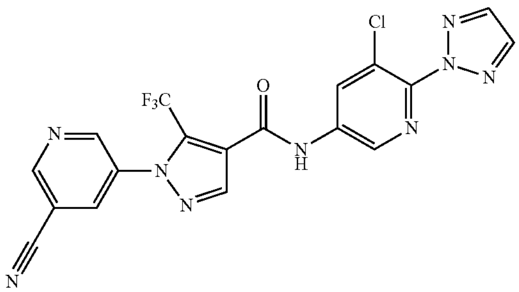 [SMILES: N#Cc1cncc(-n2ncc(C(=O)Nc3cnc(-n4nccn4)c(Cl)c3)c2C(F)(F)F)c1] | 17 | N-(5-Chloro-6-(2H-1,2,3-triazol-2-yl)pyridin-3-yl)-1-(5-cyanopyridin-3-yl)-5-(trifluoromethyl)-1H-pyrazole-4-carboxamide |
| 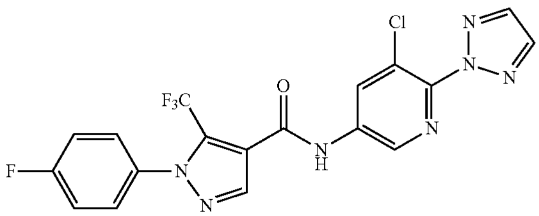 [SMILES: O=C(Nc1cnc(-n2nccn2)c(Cl)c1)c1cnn(-c2ccc(F)cc2)c1C(F)(F)F] | 18 | N-(5-chloro-6-(2H-1,2,3-triazol-2-yl)pyridin-3-yl)-1-(4-fluorophenyl)-5-(trifluoromethyl)-1H-pyrazole-4-carboxamide |
| 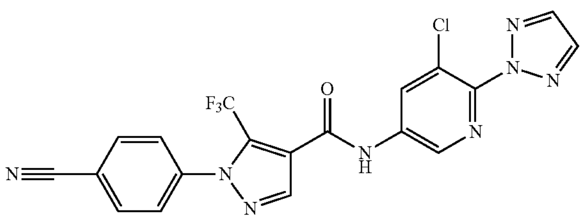 [SMILES: N#Cc1ccc(-n2ncc(C(=O)Nc3cnc(-n4nccn4)c(Cl)c3)c2C(F)(F)F)cc1] | 19 | N-(5-chloro-6-(2H-1,2,3-triazol-2-yl)pyridin-3-yl)-1-(4-cyanophenyl)-5-(trifluoromethyl)-1H-pyrazole-4-carboxamide |
| 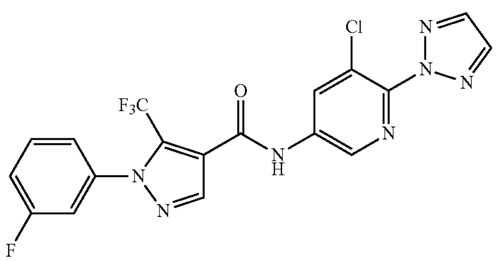 [SMILES: O=C(Nc1cnc(-n2nccn2)c(Cl)c1)c1cnn(-c2cccc(F)c2)c1C(F)(F)F] | 20 | N-(5-chloro-6-(2H-1,2,3-triazol-2-yl)pyridin-3-yl)-1-(3-fluorophenyl)-5-(trifluoromethyl)-1H-pyrazole-4-carboxamide |
| 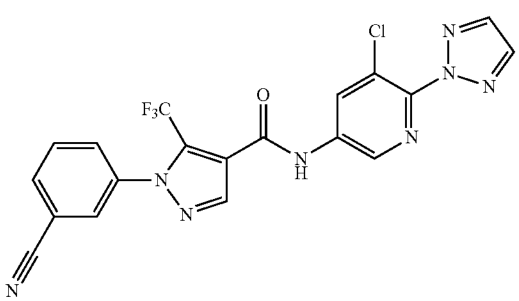 [SMILES: N#Cc1cccc(-n2ncc(C(=O)Nc3cnc(-n4nccn4)c(Cl)c3)c2C(F)(F)F)c1] | 21 | N-(5-chloro-6-(2H-1,2,3-triazol-2-yl)pyridin-3-yl)-1-(3-cyanophenyl)-5-(trifluoromethyl)-1H-pyrazole-4-carboxamide |
| 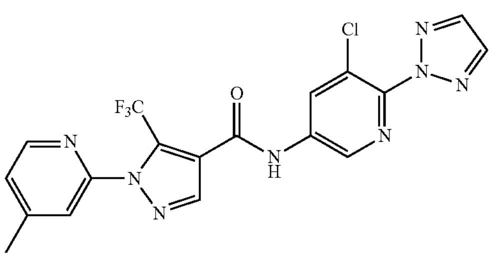 [SMILES: Cc1ccnc(-n2ncc(C(=O)Nc3cnc(-n4nccn4)c(Cl)c3)c2C(F)(F)F)c1] | 22 | N-(5-chloro-6-(2H-1,2,3-triazol-2-yl)pyridin-3-yl)-1-(4-methylpyridin-2-yl)-5-(trifluoromethyl)-1H-pyrazole-4-carboxamide |

TABLE 1-continued

| Structure | Cpd no | Name |
|---|---|---|
| 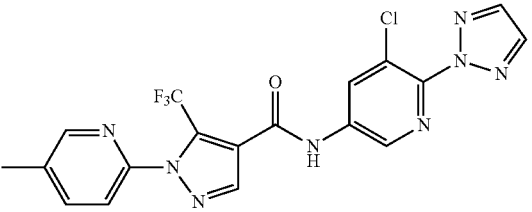 [SMILES: Cc1ccc(-n2ncc(C(=O)Nc3cnc(-n4nccn4)c(Cl)c3)c2C(F)(F)F)nc1] | 23 | N-(5-chloro-6-(2H-1,2,3-triazol-2-yl)pyridin-3-yl)-1-(5-methylpyridin-2-yl)-5-(trifluoromethyl)-1H-pyrazole-4-carboxamide |
| 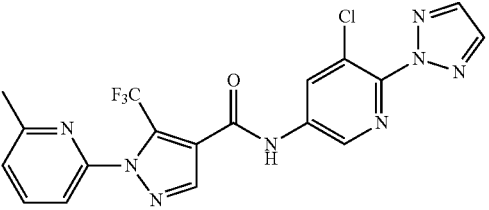 [SMILES: Cc1cccc(-n2ncc(C(=O)Nc3cnc(-n4nccn4)c(Cl)c3)c2C(F)(F)F)n1] | 24 | N-(5-chloro-6-(2H-1,2,3-triazol-2-yl)pyridin-3-yl)-1-(6-methylpyridin-2-yl)-5-(trifluoromethyl)-1H-pyrazole-4-carboxamide |
| 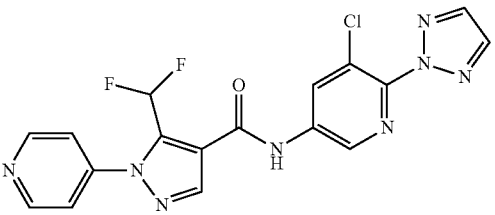 [SMILES: O=C(Nc1cnc(-n2nccn2)c(Cl)c1)c1cnn(-c2ccncc2)c1C(F)F] | 25 | N-(5-chloro-6-(2H-1,2,3-triazol-2-yl)pyridin-3-yl)-5-(difluoromethyl)-1-(pyridin-4-yl)-1H-pyrazole-4-carboxamide |
| 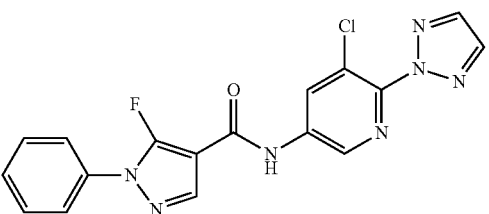 | 26 | N-(5-chloro-6-(2H-1,2,3-triazol-2-yl)pyridin-3-yl)-5-fluoro-1-phenyl-1H-pyrazole-4-carboxamide |
| 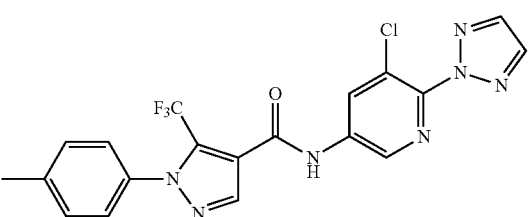 | 27 | N-(5-chloro-6-(2H-1,2,3-triazol-2-yl)pyridin-3-yl)-1-(p-tolyl)-5-(trifluoromethyl)-1H-pyrazole-4-carboxamide |
| 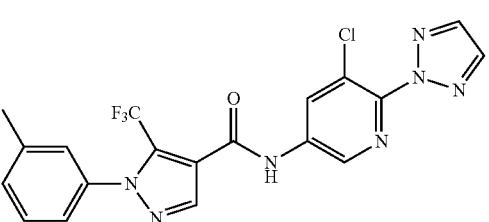 | 28 | N-(5-chloro-6-(2H-1,2,3-triazol-2-yl)pyridin-3-yl)-1-(m-tolyl)-5-(trifluoromethyl)-1H-pyrazole-4-carboxamide |
| 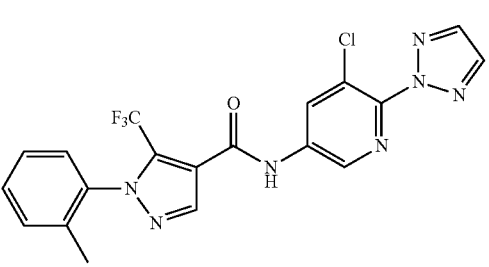 [SMILES: Cc1ccccc1-n1ncc(C(=O)Nc2cnc(-n3nccn3)c(Cl)c2)c1C(F)(F)F] | 29 | N-(5-chloro-6-(2H-1,2,3-triazol-2-yl)pyridin-3-yl)-1-(o-tolyl)-5-(trifluoromethyl)-1H-pyrazole-4-carboxamide |

TABLE 1-continued

| Structure | Cpd no | Name |
|---|---|---|
| 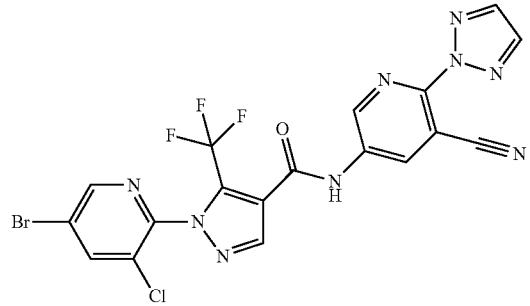 [SMILES: N#Cc1cc(NC(=O)c2cnn(-c3ncc(Br)cc3Cl)c2C(F)(F)F)cnc1-n1nccn1] | 30 | 1-(5-bromo-3-chloropyridin-2-yl)-N-(5-cyano-6-(2H-1,2,3-triazol-2-yl)pyridin-3-yl)-5-(trifluoromethyl)-1H-pyrazole-4-carboxamide |
| 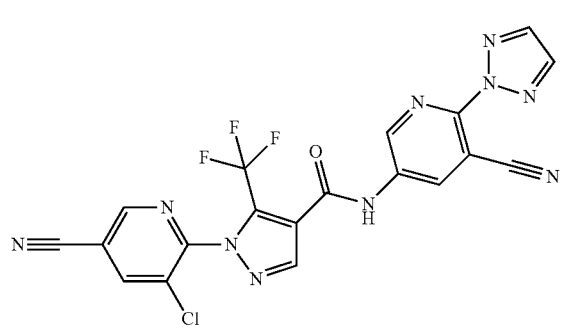 [SMILES: N#Cc1cnc(-n2ncc(C(=O)Nc3cnc(-n4nccn4)c(C#N)c3)c2C(F)(F)F)c(Cl)c1] | 31 | 1-(3-chloro-5-cyanopyridin-2-yl)-N-(5-cyano-6-(2H-1,2,3-triazol-2-yl)pyridin-3-yl)-5-(trifluoromethyl)-1H-pyrazole-4-carboxamide |
| 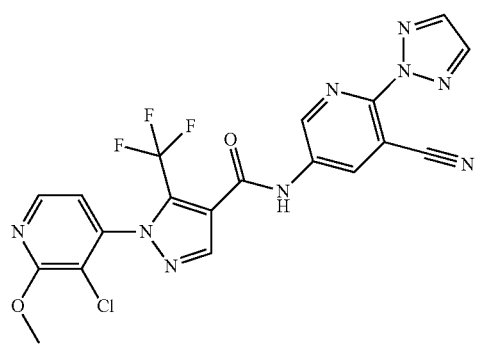 [SMILES: COc1nccc(-n2ncc(C(=O)Nc3cnc(-n4nccn4)c(C#N)c3)c2C(F)(F)F)c1Cl] | 32 | 1-(3-Chloro-2-methoxypyridin-4-yl)-N-(5-cyano-6-(2H-1,2,3-triazol-2-yl)pyridin-3-yl)-5-(trifluoromethyl)-1H-pyrazole-4-carboxamide |
| 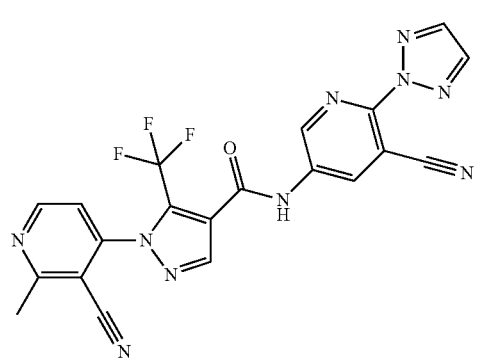 [SMILES: Cc1nccc(-n2ncc(C(=O)Nc3cnc(-n4nccn4)c(C#N)c3)c2C(F)(F)F)c1C#N] | 33 | 1-(3-Cyano-2-methylpyridin-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 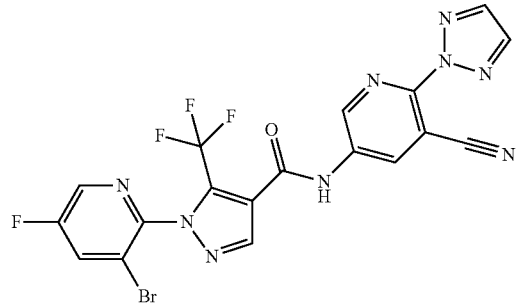 | 34 | 1-(3-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide |
| 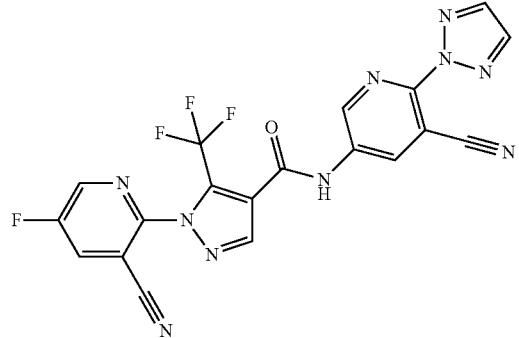 | 35 | 1-(3-cyano-5-fluoropyridin-2-yl)-N-(5-cyano-6-(2H-1,2,3-triazol-2-yl)pyridin-3-yl)-5-(trifluoromethyl)-1H-pyrazole-4-carboxamide |
| 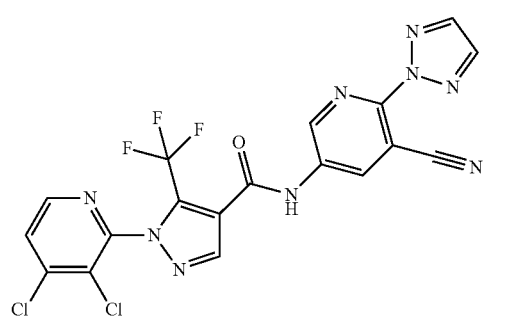 [SMILES: N#Cc1cc(NC(=O)c2cnn(-c3nccc(Cl)c3Cl)c2C(F)(F)F)cnc1-n1nccn1] | 36 | N-(5-Cyano-6-(2H-1,2,3-triazol-2-yl)pyridin-3-yl)-1-(3,4-dichloropyridin-2-yl)-5-(trifluoromethyl)-1H-pyrazole-4-carbox |
| 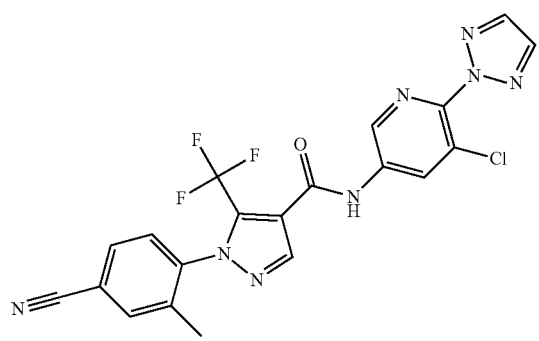 [SMILES: Cc1cc(C#N)ccc1-n1ncc(C(=O)Nc2cnc(-n3nccn3)c(Cl)c2)c1C(F)(F)F] | 37 | N-(5-chloro-6-(2H-1,2,3-triazol-2-yl)pyridin-3-yl)-1-(4-cyano-2-methylphenyl)-5-(trifluoromethyl)-1H-pyrazole-4-carboxamide |

TABLE 1-continued

| Structure | Cpd no | Name |
|---|---|---|
| 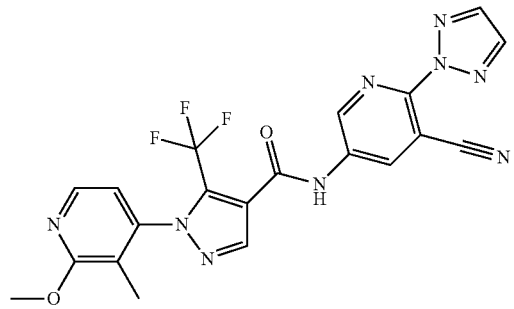 [SMILES: COc1nccc(-n2ncc(C(=O)Nc3cnc(-n4nccn4)c(C#N)c3)c2C(F)(F)F)c1C] | 38 | N-(5-cyano-6-(2H-1,2,3-triazol-2-yl)pyridin-3-yl)-1-(2-methoxy-3-methylpyridin-4-yl)-5-(trifluoromethyl)-1H-pyrazole-4-carboxamide |
| 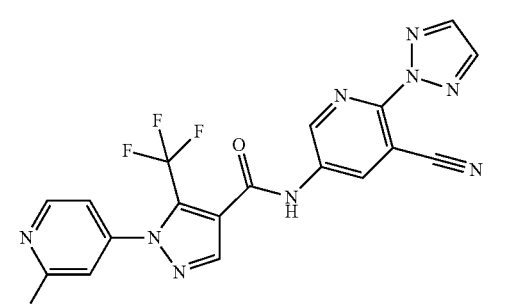 | 39 | 1-(2-chloropyridin-4-yl)-N-(5-cyano-6-(2H-1,2,3-triazol-2-yl)pyridin-3-yl)-5-(trifluoromethyl)-1H-pyrazole-4-carboxamide |
| 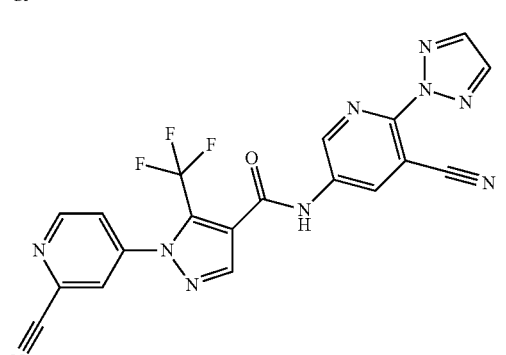 | 40 | N-(5-cyano-6-(2H-1,2,3-triazol-2-yl)pyridin-3-yl)-1-(2-cyanopyridin-4-yl)-5-(trifluoromethyl)-1H-pyrazole-4-carboxamide |
| 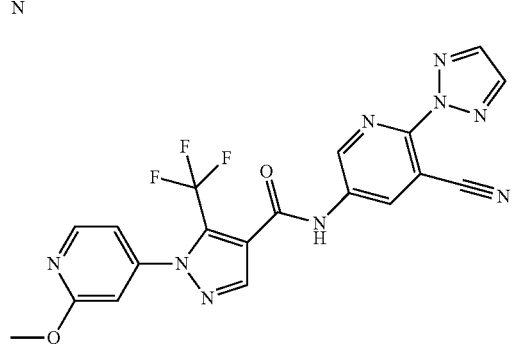 | 41 | N-(5-Cyano-6-(2H-1,2,3-triazol-2-yl)pyridin-3-yl)-1-(2-methoxypyridin-4-yl)-5-(trifluoromethyl)-1H-pyrazole-4-carboxamide |
| 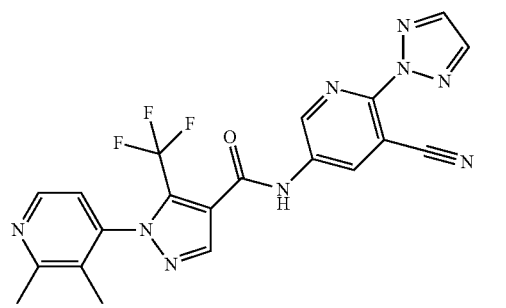 [SMILES: Cc1nccc(-n2ncc(C(=O)Nc3cnc(-n4nccn4)c(C#N)c3)c2C(F)(F)F)c1C] | 42 | N-(5-cyano-6-(2H-1,2,3-triazol-2-yl)pyridin-3-yl)-1-(2,3-dimethylpyridin-4-yl)-5-(trifluoromethyl)-1H-pyrazole-4-carboxamide |

TABLE 1-continued

| Structure | Cpd no | Name |
|---|---|---|
| 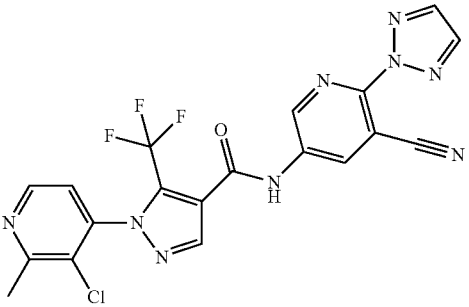 [SMILES: Cc1nccc(-n2ncc(C(=O)Nc3cnc(-n4nccn4)c(C#N)c3)c2C(F)(F)F)c1Cl] | 43 | 1-(3-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide |
| 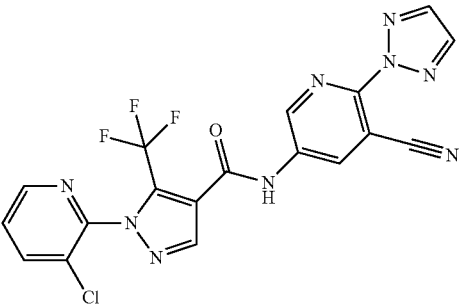 [SMILES: N#Cc1cc(NC(=O)c2cnn(-c3ncccc3Cl)c2C(F)(F)F)cnc1-n1nccn1] | 44 | 1-(3-Chloropyridin-2-yl)-N-(5-cyano-6-(2H-1,2,3-triazol-2-yl)pyridin-3-yl)-5-(trifluoromethyl)-1H-pyrazole-4-carboxamide |
| 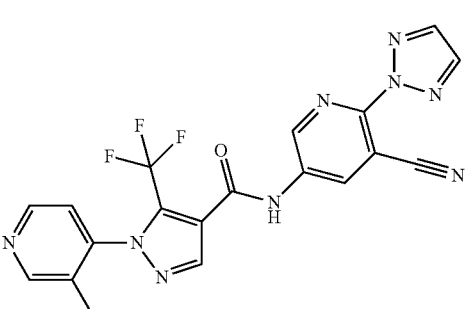 | 45 | 1-(3-chloropyridin-4-yl)-N-(5-cyano-6-(2H-1,2,3-triazol-2-yl)pyridin-3-yl)-5-(trifluoromethyl)-1H-pyrazole-4-carboxamide |
| 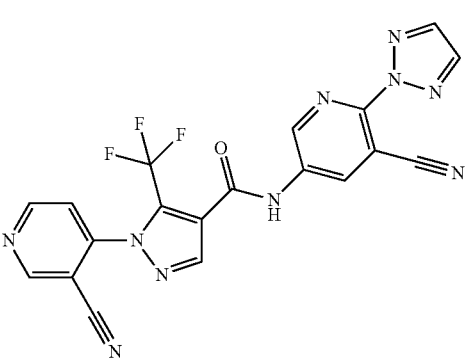 [SMILES: N#Cc1cnccc1-n1ncc(C(=O)Nc2cnc(-n3nccn3)c(C#N)c2)c1C(F)(F)F] | 46 | N-(5-cyano-6-(2H-1,2,3-triazol-2-yl)pyridin-3-yl)-1-(3-cyanopyridin-4-yl)-5-(trifluoromethyl)-1H-pyrazole-4-carboxamide |

TABLE 1-continued

| Structure | Cpd no | Name |
|---|---|---|
| 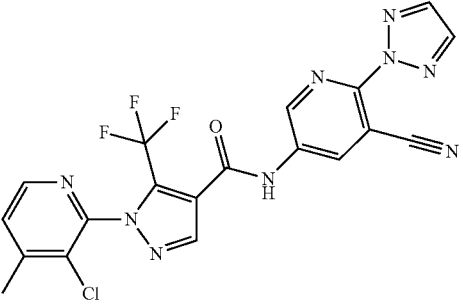 [SMILES: Cc1ccnc(-n2ncc(C(=O)Nc3cnc(-n4nccn4)c(C#N)c3)c2C(F)(F)F)c1Cl] | 47 | 1-(3-chloro-4-methylpyridin-2-yl)-N-(5-cyano-6-(2H-1,2,3-triazol-2-yl)pyridin-3-yl)-5-(trifluoromethyl)-1H-pyrazole-4-carboxamide |
| 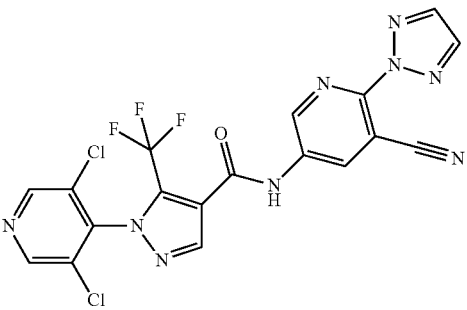 [SMILES: N#Cc1cc(NC(=O)c2cnn(-c3c(Cl)cncc3Cl)c2C(F)(F)F)cnc1-n1nccn1] | 48 | N-(5-cyano-6-(2H-1,2,3-triazol-2-yl)pyridin-3-yl)-1-(3,5-dichloropyridin-4-yl)-5-(trifluoromethyl)-1H-pyrazole-4-carboxamide |
| 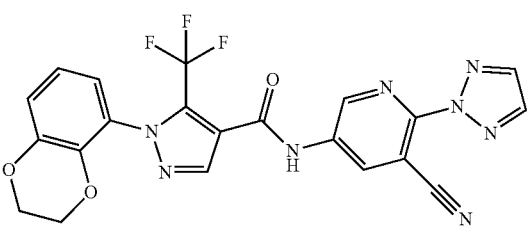 [SMILES: N#Cc1cc(NC(=O)c2cnn(-c3cccc4c3OCCO4)c2C(F)(F)F)cnc1-n1nccn1] | 49 | N-(5-cyano-6-(2H-1,2,3-triazol-2-yl)pyridin-3-yl)-1-(2,3-dihydrobenzo[b][1,4]dioxin-5-yl)-5-(trifluoromethyl)-1H-pyrazole-4-carboxamide |
| 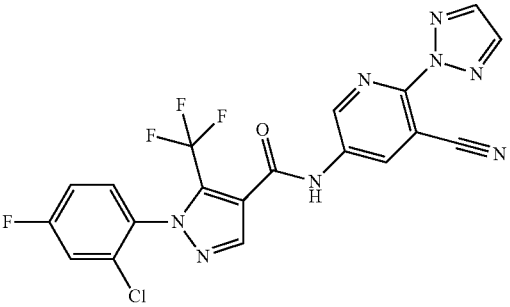 | 50 | 1-(2-bromo-4-fluorophenyl)-N-(5-cyano-6-(2H-1,2,3-triazol-2-yl)pyridin-3-yl)-5-(trifluoromethyl)-1H-pyrazole-4-carboxamide |
| 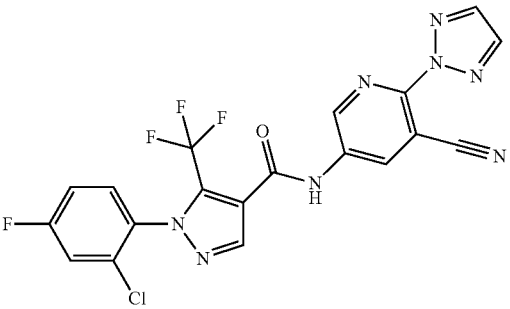 [SMILES: N#Cc1cc(NC(=O)c2cnn(-c3ccc(F)cc3Cl)c2C(F)(F)F)cnc1-n1nccn1] | 51 | 1-(2-chloro-4-fluorophenyl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 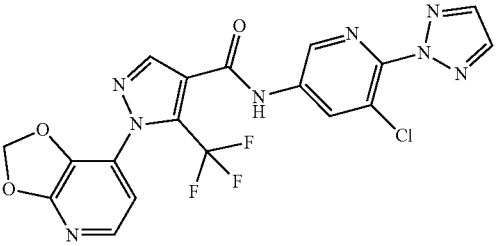 [SMILES: O=C(Nc1cnc(-n2nccn2)c(Cl)c1)c1cnn(-c2ccnc3c2OCO3)c1C(F)(F)F] | 52 | 1-([1,3]dioxolo[4,5-b]pyridin-7-yl)-N-(5-chloro-6-(2H-1,2,3-triazol-2-yl)pyridin-3-yl)-5-(trifluoromethyl)-1H-pyrazole-4-carboxamide |
| 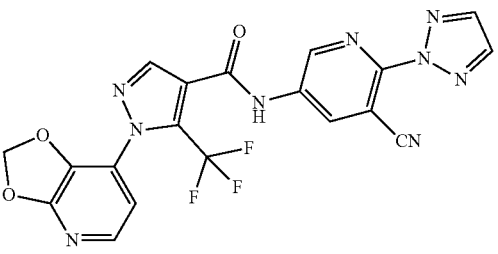 [SMILES: N#Cc1cc(NC(=O)c2cnn(-c3ccnc4c3OCO4)c2C(F)(F)F)cnc1-n1nccn1] | 53 | 1-([1,3]dioxolo[4,5-b]pyridin-7-yl)-N-(5-cyano-6-(2H-1,2,3-triazol-2-yl)pyridin-3-yl)-5-(trifluoromethyl)-1H-pyrazole-4-carboxamide |
| 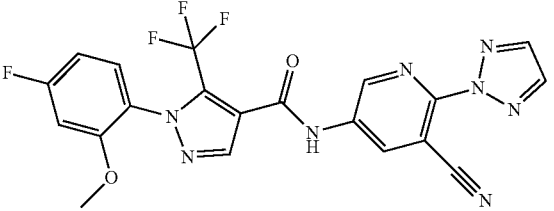 [SMILES: COc1cc(F)ccc1-n1ncc(C(=O)Nc2cnc(-n3nccn3)c(C#N)c2)c1C(F)(F)F] | 54 | N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide |
| 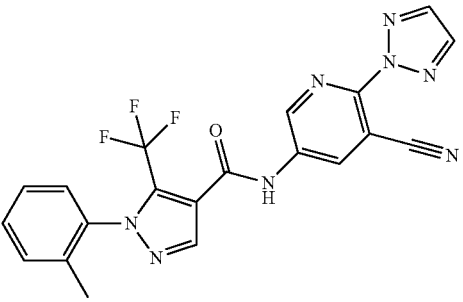 [SMILES: Cc1ccccc1-n1ncc(C(=O)Nc2cnc(-n3nccn3)c(C#N)c2)c1C(F)(F)F] | 55 | N-(5-cyano-6-(2H-1,2,3-triazol-2-yl)pyridin-3-yl)-1-(o-tolyl)-5-(trifluoromethyl)-1H-pyrazole-4-carboxamide |
| 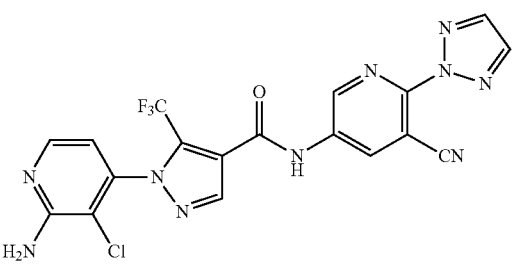 [SMILES: N#Cc1cc(NC(=O)c2cnn(-c3ccnc(N)c3Cl)c2C(F)(F)F)cnc1-n1nccn1] | 56 | 1-(2-amino-3-chloropyridin-4-yl)-N-(5-cyano-6-(2H-1,2,3-triazol-2-yl)pyridin-3-yl)-5-(trifluoromethyl)-1H-pyrazole-4-carboxamide |
| 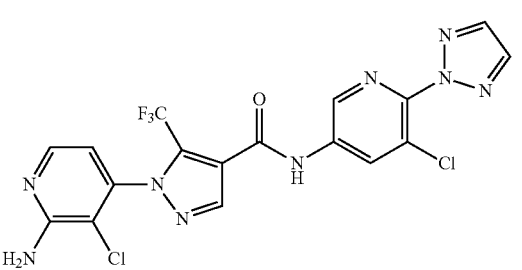 [SMILES: Nc1nccc(-n2ncc(C(=O)Nc3cnc(-n4nccn4)c(Cl)c3)c2C(F)(F)F)c1Cl] | 57 | 1-(2-amino-3-chloropyridin-4-yl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 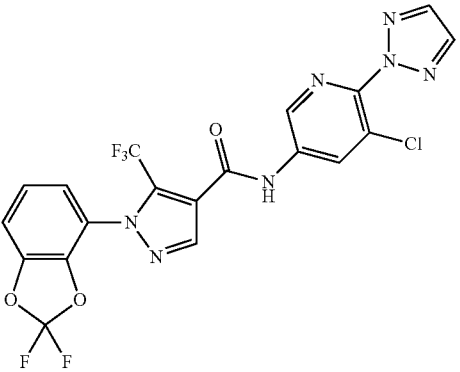 [SMILES: O=C(Nc1cnc(-n2nccn2)c(Cl)c1)c1cnn(-c2cccc3c2OC(F)(F)O3)c1C(F)(F)F] | 58 | N-(5-chloro-6-(2H-1,2,3-triazol-2-yl)pyridin-3-yl)-1-(2,2-difluorobenzo[d][1,3]dioxol-4-yl)-5-(trifluoromethyl)-1H-pyrazole-4-carboxamide |
| 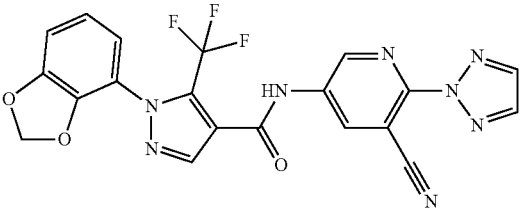 [SMILES: N#Cc1cc(NC(=O)c2cnn(-c3cccc4c3OCO4)c2C(F)(F)F)cnc1-n1nccn1] | 59 | 1-(benzo[d][1,3]dioxol-4-yl)-N-(5-cyano-6-(2H-1,2,3-triazol-2-yl)pyridin-3-yl)-5-(trifluoromethyl)-1H-pyrazole-4-carboxamide |
| 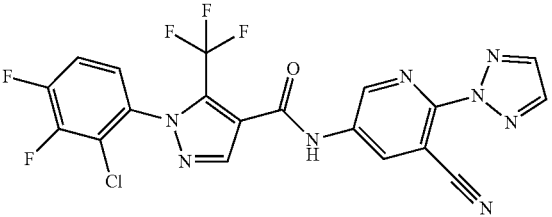 [SMILES: N#Cc1cc(NC(=O)c2cnn(-c3ccc(F)c(F)c3Cl)c2C(F)(F)F)cnc1-n1nccn1] | 60 | 1-(2-chloro-3,4-difluorophenyl)-N-(5-cyano-6-(2H-1,2,3-triazol-2-yl)pyridin-3-yl)-5-(trifluoromethyl)-1H-pyrazole-4-carboxamide |
| 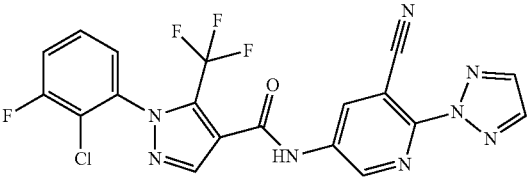 [SMILES: N#Cc1cc(NC(=O)c2cnn(-c3cccc(F)c3Cl)c2C(F)(F)F)cnc1-n1nccn1] | 61 | 1-(2-chloro-3-fluorophenyl)-N-(5-cyano-6-(2H-1,2,3-triazol-2-yl)pyridin-3-yl)-5-(trifluoromethyl)-1H-pyrazole-4-carboxamide |
| 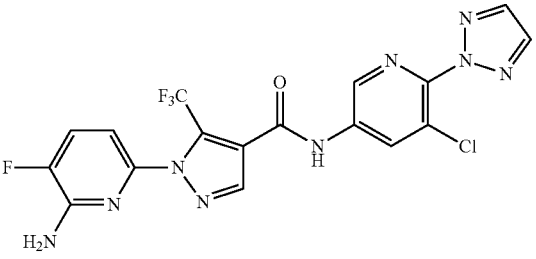 [SMILES: Nc1nc(-n2ncc(C(=O)Nc3cnc(-n4nccn4)c(Cl)c3)c2C(F)(F)F)ccc1F] | 62 | 1-(6-amino-5-fluoropyridin-2-yl)-N-(5-chloro-6-(2H-1,2,3-triazol-2-yl)pyridin-3-yl)-5-(trifluoromethyl)-1H-pyrazole-4-carboxamide |
| 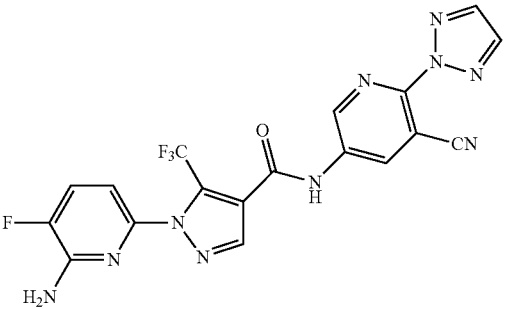 [SMILES: N#Cc1cc(NC(=O)c2cnn(-c3ccc(F)c(N)n3)c2C(F)(F)F)cnc1-n1nccn1] | 63 | 1-(6-amino-5-fluoropyridin-2-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 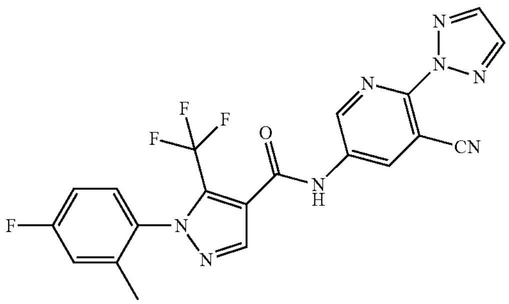 [SMILES: Cc1cc(F)ccc1-n1ncc(C(=O)Nc2cnc(-n3nccn3)c(C#N)c2)c1C(F)(F)F] | 64 | N-(5-cyano-6-(2H-1,2,3-triazol-2-yl)pyridin-3-yl)-1-(4-fluoro-2-methylphenyl)-5-(trifluoromethyl)-1H-pyrazole-4-carboxamide |
| 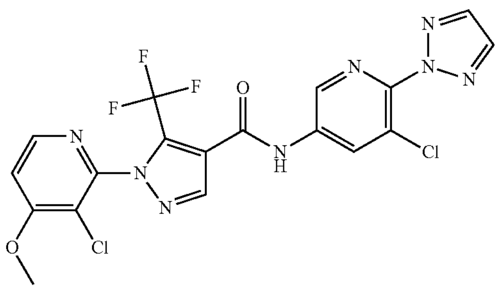 [SMILES: COc1ccnc(-n2ncc(C(=O)Nc3cnc(-n4nccn4)c(Cl)c3)c2C(F)(F)F)c1Cl] | 65 | 1-(3-chloro-4-methoxypyridin-2-yl)-N-(5-chloro-6-(2H-1,2,3-triazol-2-yl)pyridin-3-yl)-5-(trifluoromethyl)-1H-pyrazole-4-carboxamide |
| 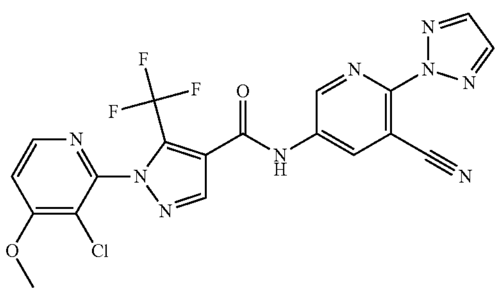 [SMILES: COc1ccnc(-n2ncc(C(=O)Nc3cnc(-n4nccn4)c(C#N)c3)c2C(F)(F)F)c1Cl] | 66 | 1-(3-chloro-4-methoxypyridin-2-yl)-N-(5-cyano-6-(2H-1,2,3-triazol-2-yl)pyridin-3-yl)-5-(trifluoromethyl)-1H-pyrazole-4-carboxamide |
| 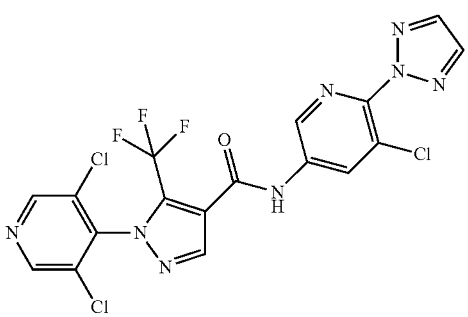 [SMILES: O=C(Nc1cnc(-n2nccn2)c(Cl)c1)c1cnn(-c2c(Cl)cncc2Cl)c1C(F)(F)F] | 67 | N-(5-chloro-6-(2H-1,2,3-triazol-2-yl)pyridin-3-yl)-1-(3,5-dichloropyridin-4-yl)-5-(trifluoropyridin-4-1H-pyrazole-4-carboxamide |
| 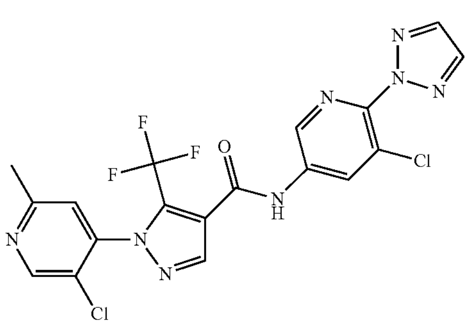 [SMILES: Cc1cc(-n2ncc(C(=O)Nc3cnc(-n4nccn4)c(Cl)c3)c2C(F)(F)F)c(Cl)cn1] | 68 | 1-(5-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 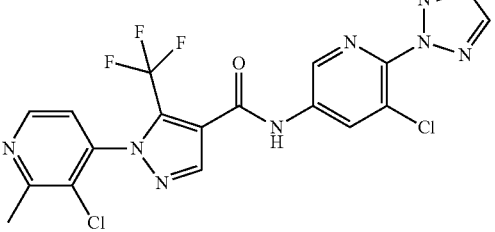 | 69 | 1-(3-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide |
| 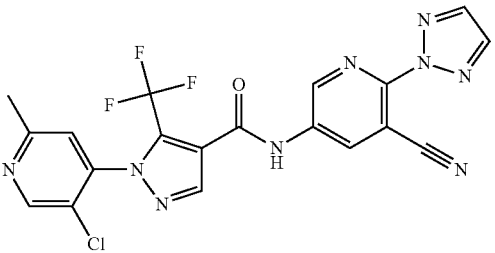 [SMILES: Cc1cc(-n2ncc(C(=O)Nc3cnc(-n4nccn4)c(C#N)c3)c2C(F)(F)F)c(Cl)cn1] | 70 | 1-(5-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide |
| 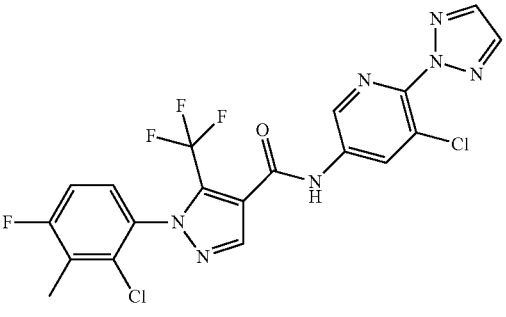 | 71 | 1-(2-chloro-4-fluoro-3-methylphenyl)-N-(5-chloro-6-(2H-1,2,3-triazol-2-yl)pyridin-3-yl)-5-(trifluoromethyl)-1H-pyrazole-4-carboxamide |
| 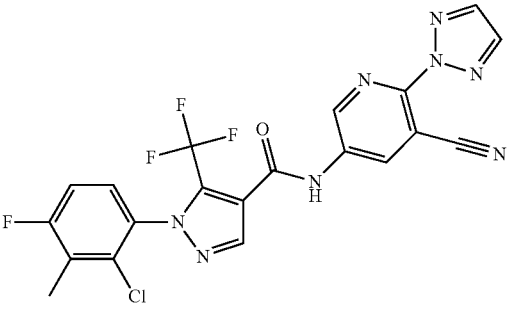 [SMILES: Cc1c(F)ccc(-n2ncc(C(=O)Nc3cnc(-n4nccn4)c(C#N)c3)c2C(F)(F)F)c1Cl] | 72 | 1-(2-chloro-4-fluoro-3-methylphenyl)-N-(5-cyano-6-(2H-1,2,3-triazol-2-yl)pyridin-3-yl)-5-(trifluoromethyl)-1H-pyrazole-4-carboxamide |
| 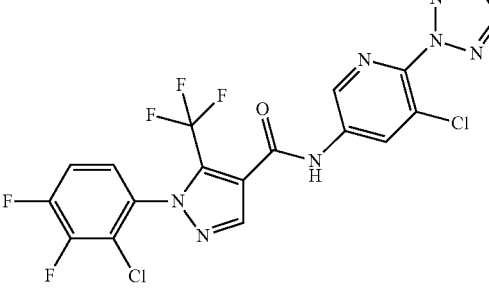 | 73 | 1-(2-chloro-3,4-difluorophenyl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 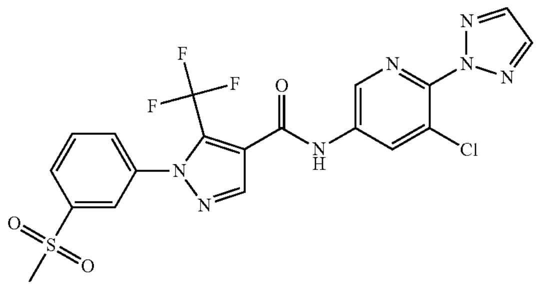 [SMILES: CS(=O)(=O)c1cccc(-n2ncc(C(=O)Nc3cnc(-n4nccn4)c(Cl)c3)c2C(F)(F)F)c1] | 74 | N-(5-chloro-6-(2H-1,2,3-triazol-2-yl)pyridin-3-yl)-1-(3-(methylsulfonyl)phenyl)-5-(trifluoromethyl)-1H-pyrazole-4-carboxamide |
| 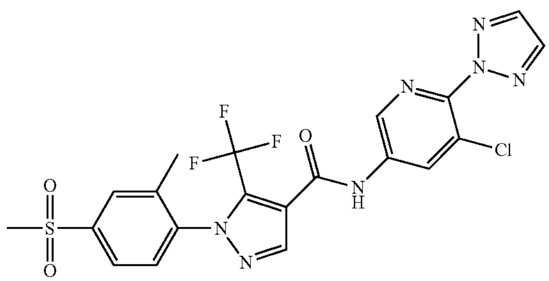 [SMILES: Cc1cc(S(C)(=O)=O)ccc1-n1ncc(C(=O)Nc2cnc(-n3nccn3)c(Cl)c2)c1C(F)(F)F] | 75 | N-(5-chloro-6-(2H-1,2,3-triazol-2-yl)pyridin-3-yl)-1-(2-methyl-4-(methyl sulfonyl)phenyl)-5-(trifluoromethyl)-1H-pyrazole-4-carboxamide |
| 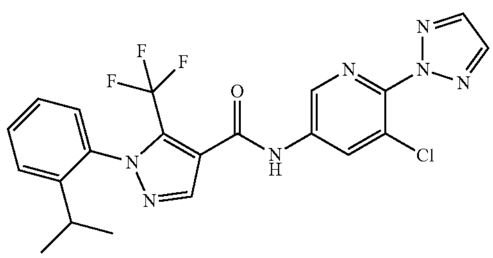 [SMILES: CC(C)c1ccccc1-n1ncc(C(=O)Nc2cnc(-n3nccn3)c(Cl)c2)c1C(F)(F)F] | 76 | N-(5-chloro-6-(2H-1,2,3-triazol-2-yl)pyridin-3-yl)-1-(2-isopropylphenyl)-5-(trifluoromethyl)-1H-pyrazole-4-carboxamide |
| 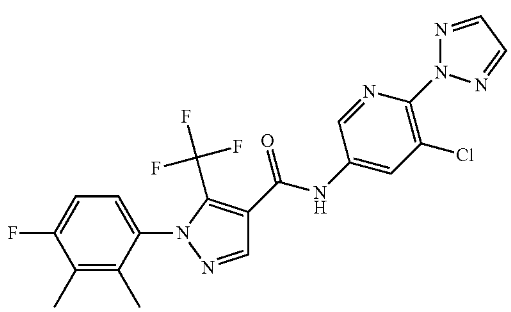 [SMILES: Cc1c(F)ccc(-n2ncc(C(=O)Nc3cnc(-n4nccn4)c(Cl)c3)c2C(F)(F)F)c1C] | 77 | N-(5-chloro-6-(2H-1,2,3-triazol-2-yl)pyridin-3-yl)-1-(4-fluoro-2,3-dimethylphenyl)-5-(trifluoromethyl)-1H-pyrazole-4-carboxamide |
| 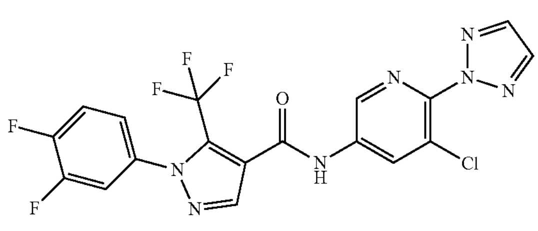 [SMILES: O=C(Nc1cnc(-n2nccn2)c(Cl)c1)c1cnn(-c2ccc(F)c(F)c2)c1C(F)(F)F] | 78 | N-(5-chloro-6-(2H-1,2,3-triazol-2-yl)pyridin-3-yl)-1-(3,4-difluorophenyl)-5-(trifluoromethyl)-1H-pyrazole-4-carboxamide |

TABLE 1-continued

| Structure | Cpd no | Name |
|---|---|---|
| 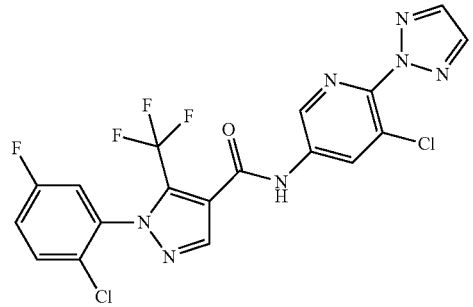 [SMILES: O=C(Nc1cnc(-n2nccn2)c(Cl)c1)c1cnn(-c2cc(F)ccc2Cl)c1C(F)(F)F] | 79 | 1-(2-chloro-5-fluorophenyl)-N-(5-chloro-6-(2H-1,2,3-triazol-2-yl)pyridin-3-yl)-5-(trifluoromethyl)-1H-pyrazole-4-carboxamide |
| 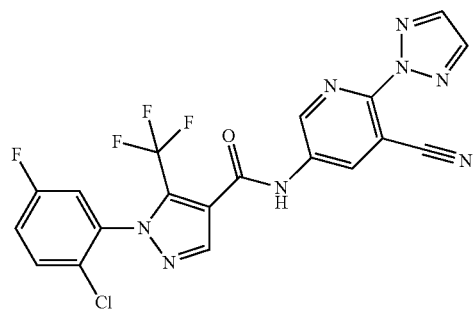 [SMILES: N#Cc1cc(NC(=O)c2cnn(-c3cc(F)ccc3Cl)c2C(F)(F)F)cnc1-n1nccn1] | 80 | 1-(2-chloro-5-fluorophenyl)-N-(5-cyano-6-(2H-1,2,3-triazol-2-yl)pyridin-3-yl)-5-(trifluoromethyl)-1H-pyrazole-4-carboxamide |
| 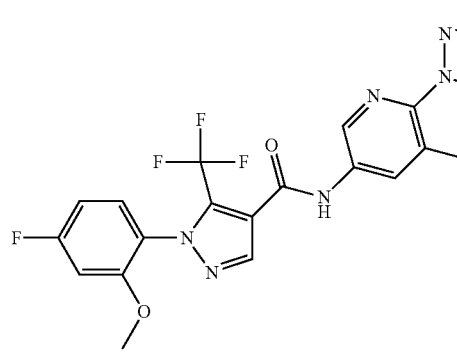 | 81 | N-(5-chloro-6-(2H-1,2,3-triazol-2-yl)pyridin-3-yl)-1-(4-fluoro-2-methoxyphenyl)-5-(trifluoromethyl)-1H-pyrazole-4-carboxamide |
| 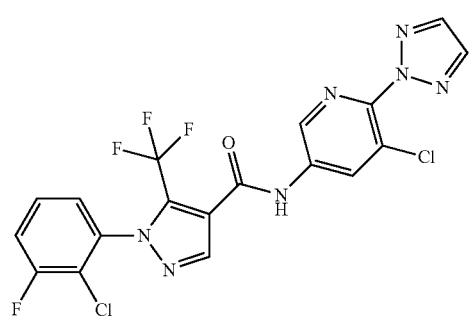 | 82 | 1-(2-chloro-3-fluorophenyl)-N-(5-chloro-6-(2H-1,2,3-triazol-2-yl)pyridin-3-yl)-5-(trifluoromethyl)-1H-pyrazole-4-carboxamide |
| 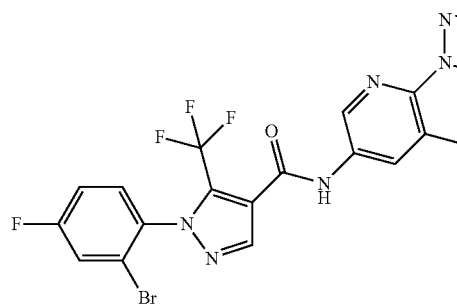 | 83 | 1-(2-bromo-4-fluorophenyl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 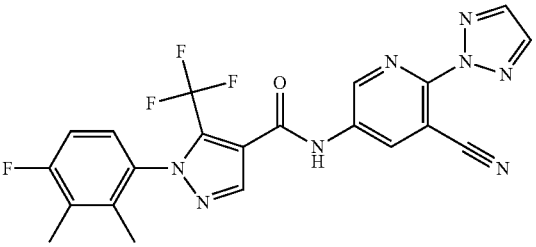 [SMILES: Cc1c(F)ccc(-n2ncc(C(=O)Nc3cnc(-n4nccn4)c(C#N)c3)c2C(F)(F)F)c1C] | 84 | N-(5-cyano-6-(2H-1,2,3-triazol-2-yl)pyridin-3-yl)-1-(4-fluoro-2,3-dimethylphenyl)-5-(trifluoromethyl)-1H-pyrazole-4-carboxamide |
| 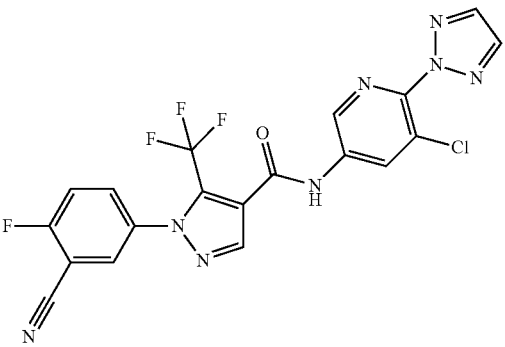 [SMILES: N#Cc1cc(-n2ncc(C(=O)Nc3cnc(-n4nccn4)c(Cl)c3)c2C(F)(F)F)ccc1F] | 85 | N-(5-chloro-6-(2H-1,2,3-triazol-2-yl)pyridin-3-yl)-1-(3-cyano-4-fluorophenyl)-5-(trifluoromethyl)-1H-pyrazole-4-carboxamide |
| 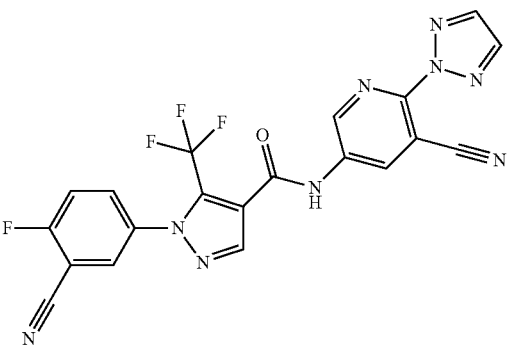 [SMILES: N#Cc1cc(-n2ncc(C(=O)Nc3cnc(-n4nccn4)c(C#N)c3)c2C(F)(F)F)ccc1F] | 86 | 1-(3-cyano-4-fluorophenyl)-N-(5-cyano-6-(2H-1,2,3-triazol-2-yl)pyridin-3-yl)-5-(trifluoromethyl)-1H-pyrazole-4-carboxamide |
| 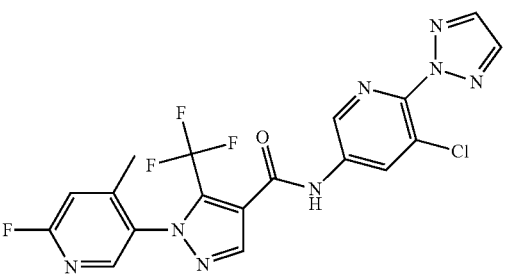 [SMILES: Cc1cc(F)ncc1-n1ncc(C(=O)Nc2cnc(-n3nccn3)c(Cl)c2)c1C(F)(F)F] | 87 | N-(5-chloro-6-(2H-1,2,3-triazol-2-yl)pyridin-3-yl)-1-(6-fluoro-4-methylpyridin-3-yl)-5-(trifluoromethyl)-1H-pyrazole-4-carboxamide |
| 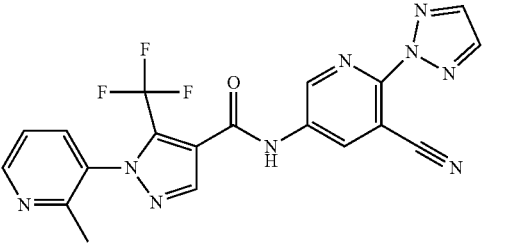 [SMILES: Cc1ncccc1-n1ncc(C(=O)Nc2cnc(-n3nccn3)c(C#N)c2)c1C(F)(F)F] | 88 | N-(5-cyano-6-(2H-1,2,3-triazol-2-yl)pyridin-3-yl)-1-(2-methylpyridin-3-yl)-5-(trifluoromethyl)-1H-pyrazole-4-carboxamide |

TABLE 1-continued

| Structure | Cpd no | Name |
|---|---|---|
| 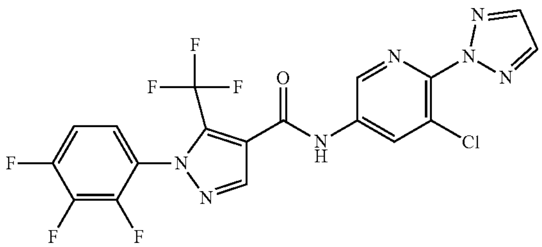 [SMILES: O=C(Nc1cnc(-n2nccn2)c(Cl)c1)c1cnn(-c2ccc(F)c(F)c2F)c1C(F)(F)F] | 89 | N-(5-chloro-6-(2H-1,2,3-triazol-2-yl)pyridin-3-yl)-5-(trifluoromethyl)-1-(2,3,4-trifluorophenyl)-1H-pyrazole-4-carboxamide |
| 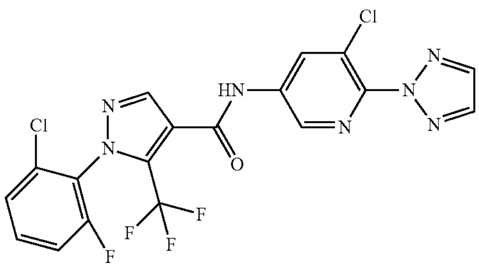 [SMILES: O=C(Nc1cnc(-n2nccn2)c(Cl)c1)c1cnn(-c2c(F)cccc2Cl)c1C(F)(F)F] | 90 | N-(5-chloro-6-(2H-1,2,3-triazol-2-yl)pyridin-3-yl)-1-(2-chloro-6-fluorophenyl)-5-(trifluoromethyl)-1H-pyrazole-4-carboxamide |
| 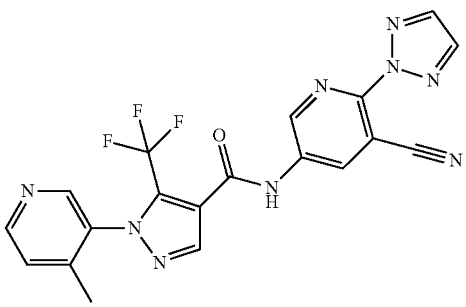 [SMILES: Cc1ccncc1-n1ncc(C(=O)Nc2cnc(-n3nccn3)c(C#N)c2)c1C(F)(F)F] | 91 | N-(5-cyano-6-(2H-1,2,3-triazol-2-yl)pyridin-3-yl)-1-(4-methylpyridin-3-yl)-5-(trifluoromethyl)-1H-pyrazole-4-carboxamide |
| 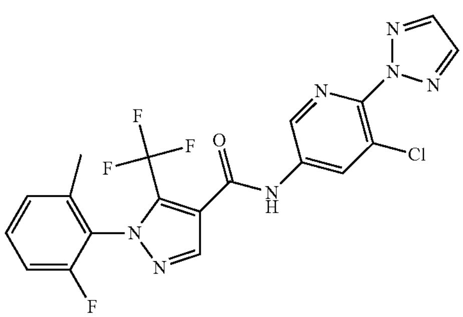 [SMILES: Cc1cccc(F)c1-n1ncc(C(=O)Nc2cnc(-n3nccn3)c(Cl)c2)c1C(F)(F)F] | 92 | N-(5-chloro-6-(2H-1,2,3-triazol-2-yl)pyridin-3-yl)-1-(2-fluoro-6-methylphenyl)-5-(trifluoromethyl)-1H-pyrazole-4-carboxamide |
| 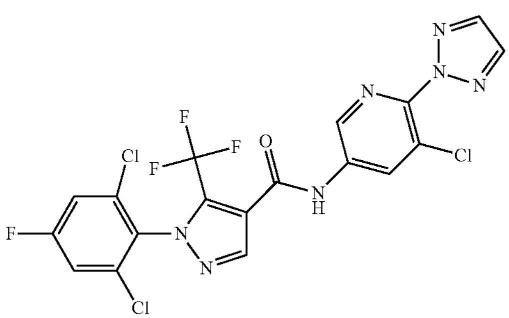 [SMILES: O=C(Nc1cnc(-n2nccn2)c(Cl)c1)c1cnn(-c2c(F)cc(F)cc2Cl)c1C(F)(F)F] | 93 | N-(5-chloro-6-(2H-1,2,3-triazol-2-yl)pyridin-3-yl)-1-(2,6-dichloro-4-fluorophenyl)-5-(trifluoromethyl)-1H-pyrazole-4-carboxamide |

TABLE 1-continued

| Structure | Cpd no | Name |
|---|---|---|
| 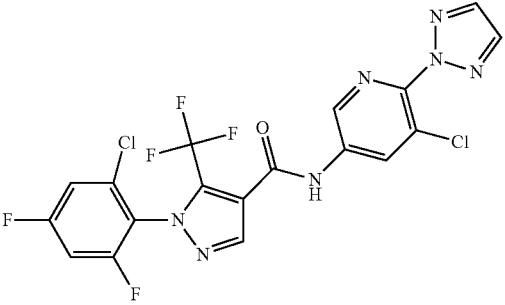 | 94 | 1-(2-chloro-4,6-difluorophenyl)-N-(5-chloro-6-(2H-1,2,3-triazol-2-yl)pyridin-3-yl)-5-(trifluoromethyl)-1H-pyrazole-4-carboxamide |
| 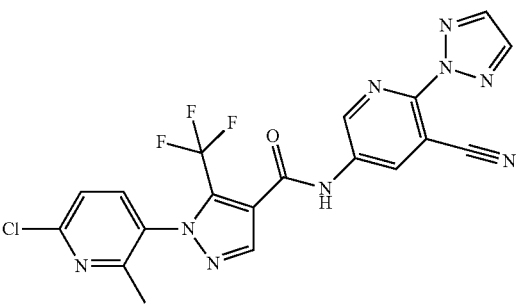 | 95 | 1-(6-chloro-2-methylpyridin-3-yl)-N-(5-cyano-6-(2H-1,2,3-triazol-2-yl)pyridin-3-yl)-5-(trifluoromethyl)-1H-pyrazole-4-carboxamide |
| 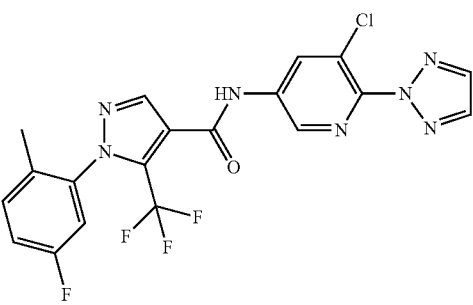 [SMILES: Cc1ccc(F)cc1-n1ncc(C(=O)Nc2cnc(-n3nccn3)c(Cl)c2)c1C(F)(F)F] | 96 | N-(5-chloro-6-(2H-1,2,3-triazol-2-yl)pyridin-3-yl)-1-(5-fluoro-2-methylphenyl)-5-(trifluoromethyl)-1H-pyrazole-4-carboxamide |
| 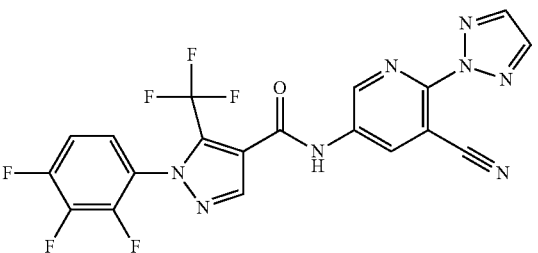 [SMILES: N#Cc1cc(NC(=O)c2cnn(-c3ccc(F)c(F)c3F)c2C(F)(F)F)cnc1-n1nccn1] | 97 | N-(5-cyano-6-(2H-1,2,3-triazol-2-yl)pyridin-3-yl)-5-(trifluoromethyl)-1-(2,3,4-trifluorophenyl)-1H-pyrazole-4-carboxamide |
| 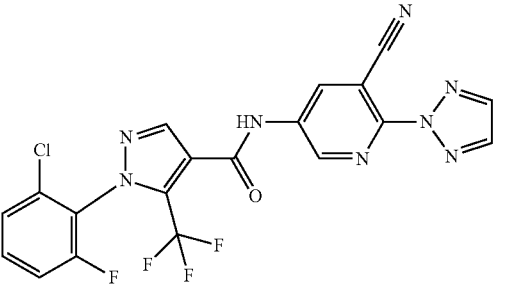 [SMILES: N#Cc1cc(NC(=O)c2cnn(-c3c(F)cccc3Cl)c2C(F)(F)F)cnc1-n1nccn1] | 98 | 1-(2-chloro-6-fluorophenyl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 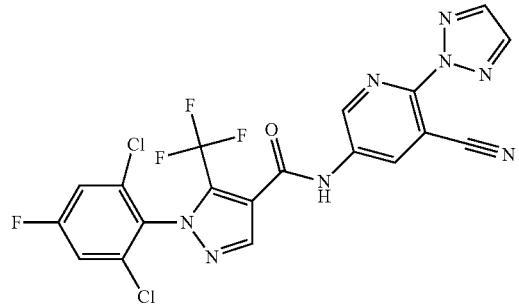 [SMILES: N#Cc1cc(NC(=O)c2cnn(-c3c(Cl)cc(F)cc3Cl)c2C(F)(F)F)cnc1-n1nccn1] | 99 | 1-(2-chloro-4,6-difluorophenyl)-N-(5-cyano-6-(2H-1,2,3-triazol-2-yl)pyridin-3-yl)-5-(trifluoromethyl)-1H-pyrazole-4-carboxamide |
| 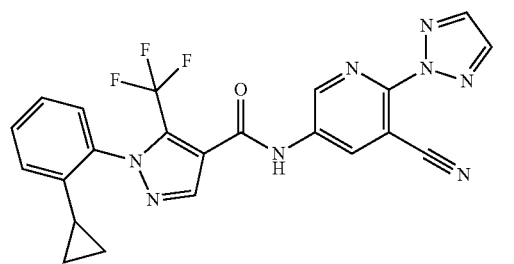 [SMILES: N#Cc1cc(NC(=O)c2cnn(-c3ccccc3C3CC3)c2C(F)(F)F)cnc1-n1nccn1] | 100 | N-(5-cyano-6-(2H-1,2,3-triazol-2-yl)pyridin-3-yl)-1-(2-cyclopropylphenyl)-5-(trifluoromethyl)-1H-pyrazole-4-carboxamide |
| 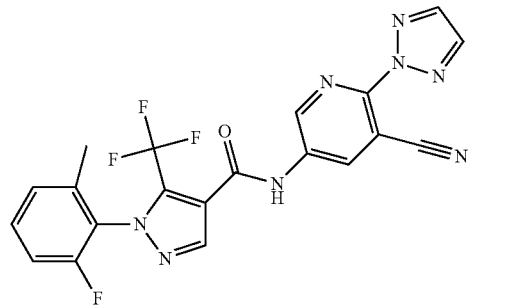 [SMILES: Cc1cccc(F)c1-n1ncc(C(=O)Nc2cnc(-n3nccn3)c(C#N)c2)c1C(F)(F)F] | 101 | N-(5-cyano-6-(2H-1,2,3-triazol-2-yl)pyridin-3-yl)-1-(2-fluoro-6-methylphenyl)-5-(trifluoromethyl)-1H-pyrazole-4-carboxamide |
| 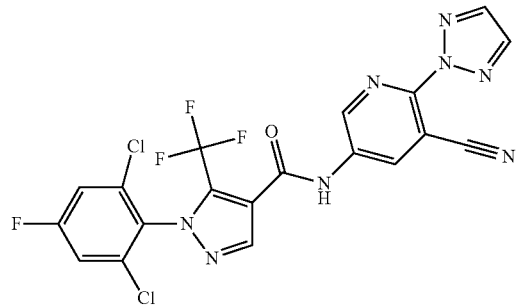 [SMILES: N#Cc1cc(NC(=O)c2cnn(-c3c(Cl)cc(F)cc3Cl)c2C(F)(F)F)cnc1-n1nccn1] | 102 | N-(5-cyano-6-(2H-1,2,3-triazol-2-yl)pyridin-3-yl)-1-(2,6-dichloro-4-fluorophenyl)-5-pyrazole-4-carboxamide |
| 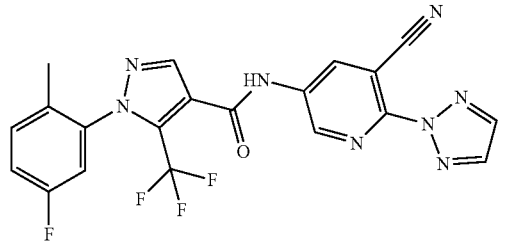 [SMILES: Cc1ccc(F)cc1-n1ncc(C(=O)Nc2cnc(-n3nccn3)c(C#N)c2)c1C(F)(F)F] | 103 | N-(5-cyano-6-(2H-1,2,3-triazol-2-yl)pyridin-3-yl)-1-(5-fluoro-2-methylphenyl)-5-(trifluoromethyl)-1H-pyrazole-4-carboxamide |

TABLE 1-continued

| Structure | Cpd no | Name |
|---|---|---|
| 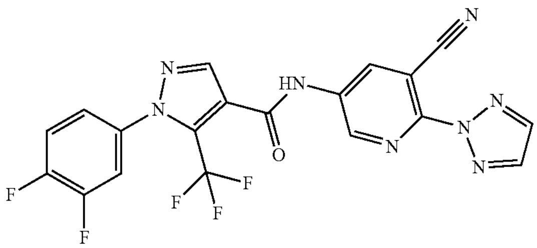 [SMILES: N#Cc1cc(NC(=O)c2cnn(-c3ccc(F)c(F)c3)c2C(F)(F)F)cnc1-n1nccn1] | 104 | N-(5-cyano-6-(2H-1,2,3-triazol-2-yl)pyridin-3-yl)-1-(3,4-difluorophenyl)-5-(trifluoromethyl)-1H-pyrazole-4-carboxamide |
| 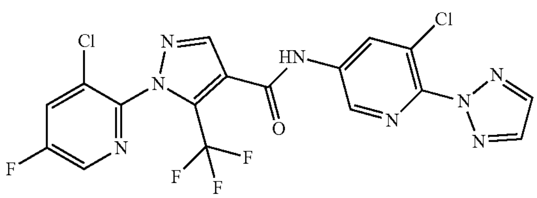 [SMILES: O=C(Nc1cnc(-n2nccn2)c(Cl)c1)c1cnn(-c2ncc(F)cc2Cl)c1C(F)(F)F] | 105 | 1-(3-chloro-5-fluoropyridin-2-yl)-N-(5-chloro-6-(2H-1,2,3-triazol-2-yl)pyridin-3-yl)-5-(trifluoromethyl)-1H-pyrazole-4-carboxamide |
| 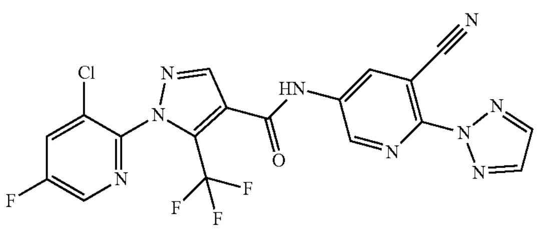 [SMILES: N#Cc1cc(NC(=O)c2cnn(-c3ncc(F)cc3Cl)c2C(F)(F)F)cnc1-n1nccn1] | 106 | 1-(3-chloro-5-fluoropyridin-2-yl)-N-(5-cyano-6-(2H-1,2,3-triazol-2-yl)pyridin-3-yl)-5-(trifluoromethyl)-1H-pyrazole-4-carboxamide |
| 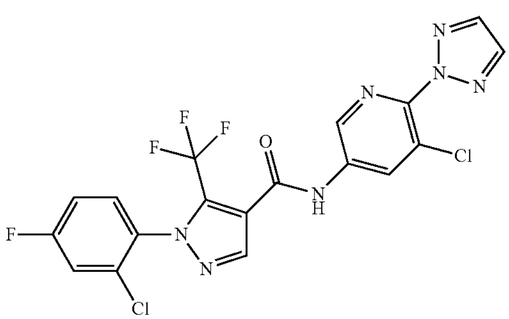 [SMILES: O=C(Nc1cnc(-n2nccn2)c(Cl)c1)c1cnn(-c2ccc(F)cc2Cl)c1C(F)(F)F] | 107 | 1-(2-chloro-4-fluorophenyl)-N-(5-chloro-6-(2H-1,2,3-triazol-2-yl)pyridin-3-yl)-5-(trifluoromethyl)-1H-pyrazole-4-carboxamide |
| 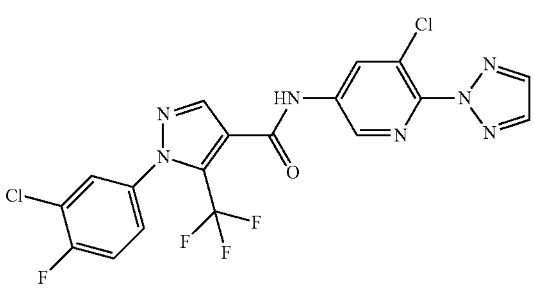 [SMILES: O=C(Nc1cnc(-n2nccn2)c(Cl)c1)c1cnn(-c2ccc(F)c(Cl)c2)c1C(F)(F)F] | 108 | 1-(3-chloro-4-fluorophenyl)-N-(5-chloro-6-(2H-1,2,3-triazol-2-yl)pyridin-3-yl)-5-(trifluoromethyl)-1H-pyrazole-4-carboxamide |
| 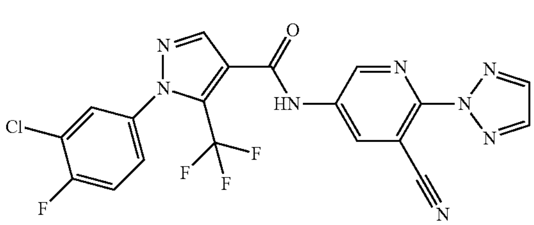 [SMILES: N#Cc1cc(NC(=O)c2cnn(-c3ccc(F)c(Cl)c3)c2C(F)(F)F)cnc1-n1nccn1] | 109 | 1-(3-chloro-4-fluorophenyl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 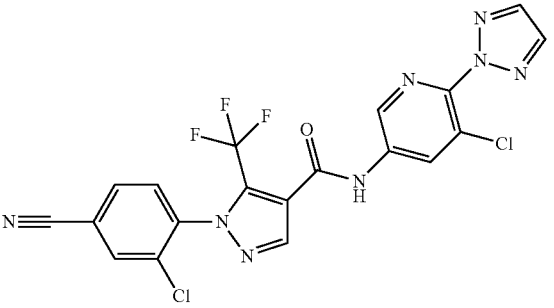 [SMILES: N#Cc1ccc(-n2ncc(C(=O)Nc3cnc(-n4nccn4)c(Cl)c3)c2C(F)(F)F)c(Cl)c1] | 110 | 1-(2-chloro-4-cyanophenyl)-N-(5-chloro-6-(2H-1,2,3-triazol-2-yl)pyridin-3-yl)-5-(trifluoromethyl)-1H-pyrazole-4-carboxamide |
| 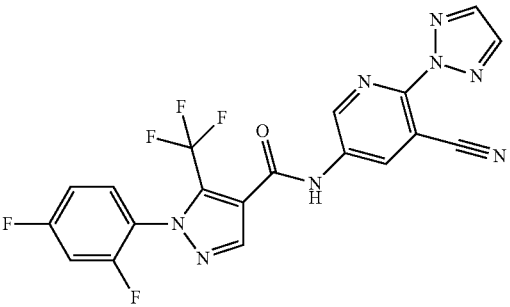 | 111 | N-(5-cyano-6-(2H-1,2,3-triazol-2-yl)pyridin-3-yl)-1-(2,4-difluorophenyl)-5-(trifluoromethyl)-1H-pyrazole-4-carboxamide |
| 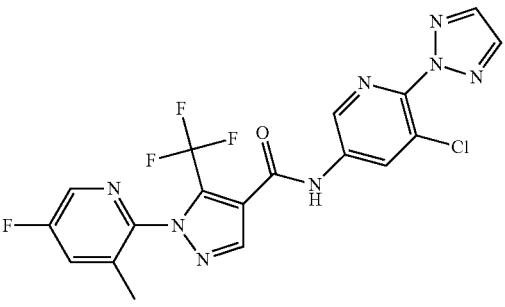 [SMILES: Cc1cc(F)cnc1-n1ncc(C(=O)Nc2cnc(-n3nccn3)c(Cl)c2)c1C(F)(F)F] | 112 | N-(5-chloro-6-(2H-1,2,3-triazol-2-yl)pyridin-3-yl)-1-(5-fluoro-3-methylpyridin-2-yl)-5-(trifluoromethyl)-1H-pyrazole-4-carboxamide |
| 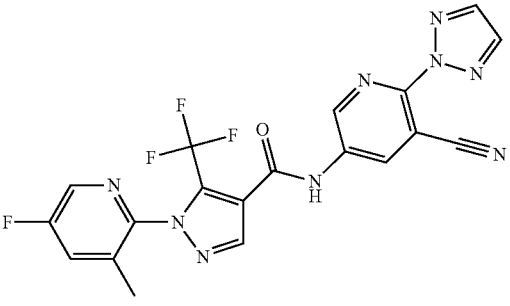 [SMILES: Cc1cc(F)cnc1-n1ncc(C(=O)Nc2cnc(-n3nccn3)c(C#N)c2)c1C(F)(F)F] | 113 | N-(5-cyano-6-(2H-1,2,3-triazol-2-yl)pyridin-3-yl)-1-(5-fluoro-3-methylpyridin-2-yl)-5-(trifluoromethyl)-1H-pyrazole-4-carboxamide |
| 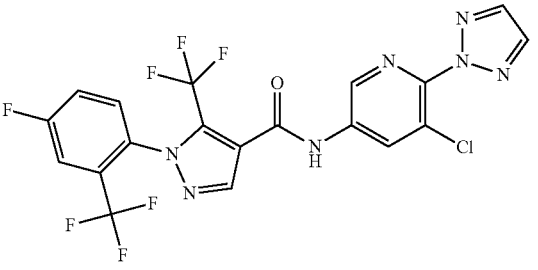 [SMILES: O=C(Nc1cnc(-n2nccn2)c(Cl)c1)c1cnn(-c2ccc(F)cc2C(F)(F)F)c1C(F)(F)F] | 114 | N-(5-chloro-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide |

TABLE 1-continued

| Structure | Cpd no | Name |
|---|---|---|
| 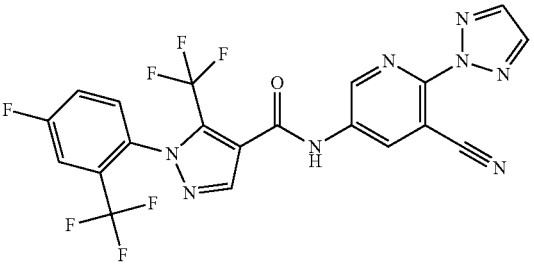 [SMILES: N#Cc1cc(NC(=O)c2cnn(-c3ccc(F)cc3C(F)(F)F)c2C(F)(F)F)cnc1-n1nccn1] | 115 | N-(5-cyano-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide |
| 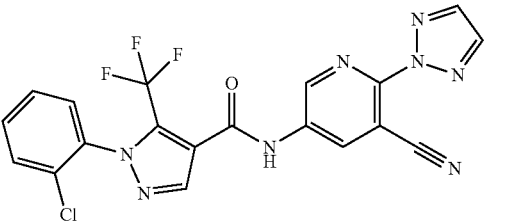 [SMILES: N#Cc1cc(NC(=O)c2cnn(-c3ccccc3Cl)c2C(F)(F)F)cnc1-n1nccn1] | 116 | 1-(2-chlorophenyl)-N-(5-cyano-6-(2H-1,2,3-triazol-2-yl)pyridin-3-yl)-5-(trifluoromethyl)-1H-pyrazole-4-carboxamide |
| 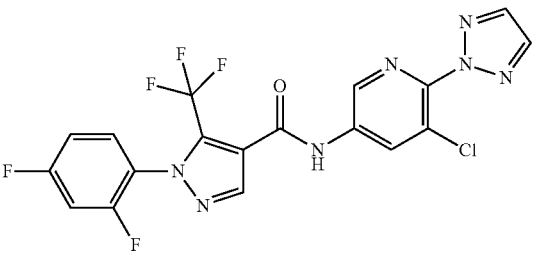 [SMILES: O=C(Nc1cnc(-n2nccn2)c(Cl)c1)c1cnn(-c2ccc(F)cc2F)c1C(F)(F)F] | 117 | N-(5-chloro-6-(2H-1,2,3-triazol-2-yl)pyridin-3-yl)-1-(2,4-difluorophenyl)-5-(trifluoromethyl)-1H-pyrazole-4-carboxamide |
| 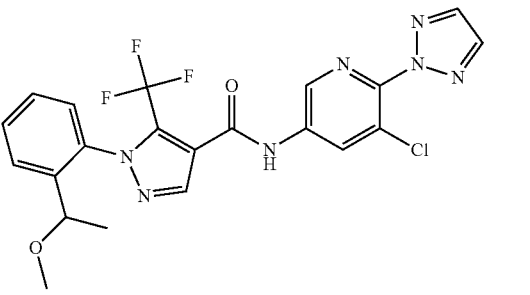 [SMILES: COC(C)c1ccccc1-n1ncc(C(=O)Nc2cnc(-n3nccn3)c(Cl)c2)c1C(F)(F)F] | 118 | N-(5-chloro-6-(2H-1,2,3-triazol-2-yl)pyridin-3-yl)-1-(2-(1-methoxyethyl)phenyl)-5-(trifluoromethyl)-1H-pyrazole-4-carboxamide |
| 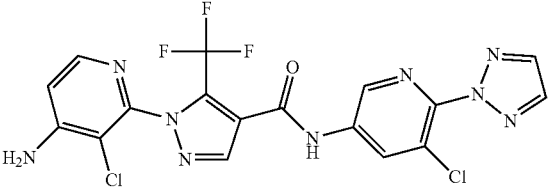 [SMILES: Nc1ccnc(-n2ncc(C(=O)Nc3cnc(-n4nccn4)c(Cl)c3)c2C(F)(F)F)c1Cl] | 119 | 1-(4-amino-3-chloropyridin-2-yl)-N-(5-chloro-6-(2H-1,2,3-triazol-2-yl)pyridin-3-yl)-5-(trifluoromethyl)-1H-pyrazole-4-carboxamide |
| 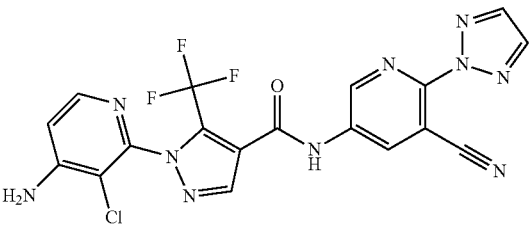 [SMILES: N#Cc1cc(NC(=O)c2cnn(-c3nccc(N)c3Cl)c2C(F)(F)F)cnc1-n1nccn1] | 120 | 1-(4-amino-3-chloropyridin-2-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 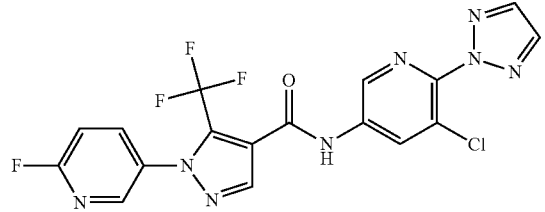 [SMILES: O=C(Nc1cnc(-n2nccn2)c(Cl)c1)c1cnn(-c2ccc(F)nc2)c1C(F)(F)F] | 121 | N-(5-chloro-6-(2H-1,2,3-triazol-2-yl)pyridin-3-yl)-1-(6-fluoropyridin-3-yl)-5-(trifluoromethyl)-1H-pyrazole-4-carboxamide |
| 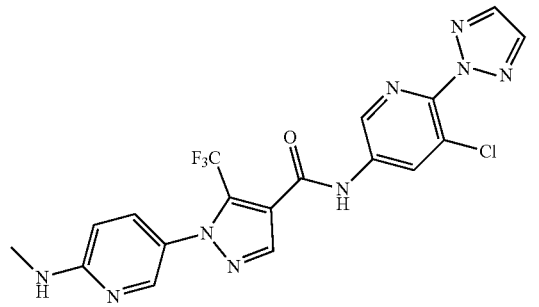 [SMILES: CNc1ccc(-n2ncc(C(=O)Nc3cnc(-n4nccn4)c(Cl)c3)c2C(F)(F)F)cn1] | 122 | N-(5-chloro-6-(2H-1,2,3-triazol-2-yl)pyridin-3-yl)-1-(6-(methylamino)pyridin-3-yl)-5-(trifluoromethyl)-1H-pyrazole-4-carboxamide |
| 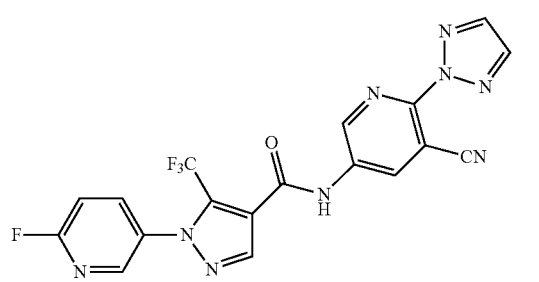 [SMILES: N#Cc1cc(NC(=O)c2cnn(-c3ccc(F)nc3)c2C(F)(F)F)cnc1-n1nccn1] | 123 | N-(5-cyano-6-(2H-1,2,3-triazol-2-yl)pyridin-3-yl)-1-(6-(fluoro)pyridin-3-yl)-5-(trifluoromethyl)-1H-pyrazole-4-carboxamide |
| 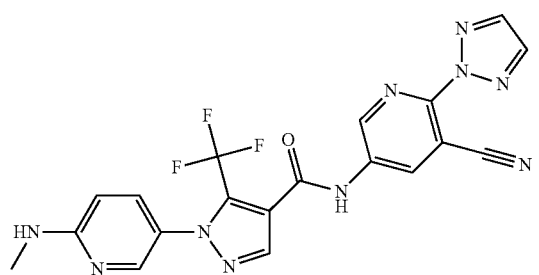 [SMILES: CNc1ccc(-n2ncc(C(=O)Nc3cnc(-n4nccn4)c(C#N)c3)c2C(F)(F)F)cn1] | 124 | N-(5-cyano-6-(2H-1,2,3-triazol-2-yl)pyridin-3-yl)-1-(6-(methylamino)pyridin-3-yl)-5-(trifluoromethyl)-1H-pyrazole-4-carboxamide |
| 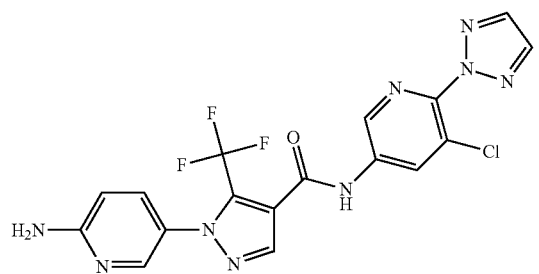 [SMILES: Nc1ccc(-n2ncc(C(=O)Nc3cnc(-n4nccn4)c(Cl)c3)c2C(F)(F)F)cn1] | 125 | 1-(6-aminopyridin-3-yl)-N-(5-chloro-6-(2H-1,2,3-triazol-2-yl)pyridin-3-yl)-5-(trifluoromethyl)-1H-pyrazole-4-carboxamide |
| 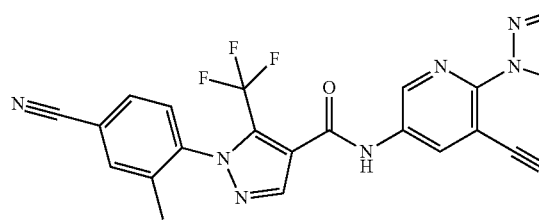 | 126 | 1-(4-cyano-2-methylphenyl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 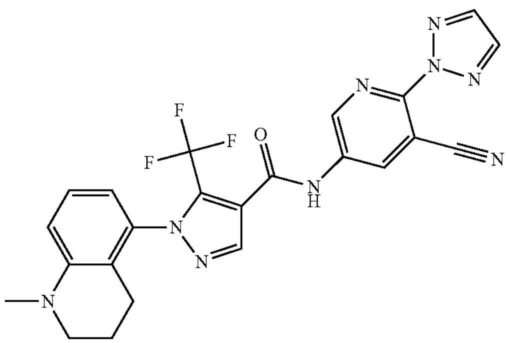 [SMILES: CN1CCCc2c1cccc2-n1ncc(C(=O)Nc2cnc(-n3nccn3)c(C#N)c2)c1C(F)(F)F] | 127 | N-(5-cyano-6-(2H-1,2,3-triazol-2-yl)pyridin-3-yl)-1-(1-methyl-1,2,3,4-tetrahydroquinolin-5-yl)-5-(trifluoromethyl)-1H-pyrazole-4-carboxamide |
| 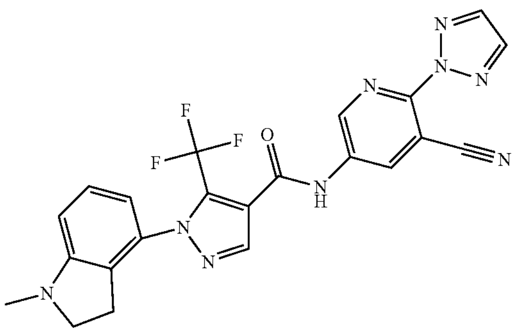 [SMILES: CN1CCc2c1cccc2-n1ncc(C(=O)Nc2cnc(-n3nccn3)c(C#N)c2)c1C(F)(F)F] | 128 | N-(5-cyano-6-(2H-1,2,3-triazol-2-yl)pyridin-3-yl)-1-(1-methylindolin-4-yl)-5-(trifluoromethyl)-1H-pyrazole-4-carboxamide |
| 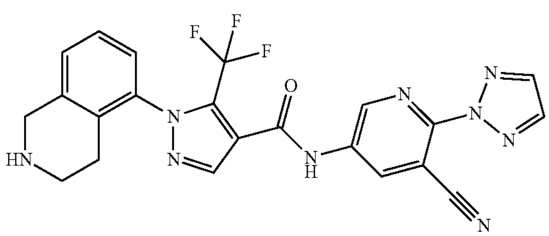 [SMILES: N#Cc1cc(NC(=O)c2cnn(-c3cccc4c3CCNC4)c2C(F)(F)F)cnc1-n1nccn1] | 129 | N-(5-cyano-6-(2H-1,2,3-triazol-2-yl)pyridin-3-yl)-1-(1,2,3,4-tetrahydroisoquinolin-5-yl)-5-(trifluoromethyl)-1H-pyrazole-4-carboxamide |
| 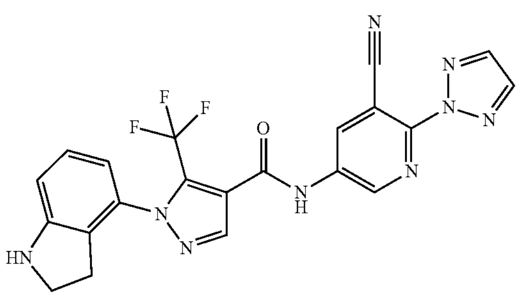 [SMILES: N#Cc1cc(NC(=O)c2cnn(-c3cccc4c3CCN4)c2C(F)(F)F)cnc1-n1nccn1] | 130 | N-(5-cyano-6-(2H-1,2,3-triazol-2-yl)pyridin-3-yl)-1-(indolin-4-yl)-5-(trifluoromethyl)-1H-pyrazole-4-carboxa |
| 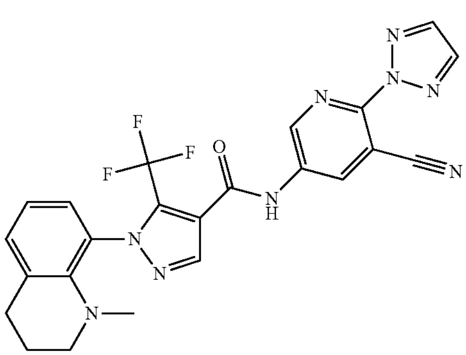 [SMILES: CN1CCCc2cccc(-n3ncc(C(=O)Nc4cnc(-n5nccn5)c(C#N)c4)c3C(F)(F)F)c21] | 131 | N-(5-cyano-6-(2H-1,2,3-triazol-2-yl)pyridin-3-yl)-1-(1-methyl-1,2,3,4-tetrahydroquinolin-8-yl)-5-(trifluoromethyl)-1H-pyrazole-4-carboxamide |

TABLE 1-continued

| Structure | Cpd no | Name |
|---|---|---|
| 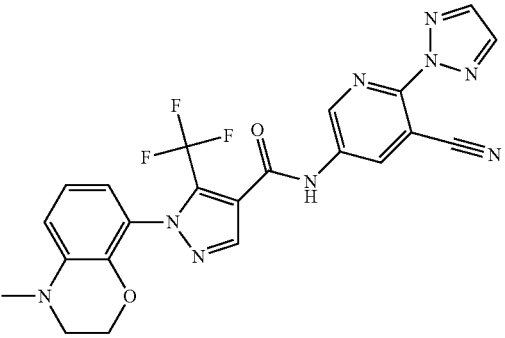 | 132 | N-(5-cyano-6-(2H-1,2,3-triazol-2-yl)pyridin-3-yl)-1-(4-methyl-3,4-dihydro-2H-benzo[b][1,4]oxazin-8-yl)-5-(trifluoromethyl)-1H-pyrazole-4-carboxamide |
| 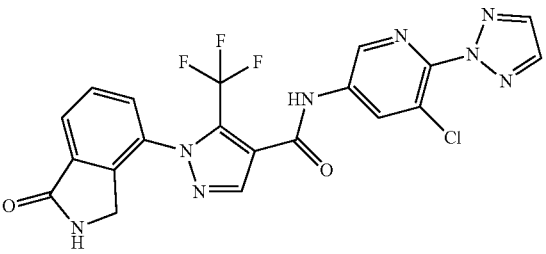 [SMILES: O=C1NCc2c1cccc2-n1ncc(C(=O)Nc2cnc(-n3nccn3)c(Cl)c2)c1C(F)(F)F] | 133 | N-(5-chloro-6-(2H-1,2,3-triazol-2-yl)pyridin-3-yl)-1-(1-oxoisoindolin-4-yl)-5-(trifluoromethyl)-1H-pyrazole-4-carboxamide |
| 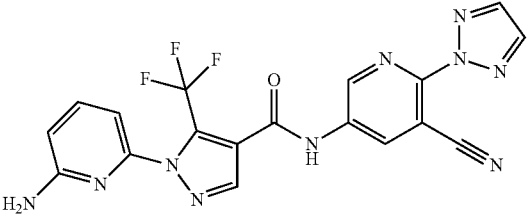 [SMILES: N#Cc1cc(NC(=O)c2cnn(-c3cccc(N)n3)c2C(F)(F)F)cnc1-n1nccn1] | 134 | 1-(6-aminopyridin-2-yl)-N-(5-cyano-6-(2H-1,2,3-triazol-2-yl)pyridin-3-yl)-5-(trifluoromethyl)-1H-pyrazole-4-carboxamide |
| 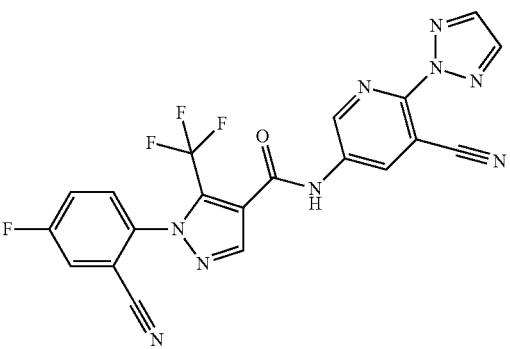 [SMILES: N#Cc1cc(F)ccc1-n1ncc(C(=O)Nc2cnc(-n3nccn3)c(C#N)c2)c1C(F)(F)F] | 135 | 1-(2-cyano-4-fluorophenyl)-N-(5-cyano-6-(2H-1,2,3-triazol-2-yl)pyridin-3-yl)-5-(trifluoromethyl)-1H-pyrazole-4-carboxamide |
| 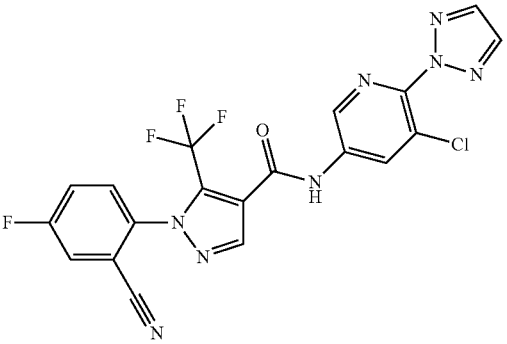 [SMILES: N#Cc1cc(F)ccc1-n1ncc(C(=O)Nc2cnc(-n3nccn3)c(Cl)c2)c1C(F)(F)F] | 136 | N-(5-chloro-6-(2H-1,2,3-triazol-2-yl)pyridin-3-yl)-1-(2-cyano-4-fluorophenyl)-5-(trifluoromethyl)-1H-pyrazole-4-carboxamide |

TABLE 1-continued

| Structure | Cpd no | Name |
|---|---|---|
| 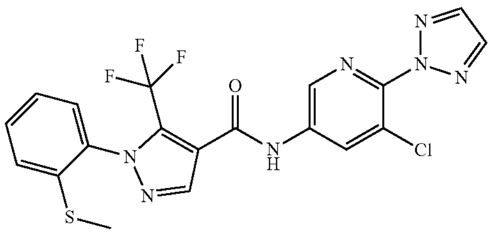 [SMILES: CSc1ccccc1-n1ncc(C(=O)Nc2cnc(-n3nccn3)c(Cl)c2)c1C(F)(F)F] | 137 | N-(5-chloro-6-(2H-1,2,3-triazol-2-yl)pyridin-3-yl)-1-(2-(methylthio)phenyl)-5-(trifluoromethyl)-1H-pyrazole-4-carboxamide |
| 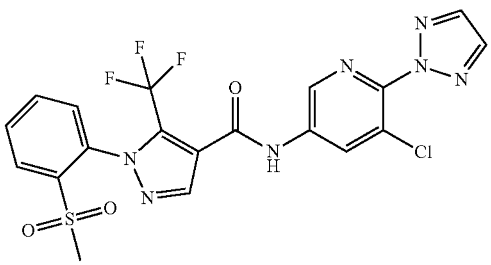 [SMILES: CS(=O)(=O)c1ccccc1-n1ncc(C(=O)Nc2cnc(-n3nccn3)c(Cl)c2)c1C(F)(F)F] | 138 | N-(5-chloro-6-(2H-1,2,3-triazol-2-yl)pyridin-3-yl)-1-(2-(methylsulfonyl)phenyl)-5-(trifluoromethyl)-1H-pyrazole-4-carboxamide |
| 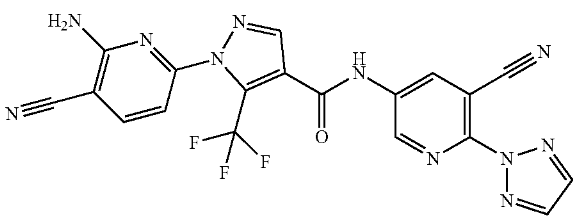 [SMILES: N#Cc1ccc(-n2ncc(C(=O)Nc3cnc(-n4nccn4)c(C#N)c3)c2C(F)(F)F)nc1N] | 139 | 1-(6-amino-5-cyanopyridin-2-yl)-N-(5-cyano-6-(2H-1,2,3-triazol-2-yl)pyridin-3-yl)-5-(trifluoromethyl)-1H-pyrazole-4-carboxamide |
| 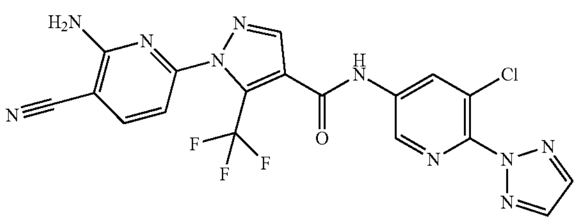 [SMILES: N#Cc1ccc(-n2ncc(C(=O)Nc3cnc(-n4nccn4)c(Cl)c3)c2C(F)(F)F)nc1N] | 140 | 1-(6-amino-5-cyanopyridin-2-yl)-N-(5-chloro-6-(2H-1,2,3-triazol-2-yl)pyridin-3-yl)-5-(trifluoromethyl)-1H-pyrazole-4-carboxamide |
| 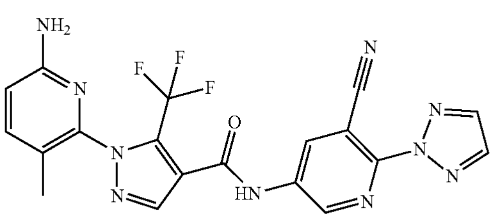 [SMILES: Cc1ccc(N)nc1-n1ncc(C(=O)Nc2cnc(-n3nccn3)c(C#N)c2)c1C(F)(F)F] | 141 | 1-(6-amino-3-methylpyridin-2-yl)-N-(5-cyano-6-(2H-1,2,3-triazol-2-yl)pyridin-3-yl)-5-(trifluoromethyl)-1H-pyrazole-4-carboxamide |
| 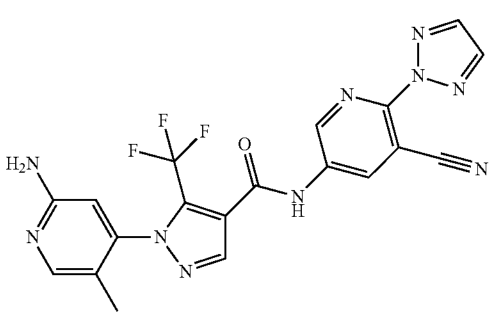 [SMILES: Cc1cnc(N)cc1-n1ncc(C(=O)Nc2cnc(-n3nccn3)c(C#N)c2)c1C(F)(F)F] | 142 | 1-(2-amino-5-methylpyridin-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 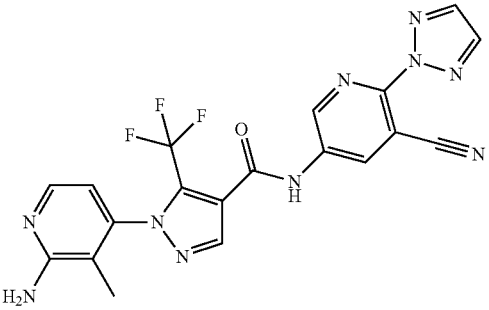 [SMILES: Cc1c(-n2ncc(C(=O)Nc3cnc(-n4nccn4)c(C#N)c3)c2C(F)(F)F)ccnc1N] | 143 | 1-(2-amino-3-methylpyridin-4-yl)-N-(5-cyano-6-(2H-1,2,3-triazol-2-yl)pyridin-3-yl)-5-(trifluoromethyl)-1H-pyrazole-4-carboxamide |
| 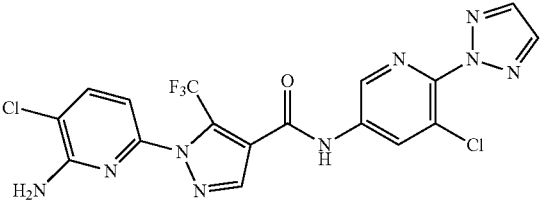 [SMILES: Nc1nc(-n2ncc(C(=O)Nc3cnc(-n4nccn4)c(Cl)c3)c2C(F)(F)F)ccc1Cl] | 144 | 1-(6-amino-5-chloropyridin-2-yl)-N-(5-cyano-6-(2H-1,2,3-triazol-2-yl)pyridin-3-yl)-5-(trifluoromethyl)-1H-pyrazole-4-carboxamide |
| 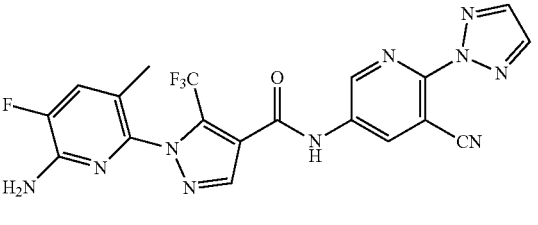 [SMILES: Cc1cc(F)c(N)nc1-n1ncc(C(=O)Nc2cnc(-n3nccn3)c(Cl)c2)c1C(F)(F)F] | 145 | 1-(6-amino-5-fluoro-3-methylpyridin-2-yl)-N-(5-cyano-6-(2H-1,2,3-triazol-2-yl)pyridin-3-yl)-5-(trifluoromethyl)-1H-pyrazole-4-carboxamide |
| 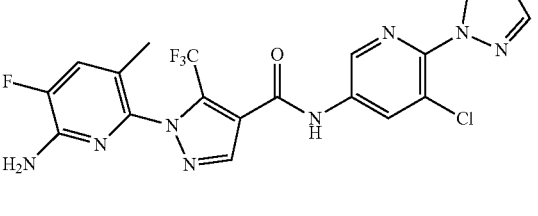 | 146 | 1-(6-amino-5-fluoro-3-methylpyridin-2-yl)-N-(5-chloro-6-(2H-1,2,3-triazol-2-yl)pyridin-3-yl)-5-(trifluoromethyl)-1H-pyrazole-4-carboxamide |
| 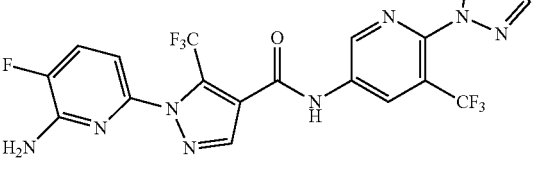 | 147 | N-(6-(2H-1,2,3-triazol-2-yl)-5-(trifluoromethyl)pyridin-3-yl)-1-(6-amino-5-fluoropyridin-2-yl)-5-(trifluoromethyl)-1H-pyrazole-4-carboxamide |
| 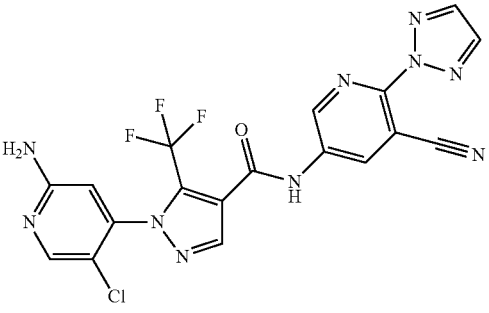 [SMILES: N#Cc1cc(NC(=O)c2cnn(-c3cc(N)ncc3Cl)c2C(F)(F)F)cnc1-n1nccn1] | 148 | 1-(2-amino-5-chloropyridin-4-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 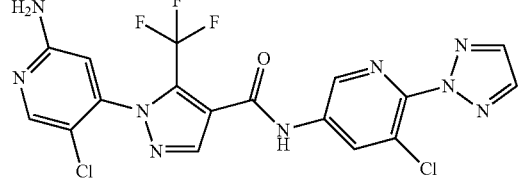 | 149 | 1-(2-amino-5-chloropyridin-4-yl)-N-(5-chloro-6-(2H-1,2,3-triazol-2-yl)pyridin-3-yl)-5-(trifluoromethyl)-1H-pyrazole-4-carboxamide |
| 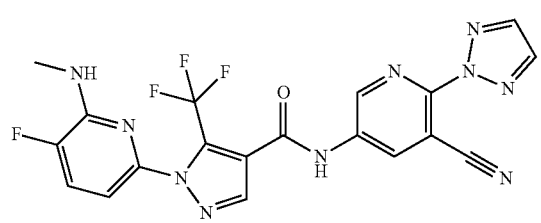 [SMILES: CNc1nc(-n2ncc(C(=O)Nc3cnc(-n4nccn4)c(C#N)c3)c2C(F)(F)F)ccc1F] | 150 | N-(5-cyano-6-(2H-1,2,3-triazol-2-yl)pyridin-3-yl)-1-(5-fluoro-6-(methylamino)pyridin-2-yl)-5-(trifluoromethyl)-1H-pyrazole-4-carboxamide |
| 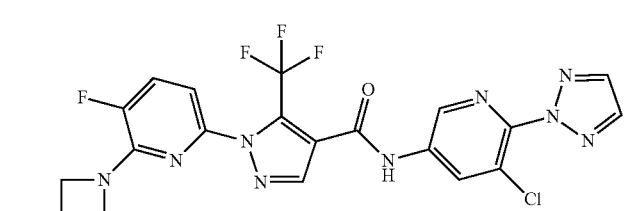 | 151 | N-(5-chloro-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide |
| 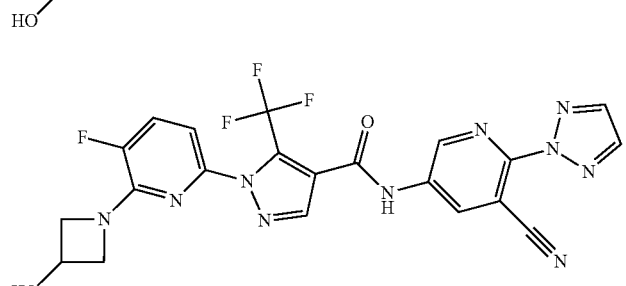 | 152 | N-(5-cyano-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide |
| 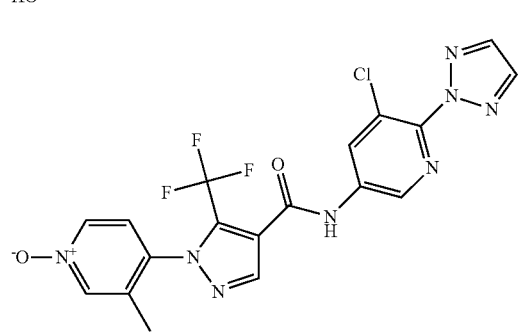 | 153 | 4-(4-((5-chloro-6-(2H-1,2,3-triazol-2-yl)pyridin-3-yl)carbamoyl)-5-(trifluoromethyl)-1H-pyrazol-1-yl)-3-methylpyridine 1-oxide |
| 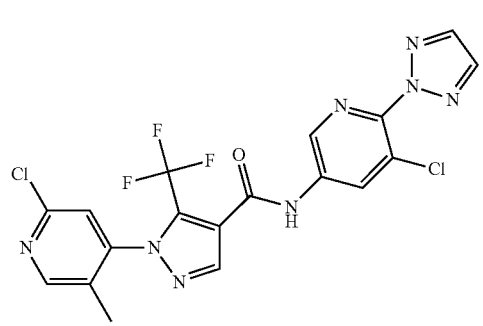 [SMILES: Cc1cnc(Cl)cc1-n1ncc(C(=O)Nc2cnc(-n3nccn3)c(Cl)c2)c1C(F)(F)F] | 154 | 1-(2-chloro-5-methyl-4-pyridyl)-N-[5-chloro-6-(triazol-2-yl)-3-pyridyl]-5-(trifluoromethyl)pyrazole-4-carboxamide |

TABLE 1-continued

| Structure | Cpd no | Name |
|---|---|---|
| 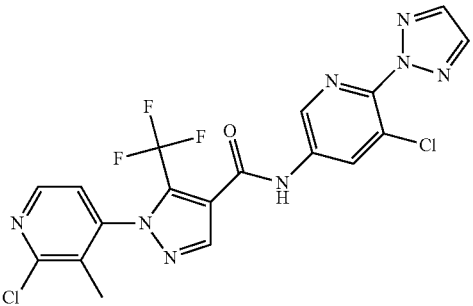 [SMILES: Cc1c(-n2ncc(C(=O)Nc3cnc(-n4nccn4)c(Cl)c3)c2C(F)(F)F)ccnc1Cl] | 155 | 1-(2-chloro-3-methylpyridin-4-yl)-N-(5-chloro-6-(2H-1,2,3-triazol-2-yl)pyridin-3-yl)-5-(trifluoromethyl)-1H-pyrazole-4-carboxamide |
| 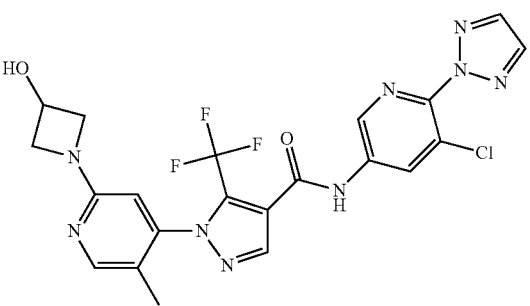 [SMILES: Cc1cnc(N2CC(O)C2)cc1-n1ncc(C(=O)Nc2cnc(-n3nccn3)c(Cl)c2)c1C(F)(F)F] | 156 | N-(5-chloro-6-(2H-1,2,3-triazol-2-yl)pyridin-3-yl)-1-(2-(3-hydroxyazetidin-1-yl)-5-methylpyridin-4-yl)-5-(trifluoromethyl)-1H-pyrazole-4-carboxamide |
| 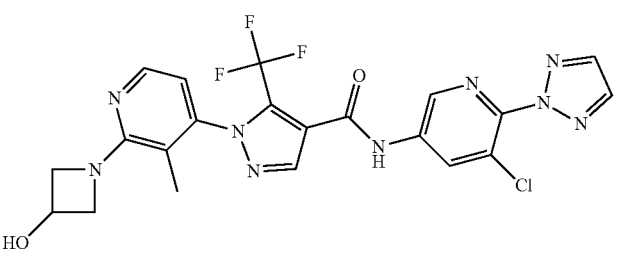 [SMILES: Cc1c(-n2ncc(C(=O)Nc3cnc(-n4nccn4)c(Cl)c3)c2C(F)(F)F)ccnc1N1CC(O)C1] | 157 | N-(5-chloro-6-(2H-1,2,3-triazol-2-yl)pyridin-3-yl)-1-(2-(3-hydroxyazetidin-1-yl)-3-methylpyridin-4-yl)-5-(trifluoromethyl)-1H-pyrazole-4-carboxamide |
| 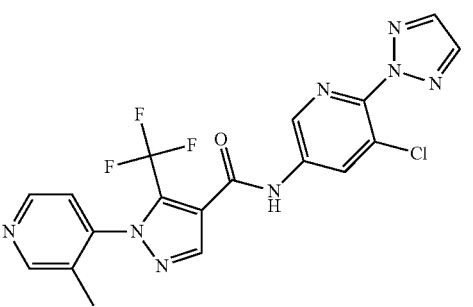 [SMILES: Cc1cnccc1-n1ncc(C(=O)Nc2cnc(-n3nccn3)c(Cl)c2)c1C(F)(F)F] | 158 | N-(5-chloro-6-(2H-1,2,3-triazol-2-yl)pyridin-3-yl)-1-(3-methylpyridin-4-yl)-5-(trifluoromethyl)-1H-pyrazole-4-carboxamide |
| 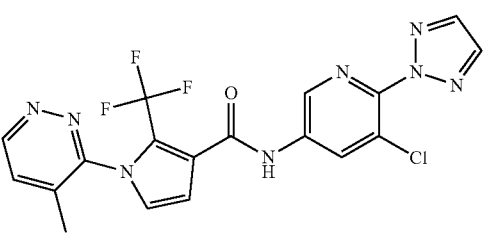 [SMILES: Cc1ccnnc1-n1ccc(C(=O)Nc2cnc(-n3nccn3)c(Cl)c2)c1C(F)(F)F] | 159 | N-(5-chloro-6-(2H-1,2,3-triazol-2-yl)pyridin-3-yl)-1-(4-methylpyridazin-3-yl)-5-(trifluoromethyl)-1H-pyrazole-4-carboxamide |

TABLE 1-continued

| Structure | Cpd no | Name |
|---|---|---|
| 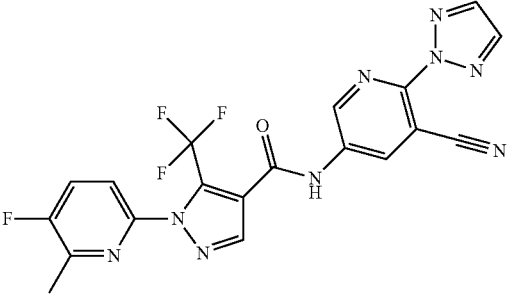 [SMILES: Cc1nc(-n2ncc(C(=O)Nc3cnc(-n4nccn4)c(C#N)c3)c2C(F)(F)F)ccc1F] | 160 | N-(5-cyano-6-(2H-1,2,3-triazol-2-yl)pyridin-3-yl)-1-(5-fluoro-6-methylpyridin-2-yl)-5-(trifluoromethyl)-1H-pyrazole-4-carboxamide |
| 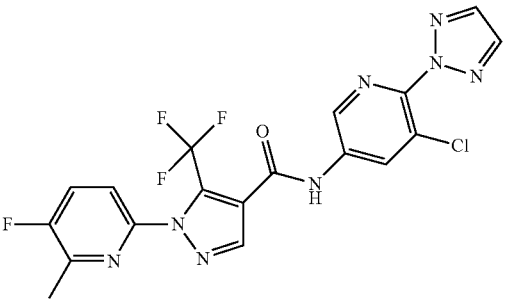 [SMILES: Cc1nc(-n2ncc(C(=O)Nc3cnc(-n4nccn4)c(Cl)c3)c2C(F)(F)F)ccc1F] | 161 | N-(5-chloro-6-(2H-1,2,3-triazol-2-yl)pyridin-3-yl)-1-(5-fluoro-6-methylpyridin-2-yl)-5-(trifluoromethyl)-1H-pyrazole-4-carboxamide |
| 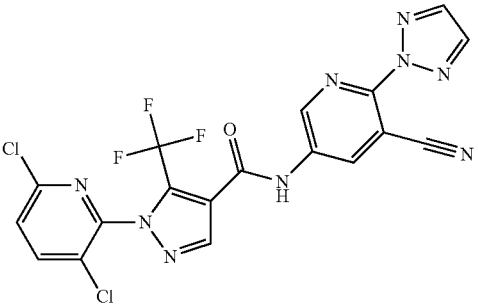 [SMILES: N#Cc1cc(NC(=O)c2cnn(-c3nc(Cl)ccc3Cl)c2C(F)(F)F)cnc1-n1nccn1] | 162 | N-(5-cyano-6-(2H-1,2,3-triazol-2-yl)pyridin-3-yl)-1-(3,6-dichloropyridin-2-yl)-5-(trifluoromethyl)-1H-pyrazole-4-carboxamide |
| 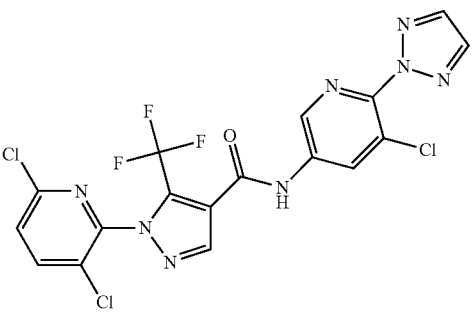 [SMILES: O=C(Nc1cnc(-n2nccn2)c(Cl)c1)c1cnn(-c2nc(Cl)ccc2Cl)c1C(F)(F)F] | 163 | N-(5-chloro-6-(2H-1,2,3-triazol-2-yl)pyridin-3-yl)-1-(3,6-dichloropyridin-2-yl)-5-(trifluoromethyl)-1H-pyrazole-4-carboxamide |
| 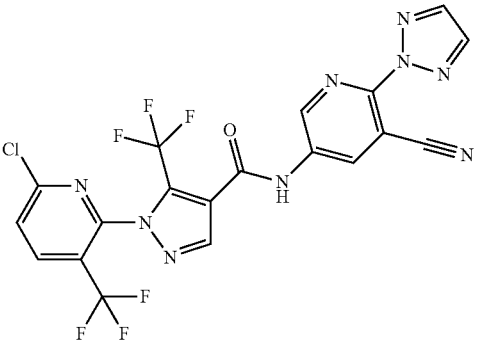 [SMILES: N#Cc1cc(NC(=O)c2cnn(-c3nc(Cl)ccc3C(F)(F)F)c2C(F)(F)F)cnc1-n1nccn1] | 164 | 1-(6-chloro-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 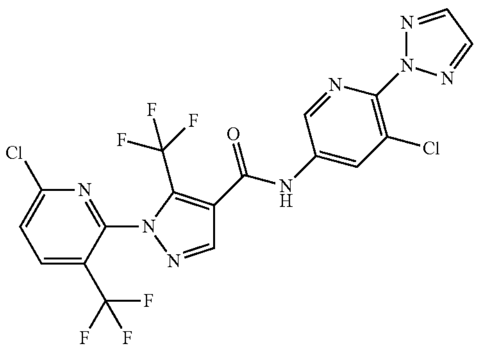 [SMILES: O=C(Nc1cnc(-n2nccn2)c(Cl)c1)c1cnn(-c2nc(Cl)ccc2C(F)(F)F)c1C(F)(F)F] | 165 | 1-(6-chloro-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide |
| 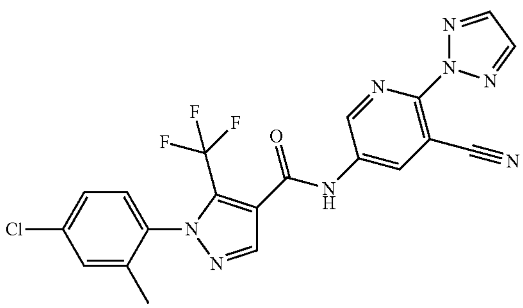 [SMILES: Cc1cc(Cl)ccc1-n1ncc(C(=O)Nc2cnc(-n3nccn3)c(C#N)c2)c1C(F)(F)F] | 166 | 1-(4-chloro-2-methylphenyl)-N-(5-cyano-6-(2H-1,2,3-triazol-2-yl)pyridin-3-yl)-5-(trifluoromethyl)-1H-pyrazole-4-carboxamide |
| 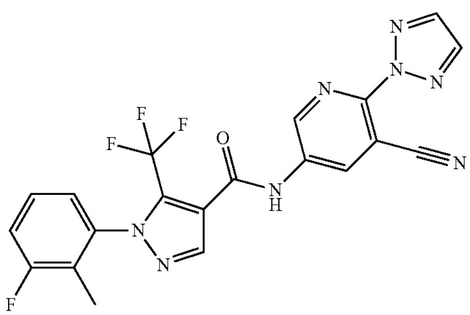 [SMILES: Cc1c(F)cccc1-n1ncc(C(=O)Nc2cnc(-n3nccn3)c(C#N)c2)c1C(F)(F)F] | 167 | N-(5-cyano-6-(2H-1,2,3-triazol-2-yl)pyridin-3-yl)-1-(3-fluoro-2-methylphenyl)-5-(trifluoromethyl)-1H-pyrazole-4-carboxamide |
| 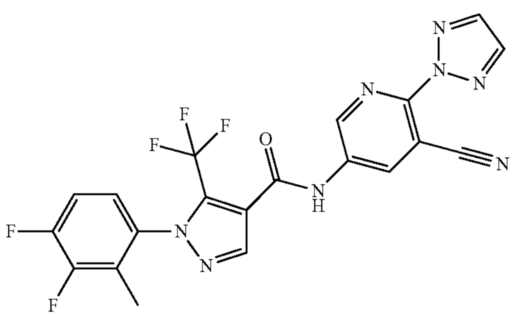 [SMILES: Cc1c(-n2ncc(C(=O)Nc3cnc(-n4nccn4)c(C#N)c3)c2C(F)(F)F)ccc(F)c1F] | 168 | N-(5-cyano-6-(2H-1,2,3-triazol-2-yl)pyridin-3-yl)-1-(3,4-difluoro-2-methylphenyl)-5-(trifluoromethyl)-1H-pyrazole-4-carboxamide |
| 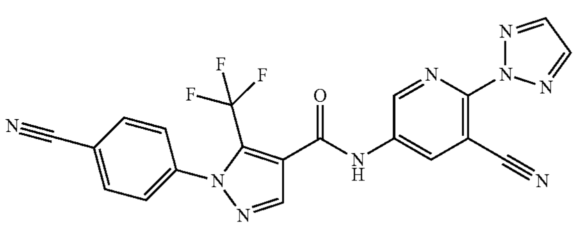 [SMILES: N#Cc1ccc(-n2ncc(C(=O)Nc3cnc(-n4nccn4)c(C#N)c3)c2C(F)(F)F)cc1] | 169 | N-(5-cyano-6-(2H-1,2,3-triazol-2-yl)pyridin-3-yl)-1-(4-cyanophenyl)-5-(trifluoromethyl)-1H-pyrazole-4-carboxamide |

TABLE 1-continued

| Structure | Cpd no | Name |
|---|---|---|
| 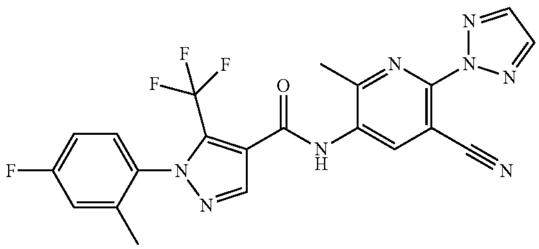 [SMILES: Cc1cc(F)ccc1-n1ncc(C(=O)Nc2cc(C#N)c(-n3nccn3)nc2C)c1C(F)(F)F] | 170 | N-(5-cyano-2-methyl-6-(2H-1,2,3-triazol-2-yl)pyridin-3-yl)-1-(4-fluoro-2-methylphenyl)-5-(trifluoromethyl)-1H-pyrazole-4-carboxamide |
| 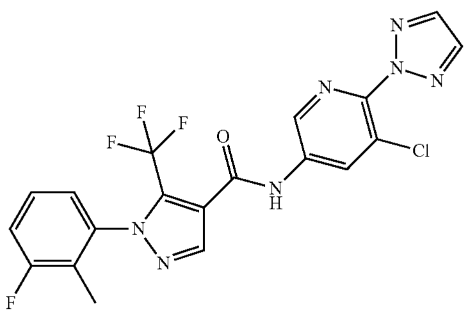 [SMILES: Cc1c(F)cccc1-n1ncc(C(=O)Nc2cnc(-n3nccn3)c(Cl)c2)c1C(F)(F)F] | 171 | N-(5-chloro-6-(2H-1,2,3-triazol-2-yl)pyridin-3-yl)-1-(3-fluoro-2-methylphenyl)-5-(trifluoromethyl)-1H-pyrazole-4-carboxamide |
| 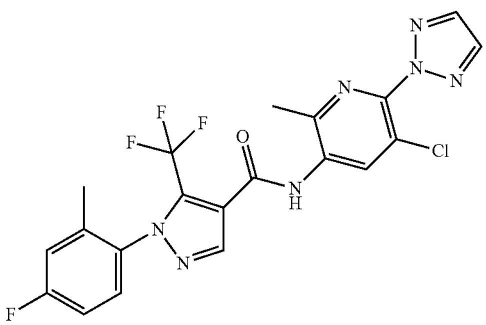 [SMILES: Cc1cc(F)ccc1-n1ncc(C(=O)Nc2cc(Cl)c(-n3nccn3)nc2C)c1C(F)(F)F] | 172 | N-(5-chloro-2-methyl-6-(2H-1,2,3-triazol-2-yl)pyridin-3-yl)-1-(4-fluoro-2-methylphenyl)-5-(trifluoromethyl)-1H-pyrazole-4-carboxamide |
| 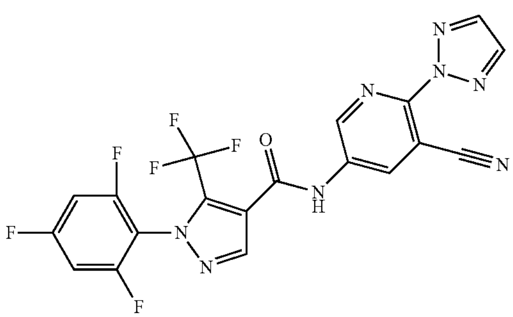 [SMILES: N#Cc1cc(NC(=O)c2cnn(-c3c(F)cc(F)cc3F)c2C(F)(F)F)cnc1-n1nccn1] | 173 | N-(5-cyano-6-(2H-1,2,3-triazol-2-yl)pyridin-3-yl)-5-(trifluoromethyl)-1-(2,4,6-trifluorophenyl)-1H-pyrazole-4-carboxamide |
| 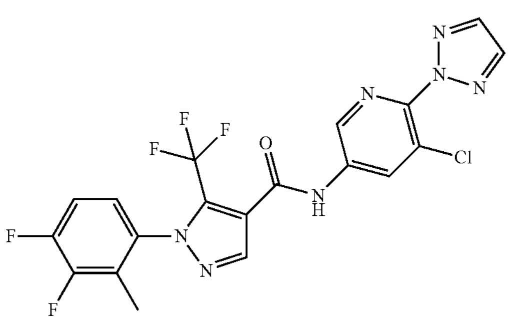 [SMILES: Cc1c(-n2ncc(C(=O)Nc3cnc(-n4nccn4)c(Cl)c3)c2C(F)(F)F)ccc(F)c1F] | 174 | N-(5-chloro-6-(2H-1,2,3-triazol-2-yl)pyridin-3-yl)-1-(3,4-difluoro-2-methylphenyl)-5-(trifluoromethyl)-1H-pyrazole-4-carboxamide |

TABLE 1-continued

| Structure | Cpd no | Name |
|---|---|---|
| 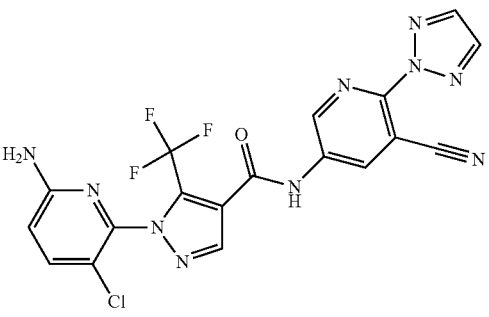 [SMILES: N#Cc1cc(NC(=O)c2cnn(-c3nc(N)ccc3Cl)c2C(F)(F)F)cnc1-n1nccn1] | 175 | 1-(6-amino-3-chloropyridin-2-yl)-N-(5-cyano-6-(2H-1,2,3-triazol-2-yl)pyridin-3-yl)-5-(trifluoromethyl)-1H-pyrazole-4-carboxamide |
| 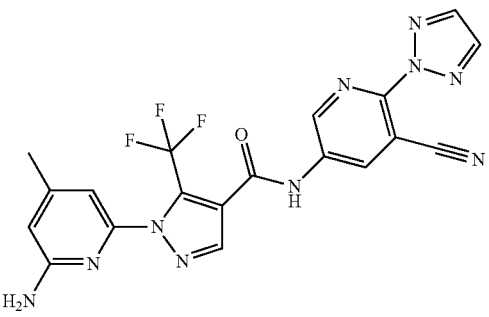 [SMILES: Cc1cc(N)nc(-n2ncc(C(=O)Nc3cnc(-n4nccn4)c(C#N)c3)c2C(F)(F)F)c1] | 176 | 1-(6-amino-4-methylpyridin-2-yl)-N-(5-cyano-6-(2H-1,2,3-triazol-2-yl)pyridin-3-yl)-5-(trifluoromethyl)-1H-pyrazole-4-carboxamide |
| 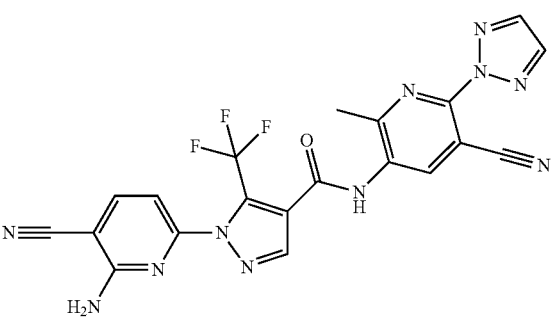 [SMILES: Cc1nc(-n2nccn2)c(C#N)cc1NC(=O)c1cnn(-c2ccc(C#N)c(N)n2)c1C(F)(F)F] | 177 | 1-(6-amino-5-cyanopyridin-2-yl)-N-(5-cyano-2-methyl-6-(2H-1,2,3-triazol-2-yl)pyridin-3-yl)-5-(trifluoromethyl)-1H-pyrazole-4-carboxamide |
| 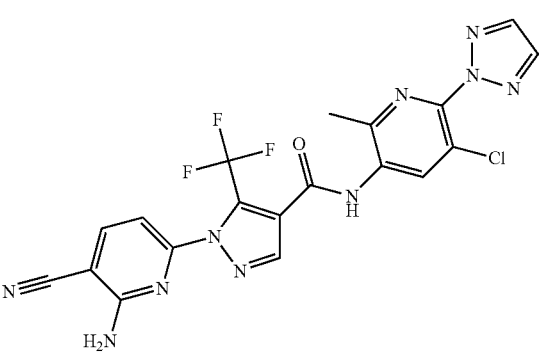 [SMILES: Cc1nc(-n2nccn2)c(Cl)cc1NC(=O)c1cnn(-c2ccc(C#N)c(N)n2)c1C(F)(F)F] | 178 | 1-(6-amino-5-cyanopyridin-2-yl)-N-(5-chloro-2-methyl-6-(2H-1,2,3-triazol-2-yl)pyridin-3-yl)-5-(trifluoromethyl)-1H-pyrazole-4-carboxamide |
| 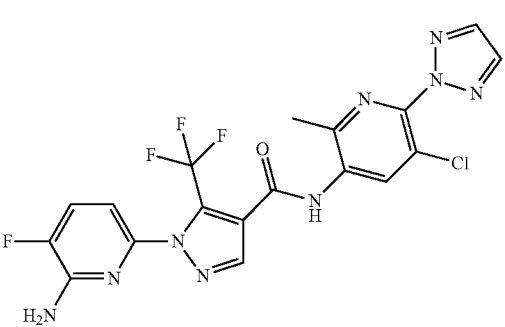 | 179 | 1-(6-amino-5-fluoropyridin-2-yl)-N-(5-chloro-2-methyl-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 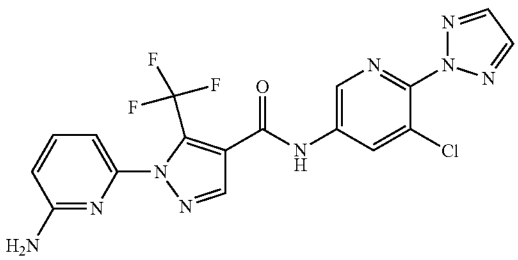 | 180 | 1-(6-aminopyridin-2-yl)-N-(5-chloro-6-(2H-1,2,3-triazol-2-yl)pyridin-3-yl)-5-(trifluoromethyl)-1H-pyrazole-4-carboxamide |
| 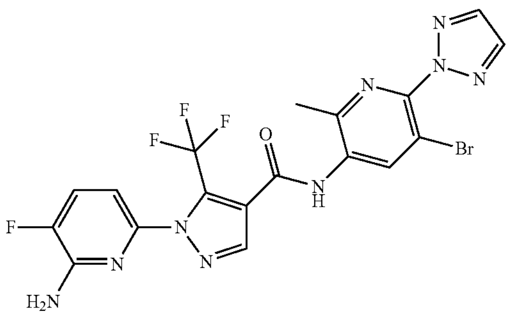 | 181 | 1-(6-amino-5-fluoropyridin-2-yl)-N-(5-bromo-2-methyl-6-(2H-1,2,3-triazol-2-yl)pyridin-3-yl)-5-(trifluoromethyl)-1H-pyrazole-4-carboxamide |
| 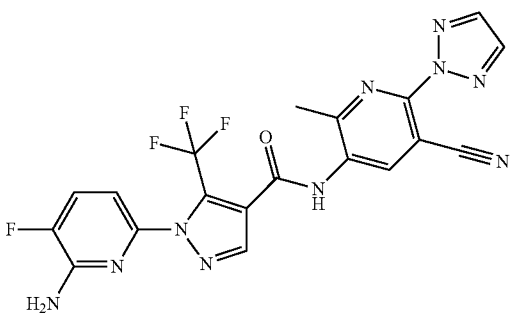 [SMILES: Cc1nc(-n2nccn2)c(C#N)cc1NC(=O)c1cnn(-c2ccc(F)c(N)n2)c1C(F)(F)F] | 182 | 1-(6-amino-5-fluoropyridin-2-yl)-N-(5-cyano-2-methyl-6-(2H-1,2,3-triazol-2-yl)pyridin-3-yl)-5-(trifluoromethyl)-1H-pyrazole-4-carboxamide |
| 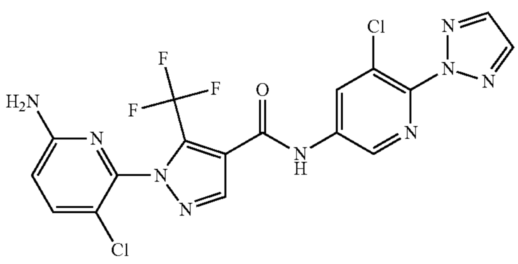 [SMILES: Nc1ccc(Cl)c(-n2ncc(C(=O)Nc3cnc(-n4nccn4)c(Cl)c3)c2C(F)(F)F)n1] | 183 | 1-(6-amino-3-chloropyridin-2-yl)-N-(5-chloro-6-(2H-1,2,3-triazol-2-yl)pyridin-3-yl)-5-(trifluoromethyl)-1H-pyrazole-4-carboxamide |
| 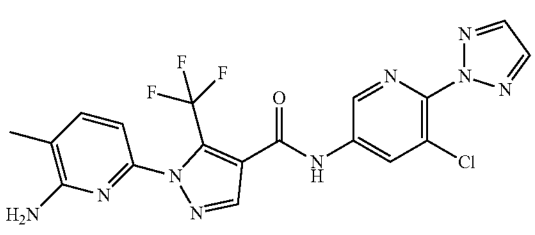 [SMILES: Cc1ccc(-n2ncc(C(=O)Nc3cnc(-n4nccn4)c(Cl)c3)c2C(F)(F)F)nc1N] | 184 | 1-(6-amino-5-methylpyridin-2-yl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 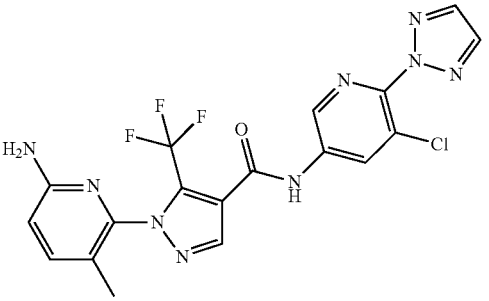 [SMILES: Cc1ccc(N)nc1-n1ncc(C(=O)Nc2cnc(-n3nccn3)c(Cl)c2)c1C(F)(F)F] | 185 | 1-(6-amino-3-methylpyridin-2-yl)-N-(5-chloro-6-(2H-1,2,3-triazol-2-yl)pyridin-3-yl)-5-(trifluoromethyl)-1H-pyrazole-4-carboxamide |
| 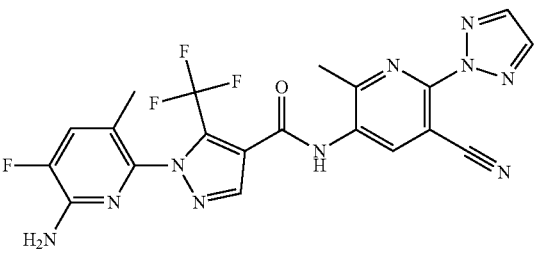 | 186 | 1-(6-amino-5-fluoro-3-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide |
| 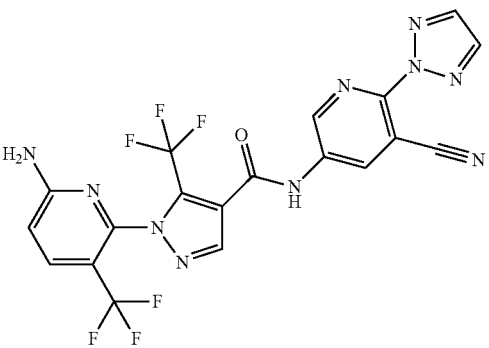 [SMILES: N#Cc1cc(NC(=O)c2cnn(-c3nc(N)ccc3C(F)(F)F)c2C(F)(F)F)cnc1-n1nccn1] | 187 | 1-(6-amino-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide |
| 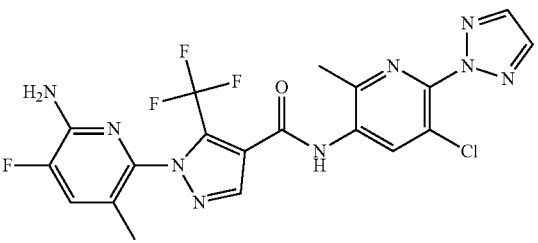 [SMILES: Cc1cc(F)c(N)nc1-n1ncc(C(=O)Nc2cc(Cl)c(-n3nccn3)nc2C)c1C(F)(F)F] | 188 | 1-(6-amino-5-fluoro-3-methylpyridin-2-yl)-N-(5-chloro-2-methyl-6-(2H-1,2,3-triazol-2-yl)pyridin-3-yl)-5-(trifluoromethyl)-1H-pyrazole-4-carboxamide |
| 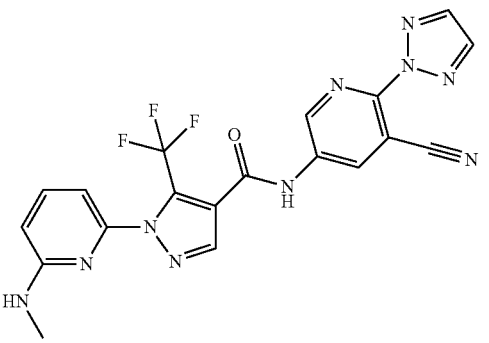 [SMILES: CNc1cccc(-n2ncc(C(=O)Nc3cnc(-n4nccn4)c(C#N)c3)c2C(F)(F)F)n1] | 189 | N-(5-cyano-6-(2H-1,2,3-triazol-2-yl)pyridin-3-yl)-1-(6-(methylamino)pyridin-2-yl)-5-(trifluoromethyl)-1H-pyrazole-4-carboxamide |

TABLE 1-continued

| Structure | Cpd no | Name |
|---|---|---|
| 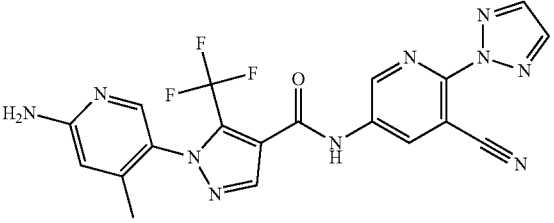 [SMILES: Cc1cc(N)ncc1-n1ncc(C(=O)Nc2cnc(-n3nccn3)c(C#N)c2)c1C(F)(F)F] | 190 | 1-(6-amino-4-methylpyridin-3-yl)-N-(5-cyano-6-(2H-1,2,3-triazol-2-yl)pyridin-3-yl)-5-fluoromethyl)-1H-pyrazole-4-carboxamide |
| 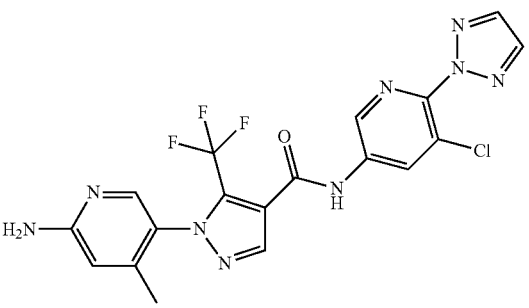 [SMILES: Cc1cc(N)ncc1-n1ncc(C(=O)Nc2cnc(-n3nccn3)c(Cl)c2)c1C(F)(F)F] | 191 | 1-(6-amino-4-methylpyridin-3-yl)-N-(5-chloro-6-(2H-1,2,3-triazol-2-yl)pyridin-3-yl)-5-(trifluoromethyl)-1H-pyrazole-4-carboxamide |
| 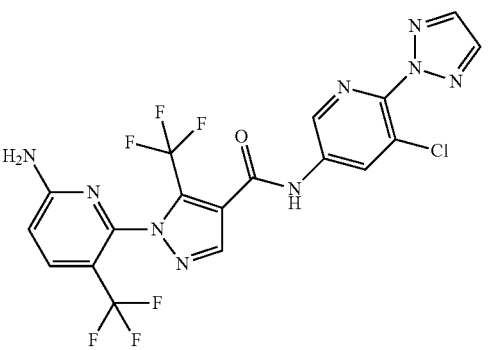 [SMILES: Nc1ccc(C(F)(F)F)c(-n2ncc(C(=O)Nc3cnc(-n4nccn4)c(Cl)c3)c2C(F)(F)F)n1] | 192 | 1-(6-amino-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide |
| 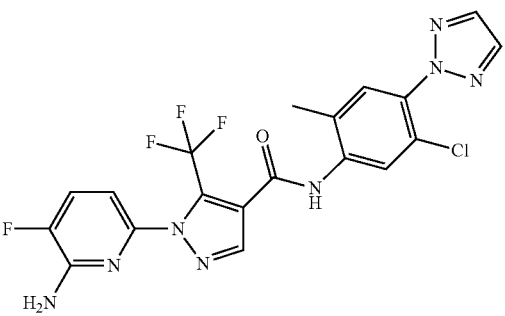 | 193 | 1-(6-amino-5-fluoropyridin-2-yl)-N-(5-chloro-2-methyl-4-(2H-1,2,3-triazol-2-yl)phenyl)-5-(trifluoromethyl)-1H-pyrazole-4-carboxamide |
| 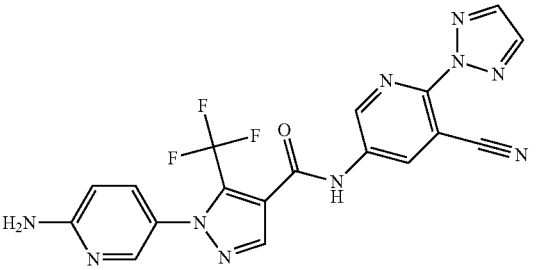 [SMILES: N#Cc1cc(NC(=O)c2cnn(-c3ccc(N)nc3)c2C(F)(F)F)cnc1-n1nccn1] | 194 | 1-(6-aminopyridin-3-yl)-N-(5-cyano-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 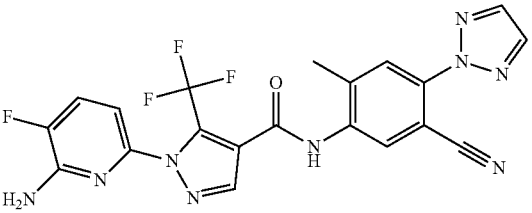 [SMILES: Cc1cc(-n2nccn2)c(C#N)cc1NC(=O)c1cnn(-c2ccc(F)c(N)n2)c1C(F)(F)F] | 195 | 1-(6-amino-5-fluoropyridin-2-yl)-N-(5-cyano-2-methyl-4-(2H-1,2,3-triazol-2-yl)phenyl)-5-(trifluoromethyl)-1H-pyrazole-4-carboxamide |
| 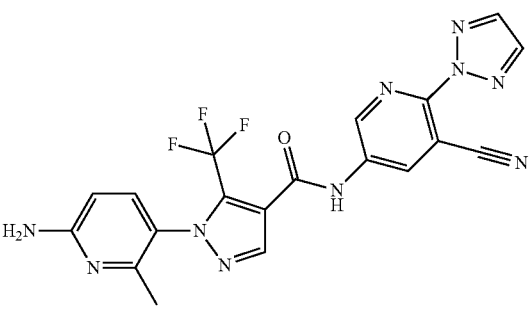 [SMILES: Cc1nc(N)ccc1-n1ncc(C(=O)Nc2cnc(-n3nccn3)c(C#N)c2)c1C(F)(F)F] | 196 | 1-(6-amino-2-methylpyridin-3-yl)-N-(5-cyano-6-(2H-1,2,3-triazol-2-yl)pyridin-3-yl)-5-(trifluoromethyl)-1H-pyrazole-4-carboxamide |
| 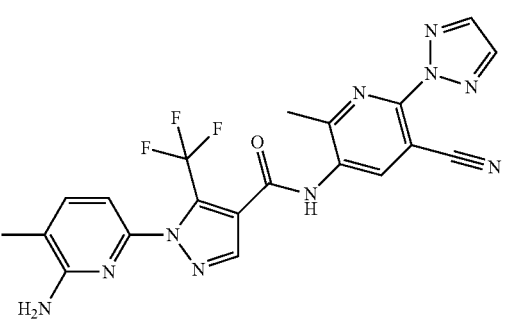 [SMILES: Cc1ccc(-n2ncc(C(=O)Nc3cc(C#N)c(-n4nccn4)nc3C)c2C(F)(F)F)nc1N] | 197 | 1-(6-amino-5-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide |
| 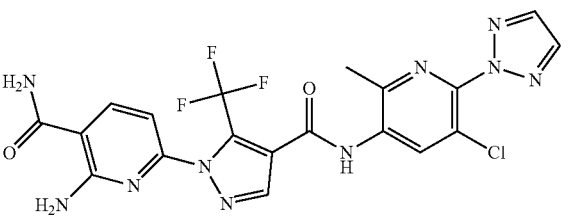 [SMILES: Cc1nc(-n2nccn2)c(Cl)cc1NC(=O)c1cnn(-c2ccc(C(N)=O)c(N)n2)c1C(F)(F)F] | 198 | 2-amino-6-(4-((5-chloro-2-methyl-6-(2H-1,2,3-triazol-2-yl)pyridin-3-yl)carbamoyl)-5-(trifluoromethyl)-1H-pyrazol-1-yl)nicotinamide |
| 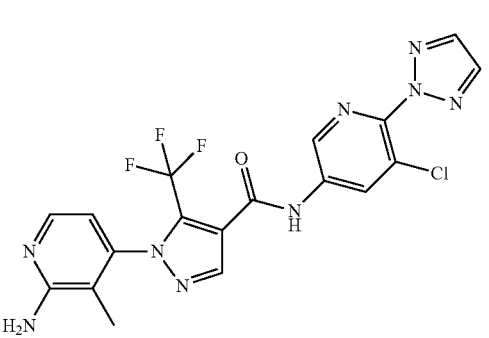 [SMILES: Cc1c(-n2ncc(C(=O)Nc3cnc(-n4nccn4)c(Cl)c3)c2C(F)(F)F)ccnc1N] | 199 | 1-(2-amino-3-methylpyridin-4-yl)-N-(5-chloro-6-(2H-1,2,3-triazol-2-yl)pyridin-3-yl)-5-(trifluoromethyl)-1H-pyrazole-4-carboxamide |

TABLE 1-continued

| Structure | Cpd no | Name |
|---|---|---|
| 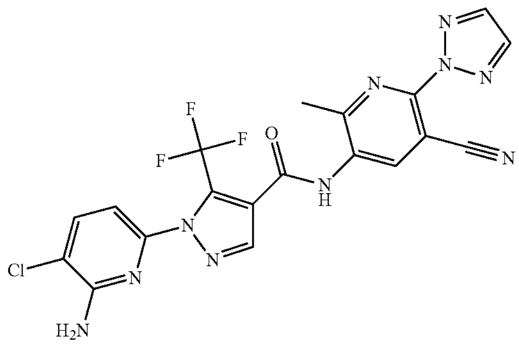 [SMILES: Cc1nc(-n2nccn2)c(C#N)cc1NC(=O)c1cnn(-c2ccc(Cl)c(N)n2)c1C(F)(F)F] | 200 | 1-(6-amino-5-chloropyridin-2-yl)-N-(5-cyano-2-methyl-6-(2H-1,2,3-triazol-2-yl)pyridin-3-yl)-5-(trifluoromethyl)-1H-pyrazole-4-carboxamide |
| 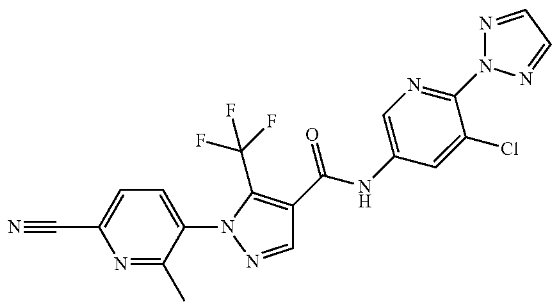 [SMILES: Cc1nc(C#N)ccc1-n1ncc(C(=O)Nc2cnc(-n3nccn3)c(Cl)c2)c1C(F)(F)F] | 201 | N-(5-chloro-6-(2H-1,2,3-triazol-2-yl)pyridin-3-yl)-1-(6-cyano-2-methylpyridin-3-yl)-5-(trifluoromethyl)-1H-pyrazole-4-carboxamide |
| 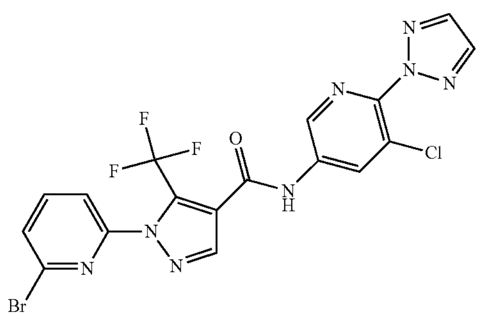 [SMILES: O=C(Nc1cnc(-n2nccn2)c(Cl)c1)c1cnn(-c2cccc(Br)n2)c1C(F)(F)F] | 202 | 1-(6-bromopyridin-2-yl)-N-(5-chloro-6-(2H-1,2,3-triazol-2-yl)pyridin-3-yl)-5-(trifluoromethyl)-1H-pyrazole-4-carboxamide |
| 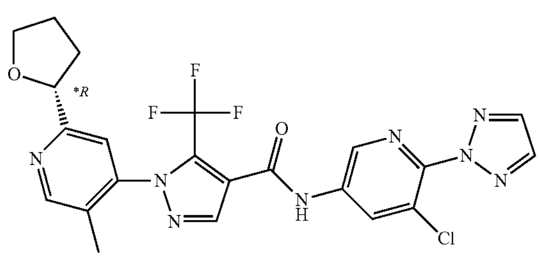 [SMILES: Cc1cnc([C@H]2CCCO2)cc1-n1ncc(C(=O)Nc2cnc(-n3nccn3)c(Cl)c2)c1C(F)(F)F] | 203 | (*R)-N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide |
| 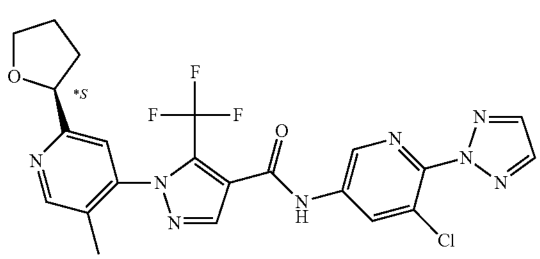 [SMILES: Cc1cnc([C@@H]2CCCO2)cc1-n1ncc(C(=O)Nc2cnc(-n3nccn3)c(Cl)c2)c1C(F)(F)F] | 204 | (*S)-N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide |

TABLE 1-continued

| Structure | Cpd no | Name |
|---|---|---|
| 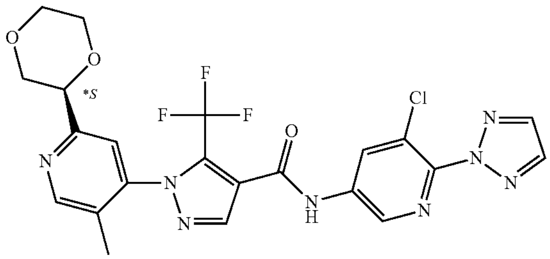 [SMILES: Cc1cnc([C@H]2COCCO2)cc1-n1ncc(C(=O)Nc2cnc(-n3nccn3)c(Cl)c2)c1C(F)(F)F] | 205 | (*S)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide |
| 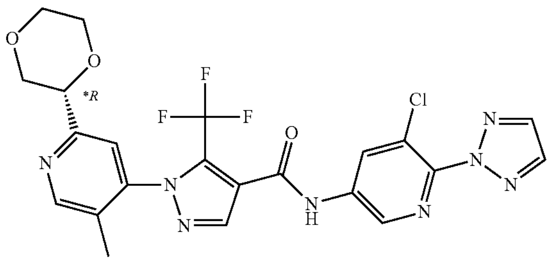 [SMILES: Cc1cnc([C@@H]2COCCO2)cc1-n1ncc(C(=O)Nc2cnc(-n3nccn3)c(Cl)c2)c1C(F)(F)F] | 206 | (*R)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide |
| 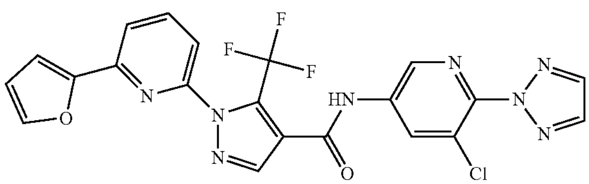 [SMILES: O=C(Nc1cnc(-n2nccn2)c(Cl)c1)c1cnn(-c2cccc(-c3ccco3)n2)c1C(F)(F)F] | 207 | N-(5-chloro-6-(2H-1,2,3-triazol-2-yl)pyridin-3-yl)-1-(6-(furan-2-yl)pyridin-2-yl)-5-(trifluoromethyl)-1H-pyrazole-4-carboxamide |
| 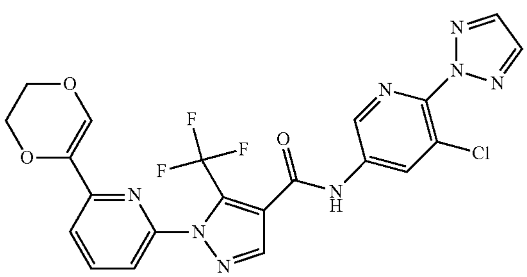 [SMILES: O=C(Nc1cnc(-n2nccn2)c(Cl)c1)c1cnn(-c2cccc(C3=COCCO3)n2)c1C(F)(F)F] | 208 | N-(5-chloro-6-(2H-1,2,3-triazol-2-yl)pyridin-3-yl)-1-(6-(5,6-dihydro-1,4-dioxin-2-yl)pyridin-2-yl)-5-(trifluoromethyl)-1H-pyrazole-4-carboxamide |

In a further embodiment, the invention is directed to a compound of Formula (I)

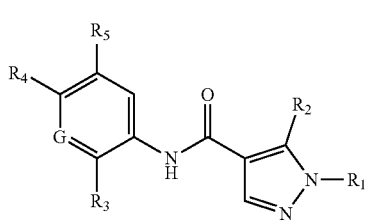

selected from the group consisting of
N-(5-Chloro-6-(2H-1,2,3-triazol-2-yl)pyridin-3-yl)-1-(4-fluoro-2-methylphenyl)-5-(trifluoromethyl)-1H-pyrazole-4-carboxamide;
1-(4-Chloro-2-methylphenyl)-N-(5-chloro-6-(2H-1,2,3-triazol-2-yl)pyridin-3-yl)-5-(trifluoromethyl)-1H-pyrazole-4-carboxamide;
N-(5-Chloro-6-(2H-1,2,3-triazol-2-yl)pyridin-3-yl)-1-(3-methylpyridin-2-yl)-5-(trifluoromethyl)-1H-pyrazole-4-carboxamide;
N-(5-Chloro-6-(2H-1,2,3-triazol-2-yl)pyridin-3-yl)-1-(pyridin-4-yl)-5-(trifluoromethyl)-1H-pyrazole-4-carboxamide;
N-(5-Chloro-6-(2H-1,2,3-triazol-2-yl)pyridin-3-yl)-1-phenyl-5-(trifluoromethyl)-1H-pyrazole-4-carboxamide;
N-(5-Chloro-6-(2H-1,2,3-triazol-2-yl)pyridin-3-yl)-1-(3-fluoropyridin-4-yl)-5-(trifluoromethyl)-1H-pyrazole-4-carboxamide;
N-(5-Chloro-6-(2H-1,2,3-triazol-2-yl)pyridin-3-yl)-1-(5-fluoropyridin-2-yl)-5-(trifluoromethyl)-1H-pyrazole-4-carboxamide;
N-(5-Chloro-6-(2H-1,2,3-triazol-2-yl)pyridin-3-yl)-1-(pyridin-2-yl)-5-(trifluoromethyl)-1H-pyrazole-4-carboxamide;
N-(5-Chloro-6-(2H-1,2,3-triazol-2-yl)pyridin-3-yl)-1-(pyrazin-2-yl)-5-(trifluoromethyl)-1H-pyrazole-4-carboxamide;
N-(5-Chloro-6-(2H-1,2,3-triazol-2-yl)pyridin-3-yl)-1-(pyrimidin-2-yl)-5-(trifluoromethyl)-1H-pyrazole-4-carboxamide;
N-(5-Chloro-6-(2H-1,2,3-triazol-2-yl)pyridin-3-yl)-1-(5-cyanopyridin-2-yl)-5-(trifluoromethyl)-1H-pyrazole-4-carboxamide;

N-(5-Chloro-6-(2H-1,2,3-triazol-2-yl)pyridin-3-yl)-1-(pyridin-3-yl)-5-(trifluoromethyl)-1H-pyrazole-4-carboxamide;
N-(5-Chloro-6-(2H-1,2,3-triazol-2-yl)pyridin-3-yl)-1-(6-methoxypyridin-3-yl)-5-(trifluoromethyl)-1H-pyrazole-4-carboxamide;
N-(5-Chloro-6-(2H-1,2,3-triazol-2-yl)pyridin-3-yl)-1-(2-methoxypyridin-3-yl)-5-(trifluoromethyl)-1H-pyrazole-4-carboxamide;
N-(5-Chloro-6-(2H-1,2,3-triazol-2-yl)pyridin-3-yl)-1-(pyrimidin-5-yl)-5-(trifluoromethyl)-1H-pyrazole-4-carboxamide;
N-(5-Chloro-6-(2H-1,2,3-triazol-2-yl)pyridin-3-yl)-1-(5-methylpyridin-3-yl)-5-(trifluoromethyl)-1H-pyrazole-4-carboxamide;
N-(5-Chloro-6-(2H-1,2,3-triazol-2-yl)pyridin-3-yl)-1-(5-cyanopyridin-3-yl)-5-(trifluoromethyl)-1H-pyrazole-4-carboxamide;
N-(5-chloro-6-(2H-1,2,3-triazol-2-yl)pyridin-3-yl)-1-(4-fluorophenyl)-5-(trifluoromethyl)-1H-pyrazole-4-carboxamide;
N-(5-chloro-6-(2H-1,2,3-triazol-2-yl)pyridin-3-yl)-1-(4-cyanophenyl)-5-(trifluoromethyl)-1H-pyrazole-4-carboxamide;
N-(5-chloro-6-(2H-1,2,3-triazol-2-yl)pyridin-3-yl)-1-(3-fluorophenyl)-5-(trifluoromethyl)-1H-pyrazole-4-carboxamide;
N-(5-chloro-6-(2H-1,2,3-triazol-2-yl)pyridin-3-yl)-1-(3-cyanophenyl)-5-(trifluoromethyl)-1H-pyrazole-4-carboxamide;
N-(5-chloro-6-(2H-1,2,3-triazol-2-yl)pyridin-3-yl)-1-(4-methylpyridin-2-yl)-5-(trifluoromethyl)-1H-pyrazole-4-carboxamide;
N-(5-chloro-6-(2H-1,2,3-triazol-2-yl)pyridin-3-yl)-1-(5-methylpyridin-2-yl)-5-(trifluoromethyl)-1H-pyrazole-4-carboxamide;
N-(5-chloro-6-(2H-1,2,3-triazol-2-yl)pyridin-3-yl)-1-(6-methylpyridin-2-yl)-5-(trifluoromethyl)-1H-pyrazole-4-carboxamide;
N-(5-chloro-6-(2H-1,2,3-triazol-2-yl)pyridin-3-yl)-5-(difluoromethyl)-1-(pyridin-4-yl)-1H-pyrazole-4-carboxamide;
N-(5-chloro-6-(2H-1,2,3-triazol-2-yl)pyridin-3-yl)-5-fluoro-1-phenyl-1H-pyrazole-4-carboxamide;
N-(5-chloro-6-(2H-1,2,3-triazol-2-yl)pyridin-3-yl)-1-(p-tolyl)-5-(trifluoromethyl)-1H-pyrazole-4-carboxamide;
N-(5-chloro-6-(2H-1,2,3-triazol-2-yl)pyridin-3-yl)-1-(m-tolyl)-5-(trifluoromethyl)-1H-pyrazole-4-carboxamide;
N-(5-chloro-6-(2H-1,2,3-triazol-2-yl)pyridin-3-yl)-1-(o-tolyl)-5-(trifluoromethyl)-1H-pyrazole-4-carboxamide;
1-(5-bromo-3-chloropyridin-2-yl)-N-(5-cyano-6-(2H-1,2,3-triazol-2-yl)pyridin-3-yl)-5-(trifluoromethyl)-1H-pyrazole-4-carboxamide;
1-(3-chloro-5-cyanopyridin-2-yl)-N-(5-cyano-6-(2H-1,2,3-triazol-2-yl)pyridin-3-yl)-5-(trifluoromethyl)-1H-pyrazole-4-carboxamide;
1-(3-Chloro-2-methoxypyridin-4-yl)-N-(5-cyano-6-(2H-1,2,3-triazol-2-yl)pyridin-3-yl)-5-(trifluoromethyl)-1H-pyrazole-4-carboxamide;
1-(3-Cyano-2-methylpyridin-4-yl)-N-(5-cyano-6-(2H-1,2,3-triazol-2-yl)pyridin-3-yl)-5-(trifluoromethyl)-1H-pyrazole-4-carboxamide;
1-(3-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide;
1-(3-cyano-5-fluoropyridin-2-yl)-N-(5-cyano-6-(2H-1,2,3-triazol-2-yl)pyridin-3-yl)-5-(trifluoromethyl)-1H-pyrazole-4-carboxamide;
N-(5-Cyano-6-(2H-1,2,3-triazol-2-yl)pyridin-3-yl)-1-(3,4-dichloropyridin-2-yl)-5-(trifluoromethyl)-1H-pyrazole-4-carboxamide;
N-(5-chloro-6-(2H-1,2,3-triazol-2-yl)pyridin-3-yl)-1-(4-cyano-2-methylphenyl)-5-(trifluoromethyl)-1H-pyrazole-4-carboxamide;
N-(5-cyano-6-(2H-1,2,3-triazol-2-yl)pyridin-3-yl)-1-(2-methoxy-3-methylpyridin-4-yl)-5-(trifluoromethyl)-1H-pyrazole-4-carboxamide;
1-(2-chloropyridin-4-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(2-cyanopyridin-4-yl)-5-(trifluoromethyl)-1H-pyrazole-4-carboxamide;
N-(5-Cyano-6-(2H-1,2,3-triazol-2-yl)pyridin-3-yl)-1-(2-methoxypyridin-4-yl)-5-(trifluoromethyl)-1H-pyrazole-4-carboxamide;
N-(5-cyano-6-(2H-1,2,3-triazol-2-yl)pyridin-3-yl)-1-(2,3-dimethylpyridin-4-yl)-5-(trifluoromethyl)-1H-pyrazole-4-carboxamide;
1-(3-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide;
1-(3-Chloropyridin-2-yl)-N-(5-cyano-6-(2H-1,2,3-triazol-2-yl)pyridin-3-yl)-5-(trifluoromethyl)-1H-pyrazole-4-carboxamide;
1-(3-chloropyridin-4-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(3-cyanopyridin-4-yl)-5-(trifluoromethyl)-1H-pyrazole-4-carboxamide;
1-(3-chloro-4-methylpyridin-2-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(3,5-dichloropyridin-4-yl)-5-(trifluoromethyl)-1H-pyrazole-4-carboxamide;
N-(5-cyano-6-(2H-1,2,3-triazol-2-yl)pyridin-3-yl)-1-(2,3-dihydrobenzo[b][1,4]dioxin-5-yl)-5-(trifluoromethyl)-1H-pyrazole-4-carboxamide;
1-(2-bromo-4-fluorophenyl)-N-(5-cyano-6-(2H-1,2,3-triazol-2-yl)pyridin-3-yl)-5-(trifluoromethyl)-1H-pyrazole-4-carboxamide;
1-(2-chloro-4-fluorophenyl)-N-(5-cyano-6-(2H-1,2,3-triazol-2-yl)pyridin-3-yl)-5-(trifluoromethyl)-1H-pyrazole-4-carboxamide;
1-([1,3]dioxolo[4,5-b]pyridin-7-yl)-N-(5-chloro-6-(2H-1,2,3-triazol-2-yl)pyridin-3-yl)-5-(trifluoromethyl)-1H-pyrazole-4-carboxamide;
1-([1,3]dioxolo[4,5-b]pyridin-7-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide;
N-(5-cyano-6-(2H-1,2,3-triazol-2-yl)pyridin-3-yl)-1-(o-tolyl)-5-(trifluoromethyl)-1H-pyrazole-4-carboxamide;
1-(2-amino-3-chloropyridin-4-yl)-N-(5-cyano-6-(2H-1,2,3-triazol-2-yl)pyridin-3-yl)-5-(trifluoromethyl)-1H-pyrazole-4-carboxamide;

1-(2-amino-3-chloropyridin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2,2-difluorobenzo[d][1,3]dioxol-4-yl)-5-(trifluoromethyl)-1H-pyrazole-4-carboxamide;

1-(benzo[d][1,3]dioxol-4-yl)-N-(5-cyano-6-(2H-1,2,3-triazol-2-yl)pyridin-3-yl)-5-(trifluoromethyl)-1H-pyrazole-4-carboxamide;

1-(2-chloro-3,4-difluorophenyl)-N-(5-cyano-6-(2H-1,2,3-triazol-2-yl)pyridin-3-yl)-5-(trifluoromethyl)-1H-pyrazole-4-carboxamide;

1-(2-chloro-3-fluorophenyl)-N-(5-cyano-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(4-fluoro-2-methylphenyl)-5-(trifluoromethyl)-1H-pyrazole-4-carboxamide;

1-(3-chloro-4-methoxypyridin-2-yl)-N-(5-chloro-6-(2H-1,2,3-triazol-2-yl)pyridin-3-yl)-5-(trifluoromethyl)-1H-pyrazole-4-carboxamide;

1-(3-chloro-4-methoxypyridin-2-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(3,5-dichloropyridin-4-yl)-5-(trifluoromethyl)-1H-pyrazole-4-carboxamide;

1-(5-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide;

1-(3-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide;

1-(5-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide;

1-(2-chloro-4-fluoro-3-methylphenyl)-N-(5-chloro-6-(2H-1,2,3-triazol-2-yl)pyridin-3-yl)-5-(trifluoromethyl)-1H-pyrazole-4-carboxamide;

1-(2-chloro-4-fluoro-3-methylphenyl)-N-(5-cyano-6-(2H-1,2,3-triazol-2-yl)pyridin-3-yl)-5-(trifluoromethyl)-1H-pyrazole-4-carboxamide;

1-(2-chloro-3,4-difluorophenyl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(3-(methylsulfonyl)phenyl)-5-(trifluoromethyl)-1H-pyrazole-4-carboxamide;

N-(5-chloro-6-(2H-1,2,3-triazol-2-yl)pyridin-3-yl)-1-(2-methyl-4-(methylsulfonyl)phenyl)-5-(trifluoromethyl)-1H-pyrazole-4-carboxamide;

N-(5-chloro-6-(2H-1,2,3-triazol-2-yl)pyridin-3-yl)-1-(2-isopropylphenyl)-5-(trifluoromethyl)-1H-pyrazole-4-carboxamide;

N-(5-chloro-6-(2H-1,2,3-triazol-2-yl)pyridin-3-yl)-1-(4-fluoro-2,3-dimethylphenyl)-5-(trifluoromethyl)-1H-pyrazole-4-carboxamide;

N-(5-chloro-6-(2H-1,2,3-triazol-2-yl)pyridin-3-yl)-1-(3,4-difluorophenyl)-5-(trifluoromethyl)-1H-pyrazole-4-carboxamide;

1-(2-chloro-5-fluorophenyl)-N-(5-chloro-6-(2H-1,2,3-triazol-2-yl)pyridin-3-yl)-5-(trifluoromethyl)-1H-pyrazole-4-carboxamide;

1-(2-chloro-5-fluorophenyl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(4-fluoro-2-methoxyphenyl)-5-(trifluoromethyl)-1H-pyrazole-4-carboxamide;

1-(2-chloro-3-fluorophenyl)-N-(5-chloro-6-(2H-1,2,3-triazol-2-yl)pyridin-3-yl)-5-(trifluoromethyl)-1H-pyrazole-4-carboxamide;

1-(2-bromo-4-fluorophenyl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(4-fluoro-2,3-dimethylphenyl)-5-(trifluoromethyl)-1H-pyrazole-4-carboxamide;

N-(5-chloro-6-(2H-1,2,3-triazol-2-yl)pyridin-3-yl)-1-(3-cyano-4-fluorophenyl)-5-(trifluoromethyl)-1H-pyrazole-4-carboxamide;

1-(3-cyano-4-fluorophenyl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-fluoro-4-methylpyridin-3-yl)-5-(trifluoromethyl)-1H-pyrazole-4-carboxamide;

N-(5-cyano-6-(2H-1,2,3-triazol-2-yl)pyridin-3-yl)-1-(2-methylpyridin-3-yl)-5-(trifluoromethyl)-1H-pyrazole-4-carboxamide;

N-(5-chloro-6-(2H-1,2,3-triazol-2-yl)pyridin-3-yl)-5-(trifluoromethyl)-1-(2,3,4-trifluorophenyl)-1H-pyrazole-4-carboxamide;

N-(5-chloro-6-(2H-1,2,3-triazol-2-yl)pyridin-3-yl)-1-(2-chloro-6-fluorophenyl)-5-(trifluoromethyl)-1H-pyrazole-4-carboxamide;

N-(5-cyano-6-(2H-1,2,3-triazol-2-yl)pyridin-3-yl)-1-(4-methylpyridin-3-yl)-5-(trifluoromethyl)-1H-pyrazole-4-carboxamide;

N-(5-chloro-6-(2H-1,2,3-triazol-2-yl)pyridin-3-yl)-1-(2-fluoro-6-methylphenyl)-5-(trifluoromethyl)-1H-pyrazole-4-carboxamide;

N-(5-chloro-6-(2H-1,2,3-triazol-2-yl)pyridin-3-yl)-1-(2,6-dichloro-4-fluorophenyl)-5-(trifluoromethyl)-1H-pyrazole-4-carboxamide;

1-(2-chloro-4,6-difluorophenyl)-N-(5-chloro-6-(2H-1,2,3-triazol-2-yl)pyridin-3-yl)-5-(trifluoromethyl)-1H-pyrazole-4-carboxamide;

1-(6-chloro-2-methylpyridin-3-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(5-fluoro-2-methylphenyl)-5-(trifluoromethyl)-1H-pyrazole-4-carboxamide;

N-(5-cyano-6-(2H-1,2,3-triazol-2-yl)pyridin-3-yl)-5-(trifluoromethyl)-1-(2,3,4-trifluorophenyl)-1H-pyrazole-4-carboxamide;

1-(2-chloro-6-fluorophenyl)-N-(5-cyano-6-(2H-1,2,3-triazol-2-yl)pyridin-3-yl)-5-(trifluoromethyl)-1H-pyrazole-4-carboxamide;

1-(2-chloro-4,6-difluorophenyl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(2-cyclopropylphenyl)-5-(trifluoromethyl)-1H-pyrazole-4-carboxamide;

N-(5-cyano-6-(2H-1,2,3-triazol-2-yl)pyridin-3-yl)-1-(2-fluoro-6-methylphenyl)-5-(trifluoromethyl)-1H-pyrazole-4-carboxamide;

N-(5-cyano-6-(2H-1,2,3-triazol-2-yl)pyridin-3-yl)-1-(2,6-dichloro-4-fluorophenyl)-5-(trifluoromethyl)-1H-pyrazole-4-carboxamide;

N-(5-cyano-6-(2H-1,2,3-triazol-2-yl)pyridin-3-yl)-1-(5-fluoro-2-methylphenyl)-5-(trifluoromethyl)-1H-pyrazole-4-carboxamide;

N-(5-cyano-6-(2H-1,2,3-triazol-2-yl)pyridin-3-yl)-1-(3,4-difluorophenyl)-5-(trifluoromethyl)-1H-pyrazole-4-carboxamide;

1-(3-chloro-5-fluoropyridin-2-yl)-N-(5-chloro-6-(2H-1,2,3-triazol-2-yl)pyridin-3-yl)-5-(trifluoromethyl)-1H-pyrazole-4-carboxamide;

1-(3-chloro-5-fluoropyridin-2-yl)-N-(5-cyano-6-(2H-1,2,3-triazol-2-yl)pyridin-3-yl)-5-(trifluoromethyl)-1H-pyrazole-4-carboxamide;

1-(2-chloro-4-fluorophenyl)-N-(5-chloro-6-(2H-1,2,3-triazol-2-yl)pyridin-3-yl)-5-(trifluoromethyl)-1H-pyrazole-4-carboxamide;

1-(3-chloro-4-fluorophenyl)-N-(5-chloro-6-(2H-1,2,3-triazol-2-yl)pyridin-3-yl)-5-(trifluoromethyl)-1H-pyrazole-4-carboxamide;

1-(3-chloro-4-fluorophenyl)-N-(5-cyano-6-(2H-1,2,3-triazol-2-yl)pyridin-3-yl)-5-(trifluoromethyl)-1H-pyrazole-4-carboxamide;

1-(2-chloro-4-cyanophenyl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(2,4-difluorophenyl)-5-(trifluoromethyl)-1H-pyrazole-4-carboxamide;

N-(5-chloro-6-(2H-1,2,3-triazol-2-yl)pyridin-3-yl)-1-(5-fluoro-3-methylpyridin-2-yl)-5-(trifluoromethyl)-1H-pyrazole-4-carboxamide;

N-(5-cyano-6-(2H-1,2,3-triazol-2-yl)pyridin-3-yl)-1-(5-fluoro-3-methylpyridin-2-yl)-5-(trifluoromethyl)-1H-pyrazole-4-carboxamide;

N-(5-chloro-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide;

N-(5-cyano-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide;

1-(2-chlorophenyl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2,4-difluorophenyl)-5-(trifluoromethyl)-1H-pyrazole-4-carboxamide;

N-(5-chloro-6-(2H-1,2,3-triazol-2-yl)pyridin-3-yl)-1-(2-(1-methoxyethyl)phenyl)-5-(trifluoromethyl)-1H-pyrazole-4-carboxamide;

1-(4-amino-3-chloropyridin-2-yl)-N-(5-chloro-6-(2H-1,2,3-triazol-2-yl)pyridin-3-yl)-5-(trifluoromethyl)-1H-pyrazole-4-carboxamide;

1-(4-amino-3-chloropyridin-2-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-fluoropyridin-3-yl)-5-(trifluoromethyl)-1H-pyrazole-4-carboxamide;

N-(5-chloro-6-(2H-1,2,3-triazol-2-yl)pyridin-3-yl)-1-(6-(methylamino)pyridin-3-yl)-5-(trifluoromethyl)-1H-pyrazole-4-carboxamide;

N-(5-cyano-6-(2H-1,2,3-triazol-2-yl)pyridin-3-yl)-1-(6-(fluoro)pyridin-3-yl)-5-(trifluoromethyl)-1H-pyrazole-4-carboxamide;

N-(5-cyano-6-(2H-1,2,3-triazol-2-yl)pyridin-3-yl)-1-(6-(methylamino)pyridin-3-yl)-5-(trifluoromethyl)-1H-pyrazole-4-carboxamide;

1-(6-aminopyridin-3-yl)-N-(5-chloro-6-(2H-1,2,3-triazol-2-yl)pyridin-3-yl)-5-(trifluoromethyl)-1H-pyrazole-4-carboxamide;

1-(4-cyano-2-methylphenyl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(1-methyl-1,2,3,4-tetrahydroquinolin-5-yl)-5-(trifluoromethyl)-1H-pyrazole-4-carboxamide;

N-(5-cyano-6-(2H-1,2,3-triazol-2-yl)pyridin-3-yl)-1-(1-methylindolin-4-yl)-5-(trifluoromethyl)-1H-pyrazole-4-carboxamide;

N-(5-cyano-6-(2H-1,2,3-triazol-2-yl)pyridin-3-yl)-1-(1,2,3,4-tetrahydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(indolin-4-yl)-5-(trifluoromethyl)-1H-pyrazole-4-carboxamide;

N-(5-cyano-6-(2H-1,2,3-triazol-2-yl)pyridin-3-yl)-1-(1-methyl-1,2,3,4-tetrahydroquinolin-8-yl)-5-(trifluoromethyl)-1H-pyrazole-4-carboxamide;

N-(5-cyano-6-(2H-1,2,3-triazol-2-yl)pyridin-3-yl)-1-(4-methyl-3,4-dihydro-2H-benzo[b][1,4]oxazin-8-yl)-5-(trifluoromethyl)-1H-pyrazole-4-carboxamide;

N-(5-chloro-6-(2H-1,2,3-triazol-2-yl)pyridin-3-yl)-1-(1-oxoisoindolin-4-yl)-5-(trifluoromethyl)-1H-pyrazole-4-carboxamide;

1-(6-aminopyridin-2-yl)-N-(5-cyano-6-(2H-1,2,3-triazol-2-yl)pyridin-3-yl)-5-(trifluoromethyl)-1H-pyrazole-4-carboxamide;

1-(2-cyano-4-fluorophenyl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2-cyano-4-fluorophenyl)-5-(trifluoromethyl)-1H-pyrazole-4-carboxamide;

N-(5-chloro-6-(2H-1,2,3-triazol-2-yl)pyridin-3-yl)-1-(2-(methylthio)phenyl)-5-(trifluoromethyl)-1H-pyrazole-4-carboxamide;

N-(5-chloro-6-(2H-1,2,3-triazol-2-yl)pyridin-3-yl)-1-(2-(methylsulfonyl)phenyl)-5-(trifluoromethyl)-1H-pyrazole-4-carboxamide;

1-(6-amino-5-cyanopyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-cyanopyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-3-methylpyridin-2-yl)-N-(5-cyano-6-(2H-1,2,3-triazol-2-yl)pyridin-3-yl)-5-(trifluoromethyl)-1H-pyrazole-4-carboxamide;

1-(2-amino-5-methylpyridin-4-yl)-N-(5-cyano-6-(2H-1,2,3-triazol-2-yl)pyridin-3-yl)-5-(trifluoromethyl)-1H-pyrazole-4-carboxamide;

1-(2-amino-3-methylpyridin-4-yl)-N-(5-cyano-6-(2H-1,2,3-triazol-2-yl)pyridin-3-yl)-5-(trifluoromethyl)-1H-pyrazole-4-carboxamide;

1-(6-amino-5-chloropyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-chloro-6-(2H-1,2,3-triazol-2-yl)pyridin-3-yl)-5-(trifluoromethyl)-1H-pyrazole-4-carboxamide;

N-(6-(2H-1,2,3-triazol-2-yl)-5-(trifluoromethyl)pyridin-3-yl)-1-(6-amino-5-fluoropyridin-2-yl)-5-(trifluoromethyl)-1H-pyrazole-4-carboxamide;

1-(2-amino-5-chloropyridin-4-yl)-N-(5-cyano-6-(2H-1,2,3-triazol-2-yl)pyridin-3-yl)-5-(trifluoromethyl)-1H-pyrazole-4-carboxamide;

1-(2-amino-5-chloropyridin-4-yl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(5-fluoro-6-(methylamino)pyridin-2-yl)-5-(trifluoromethyl)-1H-pyrazole-4-carboxamide;

N-(5-chloro-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide;

N-(5-cyano-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)-3-methylpyridine 1-oxide;

1-(2-chloro-5-methyl-4-pyridyl)-N-[5-chloro-6-(triazol-2-yl)-3-pyridyl]-5-(trifluoromethyl)pyrazole-4-carboxamide;

1-(2-chloro-3-methylpyridin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2-(3-hydroxyazetidin-1-yl)-5-methylpyridin-4-yl)-5-(trifluoromethyl)-1H-pyrazole-4-carboxamide;

N-(5-chloro-6-(2H-1,2,3-triazol-2-yl)pyridin-3-yl)-1-(2-(3-hydroxyazetidin-1-yl)-3-methylpyridin-4-yl)-5-(trifluoromethyl)-1H-pyrazole-4-carboxamide;

N-(5-chloro-6-(2H-1,2,3-triazol-2-yl)pyridin-3-yl)-1-(3-methylpyridin-4-yl)-5-(trifluoromethyl)-1H-pyrazole-4-carboxamide;

N-(5-chloro-6-(2H-1,2,3-triazol-2-yl)pyridin-3-yl)-1-(4-methylpyridazin-3-yl)-5-(trifluoromethyl)-1H-pyrazole-4-carboxamide;

N-(5-cyano-6-(2H-1,2,3-triazol-2-yl)pyridin-3-yl)-1-(5-fluoro-6-methylpyridin-2-yl)-5-(trifluoromethyl)-1H-pyrazole-4-carboxamide;

N-(5-chloro-6-(2H-1,2,3-triazol-2-yl)pyridin-3-yl)-1-(5-fluoro-6-methylpyridin-2-yl)-5-(trifluoromethyl)-1H-pyrazole-4-carboxamide;

N-(5-cyano-6-(2H-1,2,3-triazol-2-yl)pyridin-3-yl)-1-(3,6-dichloropyridin-2-yl)-5-(trifluoromethyl)-1H-pyrazole-4-carboxamide;

N-(5-chloro-6-(2H-1,2,3-triazol-2-yl)pyridin-3-yl)-1-(3,6-dichloropyridin-2-yl)-5-(trifluoromethyl)-1H-pyrazole-4-carboxamide;

1-(6-chloro-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide;

1-(6-chloro-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide;

1-(4-chloro-2-methylphenyl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(3-fluoro-2-methylphenyl)-5-(trifluoromethyl)-1H-pyrazole-4-carboxamide;

N-(5-cyano-6-(2H-1,2,3-triazol-2-yl)pyridin-3-yl)-1-(3,4-difluoro-2-methylphenyl)-5-(trifluoromethyl)-1H-pyrazole-4-carboxamide;

N-(5-cyano-6-(2H-1,2,3-triazol-2-yl)pyridin-3-yl)-1-(4-cyanophenyl)-5-(trifluoromethyl)-1H-pyrazole-4-carboxamide;

N-(5-cyano-2-methyl-6-(2H-1,2,3-triazol-2-yl)pyridin-3-yl)-1-(4-fluoro-2-methylphenyl)-5-(trifluoromethyl)-1H-pyrazole-4-carboxamide;

N-(5-chloro-6-(2H-1,2,3-triazol-2-yl)pyridin-3-yl)-1-(3-fluoro-2-methylphenyl)-5-(trifluoromethyl)-1H-pyrazole-4-carboxamide;

N-(5-chloro-2-methyl-6-(2H-1,2,3-triazol-2-yl)pyridin-3-yl)-1-(4-fluoro-2-methylphenyl)-5-(trifluoromethyl)-1H-pyrazole-4-carboxamide;

N-(5-cyano-6-(2H-1,2,3-triazol-2-yl)pyridin-3-yl)-5-(trifluoromethyl)-1-(2,4,6-trifluorophenyl)-1H-pyrazole-4-carboxamide;

N-(5-chloro-6-(2H-1,2,3-triazol-2-yl)pyridin-3-yl)-1-(3,4-difluoro-2-methylphenyl)-5-(trifluoromethyl)-1H-pyrazole-4-carboxamide;

1-(6-amino-3-chloropyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-4-methylpyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-cyanopyridin-2-yl)-N-(5-cyano-2-methyl-6-(2H-1,2,3-triazol-2-yl)pyridin-3-yl)-5-(trifluoromethyl)-1H-pyrazole-4-carboxamide;

1-(6-amino-5-cyanopyridin-2-yl)-N-(5-chloro-2-methyl-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-chloro-2-methyl-6-(2H-1,2,3-triazol-2-yl)pyridin-3-yl)-5-(trifluoromethyl)-1H-pyrazole-4-carboxamide;

1-(6-aminopyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-bromo-2-methyl-6-(2H-1,2,3-triazol-2-yl)pyridin-3-yl)-5-(trifluoromethyl)-1H-pyrazole-4-carboxamide;

1-(6-amino-5-fluoropyyridin-2-yl)-N-(5-cyano-2-methyl-6-(2H-1,2,3-triazol-2-yl)pyridin-3-yl)-5-(trifluoromethyl)-1H-pyrazole-4-carboxamide;

1-(6-amino-3-chloropyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-methylpyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-3-methylpyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide;

1-(6-amino-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-chloro-2-methyl-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(6-(methylamino)pyridin-2-yl)-5-(trifluoromethyl)-1H-pyrazole-4-carboxamide;

1-(6-amino-4-methylpyridin-3-yl)-N-(5-cyano-6-(2H-1,2,3-triazol-2-yl)pyridin-3-yl)-5-(trifluoromethyl)-1H-pyrazole-4-carboxamide;

1-(6-amino-4-methylpyridin-3-yl)-N-(5-chloro-6-(2H-1,2,3-triazol-2-yl)pyridin-3-yl)-5-(trifluoromethyl)-1H-pyrazole-4-carboxamide;

1-(6-amino-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-chloro-2-methyl-4-(2H-1,2,3-triazol-2-yl)phenyl)-5-(trifluoromethyl)-1H-pyrazole-4-carboxamide;

1-(6-aminopyridin-3-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-cyano-2-methyl-4-(2H-1,2,3-triazol-2-yl)phenyl)-5-(trifluoromethyl)-1H-pyrazole-4-carboxamide;

1-(6-amino-2-methylpyridin-3-yl)-N-(5-cyano-6-(2H-1,2,3-triazol-2-yl)pyridin-3-yl)-5-(trifluoromethyl)-1H-pyrazole-4-carboxamide;

1-(6-amino-5-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide;

2-amino-6-(4-((5-chloro-2-methyl-6-(2H-1,2,3-triazol-2-yl)pyridin-3-yl)carbamoyl)-5-(trifluoromethyl)-1H-pyrazol-1-yl)nicotinamide;

1-(2-amino-3-methylpyridin-4-yl)-N-(5-chloro-6-(2H-1,2,3-triazol-2-yl)pyridin-3-yl)-5-(trifluoromethyl)-1H-pyrazole-4-carboxamide;

1-(6-amino-5-chloropyridin-2-yl)-N-(5-cyano-2-methyl-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-cyano-2-methylpyridin-3-yl)-5-(trifluoromethyl)-1H-pyrazole-4-carboxamide;

1-(6-bromopyridin-2-yl)-N-(5-chloro-6-(2H-1,2,3-triazol-2-yl)pyridin-3-yl)-5-(trifluoromethyl)-1H-pyrazole-4-carboxamide;

(*R)—N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide;

(*S)—N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide;

(*S)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide;

(*R)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-(furan-2-yl)pyridin-2-yl)-5-(trifluoromethyl)-1H-pyrazole-4-carboxamide;

and

N-(5-chloro-6-(2H-1,2,3-triazol-2-yl)pyridin-3-yl)-1-(6-(5,6-dihydro-1,4-dioxin-2-yl)pyridin-2-yl)-5-(trifluoromethyl)-1H-pyrazole-4-carboxamide;

or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (+)-DL-lactic acid, lactobionic acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorph and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

A person of ordinary skill in the art would recognize that the compounds described herein may exist as tautomers and that other tautomeric arrangements of the structures depicted herein are possible. It is understood that all tautomeric forms are encompassed by a structure where one possible tautomeric arrangement of the groups of the compound is described, even if not specifically indicated.

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \text{ (+)-enantiomer} = \frac{(\text{mass(+)-enantiomer})}{(\text{mass(+)-enantiomer}) + (\text{mass(−)-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \text{ (−)-enantiomer} = \frac{(\text{mass(−)-enantiomer})}{(\text{mass(+)-enantiomer}) + (\text{mass(−)-enantiomer})} \times 100.$$

It is intended that within the scope of the present invention, any one or more element(s), in particular when mentioned in relation to a compound of Formula (I), shall comprise all isotopes and isotopic mixtures of said element(s), either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise one or more radioactive isotope(s) selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F.

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

An embodiment of the present invention is directed to a pharmaceutical composition for oral administration, comprising a compound of Formula (I) in an amount of from about 25 mg to about 500 mg.

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

In an embodiment, cancers that may benefit from a treatment with MALT1 inhibitors of the present invention include, but are not limited to, lymphomas, leukemias, carcinomas, and sarcomas, e.g. non-Hodgkin's lymphoma, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chonic lymphocytic leukemia (CLL), lymphoblastic T cell leukemia, chonic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head&neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, MALT1 inhibitors of the present invention may be used for the treatment of immunological diseases including, but not limited to, autoimmune and inflammatory disorders, e.g. arthritis, inflammatory bowel disease, gastritis, ankylosing spondylitis, ulcerative colitis, pancreatits, Crohn's disease, celiac disease, multiple sclerosis, systemic lupus erythematosus, lupus nephitis, rheumatic fever, gout, organ or transplact rejection, chonic allograft rejection, acute or chonic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chonic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment of the present invention, the compounds of the present invention may be employed in combination with one or more other medicinal agents, more particularly with other anti-cancer agents, e.g. chemotherapeutic, anti-proliferative or immunomodulating agents, or with adjuvants in cancer therapy, e.g. immunosuppressive or anti-inflammatory agents.

Possible combinations of the compounds of the present invention may include, but are not limited to, BTK (Bruton's tyrosine kinase) inhibitors such as ibrutinib, SYK inhibitors, PKC inhibitors, PI3K pathway inhibitors, BCL family inhibitors, JAK inhibitors, PIM kinase inhibitors, rituximab or other B cell antigen-binding antibodies, as well as immune cell redirection agents (e.g. blinatumomab or CAR T-cells) and immunomodulatory agents such as daratumumab, anti-PD 1 antibodies, and anti-PD-L1 antibodies.

It has been found that the compounds of the present invention inhibit MALT1 activity.
In some embodiments, the inhibition of MALT1 by a provided compound may be useful in treating or preventing, in particular treating, the non-limiting list of cancers described herein.

The invention relates to compounds of Formula (I) or an enantiomer, diastereomer, solvate or pharmaceutically acceptable salt form thereof, for use as a medicament. The invention relates to compounds of Formula (I) or an enantiomer, diastereomer, solvate or pharmaceutically acceptable salt form thereof, for use in the inhibition of MALT1 activity.

The invention relates to compounds of Formula (I) or an enantiomer, diastereomer, solvate or pharmaceutically acceptable salt form thereof, for use in the treatment of diseases mentioned herein.

The invention relates to compounds of Formula (I) or an enantiomer, diastereomer, solvate or pharmaceutically acceptable salt form thereof, for the treatment or prevention, in particular for the treatment, of said diseases.

The invention relates to compounds of Formula (I) or an enantiomer, diastereomer, solvate or pharmaceutically acceptable salt form thereof, for the treatment or prevention, in particular in the treatment, of MALT1 mediated diseases or conditions.

The invention relates to compounds of Formula (I) or an enantiomer, diastereomer, solvate or pharmaceutically acceptable salt form thereof, for the manufacture of a medicament.

The invention relates to compounds of Formula (I) or an enantiomer, diastereomer, solvate or pharmaceutically acceptable salt form thereof, for the manufacture of a medicament for the inhibition of MALT1.

The invention relates to compounds of Formula (I) or an enantiomer, diastereomer, solvate or pharmaceutically acceptable salt form thereof, for the manufacture of a medicament for the treatment or prevention, in particular for the treatment, of any one of the disease conditions mentioned herein.

The invention relates to compounds of Formula (I) or an enantiomer, diastereomer, solvate or pharmaceutically acceptable salt form thereof, for the manufacture of a medicament for the treatment of any one of the disease conditions mentioned herein.

The invention relates to compounds of Formula (I) or an enantiomer, diastereomer, solvate or pharmaceutically acceptable salt form thereof, can be administered to mammals, preferably humans, for the treatment or prevention of any one of the diseases mentioned herein.

In view of the utility of the compounds of Formula (I) or an enantiomer, diastereomer, solvate or pharmaceutically acceptable salt form thereof, there is provided a method of treating warm-blooded animals, including humans, suffering from or a method of preventing warm-blooded animals, including humans, to suffer from any one of the diseases mentioned herein.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. Compounds analogous to the target compounds of these examples can be made according to similar routes. The disclosed compounds are useful as pharmaceutical agents as described herein. The various starting materials used in the schemes and examples are commercially available or may be prepared by methods well within the skill of persons versed in the art.

Abbreviations used in the instant specification, particularly the schemes and examples, are as follows:
ACN acetonitrile
AcOH acetic acid
BINAP 2,2'-bis(diphenylphosphino)-1,1'-binaphthalene
Boc tert-butyl carbamate
BuLi butyllithium
Cbz benzyl carbamate
DCM dichloromethane
DMA dimethylacetamide
DME ethylene glycol dimethyl ether
DMF dimethylformamide
DMSO dimethyl sulfoxide
EA ethyl acetate
Et ethyl
Et$_2$O diethyl ether
EtOAc ethyl acetate
EtOH ethyl alcohol
FCC flash column chromatography
h hour(s)
HATU O-(7-azabenzotriazol-1-yl)-N,N,N',N'-tetramethyluronium hexafluorophosphate
HCHO formaldehyde
HCl hydrochloric acid
HPLC high performance liquid chromatography
KCN potassium cyanide
LCMS high pressure liquid chromatography with mass spectrometer
LDA lithium diisopropylamide
LiOH lithium hydroxyde
Me methyl MeCN acetonitrile
MeOH methyl alcohol
mg milligram
min minute
NaCN sodium cyanide
NaOH sodium hydroxide
NaOtBu sodium tert-butoxide
NH₄Cl ammonium chloride
Pd/C palladium on charcoal
Pd₂(dba)₃ tris(dibenzylideneacetone)dipalladium
Pd(dppf)Cl₂ [1,1'-bis(diphenylphosphino)ferrocene]dichloropalladium
Pd(OAc)₂ palladium diacetate
Pd(PPh₃)₄ tetrakis(triphenylphosphine)palladium
PPh₃ triphenyl phosphine
p-TsOH para-toluenesulfonic acid
rt or RT room temperature
TBAF tetrabutyl ammonium fluoride
TMSI iodotrimethylsilane
t-Bu tert-butyl
TFA trifluoroacetic acid
TFAA trifluoroacetic anhydride
THF tetrahydrofuran
TLC thin layer chromatography
Xantphos 4,5-Bis(diphenylphosphino)-9,9-dimethylxanthene
Xphos 2-dicyclohexylphosphino-2',4',6'-triisopropylbiphenyl Compounds of Formula (I) may be prepared according to the process outlined in Scheme 1.

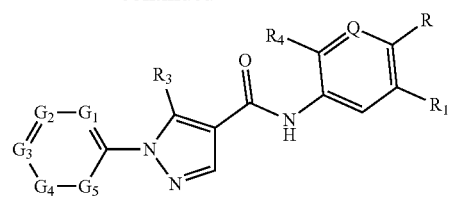

Formula I

A carboxylic acid of formula (1A) may be treated with carbonyldiimidazole followed by addition of a mono-ester of malonic acid of formula (1B), wherein R' is $C_{1-4}$alkyl, and a base, such as isopropylmagnesium chloride, to yield a ketoester of formula (1C). Condensation with triethyl orthoformate in acetic anhydride or with 1,1-dimethoxy-N,N-dimethylmethanamine may yield a 2-ethoxymethylidene-3-oxo ester (or 2-((dimethylamino)methylidene-3-oxo ester) of formula (1D). A compound of formula (1D) may be reacted with a hydrazine of formula (1E) to provide a pyrazole of formula (1F). Hydrolysis of the ester group may be effected via by treatment with aqueous sodium hydroxide in the presence of an alcohol co-solvent, to provide the corresponding carboxylic acid intermediate, which, subsequently, may be converted to a compound of Formula (I) upon amide coupling with a compound of formula (1G). The amide coupling may be carried out, for example, in the presence of phosphorus oxychloride in pyridine to afford the corresponding acid chloride, followed by treatment with a compound of formula (1G), in the presence of a base. In one embodiment, the amide coupling reaction is carried out in the presence of a suitable amide coupling reagent such as HATU, in the presence of a base such as, but not limited to, diisopropylethyl amine.

Alternatively, the pyrazole ester of formula (1F) may be directly converted to a compound of Formula (I) via treatment with a compound of formula (1G) and a base, such as potassium tert-butoxide.

An alternate route to compounds of Formula (I) is illustrated in Scheme 2.

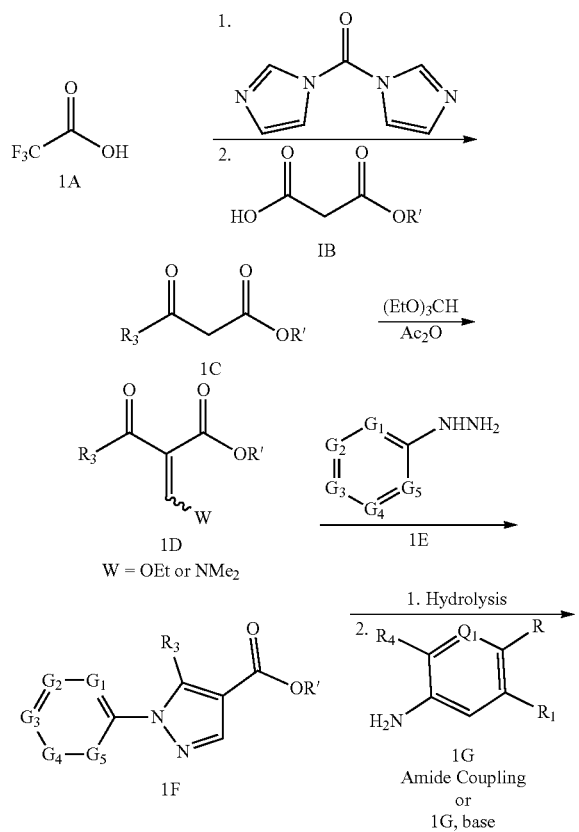

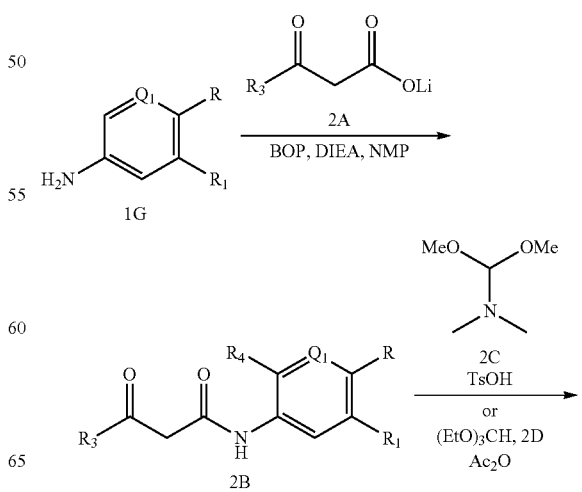

-continued

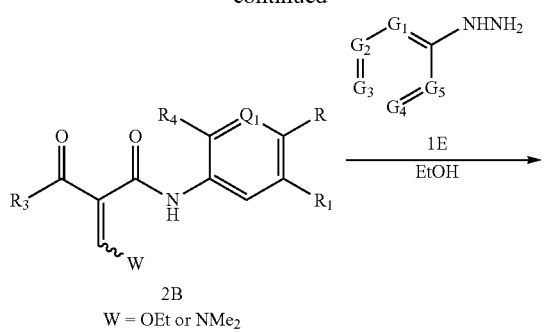

2B
W = OEt or NMe₂

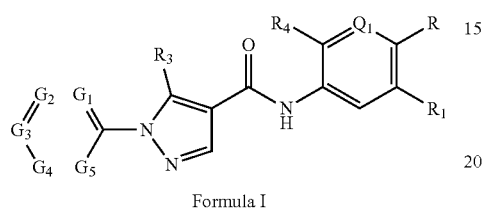

Formula I

Aniline (1G) may be coupled with a lithium acetoacetate of formula (2A) in the presence of coupling reagent such as BOP, a base such as DIPEA, and a solvent such as NMP, to provide a compound of formula (2B). A compound of formula (2B) may then be reacted with DMF-DMA (2C) in the presence of an acid, such as TsOH, or reacted with triethoxymethane (2D) in AcOH to afford a compound of formula (2E). A compound of formula (2E) may then be treated with a hydrazine of formula (1E) to afford a compound of Formula (I).

Scheme 3 illustrates the preparation of certain hydrazine intermediates of formula (1E), useful for the preparation of compounds of Formula (I) of the present invention.

Scheme 3

PATH 1

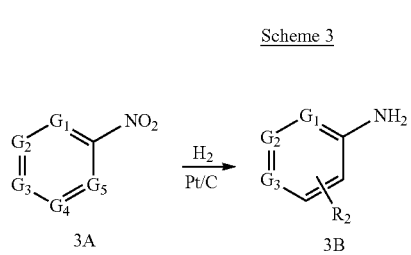

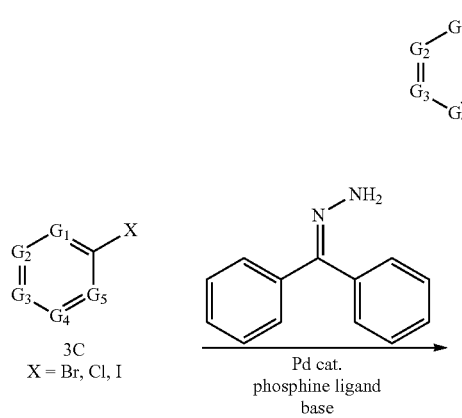

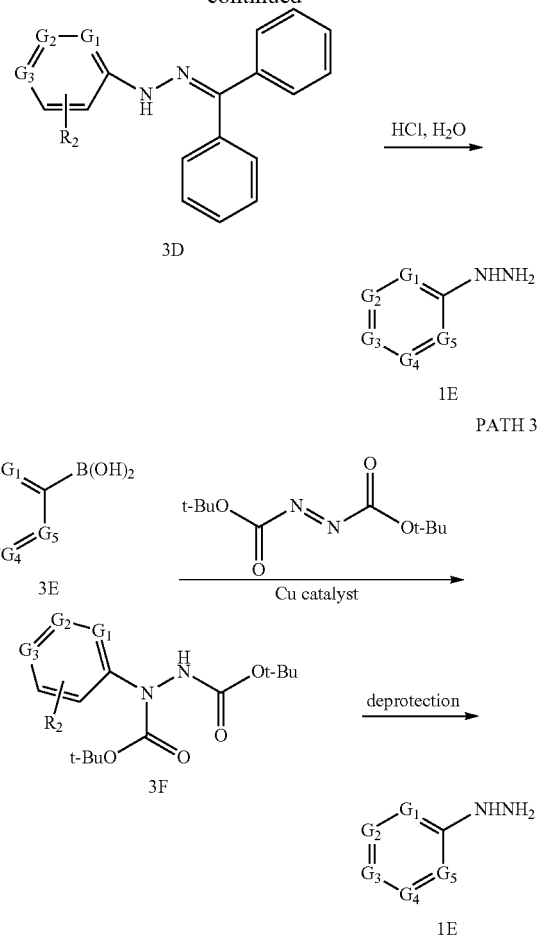

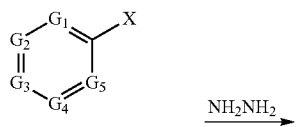
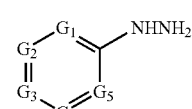

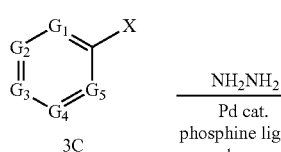

An aryl or heteroaryl amine of formula (3B) may be converted to an aryl or heteroaryl diazonium salt via treatment with sodium nitrite under acidic conditions. This intermediate may be reduced, using a reductant such as tin (II) chloride or ascorbic acid, to form the hydrazine of formula (1E). For aryl or heteroaryl amines of formula (3B) that are not commercially available, they may be accessed by reduction of the nitroarene or heteronitroarene (3A) using hydrogen and Pt/C or other conventional nitro-reducing conditions (path one).

Chlorides, bromides, or iodides substituted aryls or heteroaryls may undergo a palladium catalyzed Buchwald Hartwig coupling with benzophenone hydrazine, in the presence of a ligand, such as Xantphos, and a base, such as sodium tert-butoxide, to form a hydrazine of formula (3D). Acidic hydrolysis may afford the hydrazine of formula (1E) (path two).

Aryl or heteroaryl substituted boronic acids may also serve as a precursor to compounds of formula (1E) by the route shown in path three. A boronic acid of formula (3E) may undergo a $Cu^{2+}$-catalyzed addition to di-tert-butylazodicarboxylate to afford an intermediate of formula (3F), which may be deprotected under acidic conditions to yield the compound of formula (1E). Heteroaryl hydrazines of formula (1E), having a nitrogen atom in the ortho- or para-position with respect to the hydrazine functionality, may be prepared via direct displacement of a halogen with hydrazine or hydrazine hydrate (path four). Alternatively, halogenated (hetero)arenes of formula (311) may undergo palladium-catalyzed cross-coupling with hydrazine to directly furnish intermediate (1E) (path five).

Scheme 4 illustrates multiple pathways available for the synthesis of intermediate (1G, $Q_2$=CR),

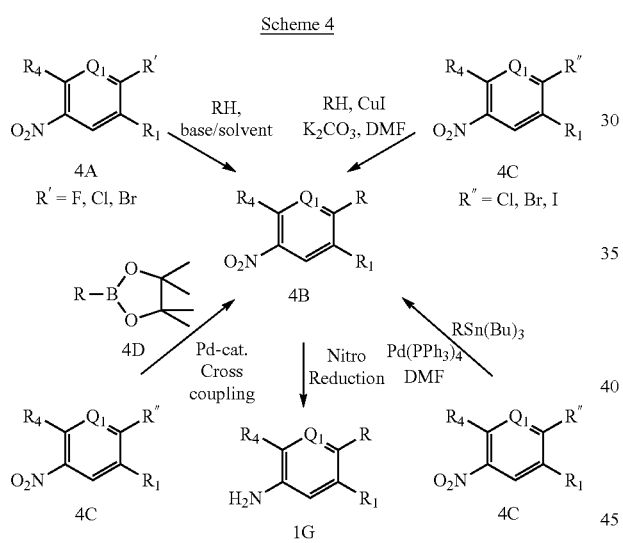

Scheme 4

Compound (4A) may be reacted with a compound of formula RH in the presence of a base, such as $Cs_2CO_3$, in a solvent, such as DMF, to yield a compound of formula (4B). Alternatively, a compound of formula (4C) may be treated with a crossing coupling reagent, such as a boron reagent of formula (4D) or a tin reagent of formula $RSn(Bu)_3$; in the presence of a palladium catalyst, including but not limited to, $Pd(dppf)Cl_2$ or $Pd(PPh_3)_4$; in a suitable solvent or solvent system such as DMF, dioxane/water, or the like; to produce a compound of formula (4B). Another suitable pathway includes the reaction of a compound of formula (4C) with a compound of formula RH, in the presence of a coupling reagent such as CuI, with a base such as $Cs_2CO_3$, and in a solvent such as DMF, to afford a compound of formula (4B). A compound of formula (4B) may be reduced to a compound of formula (1G) using a reducing agent such as Zn or Fe in the presence of $NH_4Cl$, in a solvent such as MeOH. Alternatively, intermediate 1G can be prepared via Curtius rearrangement of suitable aryl acids (Scheme 5) which can be prepared like Scheme 4 (replace $NO_2$ with acid or ester)

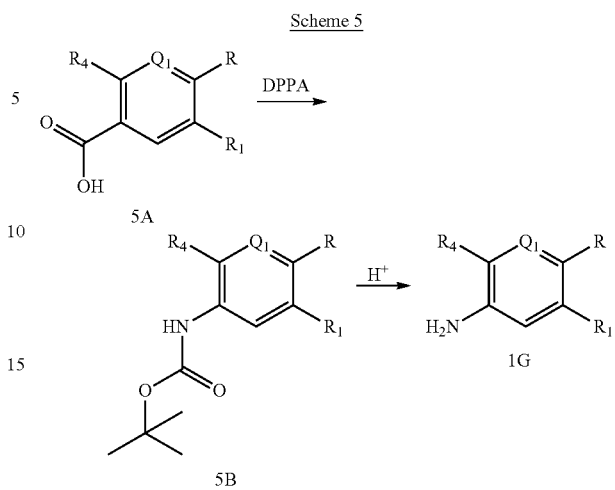

Scheme 5

Acid 5A treated with diphenyl phosphoryl azide in the present a base in t-butanol produces the t-butoxy-carbonyl protected amino compound 5B, deprotected 5B under acidic condition such as HCl or TFA to give intermediate 1G.

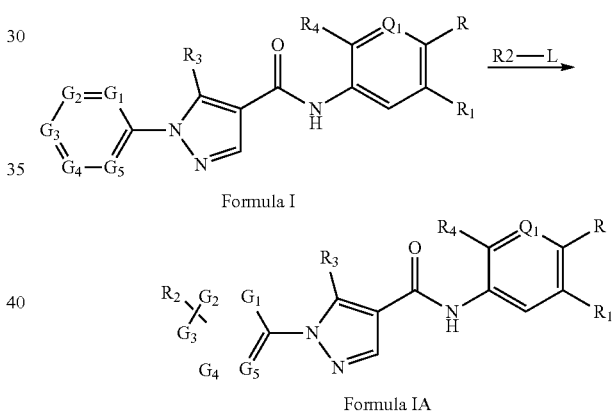

Scheme 6

In the instance when L is H, alkylation of compounds of formula Formula I may occur via formation of a radical from $R_2$-L, generated by treatment with ammonium persulfate and $(IR[DF(CF_3)PPY]_2(DTBPY))PF_6$, in a mixture of water and $CH_3CN$ or DMSO and TFA, under irradiation with blue LED. Compounds of Formula I may also be converted to their corresponding N-oxides via treatment with an oxidizing agent such as m-CPBA in DCM or THF. Said N-oxides of compounds of Formula I may also be converted to their corresponding ortho-chloro derivatives by the action of $POCl_3$, optionally in a solvent such as $CHCl_3$. Such ortho-chloro derivatives may be reacted with appropriately substituted amines to afford $C_{1-6}$alkylamino, $C_{1-6}$cycloalkylamino, or N-linked heterocyclic rings of the present invention.

SPECIFIC EXAMPLES

In the following Examples, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Intermediate 1

Ethyl 2-(ethoxymethylene)-4,4,4-trifluoro-3-oxobutanoate, INT 1

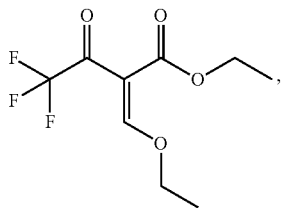

INT1

Ethyl 4,4,4-trifluoro-3-oxobutanoate (30 g, 162.9 mmol) was added to a solution of triethoxymethane (72.4 g, 488.8 mmol) in acetic anhydride (50 mL). The mixture was stirred at 135° C. for 18 h. The brown mixture was concentrated to afford ethyl 2-(ethoxymethylene)-4,4,4-trifluoro-3-oxobutanoate, INT1 (38 g, 97.1%) as a brown oil, which was used without further purification. $^1$H NMR (400 MHz, CDCl$_3$) δ ppm 1.23-1.33 (m, 3H) 1.40 (dt, J=14.18, 7.19 Hz, 3H) 4.19-4.36 (m, 4H) 7.66-7.87 (m, 1H).

Intermediate 2

A. 3-Chloro-5-nitro-2-(2H-1,2,3-triazol-2-yl)pyridine, INT2A

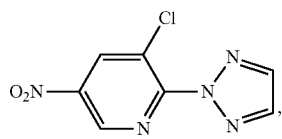

INT2A

A mixture of 2,3-dichloro-5-nitropyridine (50 g, 259.08 mmol), 1H-1,2,3-triazole (19.683 g, 284.99 mmol), potassium carbonate (46.549 g, 336.81 mmol) and CH$_3$CN (200 mL) was heated to 40° C. and stirred overnight. Ethyl acetate (500 mL) was added. The mixture was washed with water (500 mL×2) and brine (500 mL), dried over anhydrous Na$_2$SO$_4$, filtered, and concentrated to dryness under reduced pressure. The residue was triturated with DCM (100 mL), filtered, and the solid was collected to afford compound INT2A (40 g, 68%) as an off-white solid. LC-MS: (ES, m/z): [M+1]$^+$ 225.9. $^1$H NMR (400 MHz, DMSO-d$_6$) δ ppm 9.40 (d, J=2.0 Hz, 1H), 9.15 (d, J=2.0 Hz, 1H), 8.33 (s, 2H).

B. 5-Chloro-6-(2H-1,2,3-triazol-2-yl)pyridin-3-amine, INT2

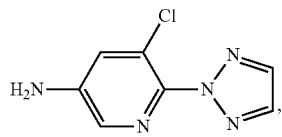

INT2

3-Chloro-5-nitro-2-(2H-1,2,3-triazol-2-yl)pyridine, INT2A (20 g, 88.656 mmol), MeOH (500 mL) and Pt/C (2 g, 5%, 0.513 mmol) were added to a 1000 mL hydrogenation bottle. The resultant mixture was stirred under a H$_2$ atmosphere (30 psi) at 25° C. for 20 h. The suspension was filtered though a pad of diatomaceous earth and the filter cake was washed with ethyl acetate (100 mL). The filtrate was concentrated to dryness under reduced pressure to afford a crude product, which was purified by preparative reverse phase HPLC (0% to 50% (v/v) CH$_3$CN and water with 0.05% NH$_3$), followed by lyophilization to dryness to afford compound INT2 (10.4 g, 60%) as an off-white solid. LC-MS: (ES, m/z): [M+1]$^+$ 196.1; $^1$H NMR (400 MHz, DMSO-d$_6$) δ ppm 8.05 (s, 2H), 7.83 (d, J=2.0 Hz, 1H), 7.21 (d, J=2.4 Hz, 1H), 6.19 (s, 2H).

Intermediate 3

A. 5-nitro-2-[1,2,3]triazol-2-yl-nicotinonitrile, INT3A

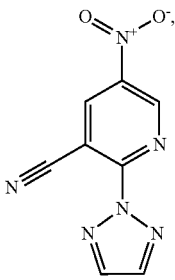

INT3A

A mixture of 2-chloro-5-nitropyridine-3-carbonitrile (9.0 g, 49 mmol), 2H-[1,2,3]Triazole (3.41 mL, 58.8 mmol) and potassium carbonate (20.32 g, 147 mmol) in acetonitrile (225 mL) was stirred at 30° C. for 2 h. Water and ethyl acetate were added and the organic phase was separated, dried with MgSO$_4$, filtered and the filtrate concentrated to afford the crude product, which was mixed with dichloromethane (30 mL) and filtered to afford pure 5-nitro-2-[1,2,3]triazol-2-yl-nicotinonitrile (8.3 g, 78.4% yield) as an orange solid. $^1$H NMR (300 MHz, DMSO-d$_6$) δ 8.46 (s, 2H), 9.45 (d, J=2.5 Hz, 1H), 9.61 (d, J=2.5 Hz, 1H). LC-MS m/z 217.0 (M+H)$^+$.

B. 5-Amino-2-[1,2,3]triazol-2-yl-nicotinonitrile, INT3

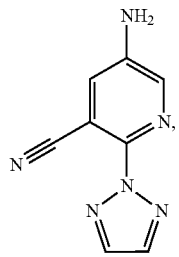

To a solution of 5-nitro-2-[1,2,3]triazol-2-yl-nicotinonitrile, INT3a (2.0 g, 9.25 mmol) in Ethyl acetate (30 mL), tin (II) chloride dihydrate (19.2 g, 92.5 mmol, 10 eq) was added in three portions in 3 h, and the mixture was stirred at room temperature for 24 h. The mixture was poured onto water/NaHCO$_3$ and diluted with ethyl acetate. The organic layer was separated and washed with brine, then dried over MgSO$_4$ and the filtrate concentrated to afford a mixture of product and starting material, which was taken in ethanol (300 mL). Tin (II) chloride dihydrate (9.6 g, 46.25 mmol, 5 eq) was added. This mixture was heated to 50° C. and stirred for 48 h to completion of the reaction. The mixture was poured onto water/NaHCO$_3$ and diluted with ethyl acetate. The organic layer was separated and washed with brine, then dried over MgSO$_4$ and the filtrate concentrated. Flash column chromatography (SiO$_2$, Methanol-dichloromethane gradient 0% to 10%) was used for purification. Pure fractions were combined and concentrated to afford pure 5-amino-2-[1,2,3]triazol-2-yl-nicotinonitrile, INT3 (899 mg, 52% yield) as an orange solid. $^1$H NMR (400 MHz, DMSO-d$_6$) δ ppm 6.26 (s, 2H), 7.45 (d, J=2.87 Hz, 1H), 8.09 (d, J=2.65 Hz, 1H), 8.13 (s, 2H). LC-MS m/z 187.1 (M+H)+.

Example 1

N-(5-Chloro-6-(2H-1,2,3-triazol-2-yl)pyridin-3-yl)-1-(4-fluoro-2-methylphenyl)-5-(trifluoromethyl)-1H-pyrazole-4-carboxamide, Cpd 1

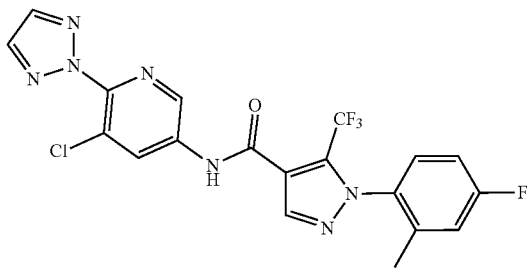 [SMILES: Cc1cc(F)ccc1-n1ncc(C(=O)Nc2cnc(-n3nccn3)c(Cl)c2)c1C(F)(F)F]

A. Ethyl 1-(4-fluoro-2-methylphenyl)-5-(triflurom-ethyl)-1H-pyrazole-4-carboxylate, Cpd 1a

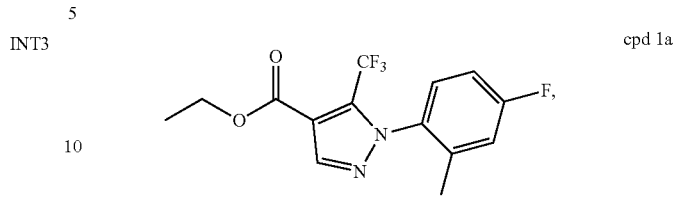

A solution consisting of ethyl 2-(ethoxymethylene)-4,4,4-trifluoro-3-oxobutanoate, INT1 (1.55 g, 6.46 mmol), (4-fluoro-2-methylphenyl)hydrazine (950 mg, 5.38 mmol), triethylamine (0.749 mL, 5.38 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=10:1) to afford the title compound (1.2 g, 71%) as a brown oil. LCMS (ESI) m/z M+1: 316.9. $^1$H NMR (400 MHz, CDCl$_3$) δ 8.16 (s, 1H), 7.27-7.21 (m, 1H), 7.08-6.98 (m, 2H), 4.39 (d, J=7.2 Hz, 2H), 2.04 (s, 3H), 1.40 (t, J=7.2 Hz, 3H).

B. N-(5-Chloro-6-(2H-1,2,3-triazol-2-yl)pyridin-3-yl)-1-(4-fluoro-2-methylphenyl)-5-(trifluoromethyl)-1H-pyrazole-4-carboxamide, Cpd 1

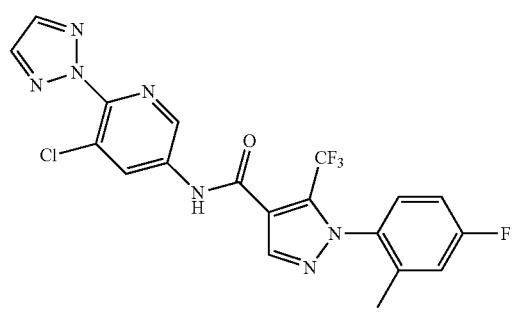 [SMILES: Cc1cc(F)ccc1-n1ncc(C(=O)Nc2cnc(-n3nccn3)c(Cl)c2)c1C(F)(F)F]

A solution consisting of 5-chloro-6-(2H-1,2,3-triazol-2-yl)pyridin-3-amine, INT2 (148 mg, 0.759 mmol) and THF (1 mL), and a solution consisting of ethyl 1-(4-fluoro-2-methylphenyl)-5-(trifluoromethyl)-1H-pyrazole-4-carboxylate, cpd 1a (200 mg, 0.632 mmol) and THF (1 mL) were added to a solution consisting of potassium tert-butoxide (3.16 mL, 3.16 mmol, 1 M in THF) at 0° C. The resultant mixture was stirred at room temperature for 16 h. Water was added to the resultant mixture and the mixture was extracted with ethyl acetate (15 mL×3). The combined organic extracts were dried over anhydrous Na$_2$SO$_4$, filtered, and concentrated to dryness under reduced pressure to afford the crude product, which was purified by preparative HPLC (42% to 72% (v/v) CH$_3$CN and H$_2$O with 0.05% NH$_3$) and lyophilized to dryness to afford the title compound (143.60 mg, 49%). LCMS (ESI) m/z M+1: 465.9. $^1$H NMR (400 MHz, CDCl$_3$) δ 8.74 (d, J=2.4 Hz, 1H), 8.49 (d, J=2.4 Hz, 1H), 8.37 (br.s., 1H), 8.11 (s, 1H), 7.94 (s, 2H), 7.28-7.25 (m, 1H), 7.11-7.00 (m, 2H), 2.05 (s, 3H).

Example 2

1-(4-Chloro-2-methylphenyl)-N-(5-chloro-6-(2H-1,2,3-triazol-2-yl)pyridin-3-yl)-5-(trifluoromethyl)-1H-pyrazole-4-carboxamide, Cpd 2

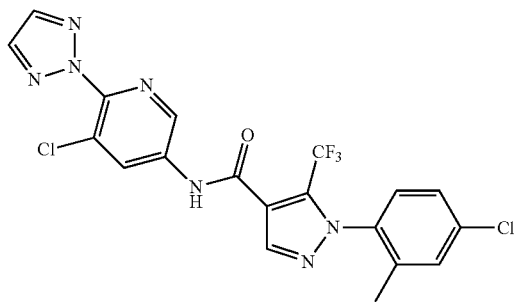 [SMILES: Cc1cc(Cl)ccc1-n1ncc(C(=O)Nc2cnc(-n3nccn3)c(Cl)c2)c1C(F)(F)F]

A. Ethyl 1-(4-chloro-2-methylphenyl)-5-(trifluoromethyl)-1H-pyrazole-4-carboxylate, Cpd 2a

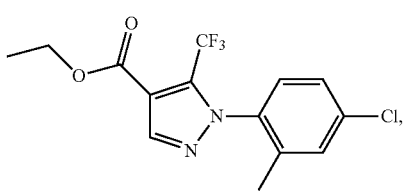

cpd 2a

A solution consisting of ethyl 2-(ethoxymethylene)-4,4,4-trifluoro-3-oxobutanoate, INT1 (0.836 g, 3.48 mmol), (4-chloro-2-methylphenyl)hydrazine (560 mg, 2.90 mmol), triethylamine (0.404 mL, 2.90 mmol), and ethanol (20 mL) was stirred at 80° C. for 16 h before cooling to room temperature. The resultant solution was concentrated to dryness under reduced pressure to afford the crude product, which was added into water (10 mL). The resultant mixture was extracted with ethyl acetate (20 mL×3). The combined organic extracts were dried over anhydrous $Na_2SO_4$, filtered, and concentrated to dryness under reduced pressure to afford the crude product, which was purified by flash column chromatography (petroleum ether:ethyl acetate=10:1) to afford the title compound (580 mg, 60%) as a yellow solid. LCMS (ESI) m/z M+1: 332.9. $^1$H NMR (400 MHz, CDCl$_3$) δ 8.16 (s, 1H), 7.35 (s, 1H), 7.33-7.28 (m, 1H), 7.19 (d, J=8.4 Hz, 1H), 4.39 (q, J=7.2 Hz, 2H), 2.04 (s, 3H), 1.40 (t, J=7.2 Hz, 3H).

B. 1-(4-Chloro-2-methylphenyl)-N-(5-chloro-6-(2H-1,2,3-triazol-2-yl)pyridin-3-yl)-5-(trifluoromethyl)-1H-pyrazole-4-carboxamide, Cpd 2

A solution consisting of 5-chloro-6-(2H-1,2,3-triazol-2-yl)pyridin-3-amine, INT2 (176 mg, 0.902 mmol) and THF (1 mL), and a solution consisting of ethyl 1-(4-chloro-2-methylphenyl)-5-(trifluoromethyl)-1H-pyrazole-4-carboxylate, cpd 2a (200 mg, 0.601 mmol) and THF (1 mL) were added to a solution consisting of potassium tert-butoxide (3.01 mL, 3.01 mmol, 1 M in THF) at 0° C. The resultant mixture was stirred at room temperature for 16 h. The resultant mixture was added water (5 mL) and extracting with ethyl acetate (15 mL×3). The combined organic extracts were dried over anhydrous $Na_2SO_4$, filtered, and the filtrate concentrated to dryness under reduced pressure to give the crude product, which was purified by preparative HPLC (45% to 75% (v/v) $CH_3CN$ and $H_2O$ with 0.05% $NH_3$) and lyophilized to afford the title compound (172.30 mg, 59%) as a brown solid. LCMS (ESI) m/z M+1: 481.8. $^1$H NMR (400 MHz, CDCl$_3$) δ 8.75 (d, J=2.4 Hz, 1H), 8.50 (d, J=2.8 Hz, 1H), 8.33 (br.s., 1H), 8.12 (s, 1H), 7.94 (s, 2H), 7.38 (d, J=2.0 Hz, 1H), 7.35-7.30 (m, 1H), 7.22 (d, J=8.4 Hz, 1H), 2.05 (s, 3H).

Example 3

N-(5-Chloro-6-(2H-1,2,3-triazol-2-yl)pyridin-3-yl)-1-(3-methylpyridin-2-yl)-5-(trifluoromethyl)-1H-pyrazole-4-carboxamide

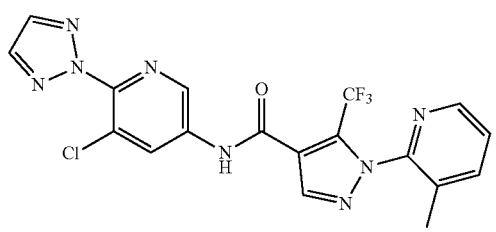 [SMILES: Cc1cccnc1-n1ncc(C(=O)Nc2cnc(-n3nccn3)c(Cl)c2)c1C(F)(F)F]

A. Ethyl 1-(3-methylpyridin-2-yl)-5-(trifluoromethyl)-1H-pyrazole-4-carboxylate, Cpd 3a

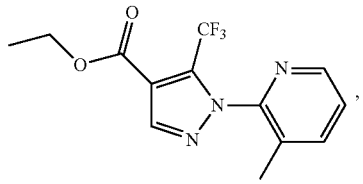

cpd 3a

A solution consisting of ethyl 2-(ethoxymethylene)-4,4,4-trifluoro-3-oxobutanoate, INT1 (2.3 g, 9.7 mmol), 2-hydrazinyl-3-methylpyridine (1.0 g, 8.1 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=4:1) to afford the title compound (1.1 g, 45%) as a brown oil. LCMS (ESI) m/z M+1: 300.0. $^1$H NMR (400 MHz, CDCl$_3$) δ 8.44 (dd, J=1.6, 4.8 Hz, 1H), 8.19 (s, 1H), 7.78-7.73 (m, 1H), 7.42 (dd, J=4.8, 8.0 Hz, 1H), 4.39 (q, J=7.2 Hz, 2H), 2.17 (s, 3H), 1.40 (t, J=7.2 Hz, 3H).

B. 1-(3-Methylpyridin-2-yl)-5-(trifluoromethyl)-1H-pyrazole-4-carboxylic Acid, Cpd 3b

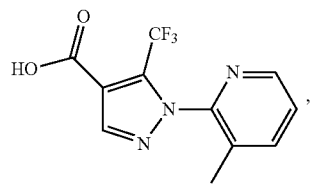

cpd 3b

A solution consisting of lithium hydroxide hydrate (126 mg, 3.01 mmol) and water (5 mL) was added to a solution consisting of ethyl 1-(3-methylpyridin-2-yl)-5-(trifluoromethyl)-1H-pyrazole-4-carboxylate, cpd 3a (300 mg, 1.00 mmol) and ethanol (10 mL). The resultant solution was stirred at room temperature for 16 h. The resultant solution was concentrated to dryness under reduced pressure to afford the crude product, which was poured into water (3 mL) and acidified with 3 N HCl to pH 5. The resultant mixture was filtered and the filter cake was washed with 3 mL of water, and dried under reduced pressure to afford the title compound (160 mg, 59%) as a white solid. LCMS (ESI) m/z M+1: 272.1. $^1$H NMR (400 MHz, DMSO-d$_6$) δ 13.43 (br.s., 1H), 8.45 (dd, J=1.2, 4.8 Hz, 1H), 8.31 (s, 1H), 8.01 (d, J=8.0 Hz, 1H), 7.61 (dd, J=4.8, 8.0 Hz, 1H), 2.11 (s, 3H).

C. N-(5-Chloro-6-(2H-1,2,3-triazol-2-yl)pyridin-3-yl)-1-(3-methylpyridin-2-yl)-5-(trifluoromethyl)-1H-pyrazole-4-carboxamide, Cpd 3

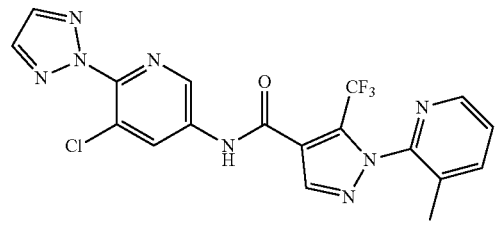 [SMILES: Cc1cccnc1-n1ncc(C(=O)Nc2cnc(-n3nccn3)c(Cl)c2)c1C(F)(F)F]

POCl$_3$ (95.0 mg, 0.619 mmol) was added drop-wise to a solution consisting of 1-(3-methylpyridin-2-yl)-5-(trifluoromethyl)-1H-pyrazole-4-carboxylic acid, cpd 3b (140 mg, 0.516 mmol), 5-chloro-6-(2H-1,2,3-triazol-2-yl)pyridin-3-amine, INT2 (121 mg, 0.619 mmol), and pyridine (5 mL) at 0° C. The resultant mixture was stirred at 0° C. for 1 h. Saturated NaHCO$_3$(10 mL) was added to the resultant mixture and the mixture was extracted with ethyl acetate (15 mL×3). The organic extracts were dried over anhydrous Na$_2$SO$_4$, filtered, and the filtrate concentrated to dryness under reduced pressure to give the crude product, which was purified by flash column chromatography (petroleum ether: ethyl acetate=3:1) to afford still impure product (200 mg). The product was further purified by preparative HPLC (30% to 60% (v/v) CH$_3$CN and H$_2$O with 0.05% NH$_3$) and lyophilized to afford the title compound (120.3 mg, 52%). LCMS (ESI) m/z M+1: 448.9. $^1$H NMR (400 MHz, DMSO-d$_6$) δ 11.20 (br.s., 1H), 8.84 (d, J=2.4 Hz, 1H), 8.66 (d, J=2.4 Hz, 1H), 8.51-8.47 (m, 2H), 8.18 (s, 2H), 8.04 (d, J=7.6 Hz, 1H), 7.63 (dd, J=4.8, 7.6 Hz, 1H), 2.16 (s, 3H).

Example 4

N-(5-Chloro-6-(2H-1,2,3-triazol-2-yl)pyridin-3-yl)-1-(pyridin-4-yl)-5-(trifluoromethyl)-1H-pyrazole-4-carboxamide, Cpd 4

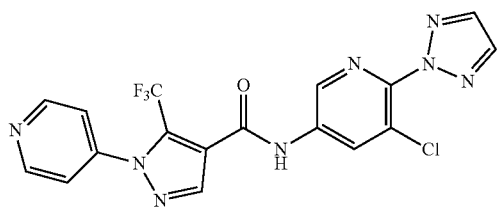 [SMILES: O=C(Nc1cnc(-n2nccn2)c(Cl)c1)c1cnn(-c2ccncc2)c1C(F)(F)F]

A. Ethyl 1-(pyridin-4-yl)-5-(trifluoromethyl)-1H-pyrazole-4-carboxylate, Cpd 4a

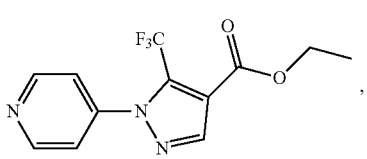

cpd 4a

A mixture consisting of 4-hydrazinylpyridine hydrochloride (1.00 g, 6.87 mmol), triethylamine (0.690 g, 6.87 mmol), ethyl 2-(ethoxymethylene)-4,4,4-trifluoro-3-oxobutanoate, INT1 (1.65 g, 6.87 mmol), and ethanol (12 mL) was stirred at 80° C. for 1 h. Then the mixture was cooled to room temperature and concentrated to dryness under reduced pressure to give a residue, which was purified by flash column chromatography (petroleum ether:ethyl acetate=8:1) to afford the title compound (215 mg, 11%). LCMS (ESI) m/z M+1: 285.8.

B. 1-(Pyridin-4-yl)-5-(trifluoromethyl)-1H-pyrazole-4-carboxylic Acid, Cpd 4b

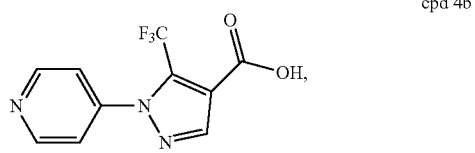

cpd 4b

A mixture consisting of ethyl 1-(pyridin-4-yl)-5-(trifluoromethyl)-1H-pyrazole-4-carboxylate, cpd 4a (210 mg, 0.740 mmol), sodium hydroxide (2.21 mL, 2.21 mmol, 1 M), and ethanol (2 mL) was stirred at room temperature for 2 h. The mixture was neutralized with 1M HCl to pH 6 and extracted with ethyl acetate (40 mL×3). The combined organic extracts were dried over anhydrous Na$_2$SO$_4$ and the filtrate concentrated to dryness under reduced pressure to give title compound (180 mg, crude), which was used in the next step without further purification. LCMS (ESI) m/z M+1: 257.7.

C. N-(5-Chloro-6-(2H-1,2,3-triazol-2-yl)pyridin-3-yl)-1-(pyridin-4-yl)-5-(trifluoromethyl)-1H-pyrazole-4-carboxamide, Cpd 4

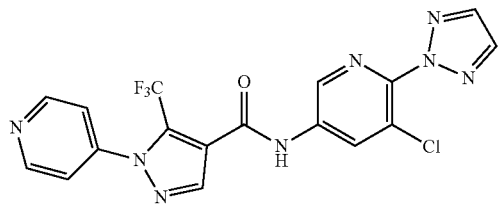 [SMILES: O=C(Nc1cnc(-n2nccn2)c(Cl)c1)c1cnn(-c2ccncc2)c1C(F)(F)F]

POCl$_3$ (0.1 mL) was added dropwise to a mixture consisting of 1-(pyridin-4-yl)-5-(trifluoromethyl)-1H-pyrazole-4-carboxylic acid, cpd 4b (140 mg, 0.540 mmol), 5-chloro-6-(2H-1,2,3-triazol-2-yl)pyridin-3-amine, INT2 (106 mg, 0.540 mmol), and pyridine (4 mL) at 0° C. The mixture was stirred at 0° C. for 1 h before quenching with sat. NaHCO$_3$ and extracting with ethyl acetate (50 mL×3). The combined organic extracts were dried over anhydrous Na$_2$SO$_4$ and concentrated to dryness under reduced pressure to give a residue, which was purified by prep-TLC (petroleum ether:ethyl acetate=1:1) to afford still impure product (80 mg). The post-chromatographic product (80 mg) was purified by preparative HPLC (28% to 58% (v/v) CH$_3$CN and H$_2$O with 0.05% NH$_3$) and lyophilized to afford the title compound (50 mg, 21%). LCMS (ESI) m/z M+1: 434.9. $^1$H NMR (400 MHz, CDCl$_3$) δ 8.85 (d, J=6.4 Hz, 2H), 8.74 (d, J=2.4 Hz, 1H), 8.50 (d, J=1.6 Hz, 1H), 8.13 (s, 1H), 8.11 (s, 1H), 7.95 (s, 2H), 7.48 (d, J=6.0 Hz, 2H).

Example 5

N-(5-Chloro-6-(2H-1,2,3-triazol-2-yl)pyridin-3-yl)-1-phenyl-5-(trifluoromethyl)-1H-pyrazole-4-carboxamide, Cpd 5

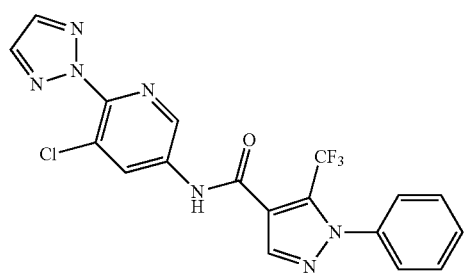 [SMILES: O=C(Nc1cnc(-n2nccn2)c(Cl)c1)c1cnn(-c2ccccc2)c1C(F)(F)F]

A. Ethyl 1-phenyl-5-(trifluoromethyl)-1H-pyrazole-4-carboxylate, cpd 5a

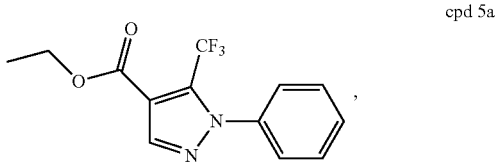 [SMILES: CCOC(=O)c1cnn(-c2ccccc2)c1C(F)(F)F]

cpd 5a

A solution consisting of ethyl 2-(ethoxymethylene)-4,4,4-trifluoro-3-oxobutanoate, INT1 (9.97 g, 41.5 mmol), phenylhydrazine (5.00 g, 34.6 mmol), triethylamine (4.81 mL, 34.6 mmol), and ethanol (20 mL) was stirred at 80° C. for 16 h before cooling to room temperature. The resultant solution was concentrated to dryness under reduced pressure to afford the crude product, which was added into water (10 mL). The resultant mixture was extracted with ethyl acetate (20 mL×3). The combined organic extracts were dried over anhydrous Na$_2$SO$_4$, filtered, and the filtrate concentrated to dryness under reduced pressure to afford the crude product, which was purified by flash column chromatography (petroleum ether:ethyl acetate=5:1) to afford the title compound (5 g, 50%) as a brown oil. LCMS (ESI) m/z M+1: 284.9. $^1$H NMR (400 MHz, CDCl$_3$) δ 8.12 (s, 1H), 7.56-7.48 (m, 3H), 7.47-7.39 (m, 2H), 4.39 (q, J=7.2 Hz, 2H), 1.40 (t, J=7.2 Hz, 3H).

B. N-(5-Chloro-6-(2H-1,2,3-triazol-2-yl)pyridin-3-yl)-1-phenyl-5-(trifluoromethyl)-1H-pyrazole-4-carboxamide, Cpd 5

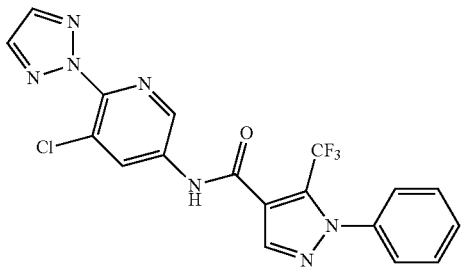

A solution consisting of 5-chloro-6-(2H-1,2,3-triazol-2-yl)pyridin-3-amine, INT2 (206 mg, 1.06 mmol) and THF (1.5 mL), and a solution consisting of ethyl 1-phenyl-5-(trifluoromethyl)-1H-pyrazole-4-carboxylate, cpd 5a (300 mg, 1.06 mmol) and THF (1.5 mL) were added to a solution consisting of potassium tert-butoxide (130 mg, 1.16 mmol) and THF (1 mL) at 0° C. The resultant mixture was stirred at room temperature for 16 h. The resultant mixture was added water (10 mL) and extracting with ethyl acetate (20 mL×3). The combined organic extracts were dried over anhydrous Na$_2$SO$_4$, filtered, and concentrated to dryness under reduced pressure to give the crude product, which was purified by preparative HPLC (40% to 70% (v/v) CH$_3$CN and H$_2$O with 0.05% NH$_3$) and lyophilized to afford the title compound (117.60 mg, 26%). LCMS (ESI) m/z M+1: 433.9. $^1$H NMR (400 MHz, CDCl$_3$) δ 8.75 (d, J=2.4 Hz, 1H), 8.49 (d, J=2.4 Hz, 1H), 8.31 (br.s., 1H), 8.07 (s, 1H), 7.94 (s, 2H), 7.58-7.51 (m, 3H), 7.49-7.42 (m, 2H).

Example 6

N-(5-Chloro-6-(2H-1,2,3-triazol-2-yl)pyridin-3-yl)-1-(3-fluoropyridin-4-yl)-5-(trifluoromethyl)-1H-pyrazole-4-carboxamide, Cpd 6

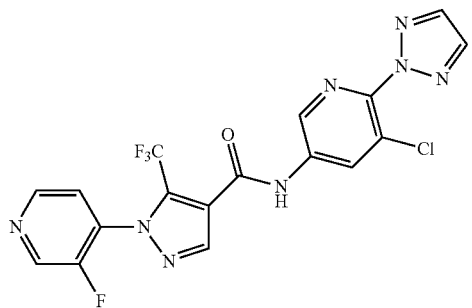 [SMILES: O=C(Nc1cnc(-n2nccn2)c(Cl)c1)c1cnn(-c2ccncc2F)c1C(F)(F)F]

A. 3-Fluoro-4-hydrazinylpyridine, Cpd 6a

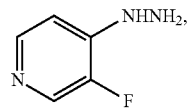

A mixture consisting of 4-chloro-3-fluoropyridine (3.00 g, 22.8 mmol) and hydrazine hydrate (30 mL, 50 wt. %) was stirred at 90° C. for 2 h. The mixture was cooled to room temperature and extracted with ethyl acetate (100 mL×3). The combined organic extracts were dried over anhydrous Na$_2$SO$_4$ and the filtrate concentrated to dryness under reduced pressure to give title compound (3 g, crude), which was used in the next step without further purification. $^1$H NMR (400 MHz, DMSO-d$_6$) δ 7.99 (d, J=4.0 Hz, 1H), 7.96 (d, J=5.2 Hz, 1H), 7.69 (br s, 1H), 7.01 (dd, J=5.6, 7.6 Hz, 1H), 4.24 (br s, 2H).

B. Ethyl 1-(3-fluoropyridin-4-yl)-5-(trifluoromethyl)-1H-pyrazole-4-carboxylate, Cpd 6b

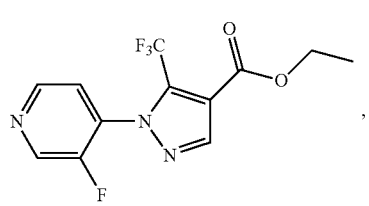

A mixture consisting of ethyl 2-(ethoxymethylene)-4,4,4-trifluoro-3-oxobutanoate, INT1 (4.41 g, 18.3 mmol), 3-fluoro-4-hydrazinylpyridine, cpd 6a (3.00 g, 18.3 mmol), and ethanol (40 mL) was stirred at 80° C. for 16 h. The mixture was cooled to room temperature and concentrated to dryness under reduced pressure to give a residue, which was purified by flash column chromatography (petroleum ether: ethyl acetate=10:1) to afford partially purified title compound (3 g, 54%) which was used in the next step without further purification.

C. 1-(3-Fluoropyridin-4-yl)-5-(trifluoromethyl)-1H-pyrazole-4-carboxylic Acid, Cpd 6c

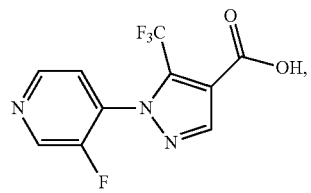

A mixture consisting of ethyl 1-(3-fluoropyridin-4-yl)-5-(trifluoromethyl)-1H-pyrazole-4-carboxylate, cpd 6b (500 mg, 1.65 mmol), sodium hydroxide (5 mL, 4.95 mmol, 1M), and ethanol (4 mL) was stirred at room temperature for 4 h. The mixture was neutralized with 1 M HCl and extracted with ethyl acetate (40 mL×3). The combined extracts were dried over anhydrous Na$_2$SO$_4$ and the filtrate concentrated to dryness under reduced pressure to afford title compound (423 mg, crude), which was used in the next step without purification.

D. N-(5-Chloro-6-(2H-1,2,3-triazol-2-yl)pyridin-3-yl)-1-(3-fluoropyridin-4-yl)-5-(trifluoromethyl)-1H-pyrazole-4-carboxamide, Cpd 6

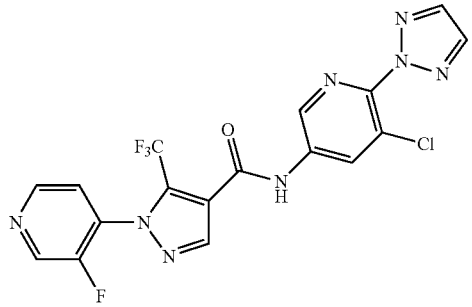 [SMILES: O=C(Nc1cnc(-n2nccn2)c(Cl)c1)c1cnn(-c2ccncc2F)c1C(F)(F)F]

POCl$_3$ (268 mg, 1.74 mmol) was added to a mixture consisting of 1-(3-fluoropyridin-4-yl)-5-(trifluoromethyl)-1H-pyrazole-4-carboxylic acid, cpd 6c (400 mg, 1.45 mmol), 5-chloro-6-(2H-1,2,3-triazol-2-yl)pyridin-3-amine, INT2 (310 mg, 1.45 mmol), and pyridine (5 mL) at 0° C. The mixture was stirred at 0° C. for 1 h. The reaction mixture was concentrated under reduced pressure to give the crude product, which was purified by preparative HPLC (34% to 44% (v/v) ACN and H$_2$O with 0.05% NH$_3$) and lyophilized to afford the title compound (221.20 mg, 33%). LCMS (ESI) m/z M+1: 452.9. $^1$H NMR (400 MHz, DMSO-d$_6$) δ 11.25 (br.s., 1H), 9.01 (d, J=1.6 Hz, 1H), 8.84 (d, J=2.0 Hz, 1H), 8.77 (d, J=4.8 Hz, 1H), 8.66 (d, J=2.4 Hz, 1H), 8.63 (s, 1H), 8.20 (s, 2H), 7.97-7.91 (m, 1H).

Example 7

N-(5-Chloro-6-(2H-1,2,3-triazol-2-yl)pyridin-3-yl)-1-(5-fluoropyridin-2-yl)-5-(trifluoromethyl)-1H-pyrazole-4-carboxamide, Cpd 7

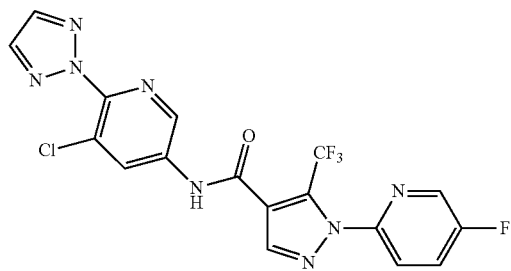 [SMILES: O=C(Nc1cnc(-n2nccn2)c(Cl)c1)c1cnn(-c2ccc(F)cn2)c1C(F)(F)F]

A. Ethyl 1-(5-fluoropyridin-2-yl)-5-(trifluoromethyl)-1H-pyrazole-4-carboxylate, Cpd 7a

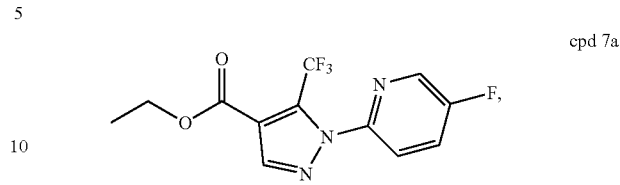

A solution consisting of ethyl 2-(ethoxymethylene)-4,4,4-trifluoro-3-oxobutanoate, INT1 (2.15 g, 8.97 mmol), 5-fluoro-2-hydrazinylpyridine (950 mg, 7.47 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=5:1) to afford the title compound (2.2 g, 97%) as a brown solid. LCMS (ESI) m/z M+1: 304.0. $^1$H NMR (400 MHz, DMSO-d$_6$) δ 8.65 (d, J=2.8 Hz, 1H), 8.34 (s, 1H), 8.13-8.08 (m, 1H), 7.91 (dd, J=4.0, 8.8 Hz, 1H), 4.32 (q, J=7.2 Hz, 2H), 1.30 (t, J=7.2 Hz, 3H)

B. N-(5-chloro-6-(2H-1,2,3-triazol-2-yl)pyridin-3-yl)-1-(5-fluoropyridin-2-yl)-5-(trifluoromethyl)-1H-pyrazole-4-carboxamide, Cpd 7

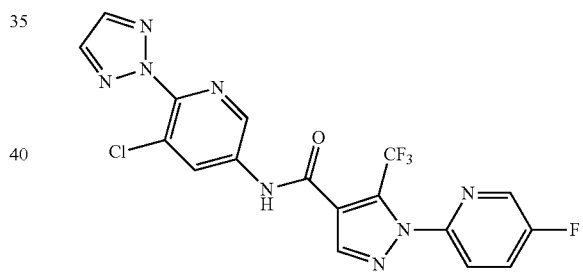

A solution consisting of 5-chloro-6-(2H-1,2,3-triazol-2-yl)pyridin-3-amine, INT2 (242 mg, 1.24 mmol) and THF (1 mL), and a solution consisting of ethyl 1-(5-fluoropyridin-2-yl)-5-(trifluoromethyl)-1H-pyrazole-4-carboxylate, cpd 7a (250 mg, 0.825 mmol) and THF (1 mL) were added to a solution consisting of potassium tert-butoxide (2.47 mL, 2.47 mmol, 1 M in THF) at 0° C. The resultant mixture was stirred at room temperature for 16 h. Water (5 mL) was added to the resultant mixture and it was extracted with ethyl acetate (15 mL×3). The combined organic extracts were dried over anhydrous Na$_2$SO$_4$, filtered, and concentrated to dryness under reduced pressure to afford the crude product, which was purified by preparative HPLC (43% to 53% (v/v) CH$_3$CN and H$_2$O with 0.05% NH$_3$) and lyophilized to dryness to afford the title compound (151.10 mg, 40%). LCMS (ESI) m/z M+1: 453.0. $^1$H NMR (400 MHz, CDCl$_3$) δ 8.71 (d, J=2.4 Hz, 1H), 8.48 (d, J=2.4 Hz, 1H), 8.42 (d, J=2.8 Hz, 1H), 8.29 (br.s., 1H), 8.06 (s, 1H), 7.94 (s, 2H), 7.76-7.71 (m, 1H), 7.70-7.64 (m, 1H).

Example 8

N-(5-Chloro-6-(2H-1,2,3-triazol-2-yl)pyridin-3-yl)-1-(pyridin-2-yl)-5-(trifluoromethyl)-1H-pyrazole-4-carboxamide, Cpd 8

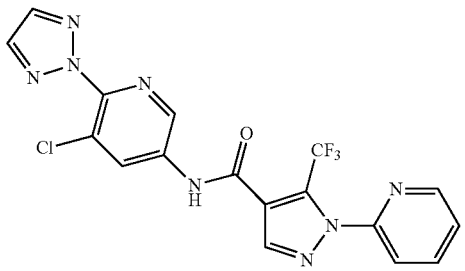 [SMILES: O=C(Nc1cnc(-n2nccn2)c(Cl)c1)c1cnn(-c2ccccn2)c1C(F)(F)F]

A. Ethyl 1-(pyridin-2-yl)-5-(trifluoromethyl)-1H-pyrazole-4-carboxylate, Cpd 8a

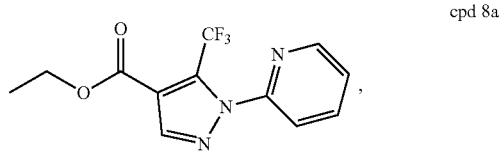 [SMILES: CCOC(=O)c1cnn(-c2ccccn2)c1C(F)(F)F]

A solution consisting of ethyl 2-(ethoxymethylene)-4,4,4-trifluoro-3-oxobutanoate, INT1 (5.3 g, 22 mmol), 2-hydrazinylpyridine (2.0 g, 18 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether: ethyl acetate=5:1) to afford the title compound (4.2 g, 80%) as a brown oil. LCMS (ESI) m/z M+1: 286.0. $^1$H NMR (400 MHz, DMSO-$d_6$) δ 8.66-8.60 (m, 1H), 8.36 (s, 1H), 8.20-8.13 (m, 1H), 7.82 (dd, J=0.8, 8.0 Hz, 1H), 7.70-7.62 (m, 1H), 4.39-4.30 (m, 2H), 1.32 (t, J=7.2 Hz, 3H)

B. N-(5-Chloro-6-(2H-1,2,3-triazol-2-yl)pyridin-3-yl)-1-(pyridin-2-yl)-5-(trifluoromethyl)-1H-pyrazole-4-carboxamide, Cpd 8

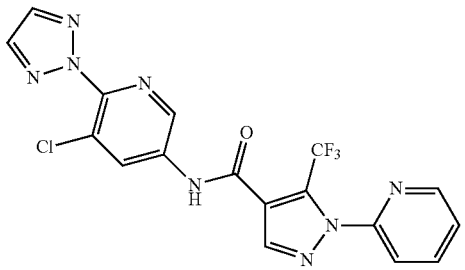 [SMILES: O=C(Nc1cnc(-n2nccn2)c(Cl)c1)c1cnn(-c2ccccn2)c1C(F)(F)F]

A solution consisting of 5-chloro-6-(2H-1,2,3-triazol-2-yl)pyridin-3-amine, INT2 (309 mg, 1.58 mmol) and THF (1 mL), and a solution consisting of ethyl 1-(pyridin-2-yl)-5-(trifluoromethyl)-1H-pyrazole-4-carboxylate, cpd 8a (300 mg, 1.05 mmol) and THF (1 mL) were added to a solution consisting of potassium tert-butoxide (1.58 mL, 1.58 mmol, 1 M in THF) at 0° C. The resultant mixture was stirred at room temperature for 16 h. Water (5 mL) was added to the resultant mixture it was extracted with ethyl acetate (15 mL×3). The combined organic extracts were dried over anhydrous Na$_2$SO$_4$, filtered, and concentrated to dryness under reduced pressure to afford the crude product, which was purified by preparative HPLC (30% to 60% (v/v) CH$_3$CN and H$_2$O with 0.05% NH$_3$) and lyophilized to dryness to afford the title compound (97.20 mg, 21%) as a brown solid. LCMS (ESI) m/z M+1: 434.9. $^1$H NMR (400 MHz, DMSO-$d_6$) δ 11.29 (br.s., 1H), 8.82 (d, J=2.4 Hz, 1H), 8.66-8.60 (m, 2H), 8.45 (s, 1H), 8.21-8.12 (m, 3H), 7.85 (d, J=8.0 Hz, 1H), 7.67-7.62 (m, 1H).

Example 9

N-(5-Chloro-6-(2H-1,2,3-triazol-2-yl)pyridin-3-yl)-1-(pyrazin-2-yl)-5-(trifluoromethyl)-1H-pyrazole-4-carboxamide, Cpd 9

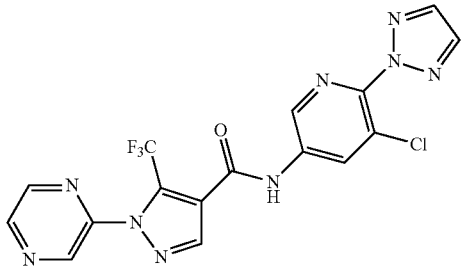 [SMILES: O=C(Nc1cnc(-n2nccn2)c(Cl)c1)c1cnn(-c2cnccn2)c1C(F)(F)F]

A. Ethyl 1-(pyrazin-2-yl)-5-(trifluoromethyl)-1H-pyrazole-4-carboxylate, Cpd 9a

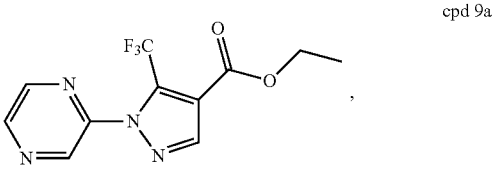 [SMILES: CCOC(=O)c1cnn(-c2cnccn2)c1C(F)(F)F]

A mixture of 2-hydrazinopyrazine (500 mg, 2.73 mmol), ethyl 2-(ethoxymethylene)-4,4,4-trifluoro-3-oxobutanoate, INT1 (849 mg, 3.01 mmol), and EtOH (5 mL) was heated to 90° C. and stirred for 20 h before cooling to room temperature. The mixture was evaporated under reduced pressure to afford a yellow oil, which was purified by flash column chromatography (ethyl acetate: petroleum ether=40:60). The title compound (610 mg, 78%) was obtained as a yellow solid. LCMS (ESI) m/z M+1: 287.0. $^1$H NMR (400 MHz, DMSO-$d_6$) δ 9.14 (d, J=1.2 Hz, 1H), 8.93 (d, J=2.4 Hz, 1H), 8.75 (d, J=2.4 Hz, 1H), 8.43 (s, 1H), 4.34 (q, J=6.8 Hz, 2H), 1.31 (t, J=6.8 Hz, 3H).

B. 1-(Pyrazin-2-yl)-5-(trifluoromethyl)-1H-pyrazole-4-carboxylic Acid, Cpd 9b

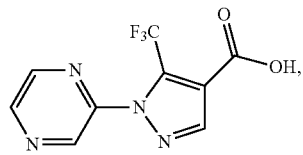

cpd 9b

A mixture of ethyl 1-(pyrazin-2-yl)-5-(trifluoromethyl)-1H-pyrazole-4-carboxylate, cpd 9a (200 mg, 0.699 mmol), lithium hydroxide (50.2 mg, 2.10 mmol), MeOH (1 mL), THF (1 mL), and $H_2O$ (1 mL) was stirred for 20 h at room temperature. Then the pH of the mixture was adjusted to pH 2 with 6 N aq. HCl. The organic solvents were removed under reduced pressure. The residue was diluted with water (30 mL) and extracted with ethyl acetate (30 mL×2). The organic layers were combined, dried over anhydrous $Na_2SO_4$, filtered, and the filtrate evaporated to afford the title compound (191 mg, 85%) as a yellow solid. LCMS (ESI) m/z M+1: 258.9.

C. N-(5-Chloro-6-(2H-1,2,3-triazol-2-yl)pyridin-3-yl)-1-(pyrazin-2-yl)-5-(trifluoromethyl)-1H-pyrazole-4-carboxamide, Cpd 9

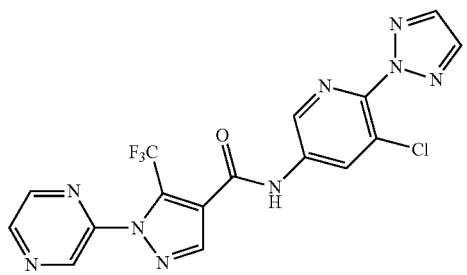 [SMILES: O=C(Nc1cnc(-n2nccn2)c(Cl)c1)c1cnn(-c2cnccn2)c1C(F)(F)F]

Phosphorus oxychloride (0.069 mL, 0.74 mmol) was added drop-wise into a solution consisting of 1-(pyrazin-2-yl)-5-(trifluoromethyl)-1H-pyrazole-4-carboxylic acid, cpd 9b (160 mg, 0.116 mmol), 5-chloro-6-(2H-1,2,3-triazol-2-yl)pyridin-3-amine, INT2 (121 mg, 0.620 mmol), and pyridine (2 mL). The mixture was stirred at 0° C. for 1 h before concentrating to dryness under reduced pressure to give the crude product, which was purified by preparative high performance liquid chromatography over Phenomenex Gemini 150×25 mm×10 m (eluent: $CH_3CN$ in Basic water (0.05% $NH_3.H_2O$) from 37% to 67%, v/v). The pure fractions were collected and the volatiles were removed under reduced pressure. The residue was re-suspended in water (10 mL) and the resulting mixture was lyophilized to dryness to remove the solvent residue completely to afford the title compound (51.70 mg, 19%) as a yellow solid. LCMS (ESI) m/z M+1: 435.9. $^1$H NMR (400 MHz, DMSO-$d_6$) δ 11.36 (br s, 1H), 9.22 (d, J=1.2 Hz, 1H), 8.93 (d, J=2.4 Hz, 1H), 8.83 (d, J=2.4 Hz, 1H), 8.77 (dd, J=1.2, 2.4 Hz, 1H), 8.65 (d, J=2.4 Hz, 1H), 8.55 (s, 1H), 8.19 (s, 2H).

Example 10

N-(5-Chloro-6-(2H-1,2,3-triazol-2-yl)pyridin-3-yl)-1-(pyrimidin-2-yl)-5-(trifluoromethyl)-1H-pyrazole-4-carboxamide, Cpd 10

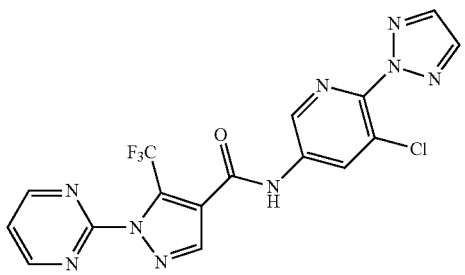 [SMILES: O=C(Nc1cnc(-n2nccn2)c(Cl)c1)c1cnn(-c2ncccn2)c1C(F)(F)F]

A. Ethyl 1-(pyrimidin-2-yl)-5-(trifluoromethyl)-1H-pyrazole-4-carboxylate, Cpd 10a cpd 10a A mixture of 2-hydrazinopyrimidine (500 mg, 2.73 mmol), ethyl 2-(ethoxymethylene)-4,4,4-trifluoro-3-oxobutanoate, INT1 (849 mg, 3.01 mmol), and EtOH (5 mL) was heated to 90° C. and stirred for 20 h before cooling to room temperature. The mixture was evaporated under reduced pressure to afford a yellow oil, which was purified by flash column chromatography (ethyl acetate: petroleum ether=40:60) to afford a yellow solid (620 mg, 79%). The crude product (250 mg) was further purified by flash column chromatography (ethyl acetate: petroleum ether=40:60) to afford the title compound (217.30 mg, 84%) as a yellow solid. LCMS (ESI) m/z M+1: 287.0. $^1$H NMR (400 MHz, DMSO-$d_6$) δ 9.09 (d, J=4.4 Hz, 2H), 8.39 (s, 1H), 7.85-7.82 (m, 1H), 4.34 (q, J=6.8 Hz, 2H), 1.31 (t, J=6.8 Hz, 3H).

B. 1-(Pyrimidin-2-yl)-5-(trifluoromethyl)-1H-pyrazole-4-carboxylic Acid, Cpd 10b

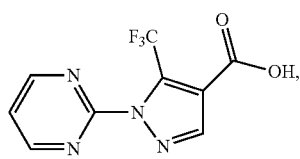

cpd 10b

A mixture of ethyl 1-(pyrimidin-2-yl)-5-(trifluoromethyl)-1H-pyrazole-4-carboxylate, cpd 10a (200 mg, 0.699 mmol), lithium hydroxide (50.2 mg, 2.10 mmol), MeOH (1 mL), THF (1 mL), and $H_2O$ (1 mL) was stirred for 20 h at room temperature.

Then the pH of the mixture was adjusted to pH 2 with 6 N aq. HCl. The organic solvents were removed under reduced pressure. The residue was diluted with water (30 mL) and extracted with ethyl acetate (30 mL×2). The organic layers were combined, dried over anhydrous Na₂SO₄, filtered, and the filtrate evaporated to afford the title compound (190 mg, 84%) as a yellow solid. LCMS (ESI) m/z M+1: 258.9.

C. N-(5-Chloro-6-(2H-1,2,3-triazol-2-yl)pyridin-3-yl)-1-(pyrimidin-2-yl)-5-(trifluoromethyl)-1H-pyrazole-4-carboxamide, Cpd 10

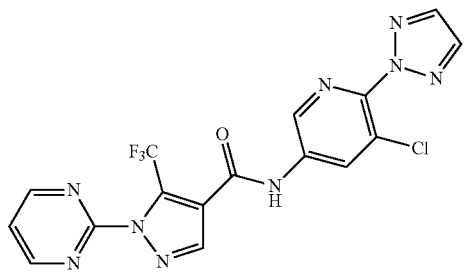

Phosphorus oxychloride (0.069 mL, 0.74 mmol) was added drop-wise into a solution consisting of 1-(pyrimidin-2-yl)-5-(trifluoromethyl)-1H-pyrazole-4-carboxylic acid, cpd 10b (160 mg, 0.620 mmol), 5-chloro-6-(2H-1,2,3-triazol-2-yl)pyridin-3-amine (121 mg, 0.620 mmol), and pyridine (2 mL). The mixture was stirred at 0° C. for 1 h before concentrating to dryness under reduced pressure to give the crude product, which was purified by preparative HPLC (CH₃CN in basic water (0.05% NH₃.H₂O) from 30% to 60%, v/v) and lyophilized to dryness to afford the title compound (75.00 mg, 28%) as a yellow solid. LCMS (ESI) m/z M+1: 435.9. ¹H NMR (400 MHz, DMSO-d₆) δ 11.32 (br s, 1H), 9.10 (d, J=5.2 Hz, 2H), 8.83 (d, J=2.4 Hz, 1H), 8.65 (d, J=2.4 Hz, 1H), 8.50 (s, 1H), 8.20 (s, 2H), 7.84-7.82 (m, 1H).

Example 11

N-(5-Chloro-6-(2H-1,2,3-triazol-2-yl)pyridin-3-yl)-1-(5-cyanopyridin-2-yl)-5-(trifluoromethyl)-1H-pyrazole-4-carboxamide, Cpd 11

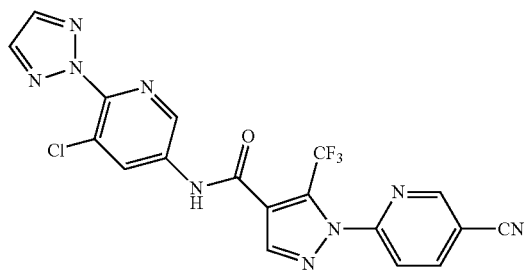 [SMILES: N#Cc1ccc(-n2ncc(C(=O)Nc3cnc(-n4nccn4)c(Cl)c3)c2C(F)(F)F)nc1]

A. Ethyl 1-(5-cyanopyridin-2-yl)-5-(trifluoromethyl)-1H-pyrazole-4-carboxylate, Cpd 11a

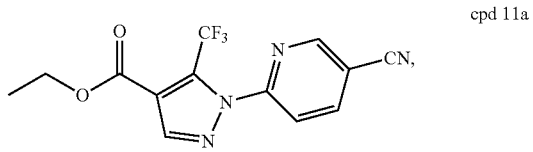 [SMILES: CCOC(=O)c1cnn(-c2ccc(C#N)cn2)c1C(F)(F)F]

A solution consisting of ethyl 2-(ethoxymethylene)-4,4,4-trifluoro-3-oxobutanoate, INT1 (2.04 g, 8.50 mmol), 6-hydrazinylnicotinonitrile (950 mg, 7.08 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=4:1) to afford the title compound (1.9 g, 86%) as a brown solid. LCMS (ESI) m/z M+1: 311.0. ¹H NMR (400 MHz, DMSO-d₆) δ 9.17-9.07 (m, 1H), 8.68 (dd, J=2.4, 8.4 Hz, 1H), 8.44 (s, 1H), 8.10-8.05 (m, 1H), 4.34 (q, J=7.2 Hz, 2H), 1.32 (t, J=7.2 Hz, 3H).

B. N-(5-chloro-6-(2H-1,2,3-triazol-2-yl)pyridin-3-yl)-1-(5-cyanopyridin-2-yl)-5-(trifluoromethyl)-1H-pyrazole-4-carboxamide, Cpd 11

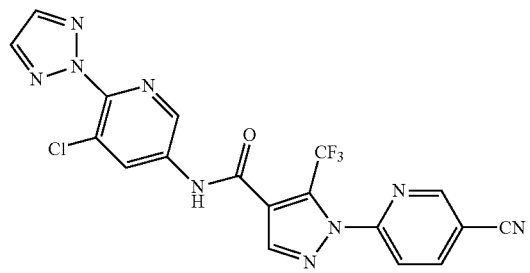 [SMILES: N#Cc1ccc(-n2ncc(C(=O)Nc3cnc(-n4nccn4)c(Cl)c3)c2C(F)(F)F)nc1]

Trimethylaluminum (0.725 mL, 1.45 mmol, 2 M in toluene) was added to a solution consisting of ethyl 1-(5-cyanopyridin-2-yl)-5-(trifluoromethyl)-1H-pyrazole-4-carboxylate, cpd 11a (300 mg, 0.967 mmol), 5-chloro-6-(2H-1,2,3-triazol-2-yl)pyridin-3-amine, INT2 (284 mg, 1.45 mmol), and toluene (5 mL) under N₂, and the resultant solution was refluxed for 16 h. The resultant mixture was added water (10 mL) and extracted with ethyl acetate (15 mL×3). The combined organic extracts were dried over anhydrous Na₂SO₄, filtered, and the filtrate concentrated to dryness under reduced pressure to afford the crude product, which was purified by preparative HPLC (35% to 55% (v/v) CH₃CN and H₂O with 10 mM NH₄HCO₃) and lyophilized to dryness to afford still-impure product (160 mg). The product was purified by flash column chromatography (petroleum ether:ethyl acetate=1:1) to give the title compound (92.40 mg, 21%) as a white solid. LCMS (ESI) m/z M+1: 459.9. ¹H NMR (400 MHz, DMSO-d₆) δ 11.38 (br.s., 1H), 9.13 (d, J=1.6 Hz, 1H), 8.81 (d, J=2.4 Hz, 1H), 8.67 (dd, J=2.4, 8.4 Hz, 1H), 8.63 (d, J=2.4 Hz, 1H), 8.53 (s, 1H), 8.19 (s, 2H), 8.13 (d, J=8.4 Hz, 1H).

Example 12

N-(5-Chloro-6-(2H-1,2,3-triazol-2-yl)pyridin-3-yl)-1-(pyridin-3-yl)-5-(trifluoromethyl)-1H-pyrazole-4-carboxamide, Cpd 12

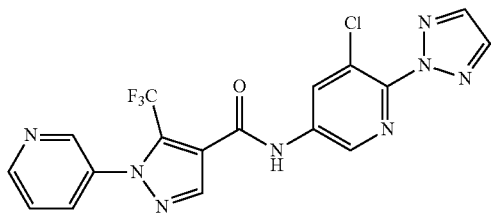 [SMILES: O=C(Nc1cnc(-n2nccn2)c(Cl)c1)c1cnn(-c2cccnc2)c1C(F)(F)F]

A. Ethyl 1-(pyridin-3-yl)-5-(trifluoromethyl)-1H-pyrazole-4-carboxylate, Cpd 12a

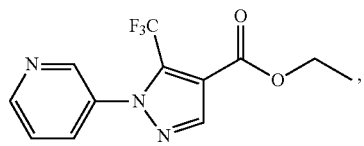
cpd 12a

A solution consisting of ethyl 2-(ethoxymethylene)-4,4,4-trifluoro-3-oxobutanoate, INT1 (1.32 g, 5.49 mmol), 3-hydrazinylpyridine (1.00 g, 5.49 mmol), triethylamine (1.11 g, 11.0 mmol), and ethanol (5 mL) was stirred at 80° C. for 16 h before cooling to room temperature and concentrating under reduced pressure to afford the crude product, which was purified by flash column chromatography (petroleum ether:ethyl acetate=100:0 to 80:20) to give the title compound (550 mg, 35%). LCMS (ESI) m/z M+1: 286.0. $^1$H NMR (400 MHz, CDCl$_3$) δ 8.81 (br s, 2H), 8.17 (s, 1H), 7.80 (d, J=8.0 Hz, 1H), 7.56-7.45 (m, 1H), 4.39 (q, J=7.2 Hz, 2H), 1.39 (t, J=7.2 Hz, 3H).

B. N-(5-Chloro-6-(2H-1,2,3-triazol-2-yl)pyridin-3-yl)-1-(pyridin-3-yl)-5-(trifluoromethyl)-1H-pyrazole-4-carboxamide, Cpd 12

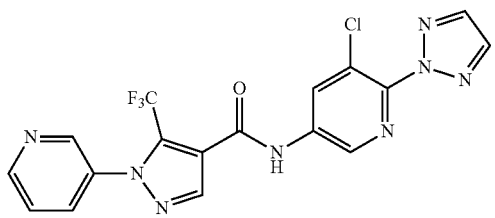 [SMILES: O=C(Nc1cnc(-n2nccn2)c(Cl)c1)c1cnn(-c2cccnc2)c1C(F)(F)F]

A solution consisting of 5-chloro-6-(2H-1,2,3-triazol-2-yl)pyridin-3-amine, INT2 (137 mg, 0.701 mmol) and THF (1 mL) was added to 1 M potassium tert-butoxide in THF (2.10 mL, 2.10 mmol) at 0° C., then a solution consisting of ethyl 1-(pyridin-3-yl)-5-(trifluoromethyl)-1H-pyrazole-4-carboxylate, cpd 12a (200 mg, 0.701 mmol) and THF (1 mL) was added. The resultant mixture was stirred at room temperature for 16 h. The reaction mixture was concentrated under reduced pressure to give the crude product, which was purified by preparative HPLC (30% to 60% (v/v) CH$_3$CN and H$_2$O with 0.05% NH$_3$) and lyophilized to dryness to give the title compound (154.30 mg, 51%). LCMS (ESI) m/z M+1: 434.9. $^1$H NMR (400 MHz, DMSO-d$_6$) δ 8.84-8.83 (m, 3H), 8.65 (d, J=2.4 Hz, 1H), 8.50 (s, 1H), 8.22-8.16 (m, 2H), 8.14-8.09 (m, 1H), 7.71 (dd, J=5.2, 8.4 Hz, 1H).

Example 13

N-(5-Chloro-6-(2H-1,2,3-triazol-2-yl)pyridin-3-yl)-1-(6-methoxypyridin-3-yl)-5-(trifluoromethyl)-1H-pyrazole-4-carboxamide, Cpd 13

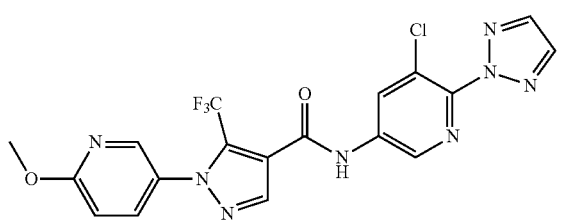 [SMILES: COc1ccc(-n2ncc(C(=O)Nc3cnc(-n4nccn4)c(Cl)c3)c2C(F)(F)F)cn1]

A. 5-Hydrazinyl-2-methoxypyridine, Cpd 13a

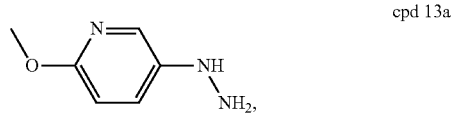
cpd 13a

A solution consisting of sodium nitrite (834 mg, 12.1 mmol) in water (1 mL) was added drop-wise to a solution consisting of 6-methoxypyridin-3-amine (1.00 g, 8.06 mmol) and concentrated aq. HCl (5 mL) at −10° C.-0° C. The mixture was stirred at −10° C.-0° C. for 1.5 h. A solution consisting of SnCl$_2$.2H$_2$O (3.64 g, 16.1 mmol) and concentrated aq. HCl (1 mL) was added drop-wise at −10° C.-0° C., then the mixture was stirred at room temperature for 16 h. The reaction mixture was basified to pH 10 with 4 M aq. NaOH at 0° C., extracted with ethyl acetate (30 mL×3) and dried over anhydrous Na$_2$SO$_4$. The extracts were concentrated to dryness under reduced pressure to give the title compound (700 mg, crude), which was used in the next step without purification. LCMS (ESI) m/z M+1: 140.2.

B. Ethyl 1-(6-methoxypyridin-3-yl)-5-(trifluoromethyl)-1H-pyrazole-4-carboxylate, 13b

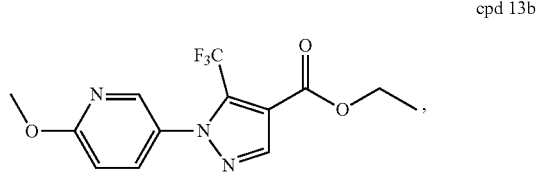 [SMILES: CCOC(=O)c1cnn(-c2ccc(OC)nc2)c1C(F)(F)F]
cpd 13b

A solution consisting of ethyl 2-(ethoxymethylene)-4,4,4-trifluoro-3-oxobutanoate, INT1 (793 mg, 3.30 mmol), 5-hydrazinyl-2-methoxypyridine, cpd 13a (700 mg, 3.30 mmol), triethylamine (668 mg, 6.60 mmol), and ethanol (5 mL) was stirred at 80° C. for 16 h before cooling to room temperature and concentrating under reduced pressure to afford the crude product, which was purified by flash column chromatography (petroleum ether:ethyl acetate=100:0 to 70:30) to give the title compound (750 mg, 72%). LCMS (ESI) m/z M+1: 316.0.

C. N-(5-Chloro-6-(2H-1,2,3-triazol-2-yl)pyridin-3-yl)-1-(6-methoxypyridin-3-yl)-5-(trifluoromethyl)-1H-pyrazole-4-carboxamide, Cpd 13

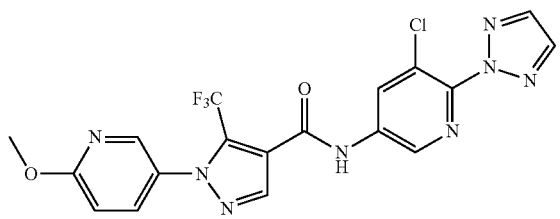 [SMILES: COc1ccc(-n2ncc(C(=O)Nc3cnc(-n4nccn4)c(Cl)c3)c2C(F)(F)F)cn1]

A solution consisting of 5-chloro-6-(2H-1,2,3-triazol-2-yl)pyridin-3-amine, INT2 (124 mg, 0.634 mmol) and THF (1 mL) were added to 1 M potassium tert-butoxide in THF (1.90 mL, 1.90 mmol) at 0° C., then a solution consisting of ethyl 1-(6-methoxypyridin-3-yl)-5-(trifluoromethyl)-1H-pyrazole-4-carboxylate, cpd 13b (200 mg, 0.634 mmol) and THF (1 mL) was added. The resultant mixture was stirred at room temperature for 16 h before concentrating under reduced pressure to give the crude product, which was purified by preparative HPLC (42% to 72% (v/v) CH$_3$CN and H$_2$O with 0.05% NH$_3$) to afford the title compound (148.50 mg, 50%). LCMS (ESI) m/z M+1: 464.9. $^1$H NMR (400 MHz, DMSO-d$_6$) δ 11.24 (br s, 1H), 8.83 (d, J=2.4 Hz, 1H), 8.65 (d, J=2.4 Hz, 1H), 8.46-8.41 (m, 2H), 8.19 (s, 2H), 7.98 (dd, J=2.8, 8.8 Hz, 1H), 7.07 (d, J=8.8 Hz, 1H), 3.96 (s, 3H).

Example 14

N-(5-Chloro-6-(2H-1,2,3-triazol-2-yl)pyridin-3-yl)-1-(2-methoxypyridin-3-yl)-5-(trifluoromethyl)-1H-pyrazole-4-carboxamide, Cpd 14

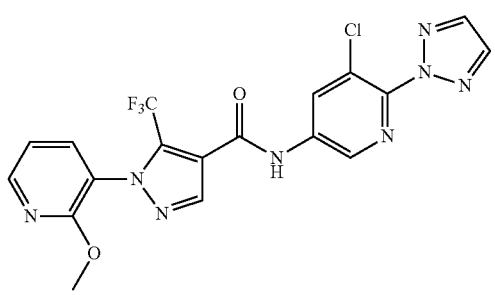 [SMILES: COc1ncccc1-n1ncc(C(=O)Nc2cnc(-n3nccn3)c(Cl)c2)c1C(F)(F)F]

A. Di-tert-butyl 1-(2-methoxypyridin-3-yl)hydrazine-1,2-dicarboxylate, Cpd 14a

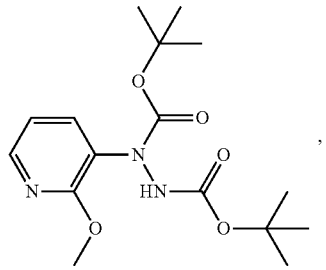

A mixture of 2-methoxypyridine-3-boronic acid (1.00 g, 6.54 mmol), di-tert-butyl azodicarboxylate (1.51 g, 6.54 mmol), copper(ii) acetate (39.2 mg, 0.216 mmol), and MeOH (10 mL) was heated to 60° C. and stirred for 1 h before cooling to room temperature. The mixture was concentrated under reduced pressure to give a yellow solid, which was solved in MTBE (100 mL) and washed with sat. aq. NaHCO$_3$(100 mL) and brine (100 mL). The organic layer was dried over anhydrous Na$_2$SO$_4$, filtered, and concentrated under reduced pressure to afford the title compound (2.2 g, 99%) as a yellow solid, which was used directly in the next step. LCMS (ESI) m/z M+1: 340.1.

B. 3-Hydrazinyl-2-methoxypyridine dihydrochloride, Cpd 14b

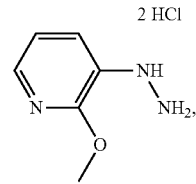

Hydrogen chloride in 1,4-dioxane (6 mL, 4 M, 24 mmol) was added to a solution consisting of di-tert-butyl 1-(2-methoxypyridin-3-yl)hydrazine-1,2-dicarboxylate, cpd 14a (1.00 g, 2.95 mmol) and 1,4-dioxane (6 mL). The mixture was stirred for 2 days at room temperature before concentrating under reduced pressure to give the crude product (510 mg, 82%) as a yellow solid, which was used directly in next step. LCMS (ESI) m/z M+1: 140.1.

C. Ethyl 1-(2-methoxypyridin-3-yl)-5-(trifluoromethyl)-1H-pyrazole-4-carboxylate, Cpd 14c

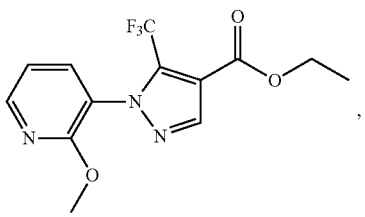

A mixture of 3-hydrazinyl-2-methoxypyridine dihydrochloride, cpd 14b (510 mg, 2.41 mmol), ethyl 2-(ethoxymethylene)-4,4,4-trifluoro-3-oxobutanoate, INT1 (747 mg, 2.65 mmol), triethylamine (1.00 mL, 7.21 mmol), and EtOH (10 mL) was heated to 90° C. and stirred for 20 h before cooling to room temperature. The mixture was evaporated under reduced pressure to afford a yellow oil, which was purified by flash column chromatography (petroleum ether: ethyl acetate=50:50) to afford the title compound (350 mg, 46%) as a yellow solid. LCMS (ESI) m/z M+1: 316.0.

D. N-(5-Chloro-6-(2H-1,2,3-triazol-2-yl)pyridin-3-yl)-1-(2-methoxypyridin-3-yl)-5-(trifluoromethyl)-1H-pyrazole-4-carboxamide, Cpd 14

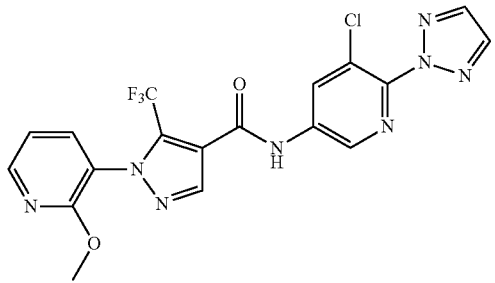 [SMILES: COc1ncccc1-n1ncc(C(=O)Nc2cnc(-n3nccn3)c(Cl)c2)c1C(F)(F)F]

A solution consisting of 5-chloro-6-(2H-1,2,3-triazol-2-yl)pyridin-3-amine, INT2 (93.1 mg, 0.476 mmol) and THF (1 mL) were added to 1 M potassium tert-butoxide in THF (1.43 mL, 1.43 mmol) at 0° C., then a solution consisting of ethyl 1-(2-methoxypyridin-3-yl)-5-(trifluoromethyl)-1H-pyrazole-4-carboxylate, cpd 14c (150 mg, 0.476 mmol) and THF (1 mL) was added. The resultant mixture was stirred at room temperature for 16 hours. The reaction mixture was concentrated under reduced pressure to give the crude product, which was purified by preparative HPLC (40% to 70% (v/v) CH$_3$CN and H$_2$O with 0.05% NH$_3$) and lyophilized to dryness to give the title compound (73.3 mg, 32%). LCMS (ESI) m/z M+1: 464.9. $^1$H NMR (400 MHz, DMSO-d$_6$) δ 11.18 (br.s., 1H), 8.84 (d, J=2.4 Hz, 1H), 8.65 (d, J=2.4 Hz, 1H), 8.49 (s, 1H), 8.43 (dd, J=2.0, 4.8 Hz, 1H), 8.19 (s, 2H), 8.06 (dd, J=2.0, 7.6 Hz, 1H), 7.26 (dd, J=5.2, 7.6 Hz, 1H), 3.90 (s, 3H).

Example 15

N-(5-Chloro-6-(2H-1,2,3-triazol-2-yl)pyridin-3-yl)-1-(pyrimidin-5-yl)-5-(trifluoromethyl)-1H-pyrazole-4-carboxamide, Cpd 15

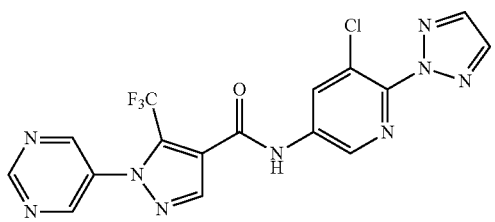 [SMILES: O=C(Nc1cnc(-n2nccn2)c(Cl)c1)c1cnn(-c2cncnc2)c1C(F)(F)F]

A. Di-tert-butyl 1-(pyrimidin-5-yl)hydrazine-1,2-dicarboxylate, Cpd 15a

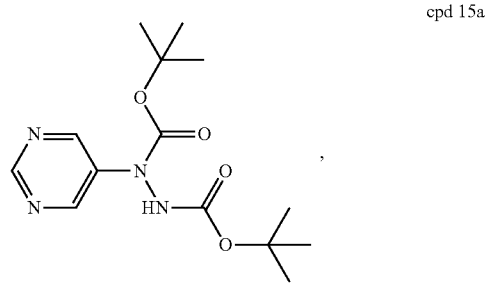 [SMILES: CC(C)(C)OC(=O)NN(C(=O)OC(C)(C)C)c1cncnc1]

A mixture consisting of pyrimidin-5-ylboronic acid (1.00 g, 8.07 mmol), di-tert-butyl diazene-1,2-dicarboxylate (1.86 g, 8.07 mmol), copper(II) acetate (147 mg, 0.807 mmol), and methanol (5 mL) was stirred at 60° C. for 1 h before cooling to room temperature, concentrating under reduced pressure, washed with water (10 mL), and extracted with ethyl acetate (10 mL×3). The extract was dried over anhydrous Na$_2$SO$_4$ and concentrated under reduced pressure to give the title compound (1.8 g, crude), which was used in the next step without purification. LCMS (ESI) m/z M+1: 311.0.

B. 5-Hydrazinylpyrimidine Dihydrochloride, Cpd 15b

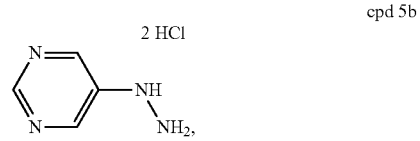

A solution consisting of di-tert-butyl 1-(pyrimidin-5-yl)hydrazine-1,2-dicarboxylate, cpd 15a (1.8 g, 5.8 mmoL), 4 M HCl in 1,4-dioxane (12 mL) and 1,4-dioxane (12 mL) was stirred at room temperature for 16 h. The suspension was filtered, and the residue was washed with ethyl acetate (10 mL×2) and dried under reduced pressure to afford the title compound (1.00 g, crude), which was used in the next step without purification.

C. Ethyl 1-(pyrimidin-5-yl)-5-(trifluoromethyl)-1H-pyrazole-4-carboxylate, Cpd 15c

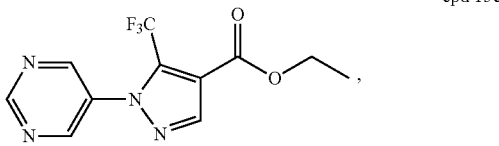

A solution consisting of ethyl 2-(ethoxymethylene)-4,4,4-trifluoro-3-oxobutanoate, INT1 (656 mg, 2.73 mmol), 5-hydrazinylpyrimidine dihydrochloride, cpd 15b (500 mg, 2.73 mmol), triethylamine (553 mg, 5.46 mmol), and ethanol (5 mL) was stirred at 80° C. for 16 h before cooling to room temperature and concentrating under reduced pressure to give the crude product, which was purified by flash column chromatography (petroleum ether:ethyl acetate=100:0 to 70:30) to afford the title compound (130 mg, 17%). LCMS (ESI) m/z M+1: 286.9.

D. N-(5-Chloro-6-(2H-1,2,3-triazol-2-yl)pyridin-3-yl)-1-(pyrimidin-5-yl)-5-(trifluoromethyl)-1H-pyrazole-4-carboxamide, Cpd 15

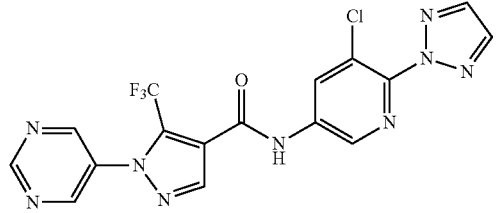 [SMILES: O=C(Nc1cnc(-n2nccn2)c(Cl)c1)c1cnn(-c2cncnc2)c1C(F)(F)F]

A solution consisting of 5-chloro-6-(2H-1,2,3-triazol-2-yl)pyridin-3-amine, INT2 (75.2 mg, 0.384 mmol) and THF (0.5 mL) were added to 1 M potassium tert-butoxide in THF (1.15 mL, 1.15 mmol) at 0° C., then a solution consisting of ethyl 1-(pyrimidin-5-yl)-5-(trifluoromethyl)-1H-pyrazole-4-carboxylate, cpd 15c (110 mg, 0.384 mmol) and THF (0.5 mL) was added. The resultant mixture was stirred at room temperature for 16 hours. The reaction mixture was concentrated under reduced pressure to give the crude product, which was purified by preparative HPLC (32% to 42% (v/v) CH$_3$CN and H$_2$O with 0.05% NH$_3$) and lyophilized to dryness to give the title compound (82.10 mg, 48%). LCMS (ESI) m/z M+1: 435.9. $^1$H NMR (400 MHz, DMSO-d$_6$) δ 9.46 (s, 1H), 9.21 (s, 2H), 8.84 (d, J=2.0 Hz, 1H), 8.66 (d, J=2.4 Hz, 1H), 8.58 (s, 1H), 8.19 (s, 2H).

Example 16

N-(5-Chloro-6-(2H-1,2,3-triazol-2-yl)pyridin-3-yl)-1-(5-methylpyridin-3-yl)-5-(trifluoromethyl)-1H-pyrazole-4-carboxamide, Cpd 16

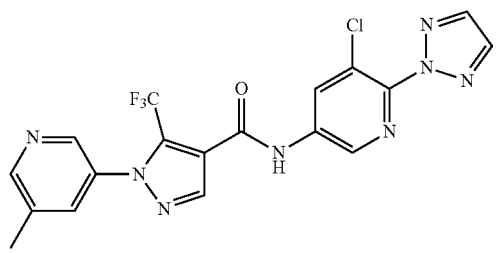 [SMILES: Cc1cncc(-n2ncc(C(=O)Nc3cnc(-n4nccn4)c(Cl)c3)c2C(F)(F)F)c1]

A. Di-tert-butyl 1-(5-methylpyridin-3-yl)hydrazine-1,2-dicarboxylate, Cpd 16a

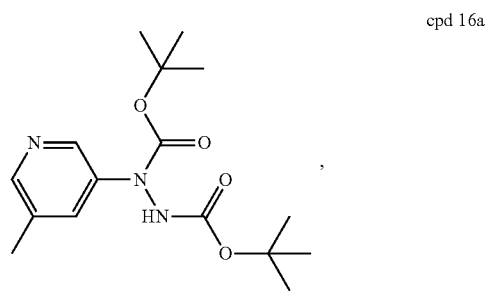 [SMILES: Cc1cncc(N(NC(=O)OC(C)(C)C)C(=O)OC(C)(C)C)c1]

A mixture consisting of (5-methylpyridin-3-yl)boronic acid (1.5 g, 11 mmol), di-tert-butyl diazene-1,2-dicarboxylate (2.5 g, 11 mmol), copper(II)acetate (66 mg, 0.36 mmol), and MeOH (10 mL) was added to a 5-10 mL microwave tube and stirred at 60° C. for 1 h. The organic layer was concentrated under reduced pressure to dryness to give a residue, and this was extracted with ethyl acetate (20 mL×3). The combined organic extracts were dried over anhydrous Na$_2$SO$_4$, filtered, and concentrated to dryness under reduced pressure to afford the crude product, which was purified by flash column chromatography (petroleum ether:ethyl acetate=10:1) to afford the title compound (2.4 g, 34%) as a white solid. LC-MS (ESI) m/z M+1: 323.9. $^1$H NMR (400 MHz, CDCl$_3$) δ 8.49 (br.s., 1H), 8.22 (s, 1H), 7.72-7.53 (m, 1H), 6.99-6.87 (m, 1H), 2.33 (s, 3H), 1.50 (s, 18H).

B. 3-Hydrazinyl-5-methylpyridine dihydrochloride, Cpd 16b

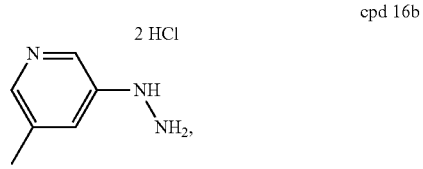

HCl in 1,4-dioxane (15 mL, 4 M) was added to a solution consisting of di-tert-butyl 1-(5-methylpyridin-3-yl)hydrazine-1,2-dicarboxylate, cpd 16a (2.4 g, 7.4 mmol) and 1,4-dioxane (15 mL), and the resultant mixture was stirred at room temperature for 16 h. The resultant mixture was concentrated to dryness under reduced pressure to afford the compound (1.5 g, crude), which was used in the next step without further purification. $^1$H NMR (400 MHz, DMSO-d$_6$) δ 9.65 (br.s., 1H), 8.38-8.30 (m, 2H), 7.94 (s, 1H), 2.41 (s, 3H).

C. Ethyl 1-(5-methylpyridin-3-yl)-5-(trifluoromethyl)-1H-pyrazole-4-carboxylate, Cpd 16c

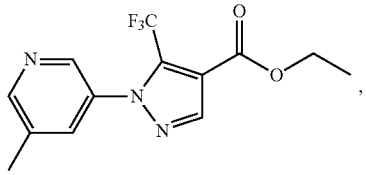

A solution consisting of ethyl 2-(ethoxymethylene)-4,4,4-trifluoro-3-oxobutanoate, INT1 (2.1 g, 8.6 mmol), 3-hydrazinyl-5-methylpyridine dihydrochloride, cpd 16b (1.4 g, 7.1 mmol), triethylamine (2.0 mL, 14 mmol), and ethanol (20 mL) was stirred at 80° C. for 16 h before cooling to room temperature. The resultant solution was concentrated to dryness under reduced pressure to afford the crude product, which was added into water (10 mL) and extracted with ethyl acetate (20 mL×3). The combined organic extracts were dried over anhydrous Na$_2$SO$_4$, filtered, and concentrated to dryness under reduced pressure to afford the crude product, which was purified by flash column chromatography (petroleum ether:ethyl acetate=5:1) to afford the title compound (900 mg, 42%) as a light yellow solid. LC-MS (ESI) m/z M+1: 300.0. $^1$H NMR (400 MHz, DMSO-d$_6$) δ 8.65 (s, 1H), 8.59 (d, J=2.0 Hz, 1H), 8.37 (s, 1H), 7.93 (s, 1H), 4.33 (q, J=7.2 Hz, 2H), 2.42 (s, 3H), 1.31 (t, J=7.2 Hz, 3H).

D. N-(5-Chloro-6-(2H-1,2,3-triazol-2-yl)pyridin-3-yl)-1-(5-methylpyridin-3-yl)-5-(trifluoromethyl)-1H-pyrazole-4-carboxamide, Cpd 16

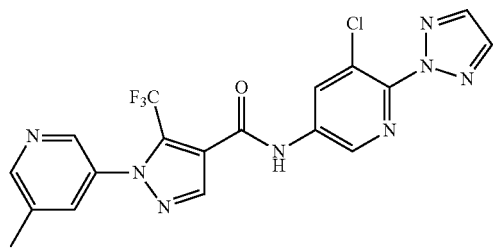 [SMILES: Cc1cncc(-n2ncc(C(=O)Nc3cnc(-n4nccn4)c(Cl)c3)c2C(F)(F)F)c1]

A solution consisting of 5-chloro-6-(2H-1,2,3-triazol-2-yl)pyridin-3-amine, INT2 (245 mg, 1.25 mmol) and THF (1 mL), and a solution consisting of ethyl 1-(5-methylpyridin-3-yl)-5-(trifluoromethyl)-1H-pyrazole-4-carboxylate, cpd 16c (250 mg, 0.835 mmol) and THF (1 mL) were added to a solution consisting of potassium tert-butoxide (2.51 mL, 2.51 mmol, 1 M in THF) at 0° C. The resultant mixture was stirred at room temperature for 16 h. The resultant mixture was treated with water (5 mL) and extracted with ethyl acetate (15 mL×3). The combined organic extracts were dried over anhydrous Na$_2$SO$_4$, filtered, and concentrated to dryness under reduced pressure to afford the crude product, which was purified by preparative HPLC (30% to 60% (v/v) CH$_3$CN and H$_2$O with 0.05% NH$_3$) and lyophilized to dryness to afford the title compound (203.90 mg, 54%) as a brown solid. LC-MS (ESI) m/z M+1: 448.9. $^1$H NMR (400 MHz, DMSO-d$_6$) δ 8.83 (d, J=2.0 Hz, 1H), 8.67 (d, J=1.2 Hz, 1H), 8.65 (d, J=2.4 Hz, 1H), 8.61 (d, J=2.4 Hz, 1H), 8.49 (s, 1H), 8.18 (s, 2H), 7.93 (s, 1H), 2.43 (s, 3H).

Example 17

N-(5-Chloro-6-(2H-1,2,3-triazol-2-yl)pyridin-3-yl)-1-(5-cyanopyridin-3-yl)-5-(trifluoromethyl)-1H-pyrazole-4-carboxamide, Cpd 17

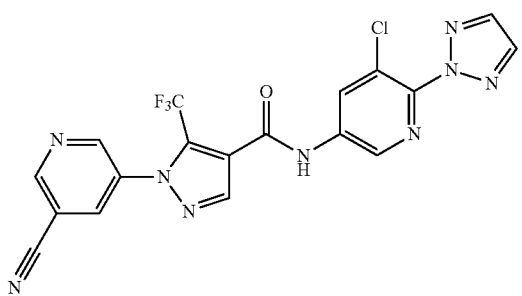 [SMILES: N#Cc1cncc(-n2ncc(C(=O)Nc3cnc(-n4nccn4)c(Cl)c3)c2C(F)(F)F)c1]

A. Di-tert-butyl 1-(5-cyanopyridin-3-yl)hydrazine-1,2-dicarboxylate, Cpd 17a

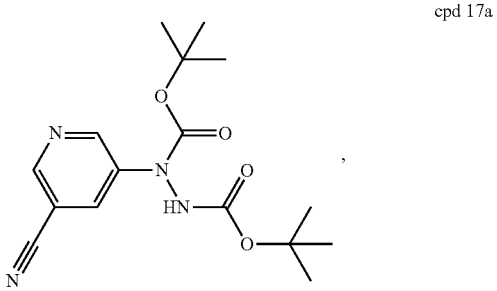 [SMILES: CC(C)(C)OC(=O)NN(C(=O)OC(C)(C)C)c1cncc(C#N)c1]

A mixture consisting of (5-cyanopyridin-3-yl)boronic acid (2.00 g, 13.5 mmol), di-tert-butyl diazene-1,2-dicarboxylate (3.11 g, 13.5 mmol), copper(II) acetate (245 mg, 1.35 mmol), and methanol (10 mL) was stirred at 60° C. for 1 hour before cooling to room temperature. The resultant mixture was concentrated under reduced pressure to give the crude product, which was purified by flash column chromatography (petroleum ether:ethyl acetate=100:0 to 70:30) to afford the title compound (1.6 g, 35%). LCMS (ESI) m/z M+1: 335.0.

B. 5-Hydrazinylnicotinonitrile Dihydrochloride Cpd 17b

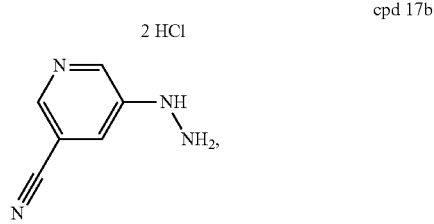

A solution consisting of di-tert-butyl 1-(5-cyanopyridin-3-yl)hydrazine-1,2-dicarboxylate, cpd17a (1.6 g, 4.79 mmoL), 4 M HCl in 1,4-dioxane (12 mL) and 1,4-dioxane (10 mL) was stirred at room temperature for 16 hours. The suspension was filtered and the residue was dried under reduced pressure to afford the crude product (1.00 g, crude), which was used in the next step without purification. LCMS (ESI) m/z M+1: 135.1.

C. Ethyl 1-(5-cyanopyridin-3-yl)-5-(trifluoromethyl)-1H-pyrazole-4-carboxylate, Cpd

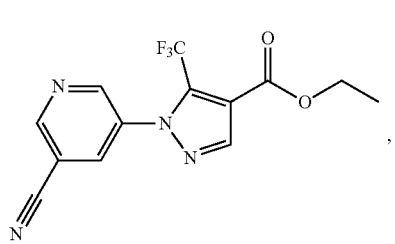

cpd 17c

A solution consisting of ethyl 2-(ethoxymethylene)-4,4,4-trifluoro-3-oxobutanoate, INT1 (580 mg, 2.42 mmol), 5-hydrazinylnicotinonitrile dihydrochloride, cpd 17b (500 mg, 2.42 mmol), triethylamine (489 mg, 4.83 mmol), and ethanol (10 mL) was stirred at 80° C. for 16 hours before cooling to room temperature. The resultant mixture was concentrated under reduced pressure to give the crude product, which was purified by flash column chromatography (petroleum ether:ethyl acetate=100:0 to 70:30) to afford the title compound (420 mg, 56%). LCMS (ESI) m/z M+1: 310.9.

D. N-(5-Chloro-6-(2H-1,2,3-triazol-2-yl)pyridin-3-yl)-1-(5-cyanopyridin-3-yl)-5-(trifluoromethyl)-1H-pyrazole-4-carboxamide, Cpd 17

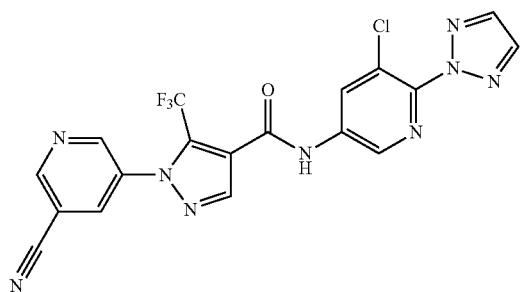 [SMILES: N#Cc1cncc(-n2ncc(C(=O)Nc3cnc(-n4nccn4)c(Cl)c3)c2C(F)(F)F)c1]

2 M AlMe$_3$ in toluene (0.363 mL, 0.725 mmol) was added to a solution consisting of 5-chloro-6-(2H-1,2,3-triazol-2-yl)pyridin-3-amine, INT2 (94.6 mg, 0.484 mmol), ethyl 1-(5-cyanopyridin-3-yl)-5-(trifluoromethyl)-1H-pyrazole-4-carboxylate, cpd 17c (150 mg, 0.484 mmol) and toluene (5 mL) under N$_2$ atmosphere. The resultant mixture was refluxed for 16 hours before cooling to room temperature. The resultant mixture was quenched with water (10 mL), extracted with ethyl acetate (10 mL×3), dried over anhydrous Na$_2$SO$_4$ and concentrated under reduced pressure to give the crude product, which was purified by preparative HPLC (35% to 65% (v/v) CH$_3$CN and H$_2$O with 0.05% NH$_3$) and then lyophilized to dryness to give the title compound (108.10 mg, 48%). LCMS (ESI) m/z M+1: 459.9. $^1$H NMR (400 MHz, DMSO-d$_6$) δ 9.30 (d, J=2.0 Hz, 1H), 9.17 (d, J=2.4 Hz, 1H), 8.86-8.81 (m, 2H), 8.66 (d, J=2.4 Hz, 1H), 8.57 (s, 1H), 8.19 (s, 2H).

Example 18

N-(5-chloro-6-(2H-1,2,3-triazol-2-yl)pyridin-3-yl)-1-(4-fluorophenyl)-5-(trifluoromethyl)-1H-pyrazole-4-carboxamide, Cpd 18

A 4 mL vial was charged with 4-fluorophenylhydrazine hydrochloride (52 mg, 0.32 mmol), THF, and 1 M potassium tert-butoxide in THF (0.35 mL, 0.354 mmol), and stirred at room temperature for ~5 min. The reaction was then treated with ethyl 2-(ethoxymethylene)-4,4,4-trifluoro-3-oxobutanoate, INT1 (0.06 mL, 0.309 mmol) and anhydrous calcium sulfate (234 mg, 1.719 mmol), and stirred at 70° C. for 10 min. The reaction was then cooled to room temperature, treated with 1 M potassium tert-butoxide in THF (0.48 mL, 0.485 mmol) and 5-chloro-6-(2H-1,2,3-triazol-2-yl)pyridin-3-amine, INT2 (65.1 mg, 0.332 mmol), and then stirred at room temperature for 40 min. The reaction was then partitioned with 5M NH$_4$Cl and EtOAc (1 mL each), and the amber organic layer was dried (Na$_2$SO$_4$), filtered, and concentrated. The residue was flash chromatographed on a 12 g Silicycle HP column (10-100% EtOAc over 25 CVs) to provide compound, cpd 18 (32.2 mg, 22% from aryl hydrazine HCl). $^1$H NMR (400 MHz, CDCl$_3$) δ 8.77 (d, J=2.02 Hz, 1H), 8.50 (d, J=2.02 Hz, 1H), 8.09 (s, 1H), 7.93-7.97 (m, 3H), 7.44-7.50 (m, 2H), 7.21-7.26 (m, 2H); MS m/e 452.3 (M+H).

Example 19

N-(5-chloro-6-(2H-1,2,3-triazol-2-yl)pyridin-3-yl)-1-(4-cyanophenyl)-5-(trifluoromethyl)-1H-pyrazole-4-carboxamide, Cpd 19

A 4 mL vial was charged with 4-cyanophenylhydrazine hydrochloride (52.5 mg, 0.31 mmol), THF (0.62 mL, 0.5 M, 0.31 mmol), and 1 M potassium tert-butoxide in THF (0.34 mL, 0.343 mmol), and stirred at room temperature for 10 min. The reaction was then treated with ethyl 2-(ethoxymethylene)-4,4,4-trifluoro-3-oxobutanoate, INT1 (0.06 mL, 1.235 g/mL, 0.309 mmol) and stirred for 20 min. The reaction was then treated with anhydrous calcium sulfate (white Drierite, 8 mesh) (204 mg, 1.498 mmol) and the mixture stirred at room temp for 10 min, then treated with 5-chloro-6-(2H-1,2,3-triazol-2-yl)pyridin-3-amine, INT2 (60.7 mg, 0.309 mmol) and 1 M potassium tert-butoxide in THF (0.46 mL, 0.464 mmol), and the resulting dark solution was stirred under air for 30 min. The reaction was then partitioned with 5 M NH$_4$Cl and EtOAc (1 mL each), and the organic layer was dried (Na$_2$SO$_4$), filtered, and concentrated to provide 133 mg of a clear dark amber oil. This was flash chromatographed on a 12 g Silicycle HP column (10-100% EtOAc/heptane over 25 CVs) to provide compound, cpd 19 as an off-white foam (41.4 mg, 29% from aryl hydrazine HCl). $^1$H NMR (400 MHz, CDCl$_3$) δ 8.76 (d, J=2.53 Hz, 1H), 8.50 (d, J=2.53 Hz, 1H), 8.14 (s, 1H), 7.86-7.96 (m, 5H), 7.65 (d, J=8.59 Hz, 2H); MS m/e 459.1 (M+H).

Example 20

N-(5-chloro-6-(2H-1,2,3-triazol-2-yl)pyridin-3-yl)-1-(3-fluorophenyl)-5-(trifluoromethyl)-1H-pyrazole-4-carboxamide, Cpd 20

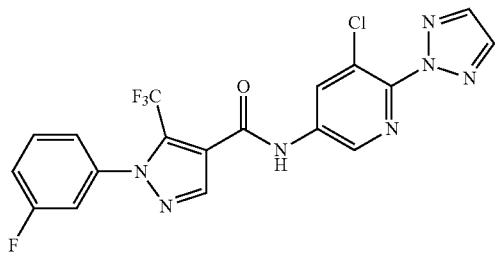 [SMILES: O=C(Nc1cnc(-n2nccn2)c(Cl)c1)c1cnn(-c2cccc(F)c2)c1C(F)(F)F]

Prepared as described for Example 19, but using 3-fluorophenylhydrazine hydrochloride (51.4 mg, 0.316 mmol) in place of 4-cyanophenylhydrazine hydrochloride to provide compound, cpd 20 as a white foam (44.8 mg, 31% aryl hydrazine HCl). $^1$H NMR (400 MHz, CDCl$_3$) δ 8.78 (d, J=2.53 Hz, 1H), 8.51 (d, J=2.53 Hz, 1H), 8.10 (s, 1H), 7.96 (s, 2H), 7.90 (s, 1H), 7.54 (dt, J=6.06, 8.08 Hz, 1H), 7.28-7.33 (m, 2H), 7.23-7.26 (m, 1H); MS m/e 452.1 (M+H).

Example 21

N-(5-chloro-6-(2H-1,2,3-triazol-2-yl)pyridin-3-yl)-1-(3-cyanophenyl)-5-(trifluoromethyl)-1H-pyrazole-4-carboxamide, Cpd 21

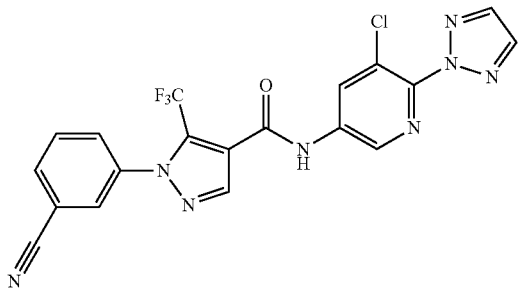 [SMILES: N#Cc1cccc(-n2ncc(C(=O)Nc3cnc(-n4nccn4)c(Cl)c3)c2C(F)(F)F)c1]

Prepared as described for Example 19, but using 3-cyanophenylhydrazine hydrochloride (72.3 mg, 0.426 mmol) in place of 4-cyanophenylhydrazine hydrochloride. Further purification with preparative HPLC (10-90% CH$_3$CN gradient, with 0.1% TFA throughout) followed by lyophilization, pH 8.5 neutralization, extraction with DCM, and concentration of the dried organic layer provided compound, cpd 21 as a white solid (15.8 mg, 11% from aryl hydrazine HCl). $^1$H NMR (400 MHz, CDCl$_3$) δ 8.76 (d, J=2.53 Hz, 1H), 8.51 (d, J=2.53 Hz, 1H), 8.13 (s, 1H), 7.95 (s, 2H), 7.84-7.90 (m, 2H), 7.82 (s, 1H), 7.68-7.78 (m, 2H); MS m/e 459.1 (M+H).

Example 22

N-(5-chloro-6-(2H-1,2,3-triazol-2-yl)pyridin-3-yl)-1-(4-methylpyridin-2-yl)-5-(trifluoromethyl)-1H-pyrazole-4-carboxamide, Cpd 22

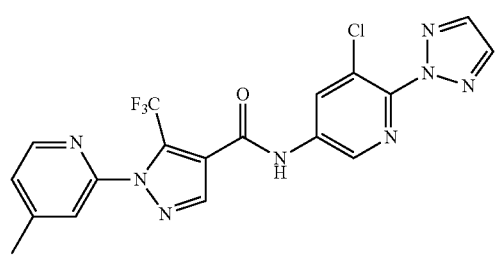 [SMILES: Cc1ccnc(-n2ncc(C(=O)Nc3cnc(-n4nccn4)c(Cl)c3)c2C(F)(F)F)c1]

A. 2-hydrazinyl-4-methylpyridine, Cpd 22a

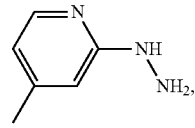

cpd 22a

A 2-5 mL capacity Biotage microwave vial with stirbar was charged with 2-fluoro-4-methylpyridine (201.3 mg, 1.81 mmol) and hydrazine (0.57 mL, 18.2 mmol). The resulting clear colorless solution was evacuated/flushed with argon 4× and stirred at 150° C. for 10 min, and then concentrated at 150° C. under a stream of argon to give an off-white slightly translucent solution. This was cooled to room temperature, partitioned with toluene (2 mL) and water (0.1 mL), and the organic layer was dried (Na$_2$SO$_4$), filtered, and concentrated to provide the title compound as a beige solid (162 mg, 73%). $^1$H NMR (400 MHz, CDCl$_3$) δ 8.00 (d, J=6.06 Hz, 1H), 6.52 (m, 2H), 5.72 (br s, 1H), 3.80 (br s, 2H), 2.27 (s, 3H).

B. N-(5-chloro-6-(2H-1,2,3-triazol-2-yl)pyridin-3-yl)-1-(4-methylpyridin-2-yl)-5-(trifluoromethyl)-1H-pyrazole-4-carboxamide, Cpd 22

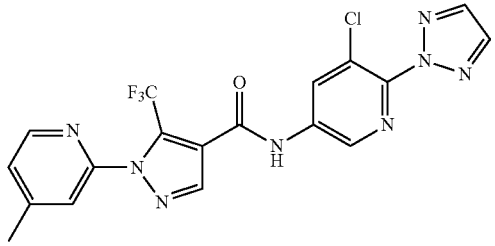 [SMILES: Cc1ccnc(-n2ncc(C(=O)Nc3cnc(-n4nccn4)c(Cl)c3)c2C(F)(F)F)c1]

A 4 mL vial with was charged with 2-hydrazinyl-4-methylpyridine, cpd 22a (33.6 mg, 0.273 mmol), THF (0.39 mL), and ethyl 2-(ethoxymethylene)-4,4,4-trifluoro-3-oxobutanoate, INT1 in THF (0.55 mL, 0.5 M, 0.275 mmol), and the reaction was stirred at room temperature for 10 min and then at 70° C. for 90 min. The reaction was then charged with calcium sulfate (white Drierite, 8 mesh) (196 mg, 1.44 mmol) and stirred at 70° C. for 10 min. The reaction was then cooled to room temperature, treated with 5-chloro-6-(2H-1,2,3-triazol-2-yl)pyridin-3-amine, INT2 (53.6 mg, 0.273 mmol) and potassium tert-butoxide (0.41 mL, 0.41 mmol, 1 M in THF), and the resulting dark reaction was stirred at room temperature for 30 min. The reaction was then partitioned with 5 M NH$_4$Cl and EtOAc (1 mL each), and the organic layer dried (Na$_2$SO$_4$), filtered, and concentrated. The 112 mg residue was purified by flash column chromatography on a 12 g Silicycle HP column (10-100% EtOAc in heptane over 25 CVs) to provide the title compound contaminated with 3 mol % 5-chloro-6-(2H-1,2,3-triazol-2-yl)pyridin-3-amine, INT2 (39.9 mg, 33%). This was combined with a similarly contaminated 8 mg previous batch (48 mg total) and re-purified by flash column chromatography as before to provide the title compound as an off-white solid (39.2 mg, 32%). $^1$H NMR (400 MHz, CDCl$_3$) δ 8.77 (s, 1H), 8.67 (d, J=2.53 Hz, 1H), 8.44 (s, 1H), 8.39 (d, J=5.30 Hz, 1H), 8.00 (s, 1H), 7.92 (s, 2H), 7.47 (s, 1H), 7.24-7.26 (m, 1H), 2.47 (s, 3H); MS m/e 449.1 (M+H).

Example 23

N-(5-chloro-6-(2H-1,2,3-triazol-2-yl)pyridin-3-yl)-1-(5-methylpyridin-2-yl)-5-(trifluoromethyl)-1H-pyrazole-4-carboxamide, Cpd 23

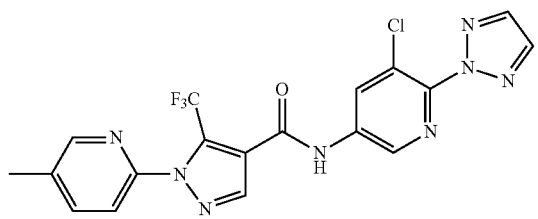 [SMILES: Cc1ccc(-n2ncc(C(=O)Nc3cnc(-n4nccn4)c(Cl)c3)c2C(F)(F)F)nc1]

A. 2-hydrazinyl-5-methylpyridine, Cpd 23a

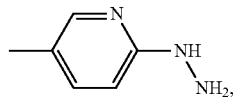

Prepared as described for 2-hydrazinyl-4-methylpyridine, cpd 22a using 2-fluoro-5-methylpyridine (206.1 mg, 1.855 mmol) in place of 2-fluoro-4-methylpyridine.

B. N-(5-chloro-6-(2H-1,2,3-triazol-2-yl)pyridin-3-yl)-1-(5-methylpyridin-2-yl)-5-(trifluoromethyl)-1H-pyrazole-4-carboxamide, Cpd 23

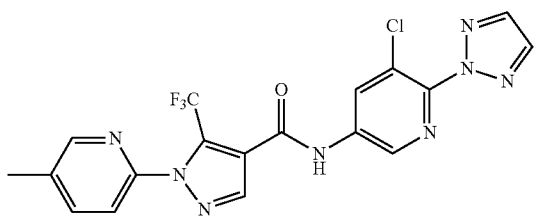 [SMILES: Cc1ccc(-n2ncc(C(=O)Nc3cnc(-n4nccn4)c(Cl)c3)c2C(F)(F)F)nc1]

Prepared as described for N-(5-chloro-6-(2H-1,2,3-triazol-2-yl)pyridin-3-yl)-1-(4-methylpyridin-2-yl)-5-(trifluoromethyl)-1H-pyrazole-4-carboxamide, Cpd 22 but using 2-hydrazinyl-5-methylpyridine, cpd 23a (45 mg, 0.365 mmol) in place of 2-hydrazinyl-4-methylpyridine, cpd 22a to provide the title compound contaminated with 2.5 mol % 5-chloro-6-(2H-1,2,3-triazol-2-yl)pyridin-3-amine, INT2. Further purification by flash chromatography on two 12 g Silicycle columns (25-75% acetone in heptane over 25 CVs, and 1:1 isocratic acetone/heptane) provided the title compound as a white solid (46.9 mg, 29%). $^1$H NMR (400 MHz, CDCl$_3$) δ 8.76 (d, J=2.02 Hz, 1H), 8.50 (d, J=2.53 Hz, 1H), 8.41 (d, J=1.52 Hz, 1H), 8.09 (s, 1H), 7.96 (s, 2H), 7.84 (s, 1H), 7.76 (dd, J=1.52, 8.08 Hz, 1H), 7.59 (d, J=8.08 Hz, 1H), 2.47 (s, 3H); MS m/e 449.3 (M+H).

Example 24

N-(5-chloro-6-(2H-1,2,3-triazol-2-yl)pyridin-3-yl)-1-(6-methylpyridin-2-yl)-5-(trifluoromethyl)-1H-pyrazole-4-carboxamide, Cpd 24

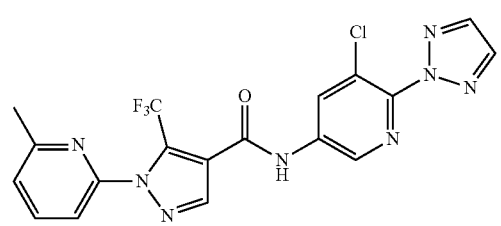

A. 2-hydrazinyl-6-methylpyridine, Cpd 24a

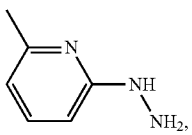

Prepared as described for 2-hydrazinyl-4-methylpyridine, cpd 22a using 2-fluoro-6-methylpyridine (201.1 mg, 1.81 mmol) in place of 2-fluoro-4-methylpyridine.

B. N-(5-chloro-6-(2H-1,2,3-triazol-2-yl)pyridin-3-yl)-1-(6-methylpyridin-2-yl)-5-(trifluoromethyl)-1H-pyrazole-4-carboxamide, Cpd 24b

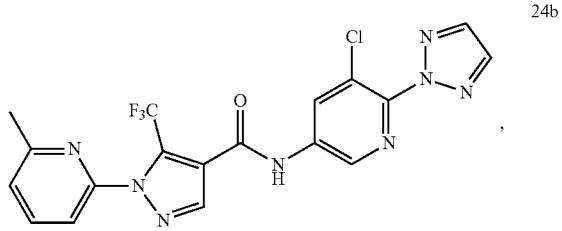 [SMILES: Cc1cccc(-n2ncc(C(=O)Nc3cnc(-n4nccn4)c(Cl)c3)c2C(F)(F)F)n1]

Prepared as described for N-(5-chloro-6-(2H-1,2,3-triazol-2-yl)pyridin-3-yl)-1-(4-methylpyridin-2-yl)-5-(trifluoromethyl)-1H-pyrazole-4-carboxamide, Cpd 22 but using 2-hydrazinyl-6-methylpyridine, cpd 24a (47.1 mg, 0.382 mmol) in place of 2-hydrazinyl-4-methylpyridine, cpd 22a to provide the title compound contaminated with a small amount of 5-chloro-6-(2H-1,2,3-triazol-2-yl)pyridin-3-amine, INT2. Further purification by flash chromatography on two 12 g Silicycle columns (25-75% acetone in heptane over 25 CVs, and 1:1 isocratic acetone/heptane) provided the title compound as a white solid (35.7 mg, 21%). $^1$H NMR (400 MHz, CDCl$_3$) δ 8.75 (d, J=2.02 Hz, 1H), 8.49 (d, J=2.02 Hz, 1H), 8.08 (s, 1H), 7.95 (s, 2H), 7.77-7.93 (m, 2H), 7.51 (d, J=7.82 Hz, 1H), 7.29-7.36 (m, 1H), 2.62 (s, 3H); MS m/e 449.3 (M+H).

Example 25

N-(5-chloro-6-(2H-1,2,3-triazol-2-yl)pyridin-3-yl)-5-(difluoromethyl)-1-(pyridin-4-yl)-1H-pyrazole-4-carboxamide, Cpd 25

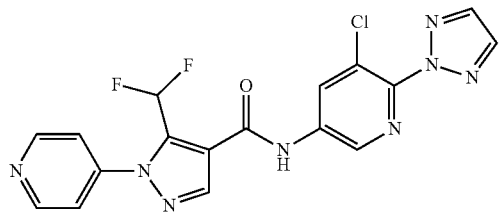 [SMILES: O=C(Nc1cnc(-n2nccn2)c(Cl)c1)c1cnn(-c2ccncc2)c1C(F)F]

An 8 mL vial was charged with 5-(difluoromethyl)-1-(pyridin-4-yl)-1H-pyrazole-4-carboxylic acid (Enamine, Catalog #EN300-185785) (55 mg, 0.23 mmol), 5-chloro-6-(2H-1,2,3-triazol-2-yl)pyridin-3-amine, INT2 (59.1 mg, 0.302 mmol), CH$_2$Cl$_2$ (3 mL), and pyridine (0.11 mL, 1.37 mmol), and the resulting mixture was treated with phosphorus oxychloride (0.063 mL, 0.69 mmol) dropwise via syringe over 15 seconds at room temperature. The reaction was stirred at room temperature overnight (14 hrs), and the resulting homogeneous yellow solution was quenched in portions with 5 M K$_2$CO$_3$ (~1 mL total; final pH>8). The aqueous layer was extracted with DCM (1×3 mL), and the combined organic layers were dried (Na$_2$SO$_4$), filtered, and concentrated to provide ~120 mg of an oil. This was purified by flash chromatography on a 12 g Silicycle HP column (neat EtOAc; 10 CVs) to provide the title compound as a white solid (45.9 mg, 48%). $^1$H NMR (400 MHz, CDCl$_3$) δ 8.81-8.85 (m, 2H), 8.71 (d, J=2.53 Hz, 1H), 8.55 (d, J=2.53 Hz, 1H), 8.17 (s, 1H), 8.02-8.13 (m, 1H), 7.96 (s, 2H), 7.45-7.75 (m, 3H); MS m/e 417.1 (M+H).

Example 26

N-(5-chloro-6-(2H-1,2,3-triazol-2-yl)pyridin-3-yl)-5-fluoro-1-phenyl-1H-pyrazole-4-carboxamide

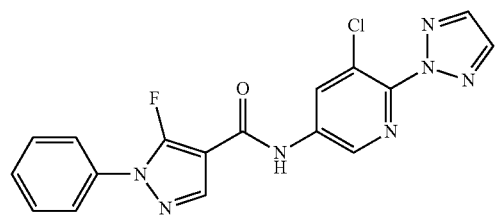 [SMILES: O=C(Nc1cnc(-n2nccn2)c(Cl)c1)c1cnn(-c2ccccc2)c1F]

Prepared essentially as described for N-(5-chloro-6-(2H-1,2,3-triazol-2-yl)pyridin-3-yl)-5-(difluoromethyl)-1-(pyridin-4-yl)-1H-pyrazole-4-carboxamide, compound 25 using 5-fluoro-1-phenylpyrazole-4-carboxylic acid (Enamine, Catalog #EN300-211840) (101.7 mg, 0.493 mmol) in place of 5-(difluoromethyl)-1-(pyridin-4-yl)-1H-pyrazole-4-carboxylic acid. Purification by flash chromatography (30%-80% EtOAc in heptane over 15 CVs) provided the title compound as a white solid (39.8 mg, 21%). $^1$H NMR (400 MHz, CDCl$_3$) δ 8.71 (d, J=2.53 Hz, 1H), 8.51 (d, J=2.02 Hz, 1H), 8.09 (d, J=3.03 Hz, 1H), 7.86-7.98 (m, 3H), 7.63-7.70 (m, 2H), 7.51-7.59 (m, 2H), 7.44-7.49 (m, 1H); MS m/e 384.1 (M+H).

Example 27

N-(5-chloro-6-(2H-1,2,3-triazol-2-yl)pyridin-3-yl)-1-(p-tolyl)-5-(trifluoromethyl)-1H-pyrazole-4-carboxamide, Cpd 27

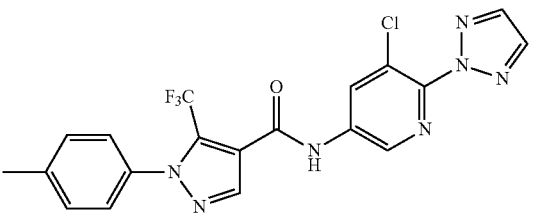 [SMILES: Cc1ccc(-n2ncc(C(=O)Nc3cnc(-n4nccn4)c(Cl)c3)c2C(F)(F)F)cc1]

A 4 mL vial was charged with 4-tolylhydrazine hydrochloride (51.9 mg, 0.327 mmol), THF (0.65 mL), potassium tert-butoxide (0.33 mL, 0.33 mmol, 1 M in THF), and the resulting slurry was stirred at room temperature for 10 min. The reaction was then treated with ethyl 2-(ethoxymethylene)-4,4,4-trifluoro-3-oxobutanoate, INT1 in THF (0.66 mL, 0.5 M, 0.33 mmol) and the mixture stirred at room temperature for 10 min and at 70° C. for 10 min. The slurry was then cooled to room temperature, treated with calcium sulfate (white Drierite, 8 mesh) (185 mg, 1.359 mmol), and stirred at 70° C. for 10 min. The reaction was then cooled to room temperature, treated with 5-chloro-6-(2H-1,2,3-triazol-2-yl)pyridin-3-amine, INT2 (64.7 mg, 0.329 mmol) and stirred for a minute, then treated with potassium tert-butoxide (0.49 mL, 0.495 mmol, 1 M in THF) in one portion at room temperature, and the resulting dark reaction was stirred for 1.5 hours. The reaction was then partitioned with 5 M NH$_4$Cl and EtOAc (1 mL each), and the organic layer dried (Na$_2$SO$_4$), filtered, and the filtrate concentrated. The residue was purified by flash chromatography on a 12 g Silicycle HP column (30-100% EtOAc in heptane over 15 CVs) to provide the title compound as a white solid (27.9 mg, 19% from aryl hydrazine HCl). $^1$H NMR (400 MHz, CDCl$_3$) δ 8.78 (d, J=2.53 Hz, 1H), 8.50 (d, J=2.53 Hz, 1H), 8.07 (s, 1H), 7.96 (s, 2H), 7.85-7.91 (m, 1H), 7.34 (s, 4H), 2.47 (s, 3H); MS m/e 448.1 (M+H).

Example 28

N-(5-chloro-6-(2H-1,2,3-triazol-2-yl)pyridin-3-yl)-1-(m-tolyl)-5-(trifluoromethyl)-1H-pyrazole-4-carboxamide, Cpd 28

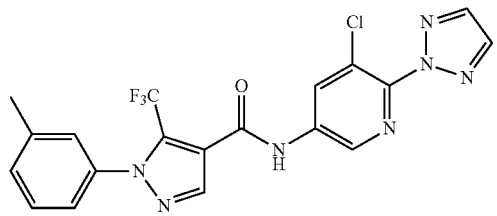 [SMILES: Cc1cccc(-n2ncc(C(=O)Nc3cnc(-n4nccn4)c(Cl)c3)c2C(F)(F)F)c1]

Prepared essentially as described for N-(5-chloro-6-(2H-1,2,3-triazol-2-yl)pyridin-3-yl)-1-(p-tolyl)-5-(trifluoromethyl)-1H-pyrazole-4-carboxamide, Cpd 27, using 3-methylphenylhydrazine hydrochloride (51.6 mg, 0.325 mmol) in place of 4-tolylhydrazine hydrochloride to provide, after purification by flash chromatography (30-90% EtOAc in heptane), the title compound as an off-white powder (57.7 mg, 40%). $^1$H NMR (400 MHz, CDCl$_3$) δ 8.76 (d, J=2.53 Hz, 1H), 8.48 (d, J=2.53 Hz, 1H), 8.03-8.11 (m, 2H), 7.94 (s, 2H), 7.34-7.44 (m, 2H), 7.23-7.26 (m, 2H), 2.45 (s, 3H); MS m/e 448.0 (M+H).

Example 29

N-(5-chloro-6-(2H-1,2,3-triazol-2-yl)pyridin-3-yl)-1-(o-tolyl)-5-(trifluoromethyl)-1H-pyrazole-4-carboxamide, Cpd 29

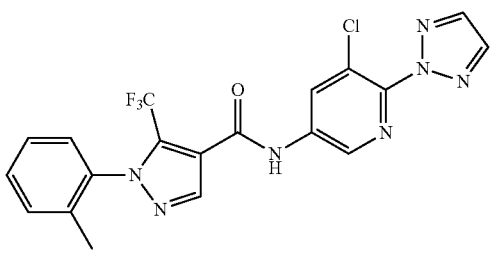 [SMILES: Cc1ccccc1-n1ncc(C(=O)Nc2cnc(-n3nccn3)c(Cl)c2)c1C(F)(F)F]

Prepared essentially as described for N-(5-chloro-6-(2H-1,2,3-triazol-2-yl)pyridin-3-yl)-1-(p-tolyl)-5-(trifluoromethyl)-1H-pyrazole-4-carboxamide, Cpd 27, using 2-methylphenylhydrazine hydrochloride (51.6 mg, 0.325 mmol) in place of 4-tolylhydrazine hydrochloride to provide, after purification by flash chromatography (40-90% EtOAc in heptane), the title compound as an orange powder (46.1 mg, 32%). $^1$H NMR (400 MHz, CDCl$_3$) δ 8.79 (d, J=2.02 Hz, 1H), 8.51 (d, J=2.53 Hz, 1H), 8.14 (s, 1H), 7.92-7.97 (m, 3H), 7.45-7.53 (m, 1H), 7.28-7.40 (m, 3H), 2.09 (s, 3H); MS m/e 448.0 (M+H).

Example 30

1-(5-bromo-3-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 30

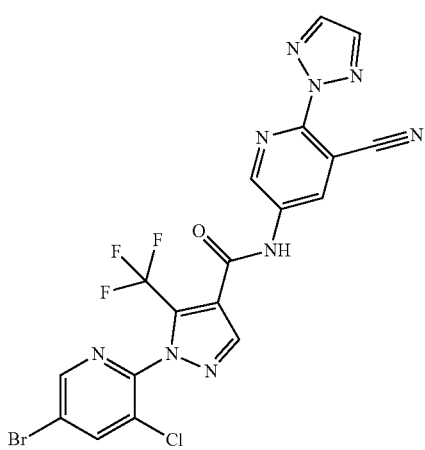 [SMILES: N#Cc1cc(NC(=O)c2cnn(-c3ncc(Br)cc3Cl)c2C(F)(F)F)cnc1-n1nccn1]

A. Ethyl 1-(5-bromo-3-chloropyridin-2-yl)-5-(trifluoromethyl)-1H-pyrazole-4-carboxylate, Cpd 30a

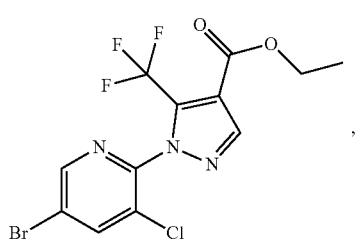

A solution of (5-bromo-3-chloro-pyridin-2-yl)-hydrazine hydrochloride (1.0 g, 3.862 mmol), ethyl 2-(ethoxymethylene)-4,4,4-trifluoro-3-oxobutanoate, INT1 (0.928 g, 3.862 mmol) and triethylamine (1.07 mL, 7.724 mmol) in ethanol (15 m) was stirred overnight at 80° C. The reaction mixture was concentrated under reduced pressure and residue purified by chromatography over silica gel (gradient of EA in heptane from 0 to 60%) to afford the title compound as a white solid (802 mg, 51%). $^1$H NMR (300 MHz, DMSO-$d_6$) δ 1.31 (t, J=7.1 Hz, 3H), 4.33 (q, J=7.1 Hz, 2H), 8.41 (s, 1H), 8.61 (d, J=2.3 Hz, 1H), 8.72 (d, J=2.3 Hz, 1H). MS m/z 398 (MH$^+$).

B. 1-(5-Bromo-3-chloro-pyridin-2-yl)-5-trifluoromethyl-1H-pyrazole-4-carboxylic Acid Cpd 30b

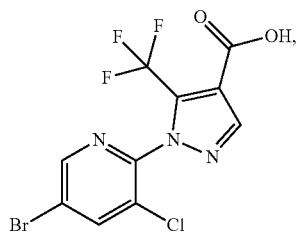

Lithium hydroxide (168 mg, 4.014 mmol) was added to a solution of ethyl 1-(5-bromo-3-chloropyridin-2-yl)-5-(trifluoromethyl)-1H-pyrazole-4-carboxylate, cpd 30A (800 mg, 2.007 mmol) in THF (8 mL) and water (2 mL). The reaction was continued 18 h at room temperature before the pH was brought to 2-3 with 2N HCl. The mixture was concentrated dry. The residue was filtered through a short column of silica gel with a mixture DCM/MeOH (9/1, v/v). Removal of solvents afforded the carboxylic acid as gum (790 mg, 105%). MS m/z 370 (MH$^+$).

C. 1-(5-bromo-3-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 30

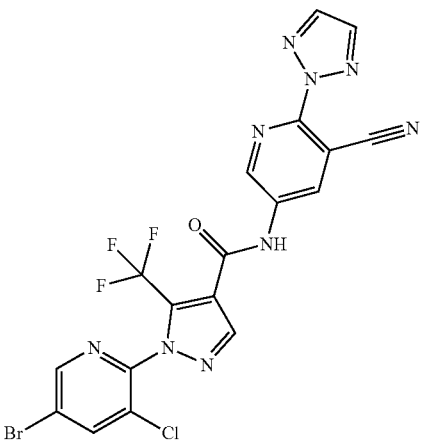 [SMILES: N#Cc1cc(NC(=O)c2cnn(-c3ncc(Br)cc3Cl)c2C(F)(F)F)cnc1-n1nccn1]

1-(5-Bromo-3-chloro-pyridin-2-yl)-5-trifluoromethyl-1H-pyrazole-4-carboxylic acid, cpd 30b (790 mg, 2.232 mmol) was taken in DCM (15 mL). DMF (1 drop) was added, followed by oxalyl chloride (0.366 mL, 4.264 mmol). The mixture was refluxed for 1 h and then concentrated dry to the crude acid chloride. It was taken in DCM (20 mL) and 5-amino-2-[1,2,3]triazol-2-yl-nicotinonitrile, INT3 (595 mg, 3.197 mmol) was added, immediately followed by triethylamine (0.891 mL, 6.394 mmol). THF (10-15 mL) was added to increase solubility and reaction continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and the filtrate was concentrated to a solid. The crude was suspended in a mixture DCM/MeOH (20 mL, 9/1, v/v) and most of the un-reacted 5-amino-2-[1,2,3]triazol-2-yl-nicotinonitrile was remove by filtration. The filtrate was concentrated and residue purified by chromatography over silica gel (gradient of EA in heptane from 15 to 75%) affording the title compound as an off-white solid (257 mg, 22%). $^1$H NMR (300 MHz, DMSO-$d_6$) δ 8.31 (s, 2H), 8.55 (s, 1H), 8.63 (d, J=2.3 Hz, 1H), 8.74 (d, J=2.3 Hz, 1H), 8.86 (d, J=2.4 Hz, 1H), 9.07 (d, J=2.5 Hz, 1H), 11.30 (s, 1H). MS m/z 539 (MH$^+$).

Example 31

1-(3-chloro-5-cyanopyridin-2-yl)-N-(5-cyano-6-(2H-1,2,3-triazol-2-yl)pyridin-3-yl)-5-(trifluoromethyl)-1H-pyrazole-4-carboxamide, Cpd 31

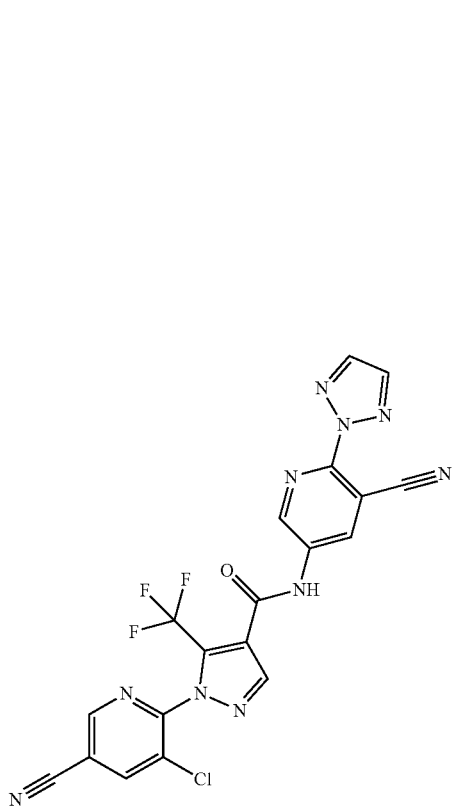 [SMILES: N#Cc1cnc(-n2ncc(C(=O)Nc3cnc(-n4nccn4)c(C#N)c3)c2C(F)(F)F)c(Cl)c1]

1-(5-Bromo-3-chloropyridin-2-yl)-N-(5-cyano-6-(2H-1,2,3-triazol-2-yl)pyridin-3-yl)-5-(trifluoromethyl)-1H-pyrazole-4-carboxamide, cpd 30 (150 mg, 0.278 mmol) was taken in DMF (3 mL) and resulting solution bubbled with nitrogen for ca. 15 minutes. Copper cyanide (50 mg, 0.557 mmol) and copper iodide (5 mg, 0.028 mmol) were added and reaction vessel closed tight with a screw cap. The mixture was then heated at 140° C. for 1.5 hour and then allowed to cool to room temperature. The reaction mixture was diluted with EA (50 mL), washed twice with 10% NH$_4$OH (2×30 mL), brine (20 mL), dried over MgSO$_4$, filtered and concentrated to the crude residue. Chromatography over silica gel (gradient of MeOH in DCM from 0 to 3%) gave the product with insufficient quality. Preparative LC (gradient from 28 to 64% of ACN/MeOH (1/1, v/v) in 25 mM aqueous ammonium acetate) followed by extraction gave the pure product as a sticky solid. Triturating in diethyl ether led to a powder (32 mg, 23%). $^1$H NMR (300 MHz, DMSO-d$_6$) δ 8.31 (s, 2H), 8.72 (s, 1H), 8.81 (d, J=2.0 Hz, 1H), 8.92 (d, J=2.4 Hz, 1H), 9.05 (d, J=2.1 Hz, 1H), 9.16 (d, J=2.4 Hz, 1H). MS m/z 485 (MH$^+$).

Example 32

1-(3-Chloro-2-methoxypyridin-4-yl)-N-(5-cyano-6-(2H-1,2,3-triazol-2-yl)pyridin-3-yl)-5-(trifluoromethyl)-1H-pyrazole-4-carboxamide, Cpd 32

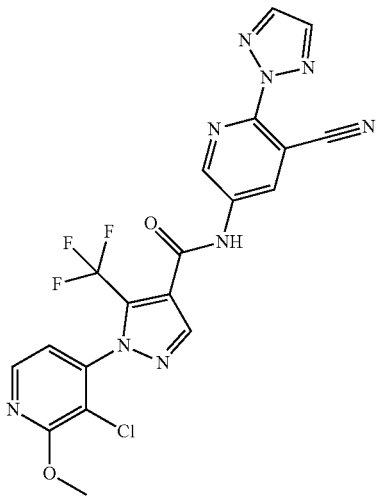 [SMILES: COc1nccc(-n2ncc(C(=O)Nc3cnc(-n4nccn4)c(C#N)c3)c2C(F)(F)F)c1Cl]

A. 3-Chloro-4-fluoro-2-methoxy-pyridine Cpd 32a

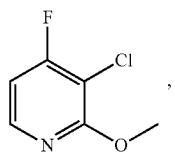

3-Chloro-2-methoxy-pyridin-4-ylamine (1.95 g, 12.296 mmol) was taken in pyridine hydrogen fluoride (15 mL) and cooled at −10° C. Sodium nitrite (1.273 g, 18.444 mmol) was added portionwise over 30 min. The mixture was allowed to come to room temperature and finally heated at 60° C. for 1 h. The mixture was poured onto crushed ice (ca 50 g). The mixture was neutralized with 1M Na$_2$CO$_3$ and organics extracted with EA (200 mL). The organic layer was further washed with brine, dried over MgSO$_4$, filtered and concentrated to the crude 3-chloro-4-fluoro-2-methoxy-pyridine as a brownish oil (2.14 g, 75%).

B. (3-Chloro-2-methoxy-pyridin-4-yl)-hydrazine Cpd 32b

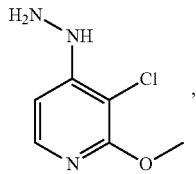

Hydrazine monohydrate (2.1 mL, 27.816 mmol) was added to a solution of 3-chloro-4-fluoro-2-methoxy-pyridine cpd 32a (2.14 g, 9.272 mmol) in ethanol (15 mL) and stirred at 80° C. overnight. The mixture was then allowed to cool to room temperature and concentrated to dark oil. Water (20 mL) and 1M Na₂CO₃ (10 mL) were added. The organics were extracted with DCM (2×40 mL). The combined extracts were dried over MgSO₄, filtered and the filtrate concentrated. Chromatography over silica gel (gradient of MeOH in DCM from 0 to 5%) afforded the desired hydrazine as a reddish solid (762 mg, 33%). MS m/z 174 (MH⁺).

C. Ethyl 1-(3-chloro-2-methoxypyridin-4-yl)-5-(trifluoromethyl)-1H-pyrazole-4-carboxylate, Cpd 32c

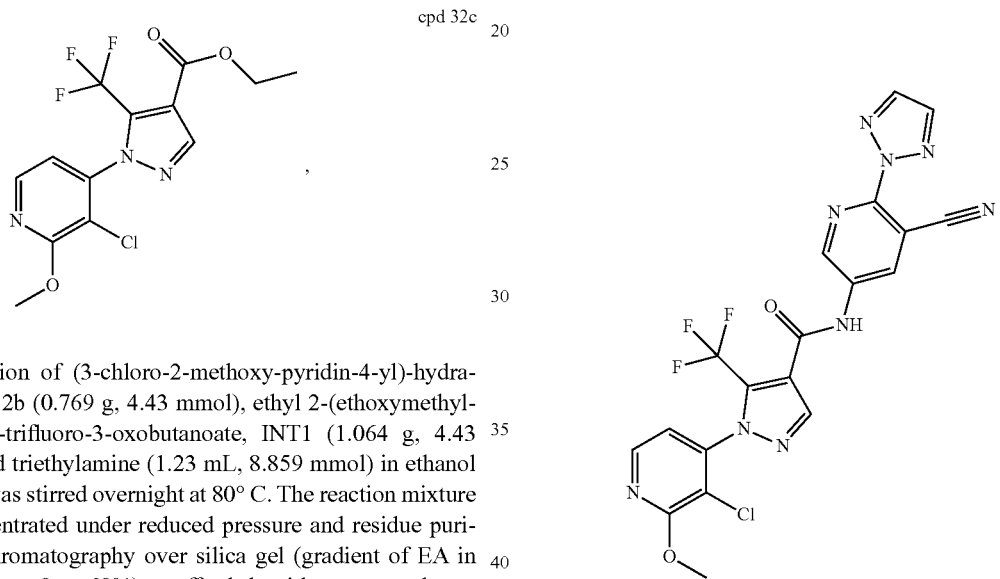

cpd 32c

A solution of (3-chloro-2-methoxy-pyridin-4-yl)-hydrazine cpd 32b (0.769 g, 4.43 mmol), ethyl 2-(ethoxymethylene)-4,4,4-trifluoro-3-oxobutanoate, INT1 (1.064 g, 4.43 mmol) and triethylamine (1.23 mL, 8.859 mmol) in ethanol (15 mL) was stirred overnight at 80° C. The reaction mixture was concentrated under reduced pressure and residue purified by chromatography over silica gel (gradient of EA in heptane from 0 to 60%) to afford the title compound as a white solid (349 mg, 21%). ¹H NMR (300 MHz, DMSO-d₆) δ 1.31 (t, J=7.1 Hz, 3H), 4.04 (s, 3H), 4.33 (q, J=7.1 Hz, 2H), 7.49 (d, J=5.3 Hz, 1H), 8.40 (d, J=5.3 Hz, 1H), 8.46 (s, 1H). MS m/z 350 (MH⁺).

C. 1-(3-Chloro-2-methoxy-pyridin-4-yl)-5-trifluoromethyl-1H-pyrazole-4-carboxylic Acid, Cpd 32d cpd 32d Lithium hydroxide (78 mg, 1.87 mmol) was added to a solution of ethyl 1-(3-chloro-2-methoxypyridin-4-yl)-5-(trifluoromethyl)-1H-pyrazole-4-carboxylate, cpd 32c (327 mg, 0.935 mmol) in THF (4 mL) and water (1 mL). The reaction was continued 18 h at room temperature before the pH was brought to 2-3 with 2N HCl. The mixture was concentrated dry. The residue was filtered through a short column of silica gel with a mixture DCM/MeOH (9/1, v/v). Removal of solvents afforded the carboxylic acid as a white crystalline solid (296 mg, 93%). MS m/z 322 (MH⁺).

E. 1-(3-Chloro-2-methoxypyridin-4-yl)-N-(5-cyano-6-(2H-1,2,3-triazol-2-yl)pyridin-3-yl)-5-(trifluoromethyl)-1H-pyrazole-4-carboxamide, Cpd 32

Oxalyl Chloride (0.158 mL, 1.841 mmol) was added to a solution of 1-(3-chloro-2-methoxy-pyridin-4-yl)-5-trifluoromethyl-1H-pyrazole-4-carboxylic acid cpd 32d (296 mg, 0.92 mmol) in DCM (10 mL) and DMF (1 drop) at room temperature. The resulting solution was then refluxed for 45 minutes and then concentrated dry. The crude acid chloride was taken in DCM (10 mL) and THF (10 mL) and 5-amino-2-[1,2,3]triazol-2-yl-nicotinonitrile, INT3 (256 mg, 1.376 mmol) was added, immediately followed by triethylamine (0.384 mL, 2.752 mmol). The reaction was continued overnight at room temperature and finally quenched with water (10 mL). After 15 min stirring, 1M Na₂CO₃ (25 mL) was added, and organics extracted with DCM (2×50 mL). The combined extracts were dried over MgSO₄, filtered and concentrated to a crude solid. Chromatography over silica gel (gradient of MeOH in DCM from 0 to 5%) afforded the contaminated title compound. Preparative LC (gradient from 30 to 73% of ACN/MeOH (1/1, v/v) in 25 mM aqueous ammonium bicarbonate) followed by extraction gave the pure product as a sticky solid. Triturating in diethyl ether led to a powder (135 mg, 29%). ¹H NMR (300 MHz, DMSO-d₆) δ 4.06 (s, 3H), 7.50 (d, J=5.3 Hz, 1H), 8.31 (s, 2H), 8.42 (d, J=5.3 Hz, 1H), 8.60 (s, 1H), 8.86 (d, J=2.5 Hz, 1H), 9.07 (d, J=2.5 Hz, 1H), 11.28 (s, 1H). MS m/z 490 (MH⁺).

Example 33

1-(3-Cyano-2-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 33

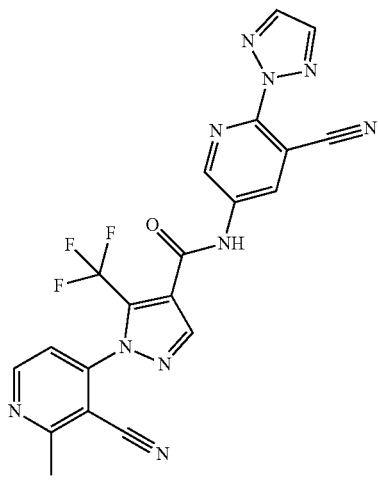 [SMILES: Cc1nccc(-n2ncc(C(=O)Nc3cnc(-n4nccn4)c(C#N)c3)c2C(F)(F)F)c1C#N]

A. 3-Bromo-4-fluoro-2-methyl-pyridine Cpd 33a

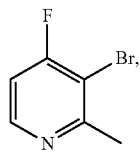

3-Bromo-2-methyl-pyridin-4-ylamine (1.98 g, 10.586 mmol) was taken in pyridine hydrogen fluoride (15 mL) and cooled at −10° C. Sodium nitrite (1.096 g, 15.879 mmol) was added portionwise over 30 min. The mixture was allowed to come to room temperature and finally heated at 60° C. for 1 h. The mixture was poured onto crushed ice (ca 50 g). The mixture was neutralized with 1M Na₂CO₃ and organics extracted with EA (200 mL). The organic layer was further washed with brine, dried over MgSO₄, filtered and the filtrate concentrated to the crude 3-bromo-4-fluoro-2-methyl-pyridine as a brownish oil, cpd 33a (1.48 g, 72%).

B. (3-Bromo-2-methyl-pyridin-4-yl)-hydrazine Cpd 33b

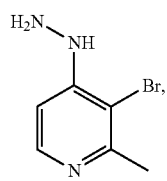

Hydrazine monohydrate (1.76 mL, 23.367 mmol) was added to a solution of 3-bromo-4-fluoro-2-methyl-pyridine, cpd 33a (1.48 g, 7.789 mmol) in ethanol (15 mL) and stirred at 80° C. overnight. The mixture was then allowed to cool to room temperature and partially concentrated till the desired product crystallized. Water was added and suspension stirred for 30 minutes. The precipitate was filtered and washed with water. Air drying afforded the pure hydrazine (737 mg, 46%). The filtrate was extracted with DCM (2×40 mL). The combined extracts were dried over MgSO₄, filtered and concentrated. Chromatography over silica gel (gradient of MeOH in DCM from 0 to 5%) afforded a second part of the desired hydrazine as an off-white solid (347 mg, 18%). MS m/z 202 (MH⁺).

C. Ethyl 1-(3-bromo-2-methylpyridin-4-yl)-5-(trifluoromethyl)-1H-pyrazole-4-carboxylate, Cpd 33c

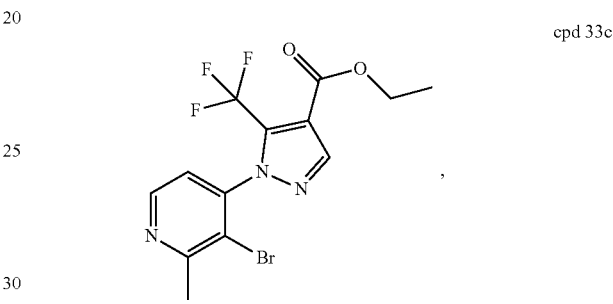

A solution of (3-bromo-2-methyl-pyridin-4-yl)-hydrazine, cpd 33b (1.084 g, 5.365 mmol), ethyl 2-(ethoxymethylene)-4,4,4-trifluoro-3-oxobutanoate, INT1 (1.289 g, 5.365 mmol) and triethylamine (1.49 mL, 10.73 mmol) in ethanol (15 mL) was stirred overnight at 80° C. The reaction mixture was concentrated under reduced pressure and residue purified by chromatography over silica gel (gradient of EA in heptane from 0 to 60%) to afford the title compound as an oil (637 mg, 31%). ¹H NMR (300 MHz, DMSO-d₆) δ 1.31 (t, J=7.1 Hz, 3H), 2.72 (s, 3H), 4.33 (q, J=7.1 Hz, 2H), 7.72 (d, J=5.1 Hz, 1H), 8.45 (s, 1H), 8.69 (d, J=5.1 Hz, 1H). MS m/z 378 (MH⁺).

D. 1-(3-bromo-2-methylpyridin-4-yl)-5-(trifluoromethyl)-1H-pyrazole-4-carboxylic Acid, Cpd 33d

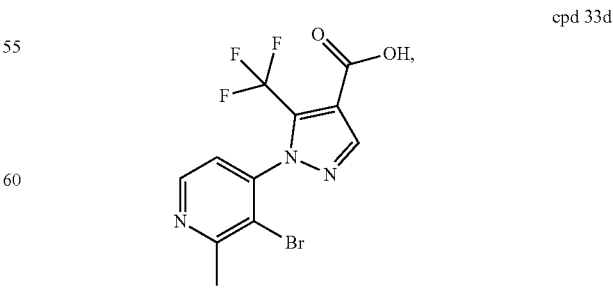

Lithium hydroxide (78 mg, 1.87 mmol) was added to a solution of ethyl 1-(3-bromo-2-methylpyridin-4-yl)-5-(trifluoromethyl)-1H-pyrazole-4-carboxylate, cpd 33c (310 mg, 0.820 mmol) in THF (4 mL) and water (1 mL). The reaction was continued 18 hours at room temperature before the pH was brought to 2-3 with 2N HCl. The mixture was concentrated dry. The residue was filtered through a short column of silica gel with a mixture DCM/MeOH (9/1, v/v). Removal of solvents afforded the carboxylic acid as an amorphous solid (262 mg, 90%). MS m/z 349 (MH$^+$).

E. 1-(3-Bromo-2-methylpyridin-4-yl)-N-(5-cyano-6-(2H-1,2,3-triazol-2-yl)pyridin-3-yl)-5-(trifluoromethyl)-1H-pyrazole-4-carboxamide Cpd 33e cpd 33e

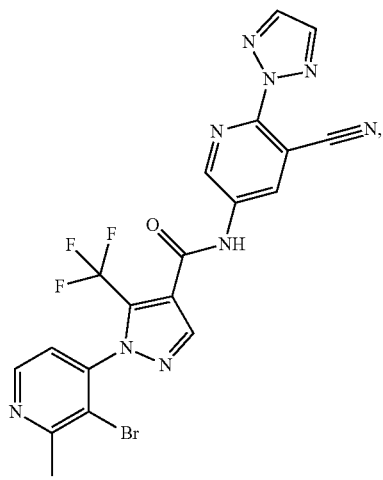

Oxalyl Chloride (0.158 mL, 1.841 mmol) was added to a solution of 1-(3-bromo-2-methyl-pyridin-4-yl)-5-trifluoromethyl-1H-pyrazole-4-carboxylic acid cpd 33d (262 mg, 0.748 mmol) in DCM (10 mL) and DMF (1 drop) at room temperature. The resulting solution was then refluxed for 45 minutes and then concentrated dry. The crude acid chloride was taken in DCM (20 mL) and THF (20 mL) and 5-amino-2-[1,2,3]triazol-2-yl-nicotinonitrile (208 mg, 1.119 mmol) was added, immediately followed by triethylamine (0.312 mL, 2.239 mmol). The reaction was continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and concentrated to a crude solid. Chromatography over silica gel (gradient of EA in heptane from 15 to 75%) afforded the title compound as a sticky solid (114 mg, 27%). MS m/z 518 (MH$^+$).

F. 1-(3-Cyano-2-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 33

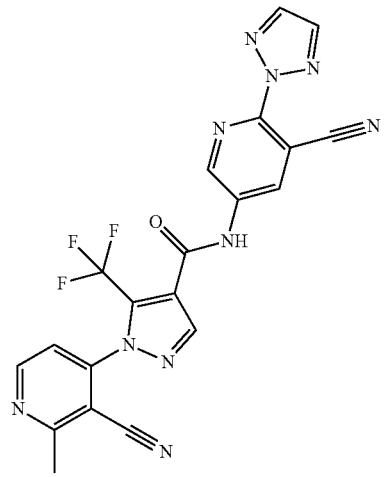 [SMILES: Cc1nccc(-n2ncc(C(=O)Nc3cnc(-n4nccn4)c(C#N)c3)c2C(F)(F)F)c1C#N]

1-(3-Bromo-2-methylpyridin-4-yl)-N-(5-cyano-6-(2H-1,2,3-triazol-2-yl)pyridin-3-yl)-5-(trifluoromethyl)-1H-pyrazole-4-carboxamide, cpd 33e (114 mg, 0.220 mmol) was taken in DMF (2 mL) and resulting solution bubbled with nitrogen for ca. 15 minutes. Copper cyanide (39 mg, 0.440 mmol) and copper iodide (5 mg, 0.028 mmol) were added and reaction vessel closed tight with a screw cap. The mixture was then heated at 140° C. for 45 minutes and then allowed to cool to room temperature. The reaction mixture was diluted with EA (50 mL), washed twice with 10% NH$_4$OH (2×30 mL), brine (20 mL), dried over MgSO$_4$, filtered and concentrated to the crude residue. Chromatography over silica gel (gradient of MeOH in DCM from 0 to 3%) gave the product as a sticky solid. Recrystallization from ACN (3 mL) afforded a white solid (43 mg, 38%). $^1$H NMR (300 MHz, DMSO-d$_6$) δ 2.84 (s, 3H), 7.88 (d, J=5.4 Hz, 1H), 8.31 (s, 2H), 8.65 (s, 1H), 8.86 (d, J=2.4 Hz, 1H), 9.04 (d, J=5.3 Hz, 1H), 9.07 (d, J=2.4 Hz, 1H), 11.38 (s, 1H). MS m/z 465 (MH$^+$).

Example 34

1-(3-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 34

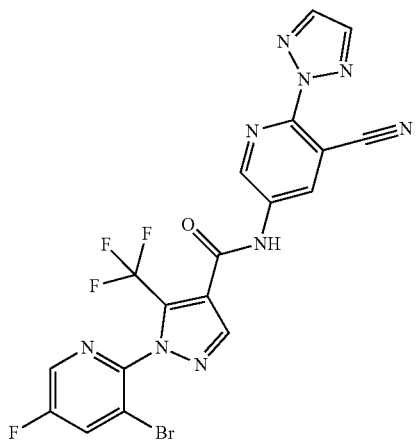 [SMILES: N#Cc1cc(NC(=O)c2cnn(-c3ncc(F)cc3Br)c2C(F)(F)F)cnc1-n1nccn1]

A. 3-Bromo-2,5-difluoro-pyridine, Cpd 34a

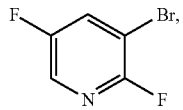

3-Bromo-5-fluoro-pyridin-2-ylamine (2.17 g, 11.361 mmol) was taken in pyridine hydrogen fluoride (15 mL) and cooled at −10° C. Sodium nitrite (1.176 g, 17.042 mmol) was added portionwise over 30 minutes. The mixture was allowed to come to room temperature and finally heated at 60° C. for 1 h. The mixture was poured onto crushed ice (ca 50 g). The mixture was neutralized with 1M $Na_2CO_3$ and organics extracted with EA (2×100 mL). The organic layers were further washed with brine, dried over $MgSO_4$, filtered and concentrated to the crude 3-bromo-2,5-difluoro-pyridine as a brownish oil (1.48 g, 66%).

B. (3-Bromo-5-fluoro-pyridin-2-yl)-hydrazine, Cpd 34b

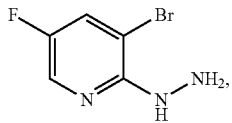

Hydrazine monohydrate (1.95 mL, 25.518 mmol) was added to a solution of 3-bromo-2,5-difluoro-pyridine, cpd 34a (1.65 g, 8.506 mmol) in ethanol (15 mL) and stirred at 80° C. overnight. The mixture was then allowed to cool to room temperature and partially concentrated till the desired product crystallized. Water was added and suspension stirred for 30 minutes. The precipitate was filtered and washed with water. Air drying afforded the pure hydrazine (1.36 g, 72%). $^1$H NMR (300 MHz, DMSO-$d_6$) δ 4.18 (s, 2H), 7.36 (s, 1H), 7.93 (dd, J=7.8, 2.5 Hz, 1H), 8.14 (d, J=2.6 Hz, 1H). MS m/z 206 (MH$^+$).

C. Ethyl 1-(3-bromo-5-fluoropyridin-2-yl)-5-(trifluoromethyl)-1H-pyrazole-4-carboxylate, Cpd 34c

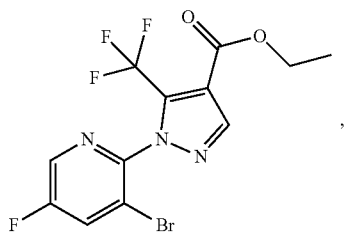

A solution of (3-bromo-5-fluoro-pyridin-2-yl)-hydrazine, cpd 34b (1.36 g, 6.601 mmol), ethyl 2-(ethoxymethylene)-4,4,4-trifluoro-3-oxobutanoate, INT1 (1.586 g, 6.601 mmol) and triethylamine (1.83 mL, 13.203 mmol) in ethanol (15 mL) was stirred overnight at 80° C. The reaction mixture was concentrated under reduced pressure and residue purified by chromatography over silica gel (gradient of EA in heptane from 0 to 60%) to afford the title compound as an oil (1.86 mg, 73%). $^1$H NMR (300 MHz, DMSO-$d_6$) δ 1.31 (t, J=7.1 Hz, 3H), 4.34 (q, J=7.1 Hz, 2H), 8.46 (s, 1H), 8.67 (dd, J=7.7, 2.6 Hz, 1H), 8.75 (d, J=2.7 Hz, 1H). MS m/z 382 (MH$^+$).

D. 1-(3-Bromo-5-fluoropyridin-2-yl)-5-(trifluoromethyl)-1H-pyrazole-4-carboxylic Acid, Cpd 34d

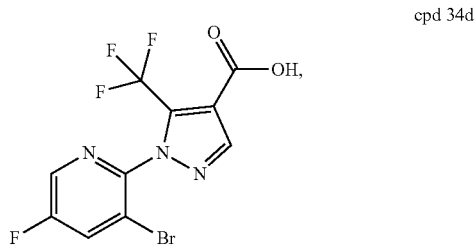 [SMILES: O=C(O)c1cnn(-c2ncc(F)cc2Br)c1C(F)(F)F]

Lithium hydroxide (180 mg, 4.287 mmol) was added to a solution of ethyl 1-(3-bromo-5-fluoropyridin-2-yl)-5-(trifluoromethyl)-1H-pyrazole-4-carboxylate, cpd 34c (819 mg, 2.143 mmol) in THF (8 mL) and water (2 mL). The reaction was continued 18 hours at room temperature before the pH was brought to 2-3 with 2N HCl. The mixture was concentrated dry. The residue was filtered through a short column of silica gel with a mixture DCM/MeOH (9/1, v/v). Removal of solvents afforded the carboxylic acid as an amorphous solid (750 mg, 98%). MS m/z 354 (MH$^+$).

E. 1-(3-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 34

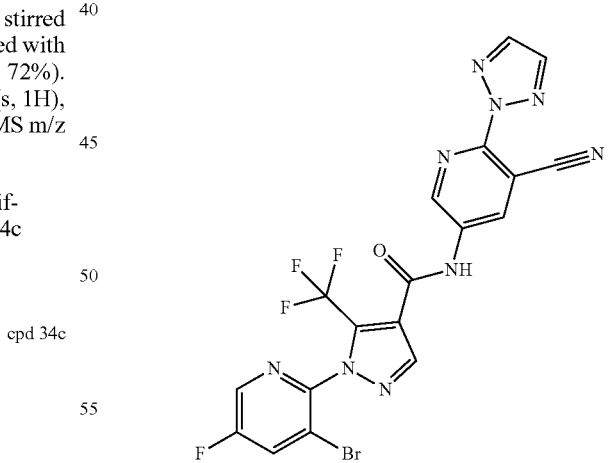

Oxalyl chloride (0.364 mL, 4.237 mmol) was added to a solution of 1-(3-bromo-5-fluoro-pyridin-2-yl)-5-trifluoromethyl-1H-pyrazole-4-carboxylic acid, cpd 34d (750 mg, 2.118 mmol) in DCM (15 mL) and DMF (1 drop) at room temperature. The resulting solution was then refluxed for 45 minutes and then concentrated dry. The crude acid chloride was taken in DCM (10 mL) and THF (30 mL) and 5-amino-2-[1,2,3]triazol-2-yl-nicotinonitrile, INT3 (591 mg, 3.177 mmol) was added, immediately followed by triethylamine (0.886 mL, 6.354 mmol). The reaction was continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and concentrated to a crude solid. Chromatography over silica gel (gradient of MeOH in DCM from 0 to 5%) afforded the compound as a sticky solid. The pure title compound was obtained after chromatography over silica gel (gradient of EA in heptane from 15 to 100%) as a white crystalline solid (252 mg, 23%). $^1$H NMR (300 MHz, DMSO-d$_6$) δ 8.31 (s, 2H), 8.59 (s, 1H), 8.70 (dd, J=7.6, 2.6 Hz, 1H), 8.78 (d, J=2.6 Hz, 1H), 8.86 (d, J=2.5 Hz, 1H), 9.07 (d, J=2.5 Hz, 1H), 11.31 (s, 1H). MS m/z 522 (MH$^+$).

Example 35

1-(3-cyano-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 35

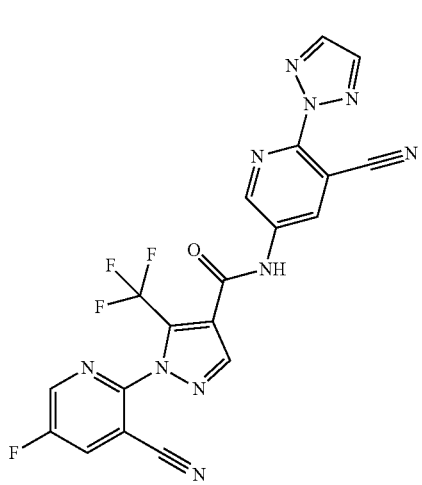 [SMILES: N#Cc1cc(NC(=O)c2cnn(-c3ncc(F)cc3C#N)c2C(F)(F)F)cnc1-n1nccn1]

1-(3-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide, cpd 34 (198 mg, 0.379 mmol) was taken in DMF (5 mL) and resulting solution bubbled with nitrogen for ca. 15 minutes. Copper cyanide (68 mg, 0.758 mmol) and copper iodide (7 mg, 0.038 mmol) were added and reaction vessel closed tight with a screw cap. The mixture was then heated at 140° C. for 90 minutes and then allowed to cool to room temperature. The reaction mixture was diluted with EA (50 mL), washed twice with 10% NH$_4$OH (2×30 mL), brine (20 mL), dried over MgSO$_4$, filtered and concentrated to the crude residue. Chromatography over silica gel (gradient of EA in heptane from 15 to 75%) gave the product as a white solid (138 mg, 77%). $^1$H NMR (300 MHz, DMSO-d$_6$) δ 8.32 (s, 2H), 8.61 (s, 1H), 8.85 (d, J=2.5 Hz, 1H), 8.92 (dd, J=7.9, 2.9 Hz, 1H), 9.02-9.10 (m, 2H), 11.43 (s, 1H). MS m/z 369 (MH$^+$).

Example 36

N-(5-Cyano-6-(2H-1,2,3-triazol-2-yl)pyridin-3-yl)-1-(3,4-dichloropyridin-2-yl)-5-(trifluoromethyl)-1H-pyrazole-4-carboxamide, Cpd 36

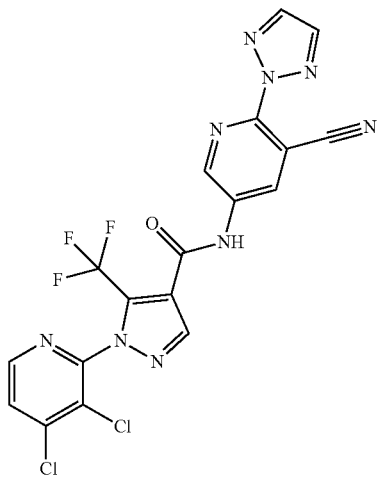 [SMILES: N#Cc1cc(NC(=O)c2cnn(-c3nccc(Cl)c3Cl)c2C(F)(F)F)cnc1-n1nccn1]

A. 3,4-Dichloro-2-fluoro-pyridine, Cpd 36a

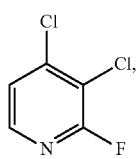

cpd 36a

3-Chloro-2-fluoro-pyridin-4-ylamine hydrochloride (2.25 g, 12.296 mmol) was taken in pyridine hydrogen fluoride (15 mL) and cooled at −10° C. Sodium nitrite (1.273 g, 18.444 mmol) was added portionwise over 30 minutes. The mixture was allowed to come to room temperature and finally heated at 60° C. for 1 hour. The mixture was poured onto crushed ice (ca 50 g). The mixture was neutralized with 1M Na$_2$CO$_3$ and organics extracted with EA (200 mL). The organic layers were further washed with brine, dried over MgSO$_4$, filtered and concentrated to the crude 3,4-dichloro-2-fluoro-pyridine as a brown solid (1.09 g, 50%). MS m/z 165 (MH$^+$).

B. (3,4-Dichloro-pyridin-2-yl)-hydrazine, Cpd 36b

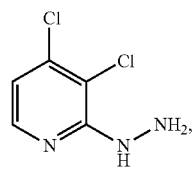

cpd 36b

Hydrazine monohydrate (1.48 mL, 19.701 mmol) was added to a solution of 3,4-dichloro-2-fluoro-pyridine, cpd 36a (1.09 g, 6.567 mmol) in ethanol (15 mL) and stirred at 60° C. overnight. The mixture was then allowed to cool to room temperature and partially concentrated till the desired product crystallized. Water was added and suspension stirred for 30 minutes. The precipitate was filtered and washed with water to afford the crude hydrazine (487 mg, 50%). MS m/z 178 (MH$^+$).

C. Ethyl 1-(3,4-dichloropyridin-2-yl)-5-(trifluoromethyl)-1H-pyrazole-4-carboxylate, Cpd 36c

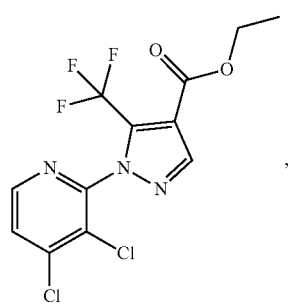

A solution of (3,4-dichloro-pyridin-2-yl)-hydrazine, cpd 36b (487 mg, 2.736 mmol), ethyl 2-(ethoxymethylene)-4,4,4-trifluoro-3-oxobutanoate, INT1 (657 mg, 2.736 mmol) and triethylamine (0.763 mL, 5.471 mmol) in ethanol (15 mL) was stirred overnight at 80° C. The reaction mixture was concentrated under reduced pressure and residue purified by chromatography over silica gel (gradient of EA in heptane from 0 to 25%) to afford the title compound as a clear oil (646 mg, 66%). $^1$H NMR (300 MHz, Chloroform-d) δ 1.39 (t, J=7.1 Hz, 3H), 4.39 (q, J=7.1 Hz, 2H), 7.63 (d, J=5.2 Hz, 1H), 8.22 (s, 1H), 8.41 (d, J=5.2 Hz, 1H). MS m/z 354 (MH$^+$).

D. 1-(3,4-Dichloro-pyridin-2-yl)-5-trifluoromethyl-1H-pyrazole-4-carboxylic Acid, Cpd 36d

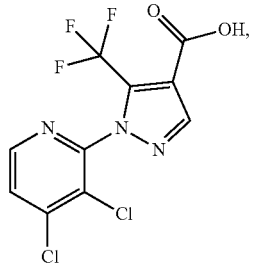

Ethyl 1-(3,4-dichloropyridin-2-yl)-5-(trifluoromethyl)-1H-pyrazole-4-carboxylate, cpd 36c (643 mg, 1.79 mmol) and lithium hydroxide (150 mg, 3.581 mmol) were stirred at room temperature in THF (6 mL) and water (2 mL). The reaction was continued 18 hours before the pH was brought to 2-3 with 2N HCl. The mixture was concentrated dry. The residue was filtered through a short column of silica gel with a mixture DCM/MeOH (9/1, v/v) to give the carboxylic acid as a white solid (645 mg, 109%). MS m/z 326 (MH$^+$).

E. N-(5-cyano-6-(2H-1,2,3-triazol-2-yl)pyridin-3-yl)-1-(3,4-dichloropyridin-2-yl)-5-(trifluoromethyl)-1H-pyrazole-4-carboxamide, Cpd 36

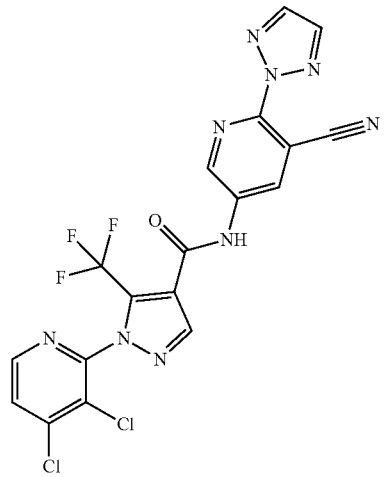 [SMILES: N#Cc1cc(NC(=O)c2cnn(-c3nccc(Cl)c3Cl)c2C(F)(F)F)cnc1-n1nccn1]

1-(3,4-Dichloro-pyridin-2-yl)-5-trifluoromethyl-1H-pyrazole-4-carboxylic acid, cpd 36e (645 mg, 1.978 mmol) was treated with oxalyl chloride (0.34 mL, 3.956 mmol) in DCM (15 mL) and DMF (1 drop) at room temperature. The mixture was then refluxed for 45 minutes and then concentrated dry. The crude acid chloride was taken in DCM (10 mL) and THF (30 mL) and 5-amino-2-[1,2,3]triazol-2-yl-nicotinonitrile, INT3 (552 mg, 2.967 mmol) was added, immediately followed by triethylamine (0.827 mL, 5.934 mmol). The reaction was continued overnight at room temperature and finally quenched with water (10 mL). After 15 minutes of stirring, 1M Na$_2$CO$_3$ (25 mL) was added, and organics extracted with DCM (2×50 mL). The combined extracts were dried over MgSO$_4$, filtered and the filtrate concentrated to a crude solid. Chromatography over silica gel (gradient of MeOH in DCM from 0 to 3%) afforded the compound as a sticky solid. The pure title compound was obtained after preparative LC (gradient from 30 to 73% of ACN/MeOH (1/1, v/v) in 25 mM aqueous ammonium bicarbonate) followed by extraction. Triturating in diethyl ether led to a white powder (233 mg, 24%). $^1$H NMR (300 MHz, DMSO-d$_6$) δ 8.17 (d, J=5.3 Hz, 1H), 8.31 (s, 2H), 8.59-8.73 (m, 2H), 8.88 (d, J=2.4 Hz, 1H), 9.11 (d, J=2.4 Hz, 1H), 11.43 (s, 1H). MS m/z 326 (MH$^+$).

Example 37

N-(5-chloro-6-(2H-1,2,3-triazol-2-yl)pyridin-3-yl)-1-(4-cyano-2-methylphenyl)-5-(trifluoromethyl)-1H-pyrazole-4-carboxamide, Cpd 37

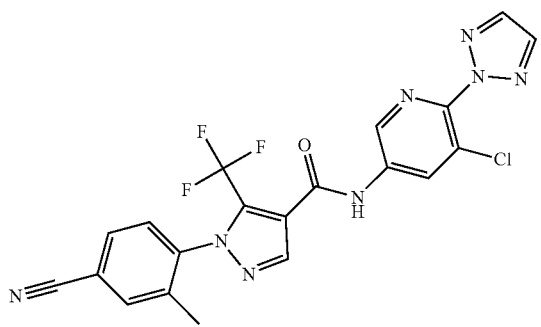 [SMILES: Cc1cc(C#N)ccc1-n1ncc(C(=O)Nc2cnc(-n3nccn3)c(Cl)c2)c1C(F)(F)F]

A. 4-Hydrazinyl-3-methylbenzonitrile, Cpd 37a

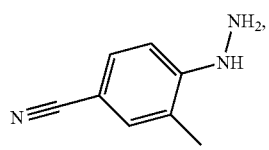

cpd 37a

The mixture of {Pd(cinnamyl)Cl}$_2$ (85.4 mg, 0.165 mmol) and Mor-DalPhos (152.9 mg, 0.33 mmol) in dioxane (5 mL) was evacuated with argon 4 times. The resulting clear yellow solution was stirred at room temp under argon for 10 min. 4-Chloro-3-methylbenzonitrile (500 mg, 3.30 mmol) and sodium t-butoxide (633.3 mg, 6.60 mmol) was added to the mixture and the mixture was evacuated with argon 4 times. The resulting yellow reaction was stirred at room temp for 5 min and was then treated with hydrazine monohydrate (337 mg, 6.60 mmol) via syringe. The reaction was evacuated with argon 4 times. Then the mixture was stirred at 50° C. under argon for 2 h. The mixture was filtered and washed with ethyl acetate (50 mL×3). The filtrate was collected and concentrated to give the product as yellow solid for next step directly.

B. Ethyl 1-(4-cyano-2-methylphenyl)-5-(trifluoromethyl)-1H-pyrazole-4-carboxylate, Cpd 37b

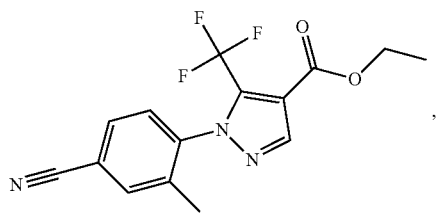

cpd 37b

A solution of 4-hydrazinyl-3-methylbenzonitrile, cpd 37a (560 mg, 3.80 mmol), ethyl 2-(ethoxymethylene)-4,4,4-trifluoro-3-oxobutanoate, INT1 (1.371 g, 5.71 mmol) and triethylamine (1.153 g, 11.42 mmol) in ethanol (10 mL) was stirred at 80° C. for 10 h. The reaction mixture was concentrated under reduced pressure and residue purified by chromatography over silica gel (petroleum ether/ethyl acetate from 100:1 to 20:1) to afford the title compound as a brown oil (670 mg, 51%). MS m/z 323.9 (MH$^+$).

C. 1-(4-Cyano-2-methylphenyl)-5-(trifluoromethyl)-1H-pyrazole-4-carboxylic Acid, Cpd 37c

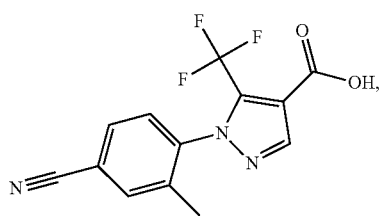

cpd 37c

Ethyl 1-(4-cyano-2-methylphenyl)-5-(trifluoromethyl)-1H-pyrazole-4-carboxylate, cpd 37b (670 mg, 1.93 mmol) and lithium hydroxide (162 mg, 3.86 mmol) were stirred at room temperature in THF (10 mL) and water (10 mL) for 3 h. The mixture was added 5% KHSO$_4$ to adjust pH 3-4. Water (100 mL) and ethyl acetate (100 mL) were added to the mixture. The organic layer was washed with brine (50 mL), dried over MgSO$_4$ and concentrated under reduced pressure to give the product as a brown solid for next step directly. Yield: 610 mg, 106.9%.

D. N-(5-chloro-6-(2H-1,2,3-triazol-2-yl)pyridin-3-yl)-1-(4-cyano-2-methylphenyl)-5-(trifluoromethyl)-1H-pyrazole-4-carboxamide, Cpd 37

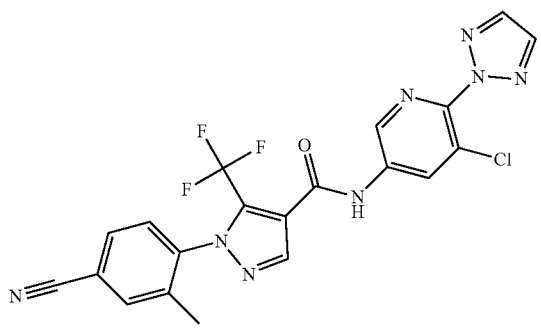 [SMILES: Cc1cc(C#N)ccc1-n1ncc(C(=O)Nc2cnc(-n3nccn3)c(Cl)c2)c1C(F)(F)F]

1-(4-Cyano-2-methylphenyl)-5-(trifluoromethyl)-1H-pyrazole-4-carboxylic acid, cpd 37c (250 mg, 0.847 mmol) was treated with oxalyl chloride (260 mg, 1.694 mmol) in DCM (15 mL) and DMF (1 drop) at room temperature. The mixture was then stirred for 45 minutes and then concentrated dry. The crude acid chloride was taken in DCM (10 mL) and 5-chloro-6-(2H-1,2,3-triazol-2-yl)pyridin-3-amine, INT2 (198.8 mg, 1.016 mmol) was added, immediately followed by pyridine (167 mg, 2.12 mmol). The reaction was stirred at room temperature for 3 hours and finally quenched with water (50 mL) and extracted with DCM (2×50 mL). The combined extracts were dried over MgSO$_4$, filtered and concentrated to a crude solid. The crude was purified by HPLC to give N-(5-chloro-6-(2H-1,2,3-triazol-2-yl)pyridin-3-yl)-1-(4-cyano-2-methylphenyl)-5-(trifluoromethyl)-1H-pyrazole-4-carboxamide, cpd 37 (129.5 mg, 32%). $^1$H NMR (400 MHz, DMSO-d$_6$) δ ppm 11.26 (s, 1H), 8.82 (d, J=2.21 Hz, 1H), 8.64 (d, J=2.21 Hz, 1H), 8.54 (s, 1H), 8.16 (s, 2H), 8.04 (s, 1H), 7.91 (dd, J=8.16, 1.54 Hz, 1H), 7.72 (d, J=8.16 Hz, 1H), 2.04 (s, 3H). LC-MS: (ES, m/z): [M+1]$^+$ 472.9.

Example 38

N-(5-cyano-6-(2H-1,2,3-triazol-2-yl)pyridin-3-yl)-1-(2-methoxy-3-methylpyridin-4-yl)-5-(trifluoromethyl)-1H-pyrazole-4-carboxamide, Cpd 38

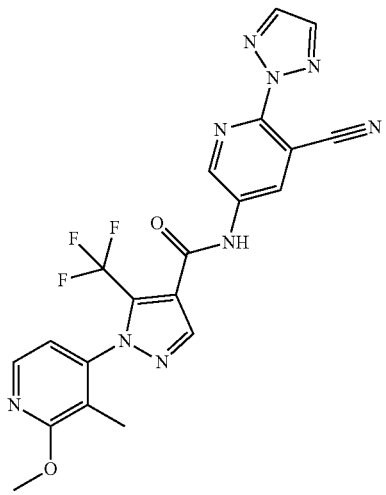 [SMILES: COc1nccc(-n2ncc(C(=O)Nc3cnc(-n4nccn4)c(C#N)c3)c2C(F)(F)F)c1C]

A. 3-Bromo-2-methoxy-pyridin-4-ylamine, Cpd 38a

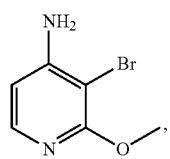

A solution of bromosuccimide (2.15 g, 12.083 mmol) in DCM (25 mL) was added dropwise to a solution of 2-methoxy-pyridin-4-ylamine (1.5 g, 12.083 mmol) in DCM (85 mL) maintaining the temperature below 5° C. The reaction was continued for 30 minutes and then concentrated dry. The residue was taken in EA (50 mL) and washed with water (40 mL) and brine (20 mL). Drying over MgSO$_4$, filtering, and solvent removal afforded the crude product that further purified by chromatography over silica gel (gradient of EA in heptane from 0 to 30%) to a pure oil (2.23 g, 90%). $^1$H NMR (300 MHz, Chloroform-d) δ 3.96 (s, 3H), 4.59 (s, 2H), 6.28 (d, J=5.6 Hz, 1H), 7.72 (d, J=5.6 Hz, 1H). MS m/z 203 (MH$^+$).

B. 3-Bromo-4-fluoro-2-methoxy-pyridine, Cpd 38b

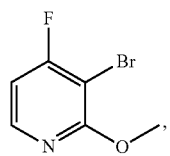

3-Bromo-2-methoxy-pyridin-4-ylamine, cpd 38a (2.2 g, 110.835 mmol) was taken in pyridine hydrogen fluoride (15 mL) and cooled at −10° C. Sodium nitrite (1.121 g, 16.253 mmol) was added portionwise over 30 minutes. The mixture was allowed to come to room temperature and finally heated at 60° C. for 1 hour. The mixture was poured onto crushed ice (ca 50 g). The mixture was neutralized with 1M Na$_2$CO$_3$ and organics extracted with EA (2×100 mL). The organic layers were further washed with brine, dried over MgSO$_4$, filtered and concentrated to the pure 3-bromo-4-fluoro-2-methoxy-pyridine (1.78 g, 79%). $^1$H NMR (300 MHz, Chloroform-d) δ 4.02 (s, 3H), 6.72 (dd, J=7.3, 5.6 Hz, 1H), 8.03 (dd, J=7.9, 5.5 Hz, 1H).

C. (3-Bromo-2-methoxy-pyridin-4-yl)-hydrazine Cpd 38c

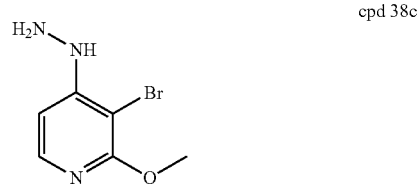

A solution of 3-bromo-4-fluoro-2-methoxy-pyridine, cpd 38b (1.75 g, 8.495 mmol) and hydrazine monohydrate (1.92 mL, 25.484 mmol) was heated at 80° C. in dioxane (15 mL) for 16 hours. The mixture was then allowed to cool to room temperature and concentrated to dark oil. Water (20 mL) and 1M Na$_2$CO$_3$ (10 mL) were added. The organics were extracted with DCM (2×40 mL). The combined extracts were dried over MgSO$_4$, filtered and concentrated. Chromatography over silica gel (gradient of MeOH in DCM from 0 to 5%) afforded the desired hydrazine as a beige solid (1.51 g, 81%). $^1$H NMR (300 MHz, DMSO-d$_6$) δ 3.82 (s, 3H), 4.35 (s, 2H), 6.76 (d, J=5.7 Hz, 1H), 7.19 (s, 1H), 7.73 (d, J=5.7 Hz, 1H). MS m/z 218 (MH$^+$).

D. Ethyl 1-(3-bromo-2-methoxypyridin-4-yl)-5-(trifluoromethyl)-1H-pyrazole-4-carboxylate, Cpd 38d

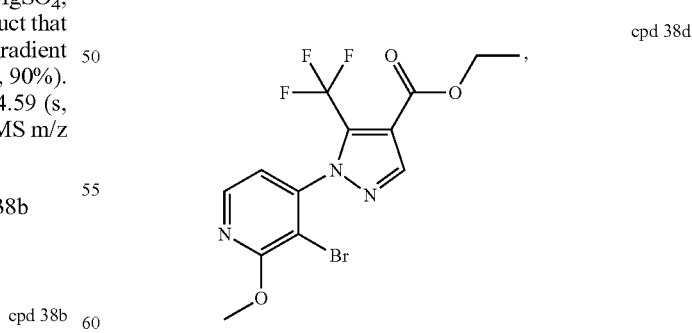

A solution of (3-bromo-2-methoxy-pyridin-4-yl)-hydrazine, cpd 38c (1.5 g, 6.879 mmol), ethyl 2-(ethoxymethylene)-4,4,4-trifluoro-3-oxobutanoate, INT 1 (1.65 g, 6.879 mmol) and triethylamine (1.92 mL, 13.758 mmol) in ethanol (25 mL) was stirred overnight at 80° C. The reaction mixture was concentrated under reduced pressure and residue purified by chromatography over silica gel (gradient of EA in heptane from 0 to 25%) to afford the title compound as a yellow oil (1.02 g, 36%). $^1$H NMR (300 MHz, chloroform-d) δ 1.39 (t, J=7.2 Hz, 3H), 4.09 (s, 3H), 4.39 (q, J=7.2 Hz, 2H), 6.95 (d, J=5.2 Hz, 1H), 8.20 (s, 1H), 8.24 (d, J=5.2 Hz, 1H). MS m/z 394 (MH$^+$).

E. Ethyl 1-(2-methoxy-3-methylpyridin-4-yl)-5-(trifluoromethyl)-1H-pyrazole-4-carboxylate, cpd 38e (VILL_chrocaboy_22472)

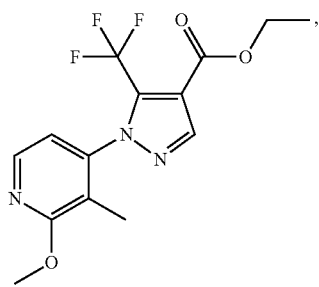

cpd 38e

A solution of ethyl 1-(3-bromo-2-methoxypyridin-4-yl)-5-(trifluoromethyl)-1H-pyrazole-4-carboxylate, cpd 38d (926 mg, 2.349 mmol) and trimethylboroxine (0.656 mL, 4.699 mmol) in dioxane (15 mL) and water (2 mL) was bubbled with nitrogen. K$_2$CO$_3$ (649 mg, 4.699 mmol) and Pd(dppf)Cl$_2$ (211 mg, 0.235 mmol) were added. The resulting mixture was heated at 100° C. for 1 hour and then allowed to cool to room temperature. The mixture was diluted with EA (50 mL) and washed with brine (20 mL). The aqueous layer was extracted back with EA (25 mL) and combined organic layers dried over MgSO$_4$, filtered and concentrated to the crude residue. Chromatography over silica gel (gradient of EA in heptane from 0 to 30%) afforded ethyl 1-(2-methoxy-3-methylpyridin-4-yl)-5-(trifluoromethyl)-1H-pyrazole-4-carboxylate as a colorless oil. $^1$H NMR (300 MHz, Chloroform-d) δ 1.38 (t, J=7.1 Hz, 3H), 1.89 (s, 3H), 4.02 (s, 3H), 4.38 (q, J=7.1 Hz, 2H), 6.80 (d, J=5.4 Hz, 1H), 8.12 (d, J=5.4 Hz, 1H), 8.16 (s, 1H). MS m/z 330 (MH$^+$).

F. 1-(2-Methoxy-3-methyl-pyridin-4-yl)-5-trifluoromethyl-1H-pyrazole-4-carboxylic Acid, Cpd 38f

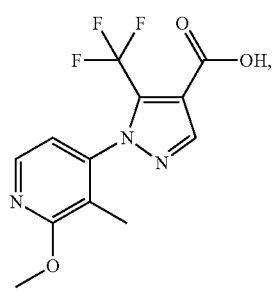

cpd 38f

Ethyl 1-(2-methoxy-3-methylpyridin-4-yl)-5-(trifluoromethyl)-1H-pyrazole-4-carboxylate, cpd 38e (642 mg, 1.95 mmol) and lithium hydroxide (164 mg, 3.899 mmol) were stirred at room temperature in THF (8 mL) and water (2 mL). The reaction was continued 18 hours before the pH was brought to 2-3 with 2N HCl. The mixture was concentrated dry. The residue was filtered through a short column of silica gel with a mixture DCM/MeOH (9/1, v/v) to give the carboxylic acid as a white solid (675 mg, 103%). MS m/z 302 (MH$^+$).

G. N-(5-cyano-6-(2H-1,2,3-triazol-2-yl)pyridin-3-yl)-1-(2-methoxy-3-methylpyridin-4-yl)-5-(trifluoromethyl)-1H-pyrazole-4-carboxamide, Cpd 38

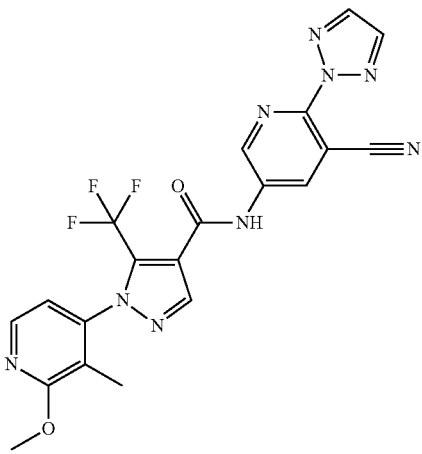 [SMILES: COc1nccc(-n2ncc(C(=O)Nc3cnc(-n4nccn4)c(C#N)c3)c2C(F)(F)F)c1C]

Oxalyl Chloride (0.385 mL, 4.482 mmol) was added to a solution of 1-(2-methoxy-3-methyl-pyridin-4-yl)-5-trifluoromethyl-1H-pyrazole-4-carboxylic acid, cpd 38e (675 mg, 2.241 mmol) in DCM (15 mL) and DMF (1 drop) and mixture refluxed for 45 minutes. Upon completion, the solution was concentrated dry. The crude acid chloride was taken in DCM (10 mL) and THF (30 mL) and 5-amino-2-[1,2,3]triazol-2-yl-nicotinonitrile (626 mg, 3.362 mmol) was added, immediately followed by triethylamine (0.937 mL, 6.723 mmol). The reaction was continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and concentrated to a crude solid. Filtration through a short column of silica gel (gradient of MeOH in DCM from 0 to 5%) afforded the title compound as a sticky solid. Final purification was performed by preparative LC (gradient from 30 to 73% of ACN/MeOH (1/1, v/v) in 25 mM aqueous ammonium bicarbonate) followed by extraction. Triturating in diethyl ether (2 mL) led to a white solid (137 mg, 13%). $^1$H NMR (300 MHz, DMSO-d$_6$) δ 1.86 (s, 3H), 3.99 (s, 3H), 7.17 (d, J=5.4 Hz, 1H), 8.25 (d, J=5.4 Hz, 1H), 8.31 (s, 2H), 8.53 (s, 1H), 8.85 (d, J=2.5 Hz, 1H), 9.07 (d, J=2.5 Hz, 1H), 11.28 (s, 1H). MS m/z 470 (MH$^+$).

Example 39

1-(2-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 39

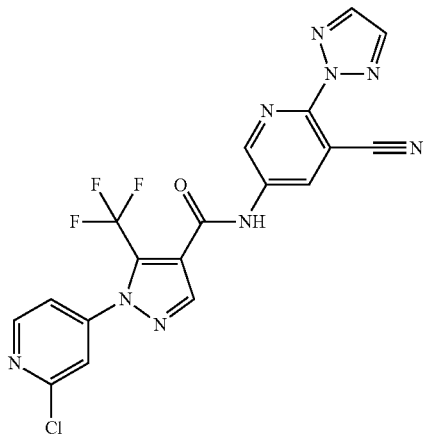 [SMILES: N#Cc1cc(NC(=O)c2cnn(-c3ccnc(Cl)c3)c2C(F)(F)F)cnc1-n1nccn1]

A. Ethyl 1-(2-chloropyridin-4-yl)-5-(trifluoromethyl)-1H-pyrazole-4-carboxylate, Cpd 39a

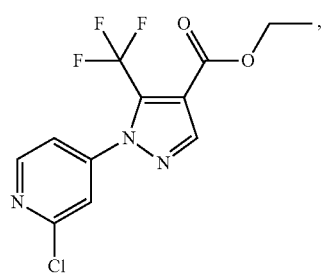

A solution of (2-chloro-pyridin-4-yl)-hydrazine (1.0 g, 6.965 mmol), ethyl 2-(ethoxymethylene)-4,4,4-trifluoro-3-oxobutanoate, INT1 (1.67 g, 6.965 mmol) and triethylamine (1.92 mL, 13.758 mmol) in ethanol (25 mL) was stirred overnight at 80° C. The reaction mixture was concentrated under reduced pressure and residue purified by chromatography over silica gel (gradient of EA in heptane from 0 to 25%) to afford the title compound as a clear oil (765 mg, 34%). $^1$H NMR (300 MHz, chloroform-d) δ 1.39 (t, J=7.2 Hz, 3H), 4.39 (q, J=7.2 Hz, 2H), 7.26 (s, OH), 7.36 (d, J=5.5 Hz, 1H), 7.51 (d, J=1.9 Hz, 1H), 8.16 (s, 1H), 8.57 (d, J=5.4 Hz, 1H). MS m/z 320 (MH$^+$).

B. 1-(2-Chloro-pyridin-4-yl)-5-trifluoromethyl-1H-pyrazole-4-carboxylic Acid, Cpd 39b

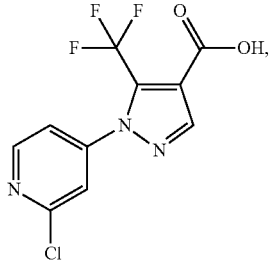

Ethyl 1-(2-chloropyridin-4-yl)-5-(trifluoromethyl)-1H-pyrazole-4-carboxylate, cpd 39a (758 mg, 2.371 mmol) and lithium hydroxide (199 mg, 4.742 mmol) were stirred at room temperature in THF (8 mL) and water (2 mL). The reaction was continued 18 hours before the pH was brought to 2-3 with 2N HCl. The mixture was concentrated dry. The residue was filtered through a short column of silica gel with a mixture DCM/MeOH (9/1, v/v) to give the carboxylic acid as a white solid (882 mg, 122%). MS m/z 292 (MH$^+$).

C. 1-(2-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 39

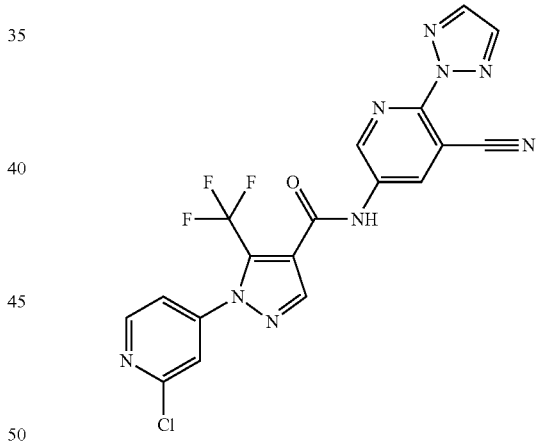

1-(2-Chloro-pyridin-4-yl)-5-trifluoromethyl-1H-pyrazole-4-carboxylic acid, cpd 39b (691 mg, 2.371 mmol) was treated with oxalyl chloride (0.407 mL, 4.742 mmol) in DCM (15 mL) and DMF (1 drop) at room temperature. The mixture was then refluxed for 45 minutes and then concentrated dry. The crude acid chloride was taken in DCM (10 mL) and THF (30 mL) and 5-amino-2-[1,2,3]triazol-2-yl-nicotinonitrile, INT3 (662 mg, 3.557 mmol) was added, immediately followed by triethylamine (0.991 mL, 7.113 mmol). The reaction was continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and concentrated to a crude solid. Chromatography over silica gel (gradient of MeOH in DCM from 0 to 3%) afforded the compound as a sticky solid. The pure title compound was obtained after preparative LC (gradient from 30 to 73% of ACN/MeOH (1/1, v/v) in 25 mM aqueous ammonium bicarbonate) followed by extraction. Triturating in diethyl ether led to a white powder (225 mg, 20%). $^1$H NMR (300 MHz, DMSO-d$_6$) δ 7.75 (dd, J=5.4, 1.8 Hz, 1H), 7.94 (d, J=1.8 Hz, 1H), 8.31 (s, 2H), 8.56 (s, 1H), 8.71 (d, J=5.4 Hz, 1H), 8.85 (d, J=2.5 Hz, 1H), 9.07 (d, J=2.5 Hz, 1H), 11.34 (s, 1H). MS m/z 460 (MH$^+$).

Example 40

N-(5-cyano-6-(2H-1,2,3-triazol-2-yl)pyridin-3-yl)-1-(2-cyanopyridin-4-yl)-5-(trifluoromethyl)-1H-pyrazole-4-carboxamide, Cpd 40

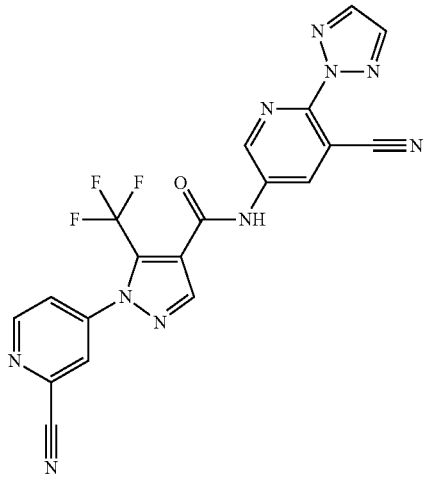 [SMILES: N#Cc1cc(-n2ncc(C(=O)Nc3cnc(-n4nccn4)c(C#N)c3)c2C(F)(F)F)ccn1]

1-(2-Chloropyridin-4-yl)-N-(5-cyano-6-(2H-1,2,3-triazol-2-yl)pyridin-3-yl)-5-(trifluoromethyl)-1H-pyrazole-4-carboxamide, cpd 39 (174 mg, 0.378 mmol) was taken in DMA (5 mL). Pd(dppf)Cl$_2$ (17 mg, 0.019 mmol) and Zn(0) (0.5 mg, 0.008 mmol) were added while bubbling nitrogen. Finally zinc cyanide (27 mg, 0.227 mmol) was added and the mixture heated at 140° C. for 2 hours. The reaction was allowed to cool to room temperature and diluted with EA (30 mL) and water (20 mL). The biphase was filtered through a short pad of diatomaceous earth, that was further rinsed with EA (2×10 mL). The organic layer was separated, washed with brine, dried over MgSO$_4$, filtered and the filtrate concentrated dry. The residue was purified by column chromatography over silica gel (gradient of MeOH in DCM from 0 to 5%) to afford a beige solid. Triturating in ACN and filtration afforded the pure compound as a white solid (116 mg, 67%). $^1$H NMR (300 MHz, DMSO-d$_6$) δ 8.07 (dd, J=5.3, 2.1 Hz, 1H), 8.32 (s, 2H), 8.49 (d, J=2.0 Hz, 1H), 8.59 (s, 1H), 8.85 (d, J=2.5 Hz, 1H), 9.00-9.11 (m, 2H), 11.35 (s, 1H). MS m/z 451 (MH$^+$).

Example 41

N-(5-Cyano-6-(2H-1,2,3-triazol-2-yl)pyridin-3-yl)-1-(2-methoxypyridin-4-yl)-5-(trifluoromethyl)-1H-pyrazole-4-carboxamide, Cpd 41

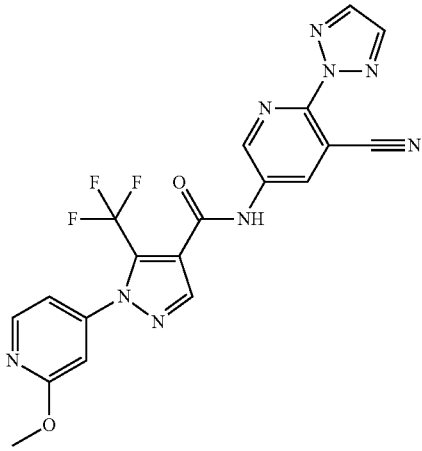 [SMILES: COc1cc(-n2ncc(C(=O)Nc3cnc(-n4nccn4)c(C#N)c3)c2C(F)(F)F)ccn1]

A. 1-(2-Methoxy-pyridin-4-yl)-5-trifluoromethyl-1H-pyrazole-4-carboxylic Acid, Cpd 41a

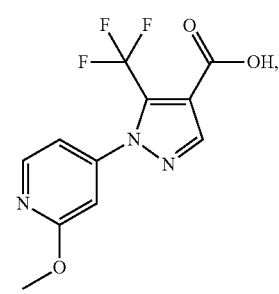

Ethyl 1-(2-chloropyridin-4-yl)-5-(trifluoromethyl)-1H-pyrazole-4-carboxylate, cpd 39a (1.38 g, 4.137 mmol) and K$_2$CO$_3$ (1.193 g, 8.634 mmol) were taken in MeOH (30 mL) and refluxed overnight. The mixture was allowed to cool to room temperature and pH adjusted to 2-3 with 2N HCl. The reaction mixture was concentrated dry. The residue was filtered through a column of silica gel with DCM/MeOH (9/1, v/v) to afford the title compound as a white solid (1.0 g, 79%). MS m/z 288 (MH$^+$).

B. N-(5-Cyano-6-(2H-1,2,3-triazol-2-yl)pyridin-3-yl)-1-(2-methoxypyridin-4-yl)-5-(trifluoromethyl)-1H-pyrazole-4-carboxamide, Cpd 41

Example 42

N-(5-cyano-6-(2H-1,2,3-triazol-2-yl)pyridin-3-yl)-1-(2,3-dimethylpyridin-4-yl)-5-(trifluoromethyl)-1H-pyrazole-4-carboxamide, Cpd 42

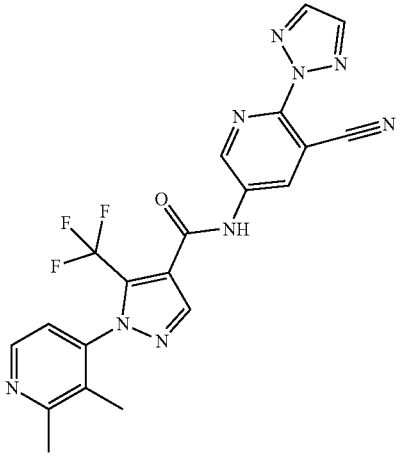 [SMILES: Cc1nccc(-n2ncc(C(=O)Nc3cnc(-n4nccn4)c(C#N)c3)c2C(F)(F)F)c1C]

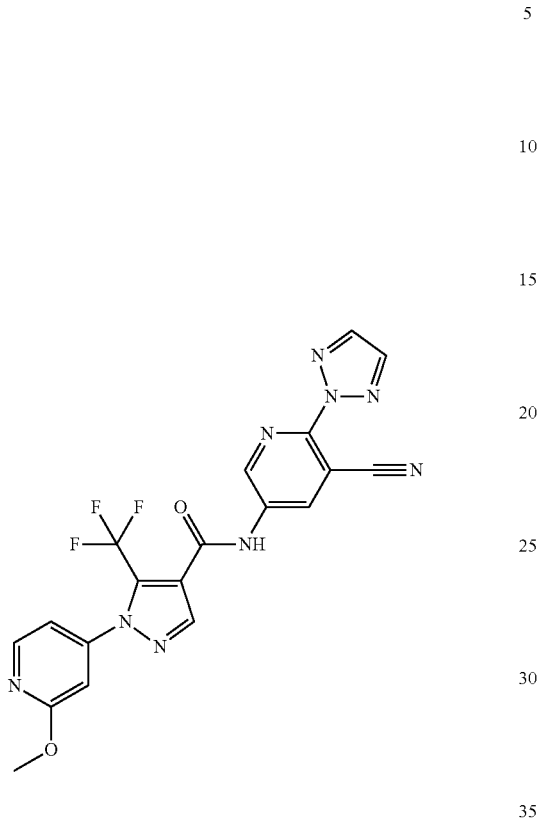

A. (2,3-Dimethyl-pyridin-4-yl)-hydrazine, Cpd 42a

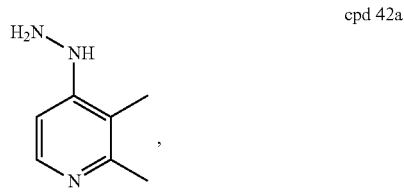

cpd 42a 1-(2-Methoxy-pyridin-4-yl)-5-trifluoromethyl-1H-pyrazole-4-carboxylic acid, cpd 41a (0.5 g, 1.741 mmol) was treated with oxalyl chloride (0.299 mL, 3.482 mmol) in DCM (15 mL) and DMF (1 drop) at reflux. After 45 minutes, the reaction mixture was concentrate dry. The crude acid chloride was taken in DCM (10 mL) and THF (30 mL) and 5-amino-2-[1,2,3]triazol-2-yl-nicotinonitrile (626 mg, 3.362 mmol) was added, immediately followed by the addition of triethylamine (0.937 mL, 6.723 mmol). The reaction was continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and concentrated to a crude solid. Chromatography over silica gel (gradient of MeOH in DCM from 0 to 5%) afforded the compound as a sticky solid. The pure title compound was obtained after preparative LC (gradient from 30 to 73% of ACN/MeOH (1/1, v/v) in 0.1% aqueous formic acid) followed by DCM/1M Na$_2$CO$_3$ extraction. N-(5-cyano-6-(2H-1,2,3-triazol-2-yl)pyridin-3-yl)-1-(2-methoxypyridin-4-yl)-5-(trifluoromethyl)-1H-pyrazole-4-carboxamide was obtained as a white solid (140 mg, 34%). $^1$H NMR (300 MHz, DMSO-d$_6$) δ 3.96 (s, 3H), 7.11 (d, J=1.8 Hz, 1H), 7.19-7.33 (m, 1H), 8.31 (s, 2H), 8.43 (d, J=5.5 Hz, 1H), 8.49 (s, 1H), 8.84 (d, J=2.4 Hz, 1H), 9.05 (d, J=2.5 Hz, 1H), 11.31 (s, 1H). MS m/z 456 (MH$^+$).

Hydrazine monohydrate (5.74 mL, 76.143 mmol) was added to a solution of 4-chloro-2,3-dimethyl-pyridine 1-oxide (4.0 g, 25.381 mmol) in dioxane (15 mL) and stirred at 140° C. in a sealed tube for 96 hours. The mixture was then allowed to cool to room temperature and concentrated dry. The residue was submitted to flash chromatography over silica gel (gradient of DCM/MeOH/NH$_4$OH, 9.0/0.9/0.1, v/v/v in DCM from 0 to 100%) to afford a white solid (1.72 g, 37%). MS m/z 138 (MH$^+$).

B. Ethyl 1-(2,3-dimethylpyridin-4-yl)-5-(trifluoromethyl)-1H-pyrazole-4-carboxylate, Cpd 42b

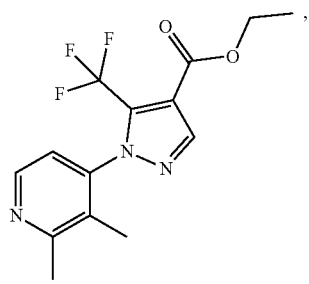

cpd 42b

A solution of (2,3-dimethyl-pyridin-4-yl)-hydrazine, cpd 42a (1.72 g, 12.538 mmol), ethyl 2-(ethoxymethylene)-4,4, 4-trifluoro-3-oxobutanoate, INT1 (3.011 g, 12.538 mmol) and triethylamine (3.495 mL, 25.076 mmol) in ethanol (50 mL) was stirred overnight at 80° C. The reaction mixture was concentrated under reduced pressure and residue purified by chromatography over silica gel (gradient of EA in heptane from 0 to 25%) to afford the title compound as a white solid (285 mg, 7%). MS m/z 314 (MH+).

C. 1-(2,3-Dimethyl-pyridin-4-yl)-5-trifluoromethyl-1H-pyrazole-4-carboxylic acid, Cpd 42c

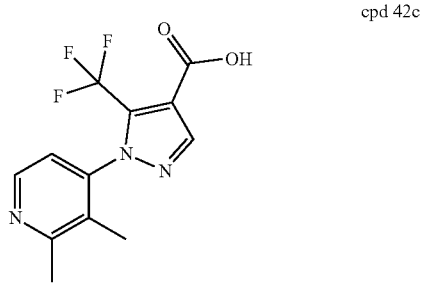

cpd 42c

Ethyl 1-(2,3-dimethylpyridin-4-yl)-5-(trifluoromethyl)-1H-pyrazole-4-carboxylate, cpd 42b (415 mg, 1.325 mmol) and lithium hydroxide (111 mg, 2.649 mmol) were stirred at room temperature in THF (8 mL) and water (2 mL). The reaction was continued 18 hours before the pH was brought to 2-3 with 2N HCl. The mixture was concentrated dry. The residue was filtered through a short column of silica gel with a mixture DCM/MeOH (9/1, v/v) to give the carboxylic acid as a white solid (472 mg, 123%). MS m/z 286 (MH+).

D. N-(5-cyano-6-(2H-1,2,3-triazol-2-yl)pyridin-3-yl)-1-(2,3-dimethylpyridin-4-yl)-5-(trifluoromethyl)-1H-pyrazole-4-carboxamide, Cpd 42

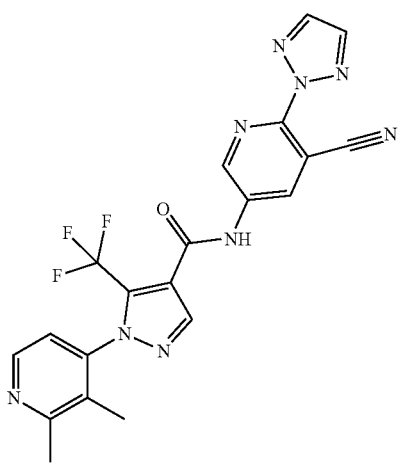 [SMILES: Cc1nccc(-n2ncc(C(=O)Nc3cnc(-n4nccn4)c(C#N)c3)c2C(F)(F)F)c1C]

1-(2,3-Dimethyl-pyridin-4-yl)-5-trifluoromethyl-1H-pyrazole-4-carboxylic acid, cpd 42c (0.472 g, 1.655 mmol) was treated with oxalyl chloride (0.284 mL, 3.310 mmol) in DCM (15 mL) and DMF (1 drop) at reflux. After 45 minutes, the reaction mixture was concentrated dry. The crude acid chloride was taken in DCM (10 mL) and THF (30 mL) and 5-amino-2-[1,2,3]triazol-2-yl-nicotinonitrile, INT3 (462 mg, 2.483 mmol) was added, immediately followed by triethylamine (0.692 mL, 4.965 mmol). The reaction was continued overnight at room temperature and finally quenched with water (10 mL). After 15 minutes stirring, 1M Na₂CO₃ (25 mL) was added, and organics extracted with DCM (2×50 mL). The combined extracts were dried over MgSO₄, filtered and the filtrate concentrated to a crude solid. Chromatography over silica gel (gradient of MeOH in DCM from 0 to 5%) afforded the compound as a solid. The pure title compound was obtained after preparative LC (gradient from 30 to 82% of ACN/MeOH (1/1, v/v) in 0.1% aqueous formic acid) followed by DCM/1M Na₂CO₃ extraction. Triturating in diethyl ether gave N-(5-cyano-6-(2H-1,2,3-triazol-2-yl)pyridin-3-yl)-1-(2,3-dimethylpyridin-4-yl)-5-(trifluoromethyl)-1H-pyrazole-4-carboxamide as a white solid (97 mg, 13%). $^1$H NMR (300 MHz, DMSO-d₆) δ 1.95 (s, 3H), 2.59 (s, 3H), 7.40 (d, J=5.2 Hz, 1H), 8.31 (s, 2H), 8.46-8.60 (m, 2H), 8.85 (d, J=2.4 Hz, 1H), 9.07 (d, J=2.4 Hz, 1H), 11.26 (s, 1H). MS m/z 454 (MH+).

Example 43

1-(3-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 43

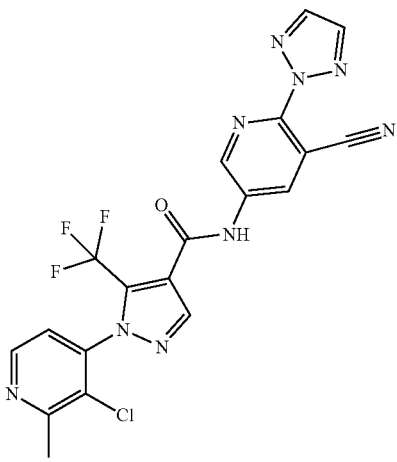 [SMILES: Cc1nccc(-n2ncc(C(=O)Nc3cnc(-n4nccn4)c(C#N)c3)c2C(F)(F)F)c1Cl]

A. (3-Chloro-2-methyl-pyridin-4-yl)-hydrazine, Cpd 43a

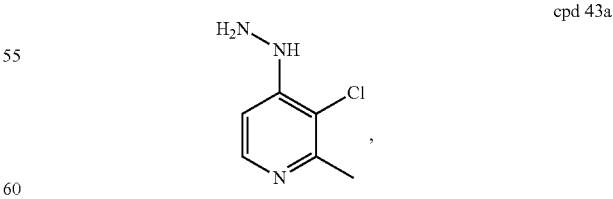

cpd 43a

Hydrazine monohydrate (5.74 mL, 76.143 mmol) was added to a solution of 3,4-dichloro-2-methyl-pyridine (2.0 g, 12.344 mmol) in dioxane (15 mL) and stirred at 100° C. overnight. The mixture was then allowed to cool to room temperature and concentrated dry. The residue treated with 1M Na₂CO₃ (10 mL) and water (20 mL). The organics were extracted with DCM (2×40 mL), dried over MgSO$_4$, filtered and the filtrate concentrated. The crude material was subjected to flash chromatography over silica gel (gradient of MeOH in DCM from 0 to 7.5%) to afford a white solid (967 mg, 49%) $^1$H NMR (300 MHz, DMSO-d$_6$) δ 2.37 (s, 3H), 4.30 (s, 2H), 6.91 (d, J=5.6 Hz, 1H), 7.39 (s, 1H), 7.94 (d, J=5.6 Hz, 1H). MS m/z 158 (MH$^+$).

B. Ethyl 1-(3-chloro-2-methylpyridin-4-yl)-5-(trifluoromethyl)-1H-pyrazole-4-carboxylate, Cpd 25b

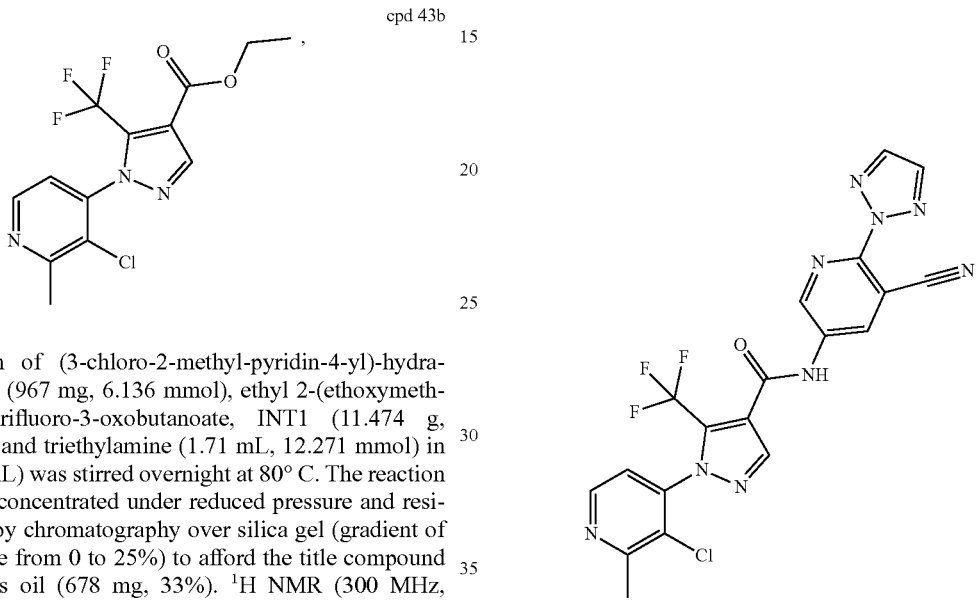

cpd 43b

A solution of (3-chloro-2-methyl-pyridin-4-yl)-hydrazine, cpd 43a (967 mg, 6.136 mmol), ethyl 2-(ethoxymethylene)-4,4,4-trifluoro-3-oxobutanoate, INT1 (11.474 g, 6.136 mmol) and triethylamine (1.71 mL, 12.271 mmol) in ethanol (25 mL) was stirred overnight at 80° C. The reaction mixture was concentrated under reduced pressure and residue purified by chromatography over silica gel (gradient of EA in heptane from 0 to 25%) to afford the title compound as a colorless oil (678 mg, 33%). $^1$H NMR (300 MHz, Chloroform-d) δ 1.39 (t, J=7.1 Hz, 3H), 2.75 (s, 3H), 4.39 (q, J=7.1 Hz, 2H), 7.23 (d, J=5.1 Hz, 1H), 8.21 (s, 1H), 8.58 (d, J=5.1 Hz, 1H). MS m/z 334 (MH$^+$).

C. 1-(3-Chloro-2-methyl-pyridin-4-yl)-5-trifluoromethyl-1H-pyrazole-4-carboxylic Acid, Cpd 43c

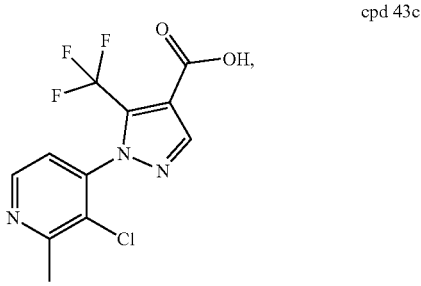 [SMILES: Cc1nccc(-n2ncc(C(=O)O)c2C(F)(F)F)c1Cl]

cpd 43c

Ethyl 1-(3-chloro-2-methylpyridin-4-yl)-5-(trifluoromethyl)-1H-pyrazole-4-carboxylate, cpd 43b (675 mg, 2.023 mmol) and lithium hydroxide (170 mg, 4.046 mmol) were stirred at room temperature in THF (8 mL) and water (2 mL). The reaction was continued for 18 hours before the pH was brought to 2-3 with 2N HCl. The mixture was concentrated dry. The residue was filtered through a short column of silica gel with a mixture DCM/MeOH (9/1, v/v) to give the carboxylic acid as a white solid (774 mg, 125%). MS m/z 306 (MH$^+$).

D. 1-(3-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 43

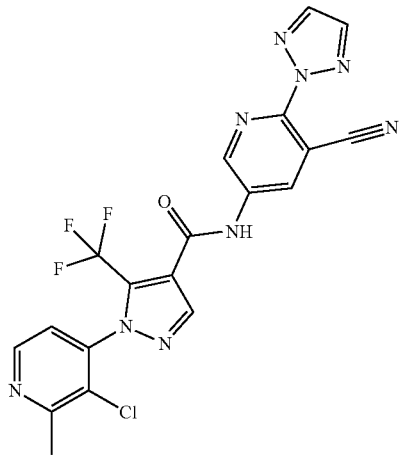 [SMILES: Cc1nccc(-n2ncc(C(=O)Nc3cnc(-n4nccn4)c(C#N)c3)c2C(F)(F)F)c1Cl]

1-(3-Chloro-2-methyl-pyridin-4-yl)-5-trifluoromethyl-1H-pyrazole-4-carboxylic acid, cpd 43c (0.618 g, 2.023 mmol) was treated with oxalyl chloride (0.695 mL, 8.092 mmol) in DCM (15 mL) and DMF (1 drop) at reflux. After 45 minutes, the reaction mixture was concentrated dry. The crude acid chloride was taken in DCM (10 mL) and THF (30 mL) and 5-amino-2-[1,2,3]triazol-2-yl-nicotinonitrile, INT3 (565 mg, 3.055 mmol) was added, immediately followed by triethylamine (0.846 mL, 6.069 mmol). DMF (10 mL) was added to increase homogeneity. The reaction was continued overnight at room temperature and finally quenched with water (10 mL). After 15 minutes stirring, 1M Na$_2$CO$_3$ (25 mL) was added, and organics extracted with DCM (2×50 mL). The combined extracts were dried over MgSO$_4$, filtered and concentrated to a crude solid. Chromatography over silica gel (gradient of MeOH in DCM from 0 to 5%) afforded the compound as an amorphous solid. Triturating in diethyl ether gave the desired product as a light yellow solid (430 mg, 44%). $^1$H NMR (300 MHz, Chloroform-d) δ 2.78 (s, 3H), 7.27 (d, J=5.0 Hz, 1H), 8.02 (s, 2H), 8.18 (s, 1H), 8.22 (s, 1H), 8.62 (d, J=5.1 Hz, 1H), 8.83 (d, J=2.5 Hz, 1H), 8.97 (d, J=2.6 Hz, 1H). MS m/z 474 (MH$^+$)

Example 44

1-(3-Chloropyridin-2-yl)-N-(5-cyano-6-(2H-1,2,3-triazol-2-yl)pyridin-3-yl)-5-(trifluoromethyl)-1H-pyrazole-4-carboxamide, Cpd 44

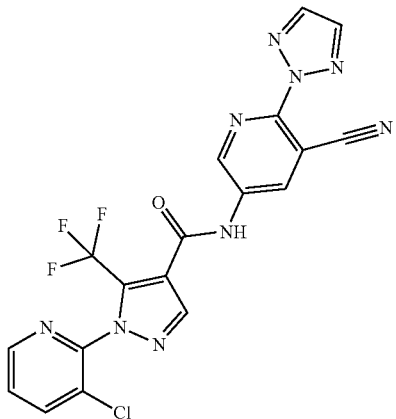 [SMILES: N#Cc1cc(NC(=O)c2cnn(-c3ncccc3Cl)c2C(F)(F)F)cnc1-n1nccn1]

A. Ethyl 1-(6-chloropyridin-2-yl)-5-(trifluoromethyl)-1H-pyrazole-4-carboxylate, Cpd 44a

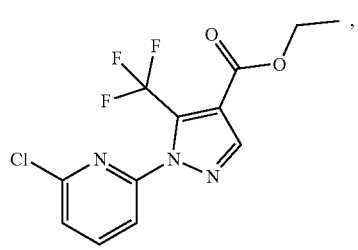
cpd 44a

A solution of (3-chloro-pyridin-2-yl)-hydrazine (0.80 g, 5.572 mmol), ethyl 2-(ethoxymethylene)-4,4,4-trifluoro-3-oxobutanoate, INT1 (1.338 g, 5.572 mmol) and triethylamine (1.545 mL, 11.144 mmol) in ethanol (15 mL) was stirred overnight at 80° C. The reaction mixture was concentrated under reduced pressure and residue purified by chromatography over silica gel (gradient of EA in heptane from 0 to 30%) to afford the title compound as a white solid (1.48 g, 80%). $^1$H NMR (300 MHz, DMSO-$d_6$) δ 1.32 (t, J=7.1 Hz, 2H), 4.34 (q, J=7.0 Hz, 1H), 7.81 (dd, J=8.2, 4.7 Hz, 1H), 8.38 (d, J=8.4 Hz, 1H), 8.45 (s, 1H), 8.65 (d, J=5.3 Hz, 1H). MS m/z 320 (MH$^+$).

B. 1-(3-Chloro-pyridin-2-yl)-5-trifluoromethyl-1H-pyrazole-4-carboxylic acid, Cpd 44b

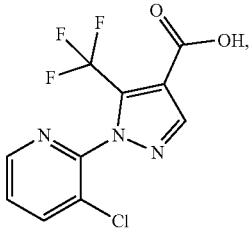
cpd 44b

Ethyl 1-(6-chloropyridin-2-yl)-5-(trifluoromethyl)-1H-pyrazole-4-carboxylate, cpd 44a (801 mg, 2.506 mmol) and lithium hydroxide (315 mg, 7.517 mmol) were stirred at room temperature in THF (8 mL) and water (2 mL). The reaction was continued 18 hours before the pH was brought to 2-3 with 1N HCl. The mixture was concentrated dry to the crude carboxylic acid (731 mg, 99%). MS m/z 292 (MH$^+$)

C. 1-(3-Chloropyridin-2-yl)-N-(5-cyano-6-(2H-1,2,3-triazol-2-yl)pyridin-3-yl)-5-(trifluoromethyl)-1H-pyrazole-4-carboxamide, Cpd 44

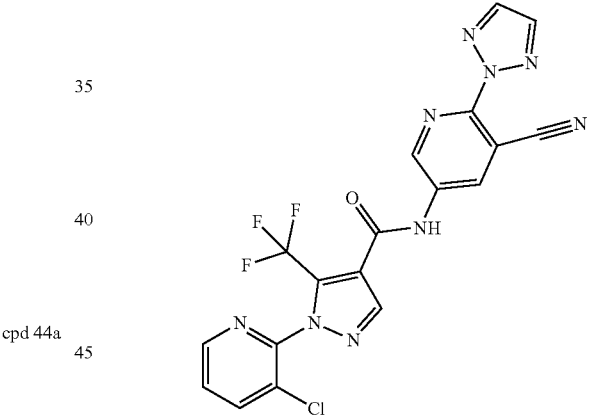

(1-Chloro-2-methyl-propenyl)-dimethyl-amine (1.375 mL, 9.979 mmol) was added portionwise to a solution of 1-(3-chloro-pyridin-2-yl)-5-trifluoromethyl-1H-pyrazole-4-carboxylic acid, cpd 44b (0.75 0 g, 2.495 mmol) in dry THF (15 mL) while monitoring by LC-MS. To the crude solution of resulting acid chloride was added and 5-amino-2-[1,2,3]triazol-2-yl-nicotinonitrile, INT3 (774 mg, 2.495 mmol) and triethylamine (0.696 mL, 4.990 mmol). The reaction was continued for 2 h and then quenched with 1M Na$_2$CO$_3$. The aqueous phase was extracted with DCM, dry over MgSO$_4$, filtered and the filtrate concentrated to dryness. The residue was purified by flash column chromatography over silica gel (gradient of MeOH in DCM from 0 to 2%) to give the pure product. Triturating in diethyl ether led to a white powder (466 mg, 58%). $^1$H NMR (300 MHz, DMSO-$d_6$) δ 7.82 (dd, J=8.1, 4.7 Hz, 1H), 8.31 (s, 2H), 8.41 (d, J=8.2 Hz, 1H), 8.58 (s, 1H), 8.67 (d, J=4.7 Hz, 1H), 8.86 (d, J=2.5 Hz, 1H), 9.08 (d, J=2.5 Hz, 1H), 11.31 (s, 1H). MS m/z 460 (MH$^+$).

Example 45

1-(3-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 45

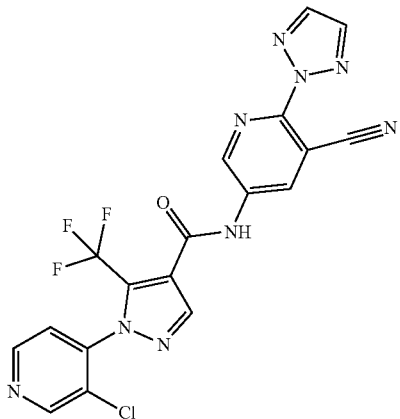 [SMILES: N#Cc1cc(NC(=O)c2cnn(-c3ccncc3Cl)c2C(F)(F)F)cnc1-n1nccn1]

A. Ethyl 1-(3-chloropyridin-4-yl)-5-(trifluoromethyl)-1H-pyrazole-4-carboxylate, Cpd 45a

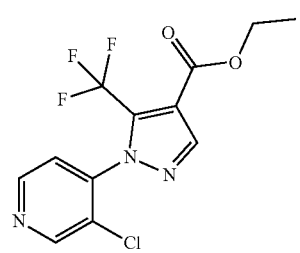

A solution of (3-chloro-pyridin-4-yl)-hydrazine (0.80 g, 5.572 mmol), ethyl 2-(ethoxymethylene)-4,4,4-trifluoro-3-oxobutanoate, INT1 (1.338 g, 5.572 mmol) and triethylamine (1.545 mL, 11.144 mmol) in ethanol (15 mL) was stirred overnight at 80° C. The reaction mixture was concentrated under reduced pressure and the residue purified by chromatography over silica gel (gradient of EA in heptane from 0 to 50%) to afford the title compound as a clear oil (541 mg, 30%). $^{1}$H NMR (300 MHz, Chloroform-d) δ 1.39 (t, J=7.1 Hz, 3H), 4.39 (q, J=7.1 Hz, 2H), 7.39 (d, J=5.1 Hz, 1H), 8.23 (s, 1H), 8.71 (d, J=5.1 Hz, 1H), 8.83 (s, 1H). MS m/z 320 (MH$^{+}$).

B. 1-(3-Chloro-pyridin-4-yl)-5-trifluoromethyl-1H-pyrazole-4-carboxylic acid, Cpd 45b

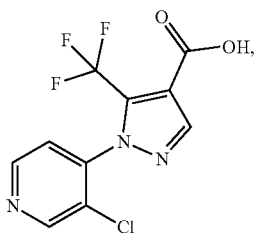

Ethyl 1-(3-chloropyridin-4-yl)-5-(trifluoromethyl)-1H-pyrazole-4-carboxylate, cpd 45a (535 mg, 1.674 mmol) and lithium hydroxide (211 mg, 5.021 mmol) were stirred at room temperature in THF (8 mL) and water (2 mL). The reaction was continued for 18 hours before the pH was brought to 2-3 with 1N HCl. The mixture was concentrated dry to the crude carboxylic acid (760 mg, 160%). MS m/z 291 (MH$^{+}$).

C. 1-(3-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 45

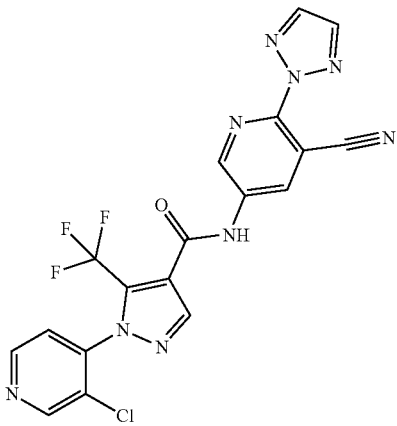 [SMILES: N#Cc1cc(NC(=O)c2cnn(-c3ccncc3Cl)c2C(F)(F)F)cnc1-n1nccn1]

(1-Chloro-2-methyl-propenyl)-dimethyl-amine (0.898 mL, 6.520 mmol) was added portionwise to a solution of 1-(3-chloro-pyridin-2-yl)-5-trifluoromethyl-1H-pyrazole-4-carboxylic acid, cpd 45b (0.490 g, 1.630 mmol) in dry THF (15 mL) while monitoring by LC-MS. To the crude solution of resulting acid chloride was added and 5-amino-2-[1,2,3]triazol-2-yl-nicotinonitrile, INT3 (202 mg, 1.087 mmol) and triethylamine (0.454 mL, 3.260 mmol). The reaction was continued for 2 hours and then quenched with 1M Na$_2$CO$_3$. The organics were extracted with DCM, dry over MgSO$_4$, filtered and the filtrate concentrated dry. The residue was purified by chromatography over silica gel (gradient of MeOH in DCM from 0 to 8%) to give the pure product. Triturating in diethyl ether led to a white solid (250 mg, 49%). $^{1}$H NMR (300 MHz, DMSO-d$_6$) δ 7.96 (d, J=5.2 Hz, 1H), 8.31 (s, 2H), 8.62 (s, 1H), 8.79-8.96 (m, 2H), 9.00-9.11 (m, 2H), 11.29 (s, 1H). MS m/z 460 (MH$^{+}$).

Example 46

N-(5-cyano-6-(2H-1,2,3-triazol-2-yl)pyridin-3-yl)-1-(3-cyanopyridin-4-yl)-5-(trifluoromethyl)-1H-pyrazole-4-carboxamide, Cpd 46 and

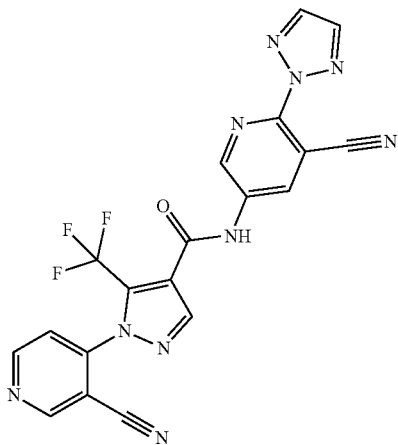 [SMILES: N#Cc1cnccc1-n1ncc(C(=O)Nc2cnc(-n3nccn3)c(C#N)c2)c1C(F)(F)F]

A. (3-Bromo-pyridin-4-yl)-hydrazine, Cpd 46a

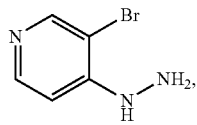
cpd 46a

A solution of 3-bromo-4-chloro-pyridine (1.295 g, 6729 mmol) and hydrazine monohydrate (1.01 mL, 13.459 mmol) was heated at 100° C. in dioxane (15 mL) for 16 hours. The mixture was then allowed to cool to room temperature and concentrated to dark oil. Water (20 mL) and 1M $Na_2CO_3$ (10 mL) were added. The organics were extracted with DCM (2×40 mL). The combined extracts were dried over $MgSO_4$, filtered and the filtrate concentrated. Chromatography over silica gel (gradient of MeOH in DCM from 0 to 7%) afforded the desired hydrazine as a beige solid (492 mg, 35%). $^1$H NMR (300 MHz, DMSO-$d_6$) δ 4.34 (s, 2H), 7.01 (d, J=5.6 Hz, 1H), 7.32 (s, 1H), 8.07 (d, J=5.6 Hz, 1H), 8.18 (s, 1H). MS m/z 188 (MH$^+$).

B. Ethyl 1-(3-bromopyridin-4-yl)-5-(trifluoromethyl)-1H-pyrazole-4-carboxylate, Cpd 46b

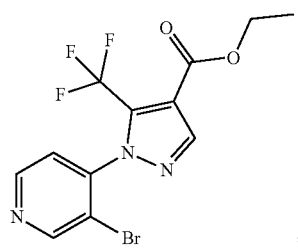
cpd 46b

A solution of (3-bromo-pyridin-4-yl)-hydrazine, cpd 46a (0.492 g, 2.617 mmol), ethyl 2-(ethoxymethylene)-4,4,4-trifluoro-3-oxobutanoate, INT1 (0.628 g, 2.617 mmol) and triethylamine (0.725 mL, 5.233 mmol) in ethanol (15 mL) was stirred overnight at 80° C. The reaction mixture was concentrated under reduced pressure and residue purified by chromatography over silica gel (gradient of EA in heptane from 0 to 30%) to afford the title compound as a white solid (300 mg, 31%). $^1$H NMR (300 MHz, DMSO-$d_6$) δ 1.31 (t, J=7.1 Hz, 3H), 4.34 (q, J=7.1 Hz, 2H), 7.93 (d, J=5.1 Hz, 1H), 8.47 (s, 1H), 8.84 (d, J=5.1 Hz, 1H), 9.08 (s, 1H). MS m/z 364 (MH$^+$).

C. Ethyl 1-(3-cyanopyridin-4-yl)-5-(trifluoromethyl)-1H-pyrazole-4-carboxylate, Cpd 46c

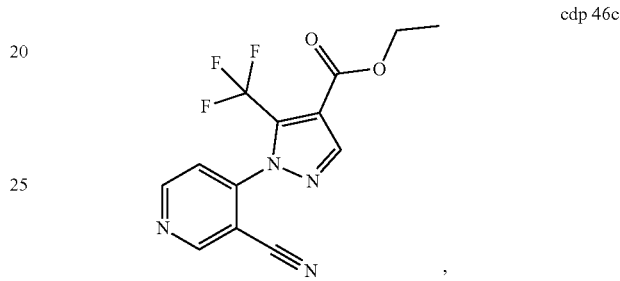
cdp 46c

Ethyl 1-(3-bromopyridin-4-yl)-5-(trifluoromethyl)-1H-pyrazole-4-carboxylate, cpd 46b (300 mg, 0.824 mmol) was taken in DMF (5 mL) and resulting solution bubbled with nitrogen for ca. 15 minutes. Copper cyanide (147 mg, 1.648 mmol) and copper iodide (15 mg, 0.082 mmol) were added and reaction vessel closed tight with a screw cap. The mixture was then heated at 140° C. for 2 hours and then allowed to cool to room temperature. The reaction mixture was diluted with EA (30 mL), and filtered through a pad of diatomaceous earth and concentrated to the crude residue. Chromatography over silica gel (gradient of EA in heptane from 0 to 30%) gave the product with sufficient quality as a viscous oil (201 mg, 64%). MS m/z 311 (MH$^+$).

D. 1-(3-Cyano-pyridin-4-yl)-5-trifluoromethyl-1H-pyrazole-4-carboxylic Acid, Cpd 46d

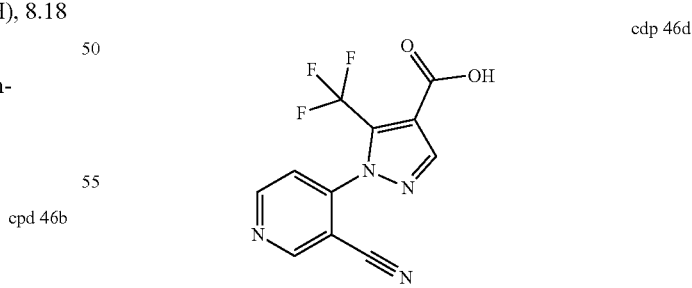
cdp 46d

Ethyl 1-(3-cyanopyridin-4-yl)-5-(trifluoromethyl)-1H-pyrazole-4-carboxylate, cpd 46c (200 mg, 0.645 mmol) and lithium hydroxide (81 mg, 1.934 mmol) were stirred at room temperature in THF (2 mL) and water (1 mL). The reaction was continued 18 hours and mixture was concentrated dry to the crude carboxylic acid (287 mg, 157%). MS m/z 283 (MH$^+$).

E. N-(5-cyano-6-(2H-1,2,3-triazol-2-yl)pyridin-3-yl)-1-(3-cyanopyridin-4-yl)-5-(trifluoromethyl)-1H-pyrazole-4-carboxamide, Cpd 46

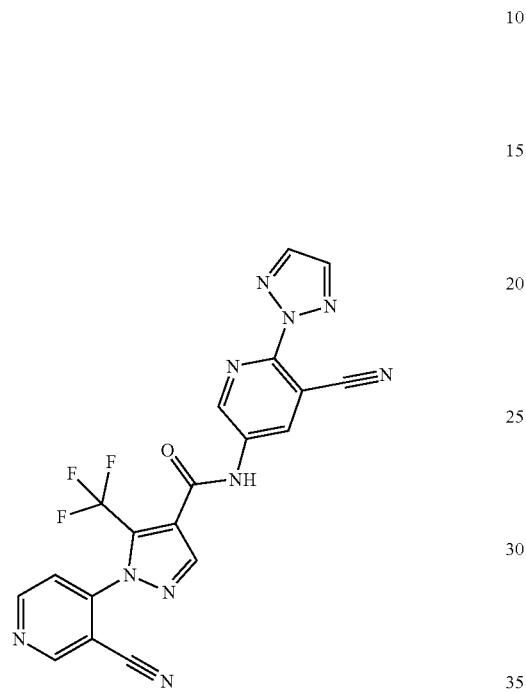

(1-Chloro-2-methyl-propenyl)-dimethyl-amine (0.345 mL, 2.503 mmol) was added portionwise to a solution of 1-(3-cyano-pyridin-4-yl)-5-trifluoromethyl-1H-pyrazole-4-carboxylic acid, cpd 46d (0.182 g, 0.626 mmol) in dry THF (10 mL) while monitoring by LC-MS. To the crude solution of resulting acid chloride was added and 5-amino-2-[1,2,3]triazol-2-yl-nicotinonitrile, INT3 (78 mg, 0.417 mmol) and triethylamine (0.175 mL, 1.252 mmol). The reaction was continued for 2 hours and then quenched with 1M Na$_2$CO$_3$. The organics were extracted with DCM, dry over MgSO$_4$, filtered and concentrated dry. The residue was purified by chromatography over silica gel (gradient of MeOH in DCM from 0 to 4%) to give a mixture of two products. Preparative LC (gradient of ACN/MeOH (1/1, v/v) in 0.1% aqueous formic acid from 19 to 55%) allowed separation of the two compounds. Both fractions were treated with 1M Na$_2$CO$_3$, extracted with DCM, dried over MgSO$_4$ and concentrated. Triturating in diethyl ether led to the white solids N-(5-cyano-6-(2H-1,2,3-triazol-2-yl)pyridin-3-yl)-1-(3-cyano-pyridin-4-yl)-5-(trifluoromethyl)-1H-pyrazole-4-carboxamide, cpd 46 (35 mg, 18%); $^1$H NMR (300 MHz, DMSO-d$_6$) δ 8.06 (d, J=5.4 Hz, 1H), 8.32 (s, 2H), 8.67 (s, 1H), 8.86 (d, J=2.5 Hz, 1H), 9.07 (d, J=2.5 Hz, 1H), 9.19 (d, J=5.4 Hz, 1H), 9.41 (s, 1H), 11.40 (s, 1H). MS m/z 451 (MH$^+$)

Example 47

1-(3-chloro-4-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 47

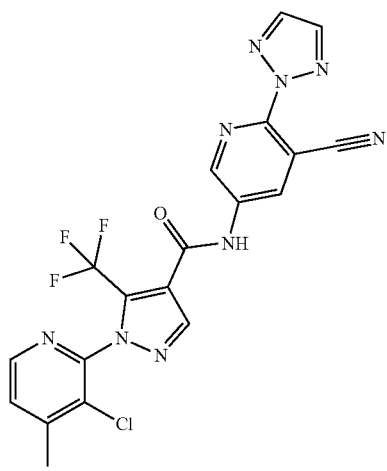 [SMILES: Cc1ccnc(-n2ncc(C(=O)Nc3cnc(-n4nccn4)c(C#N)c3)c2C(F)(F)F)c1Cl]

A. (3-Chloro-4-methyl-pyridin-2-yl)-hydrazine, Cpd 47a

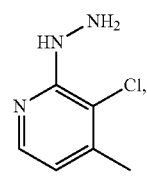

cpd 47a

Hydrazine monohydrate (3.145 mL, 55.55 mmol) was added to a solution of 2,3-dichloro-4-methyl-pyridine (1.50 g, 9.258 mmol) in dioxane (30 mL) and stirred at 110° C. overnight. The mixture was then allowed to cool to room temperature and concentrated dry. The residue was purified by chromatography over silica gel (gradient of MeOH in DCM from 0 to 10%) to afford the hydrazine as a foam (1.23 mg, 81%). $^1$H NMR (300 MHz, DMSO-d$_6$) δ 2.25 (s, 3H), 4.18 (s, 2H), 6.60 (d, J=5.0 Hz, 1H), 7.48 (s, 1H), 7.91 (d, J=5.0 Hz, 1H). MS m/z 158 (MH$^+$).

B. Ethyl 1-(3-chloro-4-methylpyridin-2-yl)-5-(trifluoromethyl)-1H-pyrazole-4-carboxylate, Cpd 47b

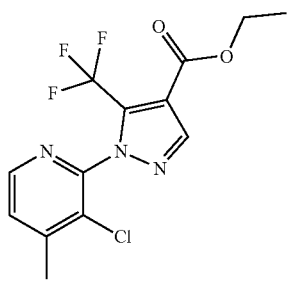

cpd 47b

A solution of (3-chloro-4-methyl-pyridin-2-yl)-hydrazine, cpd 47a (1.23 g, 7.805 mmol), ethyl 2-(ethoxymethylene)-4,4,4-trifluoro-3-oxobutanoate, INT1 (1.874 g, 7.805 mmol) and triethylamine (2.16 mL, 15.609 mmol) in ethanol (30 mL) was stirred overnight at 80° C. The reaction mixture was concentrated under reduced pressure and residue purified by chromatography over silica gel (gradient of EA in heptane from 0 to 30%) to afford the title compound as a white solid (300 mg, 31%). $^1$H NMR (300 MHz, DMSO-$d_6$) δ 1.32 (t, J=7.1 Hz, 3H), 2.52 (s, 3H), 4.34 (q, J=7.1 Hz, 2H), 7.77 (d, J=4.9 Hz, 1H), 8.44 (s, 1H), 8.50 (d, J=4.9 Hz, 1H). MS m/z 334 (MH$^+$).

C. 1-(3-Chloro-4-methyl-pyridin-2-yl)-5-trifluoromethyl-1H-pyrazole-4-carboxylic Acid, Cpd 47c

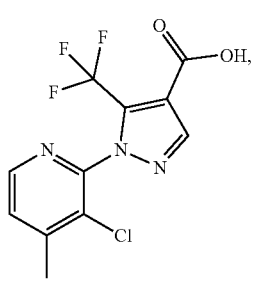

cpd 47c

Ethyl 1-(3-chloro-4-methylpyridin-2-yl)-5-(trifluoromethyl)-1H-pyrazole-4-carboxylate, cpd 47b (1.0 g, 2.997 mmol) and lithium hydroxide (377 mg, 8.99 mmol) were stirred at room temperature in THF (8 mL) and water (2 mL). The reaction was continued 18 hours before the pH was brought to 2-3 with 2N HCl. The mixture was concentrated dry to give the crude carboxylic acid (916 mg, 100%, theoretical yield). $^1$H NMR (300 MHz, DMSO-$d_6$) δ 2.51 (s, 3H), 7.77 (d, J=4.9 Hz, 1H), 8.35 (s, 1H), 8.48 (d, J=4.9 Hz, 1H). MS m/z 305 (MH$^+$).

D. 1-(3-chloro-4-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 47

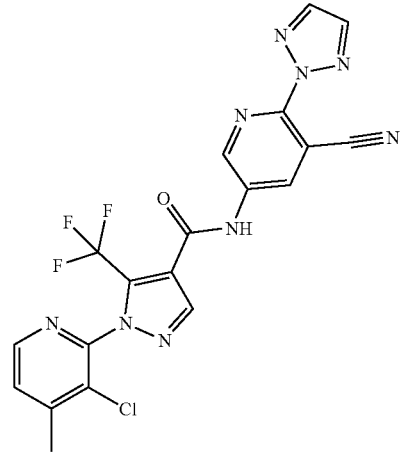 [SMILES: Cc1ccnc(-n2ncc(C(=O)Nc3cnc(-n4nccn4)c(C#N)c3)c2C(F)(F)F)c1Cl]

(1-Chloro-2-methyl-propenyl)-dimethyl-amine (1.636 mL, 11.868 mmol) was added portionwise to a solution of 1-(3-chloro-4-methyl-pyridin-2-yl)-5-trifluoromethyl-1H-pyrazole-4-carboxylic acid, cpd 47c (0.935 g, 2.967 mmol) in dry THF (15 mL) while monitoring by LC-MS. To the crude solution of resulting acid chloride was added and 5-amino-2-[1,2,3]triazol-2-yl-nicotinonitrile, INT3 (368 mg, 1.978 mmol) and triethylamine (0.827 mL, 5.934 mmol). The reaction was continued for 2 hours and then quenched with 1M Na$_2$CO$_3$. The organics were extracted with DCM, dry over MgSO$_4$, filtered and concentrated dry. The residue was purified by chromatography over silica gel (gradient of MeOH in DCM from 0 to 8%) to give the product with improved quality. Preparative LC (gradient of ACN/MeOH (1/1, v/v) in 0.1% aqueous formic acid from 19 to 55%) gave pure compound. The fractions were treated with 1M Na$_2$CO$_3$, extracted with DCM, dried over MgSO$_4$ and concentrated to a white solid (85 mg, 9%). $^1$H NMR (300 MHz, DMSO-$d_6$) δ 2.54 (s, 3H), 7.78 (d, J=4.9 Hz, 1H), 8.31 (s, 2H), 8.51 (d, J=4.9 Hz, 1H), 8.62 (s, 1H), 8.88 (d, J=2.5 Hz, 1H), 9.11 (d, J=2.5 Hz, 1H), 11.39 (s, 1H). MS m/z 305 (MH$^+$).

Example 48

N-(5-cyano-6-(2H-1,2,3-triazol-2-yl)pyridin-3-yl)-1-(3,5-dichloropyridin-4-yl)-5-(trifluoromethyl)-1H-pyrazole-4-carboxamide, Cpd 48

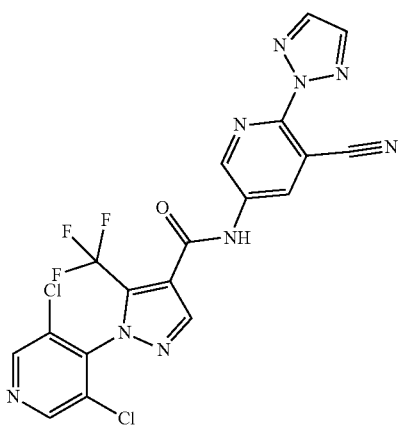 [SMILES: N#Cc1cc(NC(=O)c2cnn(-c3c(Cl)cncc3Cl)c2C(F)(F)F)cnc1-n1nccn1]

A. Ethyl 1-(3,5-dichloropyridin-4-yl)-5-(trifluoromethyl)-1H-pyrazole-4-carboxylate, Cpd 48a

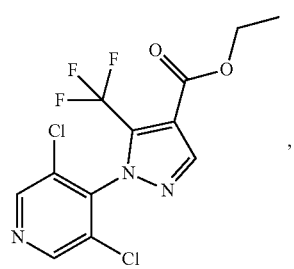

cpd 48a

A solution of (3,5-dichloro-pyridin-4-yl)-hydrazine (1.0 g, 5.617 mmol), ethyl 2-(ethoxymethylene)-4,4,4-trifluoro-3-oxobutanoate, INT1 (1.349 g, 5.617 mmol) and triethylamine (1.55 mL, 11.235 mmol) in ethanol (15 mL) was stirred overnight at 80° C. The reaction mixture was concentrated under reduced pressure and residue purified by chromatography over silica gel (gradient of MeOH in DCM from 0 to 20%) to afford the title compound as an oil (558 mg, 27%). MS m/z 354 (MH⁺)

B. 1-(3,5-Dichloro-pyridin-4-yl)-5-trifluoromethyl-1H-pyrazole-4-carboxylic Acid, Cpd 48b

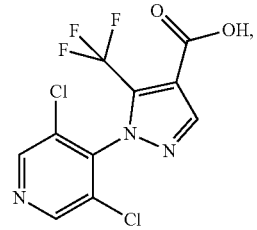

cpd 48b

Ethyl 1-(3,5-dichloropyridin-4-yl)-5-(trifluoromethyl)-1H-pyrazole-4-carboxylate, cpd 48a (558 mg, 1.576 mmol) and lithium hydroxide (132 mg, 3.152 mmol) were stirred at room temperature in THF (60 mL) and water (15 mL). The reaction was continued 18 hours before the pH was brought to 2-3 with 2N HCl. The mixture was concentrated dry to give the crude carboxylic acid (514 mg, 100%, theoretical yield). MS m/z 326 (MH⁺).

C. N-(5-cyano-6-(2H-1,2,3-triazol-2-yl)pyridin-3-yl)-1-(3,5-dichloropyridin-4-yl)-5-(trifluoromethyl)-1H-pyrazole-4-carboxamide, Cpd 48

(1-Chloro-2-methyl-propenyl)-dimethyl-amine (1.30 mL, 9.458 mmol) was added portionwise to a solution of 1-(3,5-dichloro-pyridin-4-yl)-5-trifluoromethyl-1H-pyrazole-4-carboxylic acid, cpd 48b (0.514 g, 1.576 mmol) in dry THF (16 mL) while monitoring by LC-MS. To the crude solution of resulting acid chloride was added and 5-amino-2-[1,2,3]triazol-2-yl-nicotinonitrile, INT3 (440 mg, 2.364 mmol) and triethylamine (0.659 mL, 4.728 mmol). The reaction was continued for 2 hours and then quenched with 1M Na₂CO₃. The organics were extracted with EA, dry over MgSO₄, filtered and concentrated dry. The residue was purified by chromatography over silica gel (gradient of EA in heptane from 0 to 100%). The final purification was performed via preparative LC (gradient of ACN/MeOH (1/1, v/v) in 0.1% aqueous formic acid from 30 to 73%) gave pure compound. The fractions were treated with 1M Na₂CO₃, extracted with DCM, dried over MgSO₄ and the filtrate concentrated to an amorphous solid. Triturating in diethyl ether afforded a white powder (215 mg, 27%). $^1$H NMR (300 MHz, DMSO-$d_6$) δ 8.32 (s, 2H), 8.84 (s, 1H), 8.89 (s, 1H), 9.01-9.24 (m, 3H), 11.51 (s, 1H). MS m/z 494 (MH$^+$).

Example 49

N-(5-cyano-6-(2H-1,2,3-triazol-2-yl)pyridin-3-yl)-1-(2,3-dihydrobenzo[b][1,4]dioxin-5-yl)-5-(trifluoromethyl)-1H-pyrazole-4-carboxamide, Cpd 49

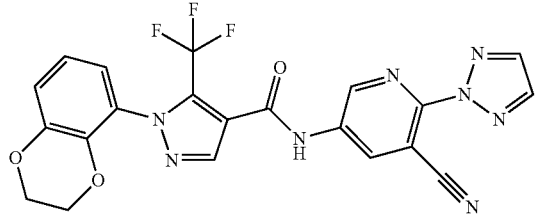 [SMILES: N#Cc1cc(NC(=O)c2cnn(-c3cccc4c3OCCO4)c2C(F)(F)F)cnc1-n1nccn1]

A. (2,3-dihydrobenzo[b][1,4]dioxin-5-yl)hydrazine, Cpd 49a

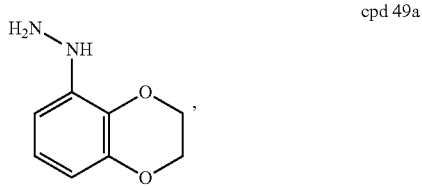 [SMILES: NNc1cccc2c1OCCO2]

To a stirring solution of 2,3-dihydrobenzo[b][1,4]dioxin-5-amine (300 mg, 1.958 mmol) in 5M HCl (10 mL) at 0° C. was added a solution of NaNO$_2$ (136.929 mg, 1.985 mmol) in water (2 mL) below 0° C. The reaction mixture was stirred at 0° C. for 30 min and a solution of SnCl$_2$ (985.2 mg, 4.366 mmol) dissolved in conc.HCl (2 mL) was added dropwise. The mixture was stirred at 60° C. for 1.5 h. Then the mixture was adjusted to pH 13 with 20% aqueous sodium hydroxide. The mixture was extracted with ethyl acetate. The organic layer was dried (Na$_2$SO$_4$), filtered, and the filtrate concentrated in under reduced pressure to afford a crude product. The crude product was purified by column chromatography over silica gel (petroleum ether/ethyl acetate=100:0 to petroleum ether/ethyl acetate=0:100). The solvent was evaporated to get the product as yellow solid (150 mg, 45.5%). LCMS (ESI) m/z M+1: 167.1.

B. Ethyl 1-(2,3-dihydrobenzo[b][1,4]dioxin-5-yl)-5-(trifluoromethyl)-1H-pyrazole-4-carboxylate, Cpd 49b

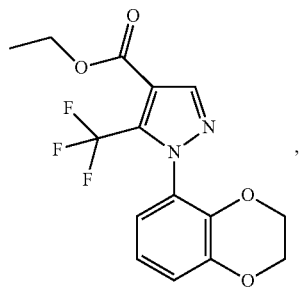

Ethyl 2-(ethoxymethylene)-4,4,4-trifluoro-3-oxobutanoate (263.04 mg, 1.095 mmol) was added to a solution of (2,3-dihydrobenzo[b][1,4]dioxin-5-yl)hydrazine, cpd 49a (140 mg, 0.842 mmol) in EtOH (4 mL) was reacted at 80° C. for 1 hour. The mixture was evaporated under reduced pressure, then was purified by FFS (petroleum ether/ethyl acetate=100:0 to petroleum ether/ethyl acetate=70:30). The desired fractions were collected and the solvent was concentrated under reduced pressure to give the product as a brown oil. LCMS (ESI) m/z M+1: 342.9.

C. 1-(2,3-dihydrobenzo[b][1,4]dioxin-5-yl)-5-(trifluoromethyl)-1H-pyrazole-4-carboxylic Acid, Cpd 49c

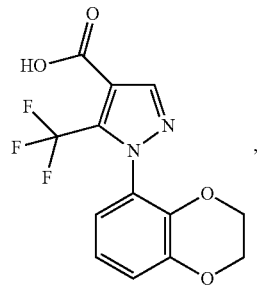

NaOH (41.53 mg, 1.038 mmol) was added to a solution of ethyl 1-(2,3-dihydrobenzo[b][1,4]dioxin-5-yl)-5-(trifluoromethyl)-1H-pyrazole-4-carboxylate, cpd 49b (120 mg, 0.346 mmol) in EtOH/H$_2$O=1:1 (5 mL) was reacted at 28° C. for 2 hours. The solvent was evaporated under reduced pressure. 1M HCl solution was add to the mixture to adjust the pH to ~5 and solid formed. The solid was collected to get the product. (115 mg, 78.1%). LCMS (ESI) m/z M+1: 314.9.

D. N-(5-cyano-6-(2H-1,2,3-triazol-2-yl)pyridin-3-yl)-1-(2,3-dihydrobenzo[b][1,4]dioxin-5-yl)-5-(trifluoromethyl)-1H-pyrazole-4-carboxamide, Cpd 49

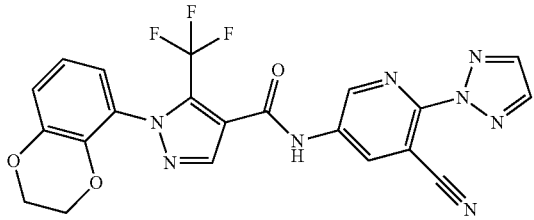 [SMILES: N#Cc1cc(NC(=O)c2cnn(-c3cccc4c3OCCO4)c2C(F)(F)F)cnc1-n1nccn1]

1-(2,3-Dihydrobenzo[b][1,4]dioxin-5-yl)-5-(trifluoromethyl)-1H-pyrazole-4-carboxylic acid, cpd 49c (95.20 mg, 0.224 mmol), 5-amino-2-(2H-1,2,3-triazol-2-yl)nicotinonitrile, INT3 (50 mg, 0.269 mmol), POCl$_3$ (41.18 mg, 0.269 mmol) were dissolved in DCM (2 mL), and pyridine (53.101 mg, 0.671 mmol) was added. The mixture was stirred at 25° C. for 1 h. Then sat NH$_4$Cl (20 mL) was added and extracted with CH$_2$Cl$_2$ (20 mL×2). The combined organic layers were dried with Na$_2$SO$_4$, filtered and the filtrates were concentrated under reduced pressure to afford crude as a brown oil, which was purified by preparative HPLC (30% to 60% (v/v) CH$_3$CN and H$_2$O with 0.05% HCl) and lyophilized to dryness to afford the title compound (34 mg, 31.49%). LCMS (ESI) m/z M+1: 482.9. 1H NMR (400 MHz, DMSO-d$_6$) δ ppm 4.13-4.35 (m, 3H), 4.24-4.35 (m, 1H), 6.96-7.02 (m, 1H), 7.03-7.07 (m, 1H), 7.09-7.13 (m, 1H), 8.29 (s, 2H), 8.41 (s, 1H), 8.83 (d, J=2.43 Hz, 1H), 9.05 (d, J=2.65 Hz, 1H), 11.21 (s, 1H).

Example 50

1-(2-bromo-4-fluorophenyl)-N-(5-cyano-6-(2H-1,2,3-triazol-2-yl)pyridin-3-yl)-5-(trifluoromethyl)-1H-pyrazole-4-carboxamide, Cpd 50

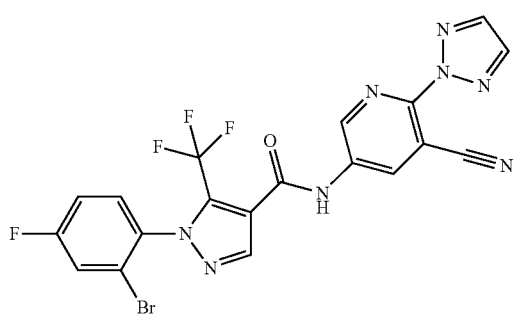

A. (2-bromo-4-fluorophenyl)hydrazine, Cpd 50a

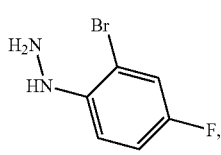

To a stirring solution of 2-bromo-4-fluoroaniline (2 g, 10.526 mmol) in 5M HCl (15.18 mL) at 0° C. was added a solution of NaNO$_2$ (1.089 g, 15.788 mmol) in H$_2$O (8 mL) below 0° C. The reaction mixture was stirred at 0° C. for 30 mins and a solution of SnCl$_2$ (5.94 mg, 15.788 mmol) dissolved in conc.HCl (2.82 mL) was added dropwise. The mixture was stirred at room temperature for 3 h. Then the mixture was adjusted to pH 12-14 with 20% aqueous sodium hydroxide. The mixture was extracted with ethyl acetate. The organic layer was dried (Na$_2$SO$_4$), filtered, and the filtrate concentrated under reduced pressure to afford the crude product (2 g, 92.7%).

B. ethyl 1-(2-bromo-4-fluorophenyl)-5-(trifluoromethyl)-1H-pyrazole-4-carboxylate, Cpd 50b

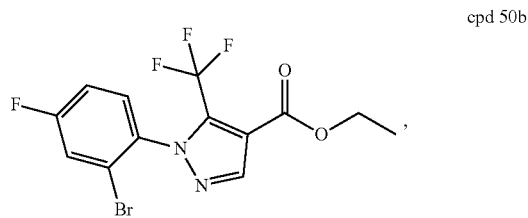 [SMILES: CCOC(=O)c1cnn(-c2ccc(F)cc2Br)c1C(F)(F)F]

Ethyl 2-(ethoxymethylene)-4,4,4-trifluoro-3-oxobutanoate, INT1 (3.162 g, 13.162 mmol) was added to a solution of (2-bromo-4-fluorophenyl)hydrazine, cpd 50a (1.8 g, 8.779 mmol) in EtOH (10 mL) was reacted at 80° C. for 1 hour. The mixture was evaporated under reduced pressure, then was purified by FFS (petroleum ether/ethyl acetate=100:0 to petroleum ether/ethyl acetate=80:20). The desired fractions were collected and the solvent was concentrated under reduced pressure to give the product as a brown oil. LCMS (ESI) m/z M+1: 382.8.

C. 1-(2-bromo-4-fluorophenyl)-5-(trifluoromethyl)-1H-pyrazole-4-carboxylic Acid, Cpd 50c

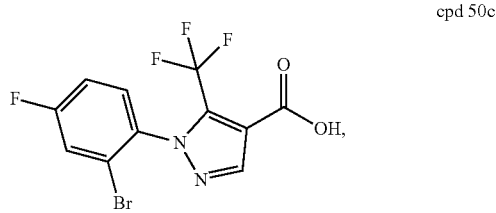 [SMILES: O=C(O)c1cnn(-c2ccc(F)cc2Br)c1C(F)(F)F]

LiOH (387.5 mg, 16.182 mmol) was added to a solution of 1-(2-bromo-4-fluorophenyl)-5-(trifluoromethyl)-1H-pyrazole-4-carboxylic acid, cpd 50b (387 mg, 16.182 mmol) in EtOH/H$_2$O=2:1 (15 mL) was reacted at 23° C. for 2 hours. The solvent was evaporated under reduced pressure. 1M HCl solution was add to the mixture to adjust the pH to ~5 and solid formed. The solid was collected by filtration to afford the product (1 g, 83.4%). LCMS (ESI) m/z M+1: 352.6.

D. 1-(2-bromo-4-fluorophenyl)-N-(5-cyano-6-(2H-1,2,3-triazol-2-yl)pyridin-3-yl)-5-(trifluoromethyl)-1H-pyrazole-4-carboxamide, Cpd 50

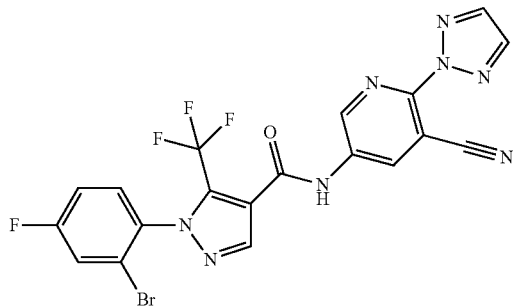 [SMILES: N#Cc1cc(NC(=O)c2cnn(-c3ccc(F)cc3Cl)c2C(F)(F)F)cnc1-n1nccn1]

1-(2-Bromo-4-fluorophenyl)-5-(trifluoromethyl)-1H-pyrazole-4-carboxylic acid, cpd 50c (200 mg, 0.540 mmol), 5-amino-2-(2H-1,2,3-triazol-2-yl)nicotinonitrile, INT3 (102.5 mg, 0.551 mmol), POCl$_3$ (99.359 mg, 0.648 mmol) were dissolved in DCM (5 mL), and pyridine (128.14 mg, 1.620 mmol) was added. The mixture was stirred at 25° C. for 1 h. Then sat.NaHCO$_3$(10 mL) was added and the mixture extracted with CH$_2$Cl$_2$ (15 mL×2). The combined organic layers were dried with Na$_2$SO$_4$, filtered and the filtrates were concentrated under reduced pressure to afford the crude product as a brown oil, which was purified by preparative HPLC (46% to 66% (v/v) CH$_3$CN and H$_2$O with 0.05% HCl) and lyophilized to dryness to afford the title compound (46 mg, 16.1%). LCMS (ESI) m/z M+1: 522.8. $^1$H NMR (400 MHz, DMSO-d$_6$) δ ppm 7.51 (td, J=8.49, 2.87 Hz, 1H), 7.85 (dd, J=8.82, 5.29 Hz, 1H), 7.93 (dd, J=8.27, 2.76 Hz, 1H), 8.29 (s, 2H), 8.50 (s, 1H), 8.83 (d, J=2.21 Hz, 1H), 9.01-9.09 (m, 1H), 11.25 (br s, 1H).

Example 51

1-(2-chloro-4-fluorophenyl)-N-(5-cyano-6-(2H-1,2,3-triazol-2-yl)pyridin-3-yl)-5-(trifluoromethyl)-1H-pyrazole-4-carboxamide, Cpd 51

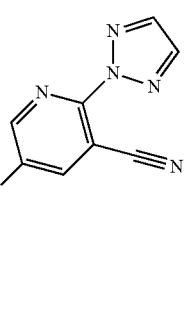

A. Ethyl 1-(2-chloro-4-fluorophenyl)-5-(trifluoromethyl)-1H-pyrazole-4-carboxylate, Cpd 51a

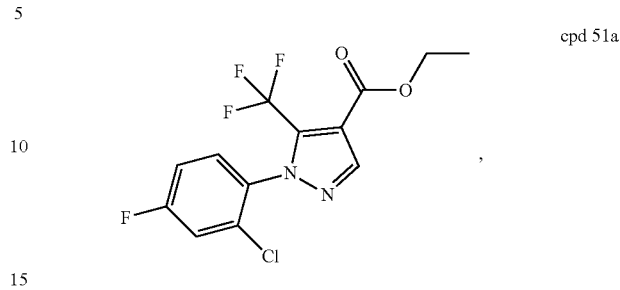

A solution of 2-chloro-4-fluorophenylhydrazine hydrochloride (400 mg, 2.030 mmol), ethyl 2-(ethoxymethylene)-4,4,4-trifluoro-3-oxobutanoate, INT1 (585.09 mg 2.436 mmol), in EtOH (5 mL) was stirred at 55° C. for 1 h. The mixture was concentrated under reduced pressure. The crude product was purified by column chromatography over silica gel (petroleum ether/ethyl acetate from 100/0 to 50/50). The desired fractions were collected and the solvent was concentrated under reduced pressure.

B. 1-(2-chloro-4-fluorophenyl)-5-(trifluoromethyl)-1H-pyrazole-4-carboxylic acid, Cpd 51b

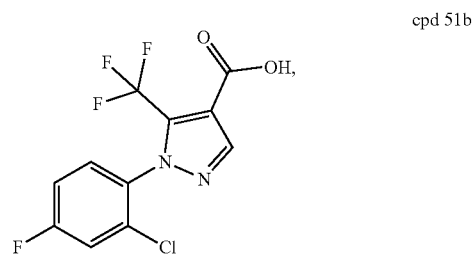 [SMILES: O=C(O)c1cnn(-c2ccc(F)cc2Cl)c1C(F)(F)F]

A solution of cpd 51a (585 mg, 1.668 mmol), LiOH (105 mg 2.502 mmol) in EtOH/H$_2$O (2/1, 5 mL) was stirred at room temperature for 2 h. IN HCl solution was added to neutralize the reaction solution. The mixture was extracted with ethyl acetate (10 mL×3). The separated organic layer was dried (MgSO$_4$), filtered, and the solvent was evaporated under reduced pressure to afford cpd 51b (500 mg, 97.124% yield) as a white solid.

C. 1-(2-chloro-4-fluorophenyl)-N-(5-cyano-6-(2H-1,2,3-triazol-2-yl)pyridin-3-yl)-5-(trifluoromethyl)-1H-pyrazole-4-carboxamide, Cpd 51

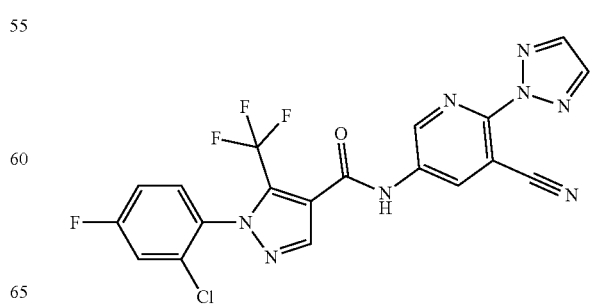

Phosphorus oxychloride (90.61 uL, 0.972 mmol) was added to a solution of 1-(2-chloro-4-fluorophenyl)-5-(trifluoromethyl)-1H-pyrazole-4-carboxylic acid, cpd 51b (120 mg, 0.389 mmol), 5-amino-2-(2H-1,2,3-triazol-2-yl)nicotinonitrile (94.11 mg, 0.505 mmol), pyridine (314.5 uL, 3.888 mmol) in CH₂Cl₂ (2 mL). The mixture was stirred at room temperature for 1 h. Water (5 mL) was added to the mixture. Sat. NaHCO₃ was added to adjust the pH of reaction mixture to 7-8. The mixture was extracted with CH₂Cl₂ (5 mL×3). The combined organic extracts were dried over anhydrous Mg₂SO₄, filtered, and the filtrate concentrated to dryness under reduced pressure to afford the crude product, which was purified by preparative HPLC (45% to 75% (v/v) CH₃CN and H₂O with 0.05% HCl) and lyophilized to dryness to afford the title compound (105 mg, 56.131%). LCMS (ESI) m/z M+1: 476.9. $^1$H NMR (400 MHz, METHANOL-d₄) δ ppm 7.35 (td, J=8.32, 2.76 Hz, 1H), 7.57 (dd, J=8.16, 2.87 Hz, 1H), 7.68 (dd, J=8.82, 5.29 Hz, 1H), 8.13 (s, 2H), 8.33 (s, 1H), 8.88 (d, J=2.65 Hz, 1H), 9.05 (d, J=2.43 Hz, 1H).

Example 52

1-([1,3]dioxolo[4,5-b]pyridin-7-yl)-N-(5-chloro-6-(2H-1,2,3-triazol-2-yl)pyridin-3-yl)-5-(trifluoromethyl)-1H-pyrazole-4-carboxamide, Cpd 52

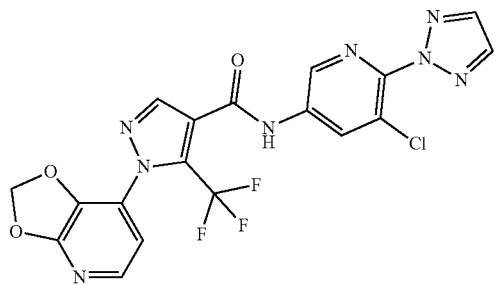 [SMILES: O=C(Nc1cnc(-n2nccn2)c(Cl)c1)c1cnn(-c2ccnc3c2OCO3)c1C(F)(F)F]

A. 7-hydrazinyl-[1,3]dioxolo[4,5-b]pyridine, Cpd 52a

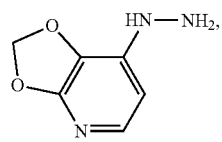

A mixture of palladium(II)(pi-cinnamyl) (19.24 mg, 0.037 mmol) chloride dimer and N-[2-(di-1-adamantylphosphino)phenyl]morpholine (34.427 mg, 0.074 mmol) in dioxane (3 mL) was evacuated with argon 4 times. The resulting clear yellow solution was stirred at room temp under argon for 10 min. 7-bromo-[1,3]dioxolo[4,5-b]pyridine (150 mg, 0.74 mmol) and tBuONa (142.72 mg, 1.49 mmol) were added to the mixture and evacuated with argon 4 times. The resulting yellow reaction was stirred at room temperature for 5 min and then treated with hydrazine (75.86 mg, 1.49 mmol) via syringe and evacuated with argon 4 times. Then the mixture was stirred at 55° C. under argon for 2 h. The mixture was filtered and washed with ethyl acetate (5 mL×3). The filtrate was concentrated under reduced pressure to afford cpd 52a (113.71 mg, crude product) as black solid.

B. ethyl 1-([1,3]dioxolo[4,5-b]pyridin-7-yl)-5-(trifluoromethyl)-1H-pyrazole-4-carboxylate, Cpd 52b

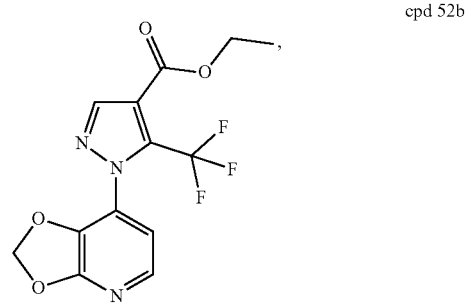 [SMILES: CCOC(=O)c1cnn(-c2ccnc3c2OCO3)c1C(F)(F)F]

A solution of 7-hydrazinyl-[1,3]dioxolo[4,5-b]pyridine. Cpd 52a (113 mg, 0.74 mmol), ethyl 2-(ethoxymethylene)-4,4,4-trifluoro-3-oxobutanoate, INT1 (283.56 mg, 1.18 mmol), in MeCN (5 mL) was stirred at 60° C. for 3 h. The mixture was concentrated under reduced pressure. The crude product was purified by column chromatography over silica gel (petroleum ether/ethyl acetate from 100/0 to 50/50). The desired fractions were collected and the solvent was concentrated under reduced pressure to afford cpd 52b (200 mg, 82.3% yield) as yellow solid. LCMS (ESI) m/z M+1: 330.1.

C. 1-([1,3]dioxolo[4,5-b]pyridin-7-yl)-5-(trifluoromethyl)-1H-pyrazole-4-carboxylic Acid, Cpd 52c

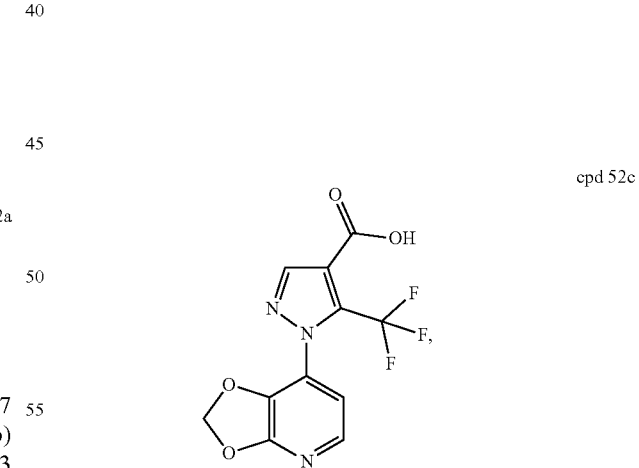

A solution of cpd 52b (200 mg, 0.607 mmol), LiOH (50.98 mg, 1.22 mmol) in THF/H₂O (2/1, 2 mL) was stirred at room temperature overnight. 1N HCl solution was added to neutralize the reaction solution. The mixture was extracted with ethyl acetate (10 mL×3). The separated organic layer was dried (MgSO₄), filtered, and the solvent was evaporated under reduced pressure to afford 1c (195 mg, 100% yield) as a yellow solid. LCMS (ESI) m/z M+1: 302.0.

D. N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide, Cpd 52

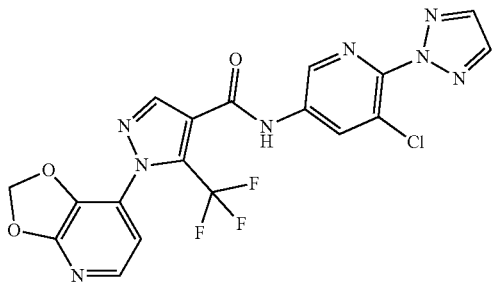 [SMILES: O=C(Nc1cnc(-n2nccn2)c(Cl)c1)c1cnn(-c2ccnc3c2OCO3)c1C(F)(F)F]

Phosphorus oxychloride (492.239 uL, 6.086 mmol) was added to a solution of 1-([1,3]dioxolo[4,5-b]pyridin-7-yl)-5-(trifluoromethyl)-1H-pyrazole-4-carboxylic acid, cpd 52c (195 mg, 0.61 mmol), 5-chloro-6-(2H-1,2,3-triazol-2-yl)pyridin-3-amine, INT2 (154.77 mg, 0.79 mmol), pyridine (492.24 uL, 6.09 mmol) in CH$_2$Cl$_2$ (2 mL). The mixture was stirred at room temperature for 2 h. Water (5 mL) was added to the mixture. Sat. NaHCO$_3$ was added to adjust the pH of reaction mixture to 7-8. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford the crude product, which was purified by preparative HPLC (32% to 62% (v/v) CH$_3$CN and H$_2$O with 0.05% HCl) and lyophilized to dryness to afford the title compound (180 mg, 60.6%). LCMS (ESI) m/z M+1: 478.9. $^1$H NMR (400 MHz, DMSO-d$_6$) δ ppm 6.31 (s, 2H), 7.16 (d, J=5.95 Hz, 1H), 7.80 (d, J=5.95 Hz, 1H), 8.19 (s, 2H), 8.55 (s, 1H), 8.64 (d, J=2.20 Hz, 1H), 8.82 (d, J=2.21 Hz, 1H), 11.27 (s, 1H).

Example 53

1-([1,3]dioxolo[4,5-b]pyridin-7-yl)-N-(5-cyano-6-(2H-1,2,3-triazol-2-yl)pyridin-3-yl)-5-(trifluoromethyl)-1H-pyrazole-4-carboxamide, Cpd 53

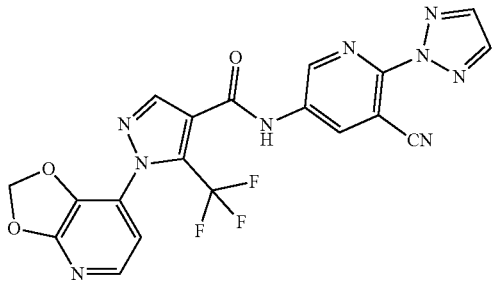 [SMILES: N#Cc1cc(NC(=O)c2cnn(-c3ccnc4c3OCO4)c2C(F)(F)F)cnc1-n1nccn1]

Phosphorus oxychloride (55.17 uL, 0.59 mmol) was added to a solution of 1-([1,3]dioxolo[4,5-b]pyridin-7-yl)-5-(trifluoromethyl)-1H-pyrazole-4-carboxylic acid, cpd 52c (90 mg, 0.30 mmol), 5-amino-2-(2H-1,2,3-triazol-2-yl)nicotinonitrile, INT3 (71.62 mg, 0.39 mmol), pyridine (239.34 uL, 2.96 mmol) in CH$_2$Cl$_2$ (2 mL). The mixture was stirred at room temperature for 1 h. Water (5 mL) was added to the mixture. Sat. NaHCO$_3$ was added to adjust the pH of reaction mixture to 7-8. The mixture was extracted with CH$_2$Cl$_2$ (5 mL×3). The combined organic extracts were dried over anhydrous Mg$_2$SO$_4$, filtered, and concentrated to dryness under reduced pressure to afford the crude product, which was purified by preparative HPLC (35% to 65% (v/v) CH$_3$CN and H$_2$O with 0.05% HCl) and lyophilized to dryness to afford the title compound (180 mg, 60.6%). LCMS (ESI) m/z M+1: 470.3. $^1$H NMR (400 MHz, DMSO-d$_6$) δ ppm 6.31 (s, 2H), 7.17 (d, J=5.95 Hz, 1H), 7.80 (d, J=5.95 Hz, 1H), 8.31 (s, 2H), 8.55 (s, 1H), 8.84 (d, J=2.43 Hz, 1H), 9.05 (d, J=2.43 Hz, 1H), 11.32 (br s, 1H).

Example 54

N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide, Cpd 54

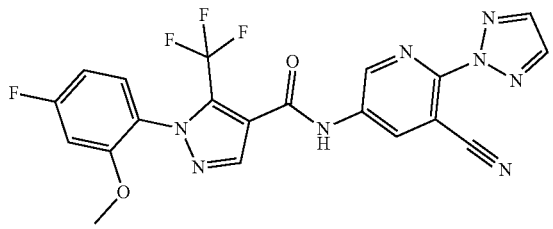 [SMILES: COc1cc(F)ccc1-n1ncc(C(=O)Nc2cnc(-n3nccn3)c(C#N)c2)c1C(F)(F)F]

A. (4-fluoro-2-methoxyphenyl)hydrazine, Cpd 54a

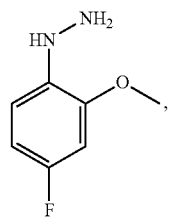

cpd 54a

To a stirring solution of 4-fluoro-2-methoxyaniline (2000 mg, 14.17 mmol) in 5 N HCl (19.84 mL, 99.19 mmol) was added a solution of NaNO$_2$ (1466 mg, 21.26 mmol) in 20 mL water at 0° C. After stirring for 30 mins, a solution of tin(II) chloride dihydrate (7994 mg, 35.43 mmol) in conc. HCl (3.543 mL, 42.51 mmol) was added dropwise. The mixture was stirred at room temperature overnight. The mixture was adjusted to pH 10-12 with 20% aqueous sodium hydroxide. The mixture was extracted with CH$_2$Cl$_2$ (5 mL×3). The combined organic extracts were dried over anhydrous Mg$_2$SO$_4$, filtered, and the filtrate concentrated to dryness under reduced pressure to afford 54a (2000 mg, 90.4%) as brown solid. TLC: petroleum ether/ethyl acetate=2/1, 4-fluoro-2-methoxyaniline Rf=0.7.

B. ethyl 1-(4-fluoro-2-methoxyphenyl)-5-(trifluoromethyl)-1H-pyrazole-4-carboxylate, Cpd 54b

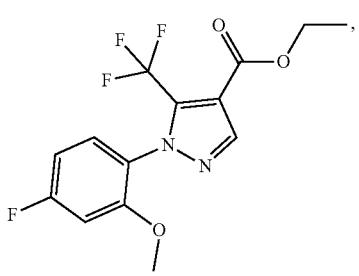

A solution of (4-fluoro-2-methoxyphenyl)hydrazine, cpd 54a (800 mg, 5.12 mmol), ethyl 2-(ethoxymethylene)-4,4,4-trifluoro-3-oxobutanoate, INT1 (1477 mg, 6.15 mmol), in MeCN (20 mL) was stirred at 60° C. for 2 h. The mixture was concentrated under reduced pressure. The crude product was purified by column chromatography over silica gel (petroleum ether/ethyl acetate from 100/0 to 50/50). The desired fractions were collected and the solvent was concentrated under reduced pressure to afford cpd 54b (1100 mg, 64.6% yield) as a yellow solid.

C. 1-(4-fluoro-2-methoxyphenyl)-5-(trifluoromethyl)-1H-pyrazole-4-carboxylic Acid, Cpd 54c

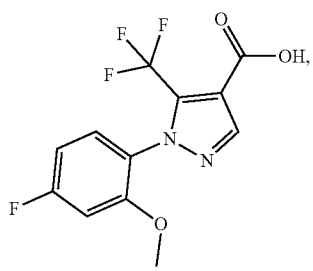

A solution of cpd 54b (1100 mg, 3.31 mmol), NaOH (264.84 mg, 6.62 mmol) in THF/H₂O (2/1, 10 mL) was stirred at room temperature overnight. 1N HCl solution was added to neutralize the reaction solution. The mixture was extracted with ethyl acetate (30 mL×3). The separated organic layer was dried (MgSO₄), filtered, and the solvent was evaporated under reduced pressure to afford cpd 54c (950 mg, 87.6% yield) as a yellow solid. LCMS (ESI) m/z M+1: 304.8.

D. N-(5-cyano-6-(2H-1,2,3-triazol-2-yl)pyridin-3-yl)-1-(4-fluoro-2-methoxyphenyl)-5-(trifluoromethyl)-1H-pyrazole-4-carboxamide, Cpd 54

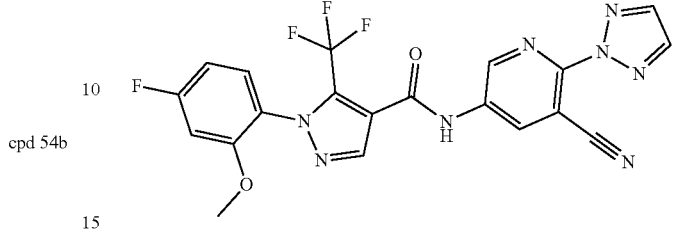

Phosphorus oxychloride (106.70 uL, 1.15 mmol) was added to a solution of 1-(4-fluoro-2-methoxyphenyl)-5-(trifluoromethyl)-1H-pyrazole-4-carboxylic acid, cpd 54c (150 mg, 0.46 mmol), 5-amino-2-(2H-1,2,3-triazol-2-yl)nicotinonitrile, INT3 (102.29 mg, 0.55 mmol), pyridine (370.32 uL, 4.58 mmol) in CH₂Cl₂ (5 mL). The mixture was stirred at room temperature for 2 h. Water (5 mL) was added to the mixture. Sat. NaHCO₃ was added to adjust the pH of reaction mixture to 7-8. The mixture was extracted with CH₂Cl₂ (5 mL×3). The combined organic extracts were dried over anhydrous MgSO₄, filtered, and the filtrate concentrated to dryness under reduced pressure to afford the crude product, which was purified by preparative HPLC (35% to 65% (v/v) CH₃CN and H₂O with 10 mM NH₄HCO₃) and lyophilized to dryness to afford the title compound (140 mg, 64.1%). LCMS (ESI) m/z M+1: 472.9. ¹H NMR (400 MHz, DMSO-d₆) δ ppm 3.81 (s, 3H), 6.99 (td, J=8.38, 2.65 Hz, 1H), 7.26 (dd, J=10.91, 2.54 Hz, 1H), 7.59 (dd, J=8.71, 6.06 Hz, 1H), 8.32 (s, 2H), 8.43 (s, 1H), 8.85 (d, J=2.65 Hz, 1H), 9.06 (d, J=2.65 Hz, 1H), 11.21 (s, 1H).

Example 55

N-(5-cyano-6-(2H-1,2,3-triazol-2-yl)pyridin-3-yl)-1-(o-tolyl)-5-(trifluoromethyl)-1H-pyrazole-4-carboxamide, Cpd 55

A. Ethyl 1-(2,3-dichloropyridin-4-yl)-5-(trifluoromethyl)-1H-pyrazole-4-carboxylate, Cpd 55a

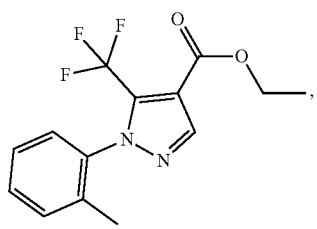

cpd 55a

A solution of (2-methylphenyl)hydrazine (200 mg, 1.64 mmol), ethyl 2-(ethoxymethylene)-4,4,4-trifluoro-3-oxobutanoate, INT1 (589.79 mg 2.46 mmol), in EtOH (5 mL) was stirred at 80° C. for 2 h. The mixture was concentrated under reduced pressure. The crude product was purified by column chromatography over silica gel (petroleum ether/ethyl acetate from 100/0 to 50/50). The desired fractions were collected and the solvent was concentrated under reduced pressure to afford cpd 55a (300 mg, 61.4% yield) as yellow solid. LCMS (ESI) m/z M+1: 298.9.

B. 1-(2-methylphenyl)-5-(trifluoromethyl)-1H-pyrazole-4-carboxylic Acid, Cpd 55b

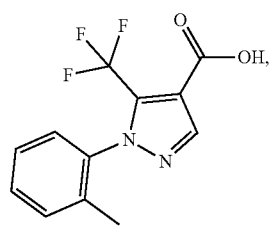

cpd 55b

A solution of cpd 55a (300 mg, 1.0 mmol), NaOH (80.46 mg 2.01 mmol) in THF/H₂O (2/1, 1 mL) was stirred at room temperature overnight. 1N HCl solution was added to neutralize the reaction solution. The mixture was extracted with ethyl acetate (10 mL×3). The separated organic layer was dried (MgSO₄), filtered, and the solvent was evaporated under reduced pressure to afford cpd 55b (270 mg, 99.3% yield) as a white solid.

C. N-(5-cyano-6-(2H-1,2,3-triazol-2-yl)pyridin-3-yl)-1-(o-tolyl)-5-(trifluoromethyl)-1H-pyrazole-4-carboxamide, Cpd 55

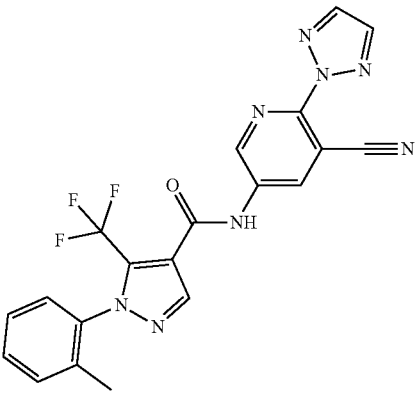 [SMILES: Cc1ccccc1-n1ncc(C(=O)Nc2cnc(-n3nccn3)c(C#N)c2)c1C(F)(F)F]

Phosphorus oxychloride (86.24 uL, 0.93 mmol) was added to a solution of 1-(2-methylphenyl)-5-(trifluoromethyl)-1H-pyrazole-4-carboxylic acid, cpd 55b (100 mg, 0.37 mmol), 5-amino-2-(2H-1,2,3-triazol-2-yl)nicotinonitrile (82.68 mg, 0.44 mmol), pyridine (299.32 uL, 3.70 mmol) in CH₂Cl₂ (5 mL). The mixture was stirred at room temperature for 1 h. Water (5 mL) was added to the mixture. Sat. NaHCO₃ was added to adjust the pH of reaction mixture to 7-8. The mixture was extracted with CH₂Cl₂ (5 mL×3). The combined organic extracts were dried over anhydrous Mg₂SO₄, filtered, and the filtrate concentrated to dryness under reduced pressure to afford the crude product, which was purified by preparative HPLC (45% to 65% (v/v) CH₃CN and H₂O with 0.05% HCl) and lyophilized to dryness to afford the title compound (38 mg, 23.1%). LCMS (ESI) m/z M+1: 438.9. ¹H NMR (400 MHz, DMSO-d₆) δ ppm 2.01 (s, 3H), 7.39-7.46 (m, 2H), 7.47-7.51 (m, 1H), 7.51-7.57 (m, 1H), 8.31 (s, 2H), 8.46 (s, 1H), 8.86 (d, J=2.21 Hz, 1H), 9.07 (d, J=2.20 Hz, 1H), 11.28 (s, 1H).

Example 56

1-(2-amino-3-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 56

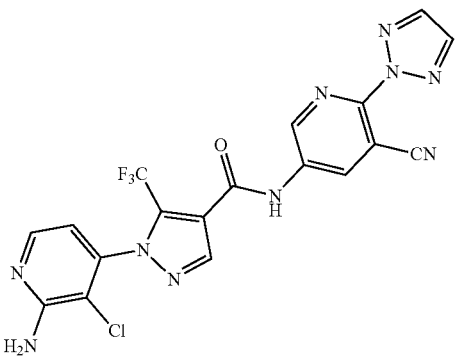 [SMILES: N#Cc1cc(NC(=O)c2cnn(-c3ccnc(N)c3Cl)c2C(F)(F)F)cnc1-n1nccn1]

A. 2,3-dichloro-4-hydrazinylpyridine, Cpd 56a

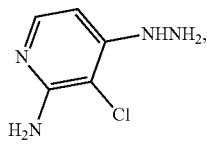

cpd 56a

A solution of 2,3,4-trichloropyridine (2000 mg, 10.96 mmol), hydrazine hydrate (1120.0 mg 21.93 mmol) in CH₃CN (5 mL) was stirred at 100° C. for 12 h. The mixture was concentrated under reduced pressure to afford cpd 56a (2200 mg>100% yield) as a white solid for next step directly. TLC: petroleum ether/ethyl acetate=0/100, Rf=0.3 1H NMR (400 MHz, CHLOROFORM-d) δ ppm 7.96-8.01 (m, 1H), 6.83-6.88 (m, 1H), 6.30-6.40 (m, 1H), 4.00 (br s, 2H).

B. Ethyl 1-(2,3-dichloropyridin-4-yl)-5-(trifluoromethyl)-1H-pyrazole-4-carboxylate, Cpd 56b

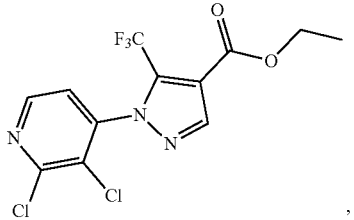

cpd 56b

A solution of 2,3-dichloro-4-hydrazinylpyridine, cpd 56a (2000 mg, 11.24 mmol), ethyl 2-(ethoxymethylene)-4,4,4-trifluoro-3-oxobutanoate, INT3 (4047.479 mg 16.85 mmol), triethylamine (3404.13 mg, 33.70 mmol) in EtOH (20 mL) was stirred at 80° C. for 12 h. The mixture was concentrated under reduced pressure. The crude product was purified by column chromatography over silica gel (petroleum ether/ethyl acetate from 20:1 to 1:1). The desired fractions were collected and the solvent was concentrated under reduced pressure to afford cpd 56b (1500 mg, 33.1% yield) as a yellow solid.

C. Ethyl 1-(2-amino-3-chloropyridin-4-yl)-5-(trifluoromethyl)-1H-pyrazole-4-carboxylate, Cpd 56c

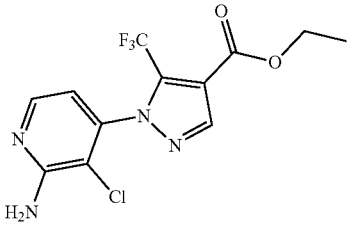

cpd 56c

Ethyl 1-(2,3-dichloropyridin-4-yl)-5-(trifluoromethyl)-1H-pyrazole-4-carboxylate, cpd 57b (1100 mg, 2.73 mmol) was added to a mixture of NH₂Boc (1596.202 mg, 13.63 mmol). K₂CO₃ (1128.21 mg, 8.18 mmol) in NMP (5 mL). The mixture was stirred at 130° C. in microwave for 1 h. The mixture was diluted with water (200 mL) and extracted with EtOAc (50 mL×3), washed with brine (100 mL), dried over MgSO₄ and concentrated under reduced pressure. The crude product was purified by column chromatography over silica gel (petroleum ether/ethyl acetate from 50:1 to 1:1). The desired fractions were collected and the solvent was concentrated under reduced pressure to afford cpd 56c (1000 mg, 94.5% yield) as a yellow solid. TLC: petroleum ether/ethyl acetate=3/1, Rf=0.4 LCMS (ESI) m/z M+1: 334.9. 1H NMR (400 MHz, CHLOROFORM-d) δ ppm 8.18-8.20 (m, 1H), 8.08 (d, J=5.51 Hz, 1H), 6.76-6.79 (m, 1H), 4.92 (br s, 2H), 4.35-4.37 (m, 2H), 1.37-1.40 (m, 3H).

D. Ethyl 1-(2-((di-(tert-butoxycarbonyl))amino)-3-chloropyridin-4-yl)-5-(trifluoromethyl)-1H-pyrazole-4-carboxylate, Cpd 56d

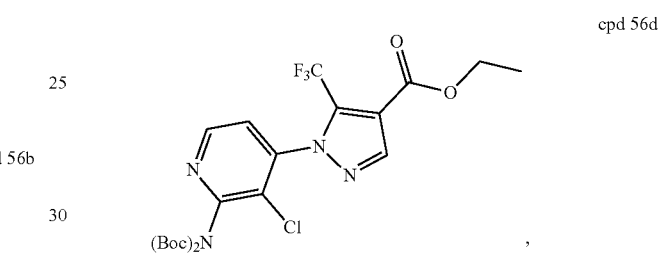

cpd 56d

A solution of ethyl 1-(2-amino-3-chloropyridin-4-yl)-5-(trifluoromethyl)-1H-pyrazole-4-carboxylate, cpd 56c (1000 mg 2.58 mmol), (Boc)₂O (1123.79 mg, 5.15 mmol), Et₃N (780.10 mg, 7.72 mmol), DMAP (31.41 mg 0.26 mmol) in CH₂Cl₂ (20 mL) was stirred at rt for 12 h. The mixture was diluted with water (100 mL) and extracted with CH₂Cl₂ (100 mL×3). The organic layer was dried (MgSO₄) and concentrated. The residue was purified by column chromatography over silica gel (eluent: petrol ether/EtOAc=100:0 to 70:30). The desired fractions were collected and the solvent was concentrated under reduced pressure to afford cpd 56d (510 mg, 34.1%) as a white solid. LCMS (ESI) m/z M+1: 535.0.

E. 1-(2-((tert-butoxycarbonyl)amino)-3-chloropyridin-4-yl)-5-(trifluoromethyl)-1H-pyrazole-4-carboxylic Acid, Cpd 56e

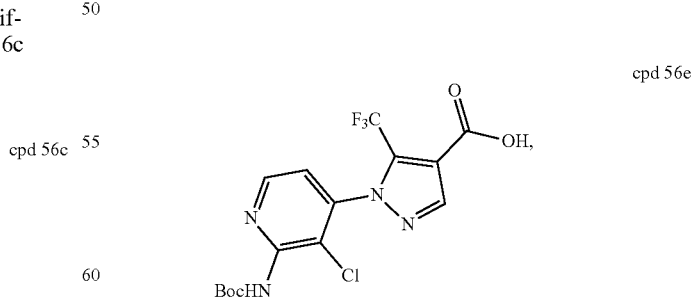

cpd 56e

A solution of cpd 56d (510 mg, 0.88 mmol), LiOH (73.652 mg 1.755 mmol) in THF (10 mL), MeOH (10 mL) and H₂O (10 mL) was stirred at rt for 3 h. The mixture was added 5% KHSO₄ to adjust pH 3-4. Water (100 mL) and ethyl acetate (100 mL) were added to the mixture. The organic layer was washed with brine (50 mL), dried over MgSO$_4$ and concentrated under reduced pressure to afford cpd 56e (370 mg, 877% yield) as a yellow solid for the next step directly. LCMS (ESI) m/z M+H: 406.9

F. Tert-butyl (3-chloro-4-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, Cpd 56f

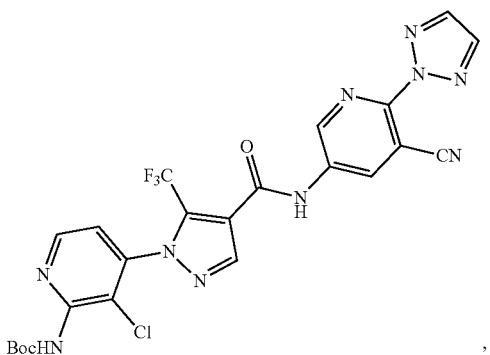

cpd 56f

POCl$_3$ (235.96 mg, 1.54 mmol) was added to a solution of 1-(2-((tert-butoxycarbonyl)amino)-3-chloropyridin-4-yl)-5-(trifluoromethyl)-1H-pyrazole-4-carboxylic acid, cpd 56e (370 mg, 0.77 mmol), 5-amino-2-(2H-1,2,3-triazol-2-yl)nicotinonitrile, INT3 (171.9 mg, 0.92 mmol), pyridine (152.16 mg 1.92 mmol) in CH$_2$Cl$_2$ (10 mL). The mixture was stirred at rt for 1 h. Water (50 mL) and CH$_2$Cl$_2$ (50 mL) were added to the mixture. The organic layer was washed with brine (50 mL), dried over MgSO$_4$ and concentrated under reduced pressure. The crude product was purified by column chromatography over silica gel (petroleum ether/ethyl acetate from 20:1 to 1:1). The desired fractions were collected and the solvent was concentrated under reduced pressure to afford cpd 56f (200 mg, 34.9% yield) as a white solid. TLC: petroleum ether/ethyl acetate=1/1), LCMS (ESI) m/z M+H: 575.0

G. 1-(2-amino-3-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 56

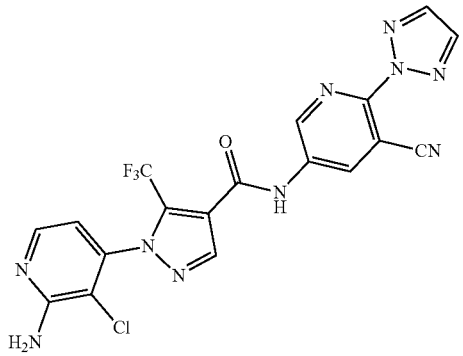 [SMILES: N#Cc1cc(NC(=O)c2cnn(-c3ccnc(N)c3Cl)c2C(F)(F)F)cnc1-n1nccn1]

tert-butyl (3-chloro-4-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, cpd 56f (200 mg, 0.27 mmol) was added to HCl/dioxane (20 mL, 4 mol/L). The mixture was stirred at rt for 1 h. The mixture was concentrated under reduced pressure to afford the crude product, which was purified by preparative HPLC (32% to 52% (v/v) CH$_3$CN and H$_2$O with 0.05% HCl) and lyophilized to dryness to afford the title compound (61.1 mg 440%) as a white solid. LCMS (ESI) m/z M+1: 474.9. 1H NMR (400 MHz, DMSO-d$_6$) δ ppm 11.27 (br s, 1H), 9.07 (d, J=2.65 Hz, 1H), 8.85 (d, J=2.43 Hz, 1H), 8.51 (s, 1H) 8.28 (s, 2H) 7.96 (d, J=5.51 Hz, 1H) 6.96 (br s, 2H) 6.88 (d, J=5.51 Hz, 1H).

Example 57

1-(2-amino-3-chloropyridin-4-yl)-N-(5-chloro-6-(2H-1,2,3-triazol-2-yl)pyridin-3-yl)-5-(trifluoromethyl)-1H-pyrazole-4-carboxamide, Cpd 57

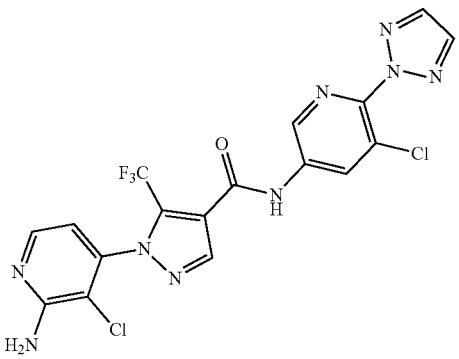 [SMILES: Nc1nccc(-n2ncc(C(=O)Nc3cnc(-n4nccn4)c(Cl)c3)c2C(F)(F)F)c1Cl]

A. Tert-butyl (3-chloro-4-(4-((5-chloro-6-(2H-1,2,3-triazol-2-yl)pyridin-3-yl)carbamoyl)-5-(trifluoromethyl)-1H-pyrazol-1-yl)pyridin-2-yl)carbamate, Cpd 57a

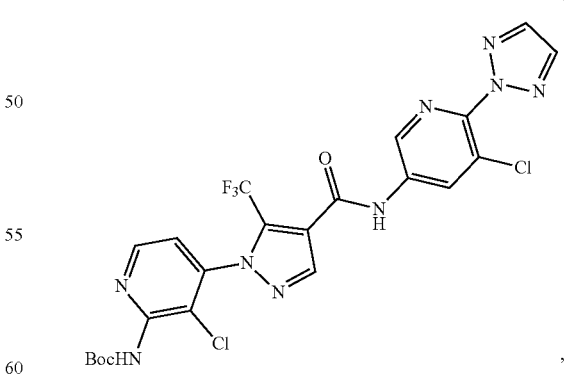

cpd 57a

POCl$_3$ (110.51 mg, 0.72 mmol) was added to a solution of 1-(2-((tert-butoxycarbonyl)amino)-3-chloropyridin-4-yl)-5-(trifluoromethyl)-1H-pyrazole-4-carboxylic acid, cpd 56c (180 mg, 0.36 mmol), 5-chloro-6-(2H-1,2,3-triazol-2-yl)pyridin-3-amine, INT2 (84.58 mg, 0.43 mmol), pyridine (71.26 mg 0.90 mmol) in CH$_2$Cl$_2$ (10 mL). The mixture was stirred at rt for 1 h. Water (50 mL) and CH₂Cl₂ (50 mL) were added to the mixture. The organic layer was washed with brine (50 mL), dried over MgSO₄ and concentrated under reduced pressure. The crude product was purified by column chromatography over silica gel (petroleum ether/ethyl acetate from 20:1 to 1:1). The desired fractions were collected and the solvent was concentrated under reduced pressure to afford 57a (160 mg, 75.5% yield) as a white solid. LCMS (ESI) m/z M-Boc: 483.9

B. 1-(2-amino-3-chloropyridin-4-yl)-N-(5-chloro-6-(2H-1,2,3-triazol-2-yl)pyridin-3-yl)-5-(trifluoromethyl)-1H-pyrazole-4-carboxamide, Cpd 57

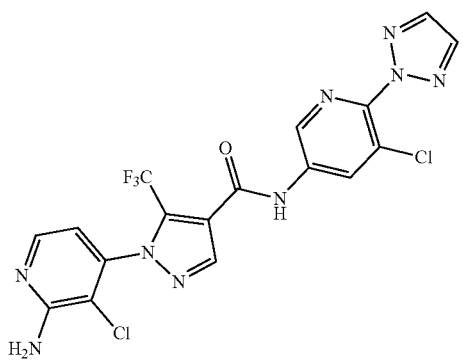 [SMILES: Nc1nccc(-n2ncc(C(=O)Nc3cnc(-n4nccn4)c(Cl)c3)c2C(F)(F)F)c1Cl]

tert-Butyl (3-chloro-4-(4-((5-chloro-6-(2H-1,2,3-triazol-2-yl)pyridin-3-yl)carbamoyl)-5-(trifluoromethyl)-1H-pyrazol-1-yl)pyridin-2-yl)carbamate, cpd 57a (150 mg 0.26 mmol) was added to HCl/dioxane (15 mL, 4 mol/L). The mixture was stirred at rt for 1 h. The mixture was concentrated under reduced pressure to afford the crude product, which was purified by preparative HPLC (30% to 60% (v/v) CH₃CN and H₂O with 0.05% HCl) and lyophilized to dryness to afford the title compound (30 mg 22.6%) as a white solid. LCMS (ESI) m/z M+1: 483.9 1H NMR (400 MHz, DMSO-d₆) δ ppm 11.46 (s, 1H), 8.87-8.94 (m, 1H), 8.66-8.73 (m, 2H), 8.16 (s, 2H), 8.10 (d, J=5.29 Hz, 1H), 6.86 (d, J=5.29 Hz, 1H).

Example 58

N-(5-chloro-6-(2H-1,2,3-triazol-2-yl)pyridin-3-yl)-1-(2,2-difluorobenzo[d][1,3]dioxol-4-yl)-5-(trifluoromethyl)-1H-pyrazole-4-carboxamide, Cpd 58

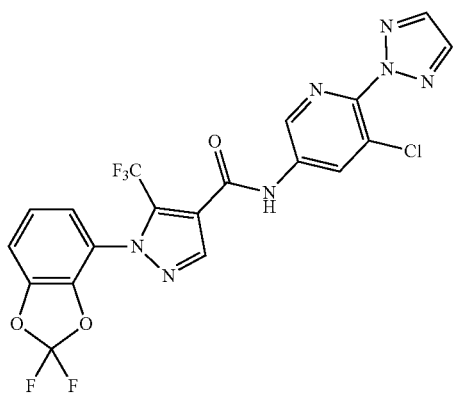 [SMILES: O=C(Nc1cnc(-n2nccn2)c(Cl)c1)c1cnn(-c2cccc3c2OC(F)(F)O3)c1C(F)(F)F]

A. (2,2-Difluorobenzo[d][1,3]dioxol-4-yl)hydrazine, Cpd 58a

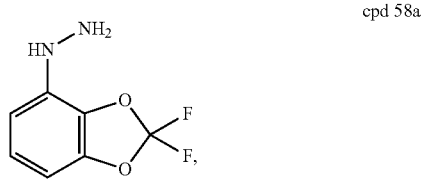 [SMILES: NNc1cccc2c1OC(F)(F)O2]

The mixture of {Pd(cinnamyl)Cl}₂ (65.58 mg, 0.13 mmol) and Mor-DalPhos (117.38 mg, 0.25 mmol) in dioxane (20 mL) was evacuated with argon 4 times. The resulting clear yellow solution was stirred at room temperature under argon for 10 min. 4-bromo-2,2-difluorobenzo[d][1,3]dioxole (600 mg, 2.53 mmol) and t-BuONa (486.08 mg, 5.06 mmol) was added to the mixture and the mixture was evacuated with argon 4 times. The resulting yellow reaction was stirred at room temp for 5 min and was then treated with hydrazine hydrate (258.65 mg, 5.06 mmol) via syringe. The reaction was evacuated with argon 4 times. Then the mixture was stirred at 50° C. under argon for 2 hrs. The mixture was filtered and washed with ethyl acetate (50 mL×3). The filtrate was collected and concentrated to afford crude cpd 58a (500 mg, 75.3% yield) as a brown solid which was used directly for the next step. LCMS (ESI) m/z M+Na: 212.9.

B. Ethyl 1-(2,2-difluorobenzo[d][1,3]dioxol-4-yl)-5-(trifluoromethyl)-1H-pyrazole-4-carboxylate, Cpd 58b A solution of (2,2-difluorobenzo[d][1,3]dioxol-4-yl)hydrazine, cpd 58a (500 mg, 1.91 mmol), ethyl 2-(ethoxymethylene)-4,4,4-trifluoro-3-oxobutanoate, INT1 (686.59 mg, 2.86 mmol), triethylamine (577.5 mg, 5.72 mmol) in EtOH (30 mL) was stirred at 80° C. for 12 h. The mixture was concentrated under reduced pressure. The crude product was purified by column chromatography over silica gel (petroleum ether/ethyl acetate from 100:1 to 20:1). The desired fractions were collected and the solvent was concentrated under reduced pressure to afford cpd 58b (410 mg, 49.8% yield) as yellow oil. LCMS (ESI) M+1: 364.8.

C. 1-(2,2-Difluorobenzo[d][1,3]dioxol-4-yl)-5-(trifluoromethyl)-1H-pyrazole-4-carboxylic Acid, Cpd 58c

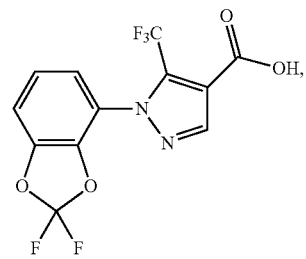

cpd 58c

A solution of ethyl 1-(2,2-difluorobenzo[d][1,3]dioxol-4-yl)-5-(trifluoromethyl)-1H-pyrazole-4-carboxylate, cpd 58b (410 mg, 0.95 mmol), LiOH (79.71 mg, 1.9 mmol) in MeOH (10 mL), THF (10 mL) and H$_2$O (10 mL) was stirred at rt for 3 h. The mixture was added 5% KHSO$_4$ to adjust to pH 3-4. Water (100 mL) and ethyl acetate (100 mL) were added to the mixture. The organic layer was washed with brine (50 mL), dried over MgSO$_4$ and concentrated under reduced pressure to afford 58c (370 mg, 77.7% yield) as yellow solid for next step directly. LCMS (ESI) m/z M+H: 337.0.

D. N-(5-Chloro-6-(2H-1,2,3-triazol-2-yl)pyridin-3-yl)-1-(2,2-difluorobenzo[d][1,3]dioxol-4-yl)-5-(trifluoromethyl)-1H-pyrazole-4-carboxamide, Cpd 58

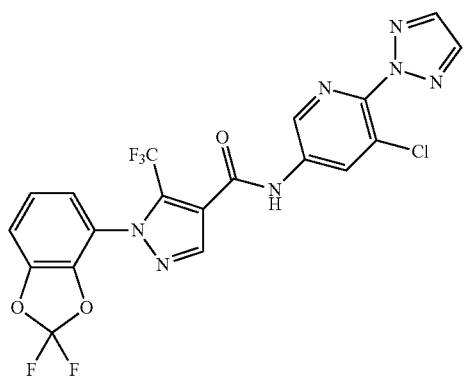 [SMILES: O=C(Nc1cnc(-n2nccn2)c(Cl)c1)c1cnn(-c2cccc3c2OC(F)(F)O3)c1C(F)(F)F]

POCl$_3$ (226.2 mg, 1.475 mmol) was added to a solution of 1-(2,2-difluorobenzo[d][1,3]dioxol-4-yl)-5-(trifluoromethyl)-1H-pyrazole-4-carboxylic acid, cpd 58c (370 mg, 0.74 mmol), 5-chloro-6-(2H-1,2,3-triazol-2-yl)pyridin-3-amine, INT2 (173.14 mg, 0.89 mmol), pyridine (145.86 mg 1.844 mmol) in CH$_2$Cl$_2$ (20 mL). The mixture was stirred at rt for 3 h. Water (50 mL) and CH$_2$Cl$_2$ (50 mL) were added to the mixture. The organic layer was washed with brine (50 mL), dried over MgSO$_4$ and concentrated under reduced pressure to afford the crude product, which was purified by preparative HPLC (50% to 80% (v/v) CH$_3$CN and H$_2$O with 0.05% HCl) and lyophilized to dryness to afford the title compound (160 mg 42.1% yield) as a white solid. LCMS (ESI) m/z M+1: 513.8. 1H NMR (400 MHz, DMSO-d$_6$) δ ppm 11.36 (br s, 1H), 8.84 (d, J=2.21 Hz, 1H), 8.65 (d, J=2.21 Hz, 1H), 8.59 (s, 1H), 8.16 (s, 2H), 7.71 (dd, J=8.16, 0.88 Hz, 1H), 7.48-7.56 (m, 1H), 7.40-7.47 (m, 1H).

Example 59

1-(benzo[d][1,3]dioxol-4-yl)-N-(5-cyano-6-(2H-1,2,3-triazol-2-yl)pyridin-3-yl)-5-(trifluoromethyl)-1H-pyrazole-4-carboxamide, Cpd 59

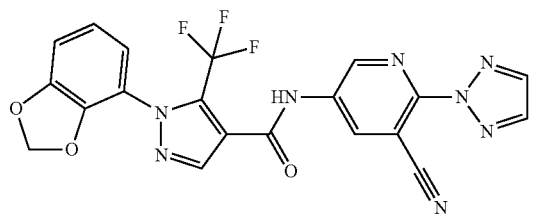 [SMILES: N#Cc1cc(NC(=O)c2cnn(-c3cccc4c3OCO4)c2C(F)(F)F)cnc1-n1nccn1]

A. Benzo[d][1,3]dioxol-4-ylhydrazine, Cpd 59a

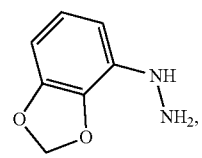

cpd 59a

To a stirring solution of benzo[d][1,3]dioxol-4-amine (250 mg, 1.44 mmol) in conc.HCl (4 mL) at −5° C. was added a solution of sodium nitrite (119.2 mg, 1.728 mmol) in water (0.5 mL) below 0° C. slowly. The reaction mixture was stirred at 0° C. for 1 h and a solution of tin(II) chloride dihydrate (649.9 mg, 2.88 mmol) dissolved in conc. HCl (1 mL) was added dropwise. Then the mixture was stirred at room temperature for 16 h. The mixture was adjusted to pH 12-14 with 20% aqueous sodium hydroxide. The mixture was extracted with ethyl acetate (20 mL×3). The combined organic layers were washed with brine, dried with anhydrous Na$_2$SO$_4$, filtered, and the filtrate concentrated under reduced pressure to afford crude product (250 mg, 114.1%) as colorless oil, which was used for the next step without further purification.

B. Ethyl 1-(benzo[d][1,3]dioxol-4-yl)-5-(trifluoromethyl)-1H-pyrazole-4-carboxylate, Cpd 59b

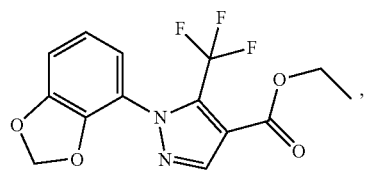

cpd 59b

A solution consisting of ethyl 2-(ethoxymethylene)-4,4,4-trifluoro-3-oxobutanoate, INT1 (250 mg, 1.64 mmol), benzo[d][1,3]dioxol-4-ylhydrazine, cpd 59a (473 mg, 1.97 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=100:0 to 60:40) to afford the title compound (200 mg, 37.1%) as a gray solid. LCMS (ESI) m/z M+1: 328.9.

C. 1-(Benzo[d][1,3]dioxol-4-yl)-5-(trifluoromethyl)-1H-pyrazole-4-carboxylic Acid. Cpd 59c

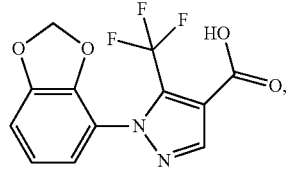

cpd 59c

Sodium hydroxide (48.7 mg, 1.22 mmol) was added to a solution of ethyl 1-(benzo[d][1,3]dioxol-4-yl)-5-(trifluoromethyl)-1H-pyrazole-4-carboxylate, cpd 59b (0.2 g, 0.61 mmol) in THF:H₂O (3:1, 8 mL). The mixture was reacted at room temperature for 3 hours. The solvent was evaporated under reduced pressure to pH 5 and extracted with ethyl acetate (30 mL×3). The combined organic layers were washed with brine, dried with anhydrous MgSO₄, and filtered. The filtrates were concentrated under reduced pressure to afford the product (167 mg, 95.1% purity, 86.8%) as a yellow solid. LCMS (ESI) m/z M+1: 300.9.

D. 1-(Benzo[d][1,3]dioxol-4-yl)-N-(5-cyano-6-(2H-1,2,3-triazol-2-yl)pyridin-3-yl)-5-(trifluoromethyl)-1H-pyrazole-4-carboxamide, Cpd 59

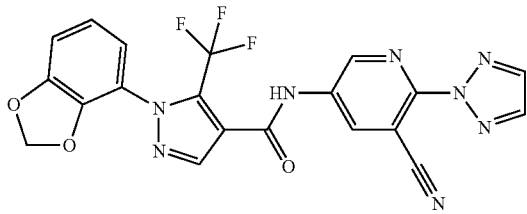 [SMILES: N#Cc1cc(NC(=O)c2cnn(-c3cccc4c3OCO4)c2C(F)(F)F)cnc1-n1nccn1]

1-(Benzo[d][1,3]dioxol-4-yl)-5-(trifluoromethyl)-1H-pyrazole-4-carboxylic acid, cpd 59c (84.79 mg, 0.27 mmol), 5-amino-2-(2H-1,2,3-triazol-2-yl)nicotinonitrile, INT 2 (50.0 mg, 0.27 mmol), pyridine (106.22 mg, 2.01 mmol) were dissolved in CH₂Cl₂ (10 mL), and phosphorus oxychloride (82.36 mg, 0.537 mmol) was added. The mixture was stirred at 25° C. for 2 h. Sat.NaHCO₃(20 mL) was added and extracted with CH₂Cl₂ (30 mL×2). The combined organic extracts were dried over anhydrous Na₂SO₄, filtered, and the filtrate concentrated to dryness under reduced pressure to afford the crude product, which was purified by preparative HPLC (45% to 75% (v/v) CH₃CN and H₂O with 0.05% HCl) and lyophilized to dryness to afford the title compound (55 mg, 43.4%). LCMS (ESI) m/z M+1: 468.9. ¹H NMR (400 MHz, DMSO-d₆) δ ppm 11.30 (1H, s), 9.07 (1H, d, J=2.43 Hz), 8.85 (1H, d, J=2.43 Hz), 8.47 (1H, s) 8.32 (2H, s), 7.15-7.23 (1H, m), 6.99-7.10 (2H, m), 6.17 (2H, s).

Example 60

1-(2-chloro-3,4-difluorophenyl)-N-(5-cyano-6-(2H-1,2,3-triazol-2-yl)pyridin-3-yl)-5-(trifluoromethyl)-1H-pyrazole-4-carboxamide, Cpd 60

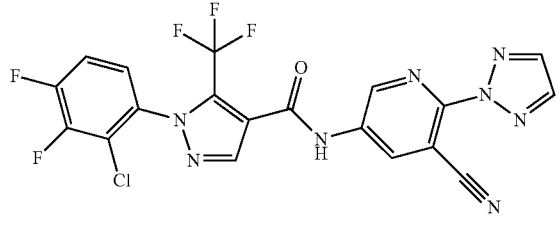 [SMILES: N#Cc1cc(NC(=O)c2cnn(-c3ccc(F)c(F)c3Cl)c2C(F)(F)F)cnc1-n1nccn1]

A. (2-chloro-3,4-difluorophenyl)hydrazine, cpd 60a

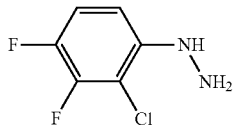

cpd 60a

To a stirring solution of 2-chloro-3,4-difluoroaniline (500 mg, 3.057 mmol) in 5M HCl (4.4 mL) at 0° C. was added a solution of sodium nitrite (316.4 mg, 5 mmol) in H₂O (2 mL) below 0° C. slowly. The reaction mixture was stirred at 0° C. for 30 min and a solution of tin (II) chloride dihydrate (1.725 g, 7.643 mmol) dissolved in conc. HCl (0.82 mL) was added dropwise. Then the mixture was stirred at room temperature for 3 h. The mixture was adjusted to pH 12-14 with 20% aqueous sodium hydroxide. The mixture was extracted with ethyl acetate (50 mL×3). The combined organic layers were washed with brine, dried with anhydrous Na₂SO₄, filtered, and concentrated under reduced pressure to afford crude product (300 mg, 55.0%) as a yellow oil, which was used for the next step without further purification. LCMS (ESI) m/z M+1: 178.9.

B. Ethyl 1-(2-chloro-3,4-difluorophenyl)-5-(trifluoromethyl)-1H-pyrazole-4-carboxylate, Cpd 60b

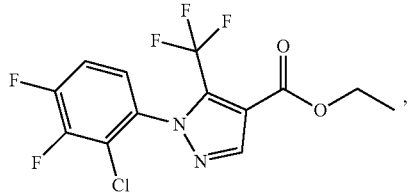

cpd 60b

A solution consisting of ethyl 2-(ethoxymethylene)-4,4,4-trifluoro-3-oxobutanoate, INT1 (0.605 g, 2.520 mmol), (2-chloro-3,4-difluorophenyl)hydrazine, cpd 60a (300 mg, 1.680 mmol) and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=100:0 to 80:20) to afford the title compound (0.77 g, 91.6% purity, 118.4%) as a brown oil. LCMS (ESI) m/z M+1: 354.9.

C. 1-(2-Chloro-3,4-difluorophenyl)-5-(trifluoromethyl)-1H-pyrazole-4-carboxylic Acid. Cpd 60c

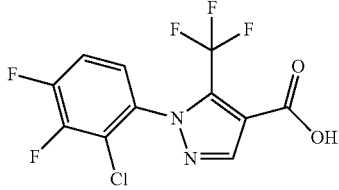

cpd 60c

Sodium hydroxide (119.33 mg, 2.984 mmol) was added to a solution of ethyl 1-(2-chloro-3,4-difluorophenyl)-5-(trifluoromethyl)-1H-pyrazole-4-carboxylate, cpd 60b (0.77 g, 1.989 mmol) in THF:H$_2$O (3:1, 8 mL). The mixture was reacted at room temperature for 3 hours. The solvent was evaporated under reduced pressure and water (10 mL) was added to the mixture. The mixture was made acidic (pH 5) by the addition of 1M hydrochloric, and then extracted with ethyl acetate (30 mL×3). The combined organic layers were washed with brine, dried with anhydrous MgSO$_4$, and filtered. The filtrates were concentrated under reduced pressure to afford product (600 mg, 82.1% purity, 75.9%) as yellow solid. LCMS (ESI) m/z M+1: 326.9.

D. 1-(2-Chloro-3,4-difluorophenyl)-N-(5-cyano-6-(2H-1,2,3-triazol-2-yl)pyridin-3-yl)-5-(trifluoromethyl)-1H-pyrazole-4-carboxamide, Cpd 60

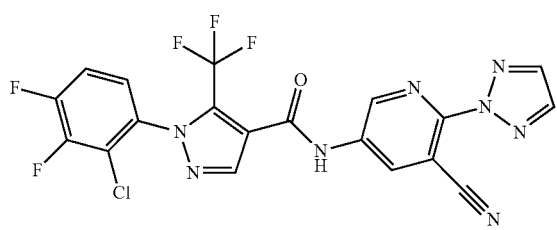 [SMILES: N#Cc1cc(NC(=O)c2cnn(-c3ccc(F)c(F)c3Cl)c2C(F)(F)F)cnc1-n1nccn1]

1-(2-Chloro-3,4-difluorophenyl)-5-(trifluoromethyl)-1H-pyrazole-4-carboxylic acid, cpd 60c (200 mg, 0.503 mmol), 5-amino-2-(2H-1,2,3-triazol-2-yl)nicotinonitrile, INT 3 (93.63 mg, 0.503 mmol), pyridine (0.20 mL, 2.012 mmol) were dissolved in CH$_2$Cl$_2$ (10 mL), and phosphorus oxychloride (0.18 mL, 2.514 mmol) was added. The mixture was stirred at 25° C. for 2 h. Sat.NaHCO$_3$(20 mL) was added and extracted with CH$_2$Cl$_2$ (30 mL×2). The combined organic extracts were dried over anhydrous Na$_2$SO$_4$, filtered, and the filtrate concentrated to dryness under reduced pressure to afford the crude product, which was purified by preparative HPLC (45% to 75% (v/v) CH$_3$CN and H$_2$O with 0.05% HCl) and lyophilized to dryness to afford the title compound (127 mg, 50.56%). LCMS (ESI) m/z M+1: 494.9. 1H NMR (400 MHz, DMSO-d$_6$) δ ppm 11.28 (1H, s), 9.04 (1H, d, J=2.65 Hz), 8.83 (1H, d, J=2.65 Hz), 8.54 (1H, s), 8.30 (2H, s), 7.71-7.84 (2H, m).

Example 61

1-(2-chloro-3-fluorophenyl)-N-(5-cyano-6-(2H-1,2,3-triazol-2-yl)pyridin-3-yl)-5-(trifluoromethyl)-1H-pyrazole-4-carboxamide, Cpd 61

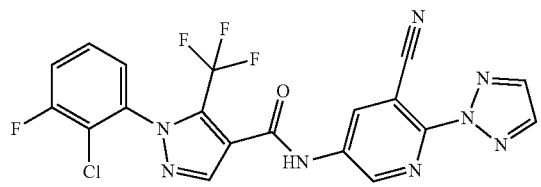 [SMILES: N#Cc1cc(NC(=O)c2cnn(-c3cccc(F)c3Cl)c2C(F)(F)F)cnc1-n1nccn1]

A. (2-chloro-3-fluorophenyl)hydrazine, Cpd 61a

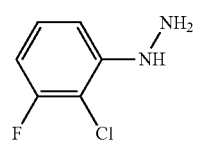

cpd 61a

To a stirring solution of 2-chloro-3-fluoroaniline (1 g, 6.870 mmol) in 5M HCl (9.6 mL) at 0° C. was added a solution of sodium nitrite (711 mg, 10 mmol) in H$_2$O (2 mL) below 0° C. slowly. The reaction mixture was stirred at 0° C. for 30 mins and a solution of tin(II) chloride dihydrate (3.875 g, 17.175 mmol) dissolved in conc.HCl (1.7 mL) was added dropwise. Then the mixture was stirred at room temperature for 3 h. The mixture was adjusted to pH 12-14 with 20% aqueous sodium hydroxide. The mixture was extracted with ethyl acetate(50 mL*3). The combined organic layers were washed with brine, dried with anhydrous Na$_2$SO$_4$, filtered, and the filtrate concentrated under reduced pressure to afford a crude product (900 mg, 81.6%) as a yellow oil, which was used for the next step without further purification. LCMS (ESI) m/z M+1: 161.0.

B. Ethyl 1-(2-chloro-3-fluorophenyl)-5-(trifluoromethyl)-1H-pyrazole-4-carboxylate, Cpd 61b

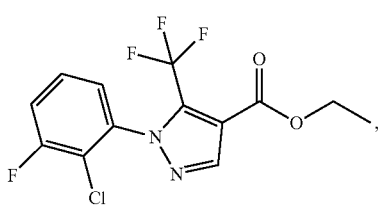

cpd 61b

A solution consisting of ethyl 2-(ethoxymethylene)-4,4,4-trifluoro-3-oxobutanoate, INT1 (1.481 g, 6.165 mmol), (2-chloro-3-fluorophenyl)hydrazine, cpd 61a (900 mg, 5.605 mmol) in ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=100/0 to 80/20) to afford the title compound (1.3 g, 69%) as a brown oil. LCMS (ESI) m/z M+1: 337.0.

C. 1-(2-Chloro-3-fluorophenyl)-5-(trifluoromethyl)-1H-pyrazole-4-carboxylic Acid. Cpd 61c

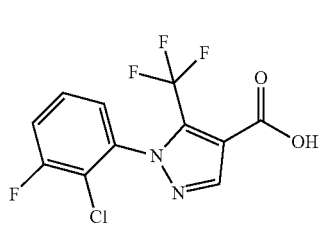

cpd 61c

Sodium hydroxide (231.67 mg, 5.792 mmol) was added to a solution of ethyl 1-(2-chloro-3-fluorophenyl)-5-(trifluoromethyl)-1H-pyrazole-4-carboxylate, cpd 61b (1.3 g, 3.861 mmol) in THF:H2O=3:1 (12 mL). The mixture was reacted at room temperature for 3 hours. The solvent was evaporated under reduced pressure and water (10 mL) was added to the mixture. The mixture was made acidic (pH 5) by the addition of 1M hydrochloric acid, and then extracted with ethyl acetate (30 mL×3). The combined organic layers were washed with brine, dried with anhydrous MgSO4, and filtered. The filtrates were concentrated under reduced pressure to afford product (660 mg, 95.9% purity, 53.1%) as brown oil. LCMS (ESI) m/z M+1: 309.0.

D. 1-(2-Chloro-3-fluorophenyl)-N-(5-cyano-6-(2H-1,2,3-triazol-2-yl)pyridin-3-yl)-5-(trifluoromethyl)-1H-pyrazole-4-carboxamide, Cpd 61

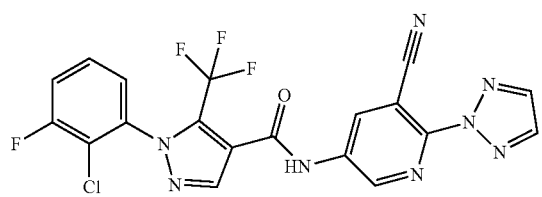 [SMILES: N#Cc1cc(NC(=O)c2cnn(-c3cccc(F)c3Cl)c2C(F)(F)F)cnc1-n1nccn1]

1-(2-Chloro-3-fluorophenyl)-5-(trifluoromethyl)-1H-pyrazole-4-carboxylic acid, cpd 61c (100 mg, 0.311 mmol), 5-amino-2-(2H-1,2,3-triazol-2-yl)nicotinonitrile, INT 3 (57.89 mg, 0.311 mmol), pyridine (0.13 mL, 1.555 mmol) were dissolved in CH2Cl2 (10 mL), and phosphorus oxychloride (0.11 mL, 1.244 mmol) was added. The mixture was stirred at 25° C. for 2 h. Sat.NaHCO3(20 mL) was added and extracted with CH2Cl2 (30 mL×2). The combined organic extracts were dried over anhydrous Na2SO4, filtered, and the filtrate concentrated to dryness under reduced pressure to afford the crude product, which was purified by preparative HPLC (44% to 74% (v/v) CH3CN and H2O with 0.05% HCl) and lyophilized to dryness to afford the title compound (52 mg, 35%). LCMS (ESI) m/z M+1: 476.9. 1H NMR (400 MHz, DMSO-d6) δ ppm 11.28 (1H, s), 9.04 (1H, d, J=2.43 Hz), 8.82 (1H, d, J=2.43 Hz), 8.53 (1H, s), 8.28 (2H, s), 7.72-7.79 (1H, m), 7.60 5-7.69 (2H, m).

Example 62

1-(6-amino-5-fluoropyridin-2-yl)-N-(5-chloro-6-(2H-1,2,3-triazol-2-yl)pyridin-3-yl)-5-(trifluoromethyl)-1H-pyrazole-4-carboxamide, Cpd 62

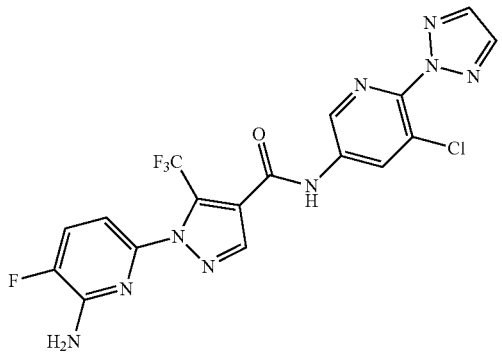 [SMILES: Nc1nc(-n2ncc(C(=O)Nc3cnc(-n4nccn4)c(Cl)c3)c2C(F)(F)F)ccc1F]

A. 2-Bromo-3-fluoro-6-hydrazinylpyridine, Cpd 62a

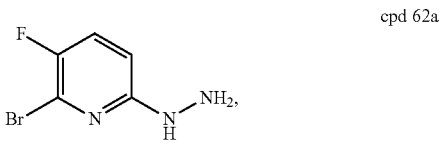

cpd 62a

2-Bromo-3,6-difluoropyridine (900 mg, 4.64 mmol) was dissolved in MeCN (10 mL) and hydrazine hydrate (474 mg, 0.279 mmol) was added. The reaction mixture was stirred at 80° C. for 16 h before cooling to room temperature. The reaction mixture was concentrated under reduced pressure to afford crude product (1 g, 38.9% purity, 40.6%) as black solid, which was used for the next step without further purification. LCMS (ESI) m/z M+1: 208.0.

B. Ethyl 1-(6-bromo-5-fluoropyridin-2-yl)-5-(trifluoromethyl)-1H-pyrazole-4-carboxylate, Cpd 62b

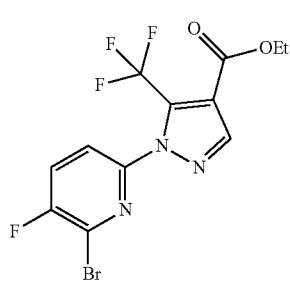

cpd 62b

2-Bromo-3-fluoro-6-hydrazinylpyridine, cpd 62a (1 g, 1.886 mmol) was dissolved in ethanol (20 mL), Ethyl 2-(ethoxymethylene)-4,4,4-trifluoro-3-oxobutanoate, INT 1 (906 mg, 3.772 mmol) was added and stirred at 60° C. for 2 h before cooling to room temperature. The combined mixture was concentrated under reduced pressure to afford crude product as a brown oil, which was purified by flash column chromatography (eluent: petroleum ether/ethyl acetate from 100/0 to 80/20) to afford the title compound (500 mg, 68.7% purity, 47.7%) as yellow solid. LCMS (ESI) m/z M+1: 384.1.

C. Ethyl 1-(6-((tert-butoxycarbonyl)amino)-5-fluoropyridin-2-yl)-5-(trifluoromethyl)-1H-pyrazole-4-carboxylate, Cpd 62c

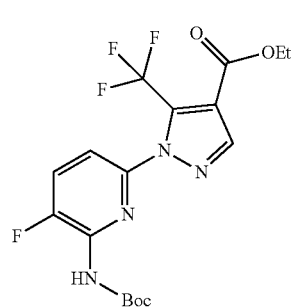

Ethyl 1-(6-bromo-5-fluoropyridin-2-yl)-5-(trifluoromethyl)-1H-pyrazole-4-carboxylate, cpd 62b (450 mg, 0.809 mmol) and tert-butyl carbamate (189.53 mg, 1.168 mmol) were dissolved in dioxane (15 mL), tris(dibenzylideneacetone)dipalladium(0) (222.23 mg, 0.243 mmol), 4,5-bis(diphenylphosphino)-9,9-dimethylxanthene (187.23 mg, 0.324 mmol) and cesium carbonate (527.15 mg, 1.618 mmol) were added and purged with $N_2$ for 1 min. The reaction mixture was stirred at 80° C. for 16 h before cooling to room temperature. The combined mixture was filtered through a pad of diatomaceous earth and the pad was washed with ethyl acetate (20 mL×3). The filtrates were concentrated under reduced pressure to afford crude product as yellow oil, which was purified by flash column chromatography (eluent: petroleum ether/ethyl acetate from 100/0 to 40/60) to afford the title compound (350 mg, 73.0% purity, 75.5%) as a yellow solid. LCMS (ESI) m/z M+1: 440.9.

D. 1-(6-((tert-Butoxycarbonyl)amino)-5-fluoropyridin-2-yl)-5-(trifluoromethyl)-1H-pyrazole-4-carboxylic Acid, Cpd 62d

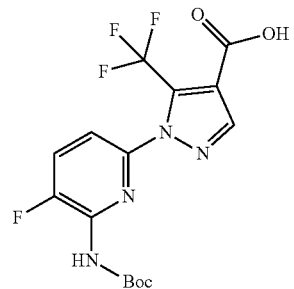

Ethyl 1-(6-((tert-butoxycarbonyl)amino)-5-fluoropyridin-2-yl)-5-(trifluoromethyl)-1H-pyrazole-4-carboxylate, cpd 62d (350 mg, 0.611 mmol) was dissolved in THF (12 mL) and water (12 mL). Lithium hydroxide (43.89 mg, 1.833 mmol) was added. The reaction mixture was stirred at 30° C. for 16 h. The reaction mixture was adjusted to pH 6 using HCl (2 N), extracted with EtOAc/MeOH (10/1, 20 mL×5). The combined organic layers were dried with $Na_2SO_4$, filtered and the filtrates were concentrated under reduced pressure to afford crude the title compound (300 mg, 69.3% purity, 87.2%) as yellow solid. LCMS (ESI) m/z M+1: 413.2.

E. Tert-Butyl (6-(4-((5-chloro-6-(2H-1,2,3-triazol-2-yl)pyridin-3-yl)carbamoyl)-5-(trifluoromethyl)-1H-pyrazol-1-yl)-3-fluoropyridin-2-yl)carbamate, Cpd 62e

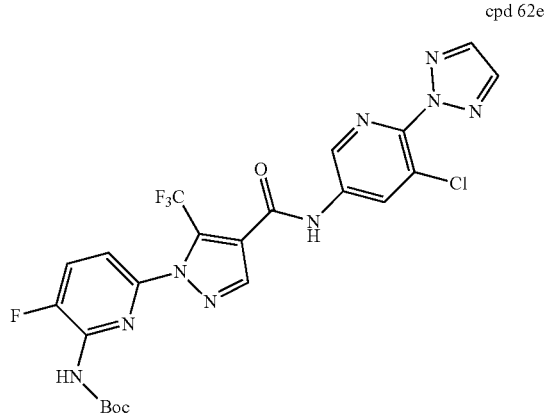 [SMILES: CC(C)(C)OC(=O)Nc1nc(-n2ncc(C(=O)Nc3cnc(-n4nccn4)c(Cl)c3)c2C(F)(F)F)ccc1F]

1-(6-((tert-Butoxycarbonyl)amino)-5-fluoropyridin-2-yl)-5-(trifluoromethyl)-1H-pyrazole-4-carboxylic acid, cpd 62d (150 mg, 0.266 mmol), 5-Chloro-6-(2H-1,2,3-triazol-2-yl)pyridin-3-amine, INT 2 (52.1 mg, 0.266 mmol), pyridine (126.41 mg, 1.598 mmol) were dissolved in $CH_2Cl_2$ (10 mL), and phosphorus oxychloride (122.52 mg, 0.799 mmol) was added. The mixture was stirred at 25° C. for 2 h. Sat.NaHCO$_3$(20 mL) was added and extracted with $CH_2Cl_2$ (30 mL×2). The combined organic layers were dried with $Na_2SO_4$, filtered and the filtrates were concentrated under reduced pressure to afford the title product (200 mg, 67.2% purity, 88.8% yield) as a yellow solid. LCMS (ESI) m/z M+1: 467.9.

F. 1-(6-Amino-5-fluoropyridin-2-yl)-N-(5-chloro-6-(2H-1,2,3-triazol-2-yl)pyridin-3-yl)-5-(trifluoromethyl)-1H-pyrazole-4-carboxamide, Cpd 62

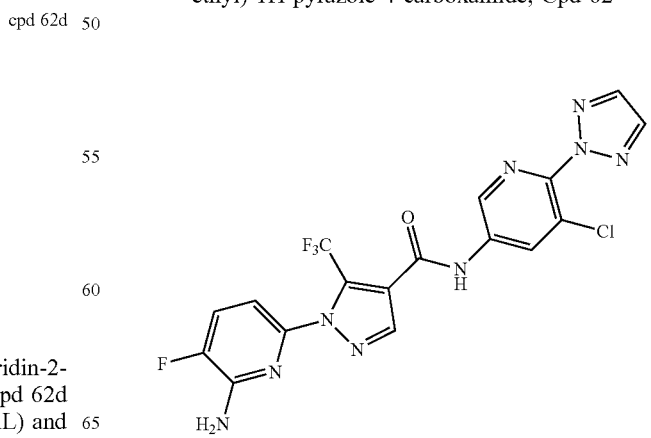

Tert-Butyl (6-(4-((5-chloro-6-(2H-1,2,3-triazol-2-yl)pyridin-3-yl)carbamoyl)-5-(trifluoromethyl)-1H-pyrazol-1-yl)-3-fluoropyridin-2-yl)carbama, cpd 62e (200 mg, 0.237 mmol) was dissolved in CH₂Cl₂ (5 mL) and trifluoroacetic acid (5 mL) was added. The reaction mixture was stirred at room temperature for 1 h. The reaction mixture was concentrated under reduced pressure to afford crude product as yellow oil, which was purified by preparative HPLC (37% to 67% (v/v) CH₃CN and H₂O with 0.05% HCl) and lyophilized to dryness to afford the title compound (57 mg, 50.441%). LCMS (ESI) m/z M+1: 467.9. ¹H NMR (400 MHz, DMSO-d₆) δ 11.23 (s, 1H), 8.82 (d, J=2.4 Hz, 1H), 8.64 (d, J=2.2 Hz, 1H), 8.37 (s, 1H), 8.18 (s, 2H), 7.62 (dd, J=8.0, 10.5 Hz, 1H), 6.81 (dd, J=2.5, 8.0 Hz, 1H), 6.76 (br s, 2H).

Example 63

1-(6-amino-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 63

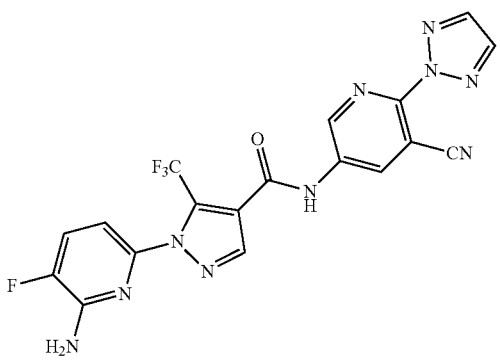 [SMILES: N#Cc1cc(NC(=O)c2cnn(-c3ccc(F)c(N)n3)c2C(F)(F)F)cnc1-n1nccn1]

A. Tert-Butyl (6-(4-((5-cyano-6-(2H-1,2,3-triazol-2-yl)pyridin-3-yl)carbamoyl)-5-(trifluoromethyl)-1H-pyrazol-1-yl)-3-fluoropyridin-2-yl)carbamate, Cpd 63a

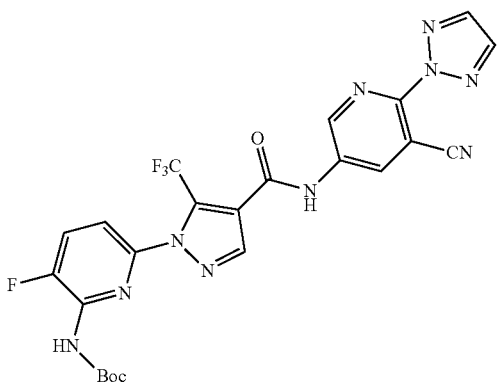

1-(6-(((tert-Butoxycarbonyl)amino)-5-fluoropyridin-2-yl)-5-(trifluoromethyl)-1H-pyrazole-4-carboxylic acid, cpd 62d (150 mg, 0.266 mmol), 5-amino-2-(2H-1,2,3-triazol-2-yl) nicotinonitrile, INT 3 (52.1 mg, 0.266 mmol), pyridine (126.41 mg, 1.598 mmol) were dissolved in CH₂Cl₂ (10 mL), and phosphorus oxychloride (122.52 mg, 0.799 mmol) was added. The mixture was stirred at 25° C. for 2 h. Sat.NaHCO₃(20 mL) was added and extracted with CH₂Cl₂ (30 mL×2). The combined organic layers were dried with Na₂SO₄, filtered and the filtrates were concentrated under reduced pressure to afford the title product (200 mg, 64.1% purity, 86.2% yield) as yellow solid. LCMS (ESI) m/z M+1: 459.1.

B. 1-(6-Amino-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 63

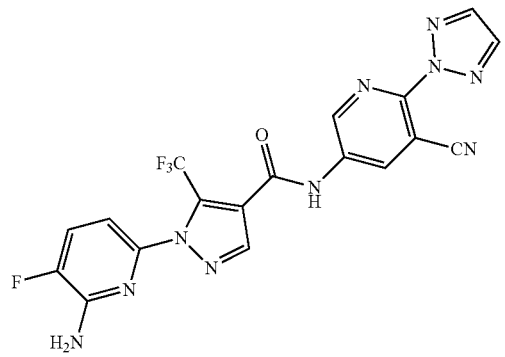 [SMILES: N#Cc1cc(NC(=O)c2cnn(-c3ccc(F)c(N)n3)c2C(F)(F)F)cnc1-n1nccn1]

Tert-Butyl (6-(4-((5-chloro-6-(2H-1,2,3-triazol-2-yl)pyridin-3-yl)carbamoyl)-5-(trifluoromethyl)-1H-pyrazol-1-yl)-3-fluoropyridin-2-yl)carbama, cpd 63a (200 mg, 0.230 mmol) was dissolved in CH₂Cl₂ (5 mL) and trifluoroacetic acid (5 mL) was added. The reaction mixture was stirred at room temperature for 1 h. The reaction mixture was concentrated under reduced pressure to afford crude product as yellow oil, which was purified by preparative HPLC (23% to 53% (v/v) CH₃CN and H₂O with 0.05% HCl) and lyophilized to dryness to afford the title compound (35 mg, 32.9%). LCMS (ESI) m/z M+1: 459.0. ¹H NMR (400 MHz, DMSO-d₆) δ 11.16 (br s, 1H), 9.03 (d, J=2.6 Hz, 1H), 8.82 (d, J=2.4 Hz, 1H), 8.34 (s, 1H), 8.29 (s, 2H), 7.61 (dd, J=8.2, 10.4 Hz, 1H), 6.80 (dd, J=2.5, 8.0 Hz, 1H), 6.74 (s, 2H).

Example 64

N-(5-cyano-6-(2H-1,2,3-triazol-2-yl)pyridin-3-yl)-1-(4-fluoro-2-methylphenyl)-5-(trifluoromethyl)-1H-pyrazole-4-carboxamide, Cpd 64

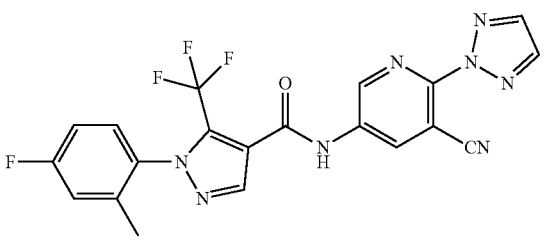 [SMILES: Cc1cc(F)ccc1-n1ncc(C(=O)Nc2cnc(-n3nccn3)c(C#N)c2)c1C(F)(F)F]

237

A. 1-(4-fluoro-2-methylphenyl)-5-(trifluoromethyl)-1H-pyrazole-4-carboxylic Acid, Cpd 64a

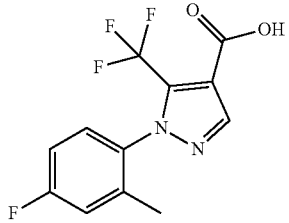

cpd 64a

Ethyl 1-(4-fluoro-2-methylphenyl)-5-(trifluoromethyl)-1H-pyrazole-4-carboxylate, Cpd 1a (6.4 g, 20.237 mmol) was dissolved in was dissolved in THF (20 mL) and water (20 mL). Lithium hydroxide (2.423 g, 101.185 mmol) was added. The reaction mixture was stirred at 30° C. for 16 h. The reaction mixture was adjusted to pH 6 using HCl (2 N), extracted with $CH_2Cl_2$/MeOH (10/1, 80 mL×5). The combined organic layers were dried with $Na_2SO_4$, filtered and the filtrates were concentrated under reduced pressure to afford the crude title compound (5.3 g, 96.8% purity, 87.9%) as yellow solid. LCMS (ESI) m/z M+1: 289.0.

B. N-(5-cyano-6-(2H-1,2,3-triazol-2-yl)pyridin-3-yl)-1-(4-fluoro-2-methylphenyl)-5-(trifluoromethyl)-1H-pyrazole-4-carboxamide, Cpd 64

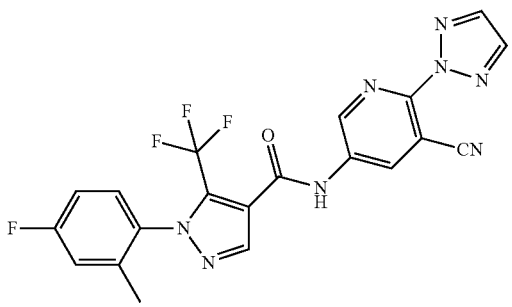 [SMILES: Cc1cc(F)ccc1-n1ncc(C(=O)Nc2cnc(-n3nccn3)c(C#N)c2)c1C(F)(F)F]

1-(4-Fluoro-2-methylphenyl)-5-(trifluoromethyl)-1H-pyrazole-4-carboxylic acid, cpd 64a (170.28 mg, 0.591 mmol), 5-amino-2-(2H-1,2,3-triazol-2-yl) nicotinonitrile, INT3 (100 mg, 0.537 mmol), pyridine (254.92 mg, 3.223 mmol) were dissolved in $CH_2Cl_2$ (10 mL), and phosphorus oxychloride (247.08 mg, 1.611 mmol) was added. The mixture was stirred at 25° C. for 16 h. Sat.$NaHCO_3$(30 mL) was added and extracted with $CH_2Cl_2$ (50 mL×2). The combined organic layers were dried with $Na_2SO_4$, filtered and the filtrates were concentrated under reduced pressure to afford the crude product, which was purified by preparative HPLC (36% to 66% (v/v) $CH_3CN$ and $H_2O$ with $NH_4HCO_3$) and lyophilized to dryness to afford the title compound (74 mg, 30.2%). LCMS (ESI) m/z M+1: 456.9. $^1$H NMR (400 MHz, DMSO-$d_6$) δ 11.28 (s, 1H), 9.07 (d, J=2.2 Hz, 1H), 8.85 (d, J=2.2 Hz, 1H), 8.47 (s, 1H), 8.31 (s, 2H), 7.55 (dd, J=5.3, 8.6 Hz, 1H), 7.40 (dd, J=2.4, 9.5 Hz, 1H), 7.27 (dt, J=2.8, 8.4 Hz, 1H), 2.01 (s, 3H).

Following the procedure described in Example 6, above, selecting and substituting the appropriate reagents, starting materials, and purification methods, and adjusting reaction temperatures, times and other variables or parameters, as needed or desirable, as would be readily recognized by those skilled in the art, the following compounds (Examples 65-70) were prepared.

Example 65

1-(3-chloro-4-methoxypyridin-2-yl)-N-(5-chloro-6-(2H-1,2,3-triazol-2-yl)pyridin-3-yl)-5-(trifluoromethyl)-1H-pyrazole-4-carboxamide, Cpd 65

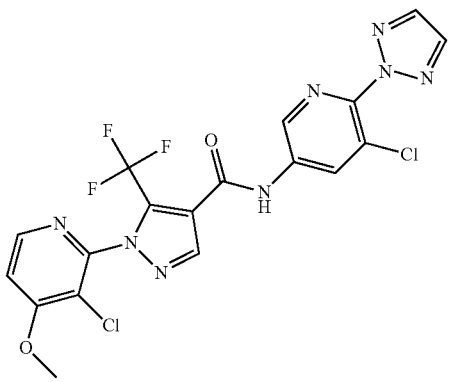 [SMILES: COc1ccnc(-n2ncc(C(=O)Nc3cnc(-n4nccn4)c(Cl)c3)c2C(F)(F)F)c1Cl]

$^1$H NMR (400 MHz, DMSO-$d_6$) δ ppm 11.22 (br s, 1H), 8.78-8.84 (m, 1H), 8.60-8.65 (m, 1H), 8.52-8.54 (m, 1H), 8.50 (d, J=5.73 Hz, 1H), 8.17 (s, 2H), 7.54 (d, J=5.95 Hz, 1H), 4.06 (s, 3H). LC-MS: (ES, m/z): [M+1]$^+$ 498.9

Example 66

1-(3-chloro-4-methoxypyridin-2-yl)-N-(5-cyano-6-(2H-1,2,3-triazol-2-yl)pyridin-3-yl)-5-(trifluoromethyl)-1H-pyrazole-4-carboxamide, Cpd 66

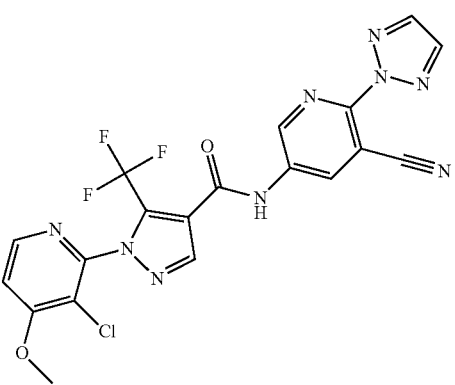 [SMILES: COc1ccnc(-n2ncc(C(=O)Nc3cnc(-n4nccn4)c(C#N)c3)c2C(F)(F)F)c1Cl]

$^1$H NMR (400 MHz, DMSO-$d_6$) δ ppm 11.29 (br s, 1H), 9.05 (d, J=2.65 Hz, 1H), 8.84 (d, J=2.65 Hz, 1H), 8.54 (s, 1H), 8.50 (d, J=5.73 Hz, 1H), 8.29 (s, 2H), 7.54 (d, J=5.95 Hz, 1H), 4.06 (s, 3H). LC-MS: (ES, m/z): [M+1]$^+$ 489.9

Example 67

N-(5-chloro-6-(2H-1,2,3-triazol-2-yl)pyridin-3-yl)-1-(3,5-dichloropyridin-4-yl)-5-(trifluoromethyl)-1H-pyrazole-4-carboxamide, Cpd 67

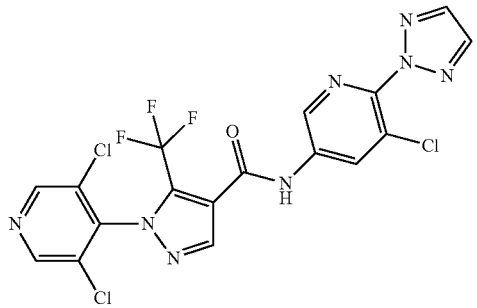 [SMILES: O=C(Nc1cnc(-n2nccn2)c(Cl)c1)c1cnn(-c2c(Cl)cncc2Cl)c1C(F)(F)F]

$^1$H NMR (400 MHz, CHLOROFORM-d) δ ppm 7.94 (s, 2H), 8.21 (s, 1H), 8.28 (s, 1H), 8.49 (br s, 1H), 8.73 (d, J=1.54 Hz, 1H), 8.75 (s, 2H). LC-MS: (ES, m/z): [M+1]$^+$ 502.8

Example 68

1-(5-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide, cpd 68

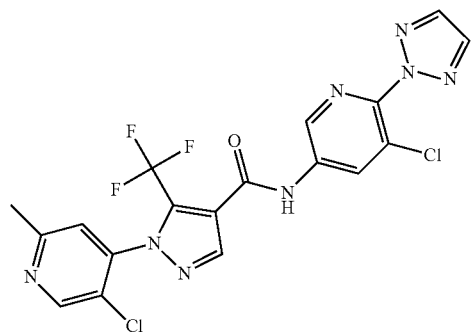 [SMILES: Cc1cc(-n2ncc(C(=O)Nc3cnc(-n4nccn4)c(Cl)c3)c2C(F)(F)F)c(Cl)cn1]

$^1$H NMR (400 MHz, DMSO-d$_6$) δ ppm 11.44 (s, 1H), 8.90-9.03 (m, 2H), 8.77 (s, 2H), 8.28 (s, 2H), 7.90 (s, 1H), 2.69 (s, 3H). LC-MS: (ES, m/z): [M+1]$^+$ 482.9

Example 69

1-(3-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide, Cpd 69

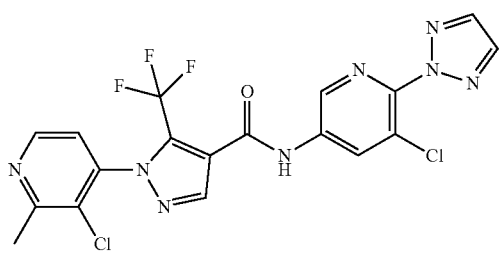 [SMILES: Cc1nccc(-n2ncc(C(=O)Nc3cnc(-n4nccn4)c(Cl)c3)c2C(F)(F)F)c1Cl]

$^1$H NMR (400 MHz, DMSO-d$_6$) δ ppm 11.35 (1H, br s), 8.86-8.93 (1H, m), 8.65-8.74 (3H, m), 8.19 (2H, s), 7.77 (1H, d, J=5.02 Hz), 2.71 (3H, s). LC-MS: (ES, m/z): [M+1]+493.0

Example 70

1-(5-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 70

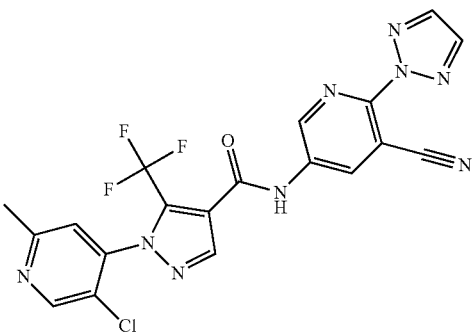 [SMILES: Cc1cc(-n2ncc(C(=O)Nc3cnc(-n4nccn4)c(C#N)c3)c2C(F)(F)F)c(Cl)cn1]

$^1$H NMR (400 MHz, DMSO-d$_6$) δ ppm 11.36 (s, 1H), 9.04-9.11 (m, 1H), 8.80-8.88 (m, 2H), 8.63 (s, 1H), 8.29 (s, 2H), 7.79 (s, 1H), 2.55-2.58 (m, 3H). LC-MS: (ES, m/z): [M+1]$^+$ 473.9

Following the procedure described in Example 50, above, selecting and substituting the appropriate reagents, starting materials, and purification methods, and adjusting reaction temperatures, times and other variables or parameters, as needed or desirable, as would be readily recognized by those skilled in the art, the following compounds (example 71-104) were prepared.

Example 71

1-(2-chloro-4-fluoro-3-methylphenyl)-N-(5-chloro-6-(2H-1,2,3-triazol-2-yl)pyridin-3-yl)-5-(trifluoromethyl)-1H-pyrazole-4-carboxamide, Cpd 71

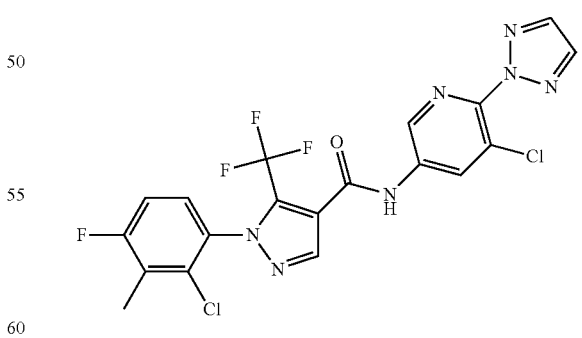

$^1$H NMR (400 MHz, DMSO-d$_6$) δ ppm 11.16-11.26 (m, 1H), 11.21 (br s, 1H), 8.82 (d, J=2.21 Hz, 1H), 8.79-8.84 (m, 1H), 8.63 (d, J=2.21 Hz, 1H), 8.50 (s, 1H), 8.16 (s, 2H), 7.70 (dd, J=8.82, 5.51 Hz, 1H), 7.45 (t, J=8.82 Hz, 1H), 2.34 (d, J=2.21 Hz, 2H), 2.31-2.38 (m, 1H), 1.20 (s, 1H). LC-MS: (ES, m/z): [M+1]$^+$ 499.9

Example 72

1-(2-chloro-4-fluoro-3-methylphenyl)-N-(5-cyano-6-(2H-1,2,3-triazol-2-yl)pyridin-3-yl)-5-(trifluoromethyl)-1H-pyrazole-4-carboxamide, Cpd 72

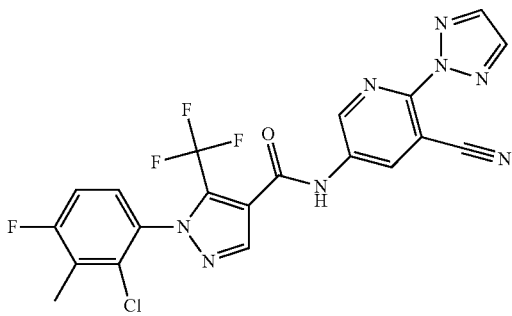 [SMILES: Cc1c(F)ccc(-n2ncc(C(=O)Nc3cnc(-n4nccn4)c(C#N)c3)c2C(F)(F)F)c1Cl]

$^1$H NMR (400 MHz, DMSO-d$_6$) δ ppm 11.32 (br s, 1H), 9.06 (d, J=2.43 Hz, 1H), 8.86 (d, J=2.43 Hz, 1H), 8.53 (s, 1H), 8.29 (s, 2H), 7.71 (dd, J=8.71, 5.40 Hz, 1H), 7.46 (t, J=8.93 Hz, 1H), 2.35 (d, J=2.20 Hz, 3H). LC-MS: (ES, m/z): [M+1]$^+$ 490.9

Example 731-(2-chloro-3,4-difluorophenyl)-N-(5-chloro-6-(2H-1,2,3-triazol-2-yl)pyridin-3-yl)-5-(trifluoromethyl)-1H-pyrazole-4-carboxamide, Cpd 73

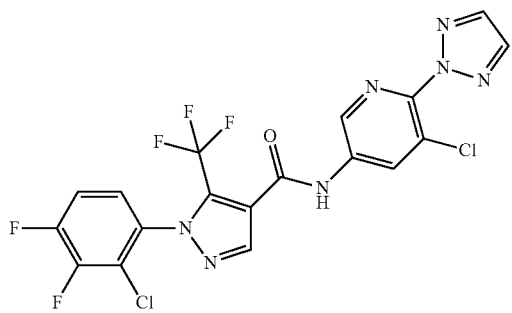 [SMILES: O=C(Nc1cnc(-n2nccn2)c(Cl)c1)c1cnn(-c2ccc(F)c(F)c2Cl)c1C(F)(F)F]

$^1$H NMR (400 MHz, DMSO-d$_6$) δ ppm 11.22 (1H, s), 8.81 (1H, d, J=2.20 Hz), 8.63 (1H, d, J=2.21 Hz), 8.54 (1H, s), 8.17 (2H, s), 7.72-7.84 (2H, m). LC-MS: (ES, m/z): [M+1]$^+$ 503.8

Example 74

N-(5-chloro-6-(2H-1,2,3-triazol-2-yl)pyridin-3-yl)-1-(3-(methylsulfonyl)phenyl)-5-(trifluoromethyl)-1H-pyrazole-4-carboxamide, Cpd 74

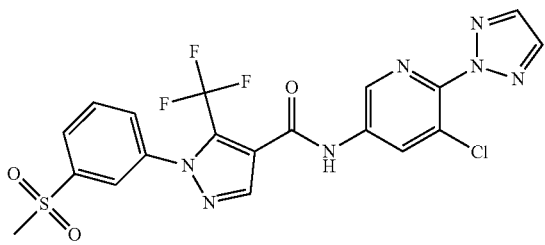 [SMILES: CS(=O)(=O)c1cccc(-n2ncc(C(=O)Nc3cnc(-n4nccn4)c(Cl)c3)c2C(F)(F)F)c1]

$^1$H NMR (400 MHz, CHLOROFORM-d) δ ppm 8.75 (d, J=2.4 Hz, 1H), 8.53 (d, J=2.2 Hz, 1H), 8.18-8.07 (m, 4H), 7.94 (s, 2H), 7.78 (d, J=5.7 Hz, 2H), 3.13 (s, 3H). LC-MS: (ES, m/z): [M+1]$^+$ 511.9

Example 75

N-(5-chloro-6-(2H-1,2,3-triazol-2-yl)pyridin-3-yl)-1-(2-methyl-4-(methylsulfonyl)phenyl)-5-(trifluoromethyl)-1H-pyrazole-4-carboxamide, Cpd 75

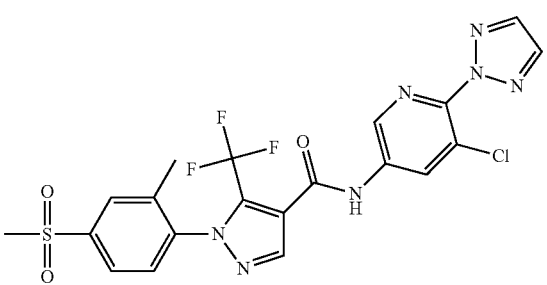 [SMILES: Cc1cc(S(C)(=O)=O)ccc1-n1ncc(C(=O)Nc2cnc(-n3nccn3)c(Cl)c2)c1C(F)(F)F]

$^1$H NMR (400 MHz, CHLOROFORM-d) δ ppm 8.76 (d, J=2.2 Hz, 1H), 8.51 (d, J=2.2 Hz, 1H), 8.18 (s, 1H), 8.03 (s, 1H), 7.99 (s, 1H), 7.98-7.91 (m, 3H), 7.50 (d, J=7.9 Hz, 1H), 3.13 (s, 3H), 2.19 (s, 3H). LC-MS: (ES, m z): [M+1]$^+$ 525.9

Example 76

N-(5-chloro-6-(2H-1,2,3-triazol-2-yl)pyridin-3-yl)-1-(2-isopropylphenyl)-5-(trifluoromethyl)-1H-pyrazole-4-carboxamide, Cpd 76

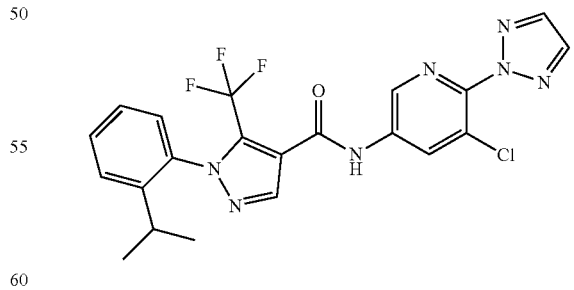

$^1$H NMR (400 MHz, CHLOROFORM-d) δ ppm 1.20 (t, J=6.39 Hz, 6H), 2.40 (quin, J=6.84 Hz, 1H), 7.23-7.26 (m, 1H), 7.31-7.36 (m, 1H), 7.48-7.52 (m, 1H), 7.53-7.59 (m, 1H), 7.88 (s, 1H), 7.96 (s, 2H), 8.13 (s, 1H), 8.51 (d, J=2.43 Hz, 1H), 8.79 (d, J=2.43 Hz, 1H). LC-MS: (ES, m/z): [M+1]$^+$ 475.9

Example 77

N-(5-chloro-6-(2H-1,2,3-triazol-2-yl)pyridin-3-yl)-1-(4-fluoro-2,3-dimethylphenyl)-5-(trifluoromethyl)-1H-pyrazole-4-carboxamide, Cpd 77

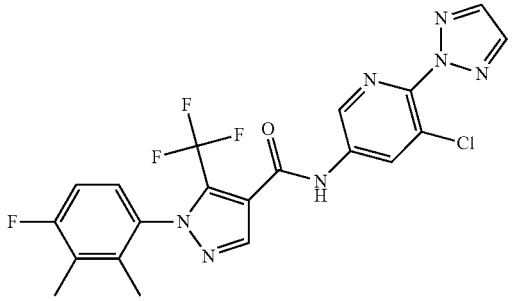 [SMILES: Cc1c(F)ccc(-n2ncc(C(=O)Nc3cnc(-n4nccn4)c(Cl)c3)c2C(F)(F)F)c1C]

$^1$H NMR (400 MHz, DMSO-d$_6$) δ ppm 11.20 (1H, s), 8.81 (1H, d, J=2.20 Hz), 8.63 (1H, d, J=2.21 Hz), 8.43 (1H, s) 8.17 (2H, s), 7.36 (1H, dd, J=8.71, 4.96 Hz), 7.18-7.25 (1H, m), 2.22 (3H, d, J=1.76 Hz), 1.86 (3H, s). LC-MS: (ES, m/z): [M+1]$^+$ 479.9

Example 78

N-(5-chloro-6-(2H-1,2,3-triazol-2-yl)pyridin-3-yl)-1-(3,4-difluorophenyl)-5-(trifluoromethyl)-1H-pyrazole-4-carboxamide, Cpd 78

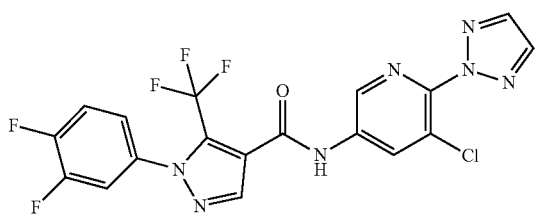 [SMILES: O=C(Nc1cnc(-n2nccn2)c(Cl)c1)c1cnn(-c2ccc(F)c(F)c2)c1C(F)(F)F]

$^1$H NMR (400 MHz, DMSO-d$_6$) δ ppm 7.49 (br d, J=9.48 Hz, 1H), 7.64-7.73 (m, 1H), 7.89 (ddd, J=10.42, 7.22, 2.65 Hz, 1H), 8.16 (s, 2H), 8.42 (s, 1H), 8.61 (d, J=2.21 Hz, 1H), 8.80 (d, J=2.21 Hz, 1H), 11.21 (s, 1H). LC-MS: (ES, m/z): [M+1]$^+$ 469.9

Example 79

1-(2-chloro-5-fluorophenyl)-N-(5-chloro-6-(2H-1,2,3-triazol-2-yl)pyridin-3-yl)-5-(trifluoromethyl)-1H-pyrazole-4-carboxamide, Cpd 79

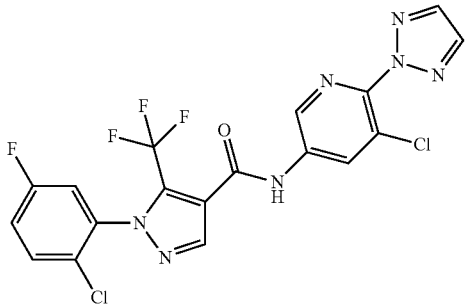 [SMILES: O=C(Nc1cnc(-n2nccn2)c(Cl)c1)c1cnn(-c2cc(F)ccc2Cl)c1C(F)(F)F]

$^1$H NMR (400 MHz, DMSO-d$_6$) δ ppm 11.20 (s, 1H), 8.83 (d, J=2.21 Hz, 1H), 8.64 (d, J=2.21 Hz, 1H), 8.54 (s, 1H), 8.17 (s, 1H), 8.13-8.21 (m, 1H), 7.93 (dd, J=8.38, 3.09 Hz, 1H), 7.84 (dd, J=9.04, 5.29 Hz, 1H), 7.62 (td, J=8.60, 3.09 Hz, 1H). LC-MS: (ES, m/z): [M+1]$^+$ 485.9

Example 80

1-(2-chloro-5-fluorophenyl)-N-(5-cyano-6-(2H-1,2,3-triazol-2-yl)pyridin-3-yl)-5-(trifluoromethyl)-1H-pyrazole-4-carboxamide, Cpd 80

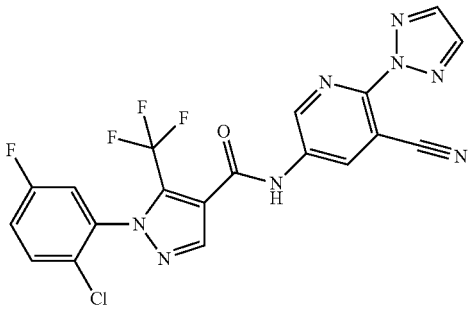 [SMILES: N#Cc1cc(NC(=O)c2cnn(-c3cc(F)ccc3Cl)c2C(F)(F)F)cnc1-n1nccn1]

$^1$H NMR (400 MHz, DMSO-d$_6$) δ ppm 11.36 (br s, 1H), 11.22-11.51 (m, 1H), 9.08 (d, J=2.43 Hz, 1H), 8.87 (d, J=2.43 Hz, 1H), 8.59 (s, 1H), 8.29 (s, 2H), 7.93 (dd, J=8.49, 2.98 Hz, 1H), 7.83 (dd, J=8.93, 5.40 Hz, 1H), 7.61 (td, J=8.60, 3.09 Hz, 1H), 2.05 (s, 1H). LC-MS: (ES, m/z): [M+1]$^+$ 476.9

Example 81

N-(5-chloro-6-(2H-1,2,3-triazol-2-yl)pyridin-3-yl)-1-(4-fluoro-2-methoxyphenyl)-5-(trifluoromethyl)-1H-pyrazole-4-carboxamide, Cpd81

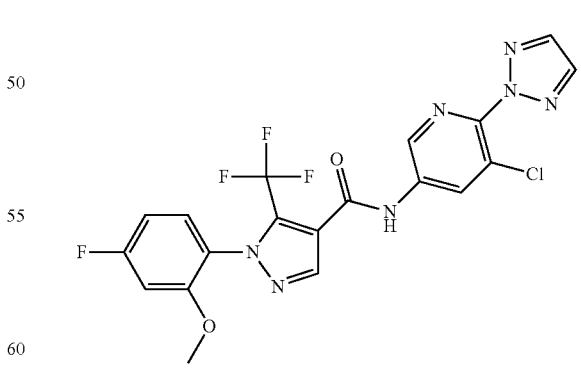

$^1$H NMR (400 MHz, DMSO-d$_6$) δ ppm 3.81 (s, 3H), 6.98 (td, J=8.49, 2.65 Hz, 1H), 7.25 (dd, J=10.91, 2.54 Hz, 1H), 7.59 (dd, J=8.71, 6.06 Hz, 1H), 8.19 (s, 2H) 8.43 (s, 1H), 8.65 (d, J=2.21 Hz, 1H), 8.83 (d, J=2.21 Hz, 1H), 11.16 (br s, 1H). LC-MS: (ES, m/z): [M+1]$^+$ 481.9

Example 82

1-(2-chloro-3-fluorophenyl)-N-(5-chloro-6-(2H-1,2,3-triazol-2-yl)pyridin-3-yl)-5-(trifluoromethyl)-1H-pyrazole-4-carboxamide, Cpd 82

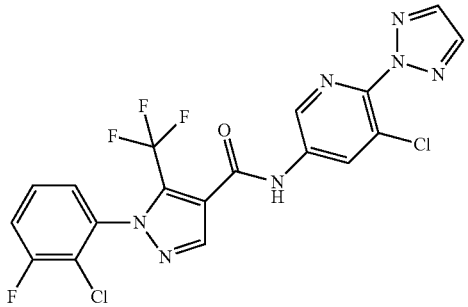

¹H NMR (400 MHz, METHANOL-d₄) δ ppm 8.77 (1H, d, J=2.21 Hz), 8.68 (1H, d, J=2.43 Hz), 8.34 (1H, s), 8.02 (2H, s), 7.54-7.62 (2H, m), 7.43-7.51 (1H, m). LC-MS: (ES, m/z): [M+1]⁺ 485.9

Example 83

1-(2-bromo-4-fluorophenyl)-N-(5-chloro-6-(2H-1,2,3-triazol-2-yl)pyridin-3-yl)-5-(trifluoromethyl)-1H-pyrazole-4-carboxamide, Cpd 83

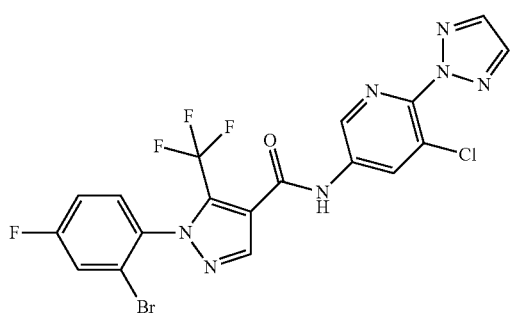 [SMILES: O=C(Nc1cnc(-n2nccn2)c(Cl)c1)c1cnn(-c2ccc(F)cc2Br)c1C(F)(F)F]

¹H NMR (400 MHz, DMSO-d₆) δ ppm 7.51 (td, J=8.49, 2.87 Hz, 1H), 7.84 (dd, J=8.82, 5.51 Hz, 1H), 7.93 (dd, J=8.27, 2.76 Hz, 1H), 8.16 (s, 2H), 8.50 (s, 1H), 8.63 (d, J=2.21 Hz, 1H), 8.81 (d, J=2.21 Hz, 1H), 11.19 (s, 1H). LC-MS: (ES, m/z): [M+1]⁺ 531.8

Example 84

N-(5-cyano-6-(2H-1,2,3-triazol-2-yl)pyridin-3-yl)-1-(4-fluoro-2,3-dimethylphenyl)-5-(trifluoromethyl)-1H-pyrazole-4-carboxamide, Cpd 84

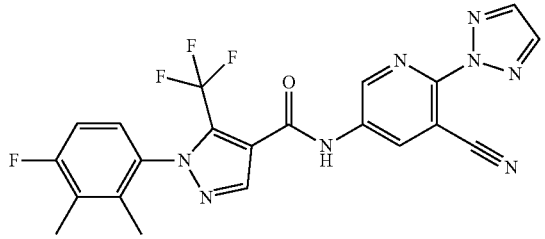 [SMILES: Cc1c(F)ccc(-n2ncc(C(=O)Nc3cnc(-n4nccn4)c(C#N)c3)c2C(F)(F)F)c1C]

¹H NMR (400 MHz, DMSO-d₆) δ ppm 11.25 (1H, s) 9.04 (1H, d, J=2.43 Hz) 8.83 (1H, d, J=2.43 Hz) 8.43 (1H, s) 8.29 (2H, s) 7.37 (1H, dd, J=8.82, 4.85 Hz) 7.22 (1H, t, J=8.93 Hz) 2.22 (3H, d, J=1.76 Hz) 1.86 (3H, s). LC-MS: (ES, m/z): [M+1]⁺ 471.0

Example 85

N-(5-chloro-6-(2H-1,2,3-triazol-2-yl)pyridin-3-yl)-1-(3-cyano-4-fluorophenyl)-5-(trifluoromethyl)-1H-pyrazole-4-carboxamide, Cpd 85

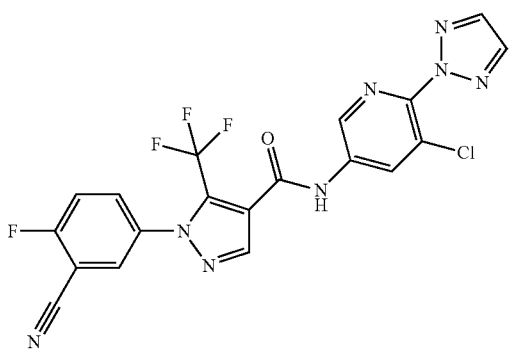 [SMILES: N#Cc1cc(-n2ncc(C(=O)Nc3cnc(-n4nccn4)c(Cl)c3)c2C(F)(F)F)ccc1F]

¹H NMR (400 MHz, DMSO-d₆) δ ppm 7.78 (t, J=8.93 Hz, 1H) 8.02-8.08 (m, 1H) 8.16 (s, 2H) 8.36 (dd, J=5.51, 2.65 Hz, 1H) 8.46 (s, 1H) 8.62 (d, J=2.43 Hz, 1H) 8.80 (d, J=2.43 Hz, 1H) 11.21 (s, 1H). LC-MS: (ES, m/z): [M+1]⁺ 476.9

Example 86

1-(3-cyano-4-fluorophenyl)-N-(5-cyano-6-(2H-1,2,3-triazol-2-yl)pyridin-3-yl)-5-(trifluoromethyl)-1H-pyrazole-4-carboxamide, Cpd 86

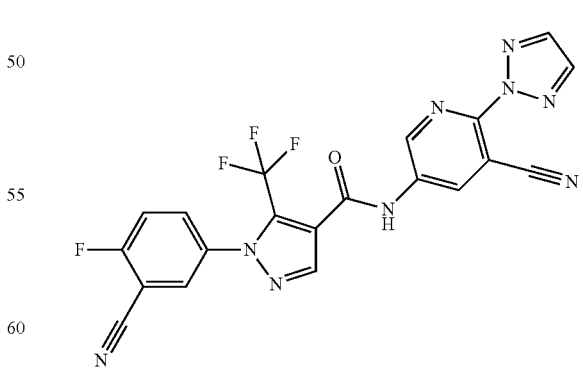

¹H NMR (400 MHz, DMSO-d₆) δ ppm 7.78 (t, J=8.93 Hz, 1H) 8.02-8.08 (m, 1H) 8.28 (s, 2H) 8.37 (dd, J=5.62, 2.76 Hz, 1H) 8.45 (s, 1H) 8.82 (d, J=2.65 Hz, 1H) 9.03 (d, J=2.43 Hz, 1H) 11.25 (s, 1H). LC-MS: (ES, m/z): [M+1]⁺ 467.9

Example 87

N-(5-chloro-6-(2H-1,2,3-triazol-2-yl)pyridin-3-yl)-1-(6-fluoro-4-methylpyridin-3-yl)-5-(trifluoromethyl)-1H-pyrazole-4-carboxamide, Cpd 87

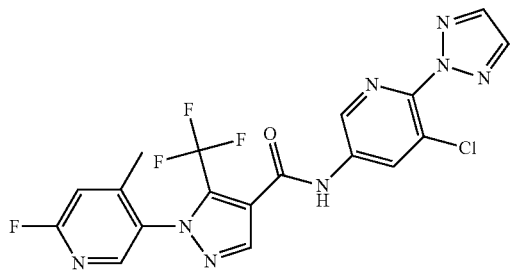 [SMILES: Cc1cc(F)ncc1-n1ncc(C(=O)Nc2cnc(-n3nccn3)c(Cl)c2)c1C(F)(F)F]

¹H NMR (400 MHz, DMSO-d₆) δ ppm 11.20 (br s, 1H), 8.81 (d, J=2.2 Hz, 1H), 8.63 (d, J=2.2 Hz, 1H), 8.52 (s, 1H), 8.46 (s, 1H), 8.16 (s, 2H), 7.43 (s, 1H), 2.10 (s, 3H). LC-MS: (ES, m/z): [M+1]⁺ 467.0

Example 88

N-(5-cyano-6-(2H-1,2,3-triazol-2-yl)pyridin-3-yl)-1-(2-methylpyridin-3-yl)-5-(trifluoromethyl)-1H-pyrazole-4-carboxamide, Cpd 88

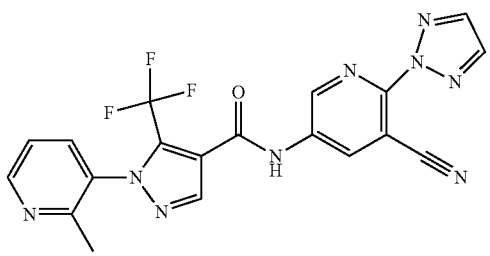 [SMILES: Cc1ncccc1-n1ncc(C(=O)Nc2cnc(-n3nccn3)c(C#N)c2)c1C(F)(F)F]

¹H NMR (400 MHz, DMSO-d₆) δ ppm 2.20 (s, 3H) 7.47-7.56 (m, 1H) 7.52 (dd, J=7.72, 4.85 Hz, 1H) 8.02 (br d, J=7.72 Hz, 1H) 8.29 (s, 2H) 8.58 (s, 1H) 8.71 (d, J=3.97 Hz, 1H) 8.87 (d, J=2.21 Hz, 1H) 9.10 (d, J=2.20 Hz, 1H) 11.39-11.49 (m, 1H). LC-MS: (ES, m/z): [M+1]⁺ 439.9

Example 89

N-(5-chloro-6-(2H-1,2,3-triazol-2-yl)pyridin-3-yl)-5-(trifluoromethyl)-1-(2,3,4-trifluorophenyl)-1H-pyrazole-4-carboxamide, Cpd 89

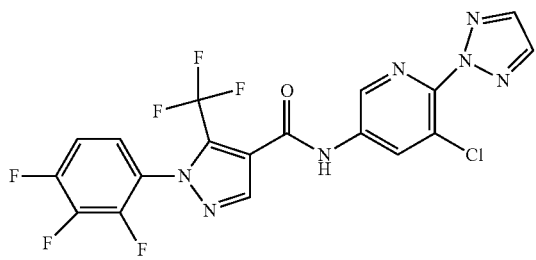 [SMILES: O=C(Nc1cnc(-n2nccn2)c(Cl)c1)c1cnn(-c2ccc(F)c(F)c2F)c1C(F)(F)F]

¹H NMR (400 MHz, DMSO-d₆) δ ppm 7.54-7.56 (m, 1H) 7.58-7.80 (m, 2H) 8.12-8.21 (m, 1H) 8.12-8.20 (m, 1H) 8.17 (s, 1H) 8.53 (s, 1H) 8.62 (d, J=2.21 Hz, 1H) 8.80 (d, J=2.20 Hz, 1H) 11.26 (s, 1H). LC-MS: (ES, m/z): [M+1]⁺ 487.8

Example 90

N-(5-chloro-6-(2H-1,2,3-triazol-2-yl)pyridin-3-yl)-1-(2-chloro-6-fluorophenyl)-5-(trifluoromethyl)-1H-pyrazole-4-carboxamide, Cpd 90

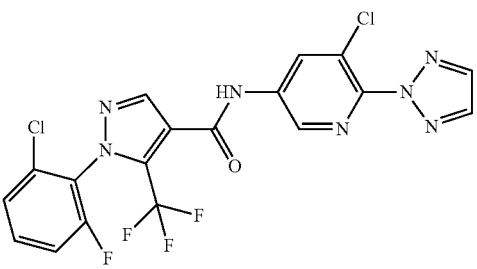 [SMILES: O=C(Nc1cnc(-n2nccn2)c(Cl)c1)c1cnn(-c2c(F)cccc2Cl)c1C(F)(F)F]

¹H NMR (400 MHz, DMSO-d₆) δ ppm 7.58-7.71 (m, 2H) 7.74-7.84 (m, 1H) 8.17 (d, J=1.10 Hz, 2H) 8.59 (s, 1H) 8.62 (s, 1H) 8.81 (s, 1H) 11.28 (s, 1H). LC-MS: (ES, m/z): [M+1]⁺ 485.9

Example 91

N-(5-cyano-6-(2H-1,2,3-triazol-2-yl)pyridin-3-yl)-1-(4-methylpyridin-3-yl)-5-(trifluoromethyl)-1H-pyrazole-4-carboxamide, Cpd 91

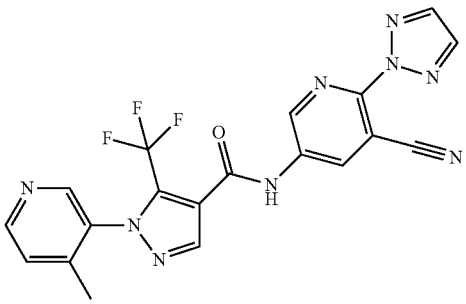 [SMILES: Cc1ccncc1-n1ncc(C(=O)Nc2cnc(-n3nccn3)c(C#N)c2)c1C(F)(F)F]

¹H NMR (400 MHz, DMSO-d₆) δ ppm 2.10 (s, 3H) 7.61 (d, J=5.07 Hz, 1H) 8.31 (s, 2H) 8.59 (s, 1H) 8.67-8.73 (m, 2H) 8.88 (d, J=2.43 Hz, 1H) 9.11 (d, J=2.65 Hz, 1H) 11.39 (s, 1H). LC-MS: (ES, m/z): [M+1]⁺ 440.0

Example 92

N-(5-chloro-6-(2H-1,2,3-triazol-2-yl)pyridin-3-yl)-1-(2-fluoro-6-methylphenyl)-5-(trifluoromethyl)-1H-pyrazole-4-carboxamide, Cpd 92

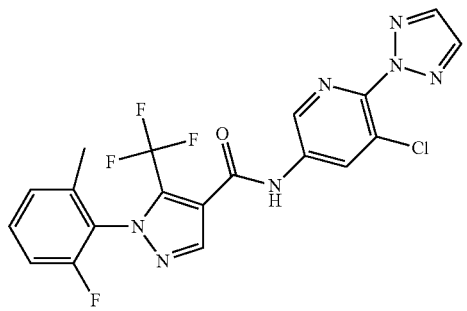 [SMILES: Cc1cccc(F)c1-n1ncc(C(=O)Nc2cnc(-n3nccn3)c(Cl)c2)c1C(F)(F)F]

$^1$H NMR (400 MHz, DMSO-d$_6$) δ ppm 11.31 (br s, 1H) 8.85 (d, J=1.54 Hz, 1H) 8.66 (d, J=1.98 Hz, 1H) 8.59 (s, 1H) 8.18 (s, 2H) 7.60 (td, J=8.10, 5.84 Hz, 1H) 7.31-7.43 (m, 2H) 2.03-2.08 (m, 3H). LC-MS: (ES, m/z): [M+1]$^+$ 465.9

Example 93

N-(5-chloro-6-(2H-1,2,3-triazol-2-yl)pyridin-3-yl)-1-(2,6-dichloro-4-fluorophenyl)-5-(trifluoromethyl)-1H-pyrazole-4-carboxamide, Cpd 93

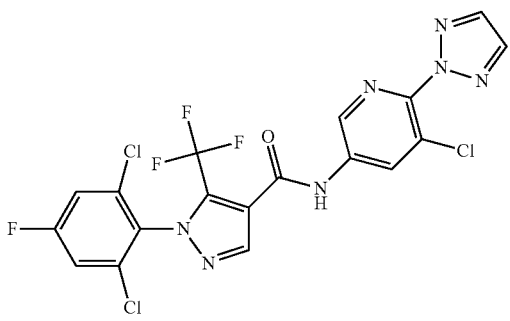 [SMILES: O=C(Nc1cnc(-n2nccn2)c(Cl)c1)c1cnn(-c2c(Cl)cc(F)cc2Cl)c1C(F)(F)F]

$^1$H NMR (400 MHz, DMSO-d$_6$) δ ppm 11.27 (br s, 1H) 8.84 (d, J=1.98 Hz, 1H) 8.67 (s, 1H) 8.64 (d, J=1.98 Hz, 1H) 8.15 (s, 2H) 7.94 (d, J=8.16 Hz, 2H). LC-MS: (ES, m/z): [M+1]$^+$ 521.8

Example 94

1-(2-chloro-4,6-difluorophenyl)-N-(5-chloro-6-(2H-1,2,3-triazol-2-yl)pyridin-3-yl)-5-(trifluoromethyl)-1H-pyrazole-4-carboxamide, Cpd 94

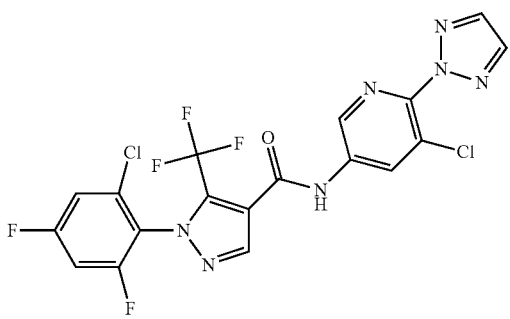

$^1$H NMR (400 MHz, DMSO-d$_6$) δ ppm 11.43 (s, 1H) 8.85 (d, J=1.98 Hz, 1H) 8.62-8.71 (m, 2H) 8.16 (s, 2H) 7.77-7.86 (m, 2H). LC-MS: (ES, m/z): [M+1]$^+$ 503.8

Example 95

1-(6-chloro-2-methylpyridin-3-yl)-N-(5-cyano-6-(2H-1,2,3-triazol-2-yl)pyridin-3-yl)-5-(trifluoromethyl)-1H-pyrazole-4-carboxamide, Cpd 95

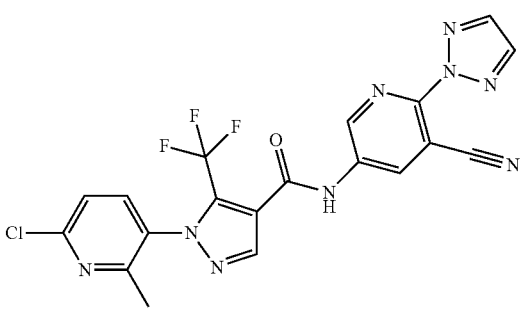 [SMILES: Cc1nc(Cl)ccc1-n1ncc(C(=O)Nc2cnc(-n3nccn3)c(C#N)c2)c1C(F)(F)F]

$^1$H NMR (400 MHz, DMSO-d$_6$) δ ppm 11.27 (s, 1H) 9.04 (d, J=2.43 Hz, 1H) 8.83 (d, J=2.43 Hz, 1H) 8.52 (s, 1H) 8.29 (s, 2H) 8.12 (d, J=8.38 Hz, 1H) 7.64 (d, J=8.38 Hz, 1H) 2.18 (s, 3H). LC-MS: (ES, m/z): [M+1]$^+$ 473.9

Example 96

N-(5-chloro-6-(2H-1,2,3-triazol-2-yl)pyridin-3-yl)-1-(5-fluoro-2-methylphenyl)-5-(trifluoromethyl)-1H-pyrazole-4-carboxamide, Cpd 96

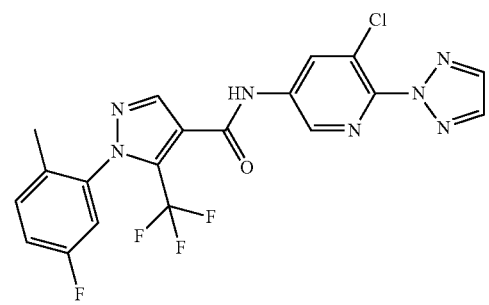 [SMILES: Cc1ccc(F)cc1-n1ncc(C(=O)Nc2cnc(-n3nccn3)c(Cl)c2)c1C(F)(F)F]

$^1$H NMR (400 MHz, DMSO-d$_6$) δ ppm 1.95 (s, 3H) 7.39-7.46 (m, 1H) 7.48-7.54 (m, 2H) 8.16 (s, 2H) 8.46 (s, 1H) 8.63 (d, J=2.43 Hz, 1H) 8.81 (d, J=2.43 Hz, 1H) 11.17 (s, 1H). LC-MS: (ES, m/z): [M+1]$^+$ 465.9

Example 97

N-(5-cyano-6-(2H-1,2,3-triazol-2-yl)pyridin-3-yl)-5-(trifluoromethyl)-1-(2,3,4-trifluorophenyl)-1H-pyrazole-4-carboxamide, Cpd 97

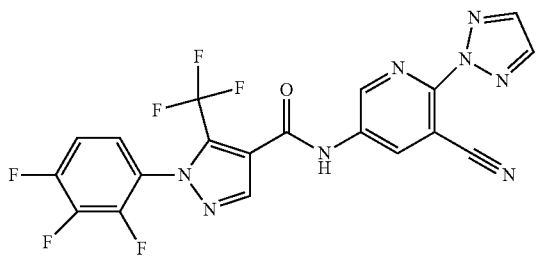 [SMILES: N#Cc1cc(NC(=O)c2cnn(-c3ccc(F)c(F)c3F)c2C(F)(F)F)cnc1-n1nccn1]

$^1$H NMR (400 MHz, DMSO-d$_6$) δ ppm 7.54-7.82 (m, 2H) 8.29 (s, 2H) 8.53 (s, 1H) 8.82 (d, J=2.65 Hz, 1H) 9.04 (d, J=2.43 Hz, 1H) 11.32 (s, 1H). LC-MS: (ES, m/z): [M+1]$^+$ 478.9

Example 98

1-(2-chloro-6-fluorophenyl)-N-(5-cyano-6-(2H-1,2,3-triazol-2-yl)pyridin-3-yl)-5-(trifluoromethyl)-1H-pyrazole-4-carboxamide, Cpd 98

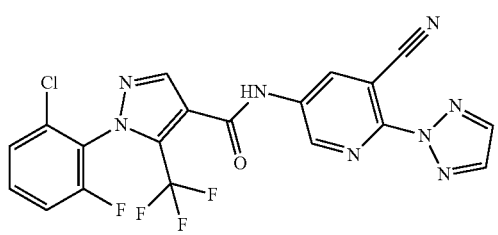 [SMILES: N#Cc1cc(NC(=O)c2cnn(-c3c(F)cccc3Cl)c2C(F)(F)F)cnc1-n1nccn1]

$^1$H NMR (400 MHz, DMSO-d$_6$) δ ppm 7.57-7.70 (m, 2H) 7.74-7.81 (m, 1H) 8.29 (s, 2H) 8.58 (s, 1H) 8.82 (d, J=2.65 Hz, 1H) 9.04 (d, J=2.43 Hz, 1H) 11.31 (s, 1H). LC-MS: (ES, m/z): [M+1]$^+$ 476.9

Example 99

1-(2-chloro-4,6-difluorophenyl)-N-(5-cyano-6-(2H-1,2,3-triazol-2-yl)pyridin-3-yl)-5-(trifluoromethyl)-1H-pyrazole-4-carboxamide, Cpd 99

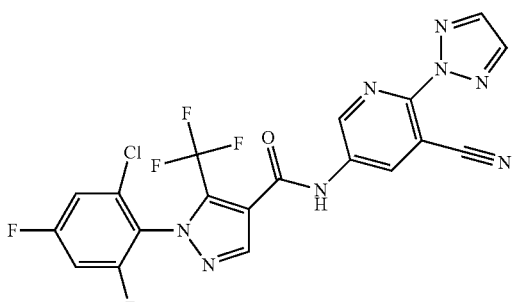

$^1$H NMR (400 MHz, DMSO-d$_6$) δ ppm 11.42 (br s, 1H) 9.07 (d, J=2.65 Hz, 1H) 8.84 (d, J=2.43 Hz, 1H) 8.65 (s, 1H) 8.28 (s, 2H) 7.77-7.86 (m, 2H). LC-MS: (ES, m/z): [M+1]+ 494.9

Example 100

N-(5-cyano-6-(2H-1,2,3-triazol-2-yl)pyridin-3-yl)-1-(2-cyclopropylphenyl)-5-(trifluoromethyl)-1H-pyrazole-4-carboxamide, Cpd 100

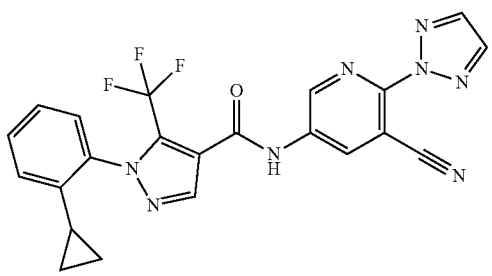 [SMILES: N#Cc1cc(NC(=O)c2cnn(-c3ccccc3C3CC3)c2C(F)(F)F)cnc1-n1nccn1]

$^1$H NMR (400 MHz, DMSO-d$_6$) δ ppm 11.24 (1H, s) 9.08 (1H, d, J=2.26 Hz) 8.86 (1H, d, J=2.26 Hz) 8.49 (1H, s) 8.32 (2H, s) 7.53 (1H, br t, J=7.28 Hz) 7.40-7.47 (1H, m) 7.32-7.40 (1H, m) 7.12 (1H, br d, J=7.78 Hz) 1.19-1.30 (1H, m) 0.85 (2H, br d, J=8.03 Hz) 0.77-0.84 (1H, m) 0.63 (1H, br s). LC-MS: (ES, m/z): [M+1]$^+$ 465.0

Example 101

N-(5-cyano-6-(2H-1,2,3-triazol-2-yl)pyridin-3-yl)-1-(2-fluoro-6-methylphenyl)-5-(trifluoromethyl)-1H-pyrazole-4-carboxamide, Cpd 101

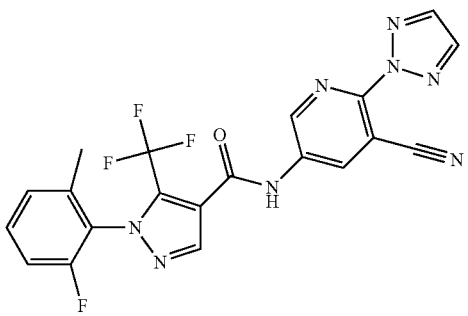 [SMILES: Cc1cccc(F)c1-n1ncc(C(=O)Nc2cnc(-n3nccn3)c(C#N)c2)c1C(F)(F)F]

$^1$H NMR (400 MHz, DMSO-d$_6$) δ ppm 11.42 (br s, 1H) 9.06-9.14 (m, 1H) 8.87 (s, 1H) 8.63 (br s, 1H) 8.28 (s, 2H) 7.58 (td, J=8.05, 5.73 Hz, 1H) 7.30-7.40 (m, 2H) 2.03 (s, 3H). LC-MS: (ES, m/z): [M+1]$^+$ 456.9

Example 102

N-(5-cyano-6-(2H-1,2,3-triazol-2-yl)pyridin-3-yl)-1-(2,6-dichloro-4-fluorophenyl)-5-(trifluoromethyl)-1H-pyrazole-4-carboxamide, Cpd 102

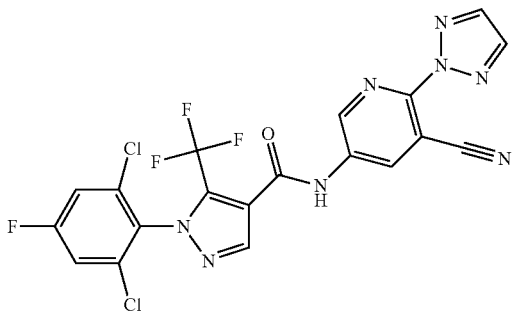 [SMILES: N#Cc1cc(NC(=O)c2cnn(-c3c(Cl)cc(F)cc3Cl)c2C(F)(F)F)cnc1-n1nccn1]

¹H NMR (400 MHz, DMSO-d₆) δ ppm 11.34 (br s, 1H) 9.07 (s, 1H) 8.84 (d, J=2.21 Hz, 1H) 8.67 (s, 1H) 8.28 (s, 2H) 7.94 (d, J=8.38 Hz, 2H). LC-MS: (ES, m/z): [M+1]⁺ 510.8

Example 103

N-(5-cyano-6-(2H-1,2,3-triazol-2-yl)pyridin-3-yl)-1-(5-fluoro-2-methylphenyl)-5-(trifluoromethyl)-1H-pyrazole-4-carboxamide, Cpd 103

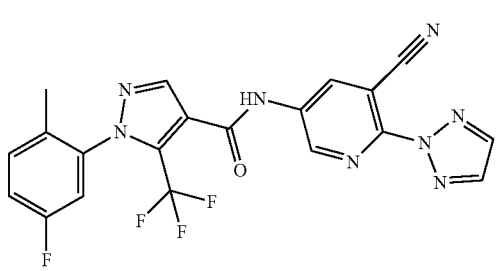 [SMILES: Cc1ccc(F)cc1-n1ncc(C(=O)Nc2cnc(-n3nccn3)c(C#N)c2)c1C(F)(F)F]

¹H NMR (400 MHz, DMSO-d₆) δ ppm 1.95 (s, 3H) 7.43 (br t, J=8.60 Hz, 1H) 7.47-7.57 (m, 2H) 8.28 (s, 2H) 8.46 (s, 1H) 8.83 (d, J=1.54 Hz, 1H) 9.04 (d, J=2.43 Hz, 1H) 11.22 (s, 1H). LC-MS: (ES, m/z): [M+1]⁺ 457.0

Example 104

N-(5-cyano-6-(2H-1,2,3-triazol-2-yl)pyridin-3-yl)-1-(3,4-difluorophenyl)-5-(trifluoromethyl)-1H-pyrazole-4-carboxamide, Cpd 104

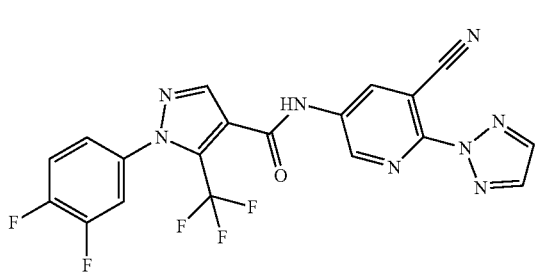 [SMILES: N#Cc1cc(NC(=O)c2cnn(-c3ccc(F)c(F)c3)c2C(F)(F)F)cnc1-n1nccn1]

¹H NMR (400 MHz, DMSO-d₆) δ ppm 7.49 (br d, J=8.82 Hz, 1H), 7.64-7.74 (m, 1H), 7.90 (ddd, J=10.31, 7.33, 2.65 Hz, 1H), 8.28 (s, 2H), 8.42 (s, 1H), 8.82 (d, J=2.43 Hz, 1H), 9.03 (d, J=2.43 Hz, 1H), 11.26 (s, 1H). LC-MS: (ES, m/z): [M+1]-460.9

Following the procedure described in Example 3, above, selecting and substituting the appropriate reagents, starting materials, and purification methods, and adjusting reaction temperatures, times and other variables or parameters, as needed or desirable, as would be readily recognized by those skilled in the art, the following compounds (105-117) were prepared.

Example 105

1-(3-chloro-5-fluoropyridin-2-yl)-N-(5-chloro-6-(2H-1,2,3-triazol-2-yl)pyridin-3-yl)-5-(trifluoromethyl)-1H-pyrazole-4-carboxamide, Cpd 105

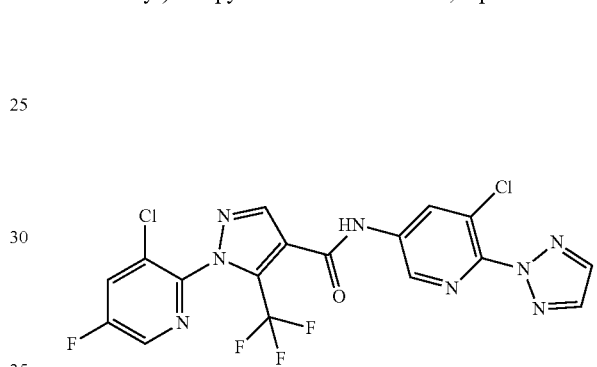

¹H NMR (400 MHz, DMSO-d₆) δ ppm 8.17 (br s, 2H), 8.60 (br d, J=19.62 Hz, 3H), 8.68-8.87 (m, 2H), 11.25 (br s, 1H). LC-MS: (ES, m/z): [M+1]⁺ 486.8

Example 106

1-(3-chloro-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 106

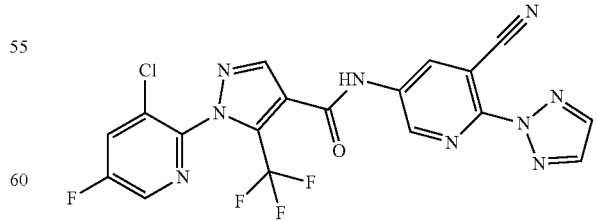

¹H NMR (400 MHz, DMSO-d₆) δ ppm 8.30 (s, 2H), 8.57 (s, 1H), 8.61 (dd, J=7.83, 2.54 Hz, 1H), 8.76 (d, J=2.65 Hz, 1H), 8.83 (d, J=2.43 Hz, 1H), 9.05 (d, J=2.43 Hz, 1H), 11.31 (s, 1H). LC-MS: (ES, m/z): [M+1]⁺ 477.9

Example 107

1-(2-chloro-4-fluorophenyl)-N-(5-chloro-6-(2H-1,2,3-triazol-2-yl)pyridin-3-yl)-5-(trifluoromethyl)-1H-pyrazole-4-carboxamide, Cpd 107

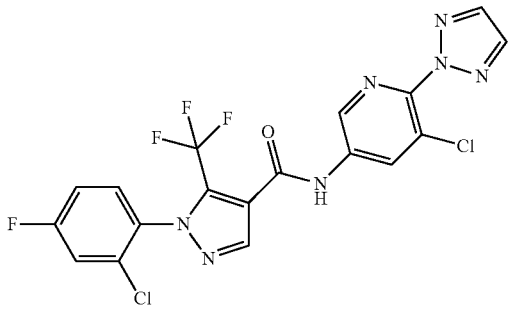 [SMILES: O=C(Nc1cnc(-n2nccn2)c(Cl)c1)c1cnn(-c2ccc(F)cc2Cl)c1C(F)(F)F]

$^1$H NMR (400 MHz, DMSO-d$_6$) δ ppm 7.52 (td, J=8.49, 2.87 Hz, 1H), 7.84-7.93 (m, 2H), 8.19 (s, 2H), 8.54 (s, 1H), 8.66 (d, J=2.21 Hz, 1H), 8.84 (d, J=2.20 Hz, 1H), 11.23 (s, 1H). LC-MS: (ES, m/z): [M+1]$^+$ 485.9.

Example 108

1-(3-chloro-4-fluorophenyl)-N-(5-chloro-6-(2H-1,2,3-triazol-2-yl)pyridin-3-yl)-5-(trifluoromethyl)-1H-pyrazole-4-carboxamide, Cpd 108

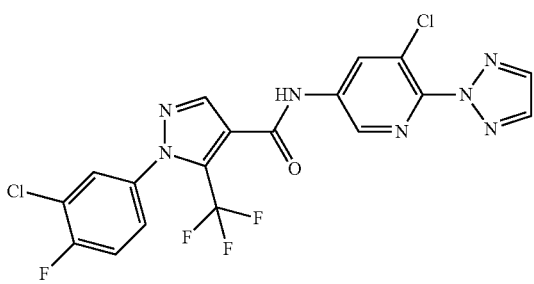 [SMILES: O=C(Nc1cnc(-n2nccn2)c(Cl)c1)c1cnn(-c2ccc(F)c(Cl)c2)c1C(F)(F)F]

$^1$H NMR (400 MHz, DMSO-d$_6$) δ ppm 7.57-7.74 (m, 2H), 7.94-8.06 (m, 1H), 8.16 (s, 2H), 8.43 (s, 1H), 8.62 (d, J=1.76 Hz, 1H), 8.81 (d, J=1.76 Hz, 1H), 11.21 (s, 1H). LC-MS: (ES, m/z): [M+1]$^+$ 485.9

Example 109

1-(3-chloro-4-fluorophenyl)-N-(5-cyano-6-(2H-1,2,3-triazol-2-yl)pyridin-3-yl)-5-(trifluoromethyl)-1H-pyrazole-4-carboxamide, Cpd 109

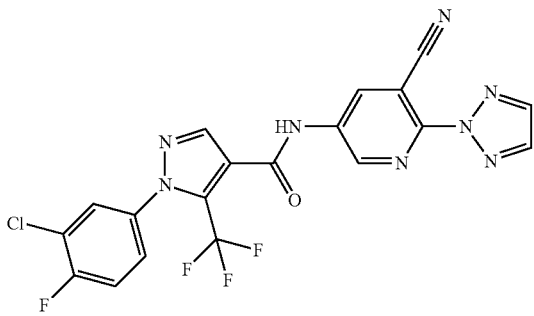 [SMILES: N#Cc1cc(NC(=O)c2cnn(-c3ccc(F)c(Cl)c3)c2C(F)(F)F)cnc1-n1nccn1]

$^1$H NMR (400 MHz, DMSO-d$_6$) δ ppm 7.65-7.68 (m, 1H), 7.65-7.68 (m, 1H), 8.00 (br d, J=6.17 Hz, 1H), 8.29 (s, 2H), 8.43 (s, 1H), 8.83 (d, J=2.43 Hz, 1H), 9.04 (d, J=2.65 Hz, 1H), 11.25 (s, 1H). LC-MS: (ES, m/z): [M+1]$^+$ 476.9

Example 110

1-(2-chloro-4-cyanophenyl)-N-(5-chloro-6-(2H-1,2,3-triazol-2-yl)pyridin-3-yl)-5-(trifluoromethyl)-1H-pyrazole-4-carboxamide, Cpd 110

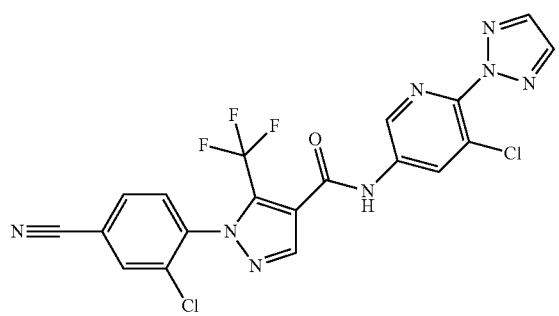 [SMILES: N#Cc1ccc(-n2ncc(C(=O)Nc3cnc(-n4nccn4)c(Cl)c3)c2C(F)(F)F)c(Cl)c1]

$^1$H NMR (400 MHz, DMSO-d$_6$) δ ppm 11.23 (s, 1H), 8.84 (d, J=2.2 Hz, 1H), 8.65 (d, J=2.2 Hz, 1H), 8.60 (s, 1H), 8.48 (d, J=1.8 Hz, 1H), 8.19 (s, 2H), 8.17-8.13 (m, 1H), 8.09-8.06 (m, 1H). LC-MS: (ES, m/z): [M+1]$^+$ 492.9

Example 111

N-(5-cyano-6-(2H-1,2,3-triazol-2-yl)pyridin-3-yl)-1-(2,4-difluorophenyl)-5-(trifluoromethyl)-1H-pyrazole-4-carboxamide, Cpd 111

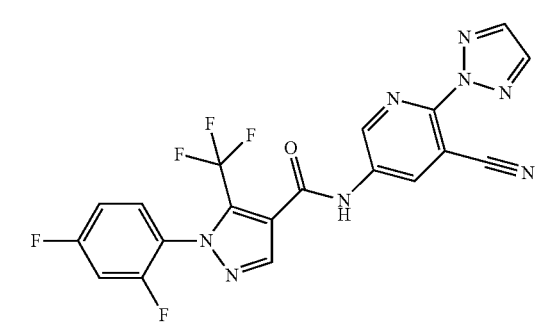

$^1$H NMR (400 MHz, METHANOL-d$_4$) δ ppm 9.06 (1H, d, J=2.51 Hz), 8.90 (1H, d, J=2.51 Hz), 8.35 (1H, s), 8.16 (2H, s), 7.70 (1H, td, J=8.72, 5.65 Hz), 7.37 (1H, ddd, J=10.10, 8.72, 2.76 Hz), 7.19-7.30 (1H, m). LC-MS: (ES, m/z): [M+1]$^+$ 531.8

Example 112

N-(5-chloro-6-(2H-1,2,3-triazol-2-yl)pyridin-3-yl)-1-(5-fluoro-3-methylpyridin-2-yl)-5-(trifluoromethyl)-1H-pyrazole-4-carboxamide, Cpd 112

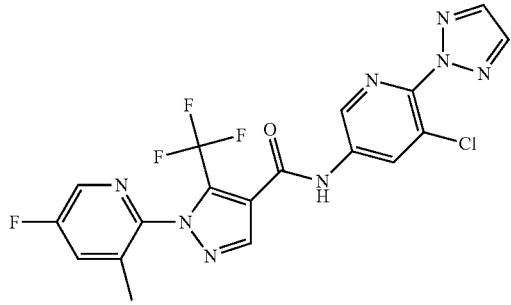 [SMILES: Cc1cc(F)cnc1-n1ncc(C(=O)Nc2cnc(-n3nccn3)c(Cl)c2)c1C(F)(F)F]

$^1$H NMR (400 MHz, DMSO-d$_6$) δ ppm 11.24 (br s, 1H), 8.82 (d, J=2.20 Hz, 1H), 8.64 (d, J=2.20 Hz, 1H), 8.46-8.54 (m, 2H), 8.17 (s, 2H), 8.06 (dd, J=8.93, 2.54 Hz, 1H), 2.15 (s, 3H). LC-MS: (ES, m/z): [M+1]$^+$ 466.9

Example 113

N-(5-cyano-6-(2H-1,2,3-triazol-2-yl)pyridin-3-yl)-1-(5-fluoro-3-methylpyridin-2-yl)-5-(trifluoromethyl)-1H-pyrazole-4-carboxamide, Cpd 113

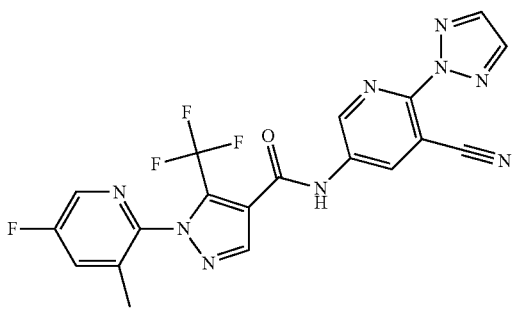 [SMILES: Cc1cc(F)cnc1-n1ncc(C(=O)Nc2cnc(-n3nccn3)c(C#N)c2)c1C(F)(F)F]

$^1$H NMR (400 MHz, DMSO-d$_6$) δ ppm 11.28 (s, 1H), 9.05 (d, J=2.43 Hz, 1H), 8.84 (d, J=2.43 Hz, 1H), 8.49-8.53 (m, 2H), 8.29 (s, 2H), 8.06 (dd, J=8.93, 2.32 Hz, 1H), 2.15 (s, 3H). LC-MS: (ES, m/z): [M+1]$^+$ 458.0

Example 114

N-(5-chloro-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide, Cpd 114

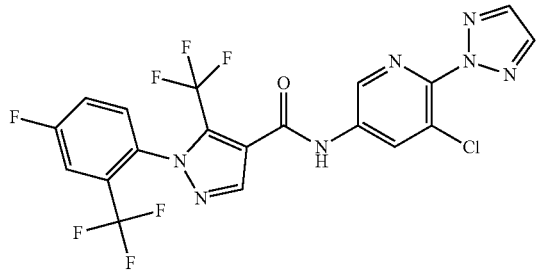 [SMILES: O=C(Nc1cnc(-n2nccn2)c(Cl)c1)c1cnn(-c2ccc(F)cc2C(F)(F)F)c1C(F)(F)F]

$^1$H NMR (400 MHz, DMSO-d$_6$) δ ppm 7.85 (td, J=8.43, 2.54 Hz, 1H) 7.97 (dd, J=8.60, 4.85 Hz, 1H) 8.05 (dd, J=8.82, 2.65 Hz, 1H) 8.19 (s, 2H) 8.53 (s, 1H) 8.66 (d, J=2.21 Hz, 1H) 8.85 (d, J=2.21 Hz, 1H) 11.21 (s, 1H). LC-MS: (ES, m/z): [M+1]$^+$ 519.9

Example 115

N-(5-cyano-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide, Cpd 115

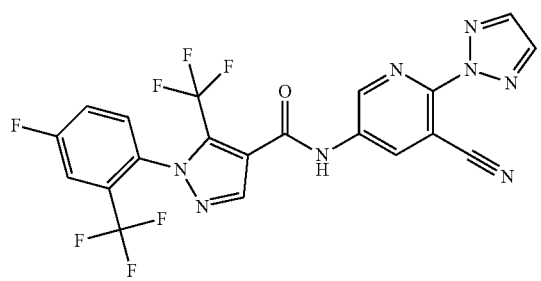 [SMILES: N#Cc1cc(NC(=O)c2cnn(-c3ccc(F)cc3C(F)(F)F)c2C(F)(F)F)cnc1-n1nccn1]

$^1$H NMR (400 MHz, DMSO-d$_6$) δ ppm 7.85 (td, J=8.38, 2.87 Hz, 1H) 7.99 (dd, J=8.82, 4.85 Hz, 1H) 8.05 (dd, J=8.49, 2.98 Hz, 1H) 8.32 (s, 2H) 8.53 (s, 1H) 8.86 (d, J=2.43 Hz, 1H) 9.07 (d, J=2.43 Hz, 1H) 11.25 (s, 1H). LC-MS: (ES, m/z): [M+1]$^+$ 510.9

Example 116

1-(2-chlorophenyl)-N-(5-cyano-6-(2H-1,2,3-triazol-2-yl)pyridin-3-yl)-5-(trifluoromethyl)-1H-pyrazole-4-carboxamide, Cpd 116

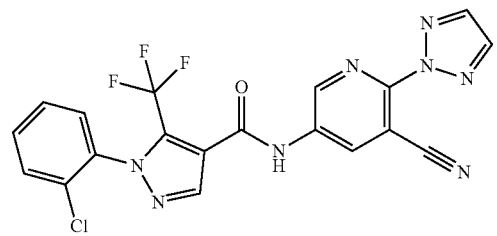 [SMILES: N#Cc1cc(NC(=O)c2cnn(-c3ccccc3Cl)c2C(F)(F)F)cnc1-n1nccn1]

$^1$H NMR (400 MHz, DMSO-d$_6$) δ ppm 11.23 (1H, s) 9.04 (1H, d, J=2.43 Hz) 8.82 (1H, d, J=2.43 Hz) 8.49 (1H, s) 8.28 (2H, s) 7.71-7.78 (2H, m) 7.67 (1H, t, J=7.72 Hz) 7.54-7.61 (1H, m). LC-MS: (ES, m/z): [M+1]$^+$ 458.9

Example 117

N-(5-chloro-6-(2H-1,2,3-triazol-2-yl)pyridin-3-yl)-1-(2,4-difluorophenyl)-5-(trifluoromethyl)-1H-pyrazole-4-carboxamide, Cpd 117

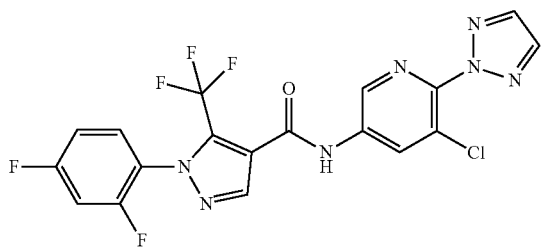 [SMILES: O=C(Nc1cnc(-n2nccn2)c(Cl)c1)c1cnn(-c2ccc(F)cc2F)c1C(F)(F)F]

$^1$H NMR (400 MHz, METHANOL-d$_4$) δ ppm 8.80 (1H, d, J=2.51 Hz), 8.72 (1H, d, J=2.26 Hz) 8.34 (1H, s), 8.06 (2H, s), 7.70 (1H, td, J=8.66, 5.52 Hz), 7.37 (1H, ddd, J=10.04, 8.66, 2.64 Hz), 7.19-7.30 (1H, m). LC-MS: (ES, m/z): [M+1]$^+$ 469.9

Example 118

V-(5-chloro-6-(2H-1,2,3-triazol-2-yl)pyridin-3-yl)-1-(2-(1-methoxyethyl)phenyl)-5-(trifluoromethyl)-1H-pyrazole-4-carboxamide, Cpd 118

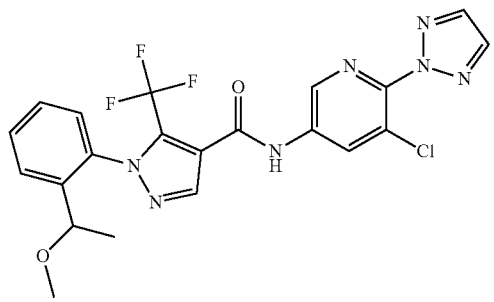 [SMILES: COC(C)c1ccccc1-n1ncc(C(=O)Nc2cnc(-n3nccn3)c(Cl)c2)c1C(F)(F)F]

A. 1-Bromo-2-(1-methoxyethyl)benzene, Cpd 118a

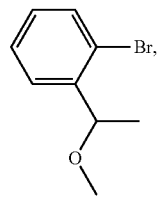

To a mixture of 1-(2-bromophenyl)ethanol (200 mg, 0.995 mmol) in THF (4 mL), cooled in an ice water bath, was added NaH (47.74 mg, 1.194 mmol). The mixture was stirred at 0° C. for 0.5 h. Then MeI (211.79 mg, 1.492 mmol) was added into the mixture. The resulted mixture was stirred at room temperature for 1 h. Water (20 mL) was added to the mixture. The mixture was extracted with ethyl acetate (30 mL). The combined organic layers were dried with Na$_2$SO$_4$, then filtered. The filtrates were concentrated under reduced pressure to afford a crude brown oil. The crude product was purified by flash column chromatography over silica gel (eluent: petroleum ether/ethyl acetate from 100/0 to 80/20). The eluent was collected and the solvent was evaporated under reduced pressure to give 1-bromo-2-(1-methoxyethyl)benzene, cpd 118a (200 mg, yield: 93.5%) as a light yellow oil.

B. (2-(1-methoxyethyl)phenyl)hydrazine, Cpd 118b

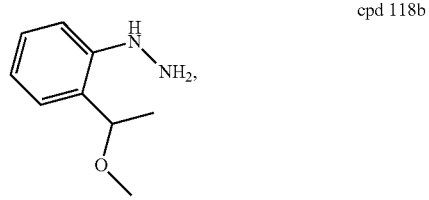

The mixture of {Pd(cinnamyl)Cl}$_2$ (24.087 mg, 0.046 mmol) and Mor-DalPhos (43.11 mg, 0.093 mmol) in dioxane (10 mL) was evacuated with argon 4 times. The resulting clear yellow solution was stirred at room temp under argon for 10 min. 1-bromo-2-(1-methoxyethyl)benzene, cpd 118a (200 mg, 0.930 mmol) and t-BuONa (178.73 mg, 1.860 mmol) was added to the mixture and the mixture was evacuated with argon 4 times. The resulting yellow reaction was then treated with NH$_2$NH$_2$.H$_2$O (95.0 mg, 1.860 mmol) via syringe. The reaction was evacuated with argon 4 times. Then the mixture was stirred at 50° C. under argon for 2 hrs. The mixture was filtered and washed with CH$_2$Cl$_2$/MeOH (20/1, 20 mL). The filtrate was collected and concentrated to give crude product, cpd 118b (154 mg, yield: 100%) which directly used in next step.

C. Ethyl 1-(2-(1-methoxyethyl)phenyl)-5-(trifluoromethyl)-1H-pyrazole-4-carboxylate, Cpd 118c

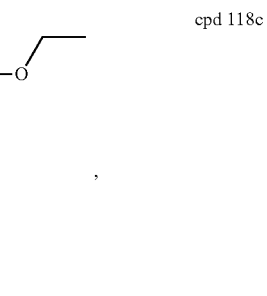

Ethyl 2-(ethoxymethylene)-4,4,4-trifluoro-3-oxobutanoate, INT1 (356.03 mg, 1.482 mmol) was added to a solution of (2-(1-methoxyethyl)phenyl)hydrazine, cpd 118b (154 mg, 0.926 mmol) in EtOH (5 mL). The mixture was stirred at 80° C. overnight. The mixture was concentrated to give a crude product. The crude product was purified by silica gel column (eluent: petroleum ether/ethyl acetate=3:1-1/1). The pure fractions were collected and evaporated to dryness to give ethyl 1-(2-(1-methoxyethyl) phenyl)-5-(trifluoromethyl)-1H-pyrazole-4-carboxylate, cpd 118c as a yellow oil (50 mg, yield: 15.8%).

D. 1-(2-(1-Methoxyethyl)phenyl)-5-(trifluoromethyl)-1H-pyrazole-4-carboxylic Acid, Cpd 118d

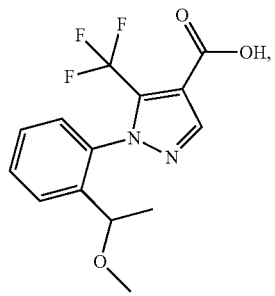

cpd 118d

To a mixture of ethyl 1-(2-(1-methoxyethyl)phenyl)-5-(trifluoromethyl)-1H-pyrazole-4-carboxylate, cpd 118c (50 mg, 0.146 mmol) in MeOH (1 mL) and water (1 mL) was added LiOH (12.26 mg, 0.292 mmol) under 0° C. The mixture was stirred at 0° C. for 1 h. The mixture was evaporated to dryness. To the residue was added water/EtOAc (2 mL/2 mL). HCl (1 M in water) was used to bring the mixture to pH 5. The organic layer was evaporated to dryness to give 1-(2-(1-methoxyethyl)phenyl)-5-(trifluoromethyl)-1H-pyrazole-4-carboxylic acid, cpd 118d (35 mg, yield: 76.2%) as a yellow solid.

E. N-(5-Chloro-6-(2H-1,2,3-triazol-2-yl)pyridin-3-yl)-1-(2-(1-methoxyethyl) phenyl)-5-(trifluoromethyl)-1H-pyrazole-4-carboxamide, Cpd 118

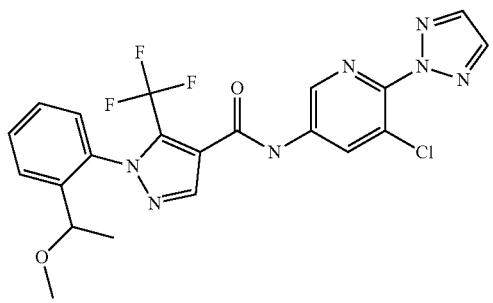 [SMILES: COC(C)c1ccccc1-n1ncc(C(=O)Nc2cnc(-n3nccn3)c(Cl)c2)c1C(F)(F)F]

POCl$_3$ (34.15 mg, 0.223 mmol) was added to a mixture of 1-(2-(1-methoxyethyl)phenyl)-5-(trifluoromethyl)-1H-pyrazole-4-carboxylic acid, cpd 118d (35 mg, 0.111 mmol), 5-chloro-6-(2H-1,2,3-triazol-2-yl)pyridin-3-amine, INT2 (21.79 mg, 0.111 mmol) and pyridine (44.05 mg, 0.557 mmol) in CH$_2$Cl$_2$ (1 mL). The reaction mixture was stirred at 20° C. for 1 h. Sat. NaHCO$_3$ solution (20 mL) was added to the mixture. The mixture was extracted with ethyl acetate (30 mL). The combined organic layers were dried with Na$_2$SO$_4$, then filtered. The filtrates were concentrated under reduced pressure to afford a crude brown oil. The residue was purified by preparative HPLC (50% to 80% (v/v) CH$_3$CN and H$_2$O with 0.05% ammonia hydroxide) and lyophilized to dryness to afford the title compound (19.5 mg, yield: 35.5%). $^1$H NMR (400 MHz, CHLOROFORM-d) δ ppm 8.77 (d, J=2.2 Hz, 1H), 8.50 (d, J=2.2 Hz, 1H), 8.11 (br s, 2H), 7.94 (s, 2H), 7.72-7.57 (m, 2H), 7.43 (t, J=7.6 I-Hz, 1H), 7.27 (s, 1H), 4.09-3.72 (m, 1H), 3.10 (br s, 3H), 1.48-1.24 (m, 3H). LC-MS: (ES, m/z): [M+1]$^+$ 491.9

Example 119

1-(4-amino-3-chloropyridin-2-yl)-N-(5-chloro-6-(2H-1,2,3-triazol-2-yl)pyridin-3-yl)-5-(trifluoromethyl)-1H-pyrazole-4-carboxamide, Cpd 119

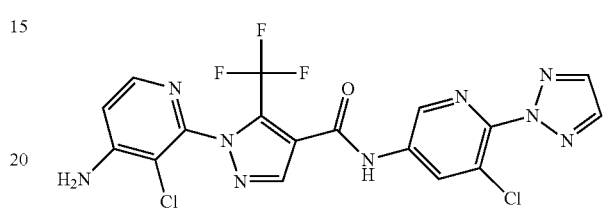

A. 4,4-tert-Butyl Carbamate-2,3-dichloropyridin-4-amine, Cpd 119a

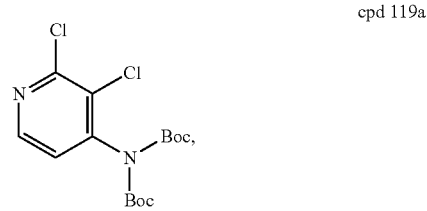 [SMILES: CC(C)(C)OC(=O)N(C(=O)OC(C)(C)C)c1ccnc(Cl)c1Cl]

cpd 119a

A solution of 2,3-dichloropyridin-4-amine (900 mg, 5.521 mmol), (Boc)$_2$O (3012.52 mg, 13.803 mmol), Et$_3$N (2230.61 mg, 22.085 mmol), DMAP (67.36 mg. 0.552 mmol) in CH$_2$Cl$_2$ was stirred at rt for 12 h. The mixture was diluted with water (100 mL) and extracted with CH$_2$-2Cl$_2$ (100 mL×3). The organic layers were dried (MgSO$_4$), filtered, and the filtrate concentrated under reduced pressure. The residue was purified by column chromatography over silica gel (eluent: petrol ether/EtOAc=100:0 to 70:30). The desired fractions were collected and the solvent was concentrated under reduced pressure to afford 4,4-tert-butyl carbamate-2,3-dichloropyridin-4-amine, cpd 119a (1600 mg, 77.7% yield) as a white solid. LCMS (ESI) m/z M+1: 362.8.

B. tert-Butyl (3-chloro-2-hydrazinylpyridin-4-yl)carbamate, Cpd 119b

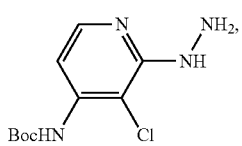

cpd 119b

A solution of 4,4-tert-butyl carbamate-2,3-dichloropyridin-4-amine, cpd 119a (1600 mg, 4.288 mmol), hydrazine hydrate (438.09 mg, 8.576 mmol) in CH₃CN (10 mL) was stirred at 100° C. in microwave for 1 h. The mixture was concentrated under reduced pressure to afford tert-butyl (3-chloro-2-hydrazinylpyridin-4-yl)carbamate, cpd 119b (1300 mg, >100% yield) as a white solid for the next step directly.

C. Ethyl 1-(4-((tert-butoxycarbonyl)amino)-3-chloropyridin-2-yl)-5-(trifluoromethyl)-1H-pyrazole-4-carboxylate, Cpd 119c

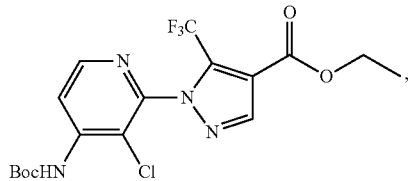

cpd 119c

A solution of tert-butyl (3-chloro-2-hydrazinylpyridin-4-yl)carbamate, cpd 119b (1300 mg, 5.025 mmol), ethyl 2-(ethoxymethylene)-4,4,4-trifluoro-3-oxobutanoate, INT1 (1810.3 mg, 7.538 mmol), Et₃N (1522.6 mg, 15.075 mmol) in EtOH (30 mL) was stirred at 80° C. for 2 h. The mixture was concentrated under reduced pressure. The crude product was purified by column chromatography over silica gel (petroleum ether/ethyl acetate from 20:1 to 1:1). The desired fractions were collected and the solvent was concentrated under reduced pressure to give 450 mg crude product as a yellow solid, which was purified by preparative HPLC (55% to 85% (v/v) CH₃CN and H₂O with 0.05% ammonia hydroxide) and lyophilized to dryness to afford ethyl 1-(4-((tert-butoxycarbonyl)amino)-3-chloropyridin-2-yl)-5-(trifluoromethyl)-1H-pyrazole-4-carboxylate, cpd 119c (150 mg, 6.9% yield) as a yellow solid.

D. 1-(4-((tert-Butoxycarbonyl)amino)-3-chloropyridin-2-yl)-5-(trifluoromethyl)-1H-pyrazole-4-carboxylic Acid, Cpd 119d

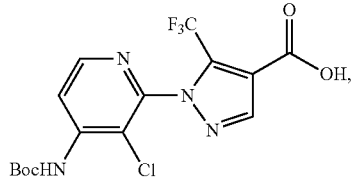

cpd 119d

A solution of ethyl 1-(4-((tert-butoxycarbonyl)amino)-3-chloropyridin-2-yl)-5-(trifluoromethyl)-1H-pyrazole-4-carboxylate, cpd 119c (150 mg, 0.345 mmol), LiOH.H₂O (28.95 mg, 0.690 mmol) in MeOH (10 mL), THF (10 mL) and water (10 mL) was stirred at rt for 3 h. To the mixture was added 5% KHSO₄ to adjust the mixture to pH 3-4. Water (100 mL) and ethyl acetate (100 mL) were added to the mixture. The organic layer was washed with brine (50 mL), dried over MgSO₄, filtered, and the filtrate concentrated under reduced pressure to afford 1-(4-((tert-butoxycarbonyl)amino)-3-chloropyridin-2-yl)-5-(trifluoromethyl)-1H-pyrazole-4-carboxylic acid, cpd 119d (130 mg, 87.5% yield) as a yellow solid to be used for the next step directly. LCMS (ESI) m/z M+H: 406.9

E. tert-Butyl (3-chloro-2-(4-((5-chloro-6-(2H-1,2,3-triazol-2-yl) Pyridin-3-yl)carbamoyl)-5-(trifluoromethyl)-1H-pyrazol-1-yl)pyridin-4-yl)carbamate, Cpd 119e

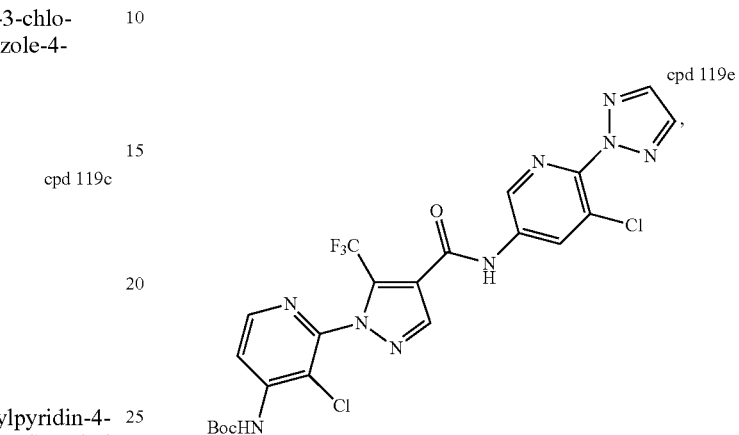

cpd 119e

POCl₃ (71.19 mg, 0.464 mmol) was added to a solution of 1-(4-((tert-butoxycarbonyl)amino)-3-chloropyridin-2-yl)-5-(trifluoromethyl)-1H-pyrazole-4-carboxylic acid, cpd 119d (100 mg, 0.232 mmol), 5-chloro-6-(2H-1,2,3-triazol-2-yl) pyridin-3-amine, INT2 (54.49 mg, 0.279 mmol), pyridine (45.90 mg 0.58 mmol) in CH₂Cl₂ (10 mL). The mixture was stirred at rt for 2 h. Water (50 mL) and CH₂Cl₂ (50 mL) were added to the mixture. The organic layer was washed with brine (50 mL), dried over MgSO₄, filtered, and the filtrate concentrated under reduced pressure. The crude product was purified by column chromatography over silica gel (petroleum ether/ethyl acetate from 20:1 to 1:1). The desired fractions were collected and the solvent was concentrated under reduced pressure to afford tert-butyl (3-chloro-2-(4-((5-chloro-6-(2H-1,2,3-triazol-2-yl)pyridin-3-yl)carbamoyl)-5-(trifluoromethyl)-1H-pyrazol-1-yl)pyridin-4-yl)carbamate, cpd 119e (60 mg, 44.2% yield) as a white solid. LCMS (ESI) m/z M+Na: 606.0.

F. 1-(4-Amino-3-chloropyridin-2-yl)-N-(5-chloro-6-(2H-1,2,3-triazol-2-yl)pyridin-3-yl)-5-(trifluoromethyl)-1H-pyrazole-4-carboxamide, Cpd 119

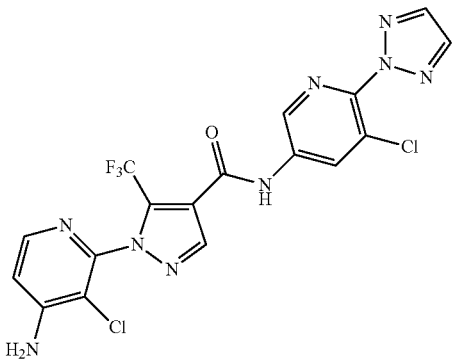 [SMILES: Nc1ccnc(-n2ncc(C(=O)Nc3cnc(-n4nccn4)c(Cl)c3)c2C(F)(F)F)c1Cl]

tert-butyl (3-chloro-2-(4-((5-chloro-6-(2H-1,2,3-triazol-2-yl)pyridin-3-yl)carbamoyl)-5-(trifluoromethyl)-1H-pyrazol-1-yl)pyridin-4-yl)carbamate, cpd 119e (60 mg 0.103 mmol) was added to HCl/dioxane (10 mL, 4 mol/L). The mixture was stirred at rt for 1 h. The mixture was concentrated under reduced pressure to afford the crude product, which was purified by preparative HPLC (32% to 62% (v/v) CH$_3$CN and H$_2$O with 0.05% HCl) and lyophilized to dryness to afford the title compound, cpd 119 (23.4 mg 43.8%) as white solid. $^1$H NMR (400 MHz, METHANOL-d$_4$) δ ppm 8.76-8.81 (m, 1H), 8.69 (d, J=2.21 Hz, 1H), 8.35 (s, 1H), 8.02 (s, 2H), 7.96 (d, J=5.95 Hz, 1H), 6.92 (d, J=5.95 Hz, 1H). LC-MS: (ES, m/z): [M+1]$^+$ 483.9

Example 120

1-(4-amino-3-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 120

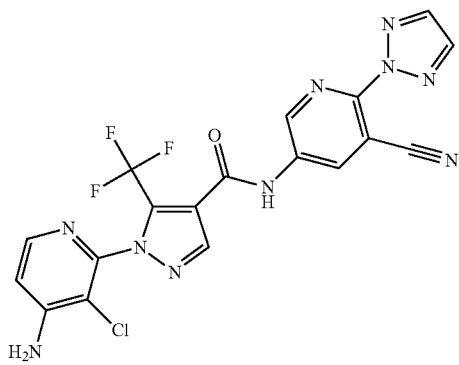 [SMILES: N#Cc1cc(NC(=O)c2cnn(-c3nccc(N)c3Cl)c2C(F)(F)F)cnc1-n1nccn1]

A. Tert-Butyl (3-chloro-2-(4-((5-cyano-6-(2H-1,2,3-triazol-2-yl) Pyridin-3-yl)carbamoyl)-5-(trifluoromethyl)-1H-pyrazol-1-yl)pyridin-4-yl)carbamate, Cpd 120a

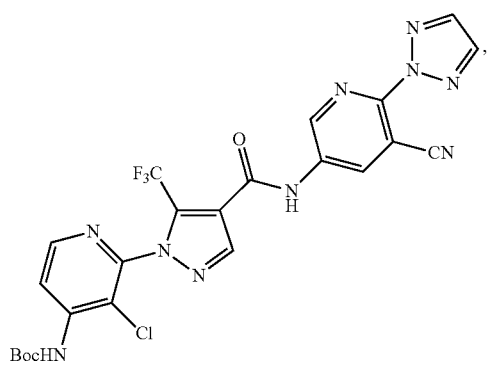

POCl$_3$ (21.356 mg, 0.139 mmol) was added to a solution of 1-(4-((tert-butoxycarbonyl)amino)-3-chloropyridin-2-yl)-5-(trifluoromethyl)-1H-pyrazole-4-carboxylic acid, cpd 119d (30 mg, 0.070 mmol), 5-amino-2-(2H-1,2,3-triazol-2-yl)nicotinonitrile, INT3 (15.558 mg, 0.084 mmol), pyridine (13.771 mg 0.174 mmol) in CH$_2$Cl$_2$ (10 mL). The mixture was stirred at rt for 2 h. Water (50 mL) and CH$_2$Cl$_2$ (50 mL) were added to the mixture. The organic layer was washed with brine (50 mL), dried over MgSO$_4$, filtered, and the filtrate concentrated under reduced pressure. The crude product was purified by column chromatography over silica gel (petroleum ether/ethyl acetate from 20:1 to 1:1). The desired fractions were collected and the solvent was concentrated under reduced pressure to afford tert-butyl (3-chloro-2-(4-((5-cyano-6-(2H-1,2,3-triazol-2-yl)pyridin-3-yl)carbamoyl)-5-(trifluoromethyl)-1H-pyrazol-1-yl)pyridin-4-yl)carbamate, cpd 120a (20 mg, 50.0% yield) as a white solid. TLC: petroleum ether/ethyl acetate=1/1, Rf=0.4; LCMS (ESI) m/z M+H: 575.1.

B. 1-(4-amino-3-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 120

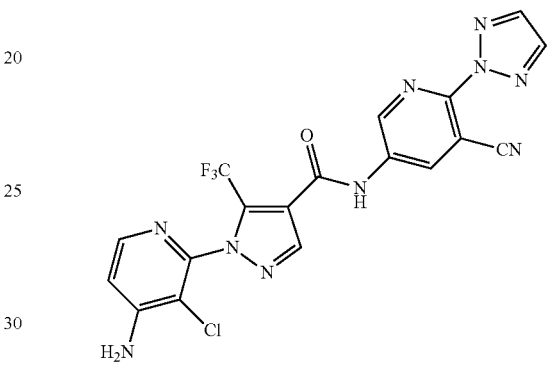

tert-Butyl (3-chloro-2-(4-((5-cyano-6-(2H-1,2,3-triazol-2-yl)pyridin-3-yl)carbamoyl)-5-(trifluoromethyl)-1H-pyrazol-1-yl)pyridin-4-yl)carbamate, cpd 120a (20 mg, 0.035 mmol) was added to HCl/dioxane (5 mL, 4 mol/L). The mixture was stirred at rt for 1 h. The mixture was concentrated under reduced pressure to afford the crude product, which was purified by preparative HPLC (35% to 55% (v/v) CH$_3$CN and H$_2$O with 0.05% HCl) and lyophilized to dryness to afford the title compound (10.3 mg 57.0%) as a white solid. $^1$H NMR (400 MHz, METHANOL-d$_4$) δ ppm 9.05 (d, J=2.43 Hz, 1H), 8.87 (d, J=2.65 Hz, 1H), 8.34 (s, 1H), 8.12 (s, 2H), 7.95 (d, J=5.73 Hz, 1H), 6.91 (d, J=5.73 Hz, 1H). LC-MS: (ES, m/z): [M+1]$^+$ 474.9

Example 121

N-(5-chloro-6-(2H-1,2,3-triazol-2-yl)pyridin-3-yl)-1-(6-fluoropyridin-3-yl)-5-(trifluoromethyl)-1H-pyrazole-4-carboxamide, Cpd 121

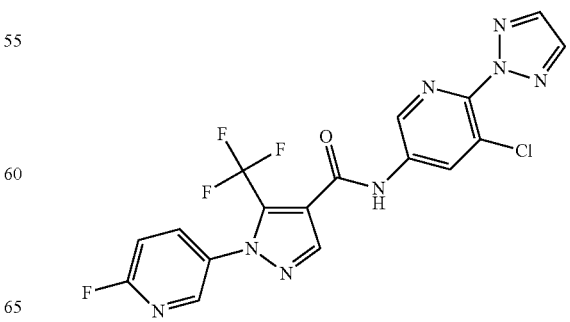

A. 2-Fluoro-5-hydrazinylpyridine, Cpd 121a

To a stirring solution of 6-fluoropyridin-3-amine (3 g, 26.761 mmol) in HCl (6 N, 20 mL) at −10° C. was added a solution of sodium nitrite (2.77 g, 40.141 mmol) in water (8 mL) below −20° C. The reaction mixture was stirred at rt for 0.5 h. Then cooled to −20° C., tin(ii) chloride dihydrate (12.077 g, 53.521 mmol) was added portions to the mixture and stirred for 1 h. The reaction mixture was made basic with 3 M NaOH, the residue was filtered and washed with EtOAc (100 mL×3). The organic layer was separated and the aqueous extracted with EtOAc (50 mL×3). The combined organic layers were dried with Na$_2$SO$_4$, filtered and the filtrates were concentrated under reduced pressure to afford crude product (3 g, 52.1% purity, 45.9%) as a yellow solid, which was used for the next step without further purification. LCMS (ESI) m/z M+23: 150.1.

B. Ethyl 1-(6-fluoropyridin-3-yl)-5-(trifluoromethyl)-1H-pyrazole-4-carboxylate, Cpd 121b

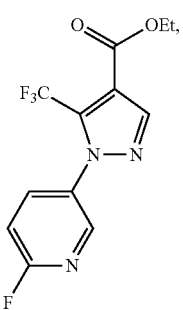

2-Fluoro-5-hydrazinylpyridine, cpd 121a (3 g, 12.295 mmol) was dissolved in ethanol (20 mL), ethyl 2-(ethoxymethylene)-4,4,4-trifluoro-3-oxobutanoate, INT1 (4.429 g, 18.442 mmol) was added and stirred at 70° C. for 2 h before cooling to room temperature. The combined mixture was concentrated under reduced pressure to afford crude product as a yellow oil, which was purified by flash column chromatography (eluent: petroleum ether/ethyl acetate from 100/0 to 85/15) to afford the title compound (2 g, 50.7%) as yellow solid. LCMS (ESI) m/z M+1: 304.0.

C. 1-(6-Fluoropyridin-3-yl)-5-(trifluoromethyl)-1H-pyrazole-4-carboxylic Acid, Cpd 121c

Ethyl 1-(6-fluoropyridin-3-yl)-5-(trifluoromethyl)-1H-pyrazole-4-carboxylate, cpd 121b (1 g, 3.298 mmol) was dissolved in THF (10 mL) and water (10 mL). Lithium hydroxide (157.96 mg, 6.596 mmol) was added. The reaction mixture was stirred at 30° C. for 16 h. The reaction mixture was adjusted to pH 5 using HCl (2 N), then extracted with CH$_2$Cl$_2$/MeOH (10/1, 60 mL×5). The combined organic layers were dried with Na$_2$SO$_4$, filtered and the filtrates were concentrated under reduced pressure to afford crude the title compound (630 mg, 85.7% purity, 59.5%) as yellow solid. LCMS (ESI) m/z M+1: 276.0.

D. N-(5-Chloro-6-(2H-1,2,3-triazol-2-yl)pyridin-3-yl)-1-(6-fluoropyridin-3-yl)-5-(trifluoromethyl)-1H-pyrazole-4-carboxamide, Cpd 121

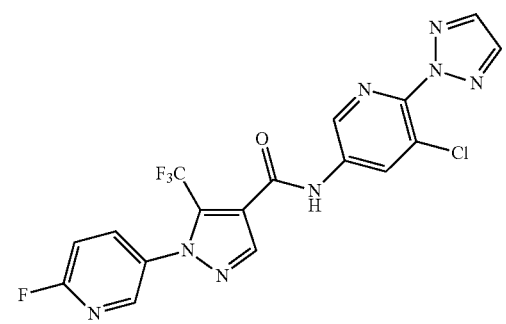 [SMILES: O=C(Nc1cnc(-n2nccn2)c(Cl)c1)c1cnn(-c2ccc(F)nc2)c1C(F)(F)F]

1-(6-Fluoropyridin-3-yl)-5-(trifluoromethyl)-1H-pyrazole-4-carboxylic acid, cpd 121c (306.85 mg, 0.956 mmol), 5-chloro-6-(2H-1,2,3-triazol-2-yl)pyridin-3-amine, (170 mg, 0.869 mmol), pyridine (412.47 mg, 5.214 mmol) were dissolved in CH$_2$Cl$_2$ (15 mL), and phosphorus oxychloride (399.77 mg, 2.607 mmol) was added. The mixture was stirred at 25° C. for 16 h. Sat.NaHCO$_3$(20 mL) was added and extracted with CH$_2$Cl$_2$ (50 mL×2). The combined organic layers were dried with Na$_2$SO$_4$, filtered and the filtrates were concentrated under reduced pressure to afford the crude product as a yellow solid, which was then purified by flash column chromatography (eluent: petroleum ether/ethyl acetate from 100/0 to 30/70) to afford the title compound (370 mg, 93.1%) as yellow solid. $^1$H NMR (400 MHz, DMSO-d$_6$) δ 8.82 (d, J=2.2 Hz, 1H), 8.65 (d, J=2.0

Hz, 1H), 8.58 (d, J=2.2 Hz, 1H), 8.50 (s, 1H), 8.39-8.30 (m, 1H), 8.19 (s, 2H), 7.51 (dd, J=2.9, 8.8 Hz, 1H). LCMS (ESI) m/z M+1: 452.9.

Example 122

N-(5-chloro-6-(2H-1,2,3-triazol-2-yl)pyridin-3-yl)-1-(6-(methylamino)pyridin-3-yl)-5-(trifluoromethyl)-1H-pyrazole-4-carboxamide, Cpd 122

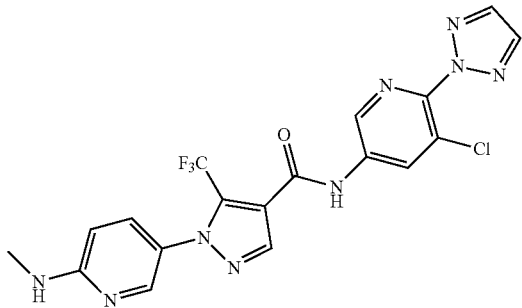 [SMILES: CNc1ccc(-n2ncc(C(=O)Nc3cnc(-n4nccn4)c(Cl)c3)c2C(F)(F)F)cn1]

N-(5-Chloro-6-(2H-1,2,3-triazol-2-yl)pyridin-3-yl)-1-(6-fluoropyridin-3-yl)-5-(trifluoromethyl)-1H-pyrazole-4-carboxamide, cpd 121 (100 mg, 0.219 mmol) and methylamine (5 mL, 2M) was stirred at 70° C. for 16 h. The reaction mixture was concentrated under reduced pressure to afford a crude product as a yellow solid, which was purified by preparative HPLC (17% to 47% (v/v) CH$_3$CN and H$_2$O with 0.05% HCl) and lyophilized to dryness to afford the title compound (85 mg, 77.736%). $^1$H NMR (400 MHz, DMSO-d$_6$) δ ppm 11.40 (s, 1H), 8.90 (d, J=2.2 Hz, 1H), 8.69 (d, J=2.2 Hz, 1H), 8.52 (s, 1H), 8.28 (d, J=2.2 Hz, 1H), 8.18 (s, 2H), 7.82 (br d, J=9.3 Hz, 1H), 6.92 (d, J=9.5 Hz, 1H), 2.94 (s, 3H). LC-MS: (ES, m/z): [M+1]$^+$ 463.9

Example 123

N-(5-cyano-6-(2H-1,2,3-triazol-2-yl)pyridin-3-yl)-1-(6-(fluoro)pyridin-3-yl)-5-(trifluoromethyl)-1H-pyrazole-4-carboxamide, Cpd 123

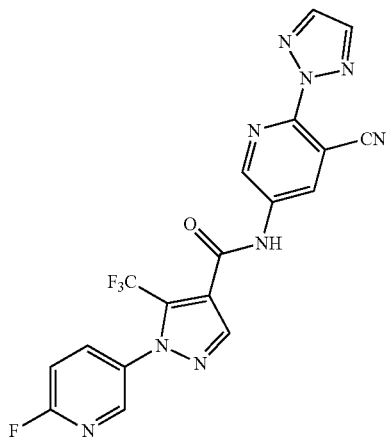 [SMILES: N#Cc1cc(NC(=O)c2cnn(-c3ccc(F)nc3)c2C(F)(F)F)cnc1-n1nccn1]

1-(6-Fluoropyridin-3-yl)-5-(trifluoromethyl)-1H-pyrazole-4-carboxylic acid, cpd 121c (303.44 mg, 0.945 mmol), 5-amino-2-(2H-1,2,3-triazol-2-yl)nicotinonitrile, INT3 (160 mg, 0.859 mmol), pyridine (407.88 mg, 5.156 mmol) were dissolved in CH$_2$Cl$_2$ (15 mL), and phosphorus oxychloride (395.33 mg, 2.578 mmol) was added. The mixture was stirred at 25° C. for 16 h. Sat.NaHCO$_3$(20 mL) was added and the mixture was extracted with CH$_2$Cl$_2$ (50 mL×2). The combined organic layers were dried with Na$_2$SO$_4$, filtered and the filtrates were concentrated under reduced pressure to afford the crude product as a yellow solid, which was purified by flash column chromatography (eluent: petroleum ether/ethyl acetate from 100/0 to 30/70) to afford the title compound (230 mg, 59.1%) as a yellow solid. $^1$H NMR (400 MHz, DMSO-d$_6$) δ 11.29 (br s, 1H), 9.06 (d, J=2.4 Hz, 1H), 8.85 (d, J=2.4 Hz, 1H), 8.59 (d, J=2.2 Hz, 1H), 8.51 (s, 1H), 8.35 (ddd, J=2.8, 6.7, 8.9 Hz, 1H), 8.32 (s, 2H), 7.51 (dd, J=2.9, 8.6 Hz, 1H). LCMS (ESI) m/z M+1: 443.9.

Example 124

N-(5-cyano-6-(2H-1,2,3-triazol-2-yl)pyridin-3-yl)-1-(6-(methylamino)pyridin-3-yl)-5-(trifluoromethyl)-1H-pyrazole-4-carboxamide, Cpd 124

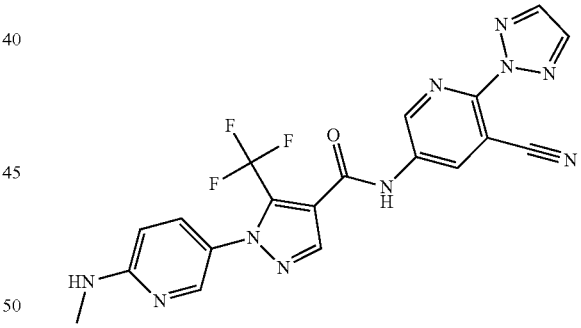

N-(5-Cyano-6-(2H-1,2,3-triazol-2-yl)pyridin-3-yl)-1-(6-(methylamino)pyridin-3-yl)-5-(trifluoromethyl)-1H-pyrazole-4-carboxamide, cpd 123 (100 mg, 0.221 mmol) and methylamine (5 mL, 2M) was stirred at 70° C. for 3 h. The reaction mixture was concentrated under reduced pressure to afford crude product as a yellow solid, which was purified by preparative HPLC (13% to 43% (v/v) CH$_3$CN and H$_2$O with 0.05% HCl) and lyophilized to dryness to afford the title compound (65 mg, 60.0%). $^1$H NMR (400 MHz, DMSO-d$_6$) δ ppm 11.43 (s, 1H), 9.12 (d, J=2.4 Hz, 1H), 8.89 (d, J=2.4 Hz, 1H), 8.49 (s, 1H), 8.31 (s, 2H), 8.26 (d, J=2.2 Hz, 1H), 7.78 (br d, J=7.7 Hz, 1H), 6.86 (br d, J=9.3 Hz, 1H), 2.92 (s, 3H). LC-MS: (ES, m/z): [M+1]-455.0

Example 125

1-(6-aminopyridin-3-yl)-N-(5-chloro-6-(2H-1,2,3-triazol-2-yl)pyridin-3-yl)-5-(trifluoromethyl)-1H-pyrazole-4-carboxamide, Cpd 125

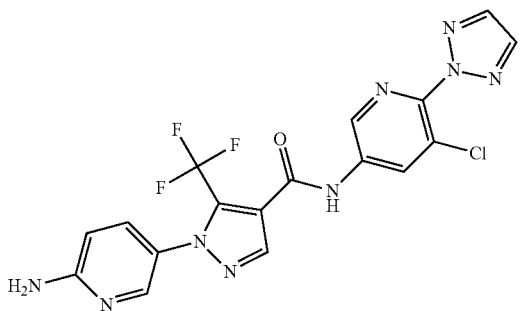 [SMILES: Nc1ccc(-n2ncc(C(=O)Nc3cnc(-n4nccn4)c(Cl)c3)c2C(F)(F)F)cn1]

N-(5-Chloro-6-(2H-1,2,3-triazol-2-yl)pyridin-3-yl)-1-(6-fluoropyridin-3-yl)-5-(trifluoromethyl)-1H-pyrazole-4-carboxamide, cpd 121 (120 mg, 0.262 mmol) and NH$_3$/MeOH (6 mL, 7M) was stirred at 70° C. for 16 h. The reaction mixture was concentrated under reduced pressure to afford crude product as a yellow solid, which was purified by preparative HPLC (25% to 55% (v/v) CH$_3$CN and H$_2$O with 0.05% HCl) and lyophilized to dryness to afford the title compound (32 mg, 24.7%). $^1$H NMR (400 MHz, DMSO-d$_6$) δ ppm 11.52 (s, 1H), 8.94 (s, 1H), 8.72 (s, 1H), 8.60 (s, 1H), 8.40 (br s, 1H), 8.18 (s, 2H), 8.01 (br d, J=8.8 Hz, 1H), 7.05 (br d, J=9.5 Hz, 1H). LC-MS: (ES, m/z): [M+1]$^+$ 449.9

Example 126

1-(4-cyano-2-methylphenyl)-N-(5-cyano-6-(2H-1,2,3-triazol-2-yl)pyridin-3-yl)-5-(trifluoromethyl)-1H-pyrazole-4-carboxamide, Cpd 126

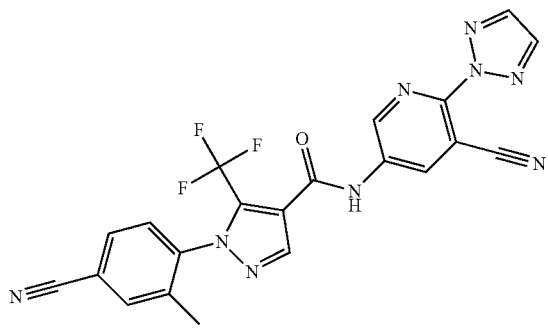 [SMILES: Cc1cc(C#N)ccc1-n1ncc(C(=O)Nc2cnc(-n3nccn3)c(C#N)c2)c1C(F)(F)F]

1-(4-Cyano-2-methylphenyl)-5-(trifluoromethyl)-1H-pyrazole-4-carboxylic acid, cpd 37c (150 mg, 0.508 mmol) was treated with oxalyl chloride (100.5 mg, 1.27 mmol) in DCM (10 mL) and DMF (1 drop) at room temperature. The mixture was then stirred for 45 minutes and then concentrated to dryness. The crude acid chloride was dissolved in DCM (10 mL) and 5-amino-2-(2H-1,2,3-triazol-2-yl)nicotinonitrile, INT3 (113.5 mg, 0.61 mmol) was added, immediately followed by pyridine (167 mg, 2.12 mmol). The reaction was stirred at room temperature for 3 hours and finally quenched with water (50 mL) and extracted with DCM (2×50 mL). The combined extracts were dried over MgSO$_4$, filtered and the filtrate concentrated to a crude solid. The crude was purified by HPLC to give 1-(4-cyano-2-methylphenyl)-N-(5-cyano-6-(2H-1,2,3-triazol-2-yl)pyridin-3-yl)-5-(trifluoromethyl)-1H-pyrazole-4-carboxamide, cpd 126 (53.6 mg, 23%). $^1$H NMR (400 MHz, DMSO-d$_6$) δ ppm 11.32 (br s, 1H), 9.10 (d, J=2.43 Hz, 1H), 8.88 (d, J=2.43 Hz, 1H), 8.58 (s, 1H), 8.32 (s, 2H), 8.07 (s, 1H), 7.95 (dd, J=8.16, 1.32 Hz, 1H), 7.76 (d, J=8.16 Hz, 1H), 2.07 (s, 3H). LC-MS: (ES, m/z): [M+1]$^+$ 472.9

Example 127

N-(5-cyano-6-(2H-1,2,3-triazol-2-yl)pyridin-3-yl)-1-(1-methyl-1,2,3,4-tetrahydroquinolin-5-yl)-5-(trifluoromethyl)-1H-pyrazole-4-carboxamide, Cpd 127

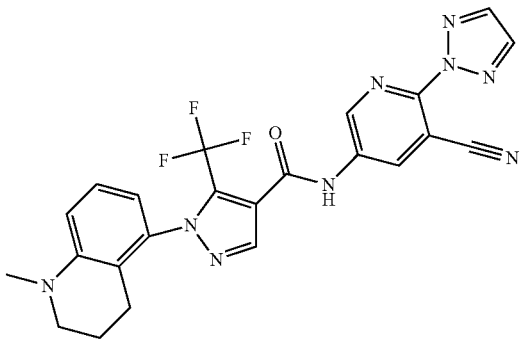 [SMILES: CN1CCCc2c1cccc2-n1ncc(C(=O)Nc2cnc(-n3nccn3)c(C#N)c2)c1C(F)(F)F]

A. Tert-Butyl 5-bromo-3,4-dihydroquinoline-1(2H)-carboxylate, Cpd 127a

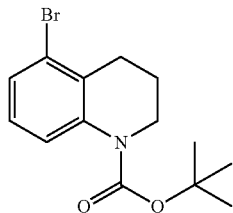

To a solution of 5-bromo-1,2,3,4-tetrahydroquinoline hydrochloride (0.90 g, 3.621 mmol) in dichloromethane (6 mL), N,N-dimethylaminopyridine (0.044 g, 0.362 mmol) and triethylamine (1.06 mL, 7.6 mmol) were added. The mixture was stirred for 30 min at room temperature, then di-tert-butyl dicarbonate (0.873 mL, 3.802 mmol) was added portionwise. The solution was stirred at room temperature overnight. The mixture was diluted with ethyl acetate. The organic layer was washed with water and brine, filtered, and the filtrate was dried and concentrated. The mixture was purified by flash chromatography (SiO$_2$, heptane-ethylacetate gradient). Pure fractions were combined and concentrated. The residue was dried under reduced pressure to yield tert-butyl 5-bromo-3,4-dihydroquinoline-1(2H)-carboxylate, cpd 127a (749 mg, 66% yield). MS m/z 213.9 (M+H-tBu)+.

B. Tert-Butyl 5-(2-(diphenylmethylene)hydrazinyl)-3,4-dihydroquinoline-1(2H)-carboxylate, Cpd 127b

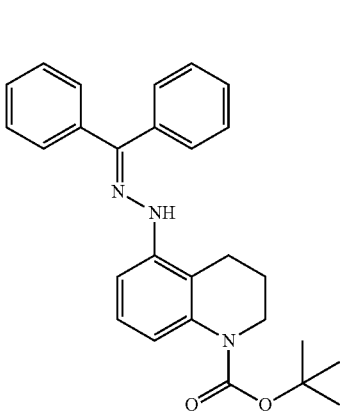

cpd 127b

To a solution of tert-butyl 5-bromo-3,4-dihydroquinoline-1(2H)-carboxylate, cpd 127a (0.749 g, 2.4 mmol) and benzophenone hydrazone (0.471 g, 2.4 mmol) in 1,4-dioxane (15 mL) at room temperature under nitrogen, BINAP (149 mg, 0.240 mmol), palladium (II) acetate (54 mg, 0.240 mmol) and sodium t-butoxyde (0.692 g, 7.2 mmol) were added and the mixture was heated at 100° C. for 16 hours. The resultant mixture was cooled to room temperature, filtered over a paper filter and the filtrate concentrated under reduce pressure to give the crude product, that was purified by silica gel chromatography ($SiO_2$, heptane-ethylacetate gradient). Pure fractions were combined and concentrated. Dried under high vacuum to afford tert-butyl 5-(2-(diphenylmethylene)hydrazinyl)-3,4-dihydroquinoline-1(2H)-carboxylate, cpd 127b (501 mg, 48.8% yield). MS m/z 328.1 (M+H-Boc)+.

C. 5-hydrazinyl-1,2,3,4-tetrahydroquinoline hydrochloride, Cpd 127c

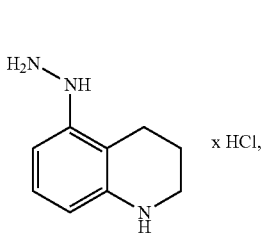

cpd 127c x HCl,

To a solution of tert-butyl 5-(2-(diphenylmethylene)hydrazinyl)-3,4-dihydroquinoline-1(2H)-carboxylate, cpd 122b (0.501 g, 1.172 mmol) in ethanol (2 mL), concentrated hydrochloric acid (4 mL) was added and the mixture was stirred at room temperature for 16 h. The reaction mixture was concentrated under reduced pressure, then treated with diethylether (25 mL) and water (10 mL). The layers were separated. The aqueous phase was concentrated under reduced pressure to give (1,2,3,4-tetrahydro-quinolin-5-yl)-hydrazine hydrochloride, that was used in the next step without purification (1.172 mmol crude, 100% yield). MS m/z 164.1 (M+H)+.

E. Ethyl 1-(1,2,3,4-tetrahydroquinolin-5-yl)-5-(trifluoromethyl)-1H-pyrazole-4-carboxylate, Cpd127d

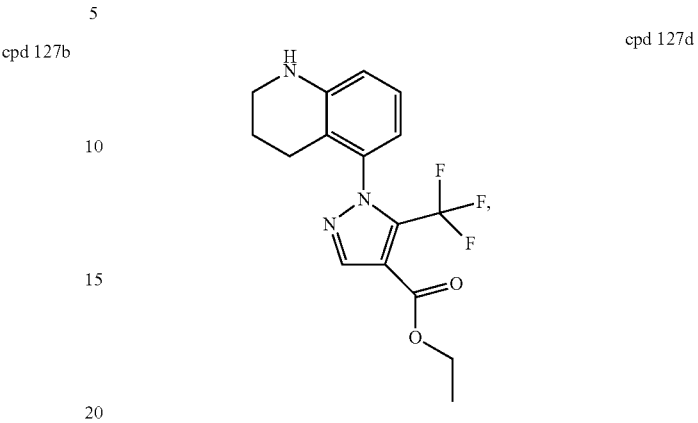

cpd 127d

To a solution of 5-hydrazinyl-1,2,3,4-tetrahydroquinoline hydrochloride, cpd 127c (1.172 mmol) and triethylamine (0.327 mL, 2.344 mmol) in ethanol (15 mL), ethyl 2-(ethoxymethylene)-4,4,4-trifluoro-3-oxobutanoate, INT1 (0.253 g, 1.055 mmol) was added and the mixture was stirred at 80° C. for 16 h. The mixture was diluted with ethyl acetate and washed with water/$NaHCO_3$, the organic layer was separated and dried with $MgSO_4$, filtered, and the filtrate was then concentrated. The crude product was purified by chromatography on silica gel (Heptane-Ethylacetate gradient). Pure fractions were combined and concentrated to yield ethyl 1-(1,2,3,4-tetrahydroquinolin-5-yl)-5-(trifluoromethyl)-1H-pyrazole-4-carboxylate, cpd 127d (265 mg, 66.6% yield). $^1$H NMR (300 MHz, Chloroform-d) δ 1.37 (t, J=7.1 Hz, 3H), 1.77-1.89 (m, 2H), 2.10-2.43 (m, 2H), 3.27 (t, J=5.5 Hz, 3H), 4.36 (q, J=7.2 Hz, 2H), 6.50-6.60 (m, 2H), 7.01 (t, J=8.0 Hz, 1H), 8.12 (s, 1H). MS m/z 340.0 (M+H)+.

E. Ethyl 1-(1-methyl-1,2,3,4-tetrahydroquinolin-5-yl)-5-(trifluoromethyl)-1H-pyrazole-4-carboxylate, Cpd 127e

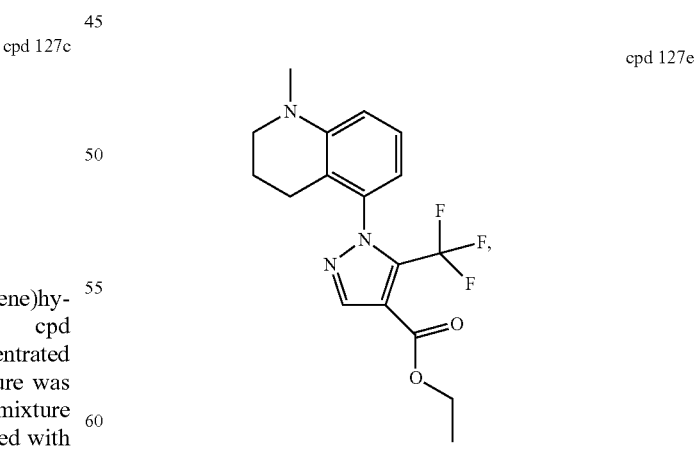

cpd 127e

To a solution of ethyl 1-(1,2,3,4-tetrahydroquinolin-5-yl)-5-(trifluoromethyl)-1H-pyrazole-4-carboxylate, cpd 127d (598 mg, 1.76 mmol) in acetic acid (9.6 mL) at RT, was added paraformaldehyde (529 mg, 17.62 mmol). The mixture was stirred at room temperature for 15 min then sodium cyanoborohydride (0.554 g, 8.812 mmol) was added and the mixture was stirred at RT for 4 h. The reaction was quenched with saturated Na₂CO₃ aqueous solution, then extracted with dichloromethane. The organic layer was separated, dried over MgSO₄, filtered and the filtrate concentrated to yield ethyl 1-(1-methyl-1,2,3,4-tetrahydroquinolin-5-yl)-5-(trifluoromethyl)-1H-pyrazole-4-carboxylate, cpd 127e (580 mg, 93%) as a sticky solid. MS m/z 354.0 (M+H)+.

F. 1-(1-Methyl-1,2,3,4-tetrahydroquinolin-5-yl)-5-(trifluoromethyl)-1H-pyrazole-4-carboxylic Acid, Cpd 127f

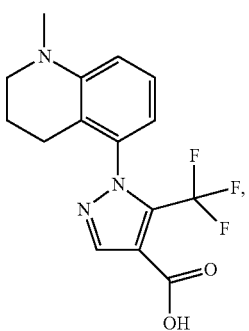

cpd 127f

To a solution of ethyl 1-(1-methyl-1,2,3,4-tetrahydroquinolin-5-yl)-5-(trifluoromethyl)-1H-pyrazole-4-carboxylate, cpd 127e (0.623 g, 1.762 mmol) in ethanol (22 mL), sodium hydroxide (141 mg, 3.52 mmol) was added and the mixture was heated at 60° C. for 3 h. The mixture was cooled to room temperature and poured onto a stirred 1N HCl/ice/ethyl acetate mixture. The organic layer was separated and washed with brine, then dried (MgSO₄) and the filtrate was concentrated to give 1-(1-methyl-1,2,3,4-tetrahydroquinolin-5-yl)-5-(trifluoromethyl)-1H-pyrazole-4-carboxylic acid, cpd 127f (512 mg, 89% yield). MS m/z 326.0 (M+H)+.

G. 1-(1-methyl-1,2,3,4-tetrahydroquinolin-5-yl)-5-(trifluoromethyl)-1H-pyrazole-4-carbonyl Chloride, Cpd 127g

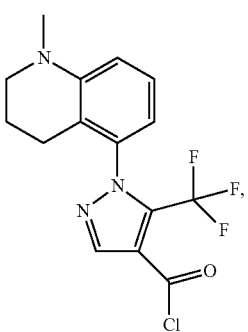

cpd 127g

To a solution of 1-(1-methyl-1,2,3,4-tetrahydroquinolin-5-yl)-5-(trifluoromethyl)-1H-pyrazole-4-carboxylic acid, cpd 127f (512 mg, 1.574 mmol) in dichloromethane (30 mL) and N,N-dimethylformamide (0.1 mL), oxalyl chloride (0.270 mL, 3.14 mmol) was added and the mixture was heated to a refluxing temperature for 1 h. The mixture was concentrated to dryness and the residue was dried under reduced pressure to constant weight to yield the crude 1-(1-methyl-1,2,3,4-tetrahydroquinolin-5-yl)-5-(trifluoromethyl)-1H-pyrazole-4-carbonyl chloride, cpd 127g (1.574 mmol) as an oil, which was immediately used as such.

H. N-(5-cyano-6-(2H-1,2,3-triazol-2-yl)pyridin-3-yl)-1-(1-methyl-1,2,3,4-tetrahydroquinolin-5-yl)-5-(trifluoromethyl)-1H-pyrazole-4-carboxamide, Cpd 127

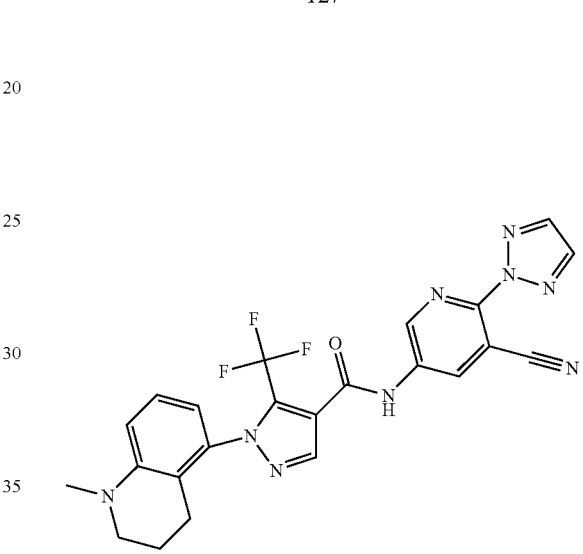

To a solution of 1-(1-methyl-1,2,3,4-tetrahydroquinolin-5-yl)-5-(trifluoromethyl)-1H-pyrazole-4-carbonyl chloride, cpd 127g (1.574 mmol) in dichoromethane (20 mL) and tethahydrofurane (60 mL) at room temperature, 5-amino-2-[1,2,3]triazol-2-yl-nicotinonitrile, INT3 (440 mg, 2.361 mmol) was added followed by triethylamine (0.878 mL, 6.296 mmol), and the reaction was stirred at room temperature for 20 h. The mixture was diluted with ethyl acetate and washed with water and brine. The organic layer was dried (MgSO₄), filtered and the filtrate concentrated. Purification by flash chromatography (SiO₂, ethylacetate-heptane gradient) afforded a mixture of product and starting material. The product was purified by reverse phase chromatography eluting with ammonium bicarbonate-water-acetonitrile gradient. Product fractions were combined and extracted with dichloromethane. The organic layer was dried (MgSO₄), filtered, and the filtrate concentrated to afford pure N-(5-cyano-6-(2H-1,2,3-triazol-2-yl)pyridin-3-yl)-1-(1-methyl-1,2,3,4-tetrahydroquinolin-5-yl)-5-(trifluoromethyl)-1H-pyrazole-4-carboxamide, cpd 127 (45 mg, 5.8%). ¹H NMR (300 MHz, DMSO-d₆) δ 1.73-1.89 (m, 2H), 1.98-2.18 (m, 1H), 2.21-2.36 (m, 1H), 2.92 (s, 3H), 3.24 (t, J=5.7 Hz, 2H), 6.60 (d, J=7.7 Hz, 1H), 6.79 (d, J=8.4 Hz, 1H), 7.10-7.25 (m, 1H), 8.31 (s, 2H), 8.45 (s, 1H), 8.87 (d, J=2.4 Hz, 1H), 9.11 (d, J=2.4 Hz, 1H), 11.33 (s, 1H). MS m/z 494.1 (M+H)+.

Example 128

N-(5-cyano-6-(2H-1,2,3-triazol-2-yl)pyridin-3-yl)-1-(1-methylindolin-4-yl)-5-(trifluoromethyl)-1H-pyrazole-4-carboxamide, Cpd 128

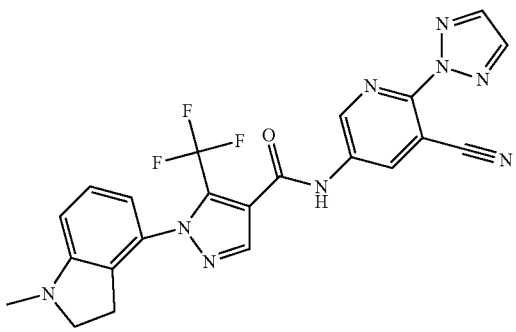 [SMILES: CN1CCc2c1cccc2-n1ncc(C(=O)Nc2cnc(-n3nccn3)c(C#N)c2)c1C(F)(F)F]

A. 4-bromo-1-methylindoline, Cpd 128a

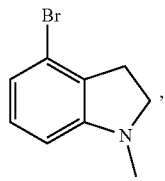

To a solution of 4-bromo-indole (2.15 g, 10.967 mmol) in acetic acid (59.6 mL) at RT, was added paraformaldehyde (3.293 g, 109.7 mmol). The mixture was stirred at room temperature for 15 min then sodium cyanoborohydride (3.446 g, 54.83 mmol) was added and the mixture was stirred at RT for 4 hr. The reaction was quenched with saturated $Na_2CO_3$ aqueous solution, then extracted with dichloromethane. The organic layer was separated, dried over $MgSO_4$, filtered and concentrated to yield the crude product. Purification by flash chromatography ($SiO_2$, ethylacetate-heptane gradient 5% to 100%). Pure fractions were combined and concentrated to afford pure 4-bromo-1-methylindoline (1.545 g, 66.4%) as a sticky solid. MS m/z 211.9 (M+H)+.

B. 4-(2-(diphenylmethylene)hydrazinyl)-1-methylindoline, Cpd 128b

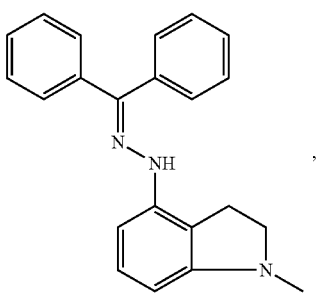

To a solution of 4-bromo-1-methylindoline, cpd 128a (1.545 g, 7.285 mmol) and benzophenone hydrazone (1.573 g, 8.013 mmol) in 1,4-dioxane (16 mL) at room temperature under nitrogen, BINAP (454 mg, 0.728 mmol), palladium (II) acetate (164 mg, 0.728 mmol) and sodium t-butoxide (2.10 g, 21.85 mmol) were added and the mixture was heated at 100° C. for 16 h. The resultant mixture was cooled to room temperature, filtered and the filtrate concentrated under reduce pressure to give the crude product, which was purified by silica gel chromatography ($SiO_2$, heptane-ethyl acetate gradient). Pure fractions were combined and concentrated. The solids were dried under reduced pressure to afford 4-(2-(diphenylmethylene)hydrazinyl)-1-methylindoline, 128b (2.012 g, 84.3% yield). MS m/z 328.1 (M+H)+.

C. 4-hydrazinyl-1-methylindoline Hydrochloride, Cpd 128c (VILL_ltrabalon_2205_1)

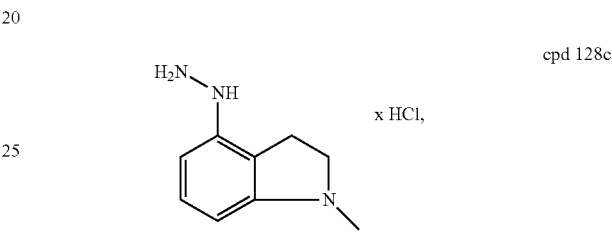

To a solution of 4-(2-(diphenylmethylene)hydrazinyl)-1-methylindoline, cpd 128b (2.012 g 6.145 mmol) in ethanol (6 mL), concentrated hydrochloric acid (12 mL) was added and the mixture was stirred at room temperature for 16 h. The reaction mixture was concentrated under reduced pressure, then treated with diethyl ether (25 mL) and water (10 mL), and the layers were separated. The aqueous phase was concentrated under reduced pressure to give 4-hydrazinyl-1-methylindoline hydrochloride, cpd 128c, which was used in the next step without purification (6.145 mmol crude, 100% yield). MS m/z 164.1 (M+H)+.

D. Ethyl 1-(1-methylindolin-4-yl)-5-(trifluoromethyl)-1H-pyrazole-4-carboxylate, Cpd 128d

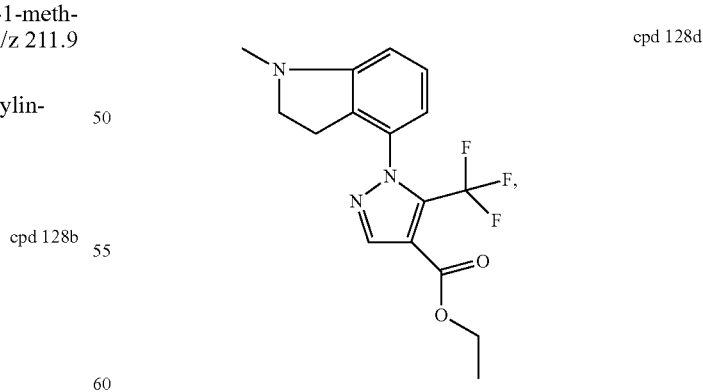

To a solution of 4-hydrazinyl-1-methylindoline hydrochloride, cpd128c (6.145 mmol) and triethylamine (4.282 mL, 30.72 mmol) in ethanol (60 mL), ethyl 2-(ethoxymethylene)-4,4,4-trifluoro-3-oxobutanoate, INT1 (1.476 g, 6.145 mmol) was added and the mixture was stirred at 80° C. for 16 h. The mixture was diluted with ethyl acetate and washed with water/NaHCO₃, the organic layer was separated and dried with MgSO₄, filtered, and the filtrate then concentrated. The crude product was purified by silica gel chromatography (SiO₂, heptane-ethylacetate gradient). Pure fractions were combined and concentrated to ethyl 1-(1-methylindolin-4-yl)-5-(trifluoromethyl)-1H-pyrazole-4-carboxylate, cpd 128d (1.290 g, 61.8% yield). MS m/z 340.0 (M+H)+.

E. 1-(1-methylindolin-4-yl)-5-(trifluoromethyl)-1H-pyrazole-4-carboxylic Acid, Cpd 128e

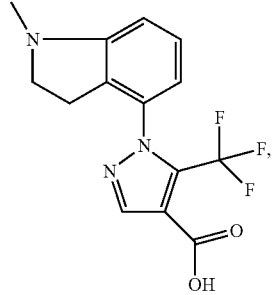

cpd 128e

To a solution of ethyl 1-(1-methylindolin-4-yl)-5-(trifluoromethyl)-1H-pyrazole-4-carboxylate, cpd 128d (1.29 g, 3.80 mmol) in ethanol (25 mL), sodium hydroxide (304 mg, 7.60 mmol) was added and the mixture was heated at 60° C. for 3 h. The mixture was cooled to room temperature and poured onto a stirred 1N HCl/ice/ethyl acetate mixture. The organic layer was separated and washed with brine, then dried (MgSO₄), filtered, and the filtrate concentrated to give 1-(1-methylindolin-4-yl)-5-(trifluoromethyl)-1H-pyrazole-4-carboxylic acid, cpd 128e (1.180 g, 99% yield). MS m/z 312.0 (M+H)+.

F. 1-(1-methylindolin-4-yl)-5-(trifluoromethyl)-1H-pyrazole-4-carbonyl Chloride, Cpd 128f

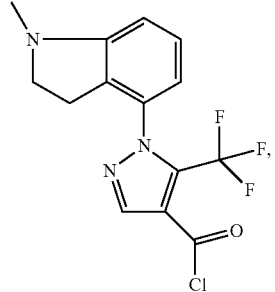

cpd 128f

To a solution of 1-(1-methylindolin-4-yl)-5-(trifluoromethyl)-1H-pyrazole-4-carboxylic acid, cpd 128e (1.17 g, 3.759 mmol) in dichloromethane (30 mL) and N,N-dimethylformamide (0.1 mL), oxalyl chloride (0.645 mL, 7.52 mmol) was added and the mixture was heated to reflux temperature for 1 h. The mixture was concentrated to dryness and the residue was dried under reduced pressure to constant weight to yield the crude 1-(1-methylindolin-4-yl)-5-(trifluoromethyl)-1H-pyrazole-4-carbonyl chloride, cpd 128f (3.759 mmol) as an oil, which was immediately used as such.

G. N-(5-cyano-6-(2H-1,2,3-triazol-2-yl)pyridin-3-yl)-1-(1-methylindolin-4-yl)-5-(trifluoromethyl)-1H-pyrazole-4-carboxamide, Cpd 128

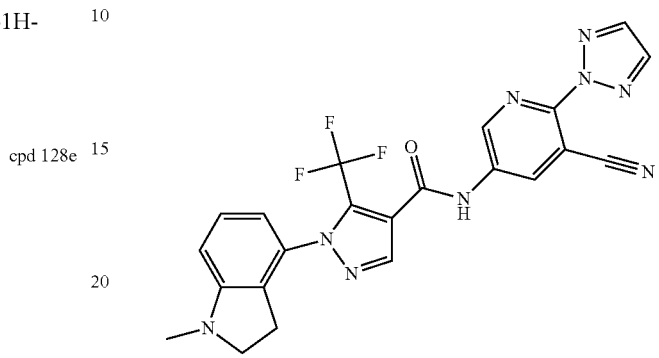

To a solution of 1-(1-methylindolin-4-yl)-5-(trifluoromethyl)-1H-pyrazole-4-carbonyl chloride, cpd 128f (3.759 mmol) in dichoromethane (20 mL) and tetrahydrofuran (60 mL) at room temperature, 5-amino-2-[1,2,3]triazol-2-yl-nicotinonitrile (1.40 g, 7.52 mmol) INT3 was added followed by triethylamine (2.1 mL, 15 mmol), and the reaction was stirred at room temperature for 25 h. The mixture was diluted with ethyl acetate and washed with water and brine. The organic layer was dried (MgSO₄), filtered, and the filtrate concentrated. Purification by flash chromatography (SiO₂, ethyl acetate-heptane gradient) afforded a mixture of product and starting material. The product was purified by reverse phase chromatography eluting with formic acid-water-acetonitrile gradient. Product fractions were combined and extracted with dichloromethane. The organic layer was dried (MgSO₄), filtered, and the filtrate concentrated to afford pure N-(5-cyano-6-(2H-1,2,3-triazol-2-yl)pyridin-3-yl)-1-(1-methylindolin-4-yl)-5-(trifluoromethyl)-1H-pyrazole-4-carboxamide, cpd 128 (526 mg, 29.2% yield). ¹H NMR (300 MHz, DMSO-d₆) δ 2.72 (t, J=8.4 Hz, 2H), 2.78 (s, 3H), 3.31-3.41 (m, 3H), 6.63 (d, J=7.9 Hz, 1H), 6.69 (d, J=7.8 Hz, 1H), 7.20 (t, J=7.9 Hz, 1H), 8.30 (s, 2H), 8.40 (s, 1H), 8.86 (d, J=2.5 Hz, 1H), 9.05 (d, J=2.5 Hz, 1H). MS m/z 480.1 (M+H)+.

Example 129

N-(5-cyano-6-(2H-1,2,3-triazol-2-yl)pyridin-3-yl)-1-(1,2,3,4-tetrahydroisoquinolin-5-yl)-5-(trifluoromethyl)-1H-pyrazole-4-carboxamide, Cpd 129

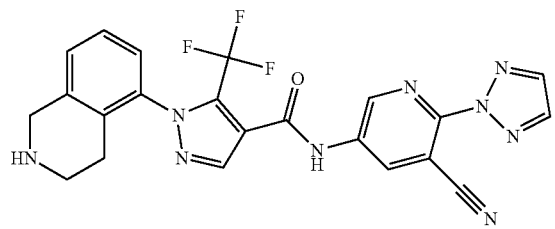 [SMILES: N#Cc1cc(NC(=O)c2cnn(-c3cccc4c3CCNC4)c2C(F)(F)F)cnc1-n1nccn1]

A. Tert-butyl 5-(2-(diphenylmethylene)hydrazinyl)-3,4-dihydroisoquinoline-2(1H)carboxylate, Cpd 129a

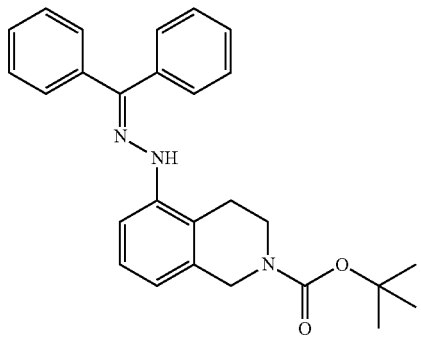

cpd 129a

To a solution tert-butyl 5-bromo-3,4-dihydroisoquinoline-2(1H)-carboxylate (1.0 g, 3.203 mmol) and benzophenone hydrazone (0.629 g, 3.203 mmol) in 1,4-dioxane (15 mL) at room temperature under nitrogen, BINAP (199 mg, 0.320 mmol), palladium (II) acetate (72 mg, 0.320 mmol) and sodium t-butoxide (923 mg, 9.61 mmol) were added and the mixture was heated at 100° C. for 16 h. The resultant mixture was cooled to room temperature, filtered, and the filtrate concentrated under reduced pressure to give the crude product, which was purified by silica gel chromatography (SiO₂, heptane-ethyl acetate gradient). Pure fractions were combined and concentrated. The solids were dried under reduced pressure to afford tert-butyl 5-(2-(diphenylmethylene)hydrazinyl)-3,4-dihydroisoquinoline-2(1H)-carboxylate, cpd 129a (955 mg, 69.7% yield). MS m/z 372.0 (M+H-tBu)+.

B. 5-Hydrazinyl-1,2,3,4-tetrahydroisoquinoline, Cpd 129b

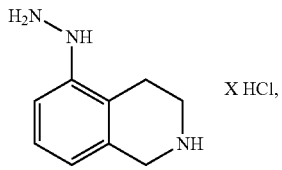

cpd 129b

X HCl,

To a solution of tert-butyl 5-(2-(diphenylmethylene)hydrazinyl)-3,4-dihydroisoquinoline-2(1H)-carboxylate, cpd 129a (955 mg, 2.234 mmol) in ethanol (2.2 mL), concentrated hydrochloric acid (4.4 mL) was added and the mixture was stirred at room temperature for 16 h. The reaction mixture was concentrated under reduced pressure, then treated with diethyl ether (25 mL) and water (10 mL), and the layers were separated. The aqueous phase was concentrated under reduced pressure to 5-hydrazinyl-1,2,3,4-tetrahydroisoquinoline, cpd 129b, which was used in the next step without purification (2.234 mmol crude, 100% yield). MS m/z 164.1 (M+H)+.

C. Ethyl 1-(1,2,3,4-tetrahydroisoquinolin-5-yl)-5-(trifluoromethyl)-1H-pyrazole-4-carboxylate, Cpd 129c

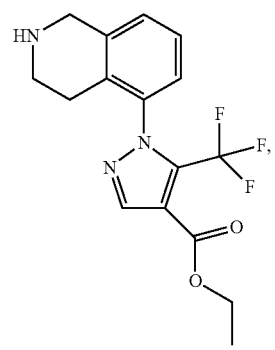

cpd 129c

To a solution of 5-hydrazinyl-1,2,3,4-tetrahydroisoquinoline, cpd 129b (2.234 mmol) and triethylamine (0.623 mL, 4.468 mmol) in ethanol (25 mL), ethyl 2-(ethoxymethylene)-4,4,4-trifluoro-3-oxobutanoate, INT1 (0.483 g, 2.011 mmol) was added and the mixture was stirred at 80° C. for 16 h. The mixture was diluted with ethyl acetate and washed with water/NaHCO₃, the organic layer was separated and dried with MgSO₄, filtered, and the filtrate then concentrated. The crude product was purified by silica gel chromatography (SiO₂, methanol-dichloromethane gradient). Pure fractions were combined and concentrated to yield ethyl 1-(1,2,3,4-tetrahydroisoquinolin-5-yl)-5-(trifluoromethyl)-1H-pyrazole-4-carboxylate, cpd 129c (423 mg, 55.8% yield). MS m/z 340.1 (M+H)+.

D. Tert-Butyl 5-(4-(ethoxycarbonyl)-5-(trifluoromethyl)-1H-pyrazol-1-yl)-3,4-dihydroisoquinoline-2(1H)-carboxylate, Cpd 129d

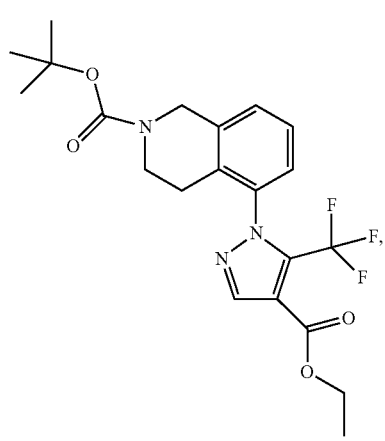

cpd 129d

To a solution of ethyl 1-(1,2,3,4-tetrahydroisoquinolin-5-yl)-5-(trifluoromethyl)-1H-pyrazole-4-carboxylate, cpd 129c (0.160 g, 0.472 mmol) in dichloromethane (5 mL), N,N-dimethylaminopyridine (0.006 g, 0.047 mmol) and triethylamine (0.139 mL, 0.990 mmol) were added. The mixture was stirred for 30 min at room temperature, then di-tert-butyl dicarbonate (0.206 g, 0.943 mmol) was added portionwise. The solution was stirred at room temperature overnight. The mixture was diluted with ethyl acetate. The organic layer was washed with water and brine, filtered, dried and concentrated. The mixture was purified by flash chromatography (SiO₂, heptane-ethyl acetate gradient). Pure fractions were combined and concentrated, then dried under high reduced pressure to yield tert-butyl 5-(4-(ethoxycarbonyl)-5-(trifluoromethyl)-1H-pyrazol-1-yl)-3,4-dihydroisoquinoline-2(1H)-carboxylate, cpd 129d (127 mg, 61.3% yield). MS m/z 384.0 (M+H-tBu)+.

E. 1-(2-(tert-butoxycarbonyl)-1,2,3,4-tetrahydroisoquinolin-5-yl)-5-(trifluoromethyl)-1H-pyrazole-4-carboxylic Acid, Cpd 129e

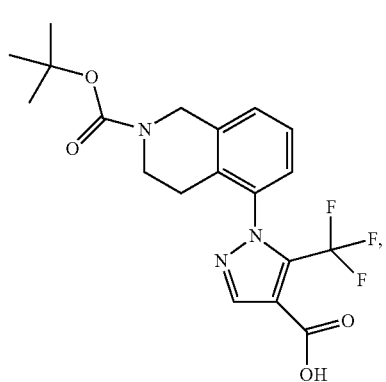

cpd 129e

To a solution of tert-butyl 5-(4-(ethoxycarbonyl)-5-(trifluoromethyl)-1H-pyrazol-1-yl)-3,4-dihydroisoquinoline-2(1H)-carboxylate, cpd 129d (0.127 g, 0.289 mmol) in ethanol (5 mL), sodium hydroxide (23 mg, 0.578 mmol) was added and the mixture was heated at 60° C. for 3 h. The mixture was cooled to room temperature and poured into a stirred 1N HCl/ice/ethyl acetate mixture. The organic layer was separated and washed with brine, then dried (MgSO₄), filtered, and the filtrate concentrated to give 1-(2-(tert-butoxycarbonyl)-1,2,3,4-tetrahydroisoquinolin-5-yl)-5-(trifluoromethyl)-1H-pyrazole-4-carboxylic acid, cpd 129e (102 mg g, 85.8% yield). MS m/z 356.0 (M-tBu+H)+.

F. Tert-Butyl 5-(4-(chlorocarbonyl)-5-(trifluoromethyl)-1H-pyrazol-1-yl)-3,4-dihydroisoquinoline-2(1H)-carboxylate, Cpd 129f

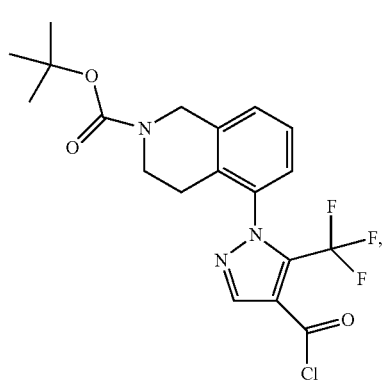

cpd 129f

To a solution of 1-(2-(tert-butoxycarbonyl)-1,2,3,4-tetrahydroisoquinolin-5-yl)-5-(trifluoromethyl)-1H-pyrazole-4-carboxylic acid, cpd 129e (36 mg, 0.088 mmol) in dichloromethane (2 mL), 1-chloro-N,N,2-trimethyl-1-propenylamine (0.046 mL, 0.350 mmol) was added and the mixture was stirred at room temperature for 30 min to give tert-butyl 5-(4-(chlorocarbonyl)-5-(trifluoromethyl)-1H-pyrazol-1-yl)-3,4-dihydroisoquinoline-2(1H)-carboxylate, cpd 129f (0.088 mmol) as a crude solution, which was immediately used as such.

G. Tert-Butyl 5-(4-((5-cyano-6-(2H-1,2,3-triazol-2-yl)pyridin-3-yl)carbamoyl)-5-(trifluoromethyl)-1H-pyrazol-1-yl)-3,4-dihydroisoquinoline-2(1H)-carboxylate, Cpd 129g

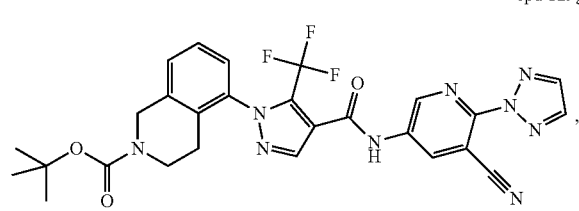

cpd 129g

To a solution of tert-butyl 5-(4-(chlorocarbonyl)-5-(trifluoromethyl)-1H-pyrazol-1-yl)-3,4-dihydroisoquinoline-2(1H)-carboxylate, cpd 129f (0.088 mmol) in pyridine (1 mL) at room temperature, was added 5-amino-2-[1,2,3]triazol-2-yl-nicotinonitrile, INT3 (25 mg, 0.132 mmol) in pyridine (1 mL), and the reaction was stirred at room temperature for 20 h. The mixture was diluted with ethyl acetate and washed with water and brine. The organic layer was dried (MgSO₄), filtered, and the filtrate concentrated. Purification by flash chromatography (SiO₂, ethyl acetate-heptane gradient) afforded pure tert-butyl 5-(4-((5-cyano-6-(2H-1,2,3-triazol-2-yl)pyridin-3-yl)carbamoyl)-5-(trifluoromethyl)-1H-pyrazol-1-yl)-3,4-dihydroisoquinoline-2(1H)-carboxylate, cpd 129g (32 mg, 62.7%). MS m/z 524.0 (M-tBu+H)+.

H. N-(5-cyano-6-(2H-1,2,3-triazol-2-yl)pyridin-3-yl)-1-(1,2,3,4-tetrahydroisoquinolin-5-yl)-5-(trifluoromethyl)-1H-pyrazole-4-carboxamide, Cpd 129

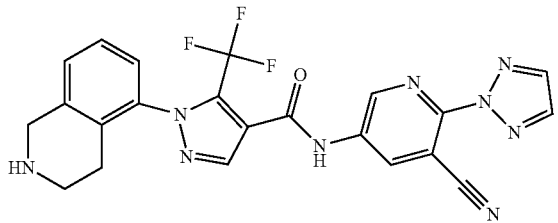 [SMILES: N#Cc1cc(NC(=O)c2cnn(-c3cccc4c3CCNC4)c2C(F)(F)F)cnc1-n1nccn1]

To a solution of tert-butyl 5-(4-((5-cyano-6-(2H-1,2,3-triazol-2-yl)pyridin-3-yl)carbamoyl)-5-(trifluoromethyl)-1H-pyrazol-1-yl)-3,4-dihydroisoquinoline-2(1H)-carboxylate, cpd 129g (32 mg, 0.055 mmol) in dichloromethane (3 mL), trifluoroacetic acid (2 mL) was added and the mixture was stirred for 3 h at room temperature. The mixture was concentrated under reduced pressure to dryness and the residue was diluted with ethyl acetate and washed with NaHCO₃. The organic layer was dried over MgSO₄, filtered, and the filtrate concentrated. The residue was purified by reverse phase chromatography (ammonium bicarbonate-water-acetonitrile gradient). The product fractions were combined and extracted with dichloromethane. The organic layer was dried (MgSO₄), filtered, and the filtrate concentrated to afford pure N-(5-cyano-6-(2H-1,2,3-triazol-2-yl)pyridin-3-yl)-1-(1,2,3,4-tetrahydroisoquinolin-5-yl)-5-(trifluoromethyl)-1H-pyrazole-4-carboxamide, cpd 129 (2 mg, 7.6%). 1H NMR (300 MHz, methanol-d₄) δ 3.00-3.19 (m, 2H), 4.05-4.18 (m, 2H), 4.51-4.69 (m, 2H), 7.22-7.42 (m, 3H), 8.14 (s, 2H), 8.29 (s, 1H), 8.89 (d, J=2.5 Hz, 1H), 9.05 (d, J=2.5 Hz, 1H). MS m/z 480.1 (M+H)+.

Example 130

N-(5-cyano-6-(2H-1,2,3-triazol-2-yl)pyridin-3-yl)-1-(indolin-4-yl)-5-(trifluoromethyl)-1H-pyrazole-4-carboxamide, Cpd 130

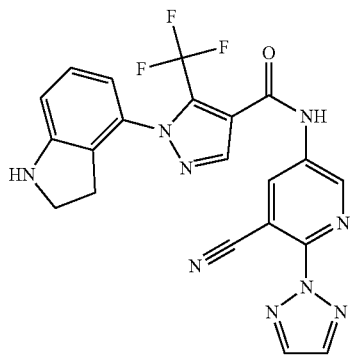 [SMILES: N#Cc1cc(NC(=O)c2cnn(-c3cccc4c3CCN4)c2C(F)(F)F)cnc1-n1nccn1]

A. Tert-Butyl 4-(2-(diphenylmethylene)hydrazinyl)indoline-1-carboxylate, Cpd 130a

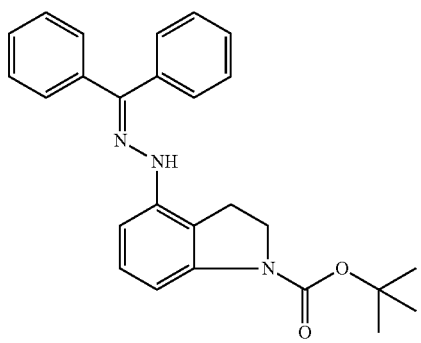

To a solution tert-butyl 4-bromoindoline-1-carboxylate (1.0 g, 3.354 mmol) and benzophenone hydrazone (0.658 g, 3.354 mmol) in 1,4-dioxane (15 mL) at room temperature under nitrogen, BINAP (209 mg, 0.335 mmol), palladium (II) acetate (75 mg, 0.335 mmol) and sodium t-butoxide (967 mg, 10.061 mmol) were added and the mixture was heated at 100° C. for 16 h. The resultant mixture was cooled to room temperature, filtered and the filtrate concentrated under reduced pressure to give the crude product, which was purified by flash chromatography (SiO₂, heptane-ethyl acetate gradient). Pure fractions were combined and concentrated. The resultant solids were dried under reduce pressure to afford tert-butyl 4-(2-(diphenylmethylene)hydrazinyl)indoline-1-carboxylate, cpd 130a (912 mg, 65.8% yield). MS m/z 414.1 (M+H)+.

B. 4-hydrazinylindoline Hydrochloride, Cpd130b

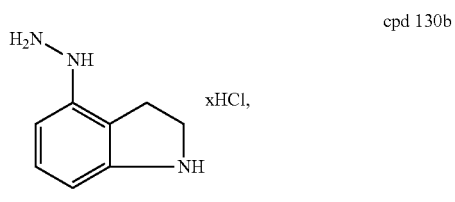 [SMILES: NNc1cccc2c1CCN2]

To a solution of tert-butyl 4-(2-(diphenylmethylene)hydrazinyl)indoline-1-carboxylate, cpd 130a (912 mg, 2.206 mmol) in Ethanol (2.2 mL), concentrated hydrochloric acid (4.4 mL) was added and the mixture was stirred at room temperature for 16 h. The reaction mixture was concentrated under reduced pressure, then treated with diethyl ether (25 mL) and water (10 mL). The layers were separated. The aqueous phase was concentrated under reduced pressure to yield 4-hydrazinylindoline hydrochloride, cpd 130b, which was used in the next step without purification (2.206 mmol, crude, 100% yield). MS m/z 150.1 (M+H)+.

C. Ethyl 1-(indolin-4-yl)-5-(trifluoromethyl)-1H-pyrazole-4-carboxylate, Cpd 130c

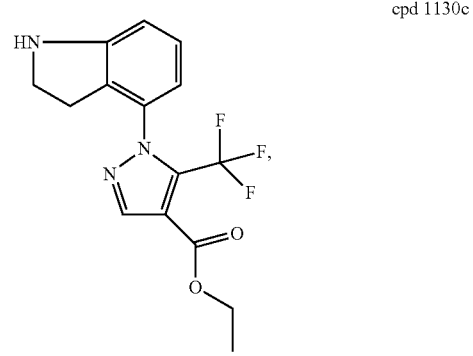 [SMILES: CCOC(=O)c1cnn(-c2cccc3c2CCN3)c1C(F)(F)F]

To a solution of 4-hydrazinylindoline hydrochloride, cpd 130b (2.206 mmol) and triethylamine (0.615 mL, 4.412 mmol) in ethanol (25 mL), ethyl 2-(ethoxymethylene)-4,4,4-trifluoro-3-oxobutanoate, INT1 (0.477 g, 1.985 mmol) was added and the mixture was stirred at 80° C. for 16 h. The mixture was diluted with ethyl acetate and washed with water/NaHCO₃, the organic layer was separated and dried with MgSO₄, filtered, and the filtrate concentrated. The crude product was purified by flash chromatography (SiO₂, methanol-dichloromethane gradient). Pure fractions were combined and concentrated to yield ethyl 1-(indolin-4-yl)-5-(trifluoromethyl)-1H-pyrazole-4-carboxylate, cpd 130c (528 mg, 73.6% yield). MS m/z 326.0 (M+H)+.

D. Tert-Butyl 4-(4-(ethoxycarbonyl)-5-(trifluoromethyl)-1H-pyrazol-1-yl)indoline-1-carboxylate, Cpd 130d

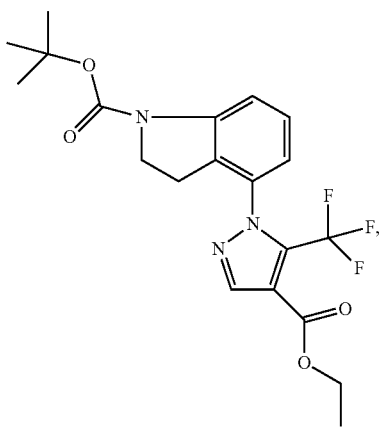

cpd 130d

To a solution of ethyl 1-(indolin-4-yl)-5-(trifluoromethyl)-1H-pyrazole-4-carboxylate, cpd 130c (0.497 g, 1.528 mmol) in dichloromethane (5 mL), N,N-dimethylaminopyridine (0.019 g, 0.153 mmol) and triethylamine (0.446 mL, 3.209 mmol) were added. The mixture was stirred for 30 min at room temperature, then di-tert-butyl dicarbonate (0.369 mL, 1.604 mmol) was added portionwise. The solution was stirred at room temperature overnight. The mixture was diluted with ethyl acetate. Organic layer was washed with water and brine, filtered, dried and the filtrate concentrated. The mixture was purified by flash chromatography (SiO$_2$, heptane-ethyl acetate gradient). Pure fractions were combined and concentrated. The resultant product was dried under reduced pressure to yield tert-butyl 4-(4-(ethoxycarbonyl)-5-(trifluoromethyl)-1H-pyrazol-1-yl)indoline-1-carboxylate, cpd 1303d ((366 mg, 56.3% yield). MS m/z 426.0 (M+H−)+.

E. 1-(1-(tert-Butoxycarbonyl)indolin-4-yl)-5-(trifluoromethyl)-1H-pyrazole-4-carboxylic Acid, Cpd 103e

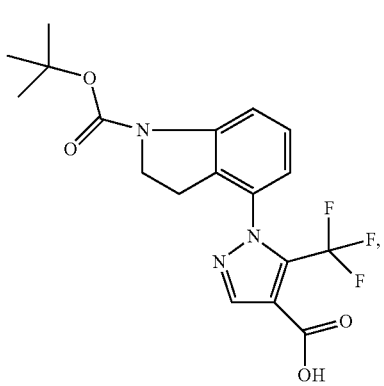

cpd 130e

To a solution tert-butyl 4-(4-(ethoxycarbonyl)-5-(trifluoromethyl)-1H-pyrazol-1-yl)indoline-1-carboxylate, cpd 130d ((0.403 g, 0.947 mmol) in ethanol (16 mL), sodium hydroxide (76 mg, 1.895 mmol) was added and the mixture was heated at 60° C. for 3 h. The mixture was cooled to room temperature and poured onto a stirred IN HCl/ice/ethyl acetate mixture. The organic layer was separated and washed with brine, then dried (MgSO$_4$), filtered, and the filtrate concentrated to afford 1-(1-(tert-butoxycarbonyl)indolin-4-yl)-5-(trifluoromethyl)-1H-pyrazole-4-carboxylic acid, cpd 130e (356 mg g, 94.6% yield). $^1$H NMR (300 MHz, Chloroform-d) δ 1.58 (s, 9H), 2.92 (t, J=8.7 Hz, 2H), 4.02 (t, J=8.7 Hz, 2H), 6.89 (d, J=8.0 Hz, 1H), 7.22-7.34 (m, 2H), 8.20 (s, 1H). MS m/z 398.0 (M+H)+.

F. Tert-Butyl 4-(4-(chlorocarbonyl)-5-(trifluoromethyl)-1H-pyrazol-1-yl)indoline-1-carboxylate, Cpd 130f

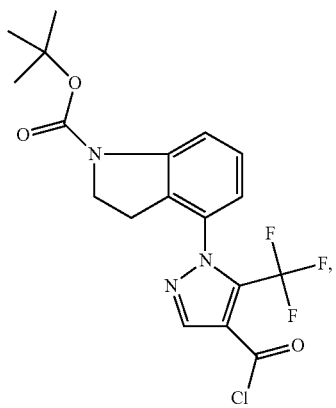

cpd 130f

To a solution 1-(1-(tert-butoxycarbonyl)indolin-4-yl)-5-(trifluoromethyl)-1H-pyrazole-4-carboxylic acid, cpd 130e (294 mg, 0.740 mmol) in dichloromethane (12 mL), 1-chloro-N,N,2-trimethyl-1-propenylamine (0.392 mL, 2.960 mmol) was added and the mixture was stirred at room temperature for 30 min to give tert-butyl 4-(4-(chlorocarbonyl)-5-(trifluoromethyl)-1H-pyrazol-1-yl)indoline-1-carboxylate, cpd 130f (0.740 mmol) crude solution, which was immediately used as such.

G. Tert-Butyl 4-(4-((5-cyano-6-(2H-1,2,3-triazol-2-yl)pyridin-3-yl)carbamoyl)-5-(trifluoromethyl)-1H-pyrazol-1-yl)indoline-1-carboxylate, Cpd 130g

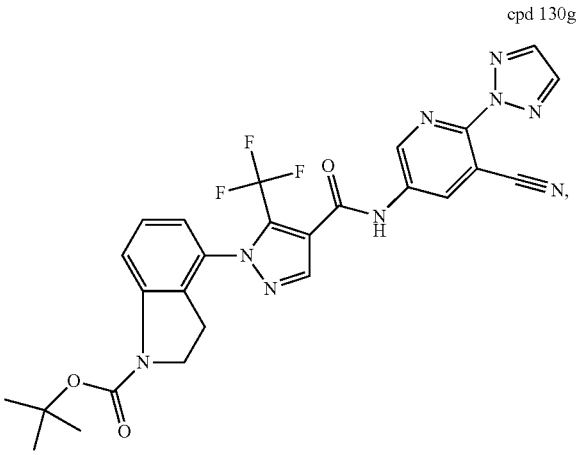 [SMILES: CC(C)(C)OC(=O)N1CCc2c1cccc2-n1ncc(C(=O)Nc2cnc(-n3nccn3)c(C#N)c2)c1C(F)(F)F]

cpd 130g

To a solution 4-tert-butyl 4-(4-(chlorocarbonyl)-5-(trifluoromethyl)-1H-pyrazol-1-yl)indoline-1-carboxylate, cpd 130 f (0.740 mmol) in pyridine (6 mL) at room temperature, 5-amino-2-[1,2,3]triazol-2-yl-nicotinonitrile, INT3 (207 mg, 1.11 mmol) in pyridine (6 mL), and the reaction was stirred at room temperature for 20 h. The mixture was diluted with ethyl acetate and washed with water and brine. The organic layer was dried (MgSO₄). filtered, and the filtrate concentrated. Purification by flash chromatography (SiO₂, ethyl acetate-heptane gradient) afforded tert-butyl 4-(4-((5-cyano-6-(2H-1,2,3-triazol-2-yl)pyridin-3-yl)carbamoyl)-5-(trifluoromethyl)-1H-pyrazol-1-yl)indoline-1-carboxylate, cpd 130g (300 mg, 71.7%). A portion (60 mg) of this product were further purified by reverse phase chromatography eluting with sodium bicarbonate-water/methanol-acetonitrile gradient, to afford 33 mg of pure product. ¹H NMR (300 MHz, Chloroform-d) δ 1.58 (s, 9H), 2.94 (t, J=8.7 Hz, 2H), 4.03 (t, J=8.7 Hz, 2H), 6.91 (d, J=8.0 Hz, 1H), 7.31 (t, J=8.1 Hz, 1H), 8.02 (s, 2H), 8.14 (s, 1H), 8.20 (s, 1H), 8.84 (d, J=2.6 Hz, 1H), 8.97 (d, J=2.5 Hz, 1H). MS m/z 566.1 (M+H)+.

H. N-(5-cyano-6-(2H-1,2,3-triazol-2-yl)pyridin-3-yl)-1-(indolin-4-yl)-5-(trifluoromethyl)-1H-pyrazole-4-carboxamide, Cpd 130

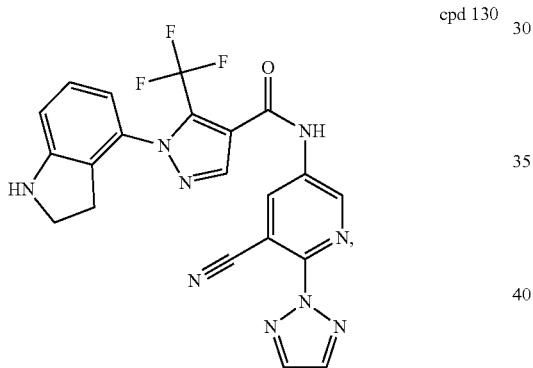

cpd 130

To a solution of tert-butyl 4-(4-((5-cyano-6-(2H-1,2,3-triazol-2-yl)pyridin-3-yl)carbamoyl)-5-(trifluoromethyl)-1H-pyrazol-1-yl)indoline-1-carboxylate, cpd 130g (300 mg, 0.530 mmol) in dichloromethane (9 mL), trifluoroacetic acid (6 mL) was added and the mixture was stirred for 3 h at room temperature. The mixture was concentrated under reduced pressure to dryness and the residue was diluted with ethyl acetate and washed with NaHCO₃. The organic layer was dried with MgSO₄, filtered, and the filtrate concentrated. The residue was purified by reverse phase chromatography (ammonium bicarbonate-water-acetonitrile gradient). The product-containing fractions were combined and extracted with dichloromethane. The organic layer was dried (MgSO₄), filtered, and the filtrate concentrated, and the product was further purified by reverse phase chromatography eluting with sodium bicarbonate-water/Methanol-acetonitrile gradient to yield pure N-(5-cyano-6-(2H-1,2,3-triazol-2-yl)pyridin-3-yl)-1-(indolin-4-yl)-5-(trifluoromethyl)-1H-pyrazole-4-carboxamide, cpd 130 (113 mg 45.8%). ¹H NMR (300 MHz, Chloroform-d) δ 2.91 (t, J=8.5 Hz, 3H), 3.63 (t, J=8.5 Hz, 2H), 6.65 (d, J=7.9 Hz, 1H), 6.75 (d, J=7.8 Hz, 1H), 7.12 (t, J=7.9 Hz, 1H), 8.02 (s, 3H), 8.10 (s, 1H), 8.80 (d, J=2.5 Hz, 1H), 8.96 (d, J=2.5 Hz, 1H). MS m/z 466.0 (M+H)+.

Example 134

N-(5-cyano-6-(2H-1,2,3-triazol-2-yl)pyridin-3-yl)-1-(1-methyl-1,2,3,4-tetrahydroquinolin-8-yl)-5-(trifluoromethyl)-1H-pyrazole-4-carboxamide, Cpd 131

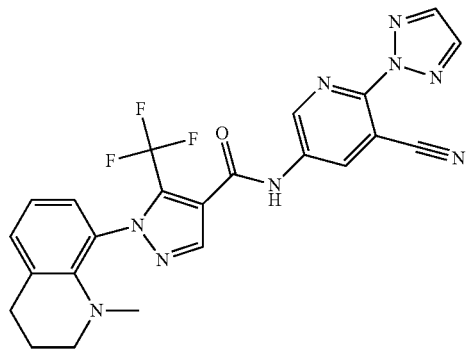 [SMILES: CN1CCCc2cccc(-n3ncc(C(=O)Nc4cnc(-n5nccn5)c(C#N)c4)c3C(F)(F)F)c21]

A. 8-Bromo-1-methyl-1,2,3,4-tetrahydroquinoline, Cpd 131a

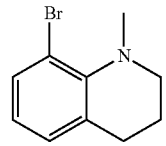

To a solution of 8-bromo-1,2,3,4-tetrahydroquinoline hydrochloride (1.0 g, 4.023 mmol) in acetic acid (21.8 mL) at RT, was added paraformaldehyde (1.208 g, 40.23 mmol). The mixture was stirred at room temperature for 15 min then sodium cyanoborohydride (1.264 g, 20.12 mmol) was added and the mixture was stirred at RT for 4 h. The reaction was quenched with saturated Na₂CO₃ aqueous solution, then extracted with dichloromethane. The organic layer was separated, dried over MgSO₄, filtered and the filtrate concentrated to yield the crude product. The crude product was purified by flash chromatography (SiO₂, ethyl acetate-heptane gradient 5% to 100%). The pure fractions were combined and concentrated to afford pure 8-bromo-1-methyl-1,2,3,4-tetrahydroquinoline, cpd 131a (0.863 g, 95%). MS m/z 227.9 (M+H)+.

B. 8-(2-(Diphenylmethylene)hydrazinyl)-1-methyl-1,2,3,4-tetrahydroquinoline, Cpd 131b

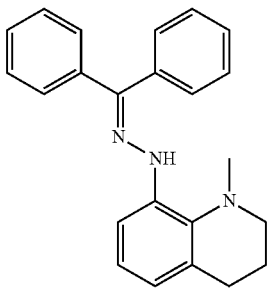 [SMILES: CN1CCCc2cccc(NN=C(c3ccccc3)c3ccccc3)c21]

To a solution of 8-bromo-1-methyl-1,2,3,4-tetrahydroquinoline, cpd 131a (0.817 g, 3.613 mmol) and benzophenone hydrazone (0.709 g, 3.613 mmol) in 1,4-dioxane (17 mL) at room temperature under nitrogen, BINAP (225 mg, 0.361 mmol), palladium (II) acetate (81 mg, 0.361 mmol) and sodium t-butoxide (1.042 mg, 10.84 mmol) were added and the mixture was heated at 100° C. for 16 h. The resultant mixture was cooled to room temperature, filtered and the filtrate concentrated under reduced pressure to give the crude product, which was purified by flash chromatography (SiO₂, heptane-ethyl acetate gradient). Pure fractions were combined and concentrated. The resultant solid was dried under reduced pressure to afford 8-(2-(diphenylmethylene) hydrazinyl)-1-methyl-1,2,3,4-tetrahydroquinoline, cpd 131b (1.195 g, 96.9% yield). MS m/z 342.1 (M+H)+.

C.
8-Hydrazinyl-1-methyl-1,2,3,4-tetrahydroquinoline Hydrochloride, Cpd 131c

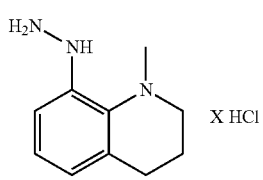

cpd 131c

X HCl

To a solution of 8-(2-(diphenylmethylene)hydrazinyl)-1-methyl-1,2,3,4-tetrahydroquinoline, cpd 131b (1.195 g, 3.5 mmol) in ethanol (3.5 mL), concentrated hydrochloric acid (7.0 mL) was added and the mixture was stirred at room temperature for 16 h. The reaction mixture was concentrated under reduced pressure, then treated with diethyl ether (25 mL) and water (10 mL). The layers were separated. The aqueous phase was concentrated under reduced pressure to yield 8-hydrazinyl-1-methyl-1,2,3,4-tetrahydroquinoline hydrochloride, cpd 131c, which was used in the next step without purification (3.5 mmol crude, 100% yield). MS m/z 178.1 (M+H)+.

D. Ethyl 1-(1-methyl-1,2,3,4-tetrahydroquinolin-8-yl)-5-(trifluoromethyl)-1H-pyrazole-4-carboxylate, Cpd 131d

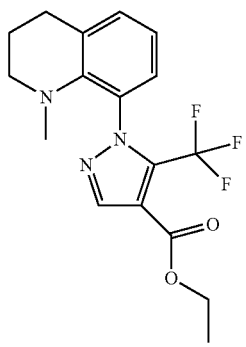 [SMILES: CCOC(=O)c1cnn(-c2cccc3c2N(C)CCC3)c1C(F)(F)F]

To a solution of 8-hydrazinyl-1-methyl-1,2,3,4-tetrahydroquinoline hydrochloride, cpd 131c (3.50 mmol) and triethylamine (0.976 mL, 7.0 mmol) in ethanol (46 mL), ethyl 2-(ethoxymethylene)-4,4,4-trifluoro-3-oxobutanoate, INT1 (0.672 g, 2.80 mmol) was added and the mixture was stirred at 80° C. for 16 h. The mixture was diluted with ethyl acetate and washed with water/NaHCO₃, the organic layer was separated and dried with MgSO₄, filtered, and the filtrate concentrated. The crude product was purified by flash chromatography (SiO₂, methanol-dichloromethane gradient). Pure fractions were combined and concentrated to yield ethyl 1-(1-methyl-1,2,3,4-tetrahydroquinolin-8-yl)-5-(trifluoromethyl)-1H-pyrazole-4-carboxylate, cpd 131d (684 mg, 55.3% yield). ¹H NMR (300 MHz, Chloroform-d) δ 1.38 (t, J=7.1 Hz, 3H), 1.69-2.06 (m, 2H), 2.18 (s, 3H), 2.77 (t, J=6.4 Hz, 2H), 2.97-3.19 (m, 2H), 4.37 (q, J=7.2 Hz, 2H), 6.80 (t, J=7.6 Hz, 1H), 6.97-7.12 (m, 2H), 8.16 (s, 1H). MS m/z 354.0 (M+H)+.

E. 1-(1-Methyl-1,2,3,4-tetrahydroquinolin-8-yl)-5-(trifluoromethyl)-1H-pyrazole-4-carboxylic Acid, Cpd 131e

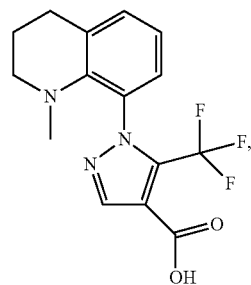

To a ethyl 1-(1-methyl-1,2,3,4-tetrahydroquinolin-8-yl)-5-(trifluoromethyl)-1H-pyrazole-4-carboxylate, cpd 131d (0.684 g, 1.936 mmol) in ethanol (35 mL), sodium hydroxide (155 mg, 3.872 mmol) was added and the mixture was heated at 60° C. for 3 h. The mixture was cooled to room temperature and poured onto a stirred 1N HCl/ice/ethyl acetate mixture. The organic layer was separated and washed with brine, then dried (MgSO₄), filtered and the filtrate concentrated to afford 1-(1-methyl-1,2,3,4-tetrahydroquinolin-8-yl)-5-(trifluoromethyl)-1H-pyrazole-4-carboxylic acid, cpd 131e (579 mg, 91.9% yield). MS m/z 326.0 (M+H)+.

F. 1-(1-Methyl-1,2,3,4-tetrahydroquinolin-8-yl)-5-(trifluoromethyl)-1H-pyrazole-4-carbonyl Chloride, Cpd 131f

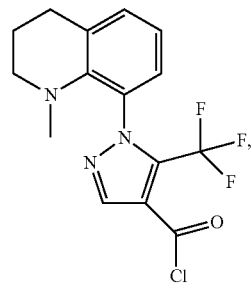

To a solution 1-(1-methyl-1,2,3,4-tetrahydroquinolin-8-yl)-5-(trifluoromethyl)-1H-pyrazole-4-carboxylic acid, cpd 131e (189 mg, 0.581 mmol) in dichloromethane (10 mL), 1-chloro-N,N,2-trimethyl-1-propenylamine (0.307 mL, 2.324 mmol) was added and the mixture was stirred at room temperature for 30 min to afford 1-(1-methyl-1,2,3,4-tetrahydroquinolin-8-yl)-5-(trifluoromethyl)-1H-pyrazole-4-carbonyl chloride, cpd 131f (0.581 mmol) crude solution, which was immediately used as such.

G. N-(5-Cyano-6-(2H-1,2,3-triazol-2-yl)pyridin-3-yl)-1-(1-methyl-1,2,3,4-tetrahydroquinolin-8-yl)-5-(trifluoromethyl)-1H-pyrazole-4-carboxamide, Cpd 131

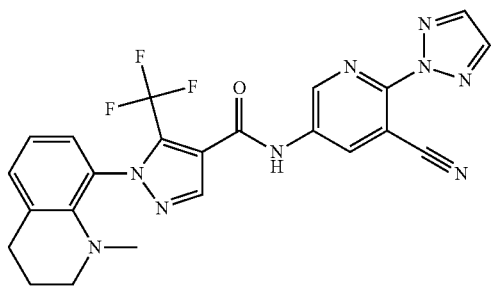 [SMILES: CN1CCCc2cccc(-n3ncc(C(=O)Nc4cnc(-n5nccn5)c(C#N)c4)c3C(F)(F)F)c21]

1-(1-Methyl-1,2,3,4-tetrahydroquinolin-8-yl)-5-(trifluoromethyl)-1H-pyrazole-4-carbonyl chloride, cpd 131f (0.581 mmol) in pyridine (5 mL) at room temperature, 5-amino-2-[1,2,3]triazol-2-yl-nicotinonitrile, INT3 (162 mg, 0.872 mmol) in pyridine (5 mL), and the reaction was stirred at room temperature for 20 h. The mixture was diluted with ethyl acetate and washed with water and brine. The organic layer was dried (MgSO$_4$), filtered, and the filtrate concentrated. Purification by flash chromatography (SiO$_2$, methanol-dichloromethane gradient) afforded N-(5-cyano-6-(2H-1,2,3-triazol-2-yl)pyridin-3-yl)-1-(1-methyl-1,2,3,4-tetrahydroquinolin-8-yl)-5-(trifluoromethyl)-1H-pyrazole-4-carboxamide, cpd 131 which was further purified by reverse phase chromatography eluting with sodium bicarbonate-water/Methanol-acetonitrile gradient, to afford pure product (67 mg, 23.4%). $^1$H NMR (300 MHz, Chloroform-d) δ 1.73-1.85 (m, 1H), 1.89-2.06 (m, 1H), 2.23 (s, 3H), 2.78 (t, J=6.4 Hz, 2H), 2.94-3.22 (m, 2H), 6.82 (t, J=7.7 Hz, 1H), 7.03 (d, J=7.8 Hz, 1H), 7.12 (d, J=7.5 Hz, 1H), 8.01 (s, 2H), 8.18 (s, 1H), 8.35 (s, 1H), 8.84 (d, J=2.6 Hz, 1H), 8.95 (d, J=2.6 Hz, 1H). MS m/z 494.1 (M+H)+.

Example 132

N-(5-cyano-6-(2H-1,2,3-triazol-2-yl)pyridin-3-yl)-1-(4-methyl-3,4-dihydro-2H-benzo[b][1,4]oxazin-8-yl)-5-(trifluoromethyl)-1H-pyrazole-4-carboxamide, Cpd132

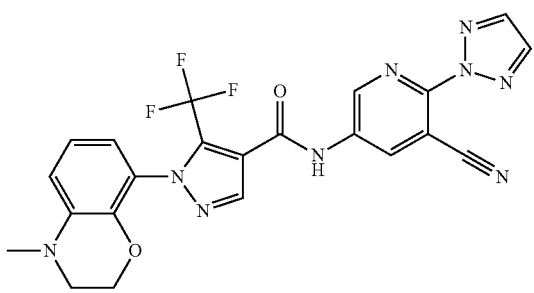 [SMILES: CN1CCOc2c1cccc2-n1ncc(C(=O)Nc2cnc(-n3nccn3)c(C#N)c2)c1C(F)(F)F]

A. Tert-Butyl 8-bromo-2,3-dihydro-4H-benzo[b][1,4]oxazine-4-carboxylate, Cpd 132a

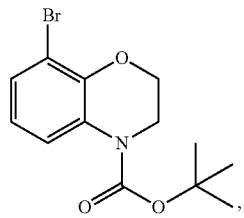

To a solution of 8-bromo-3,4-dihydro-2H-1,4-benzoxazine (1.0 g, 4.672 mmol) in dichloromethane (15 mL), N,N-dimethylaminopyridine (0.057 g, 0.467 mmol) and triethylamine (1.36 mL, 9.8 mmol) were added. The mixture was stirred for 30 min at room temperature, then di-tert-butyl dicarbonate (1.13 mL, 4.905 mmol) was added portionwise. The solution was stirred at room temperature overnight. The mixture was diluted with ethyl acetate. The organic layer was washed with water and brine, filtered, dried and the filtrate concentrated. The mixture was purified by flash chromatography (SiO$_2$, heptane-ethyl acetate gradient). Pure fractions were combined and concentrated. The resultant solids were dried under reduced pressure to yield tert-butyl 8-bromo-2,3-dihydro-4H-benzo[b][1,4]oxazine-4-carboxylate, cpd 135a (1.208 g, 82.3% yield). MS m/z 259.9 (M+H-tBu)+.

B. Tert-Butyl 8-(2-(diphenylmethylene)hydrazinyl)-2,3-dihydro-4H-benzo[b][1,4]oxazine-4-carboxylate, Cpd 132b

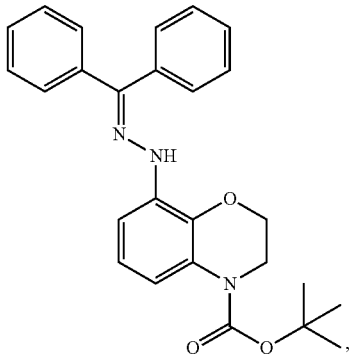

To a solution of tert-butyl 8-bromo-2,3-dihydro-4H-benzo[b][1,4]oxazine-4-carboxylate, cpd 132a (1.156 g, 3.679 mmol) and benzophenone hydrazone (0.722 g, 3.679 mmol) in 1,4-dioxane (10 mL) at room temperature under nitrogen, BINAP (229 mg, 0.368 mmol), palladium (II) acetate (83 mg, 0.368 mmol) and sodium t-butoxide (1.061 g, 11.038 mmol) were added and the mixture was heated at 100° C. for 16 h. The resultant mixture was cooled to room temperature, filtered, and the filtrate concentrated under reduced pressure to give the crude product, which was purified by flash chromatography (SiO$_2$, heptane-ethyl acetate gradient). Pure fractions were combined and concentrated. The resultant solids were dried under reduced pressure to afford tert-butyl 8-(2-(diphenylmethylene)hydrazinyl)-2,3-dihydro-4H-benzo[b][1,4]oxazine-4-carboxylate, cpd 132b (0.820 g, 51.9% yield). MS m/z 430.1 (M+H)+.

C. 8-Hydrazinyl-3,4-dihydro-2H-benzo[b][1,4]oxazine Hydrochloride, cpd 132c

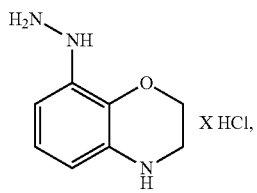

cpd 132c

To a solution of tert-butyl 8-(2-(diphenylmethylene)hydrazinyl)-2,3-dihydro-4H-benzo[b][1,4]oxazine-4-carboxylate, cpd 132b (0.901 g, 2.098 mmol) in ethanol (2.2 mL), concentrated hydrochloric acid (4.4 mL) was added and the mixture was stirred at room temperature for 16 h. The reaction mixture was concentrated under reduced pressure, then treated with diethylether (25 mL) and water (10 mL). The layers were separated. The aqueous phase was concentrated under reduced pressure to yield 8-hydrazinyl-3,4-dihydro-2H-benzo[b][1,4]oxazine hydrochloride, cpd 132c, which was used in the next step without purification (2.098 mmol crude, 100% yield). MS m/z 166.1 (M+H)+.

D. Ethyl 1-(3,4-dihydro-2H-benzo[b][1,4]oxazin-8-yl)-5-(trifluoromethyl)-1H-pyrazole-4-carboxylate, Cpd 132d

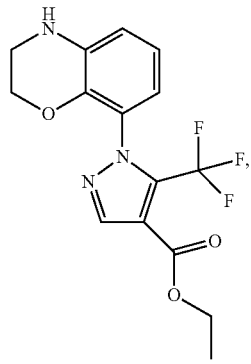

cpd 132d

To a solution of 8-hydrazinyl-3,4-dihydro-2H-benzo[b][1,4]oxazine hydrochloride, cpd 132c (1.998 mmol) and triethylamine (0.557 mL, 4.0 mmol) in ethanol (15 mL), ethyl 2-(ethoxymethylene)-4,4,4-trifluoro-3-oxobutanoate, INT1 (0.432 g, 1.80 mmol) was added and the mixture was stirred at 80° C. for 16 h. The mixture was diluted with ethyl acetate and washed with water/NaHCO$_3$, the organic layer was separated and dried with MgSO$_4$, filtered, and the filtrate concentrated. The crude product was purified by flash chromatography (SiO$_2$, methanol-dichloromethane gradient). Pure fractions were combined and concentrated to yield ethyl 1-(3,4-dihydro-2H-benzo[b][1,4]oxazin-8-yl)-5-(trifluoromethyl)-1H-pyrazole-4-carboxylate, cpd 132d (494 mg, 72.4% yield). $^1$H NMR (300 MHz, Chloroform-d) δ 1.37 (t, J=7.1 Hz, 3H), 3.33-3.50 (m, 2H), 4.10-4.28 (m, 2H), 4.36 (q, J=7.1 Hz, 2H), 6.66-6.75 (m, 2H), 6.82 (t, J=7.9 Hz, 1H), 8.14 (s, 1H). MS m/z 342.0 (M+H)+.

E. Ethyl 1-(4-methyl-3,4-dihydro-2H-benzo[b][1,4]oxazin-8-yl)-5-(trifluoromethyl)-1H-pyrazole-4-carboxylate, Cpd 132e

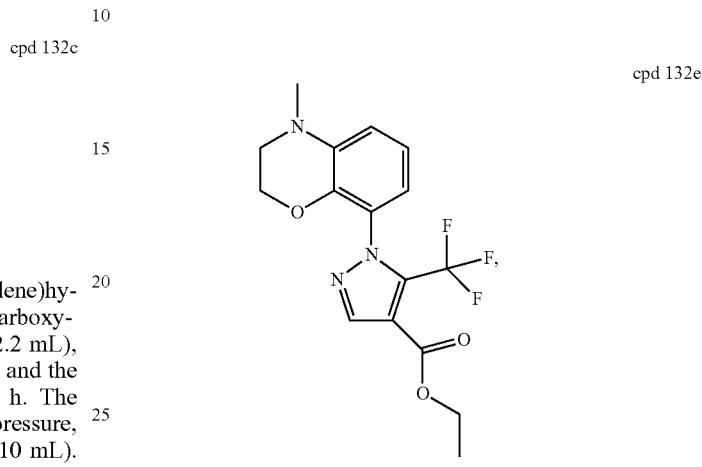

cpd 132e

To a solution of ethyl 1-(3,4-dihydro-2H-benzo[b][1,4]oxazin-8-yl)-5-(trifluoromethyl)-1H-pyrazole-4-carboxylate, cpd 132d (0.494 g, 1.447 mmol) in acetic acid (7.9 mL) at RT, was added paraformaldehyde (0.435 g, 14.475 mmol). The mixture was stirred at room temperature for 15 min then sodium cyanoborohydride (0.455 g, 7.237 mmol) was added and the mixture was stirred at RT for 4 h. The reaction was quenched with a saturated Na$_2$CO$_3$ aqueous solution, then extracted with dichloromethane. The organic layer was separated, dried over MgSO$_4$, filtered and the filtrate concentrated to yield ethyl 1-(4-methyl-3,4-dihydro-2H-benzo[b][1,4]oxazin-8-yl)-5-(trifluoromethyl)-1H-pyrazole-4-carboxylate, cpd 132e (0.514 g, 99%). MS m/z 356.0 (M+H)+.

F. 1-(4-Methyl-3,4-dihydro-2H-benzo[b][1,4]oxazin-8-yl)-5-(trifluoromethyl)-1H-pyrazole-4-carboxylic Acid, Cpd 132f

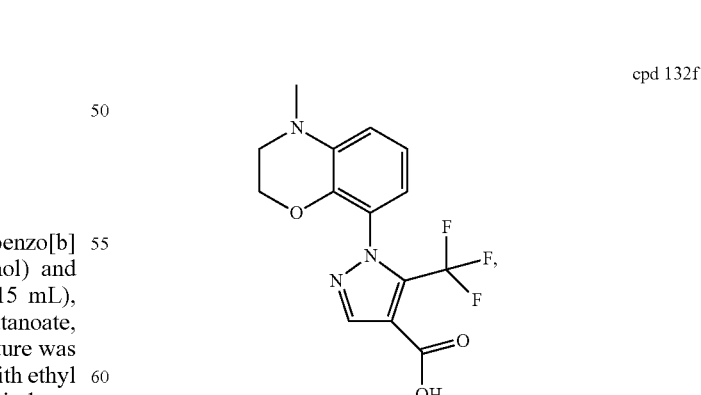

cpd 132f

To a solution of ethyl 1-(4-methyl-3,4-dihydro-2H-benzo[b][1,4]oxazin-8-yl)-5-(trifluoromethyl)-1H-pyrazole-4-carboxylate, cpd 132e (0.514 g, 1.447 mmol) in ethanol (18 mL), sodium hydroxide (116 mg, 2.894 mmol) was added and the mixture was heated at 60° C. for 3 h. The mixture was cooled to room temperature and poured onto a stirred 1N HCl/ice/ethylacetate mixture. The organic layer was separated and washed with brine, then dried (MgSO4), filtered, and the filtrate concentrated to afford 1-(4-methyl-3,4-dihydro-2H-benzo[b][1,4]oxazin-8-yl)-5-(trifluoromethyl)-1H-pyrazole-4-carboxylic acid, cpd 132f (473 mg, 99% yield). MS m/z 328.0 (M+H)+.

G. 1-(4-Methyl-3,4-dihydro-2H-benzo[b][1,4]oxazin-8-yl)-5-(trifluoromethyl)-1H-pyrazole-4-carbonyl Chloride, Cpd 132g

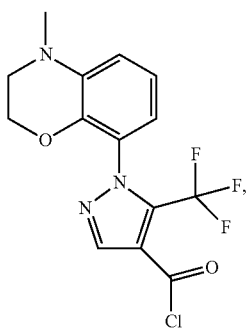

cpd 132g

To a solution of 1-(4-methyl-3,4-dihydro-2H-benzo[b][1,4]oxazin-8-yl)-5-(trifluoromethyl)-1H-pyrazole-4-carboxylic acid, cpd 132f (474 mg, 1.447 mmol) in dichloromethane (12 mL) and N,N-dimethylformamide (0.1 mL), oxalyl chloride (0.248 mL, 2.894 mmol) was added and the mixture was heated to reflux temperature for 1 h. The mixture was concentrated to dryness and the residue was dried under reduced pressure to constant weight to yield the crude 1-(4-methyl-3,4-dihydro-2H-benzo[b][1,4]oxazin-8-yl)-5-(trifluoromethyl)-1H-pyrazole-4-carbonyl chloride, cpd 132g (1.447 mmol) as an oil, which was immediately used as such.

H. N-(5-cyano-6-(2H-1,2,3-triazol-2-yl)pyridin-3-yl)-1-(4-methyl-3,4-dihydro-2H-benzo[b][1,4]oxazin-8-yl)-5-(trifluoromethyl)-1H-pyrazole-4-carboxamide, Cpd 132

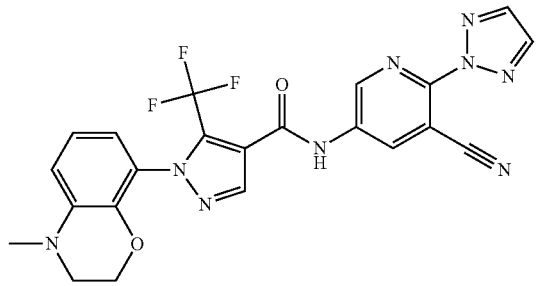 [SMILES: CN1CCOc2c1cccc2-n1ncc(C(=O)Nc2cnc(-n3nccn3)c(C#N)c2)c1C(F)(F)F]

To a solution of 1-(4-methyl-3,4-dihydro-2H-benzo[b][1,4]oxazin-8-yl)-5-(trifluoromethyl)-1H-pyrazole-4-carbonyl chloride, cpd 132g (1.447 mmol) in dichloromethane (8 mL) and tetrahydrofuran (24 mL) at room temperature, 5-amino-2-[1,2,3]triazol-2-yl-nicotinonitrile (539 mg, 2.894 mmol) was added followed by triethylamine (0.807 mL, 5.788 mmol), and the reaction was stirred at room temperature for 20 h. The mixture was diluted with ethyl acetate and washed with water and brine. The organic layer was dried (MgSO4), filtered and the filtrate concentrated. Purification by flash chromatography (SiO2, ethyl acetate-heptane gradient) afforded a mixture of product and starting material. The product was purified by reverse phase chromatography eluting with ammonium bicarbonate-water-acetonitrile gradient. The product fractions were combined and extracted with dichloromethane. The organic layer was dried (MgSO4) and concentrated to afford pure N-(5-cyano-6-(2H-1,2,3-triazol-2-yl)pyridin-3-yl)-1-(4-methyl-3,4-dihydro-2H-benzo[b][1,4]oxazin-8-yl)-5-(trifluoromethyl)-1H-pyrazole-4-carboxamide, cpd 132 (185 mg, 2 5.8%). $^1$H NMR (300 MHz, DMSO-$d_6$) δ 2.92 (s, 3H), 3.23-3.35 (m, 2H), 4.03-4.37 (m, 2H), 6.67-6.77 (m, 1H), 6.84-6.99 (m, 2H), 8.31 (s, 2H), 8.49 (s, 1H), 8.90 (d, J=2.5 Hz, 1H), 9.15 (d, J=2.4 Hz, 1H), 11.38 (s, 1H). MS m/z 496.1 (M+H)+.

Example 133

N-(5-chloro-6-(2H-1,2,3-triazol-2-yl)pyridin-3-yl)-1-(1-oxoisoindolin-4-yl)-5-(trifluoromethyl)-1H-pyrazole-4-carboxamide, Cpd 133

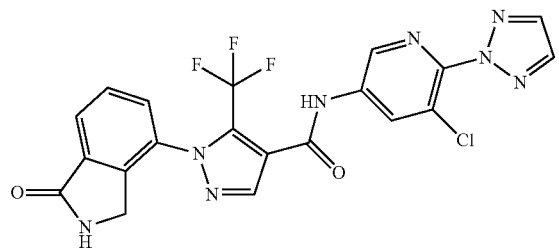 [SMILES: O=C1NCc2c1cccc2-n1ncc(C(=O)Nc2cnc(-n3nccn3)c(Cl)c2)c1C(F)(F)F]

A. 4-(2-(diphenylmethylene)hydrazinyl)isoindolin-1-one, Cpd 133a

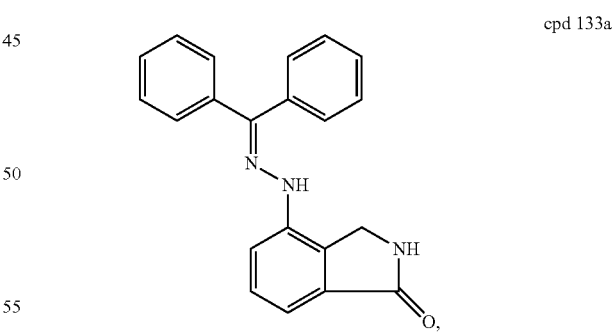

cpd 133a

To a solution of 4-bromoisoindolin-1-one (1.0 g, 4.72 mmol) and benzophenone hydrazone (2.78 g, 14.15 mmol) in 1,4-dioxane (25 mL) at room temperature under nitrogen, BINAP (587 mg, 0.94 mmol), palladium (II) acetate (212 mg, 0.94 mmol) and sodium t-butoxide (1.36 g, 11.15 mmol) were added and the mixture was heated at 100° C. for 16 h. The resultant mixture was cooled to room temperature, filtered, and the filtrate concentrated under reduced pressure to give the crude product, which was purified by flash chromatography (SiO2, heptane-ethyl acetate gradient). Pure fractions were combined and concentrated. The product was dried under reduced pressure to afford 4-(2-(diphenylmethylene)hydrazinyl)isoindolin-1-one, cpd 133a (1.544 g, 90.7% yield). MS m/z 328.0 (M+H)+

B. 4-hydrazinylisoindolin-1-one Hydrochloride, Cpd 133b

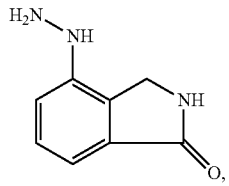

cpd 133b

To a solution of 4-(2-(diphenylmethylene)hydrazinyl)isoindolin-1-one, cpd 133a (1.4 g, 4.28 mmol) in ethanol (4.3 mL), concentrated hydrochloric acid (8.6 mL) was added and the mixture was stirred at room temperature for 16 h. The reaction mixture was concentrated under reduced pressure, then treated with diethyl ether (25 mL) and water (10 mL). The layers were separated. The aqueous phase was concentrated under reduced pressure to yield 4-hydrazinylisoindolin-1-one hydrochloride, cpd 133b, which was used in the next step without purification (3.20 mmol crude, 75% yield). MS m/z 164.0 (M+H)+.

C. Ethyl 1-(1-oxoisoindolin-4-yl)-5-(trifluoromethyl)-1H-pyrazole-4-carboxylate, Cpd 133c

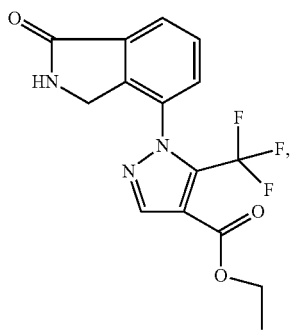

cpd 133c

To a solution of 4-hydrazinylisoindolin-1-one hydrochloride, cpd 133b (755 mg, 3.20 mmol) and triethylamine (2.30 mL, 15.99 mmol) in ethanol (15 mL), ethyl 2-(ethoxymethylene)-4,4,4-trifluoro-3-oxobutanoate, INT1 (768 mg, 3.20 mmol) was added and the mixture was stirred at 80° C. for 16 h. The mixture was diluted with ethyl acetate and washed with water/NaHCO$_3$, the organic layer was separated and dried with MgSO$_4$, filtered, and the filtrate then concentrated. The crude product was purified by flash chromatography (SiO$_2$, methanol-dichloromethane gradient). The pure fractions were combined and concentrated to yield ethyl 1-(1-oxoisoindolin-4-yl)-5-(trifluoromethyl)-1H-pyrazole-4-carboxylate, cpd 133c (120 mg, 9.4% yield). $^1$H NMR (300 MHz, Chloroform-d) d 1.40 (t, J=7.1 Hz, 3H), 4.24-4.49 (m, 4H), 6.56 (s, 1H), 7.54 (d, J=7.8 Hz, 1H), 7.65 (t, 1H), 8.04 (d, J=7.5 Hz, 1H), 8.18 (s, 1H). MS m/z 340.1 (M+H)+.

D. (1-oxoisoindolin-4-yl)-5-(trifluoromethyl)-1H-pyrazole-4-carboxylic Acid, Cpd 133d

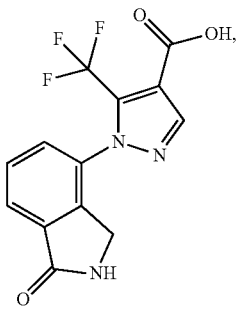

cpd 133d

To a solution of ethyl 1-(1-oxoisoindolin-4-yl)-5-(trifluoromethyl)-1H-pyrazole-4-carboxylate, cpd 133c (70 mg, 0.21 mmol) in THF-H$_2$O (8 mL), sodium hydroxide (12.4 mg, 0.31 mmol) was added and the mixture was stirred at RT for 3 h. The mixture was poured onto a stirred IN HCl/ice/ethyl acetate mixture. The organic layer was separated and washed with brine, then dried (MgSO$_4$), filtered, and the filtrate concentrated to afford 1-(1-oxoisoindolin-4-yl)-5-(trifluoromethyl)-1H-pyrazole-4-carboxylic acid, cpd 133d (66 mg, 97% yield). MS m/z 311.9 (M+H)+.

E. 1-(2-(tert-butoxycarbonyl)-1-oxoisoindolin-4-yl)-5-(trifluoromethyl)-1H-pyrazole-4-carboxylic Acid, Cpd 133e

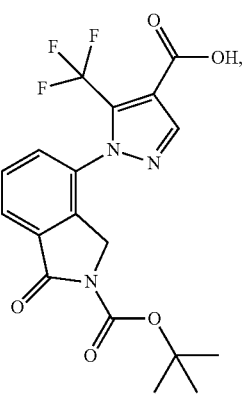

cpd 133e di-tert-Butyl decarbonate (56.8 mg, 0.26 mmol), DMAP (4.24 mg, 0.035 mmol) and triethylamine (52.7 mg, 0.52 mmol) were added to a solution of 1-(1-oxoisoindolin-4-yl)-5-(trifluoromethyl)-1H-pyrazole-4-carboxylic acid, cpd 133d (54 mg, 0.17 mmol) in dichloromethane (5 mL). The mixture was stirred at 30° C. for 48 h. The crude product was purified by preparative high-performance liquid chromatography to give 1-(2-(tert-butoxycarbonyl)-1-oxoisoindolin-4-yl)-5-(trifluoromethyl)-1H-pyrazole-4-carboxylic acid, cpd 133e as a yellow solid (33 mg, 46.24%). [M+1]$^+$ 356.0

F. Tert-Butyl 4-(4-((5-chloro-6-(2H-1,2,3-triazol-2-yl)pyridin-3-yl)carbamoyl)-5-(trifluoromethyl)-1H-pyrazol-1-yl)-1-oxoisoindoline-2-carboxylate, Cpd 133f

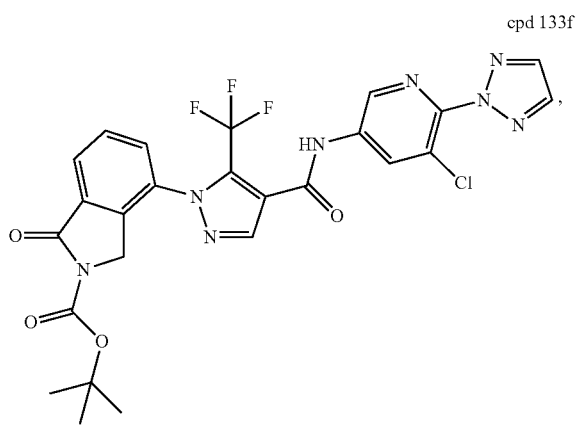 [SMILES: CC(C)(C)OC(=O)N1Cc2c(cccc2-n2ncc(C(=O)Nc3cnc(-n4nccn4)c(Cl)c3)c2C(F)(F)F)C1=O]

cpd 133f

Phosphorus oxychloride (29.4 uL, 0.32 mmol) was added to a solution of 1-(2-(tert-butoxycarbonyl)-1-oxoisoindolin-4-yl)-5-(trifluoromethyl)-1H-pyrazole-4-carboxylic acid, cpd 133e (33 mg, 0.08 mmol), 5-chloro-6-(2H-1,2,3-triazol-2-yl)pyridin-3-amine, INT2 (15.70 mg, 0.08 mmol), pyridine (32.4 uL, 0.40 mmol) in CH$_2$Cl$_2$ (5 mL). The mixture was stirred at room temperature for 2 h. 5 mL H$_2$O was added to the mixture. Sat. NaHCO$_3$ was added to adjust the pH of reaction mixture to 7-8. The mixture was extracted with CH$_2$Cl$_2$ (5 mL*3). The combined organic extracts were dried over anhydrous Mg$_2$SO$_4$, filtered, and concentrated to dryness under reduced pressure to afford the crude tert-butyl 4-(4-((5-chloro-6-(2H-1,2,3-triazol-2-yl)pyridin-3-yl)carbamoyl)-5-(trifluoromethyl)-1H-pyrazol-1-yl)-1-oxoisoindoline-2-carboxylate, cpd 133f (55.2 mg, 85%).

G. N-(5-chloro-6-(2H-1,2,3-triazol-2-yl)pyridin-3-yl)-1-(1-oxoisoindolin-4-yl)-5-(trifluoromethyl)-1H-pyrazole-4-carboxamide, Cpd 133

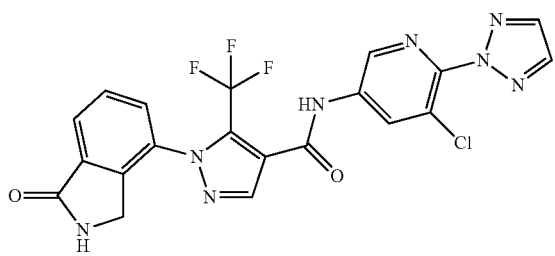 [SMILES: O=C1NCc2c1cccc2-n1ncc(C(=O)Nc2cnc(-n3nccn3)c(Cl)c2)c1C(F)(F)F]

HCl in dioxane (1 M) was added to a solution of tert-butyl 4-(4-((5-chloro-6-(2H-1,2,3-triazol-2-yl)pyridin-3-yl)carbamoyl)-5-(trifluoromethyl)-1H-pyrazol-1-yl)-1-oxoisoindoline-2-carboxylate, cpd 133f (50 mg, 0.073 mmol) in CH$_2$Cl$_2$ (3 mL). The mixture was stirred at rt for 2 h. The solvent was evaporated under reduced pressure. The reaction mixture was purified by preparative high-performance liquid chromatography to give N-(5-chloro-6-(2H-1,2,3-triazol-2-yl)pyridin-3-yl)-1-(1-oxoisoindolin-4-yl)-5-(trifluoromethyl)-1H-pyrazole-4-carboxamide, cpd 133 as a pale white solid (13 mg, 36.6%). $^1$H NMR (400 MHz, DMSO-d$_6$) δ ppm 11.26 (1H, s), 8.81 (2H, d, J=2.20 Hz), 8.63 (1H, d, J=2.43 Hz), 8.50 (1H, s) 8.16 (2H, s), 7.91 (1H, dd, J=7.06, 1.32 Hz), 7.69-7.78 (2H, m), 4.31 (2H, s). LC-MS: (ES, m/z): [M+1]$^+$ 488.9.

Example 134

1-(6-aminopyridin-2-yl)-N-(5-cyano-6-(2H-1,2,3-triazol-2-yl)pyridin-3-yl)-5-(trifluoromethyl)-1H-pyrazole-4-carboxamide, Cpd 134

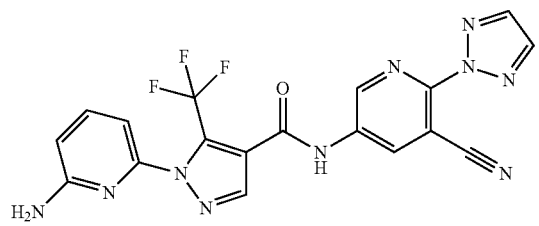

A. Ethyl 1-(6-bromopyridin-2-yl)-5-(trifluoromethyl)-1H-pyrazole-4-carboxylate, Cpd 134a

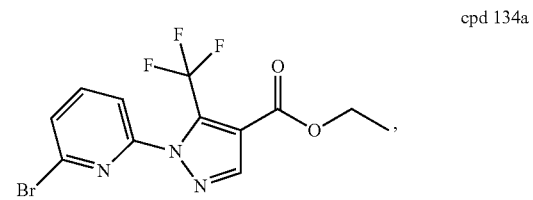 [SMILES: CCOC(=O)c1cnn(-c2cccc(Br)n2)c1C(F)(F)F]

cpd 134a

A solution of 2-bromo-6-hydrazinylpyridine (3.0 g, 15.96 mmol) and ethyl 2-(ethoxymethylene)-4,4,4-trifluoro-3-oxobutanoate, INT1 (5.75 g, 23.93 mmol) in ethanol (150 mL) was stirred at 80° C. overnight then cooled to rt. The solvent was removed under reduced pressure to give a yellow oil. The oil was purified by flash column chromatography over silica gel (eluent: petroleum ether/EtOAc 100/0 to petroleum ether/EtOAc 80/20). The desired fractions were collected and the solvent was concentrated to dryness under reduced pressure to give the desired product as a yellow solid. LC-MS: (ES, m/z): [M+1]$^+$ 365.6.

B. Ethyl 1-(6-((tert-butoxycarbonyl)amino)pyridin-2-yl)-5-(trifluoromethyl)-1H-pyrazole-4-carboxylate, Cpd 134b

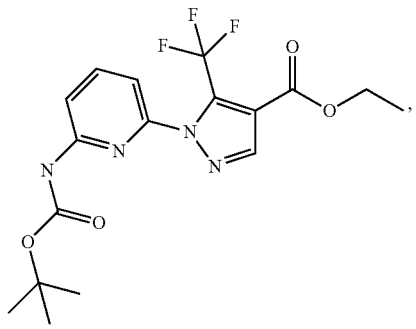

cpd 134b

Palladium acetate (93.23 mg, 0.41 mmol) and Xantphos (238.36 mg, 0.41 mmol) in dioxane (75 mL) were stirred at rt for 10 min under nitrogen. Ethyl 1-(6-bromopyridin-2-yl)-5-(trifluoromethyl)-1H-pyrazole-4-carboxylate, cpd 134a (3.0 g, 8.24 mmol), $Cs_2CO_3$ (8.05 g, 24.72 mmol) and tert-butyl carbamate (1.16 g, 9.89 mmol) were then added at room temperature. The reaction mixture was then allowed to heat at 90° C. overnight and then cooled to rt. The reaction mixture was filtered through a pad of diatomaceous earth. The filtrate was concentrated under reduced pressure. The resultant residue was purified by flash column chromatography over silica gel (eluent: petroleum ether/EtOAc 100/0 to petroleum ether/EtOAc 80/20). The desired fractions were collected and the solvent was concentrated to dryness under reduced pressure to give the desired product as a white solid.

C. 1-(6-((tert-Butoxycarbonyl)amino)pyridin-2-yl)-5-(trifluoromethyl)-1H-pyrazole-4-carboxylic Acid, Cpd 134c

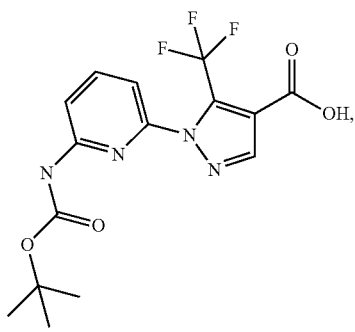

cpd 134c

To a solution ethyl 1-(6-((tert-butoxycarbonyl)amino)pyridin-2-yl)-5-(trifluoromethyl)-1H-pyrazole-4-carboxylate, cpd 134b (100 mg, 0.25 mmol) in THF/Methanol/$H_2O$ (1:1:1) (3 mL), lithium hydroxide (31.44 mg, 0.75 mmol) was added and the mixture was stirred at rt for 3 h. The mixture was poured onto a stirred 1N HCl/ice/ethylacetate mixture. The organic layer was separated and washed with brine, then dried ($MgSO_4$), filtered, and the filtrate concentrated and concentrated to afford cpd 134c (90 mg, 96.8% yield).

D. Tert-Butyl (6-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, Cpd 134d

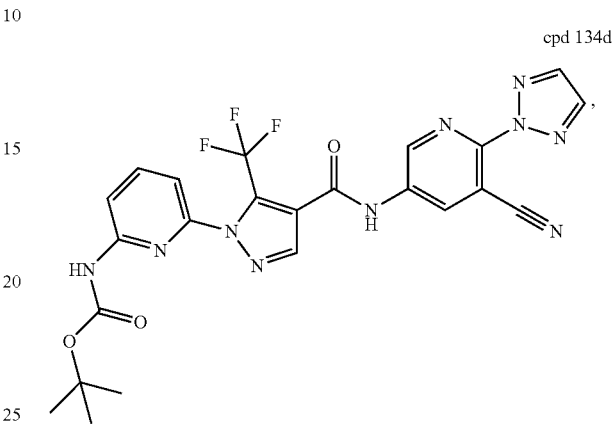

cpd 134d $POCl_3$ (41.8 μL, 0.47 mmol) was added to a solution of 1-(6-((tert-butoxycarbonyl)amino)pyridin-2-yl)-5-(trifluoromethyl)-1H-pyrazole-4-carboxylic acid, cpd 134c (70 mg, 0.19 mmol), 5-amino-2-(2H-1,2,3-triazol-2-yl)nicotinonitrile, INT3 (45.51 mg, 0.24 mmol), pyridine (152 μL 0.98 mmol) in $CH_2Cl_2$ (3 mL). The mixture was stirred at rt for 1 h. Water (5 mL) and $CH_2Cl_2$ (10 mL) were added to the mixture. The organic layer was washed with brine (5 mL), dried over $MgSO_4$, filtered, and the filtrate concentrated under reduced pressure. The crude product was purified by column chromatography over silica gel (petroleum ether/ethyl acetate from 20:1 to 1:1). The desired fractions were collected and the solvent was concentrated under reduced pressure to afford cpd 134d (70 mg, 68.9% yield) as a white solid. LCMS (ESI) m/z M+H: 563.1

E. 1-(6-aminopyridin-2-yl)-N-(5-cyano-6-(2H-1,2,3-triazol-2-yl)pyridin-3-yl)-5-(trifluoromethyl)-1H-pyrazole-4-carboxamide, Cpd 134

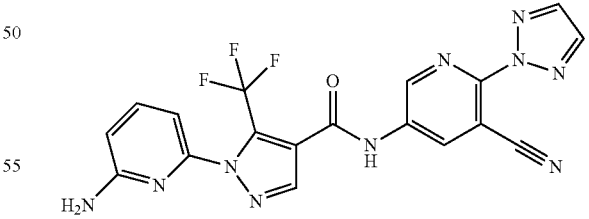

tert-Butyl (6-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, cpd 134d (70 mg 0.13 mmol) was added to TFA/DCM (2 mL, 1:4). The mixture was stirred at rt for 4 h. A 1 M NaOH solution was added to adjust the pH to 7-8. The aqueous was extracted with DCM (5 mL×3). The separated organic layer was dried ($MgSO_4$), filtered, and the filtrate was concentrated under reduced pressure to give a crude product. The crude product was purified by flash column chromatography over silica gel (eluent: petroleum ether/ethyl acetate from 100/0 to 0/100), evaporated and dried to give cpd 134 (57.9 mg 43.2%) as white solid. $^1$H NMR (400 MHz, DMSO-d$_6$) δ ppm 6.37 (s, 2H) 6.58 (d, J=8.38 Hz, 1H) 6.74 (d, J=7.72 Hz, 1H) 7.60 (t, J=8.05 Hz, 1H) 8.28 (s, 2H) 8.33 (s, 1H) 8.82 (d, J=2.43 Hz, 1H) 9.03 (d, J=1.98 Hz, 1H) 11.25 (br s, 1H). LC-MS: (ES, m/z): [M+1]-441.0

Example 135

1-(2-cyano-4-fluorophenyl)-N-(5-cyano-6-(2H-1,2,3-triazol-2-yl)pyridin-3-yl)-5-(trifluoromethyl)-1H-pyrazole-4-carboxamide, Cpd 135

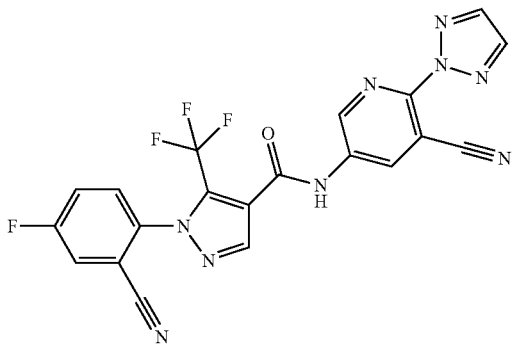 [SMILES: N#Cc1cc(F)ccc1-n1ncc(C(=O)Nc2cnc(-n3nccn3)c(C#N)c2)c1C(F)(F)F]

Pd(dba)$_2$ (7.03 mg, 0.0077 mmol) and dppf (8.51 mg, 0.015 mmol) was added to a solution of 1-(2-bromo-4-fluorophenyl)-N-(5-cyano-6-(2H-1,2,3-triazol-2-yl)pyridin-3-yl)-5-(trifluoromethyl)-1H-pyrazole-4-carboxamide, Cpd 50 (100 mg, 0.19 mmol), dicyanozinc (13.52 mg, 0.12 mmol) and zinc (3.01 mg, 0.046 mmol) in DMA (2 mL) under N$_2$ atmosphere. The reaction mixture was heated at 120° C. for 4 h. The mixture was filtered and the filtrate was concentrated to give a crude product. The crude product was purified by preparative high-performance liquid chromatography. The pure fractions were collected and the solvent was evaporated under reduced pressure to give cpd 135 as a white solid (50 mg, 56%). $^1$H NMR (400 MHz, DMSO-d$_6$) δ ppm 7.91 (td, J=8.54, 2.98 Hz, 1H) 8.04 (dd, J=8.93, 4.74 Hz, 1H) 8.26 (dd, J=8.27, 2.98 Hz, 1H) 8.31 (s, 2H) 8.58 (s, 1H) 8.86 (d, J=2.43 Hz, 1H) 9.08 (d, J=2.43 Hz, 1H) 11.36 (s, 1H). LC-MS: (ES, m/z): [M+1]$^+$ 467.9

Example 136

N-(5-chloro-6-(2H-1,2,3-triazol-2-yl)pyridin-3-yl)-1-(2-cyano-4-fluorophenyl)-5-(trifluoromethyl)-1H-pyrazole-4-carboxamide, Cpd 136

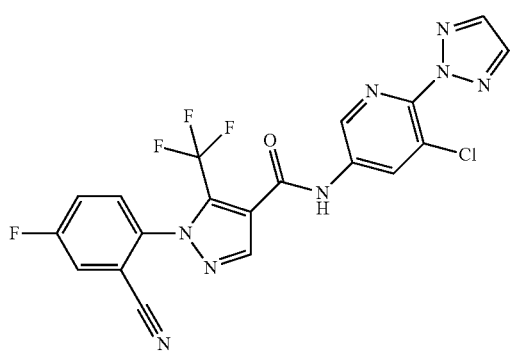 [SMILES: N#Cc1cc(F)ccc1-n1ncc(C(=O)Nc2cnc(-n3nccn3)c(Cl)c2)c1C(F)(F)F]

Pd(dba)$_2$ (6.90 mg, 0.0075 mmol) and dppf (6.27 mg, 0.011 mmol) was added to a solution of 1-(2-bromo-4-fluorophenyl)-N-(5-chloro-6-(2H-1,2,3-triazol-2-yl)pyridin-3-yl)-5-(trifluoromethyl)-1H-pyrazole-4-carboxamide, cpd 84 (100 mg, 0.19 mmol), dicyanozinc (11.51 mg, 0.10 mmol) and zinc (1.48 mg, 0.023 mmol) in DMA (2 mL) under N$_2$ atmosphere. The reaction mixture was heated at 120° C. for 4 h. The mixture was filtered and the filtrate was concentrated to give a crude product. The crude product was purified by preparative high-performance liquid chromatography. The pure fractions were collected and the solvent was concentrated under reduced pressure to give cpd 136 as a white solid (40 mg, 44%). $^1$H NMR (400 MHz, DMSO-d$_6$) δ ppm 7.91 (td, J=8.49, 3.09 Hz, 1H), 8.03 (dd, J=8.93, 4.74 Hz, 1H), 8.19 (s, 2H), 8.26 (dd, J=8.05, 2.76 Hz, 1H), 8.59 (s, 1H), 8.66 (d, J=2.21 Hz, 1H), 8.85 (d, J=1.98 Hz, 1H), 11.32 (s, 1H). LC-MS: (ES, m/z): [M+1]$^+$ 476.9

Example 137

N-(5-chloro-6-(2H-1,2,3-triazol-2-yl)pyridin-3-yl)-1-(2-(methylthio)phenyl)-5-(trifluoromethyl)-1H-pyrazole-4-carboxamide, Cpd 137

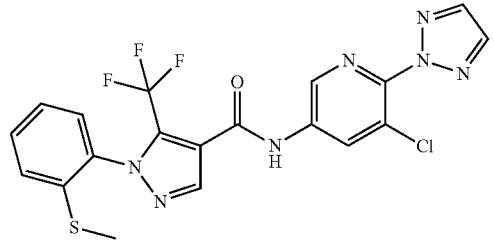 [SMILES: CSc1ccccc1-n1ncc(C(=O)Nc2cnc(-n3nccn3)c(Cl)c2)c1C(F)(F)F]

A. (2-(Methylthio)phenyl)hydrazine, Cpd 137a cpd 137a

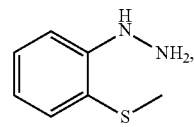

To a stirring solution of 2-(methylthio)aniline (500 mg, 2.85 mmol) in conc.HCl (4.1 mL) at −5° C. was slowly added a solution of sodium nitrite (295 mg, 4.27 mmol) in water (1.0 mL) below 0° C. The reaction mixture was stirred at 0° C. for 1 h and a solution of tin (II) chloride dihydrate (1.606 g, 7.12 mmol) dissolved in conc.HCl (1 mL) was added dropwise. Then the mixture was stirred at room temperature for 16 h. The mixture was adjusted to pH 12-14 with 20% aqueous sodium hydroxide. The mixture was extracted with ethyl acetate (30 mL×3). The combined organic layers were washed with brine, dried with anhydrous Na$_2$SO$_4$, filtered, and the filtrate concentrated under reduced pressure to afford a crude product (400 mg, 91.1%) as a brown solid, which was used for the next step without further purification.

B. Ethyl 1-(2-(methylthio)phenyl)-5-(trifluoromethyl)-1H-pyrazole-4-carboxylate, Cpd 137b

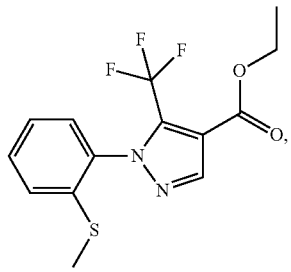

cpd 137b

A solution consisting of ethyl 2-(ethoxymethylene)-4,4,4-trifluoro-3-oxobutanoate, INT1 (1246 mg, 5.19 mmol), (2-(methylthio)phenyl)hydrazine, cpd 137a (400 mg, 2.59 mmol), and ethanol (20 mL) was stirred at 80° C. for 16 h before cooling to room temperature. The resultant solution was concentrated to dryness under reduced pressure to afford the crude product, which was purified by flash column chromatography (petroleum ether:ethyl acetate=100:0 to 80:20) to afford the title compound (800 mg, 92.5%) as a gray solid. LCMS (ESI) m/z M+1: 330.9.

C. 1-(2-(Methylthio)phenyl)-5-(trifluoromethyl)-1H-pyrazole-4-carboxylic Acid. Cpd 137c

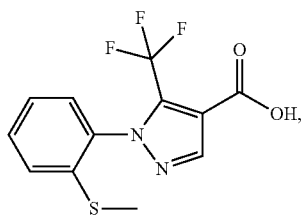

cpd 137c

Lithium hydroxide (100.7 mg, 2.40 mmol) was added to a solution of ethyl 1-(2-(methylthio)phenyl)-5-(trifluoromethyl)-1H-pyrazole-4-carboxylate, cpd 137b (400 mg, 1.2 mmol) in MeOH:H$_2$O=1:1 (10 mL). The mixture was reacted at room temperature for 3 h. The solvent was evaporated under reduced pressure and water (10 mL) was added to the mixture. The mixture was made acidic (pH 5) via the addition of 1M hydrochloric and extracted with ethyl acetate (30 mL×3). The combined organic layers were washed with brine, dried with anhydrous MgSO$_4$, and filtered. The filtrates were concentrated under reduced pressure to afford a product (350 mg, 96.5%) as a yellow solid. $^1$H NMR (400 MHz, CHLOROFORM-d) δ ppm 8.20 (s, 1H), 7.48-7.42 (m, 1H), 7.32 (d, J=7.9 Hz, 1H), 7.23 (d, J=4.4 Hz, 2H), 2.36 (s, 3H).

D. N-(5-Chloro-6-(2H-1,2,3-triazol-2-yl)pyridin-3-yl)-1-(2-(methylthio)phenyl)-5-(trifluoromethyl)-1H-pyrazole-4-carboxamide, Cpd 137

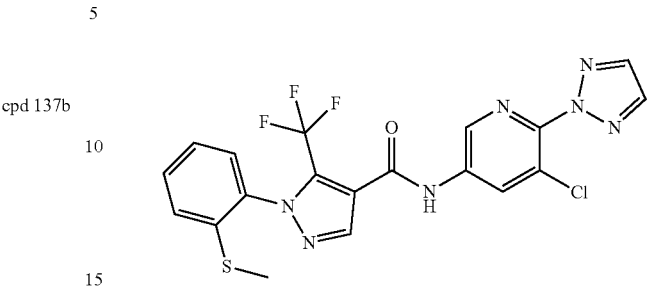

1-(2-(Methylthio)phenyl)-5-(trifluoromethyl)-1H-pyrazole-4-carboxylic acid, cpd 137c (350 mg, 1.16 mmol), 5-amino-2-(2H-1,2,3-triazol-2-yl)nicotinonitrile, INT 2 (226.5 mg, 1.16 mmol), pyridine (106.218 mg, 2.012 mmol) were dissolved in CH$_2$Cl$_2$ (10 mL), and phosphorus oxychloride (335.1 mg, 2.32 mmol) was added. The mixture was stirred at 25° C. for 2 h. Sat.NaHCO$_3$(20 mL) was added and extracted with CH$_2$Cl$_2$ (30 mL×2). The combined organic extracts were dried over anhydrous Na$_2$SO$_4$, filtered, and the filtrate concentrated under reduced pressure to afford the crude product, which was purified by preparative HPLC (50% to 80% (v/v) CH$_3$CN and H$_2$O with 0.05% HCl) and lyophilized to dryness to afford the title compound (80 mg, 13.7%). $^1$H NMR (400 MHz, CHLOROFORM-d) δ ppm 8.77 (d, J=2.2 Hz, 1H), 8.51 (d, J=2.2 Hz, 1H), 8.16 (s, 1H), 8.04 (s, 1H), 7.95 (s, 2H), 7.60-7.52 (m, 1H), 7.42 (d, J=7.9 Hz, 1H), 7.36-7.31 (m, 2H), 2.45 (s, 3H). LC-MS: (ES, m/z): [M+1]$^+$ 480.0.

Example 138

N-(5-chloro-6-(2H-1,2,3-triazol-2-yl)pyridin-3-yl)-1-(2-(methylsulfonyl)phenyl)-5-(trifluoromethyl)-1H-pyrazole-4-carboxamide, Cpd 138

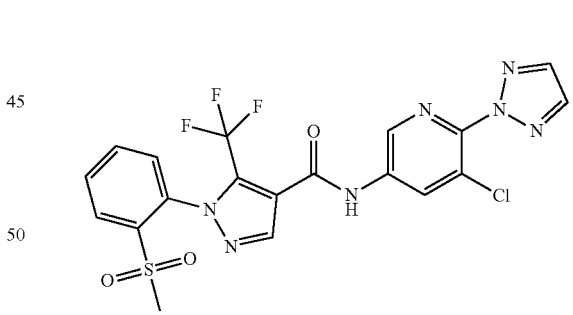

To a solution of N-(5-chloro-6-(2H-1,2,3-triazol-2-yl)pyridin-3-yl)-1-(2-(methylthio)phenyl)-5-(trifluoromethyl)-1H-pyrazole-4-carboxamide, cpd 137 (100 mg, 0.20 mmol) in CH$_2$Cl$_2$ (2 mL) was added m-CPBA (93.1 mg, 0.46 mmol). The mixture was stirred at rt for 3 h. To the mixture was added saturated Na$_2$SO$_3$ (5 mL) and saturated NaHCO$_3$(5 mL). The resulting mixture was extracted with CH$_2$Cl$_2$ (10 mL×2). The combined organic layers were dried over Na$_2$SO$_4$, filtered and the filtrate concentrated to dryness. The residue was purified by flash column chromatography (petroleum ether:EtOAc=3:1-0:1). The desired fractions were evaporated to dryness to give cpd 138 as a white solid. $^1$H NMR (400 MHz, CHLOROFORM-d) δ ppm 8.73

(d, J=2.4 Hz, 1H), 8.51 (d, J=2.4 Hz, 1H), 8.31 (s, 1H), 8.27-8.22 (m, 1H), 8.12 (s, 1H), 7.94 (s, 2H), 7.88-7.82 (m, 2H), 7.54 (br d, J=8.4 Hz, 1H), 3.21 (s, 3H). LC-MS: (ES, m/z): [M+1]$^+$ 512.0

Example 139

1-(6-amino-5-cyanopyridin-2-yl)-N-(5-cyano-6-(2H-H-1,2,3-triazol-2-yl)pyridin-3-yl)-5-(trifluoromethyl)-1H-pyrazole-4-carboxamide, Cpd 139

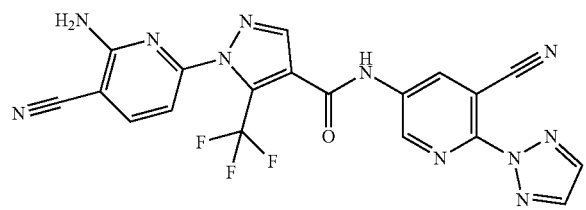 [SMILES: N#Cc1ccc(-n2ncc(C(=O)Nc3cnc(-n4nccn4)c(C#N)c3)c2C(F)(F)F)nc1N]

15A. Tert-Butyl (6-chloro-3-cyanopyridin-2-yl)carbamate, Cpd 139a

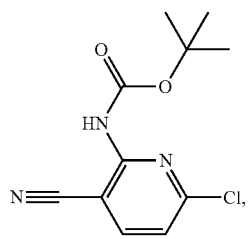

A solution of 2-amino-6-chloronicotinonitrile (118.9 mg, 6.5 mmol) mg, DMAP (31.8 mg, 0.26 mmol) and TEA (988.4 mg, 9.8 mmol) in dichloromethane (15 mL) was added di-tert-butyl decarbonate (4263.5 mg, 19.5 mmol) at RT and the mixture was stirred at RT for 12 h. Sat. NaHCO$_3$(15 mL) was added and the mixture was extracted with EtOAc (20 mL×2). The combined organic layers were dried with Na$_2$SO$_4$. After filtering, the solvent was concentrated under reduced pressure and the resultant residue was purified by column chromatography over silica gel (eluent: petrol ether/EtOAc=100:0 to 70:30). The desired fractions were collected and the solvent was removed to give a white solid (1500 mg, 90.8 mmol). LCMS (ESI) m/z M-55: 198.0.

B. Tert-Butyl (3-cyano-6-hydrazinylpyridin-2-yl)carbamate, Cpd 139b

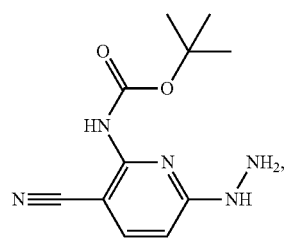

A mixture of palladium(II)(pi-cinnamyl) (153.2 mg, 0.27 mmol) chloride dimer and N-[2-(di-1-adamantylphosphino)phenyl]morpholine (274.1 mg, 0.59 mmol) in dioxane (20 mL) was evacuated with argon 4 times. The resulting clear yellow solution was stirred at RT under argon for 10 min. tert-Butyl (6-chloro-3-cyanopyridin-2-yl)carbamate, cpd 139a (1500 mg, 5.9 mmol) and tBuONa (1136.5 mg, 11.8 mmol) were added to the mixture and evacuated with argon 4 times. The resulting yellow reaction mixture was stirred at RT for 5 min and then treated with hydrazine (592.0 mg, 11.8 mmol) via syringe and then evacuated with argon 4 times. The mixture was stirred at 50° C. under argon for 2 h. After filtering the reaction mixture, the solvent was concentrated under reduced pressure to give the crude product as a yellow solid. LCMS (ESI) m/z M-55: 194.1.

C. Ethyl 1-(6-((tert-butoxycarbonyl)amino)-5-cyanopyridin-2-yl)-5-(trifluoromethyl)-1H-pyrazole-4-carboxylate, Cpd 139c

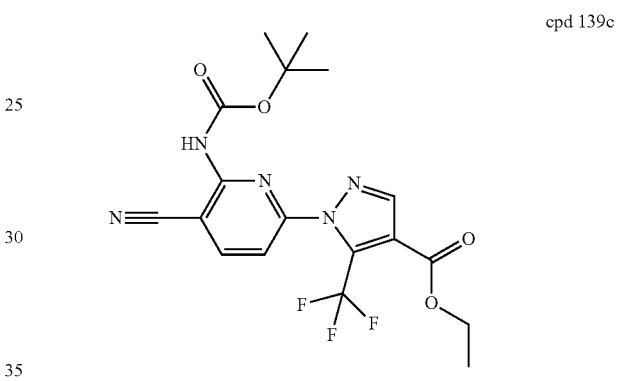

tert-Butyl (3-cyano-6-hydrazinylpyridin-2-yl)carbamate (1100 mg, 1.45 mmol) was added to a solution of ethyl 2-(ethoxymethylene)-4,4,4-trifluoro-3-oxobutanoate, INT1 (522.7 mg, 2.18 mmol) in EtOH (20 mL) was reacted at 80° C. for 1 h. The mixture was concentrated under reduced pressure, then was purified by FFS (petroleum ether/ethyl acetate=100:0 to petroleum ether/ethyl acetate=80:20). The desired fractions were collected and the solvent was concentrated under reduced pressure to afford the product as a white solid. LCMS (ESI) m/z M-55: 370.0.

D. 1-(6-((tert-butoxycarbonyl)amino)-5-cyanopyridin-2-yl)-5-(trifluoromethyl)-1H-pyrazole-4-carboxylic Acid, Cpd 139d

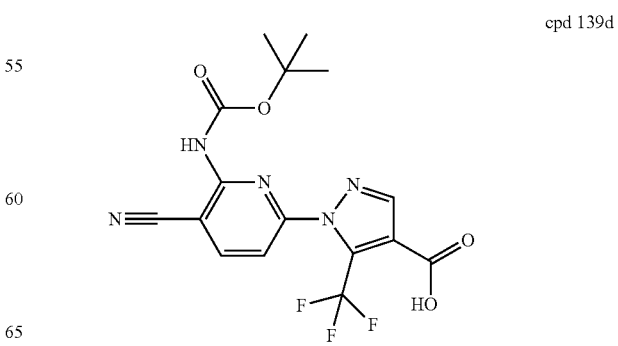

LiOH (125.58 mg, 5.24 mmol) was added to a solution of ethyl 1-(6-((tert-butoxycarbonyl)amino)-5-cyanopyridin-2-yl)-5-(trifluoromethyl)-1H-pyrazole-4-carboxylate (500 mg, 5.24 mmol) in THF/H$_2$O (1:1, 12 mL) was reacted at 23° C. for 2 h. The solvent was concentrated under reduced pressure. 1M HCl solution was added to the mixture to adjust the mixture to pH 5, and the mixture was extracted with EtOAc (30 mL×3). The combined organic layers were dried with Na$_2$SO$_4$, filtered and the filtrates were concentrated under reduced pressure to afford a crude product as a brown oil (470 mg, 94.0%). LCMS (ESI) m/z M-55: 341.8.

E. Tert-Butyl(3-cyano-6-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, cpd 139e

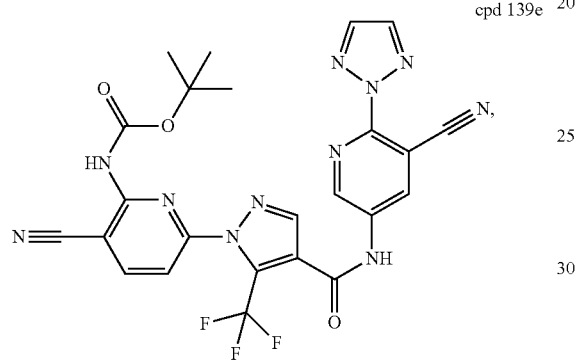

cpd 139e 1-(6-((tert-Butoxycarbonyl)amino)-5-cyanopyridin-2-yl)-5-(trifluoromethyl)-1H-pyrazole-4-carboxylic acid (230 mg, 0.43 mmol), 5-amino-2-[1,2,3]triazol-2-yl-nicotinonitrile, INT3 (94.3 mg, 0.51 mmol), POCl$_3$ (88.8 mg, 0.58 mmol) were dissolved in CH$_2$Cl$_2$ (8 mL), and pyridine (114.5 mg, 1.45 mmol) was added. The mixture was stirred at 25° C. for 1 h. Sat. NaHCO$_3$(10 mL) was added and the mixture extracted with CH$_2$Cl$_2$ (15 mL×2). The combined organic layers were dried with Na$_2$SO$_4$, filtered and the filtrates were concentrated under reduced pressure to afford a crude product as a brown oil, which was purified by FFS (petroleum ether/ethyl acetate=50:50 to petroleum ether/ethyl acetate=0:100). The desired fractions were collected and the solvent was concentrated under reduced pressure to afford the desired product as a yellow solid. LCMS (ESI) m/z M-55: 466.1.

F. 1-(6-Amino-5-cyanopyridin-2-yl)-N-(5-cyano-6-(2H-1,2,3-triazol-2-yl)pyridin-3-yl)-5-(trifluoromethyl)-1H-pyrazole-4-carboxamide, Cpd 139

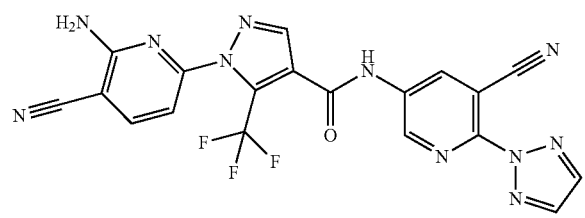 [SMILES: N#Cc1ccc(-n2ncc(C(=O)Nc3cnc(-n4nccn4)c(C#N)c3)c2C(F)(F)F)nc1N]

Silica gel (214.4 mg, 3.57 mmol) was added to a solution of tert-butyl(3-cyano-6-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate (150 mg, 0.24 mmol) in toluene (10 mL). The mixture was reacted at 110° C. for 1 h. The solution was concentrated to afford a white solid, which was then purified by preparative HPLC (63% to 33% (v/v) CH$_3$CN and H$_2$O with 0.05% HCl) and the resultant residue was lyophilized to dryness to afford the title compound (35.2 mg, 30.9%). LCMS (ESI) m/z M+1: 466.0. $^1$H NMR (400 MHz, DMSO-d$_6$) δ ppm 6.99 (d, J=8.16 Hz, 1H), 7.33 (s, 2H), 8.15 (d, J=8.16 Hz, 1H), 8.27 (s, 2H), 8.40 (s, 1H), 8.80 (d, J=2.43 Hz, 1H), 9.03 (d, J=2.43 Hz, 1H).

Example 140

1-(6-amino-5-cyanopyridin-2-yl)-N-(5-chloro-6-(2H-1,2,3-triazol-2-yl)pyridin-3-yl)-5-(trifluoromethyl)-1H-pyrazole-4-carboxamide, Cpd 140

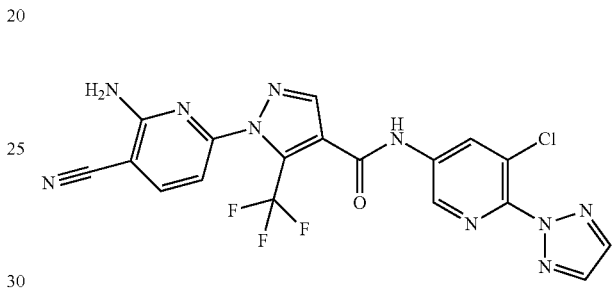

A. Tert-Butyl(6-(4-((5-chloro-6-(2H-1,2,3-triazol-2-yl)pyridin-3-yl)carbamoyl)-5-(trifluoromethyl)-1H-pyrazol-1-yl)-3-cyanopyridin-2-yl)carbamate, Cpd 140a

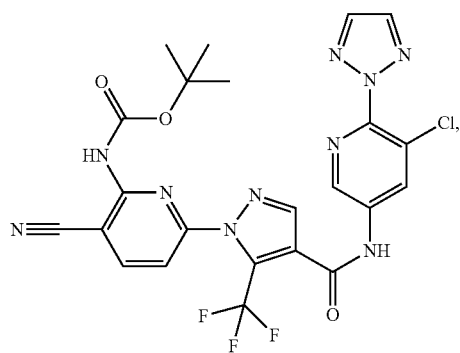

cpd 140a 1-(6-((tert-Butoxycarbonyl)amino)-5-cyanopyridin-2-yl)-5-(trifluoromethyl)-1H-pyrazole-4-carboxylic acid (230 mg, 0.58 mmol), 5-chloro-6-(2H-1,2,3-triazol-2-yl) pyridin-3-amine, INT2 (118.9 mg, 0.61 mmol), POCl$_3$ (88.8 mg, 0.58 mmol) were dissolved in CH$_2$Cl$_2$ (8 mL), and pyridine (106.5 mg, 0.70 mmol) was added. The mixture was stirred at 25° C. for 1 h. Sat. NaHCO$_3$(10 mL) was added and extracted with CH$_2$Cl$_2$ (15 mL×2). The combined organic layers were dried with Na$_2$SO$_4$, filtered and the filtrates were concentrated under reduced pressure to afford a crude product as a brown oil. The oil was purified by FFS (petroleum ether/ethyl acetate=50:50 to petroleum ether/ethyl acetate=0:100). The desired fractions were collected and the solvent was concentrated under reduced pressure to afford the product as a yellow solid. LCMS (ESI) m/z M+23: 597.3.

B. 1-(6-amino-5-cyanopyridin-2-yl)-N-(5-chloro-6-(2H-1,2,3-triazol-2-yl)pyridin-3-yl)-5-(trifluoromethyl)-1H-pyrazole-4-carboxamide, Cpd 140

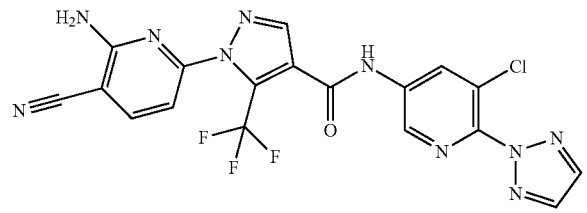 [SMILES: N#Cc1ccc(-n2ncc(C(=O)Nc3cnc(-n4nccn4)c(Cl)c3)c2C(F)(F)F)nc1N]

Silica gel (344.890 mg, 5.740 mmol) was added to a solution of tert-butyl(6-(4-((5-chloro-6-(2H-1,2,3-triazol-2-yl)pyridin-3-yl)carbamoyl)-5-(trifluoromethyl)-1H-pyrazol-1-yl)-3-cyanopyridin-2-yl)carbamate (220 mg, 0.38 mmol) in toluene (10 mL). The mixture was reacted at 110° C. for 1 h. The solution was concentrated to afford a white solid which was purified by preparative HPLC (63% to 33% (v/v) CH$_3$CN and H$_2$O with 0.05% HCl) and lyophilized to dryness to afford the title compound (110 mg, 59.1%). LCMS (ESI) m/z M+1: 474.9. $^1$H NMR (400 MHz, DMSO-d$_6$) δ ppm 6.99 (d, J=8.16 Hz, 1H), 7.33 (s, 2H), 8.05-8.19 (m, 3H), 8.38 (s, 1H), 8.59 (d, J=2.21 Hz, 1H), 8.76 (d, J=2.21 Hz, 1H), 11.11 (s, 1H).

Example 141

1-(6-amino-3-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 141

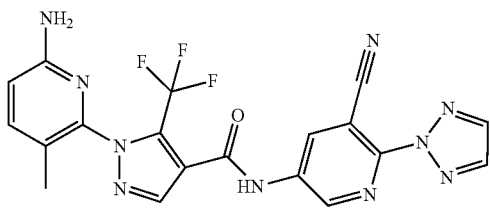 [SMILES: Cc1ccc(N)nc1-n1ncc(C(=O)Nc2cnc(-n3nccn3)c(C#N)c2)c1C(F)(F)F]

A. 2-hydrazinyl-3-methylpyridine, Cpd 141a

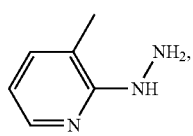

A solution consisting of 2-fluoro-3-methylpyridine (4 g, 36.0 mmol) in hydrazine (1 mL) was stirred at 60° C. for 3 h. The resultant solution was cooled to room temperature and concentrated to dryness under reduced pressure to afford the crude title product 141a (4 g, 90.2% yield).

B. Ethyl 1-(3-methylpyridin-2-yl)-5-(trifluoromethyl)-1H-pyrazole-4-carboxylate, Cpd 141b

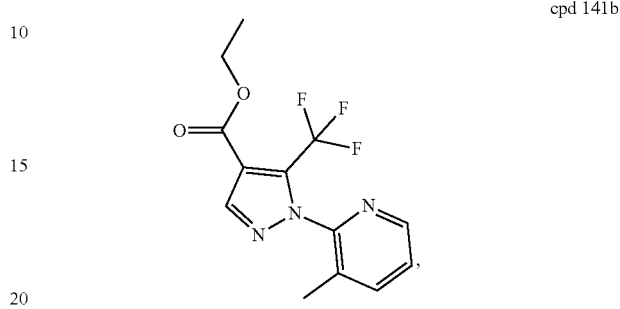

A solution consisting of 2-hydrazinyl-3-methylpyridine (4 g, 32.5 mmol) and ethyl 2-(ethoxymethylene)-4,4,4-trifluoro-3-oxobutanoate (7.8 g, 32.5 mmol) in EtOH (5 mL) was stirred at 60° C. for 3 h. The resultant solution was cooled to room temperature and concentrated to dryness under reduced pressure to afford the crude title product. The crude product was purified by column chromatography over silica gel (petroleum ether/ethyl acetate=100:0 to 70:30). The solvent was concentrated under reduced pressure to afford the title compound (8 g, 82.3% yield) as a yellow solid. LCMS (ESI) m/z M+1: 299.9

C. 2-(4-(ethoxycarbonyl)-5-(trifluoromethyl)-1H-pyrazol-1-yl)-3-methylpyridine 1-oxide, Cpd 141c

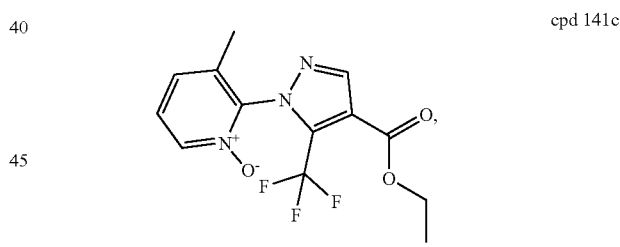

To a cooled solution (0° C.) of ethyl 1-(3-methylpyridin-2-yl)-5-(trifluoromethyl)-1H-pyrazole-4-carboxylate (8 g, 26.7 mmol) in CH$_2$Cl$_2$ (50 mL) was added 3-chlorobenzoperoxoic acid (1.38 g, 80.2 mmol) over 10 min. The mixture was warmed to rt and allowed to stir overnight. The solution was washed twice with a half-saturated aqueous solution of sodium bisulfite (50 mL) to destroy excess oxidant. The mixture was then washed (2×) with half-saturated aqueous potassium carbonate (50 mL), and brine (50 mL). The extracts were dried over magnesium sulfate, filtered and the filtrate concentrated to afford a crude oil. The residue was purified by flash column chromatography over silica gel (eluent: petroleum ether/ethyl acetate from 100/0 to 20/80). The desired fractions were collected and concentrated to dryness under reduced pressure to give Cpd 141c (3.8 g, 38.6% yield) as a yellow solid. LCMS (ESI) m/z M+1: 315.9.

D. Ethyl 1-(6-chloro-3-methylpyridin-2-yl)-5-(trifluoromethyl)-1H-pyrazole-4-carboxylate, Cpd 141d

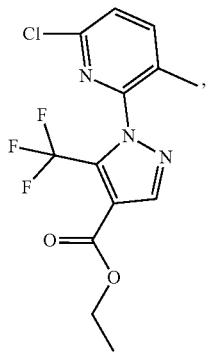

cpd 141d

A solution consisting of phosphoryl trichloride (3.16 g, 20.6 mmol) and 2-(4-(ethoxycarbonyl)-5-(trifluoromethyl)-1H-pyrazol-1-yl)-3-methylpyridine 1-oxide (3.8 g, 10.3 mmol) in CHCl$_3$ (20 mL) was stirred at 60° C. for 3 h. Sat. NaHCO$_3$ solution (50 mL) was added to the mixture. The resultant solution was cooled to room temperature and concentrated to dryness under reduced pressure to afford the crude title product. The crude product was purified by column chromatography over silica gel (petroleum ether/ethyl acetate=100:0 to 70:30). The solvent was concentrated under reduced pressure to afford the title compound (2.6 g, 75.5% yield) as a yellow solid. LCMS (ESI) m/z M+1: 333.9.

E. Ethyl 1-(6-((tert-butoxycarbonyl)amino)-3-methylpyridin-2-yl)-5-(trifluoromethyl)-1H-pyrazole-4-carboxylate, Cpd 141e

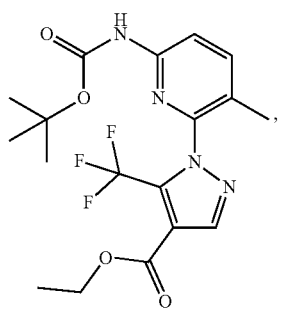

cpd 141e 2-(4-(ethoxycarbonyl)-5-(trifluoromethyl)-1H-pyrazol-1-yl)-3-methylpyridine 1-oxide (2.6 g, 7.79 mmol), tert-butyl carbamate (1.10 g, 9.35 mmol) and cesium carbonate (5.08 g, 15.58 mmol) were dissolved in dioxane, Pd$_2$(dba)$_3$ (356.7 mg, 0.39 mmol) and Xantphos (450.8 mg, 0.78 mmol) were added and purged with N$_2$ for 1 min. The reaction mixture was stirred at 100° C. for 16 hrs. The mixture was filtered through a pad of celite and the pad was washed with ethyl acetate (50 mL×2). The crude product was purified by column chromatography over silica gel (petroleum ether/ethyl acetate=100:0 to 70:30). The solvent was evaporated to get the product the title compound (1.5 g, 46.5% yield) as yellow solid. LCMS (ESI) m/z M+1: 359.0.

F. 1-(6-((tert-butoxycarbonyl)amino)-3-methylpyridin-2-yl)-5-(trifluoromethyl)-1H-pyrazole-4-carboxylic Acid, Cpd 141f

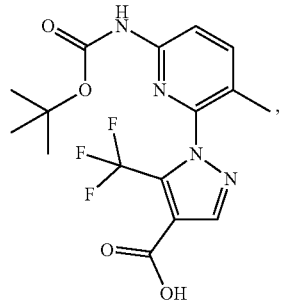

cpd 141f

Lithium hydroxide (433.4 mg, 18.10 mmol) was added to a solution of ethyl 1-(6-((tert-butoxycarbonyl)amino)-3-methylpyridin-2-yl)-5-(trifluoromethyl)-1H-pyrazole-4-carboxylate (1.5 g, 3.62 mmol) in THF/H$_2$O=1:1 (10 mL). The mixture was reacted at 23° C. for 2 h. The solvent was concentrated under reduced pressure. 1M HCl solution was added to the mixture to adjust the mixture to pH 5 and a solid formed. The solid was collected by filtration to afford the title compound 141f (1.3 g, 71.1% yield). LCMS (ESI) m/z M+1: 330.9.

G. Tert-Butyl(6-(4-((5-cyano-6-(2H-1,2,3-triazol-2-yl)pyridin-3-yl)carbamoyl)-5-(trifluoromethyl)-1H-pyrazol-1-yl)-5-methylpyridin-2-yl)carbamate, Cpd 141g

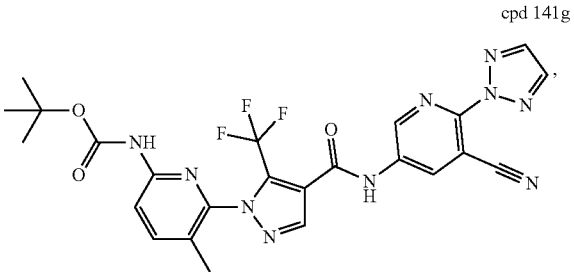 [SMILES: Cc1ccc(NC(=O)OC(C)(C)C)nc1-n1ncc(C(=O)Nc2cnc(-n3nccn3)c(C#N)c2)c1C(F)(F)F]

cpd 141g

POCl$_3$ (0.29 mL) was added to a mixture of 5-amino-2-(2H-1,2,3-triazol-2-yl)nicotinonitrile, INT3 (147.4 mg, 0.79 mmol), 1-(6-((tert-butoxycarbonyl)amino)-3-methylpyridin-2-yl)-5-(trifluoromethyl)-1H-pyrazole-4-carboxylic acid (400 mg, 0.792 mmol) and pyridine (0.32 mL, 3.96 mmol) in CH$_2$Cl$_2$ (10 mL). The reaction mixture was stirred at 25° C. for 2 h. Sat. NaHCO$_3$ solution (20 mL) was added to the mixture. The mixture was extracted with CH$_2$Cl$_2$ (30 mL×2). The combined organic layers were washed with brine, dried with anhydrous Na$_2$SO$_4$, and filtered. The filtrates were concentrated under reduced pressure to afford a crude product as a brown oil, 141g (500 mg, 44.7.% yield). LCMS (ESI) m/z M+1: 555.2.

H. 1-(6-amino-3-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 141

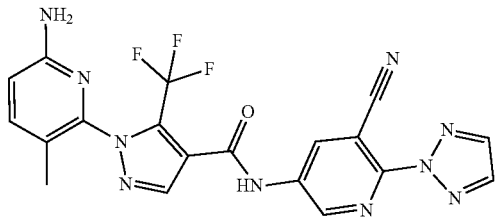 [SMILES: Cc1ccc(N)nc1-n1ncc(C(=O)Nc2cnc(-n3nccn3)c(C#N)c2)c1C(F)(F)F]

HCl/dioxane (0.663 mL) was added to a mixture of tert-butyl(6-(4-((5-cyano-6-(2H-1,2,3-triazol-2-yl)pyridin-3-yl)carbamoyl)-5-(trifluoromethyl)-1H-pyrazol-1-yl)-5-methylpyridin-2-yl)carbamate (500 mg, 0.35 mmol) and CH$_2$Cl$_2$ (5 mL). The reaction mixture was stirred at 25° C. for 2 h. Sat. NaHCO$_3$ solution (20 mL) was added to the mixture. The mixture was extracted with CH$_2$Cl$_2$ (30 mL×2). The combined organic layers were washed with brine, dried with anhydrous Na$_2$SO$_4$, filtered. The filtrates were concentrated under reduced pressure to afford a crude product as a brown oil. The crude product purified by preparative high-performance liquid chromatography. Column: Phenomenex Gemini 150*25 mm*10 um; Condition: A: water(0.05% HCl); B: MeCN; at the beginning: A (90%) and B (10%), at the end: A (10%) and B (90%). The pure fractions were collected and the organic solvent was concentrated under reduced pressure. The aqueous layer was lyophilized to dryness to give the product as a white solid (45 mg, 27.8% yield). LCMS (ESI) m/z M+1: 455.0. $^1$H NMR (400 MHz, DMSO-d$_6$) δ ppm 1.88 (s, 3H), 6.62 (d, J=8.28 Hz, 1H), 7.52 (d, J=8.53 Hz, 1H), 8.32 (s, 2H), 8.44 (s, 1H), 8.87 (d, J=2.51 Hz, 1H), 9.09 (d, J=2.26 Hz, 1H), 11.22 (s, 1H).

Example 142

1-(2-amino-5-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 142

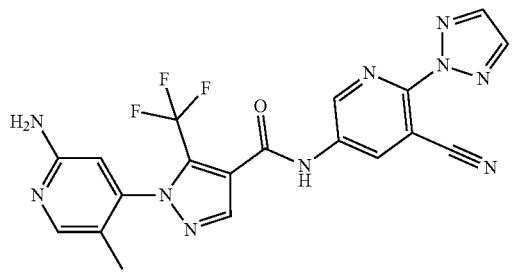 [SMILES: Cc1cnc(N)cc1-n1ncc(C(=O)Nc2cnc(-n3nccn3)c(C#N)c2)c1C(F)(F)F]

A. 4-chloro-3-methylpyridine 1-oxide, Cpd 142a

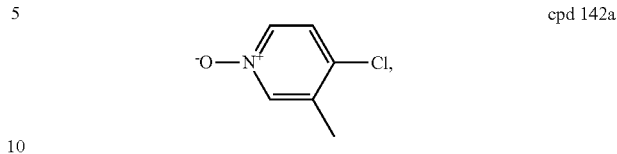

A solution of 4-chloro-3-methylpyridine (6 g, 47.0 mmol) in CH$_2$Cl$_2$ (30 mL) was stirred at room temperature overnight. Sat. NaHCO$_3$ was added to quench the reaction (pH 8-9). The mixture was extracted with CH$_2$Cl$_2$ (50 mL×3). The combined organic layers were dried with Na$_2$SO$_4$, filtered and the filtrates were concentrated. The crude product was purified by column chromatography over silica gel (petroleum ether/ethyl acetate from 100/0 to 0/100). The desired fractions were collected and the solvent was concentrated under reduced pressure to afford the title compound (2.9 g, 42.9% yield) as a yellow solid. $^1$H NMR (400 MHz, CHLOROFORM-d) δ ppm 2.33 (s, 3H), 7.25 (d, J=6.84 Hz, 1H), 8.01 (br d, J=6.61 Hz, 1H), 8.11 (s, 1H).

B. 4-hydrazinyl-3-methylpyridine 1-oxide, Cpd 142b

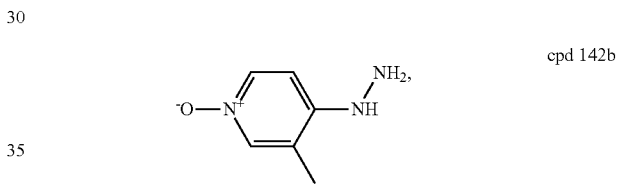

A solution of 4-chloro-3-methylpyridine 1-oxide (2.9 g, 20.2 mmol) in hydrazine (5.16 g, 98%) was stirred at 80° C. overnight. The mixture was concentrated to afford the title compound (2.8 g, crude product) as a yellow solid.

C. 4-(4-(ethoxycarbonyl)-5-(trifluoromethyl)-1H-pyrazol-1-yl)-3-methylpyridine 1-oxide, Cpd 142c

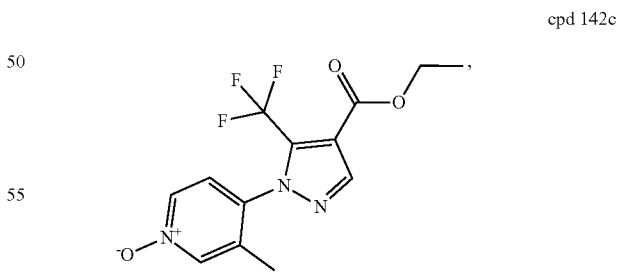

A solution of 4-hydrazinyl-3-methylpyridine 1-oxide (2.8 g, 20.1 mmol), ethyl 2-(ethoxymethylene)-4,4,4-trifluoro-3-oxobutanoate, INT1 (9.67 g, 40.2 mmol), in EtOH (30 mL) was stirred at 80° C. for 1 h. The mixture was concentrated under reduced pressure. The crude product was purified by column chromatography over silica gel (petroleum ether/ethyl acetate from 100/0 to 0/100). The desired fractions were collected and the solvent was concentrated under

D. Ethyl 1-(2-chloro-5-methylpyridin-4-yl)-5-(trifluoromethyl)-1H-pyrazole-4-carboxylate and ethyl 1-(2-chloro-3-methylpyridin-4-yl)-5-(trifluoromethyl)-1H-pyrazole-4-carboxylate, Cpd 142d

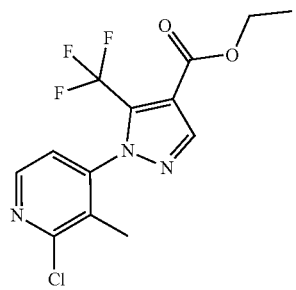

cpd 142d

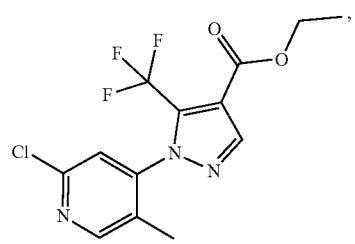

A solution of 4-(4-(ethoxycarbonyl)-5-(trifluoromethyl)-1H-pyrazol-1-yl)-3-methylpyridine 1-oxide (2.3 g, 7.3 mmol) in POCl₃ (15 mL) was stirred at 100° C. for 2 h. The mixture was diluted by CH₂Cl₂ (30 mL). Sat.Na₂CO₃ solution was added dropwise to the mixture with stirring at 0° C. to bring the solution to pH 8-9. The mixture was extracted with CH₂Cl₂ (50 mL×3). The combined organic layers were dried with Na₂SO₄, filtered and the filtrates were concentrated. The crude product was purified by column chromatography over silica gel (petroleum ether/ethyl acetate from 100/0 to 50/50). The desired fractions were collected and the solvent was concentrated under reduced pressure to afford the title compound (1.57 g, 64% yield) as a yellow solid. LCMS (ESI) m/z M+1: 333.8, $^1$H NMR (400 MHz, CHLOROFORM-d) δ ppm 1.40 (t, J=7.06 Hz, 3H), 2.08 (s, 3H), 4.40 (q, J=7.06 Hz, 2H), 7.29 (s, 1H), 8.21 (s, 1H), 8.45 (s, 1H); $^1$H NMR (400 MHz, CHLOROFORM-d) δ ppm 1.40 (t, J=7.06 Hz, 3H), 2.12 (s, 3H), 4.40 (q, J=7.06 Hz, 2H), 7.19 (d, J=5.29 Hz, 1H), 8.21 (s, 1H), 8.43 (d, J=5.07 Hz, 1H).

E. Ethyl 1-(2-((tert-butoxycarbonyl)amino)-5-methylpyridin-4-yl)-5-(trifluoromethyl)-1H-pyrazole-4-carboxylate, Cpd 142e

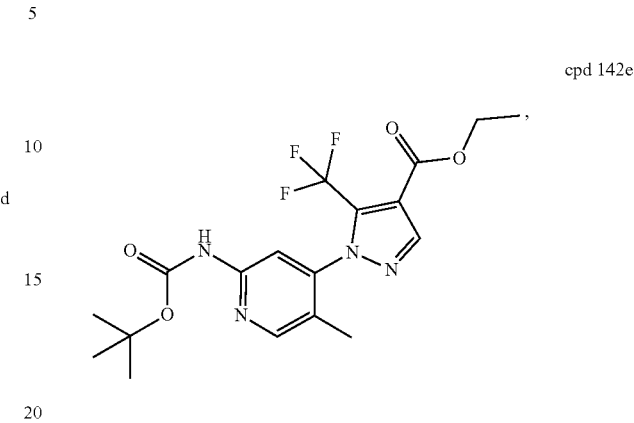

cpd 142e

To a solution of ethyl 1-(2-chloro-3-methylpyridin-4-yl)-5-(trifluoromethyl)-1H-pyrazole-4-carboxylate (1.7 g, 0.61 mmol), tert-butyl carbamate (1.7 g, 2.55 mmol) and Cs₂CO₃ (4.98 g, 15.3 mmol) in dioxane (20 mL), Pd(OAc)₂ (80.1 mg, 0.36 mmol) and Xantphos (206.3 mg, 0.36 mmol) were added under N₂ bubbling. The mixture was stirred at 100° C. overnight under N₂ atmosphere. The reaction solution was filtered and washed by ethyl acetate (30 mL). The filtrate was concentrated to give a crude product. The crude product was purified by column chromatography over silica gel (petroleum ether/ethyl acetate from 100/0 to 0/100). The desired fractions were collected and the solvent was concentrated under reduced pressure to afford the title compound (1.2 g, 57% yield) as a yellow solid. LCMS (ESI) m/z M+1: 315.1.

F. 1-(quinolin-4-yl)-5-(trifluoromethyl)-1H-pyrazole-4-carboxylic Acid, Cpd 142f

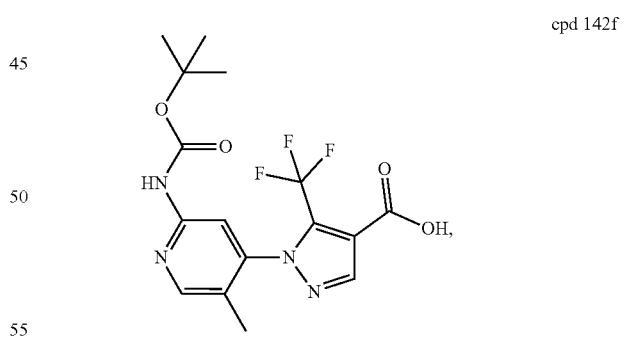

cpd 142f

A solution of ethyl 1-(2-((tert-butoxycarbonyl)amino)-5-methylpyridin-4-yl)-5-(trifluoromethyl)-1H-pyrazole-4-carboxylate (1.2 g, 0.61 mmol), LiOH.H₂O (243.0 mg, 0.39 mmol) in THF/H₂O (2/1, 10 mL) was stirred at room temperature for 3 h. 1N HCl solution was added to neutralize the reaction solution. The mixture was extracted with ethyl acetate (5 mL×3). The organic layer was isolated, dried (Na₂SO₄), filtered, and the filtrate concentrated under reduced pressure to afford the title compound (119 mg, crude product) as a yellow solid. LCMS (ESI) m/z M+1: 331.1.

G. Tert-butyl (4-(4-((5-cyano-6-(2H-1,2,3-triazol-2-yl)pyridin-3-yl)carbamoyl)-5-(trifluoromethyl)-1H-pyrazol-1-yl)-5-methylpyridin-2-yl)carbamate, Cpd 142g

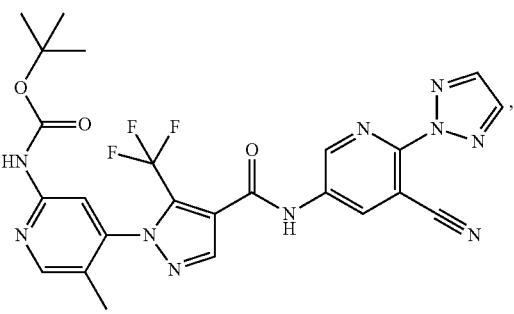

cpd 142g

Phosphorus oxychloride (219.6 uL, 0.42 mmol) was added to a solution of 1-(quinolin-4-yl)-5-(trifluoromethyl)-1H-pyrazole-4-carboxylic acid (500 mg, 1.18 mmol), 5-amino-2-[1,2,3]triazol-2-yl-nicotinonitrile, INT3 (263.1 mg, 1.41 mmol), pyridine (952.6 uL, 11.78 mmol) in $CH_2Cl_2$ (5 mL). The mixture was stirred at room temperature for 1 h. Water (5 mL) was added to the mixture. Sat. $NaHCO_3$ was added to adjust the pH of the reaction mixture to 7-8. The mixture was extracted with $CH_2Cl_2$ (10 mL×3). The combined organic extracts were dried over anhydrous $MgSO_4$, filtered, and the filtrate was concentrated to dryness under reduced pressure to afford the title compound (600 mg, crude product). LCMS (ESI) m/z M+1: 555.2.

H. 1-(1-aminoisoquinolin-4-yl)-N-(5-cyano-6-(2H-1,2,3-triazol-2-yl)pyridin-3-yl)-5-(trifluoromethyl)-1H-pyrazole-4-carboxamide, Cpd 142

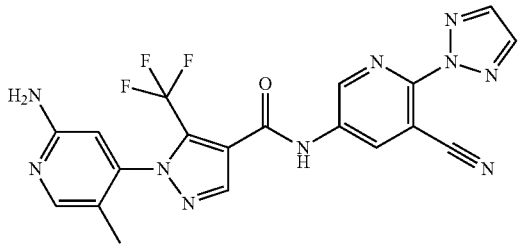 [SMILES: Cc1cnc(N)cc1-n1ncc(C(=O)Nc2cnc(-n3nccn3)c(C#N)c2)c1C(F)(F)F]

A mixture of tert-butyl (4-(4-((5-cyano-6-(2H-1,2,3-triazol-2-yl)pyridin-3-yl)carbamoyl)-5-(trifluoromethyl)-1H-pyrazol-1-yl)-5-methylpyridin-2-yl)carbamate (600 mg, 0.74 mmol) and silica gel (1334.9 mg, 22.22 mmol) in toluene (10 mL) was stirred at 120° C. overnight. The mixture was concentrated to give a crude product, which was purified by column chromatography over silica gel (petroleum ether/ethyl acetate from 100/0 to 0/100). The desired fractions were collected and evaporated to afford the product, which was further purified by preparative HPLC (10% to 40% (v/v) $CH_3CN$ and $H_2O$ with 0.05% HCl) and lyophilized to dryness to afford the title compound (80 mg, 23.2%). LCMS (ESI) m/z M+1: 454.9. $^1$H NMR (400 MHz, DMSO-$d_6$) δ ppm 1.88 (s, 3H), 6.99 (s, 1H), 8.10 (s, 1H), 8.30 (s, 2H), 8.61 (s, 1H), 8.86 (d, J=2.43 Hz, 1H), 9.10 (d, J=2.43 Hz, 1H), 11.42 (s, 1H).

Example 143

1-(2-amino-3-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 143

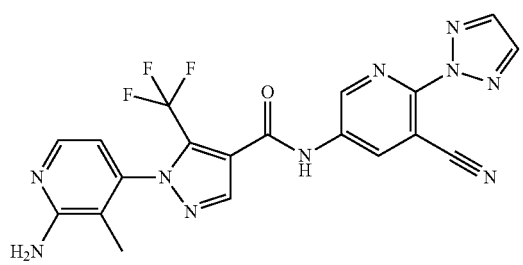 [SMILES: Cc1c(-n2ncc(C(=O)Nc3cnc(-n4nccn4)c(C#N)c3)c2C(F)(F)F)ccnc1N]

A. Ethyl 1-(2-amino-3-methylpyridin-4-yl)-5-(trifluoromethyl)-1H-pyrazole-4-carboxylate, Cpd 143a

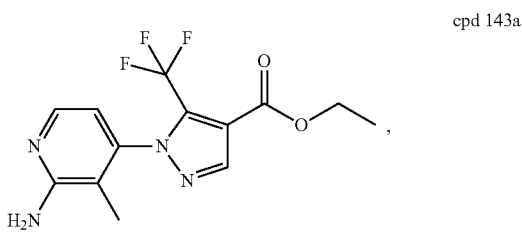 [SMILES: CCOC(=O)c1cnn(-c2ccnc(N)c2C)c1C(F)(F)F]

cpd 143a

To a solution of ethyl 1-(2-chloro-5-methylpyridin-4-yl)-5-(trifluoromethyl)-1H-pyrazole-4-carboxylate (750 mg, 1.12 mmol), tert-butyl carbamate (533.6 mg, 2.55 mmol) and $Cs_2CO_3$ (2.23 g, 6.83 mmol) in dioxane (20 mL), Pd(OAc)$_2$ (25.6 mg, 0.36 mmol) and Xantphos (65.9 mg, 0.11 mmol) were added under $N_2$ bubbling. The mixture was stirred at 110° C. overnight under a $N_2$ atmosphere. The reaction mixture was filtered and washed by ethyl acetate (20 mL). The filtrate was concentrated to give a crude product. The crude product was purified by column chromatography over silica gel (petroleum ether/ethyl acetate from 100/0 to 0/100). The desired fractions were collected and the solvent was concentrated under reduced pressure to afford the title compound (150 mg, 21% yield) as a yellow solid. LCMS (ESI) m/z M+1: 315.1.

B. Ethyl 1-(2-((tert-butoxycarbonyl)amino)-3-methylpyridin-4-yl)-5-(trifluoromethyl)-1H-pyrazole-4-carboxylate, Cpd 143b

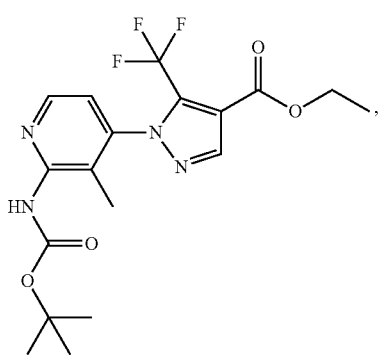

cpd 143b

A solution of ethyl 1-(2-amino-3-methylpyridin-4-yl)-5-(trifluoromethyl)-1H-pyrazole-4-carboxylate (150 mg, 0.24 mmol) and Boc$_2$O (416.7 mg, 1.91 mmol), DMAP (5.83 mg, 0.048 mmol) and TEA (200 μL, 1.43 mmol) in THF (5 mL) was stirred at room temperature overnight. The mixture was evaporated to give a crude product. The crude product was purified by column chromatography over silica gel (petroleum ether/ethyl acetate from 100/0 to 50/50). The desired fractions were collected and the solvent was concentrated under reduced pressure to afford the title compound (120 mg, 60% yield) as a yellow solid. LCMS (ESI) m/z M+1: 359.1.

C. 1-(2-((tert-butoxycarbonyl)amino)-3-methylpyridin-4-yl)-5-(trifluoromethyl)-1H-pyrazole-4-carboxylic Acid, Cpd 143c

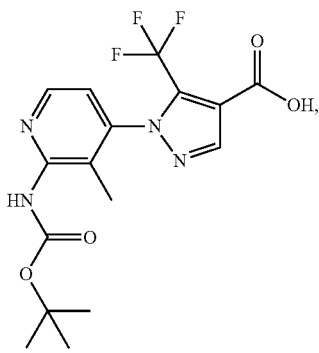

cpd 143c

A solution of ethyl 1-(2-((tert-butoxycarbonyl)amino)-3-methylpyridin-4-yl)-5-(trifluoromethyl)-1H-pyrazole-4-carboxylate (1.2 g, 0.61 mmol), LiOH.H$_2$O (243.0 mg, 0.39 mmol) in THF/H$_2$O (2/1, 2 mL) was stirred at room temperature for 3 h. 1N HCl solution was added to neutralize the reaction solution (pH 5-6). The mixture was extracted with ethyl acetate (10 mL×3). The separated organic layer was dried (Na$_2$SO$_4$), filtered, and the solvent was concentrated under reduced pressure to afford the title compound (110 mg, 98% yield) as a yellow solid.

D. Tert-butyl (4-(4-((5-cyano-6-(2H-1,2,3-triazol-2-yl)pyridin-3-yl)carbamoyl)-5-(trifluoromethyl)-1H-pyrazol-1-yl)-3-methylpyridin-2-yl)carbamate, Cpd 143d

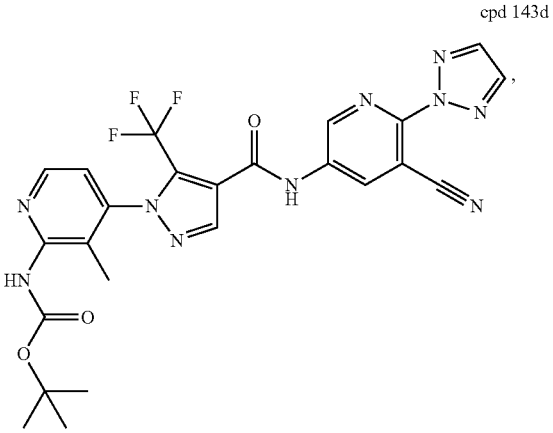 [SMILES: Cc1c(-n2ncc(C(=O)Nc3cnc(-n4nccn4)c(C#N)c3)c2C(F)(F)F)ccnc1NC(=O)OC(C)(C)C]

cpd 143d

Phosphorus oxychloride (53 μL, 0.57 mmol) was added to a solution of 1-(2-((tert-butoxycarbonyl)amino)-3-methylpyridin-4-yl)-5-(trifluoromethyl)-1H-pyrazole-4-carboxylic acid (110 mg, 0.29 mmol), 5-amino-2-[1,2,3]triazol-2-yl-nicotinonitrile, INT3 (79.5 mg, 0.43 mmol), pyridine (460 uL, 5.7 mmol) in CH$_2$Cl$_2$ (5 mL). The mixture was stirred at room temperature for 1 h. Water (5 mL) was added to the mixture. Sat. NaHCO$_3$ was added to adjust the pH of the reaction mixture to 7-8. The mixture was extracted with CH$_2$Cl$_2$ (10 mL×3). The combined organic extracts were dried over anhydrous MgSO$_4$, filtered, and the filtrate was concentrated to dryness under reduced pressure to afford the title compound (200 mg, crude product). LCMS (ESI) m/z M+1: 499.1.

E. 1-(2-amino-3-methylpyridin-4-yl)-N-(5-cyano-6-(2H-1,2,3-triazol-2-yl)pyridin-3-yl)-5-(trifluoromethyl)-1H-pyrazole-4-carboxamide, Cpd 143

A mixture of tert-butyl (4-(4-((5-cyano-6-(2H-1,2,3-triazol-2-yl)pyridin-3-yl)carbamoyl)-5-(trifluoromethyl)-1H-pyrazol-1-yl)-3-methylpyridin-2-yl)carbamate (200 mg, 0.213 mmol) and silica gel (510.7 mg, 8.5 mmol) in toluene (5 mL) was stirred at 120° C. overnight. The mixture was filtered and concentrated to give a crude product, which was purified by preparative HPLC (35% to 65% (v/v) CH$_3$CN and H$_2$O with 0.05% HCl) and lyophilized to dryness to afford the title compound (25 mg, 25.0%). LCMS (ESI) m/z M+1: 455.2. $^1$H NMR (400 MHz, DMSO-d$_6$) δ ppm 1.82 (s, 3H), 6.99 (d, J=6.39 Hz, 1H), 8.06 (d, J=6.62 Hz, 1H), 8.27 (s, 2H), 8.65 (s, 1H), 8.86 (d, J=2.43 Hz, 1H), 9.11 (d, J=2.43 Hz, 1H), 11.46 (s, 1H).

Example 144

1-(6-amino-5-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 144

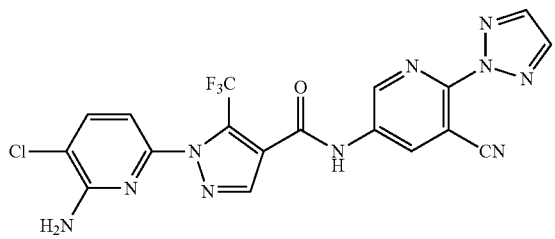 [SMILES: N#Cc1cc(NC(=O)c2cnn(-c3ccc(Cl)c(N)n3)c2C(F)(F)F)cnc1-n1nccn1]

A. Di-tert-butyl (3,6-dichloropyridin-2-yl)carbamate, Cpd 144a

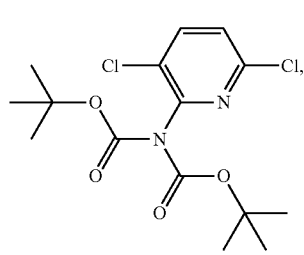

A solution of 3,6-dichloropyridin-2-amine (1 g, 6.14 mmol), (Boc)$_2$O (2677.8 mg, 12.27 mmol), Et$_3$N (1858.8 mg, 18.40 mmol), DMAP (74.84 mg, 0.61 mmol) in CH$_2$Cl$_2$ (30 mL) was stirred at rt for 12 h. The mixture was diluted with water (100 mL) and extracted with CH$_2$Cl$_2$ (100 mL×3). The organic layers were dried (MgSO$_4$) and concentrated under reduced pressure. The residue was purified by column chromatography over silica gel (eluent: petrol ether/EtOAc=100:0 to 10:1). The desired fractions were collected and the solvent was concentrated under reduced pressure to afford the title compound (2.2 g, 98.7% yield) as colorless oil. LCMS (ESI) m/z M+1: 384.9.

B. Tert-butyl (3-chloro-6-hydrazinylpyridin-2-yl)carbamate, Cpd 144b

The mixture of {Pd(cinnamyl)Cl}$_2$ (78. Mg, 0.15 mmol) and Mor-DalPhos (140.4 mg, 0.30 mmol) in dioxane (5 mL) was evacuated with argon 4 times. The resulting clear yellow solution was stirred at rt under argon for 10 min. Di-tert-butyl (3,6-dichloropyridin-2-yl)carbamate (1.1 g 3.0 mmol) and t-BuONa (581.4 mg 6.06 mmol) was added to the mixture and the mixture was evacuated with argon 4 times. The resulting yellow reaction was stirred at rt for 5 min and was then treated with. N$_2$H$_4$—H$_2$O (309.4 mg 6.06 mmol) via syringe. The reaction was evacuated with argon 4 times, then the mixture was stirred at 50° C. under argon for 2 h. The mixture was filtered and washed with ethyl acetate (50 mL×3). The filtrate was collected and concentrated to afford the title compound (1.3 g, 96.6% yield) as a yellow solid. LCMS (ESI) m/z M+1: 258.9.

C. Ethyl 1-(6-((tert-butoxycarbonyl)amino)-5-chloropyridin-2-yl)-5-(trifluoromethyl)-1H-pyrazole-4-carboxylate, Cpd 144c

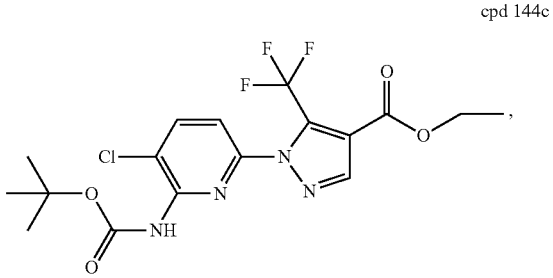 [SMILES: CCOC(=O)c1cnn(-c2ccc(Cl)c(NC(=O)OC(C)(C)C)n2)c1C(F)(F)F]

A solution of tert-butyl (3-chloro-6-hydrazinylpyridin-2-yl)carbamate (1.3 g, 2.92 mmol), ethyl 2-(ethoxymethylene)-4,4,4-trifluoro-3-oxobutanoate (1.05 g, 4.4 mmol), Et$_3$N (0.89 g, 8.8 mmol) in EtOH (30 mL) was stirred at 80° C. for 12 h. The mixture was concentrated under reduced pressure. The crude product was purified by column chromatography over silica gel (petroleum ether/ethyl acetate from 20:1 to 3:1). The desired fractions were collected and the solvent was concentrated under reduced pressure to give the crude product as a yellow oil. The product was purified by preparative high-performance liquid chromatography over Column: Gemini 150*25 5u Condition: A: water (0.05% ammonia hydroxide v/v) B: CH$_3$CN. At the beginning: A (45%) and B (55%) At the end: A: (15%) and B (85%) Gradient Time (min) 10; 100% B Hold Time (min) 2; Flow Rate(mL/min) 25. The pure fractions were collected and the solvent was concentrated under reduced pressure. The aqueous layer was lyophilized to dryness to afford the title compound (120 mg, 9.4% yield) as a yellow oil. LCMS (ESI) m/z M+1: 457.0.

D. 1-(6-((tert-butoxycarbonyl)amino)-5-chloropyridin-2-yl)-5-(trifluoromethyl)-1H-pyrazole-4-carboxylic Acid, Cpd 144d

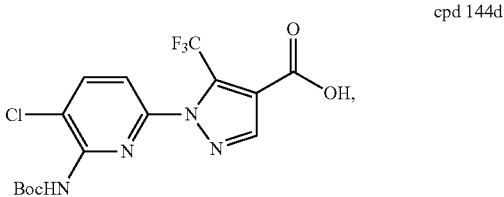 [SMILES: CC(C)(C)OC(=O)Nc1nc(-n2ncc(C(=O)O)c2C(F)(F)F)ccc1Cl]

LiOH (3.2 mg 0.55 mmol) was added to a solution of ethyl 1-(6-((tert-butoxycarbonyl)amino)-5-chloropyridin-2-yl)-5-(trifluoromethyl)-1H-pyrazole-4-carboxylate (120 mg, 0.28 mmol), THF (10 mL) in water (10 mL). The mixture was stirred at rt for 2 h. The mixture was added 5% $KHSO_4$ to adjust the pH to 3-4. Water (100 mL) and ethyl acetate (100 mL) were added to the mixture. The organic layer was washed with brine (50 mL), dried over $MgSO_4$ and concentrated under reduced pressure to afford the title compound (100 mg, 89.1% yield) as a yellow solid, used for next step directly. LCMS (ESI) m/z M+1: 428.9.

E. Tert-butyl (3-chloro-6-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, Cpd 144e

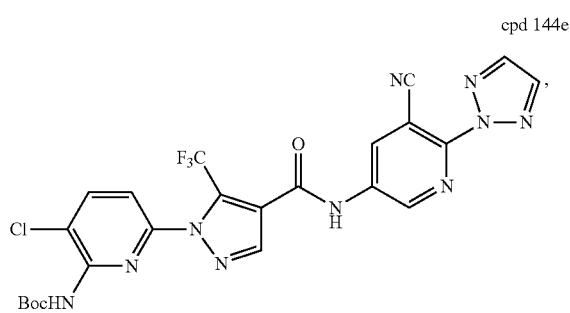 [SMILES: CC(C)(C)OC(=O)Nc1nc(-n2ncc(C(=O)Nc3cnc(-n4nccn4)c(C#N)c3)c2C(F)(F)F)ccc1Cl]

$POCl_3$ (75.395 mg 0.492 mmol) was added to a solution of 1-(6-((tert-butoxycarbonyl)amino)-5-chloropyridin-2-yl)-5-(trifluoromethyl)-1H-pyrazole-4-carboxylic acid (100 mg, 0.25 mmol), 5-Amino-2-[1,2,3]triazol-2-yl-nicotinonitrile, INT3 (54.9 mg, 0.30 mmol), pyridine (8.6 mg, 0.62 mmol) in $CH_2Cl_2$ (10 mL). The mixture was stirred at rt for 2 h. 50 mL $H_2O$ and 50 mL $CH_2Cl_2$ were added to the mixture. The organic layer was washed with brine (50 mL), dried over $MgSO_4$ and concentrated under reduced pressure to afford the title compound (200 mg, 88.2% yield) as a brown solid for the next step directly. LCMS (ESI) m/z M+1: 597.0.

F. 1-(6-amino-5-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 144

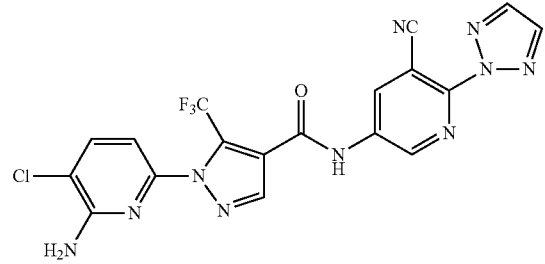 [SMILES: N#Cc1cc(NC(=O)c2cnn(-c3ccc(Cl)c(N)n3)c2C(F)(F)F)cnc1-n1nccn1]

tert-Butyl (3-chloro-6-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate (200 mg, 0.22 mmol) was added to HCl/dioxane (10 mL). The mixture was stirred at rt for 2 h. The mixture was concentrated under reduced pressure. The crude material was purified by preparative high-performance liquid chromatography. Column: Phenomenex Gemini 150*25 mm*10 um. Condition: A: water (0.05% HCl). B: $CH_3CN$. At the beginning: A (60%) and B (40%) At the end: A: (40%) and B (60%). Gradient Time (min) 10; 100% B Hold Time (min) 3; Flow Rate(mL/min) 25. The pure fractions were collected and the solvent was concentrated under reduced pressure. The aqueous layer was lyophilized to dryness to afford the title compound (21.1 mg, 19.0% yield) as a yellow solid. LCMS (ESI) m/z M+1: 474.9. $^1$H NMR (400 MHz, DMSO-$d_6$) δ ppm 6.77 (s, 2H), 6.84 (d, J=7.94 Hz, 1H), 7.83 (d, J=7.94 Hz, 1H), 8.27 (s, 2H), 8.36 (s, 1H), 8.81 (d, J=2.43 Hz, 1H), 9.03 (d, J=2.65 Hz, 1H), 11.29 (br s, 1H).

Example 145

1-(6-amino-5-fluoro-3-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 145

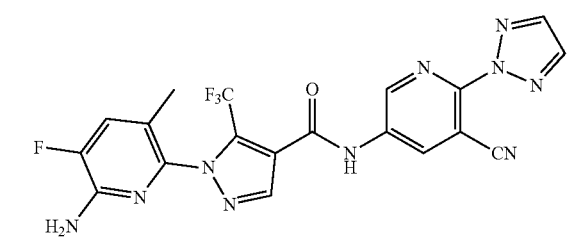 [SMILES: Cc1cc(F)c(N)nc1-n1ncc(C(=O)Nc2cnc(-n3nccn3)c(C#N)c2)c1C(F)(F)F]

A. 5-fluoro-2-hydrazinyl-3-methylpyridine, Cpd 145a

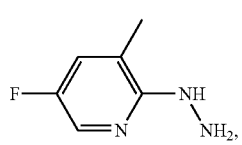

A mixture of {Pd(cinnamyl)Cl}₂ (711.8 mg, 1.37 mmol) and Mor-DalPhos (1274.1 mg, 2.75 mmol) in dioxane (80 mL) was evacuated with argon 4 times. The resulting clear yellow solution was stirred at rt under argon for 10 min. 2-Chloro-5-fluoro-3-methylpyridine (4 g, 27.48 mmol) and t-BuONa (5.28 g, 54.96 mmol) was added to the mixture and the mixture was evacuated with argon 4 times. The resulting yellow reaction mixture was stirred at rt for 5 min and was then treated with hydrazine hydrate (2.81 g, 54.96 mmol) via syringe. The reaction was evacuated with argon 4 times. The mixture was then stirred at 50° C. under argon for 2 h. The mixture was filtered and washed with ethyl acetate (100 mL×3). The filtrate was collected and concentrated to give the title compound (5 g, 128.9% crude yield) as a brown solid that was used directly for next the step.

B. Ethyl 1-(5-fluoro-3-methylpyridin-2-yl)-5-(trifluoromethyl)-1H-pyrazole-4-carboxylate, Cpd 145b

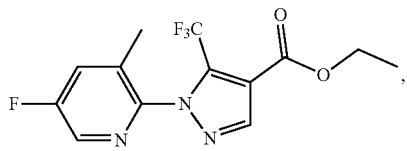

A solution of 5-fluoro-2-hydrazinyl-3-methylpyridine (5 g, 35.4 mmol), ethyl 2-(ethoxymethylene)-4,4,4-trifluoro-3-oxobutanoate, INT1 (12.77 g, 53.14 mmol), TEA (10.73 g, 106.27 mmol) in EtOH (100 mL) was stirred at 80° C. for 12 h. The mixture was concentrated under reduced pressure. The crude product was purified by column chromatography over silica gel (petroleum ether/ethyl acetate from 20:1 to 5:1). The desired fractions were collected and the solvent was concentrated under reduced pressure to give the product 145b (10 g, 81.8% yield) as a yellow oil. LCMS (ESI) m/z M+1: 317.9.

C. 2-(4-(ethoxycarbonyl)-5-(trifluoromethyl)-1H-pyrazol-1-yl)-5-fluoro-3-methylpyridine 1-oxide, Cpd 145c

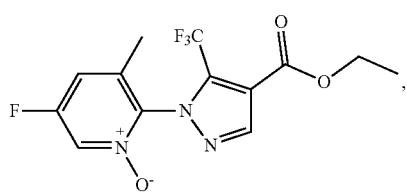

A solution of ethyl 1-(5-fluoro-3-methylpyridin-2-yl)-5-(trifluoromethyl)-1H-pyrazole-4-carboxylate (10 g, 28.96 mmol), 3-chlorobenzoperoxoic acid (18.74 g, 86.89 mmol) in 1,2-dichloroethane (100 mL) was stirred at 80° C. for 16 h. The reaction mixture was quenched with sat. NaHCO₃ (1000 mL) and the mixture was extracted with ethyl acetate (500 mL×3). The organic layers were combined, dried over Na₂SO₄, filtered and concentrated under reduced pressure to give the crude product as a colorless oil. The crude product was purified by chromatography column on silica gel (eluent: petroleum ether/ethyl acetate=10/1 to 1/1). The desired fractions were collected and the solvent was concentrated under reduced pressure to afford the product (4.5 g, 45.8% yield) as a yellow oil. LCMS (ESI) m/z M+1: 334.3.

D. Ethyl 1-(6-chloro-5-fluoro-3-methylpyridin-2-yl)-5-(trifluoromethyl)-1H-pyrazole-4-carboxylate, Cpd 145d

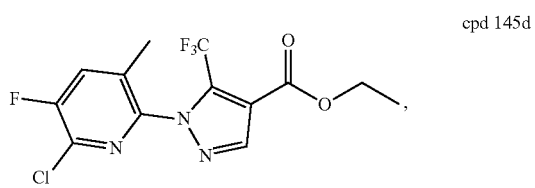 [SMILES: CCOC(=O)c1cnn(-c2nc(Cl)c(F)cc2C)c1C(F)(F)F]

2-(4-(Ethoxycarbonyl)-5-(trifluoromethyl)-1H-pyrazol-1-yl)-5-fluoro-3-methylpyridine 1-oxide (4.5 g, 13.26 mmol) was added to a solution of POCl₃ (122 g, 795.66 mmol) in CHCl₃ (40 mL). The mixture was stirred at 90° C. for 18 h. The mixture was diluted with water (50 mL) and extracted with CH₂Cl₂ (30 mL×3). The organic layer was dried (MgSO₄) and concentrated. The crude product was purified by column chromatography over silica gel (petroleum ether/ethyl acetate from 20:1 to 5:1). The desired fractions were collected and the solvent was concentrated under reduced pressure to give the product Id (4.3 g, 90.0% yield) as a yellow oil. LCMS (ESI) m/z M+1: 351.9. ¹H NMR (400 MHz, CHLOROFORM-d) δ ppm 1.37 (t, J=7.17 Hz, 3H), 2.15 (s, 3H), 4.36 (d, J=7.06 Hz, 2H), 7.50-7.60 (m, 1H), 8.12-8.20 (m, 1H).

E. Ethyl 1-(6-((tert-butoxycarbonyl)amino)-5-fluoro-3-methylpyridin-2-yl)-5-(trifluoromethyl)-1H-pyrazole-4-carboxylate, Cpd 145e

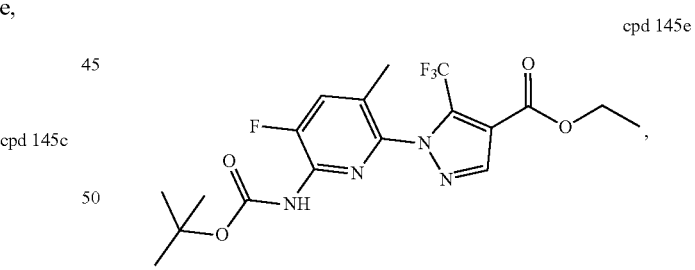

A mixture of ethyl 1-(6-chloro-5-fluoro-3-methylpyridin-2-yl)-5-(trifluoromethyl)-1H-pyrazole-4-carboxylate (2.0 g, 5.55 mmol), tert-butyl carbamate (2.60 g, 22.21 mmol) and Cs₂CO₃ (3.62 g, 11.11 mmol) in dioxane (50 mL) was added Pd(OAc)₂ (124.7 mg, 0.56 mmol) and Xantphos (642.6 mg, 1.11 mmol) under N₂ and heated to 100° C. for 10 h. The mixture was concentrated under reduced pressure. The crude product was purified by column chromatography over silica gel (petroleum ether/ethyl acetate from 100:1 to 1:1). The desired fractions were collected and the solvent was concentrated under reduced pressure to give the product 145e (2.1 g, 48.5% yield) as a yellow oil. LCMS (ESI) m/z M+1: 332.9 (-Boc).

F. 1-(6-((tert-butoxycarbonyl)amino)-5-fluoro-3-methylpyridin-2-yl)-5-(trifluoromethyl)-1H-pyrazole-4-carboxylic Acid, Cpd 145f

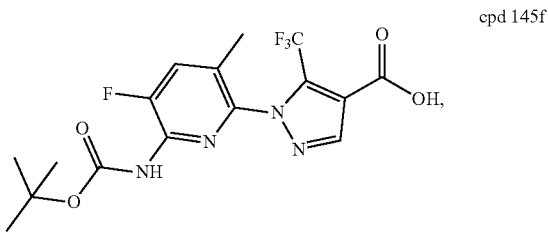 [SMILES: Cc1cc(F)c(NC(=O)OC(C)(C)C)nc1-n1ncc(C(=O)O)c1C(F)(F)F]

cpd 145f

LiOH (349.4 mg, 8.33 mmol) was added to a solution of ethyl 1-(6-((tert-butoxycarbonyl)amino)-5-fluoro-3-methylpyridin-2-yl)-5-(trifluoromethyl)-1H-pyrazole-4-carboxylate, ethyl 1-(6-((tert-butoxycarbonyl)amino)-5-fluoro-3-methylpyridin-2-yl)-5-(trifluoromethyl)-1H-pyrazole-4-carboxylate (1.8 g, 4.16 mmol), THF (30 mL) in water (30 mL). The mixture was stirred at rt for 3 h. To the mixture was added 5% KHSO$_4$ to adjust the pH to 3-4. Water (100 mL) and ethyl acetate (100 mL) were added to the mixture. The organic layer was washed with brine (50 mL), dried over MgSO$_4$, filtered, and the filtrate concentrated under reduced pressure to give the product (1.6 g, 78.5% yield) as a white solid to be used directly in the next step. LCMS (ESI) m/z M+1: 426.9 (+Na).

G. Tert-Butyl (6-(4-((5-cyano-6-(2H-1,2,3-triazol-2-yl)pyridin-3-yl)carbamoyl)-5-(trifluoromethyl)-1H-pyrazol-1-yl)-3-fluoro-5-methylpyridin-2-yl)carbamate, Cpd 145g

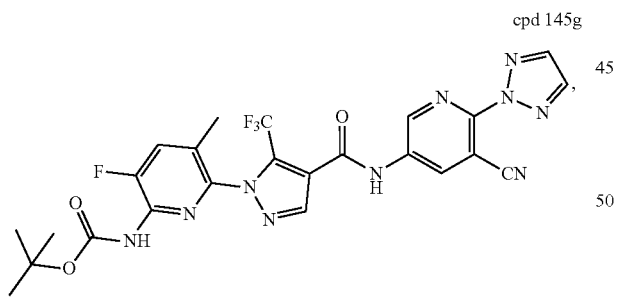

cpd 145g

POCl$_3$ (187.97 mg, 1.23 mmol) was added to a solution of 1-(6-((tert-butoxycarbonyl)amino)-5-fluoro-3-methylpyridin-2-yl)-5-(trifluoromethyl)-1H-pyrazole-4-carboxylic acid (300 mg, 0.61 mmol), 5-amino-2-(2H-1,2,3-triazol-2-yl) nicotinonitrile, INT3 (136.9 mg, 0.74 mmol) and pyridine (121.2 mg, 1.53 mmol) in CH$_2$Cl$_2$ (10 mL). The mixture was stirred at rt for 2 h. Water (50 mL) and CH$_2$Cl$_2$ (50 mL) were added to the mixture. The organic layer was washed with brine (50 mL), dried over MgSO$_4$, filtered, and the filtrate concentrated under reduced pressure to give the product (400 mg, 70.4% yield) as a brown solid to be used directly in the next step. LCMS (ESI) M+1: 595.1(+Na).

H. 1-(6-amino-5-fluoro-3-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 145

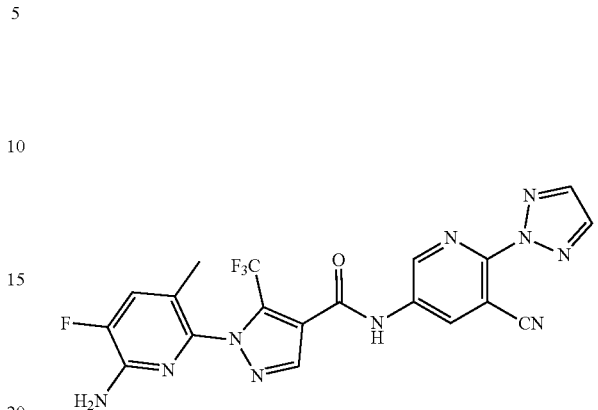

tert-Butyl (6-(4-((5-cyano-6-(2H-1,2,3-triazol-2-yl)pyridin-3-yl)carbamoyl)-5-(trifluoromethyl)-1H-pyrazol-1-yl)-3-fluoro-5-methylpyridin-2-yl)carbamate (400 mg, 0.43 mmol) was added to silica gel (214.4 mg, 3.57 mmol) in toluene (10 mL). The mixture was stirred at rt for 2 h. The mixture was concentrated under reduced pressure. The crude material was purified by preparative high-performance liquid chromatography over Column: Phenomenex Gemini 150*25 mm*10 um. Condition: A: water (0.05% HCl), B: CH$_3$CN; at the beginning: A (68%) and B (32%), at the end: A: (38%) and B (62%); Gradient Time(min) 10; 100% B Hold Time(min) 3; Flow Rate(mL/min) 25. The pure fractions were collected and the solvent was concentrated under reduced pressure. The aqueous layer was lyophilized to dryness to give the product (77.9 mg, 38.1% yield) as a white solid. LCMS (ESI) m/z M+1: 472.9. $^1$H NMR (400 MHz, DMSO-d$_6$) δ ppm 1.86 (s, 3H), 6.52 (s, 2H), 7.55 (d, J=11.03 Hz, 1H), 8.28 (s, 2H), 8.43 (s, 1H), 8.83 (d, J=2.43 Hz, 1H), 9.05 (d, J=2.43 Hz, 1H), 11.18 (br s, 1H).

Example 146

1-(6-amino-5-fluoro-3-methylpyridin-2-yl)-N-(5-chloro-6-(2H-1,2,3-triazol-2-yl)pyridin-3-yl)-5-(trifluoromethyl)-1H-pyrazole-4-carboxamide, Cpd 146

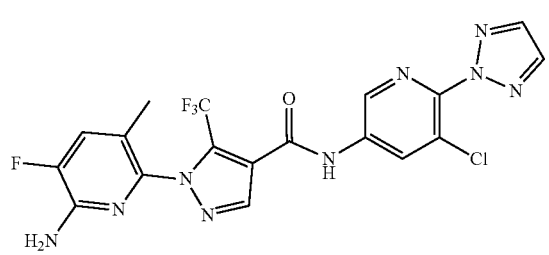 [SMILES: Cc1cc(F)c(N)nc1-n1ncc(C(=O)Nc2cnc(-n3nccn3)c(Cl)c2)c1C(F)(F)F]

A. Tert-butyl (6-(4-((5-chloro-6-(2H-1,2,3-triazol-2-yl)pyridin-3-yl)carbamoyl)-5-(trifluoromethyl)-1H-pyrazol-1-yl)-3-fluoro-5-methylpyridin-2-yl)carbamate, Cpd 146a

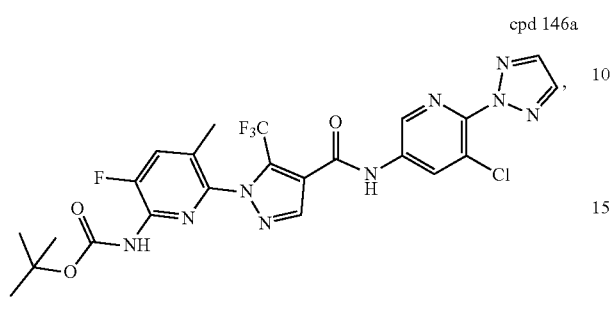

POCl$_3$ (188.0 mg, 1.23 mmol) was added to a solution of 1-(6-((tert-butoxycarbonyl)amino)-5-fluoro-3-methylpyridin-2-yl)-5-(trifluoromethyl)-1H-pyrazole-4-carboxylic acid (300 mg, 0.61 mmol), 5-chloro-6-(2H-1,2,3-triazol-2-yl) pyridin-3-amine, INT2 (136.9 mg, 0.74 mmol) and pyridine (121.2 mg, 1.53 mmol) in CH$_2$Cl$_2$ (10 mL). The mixture was stirred at rt for 3 h. Water (100 mL) and CH$_2$Cl$_2$ (100 mL) were added to the mixture. The organic layer was washed with brine (100 mL), dried over MgSO$_4$ and concentrated under reduced pressure to give the title compound (400 mg, 68.7% yield) as a brown solid to be used directly in the next step. LCMS (ESI) m/z M+1: 604.0(+Na).

B. 1-(6-amino-5-fluoro-3-methylpyridin-2-yl)-N-(5-chloro-6-(2H-1,2,3-triazol-2-yl)pyridin-3-yl)-5-(trifluoromethyl)-1H-pyrazole-4-carboxamide, Cpd 146

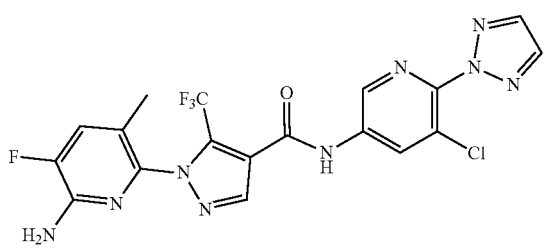 [SMILES: Cc1cc(F)c(N)nc1-n1ncc(C(=O)Nc2cnc(-n3nccn3)c(Cl)c2)c1C(F)(F)F]

tert-Butyl (6-(4-((5-chloro-6-(2H-1,2,3-triazol-2-yl)pyridin-3-yl)carbamoyl)-5-(trifluoromethyl)-1H-pyrazol-1-yl)-3-fluoro-5-methylpyridin-2-yl)carbamate (400 mg, 0.42 mmol) was added to HCl/dioxane (20 mL). The mixture was stirred at rt for 2 h. The mixture was concentrated under reduced pressure. The crude material was purified by preparative high-performance liquid chromatography over Column: Phenomenex Synergi C18 150*30 mm*4 um; Condition: A: water (0.05% HCl); B: CH$_3$CN at the beginning: A (60%) and B (40%), at the end: A: (50%) and B (50%) Gradient Time(min) 12; 100% B Hold Time(min) 2.2; Flow Rate(mL/min) 25. The pure fractions were collected and the solvent was concentrated under reduced pressure. The aqueous layer was lyophilized to dryness to give the title product (60.5 mg, 29.6% yield) as a white solid. LCMS (ESI) m/z M+1: 481.9. $^1$H NMR (400 MHz, DMSO-d$_6$) δ ppm 1.86 (s, 3H), 6.52 (s, 2H), 7.55 (d, J=10.80 Hz, 1H), 8.15 (s, 2H), 8.42 (s, 1H), 8.62 (d, J=2.21 Hz, 1H), 8.81 (d, J=2.21 Hz, 1H), 11.14 (br s, 1H).

Example 147

N-(6-(2H-1,2,3-triazol-2-yl)-5-(trifluoromethyl)pyridin-3-yl)-1-(6-amino-5-fluoropyridin-2-yl)-5-(trifluoromethyl)-1H-pyrazole-4-carboxamide, Cpd 147

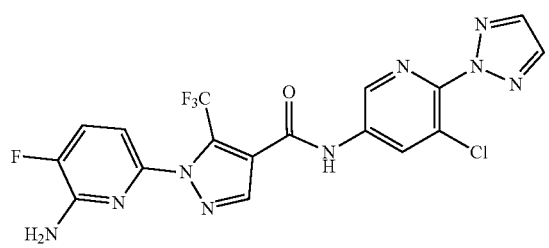 [SMILES: Nc1nc(-n2ncc(C(=O)Nc3cnc(-n4nccn4)c(Cl)c3)c2C(F)(F)F)ccc1F]

A. 5-Nitro-2-(2H-1,2,3-triazol-2-yl)-3-(trifluoromethyl)pyridine, Cpd 147a

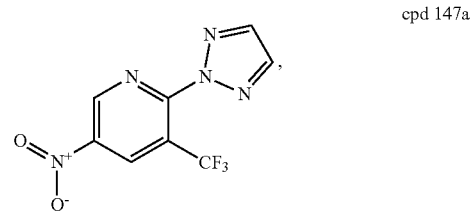 [SMILES: O=[N+]([O-])c1cnc(-n2nccn2)c(C(F)(F)F)c1]

1-Chloro-4-nitro-2-(trifluoromethyl)pyridine (950 mg, 4.19 mmol), 1H-1,2,3-triazole (579.3 mg, 8.39 mmol) and potassium carbonate (1.45 g, 10.48 mmol) were added to MeCN (20 mL) and stirred at room temperature for 16 h. Water (200 mL) and ethyl acetate (200 mL) were added to the mixture. The organic layer was washed with brine (150 mL), dried over MgSO$_4$, filtered, and the filtrate concentrated under reduced pressure to afford a crude product, which was purified by FCC (petroleum ether/ethyl acetate from 95:5 to 83:17) to afford the title compound (720 mg, 66.0%) as a white solid. $^1$H NMR (400 MHz, CHLOROFORM-d) δ 9.07 (d, J=2.43 Hz, 1H), 9.59 (d, J=2.43 Hz, 1H). 8.06 (s, 2H). LCMS (ESI) m/z M+1: 259.8.

B. 6-(2H-1,2,3-triazol-2-yl)-5-(trifluoromethyl)pyridin-3-amine, Cpd 147b

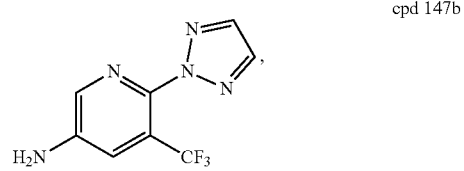 [SMILES: Nc1cnc(-n2nccn2)c(C(F)(F)F)c1]

5-Nitro-2-(2H-1,2,3-triazol-2-yl)-3-(trifluoromethyl)pyridine (720 mg, 2.77 mmol) was dissolved in methyl alcohol (30 mL), zinc powder (1.799 g, 27.7 mmol), aq.NH₄Cl (30 mL) were added. The reaction mixture was stirred at room temperature for 16 h. To the suspension was added aq. NaHCO₃ to adjust the mixture to pH 9-10, and the mixture was filtered through a pad of diatomaceous earth and the pad was washed with CH₂Cl₂ (100 mL×3). The combined filtrates were washed with brine (200 mL), dried over MgSO₄, filtered, and the filtrate concentrated under reduced pressure to give the product (650 mg, 98.9%) as a yellow oil to be used directly in the next step. LCMS (ESI) m/z M+1: 229.9.

C. Tert-Butyl (6-(4-(((6-(2H-1,2,3-triazol-2-yl)-5-(trifluoromethyl)pyridin-3-yl)carbamoyl)-5-(trifluoromethyl)-1H-pyrazol-1-yl)-3-fluoropyridin-2-yl)carbamate, Cpd 147c

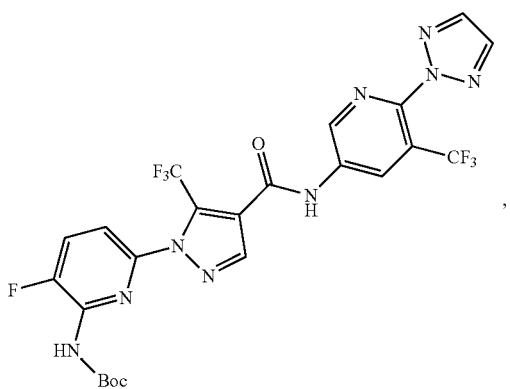

cpd 147c 1-(6-((tert-Butoxycarbonyl)amino)-5-fluoropyridin-2-yl)-5-(trifluoromethyl)-1H-pyrazole-4-carboxylic acid, cpd 62d (200 mg, 0.51 mmol), 6-(2H-1,2,3-triazol-2-yl)-5-(trifluoromethyl)pyridin-3-amine (146.0 mg, 0.62 mmol), pyridine (101.3 mg, 1.28 mmol) were dissolved in CH₂Cl₂ (20 mL), and phosphorus oxychloride (157.1 mg, 1.03 mmol) was added. The mixture was stirred at room temperature for 2 h. Water (50 mL) was added and the mixture was extracted with CH₂Cl₂ (50 mL). The organic layer was washed with brine (50 mL), dried with Na₂SO₄, filtered and the filtrates were concentrated under reduced pressure to afford the title product (350 mg, 57.193% purity, 65.0%) as a brown solid. LCMS (ESI) m/z M+23: 624.0.

D. N-(6-(2H-1,2,3-triazol-2-yl)-5-(trifluoromethyl)pyridin-3-yl)-1-(6-amino-5-fluoropyridin-2-yl)-5-(trifluoromethyl)-1H-pyrazole-4-carboxamide, Cpd 147

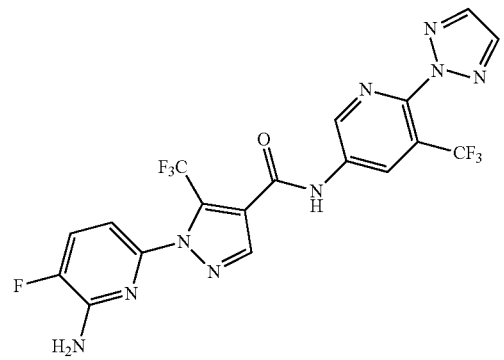 [SMILES: Nc1nc(-n2ncc(C(=O)Nc3cnc(-n4nccn4)c(C(F)(F)F)c3)c2C(F)(F)F)ccc1F]

tert-Butyl (6-(4-(((6-(2H-1,2,3-triazol-2-yl)-5-(trifluoromethyl)pyridin-3-yl)carbamoyl)-5-(trifluoromethyl)-1H-pyrazol-1-yl)-3-fluoropyridin-2-yl)carbamate, (300 mg, 0.29 mmol) was added to HCl/dioxane (15 mL). The reaction mixture was stirred at room temperature for 2 h. The reaction mixture was concentrated under reduced pressure to afford a crude product as a yellow oil, which was purified by preparative HPLC (40% to 70% (v/v) CH₃CN and H₂O with 0.05% HCl) and lyophilized to dryness to afford the title compound (96.5 mg, 67.5%). LCMS (ESI) m/z M+1: 501.9. ¹H NMR (400 MHz, DMSO-d₆) δ ppm 6.71 (br s, 1H), 6.79 (dd, J=8.05, 2.54 Hz, 1H), 7.59 (dd, J=10.58, 8.16 Hz, 1H), 8.14-8.21 (m, 2H), 8.35 (s, 1H), 8.83 (d, J=2.20 Hz, 1H), 9.10 (d, J=2.21 Hz, 1H), 11.31 (s, 1H).

Example 148

1-(2-amino-5-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 148

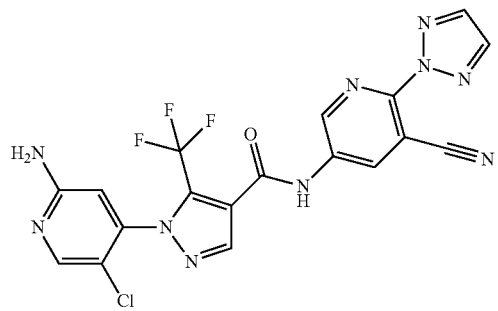 [SMILES: N#Cc1cc(NC(=O)c2cnn(-c3cc(N)ncc3Cl)c2C(F)(F)F)cnc1-n1nccn1]

A. Tert-butyl (4-bromo-5-chloropyridin-2-yl)carbamate, Cpd 148a

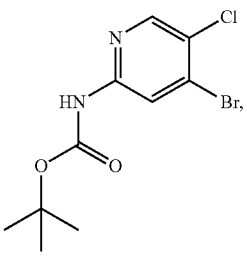

cpd 148a

A solution of 4-bromo-5-chloropyridin-2-amine (2 g, 9.64 mmol), di-tert-butyldicarbonate (4.21 g, 19.28 mmol), TEA (2.93 g, 28.92 mmol), N,N-dimethylpyridin-4-amine (117.8 mg, 0.96 mmol) in CH₂Cl₂ (20 mL) was stirred at rt for 2 h. The mixture was diluted with water (40 mL) and extracted with CH₂Cl₂ (40 mL×3). The combined organic layers were dried (MgSO₄), filtered, and the filtrate concentrated to give the crude product as a white solid. The crude product was purified by FCC (petroleum ether/ethyl acetate=100:0 to 70:30). The solvents were evaporated to afford the title compound as a white solid (1.2 g).

B. Tert-butyl (5-chloro-4-hydrazinylpyridin-2-yl)carbamate, Cpd 148b

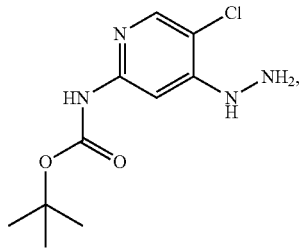

cpd 148b

{Pd(cinnamyl)Cl}$_2$ (66.0 mg, 0.13 mmol) and Mor-Dal-Phos (118.1 mg, 0.26 mmol) was added to dioxane (10 mL), and the reaction vessel was immediately evacuated with N$_2$. The resulting solution was stirred at rt under N$_2$ for 10 min. The vessel was then charged with sodium tert-butoxide (489.5 mg, 5.09 mmol) and tert-butyl (4-bromo-5-chloro-pyridin-2-yl)carbamate (0.8 g, 2.55 mmol), sealed, and evacuated with N$_2$. The resulting reaction was stirred at rt for 5 min and was then treated with hydrazine hydrate (382.4 mg, 7.64 mmol) via syringe. The reaction was stirred at 50° C. under N$_2$ for 1.5 h. The reaction mixture was filtered. The filtrate was concentrated under reduced pressure to give the crude product as a yellow oil (1.0 g). LCMS (ESI) m/z M+1: 259.1

C. Ethyl 1-(2-((tert-butoxycarbonyl)amino)-5-chloropyridin-4-yl)-5-(trifluoromethyl)-1H-pyrazole-4-carboxylate, Cpd 148c

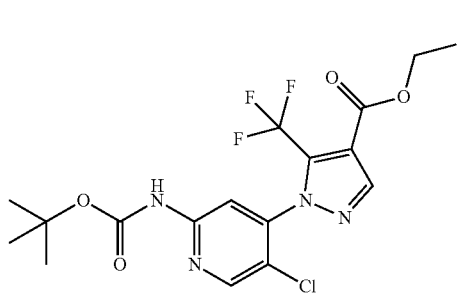

cpd 148c

Ethyl 2-(ethoxymethylene)-4,4,4-trifluoro-3-oxobutanoate, INT1 (136.9 mg, 0.57 mmol) was added to a solution of crude tert-butyl (5-chloro-4-hydrazinylpyridin-2-yl)carbamate (1 g) in EtOH (15 mL). The mixture was reacted at 80° C. for 1 h. The solvent was concentrated under reduced pressure to give the crude product as a brown oil. The crude product was purified by FCC (petroleum ether/ethyl acetate=100:0 to 90:10). The solvents were evaporated to afford the product as a white solid (250 mg). LCMS (ESI) m/z M+1: 379.1.

D. 1-(2-((tert-butoxycarbonyl)amino)-5-chloropyridin-4-yl)-5-(trifluoromethyl)-1H-pyrazole-4-carboxylic Acid, Cpd 148d

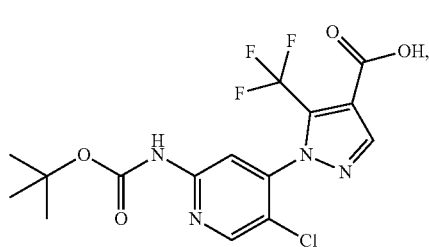

cpd 148d

NaOH (11.5 mg, 0.29 mmol) was added to a solution of crude ethyl 1-(2-((tert-butoxycarbonyl)amino)-5-chloro-pyridin-4-yl)-5-(trifluoromethyl)-1H-pyrazole-4-carboxylate (250 mg) in THF/H$_2$O=1:1 (8 mL). The mixture was reacted at room temperature for 24 h. The reaction mixture was extracted with ethyl acetate (20 mL×2). The aqueous layer was acidified by 1M hydrochloric to pH 5 and extracted with ethyl acetate (30 mL×3). The combined organic layers were washed with brine, dried with anhydrous MgSO$_4$, and filtered. The filtrates were concentrated under reduced pressure to afford a product as a white solid (70 mg, 88.4% purity, 79.0%). LCMS (ESI) m/z M+1: 351.0

E. Tert-butyl (5-chloro-4-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate, Cpd 148e

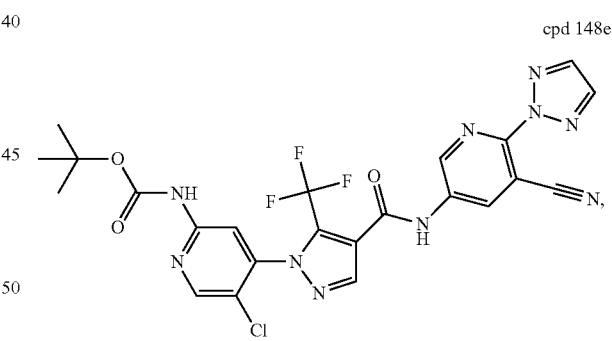

cpd 148e 1-(2-((tert-Butoxycarbonyl)amino)-5-chloropyridin-4-yl)-5-(trifluoromethyl)-1H-pyrazole-4-carboxylic acid (70 mg, 0.15 mmol), 5-amino-2-(2H-1,2,3-triazol-2-yl) nicotinonitrile, INT3 (28.3 mg, 0.15 mmol), pyridine (0.061 mL, 0.76 mmol) were dissolved in CH$_2$Cl$_2$ (10 mL), and phosphorus oxychloride (0.056 mL, 0.61 mmol) was added. The mixture was stirred at 25° C. for 2 h. Sat.NaHCO$_3$(20 mL) was added and the mixture was extracted with CH$_2$Cl$_2$ (30 mL×2). The combined organic extracts were dried over anhydrous Na$_2$SO$_4$, filtered, and the filtrate concentrated to dryness under reduced pressure to afford the crude product as a brown oil (120 mg, 62.2% purity, 85.3%). LCMS (ESI) m/z M+1: 475.1

339

F. 1-(2-amino-5-chloropyridin-4-yl)-N-(5-cyano-6-(2H-1,2,3-triazol-2-yl)pyridin-3-yl)-5-(trifluoromethyl)-1H-pyrazole-4-carboxamide, Cpd 148

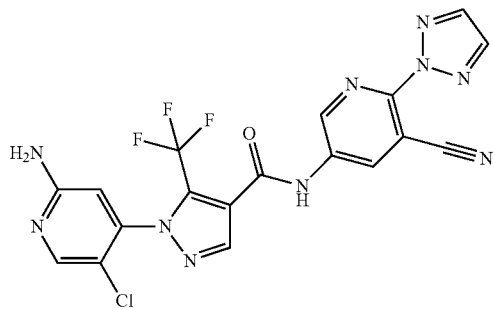 [SMILES: N#Cc1cc(NC(=O)c2cnn(-c3cc(N)ncc3Cl)c2C(F)(F)F)cnc1-n1nccn1]

tert-Butyl (5-chloro-4-(4-((5-cyano-6-(2H-1,2,3-triazol-2-yl)pyridin-3-yl)carbamoyl)-5-(trifluoromethyl)-1H-pyrazol-1-yl)pyridin-2-yl)carbamate (120 mg, 0.13 mmol) was added to HCl/dioxane (10 mL). The mixture was stirred at rt 16 h. The solvent was concentrated under reduced pressure to afford a crude product as a yellow solid, which was purified by preparative HPLC (35% to 60% (v/v) $CH_3CN$ and $H_2O$ with 0.05% ammonia hydroxide) and the pure fractions were collected and the organic solvent was concentrated under reduced pressure. The aqueous layer was lyophilized to dryness to give the product as a pale yellow solid (22 mg, 99.1% purity, 35.4%). LCMS (ESI) m/z M+1: 474.9; $^1$H NMR (400 MHz, DMSO-$d_6$) δ ppm 6.70 (s, 1H), 8.18 (s, 1H), 8.28 (s, 2H), 8.54 (s, 1H), 8.83 (d, J=2.43 Hz, 1H), 9.06 (d, J=2.65 Hz, 1H), 11.31 (s, 1H).

Example 149

1-(2-amino-5-chloropyridin-4-yl)-N-(5-chloro-6-(2H-1,2,3-triazol-2-yl)pyridin-3-yl)-5-(trifluoromethyl)-1H-pyrazole-4-carboxamide, Cpd 149

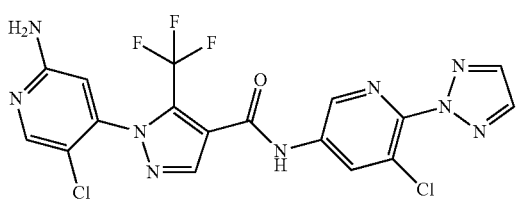 [SMILES: Nc1cc(-n2ncc(C(=O)Nc3cnc(-n4nccn4)c(Cl)c3)c2C(F)(F)F)c(Cl)cn1]

340

A. Tert-butyl (5-chloro-4-(4-((5-chloro-6-(2H-1,2,3-triazol-2-yl)pyridin-3-yl) carbamoyl)-5-(trifluoromethyl)-1H-pyrazol-1-yl)pyridin-2-yl)carbamate, Cpd 149a

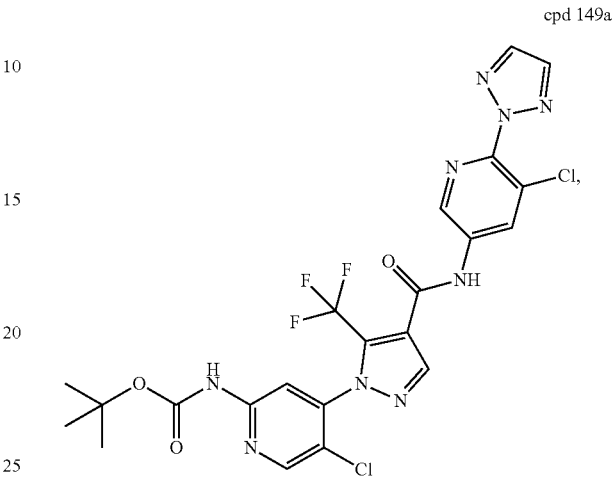

cpd 149a 1-(2-((tert-Butoxycarbonyl)amino)-5-chloropyridin-4-yl)-5-(trifluoromethyl)-1H-pyrazole-4-carboxylic acid (110 mg, 0.27 mmol), 5-chloro-6-(2H-1,2,3-triazol-2-yl) pyridin-3-amine, INT2 (58.19 mg, 0.30 mmol), pyridine (0.109 mL, 1.35 mmol) were dissolved in $CH_2Cl_2$ (10 mL), and phosphorus oxychloride (0.099 mL, 1.08 mmol) was added. The mixture was stirred at 25° C. for 2 h. Sat.NaHCO$_3$(20 mL) was added and the mixture was extracted with $CH_2Cl_2$ (30 mL×2). The combined organic extracts were dried over anhydrous $Na_2SO_4$, filtered, and the filtrate concentrated to dryness under reduced pressure to afford the crude product as a brown oil (160 mg, 68.6% purity, 69.4%). LCMS (ESI) m/z M+1: 483.7

B. 1-(2-amino-5-chloropyridin-4-yl)-N-(5-chloro-6-(2H-1,2,3-triazol-2-yl)pyridin-3-yl)-5-(trifluoromethyl)-1H-pyrazole-4-carboxamide Cpd 149

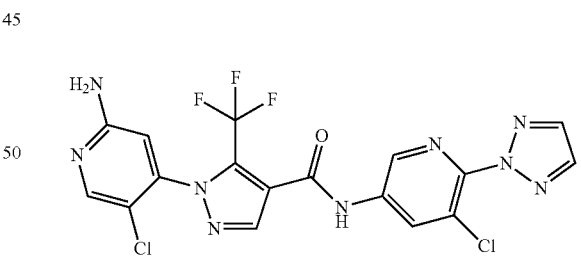

tert-Butyl (5-chloro-4-(4-((5-chloro-6-(2H-1,2,3-triazol-2-yl)pyridin-3-yl)carbamoyl)-5-(trifluoromethyl)-1H-pyrazol-1-yl)pyridin-2-yl)carbamate (140 mg, 0.16 mmol) was added to HCl/dioxane (5 mL) and $CH_2Cl_2$ (5 mL). The mixture was stirred at rt for 16 h. The solvent was concentrated under reduced pressure to afford a crude yellow solid, which was purified by preparative HPLC (35% to 55% (v/v) $CH_3CN$ and $H_2O$ with 0.05% HCl) and the pure fractions were collected and the organic solvent was concentrated under reduced pressure. The aqueous layer was lyophilized to dryness to give the product as a pale yellow solid (40 mg, 91.8% purity). The product was purified by preparative HPLC again (35% to 65% (v/v) CH₃CN and H₂O with 0.05% ammonia hydroxide) and the pure fractions were collected and the organic solvent concentrated under reduced pressure. The aqueous layer was lyophilized to dryness to afford the product as a pale yellow solid (25 mg, 99.80% purity, 31.4%). LCMS (ESI) m/z M+1: 483.9, $^1$H NMR (400 MHz, DMSO-d₆) δ ppm 6.71 (s, 1H), 6.73 (s, 2H), 8.19 (s, 2H), 8.21 (s, 1H), 8.54 (s, 1H), 8.65 (d, J=2.26 Hz, 1H), 8.83 (s, 1H), 11.16 (s, 1H).

Example 150

N-(5-cyano-6-(2H-1,2,3-triazol-2-yl)pyridin-3-yl)-1-(5-fluoro-6-(methylamino)pyridin-2-yl)-5-(trifluoromethyl)-1H-pyrazole-4-carboxamide, Cpd 150

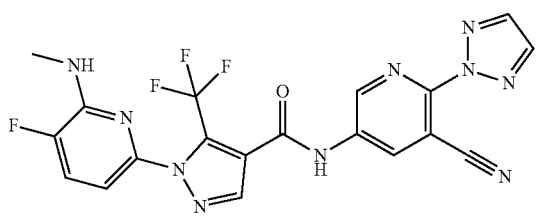 [SMILES: CNc1nc(-n2ncc(C(=O)Nc3cnc(-n4nccn4)c(C#N)c3)c2C(F)(F)F)ccc1F]

A. 6-chloro-3-fluoro-N-methylpyridin-2-amine, Cpd 150a

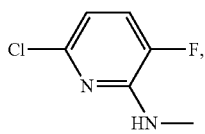

2,6-Dichloro-3-fluoropyridine (1500 mg, 9.04 mmol) in methylamine in THF (2M) was reacted at 80° C. for 16 h. The solvent was concentrated under reduced pressure to give the crude compound, which was purified by FFS (petroleum ether/ethyl acetate=100:0 to petroleum ether/ethyl acetate=60:40). The desired fractions were collected and the solvent was concentrated under reduced pressure to give the product as a colorless oil (200 mg, 13.8%). LCMS (ESI) m/z M+1: 161.1. $^1$H NMR (400 MHz, CHLOROFORM-d) δ ppm 3.00 (d, J=5.07 Hz, 3H), 4.68 (br s, 1H), 6.43 (dd, J=8.05, 2.76 Hz, 1H), 7.02 (dd, J=10.25, 8.05 Hz, 1H).

B. 3-fluoro-6-hydrazinyl-N-methylpyridin-2-amine, Cpd 150b

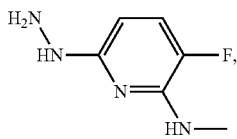

A mixture of palladium(II)(pi-cinnamyl) (25.8 mg, 0.05 mmol) chloride dimer and N-[2-(di-1-adamantylphosphino) phenyl]morpholine (46.2 mg, 0.10 mmol) in dioxane (5 mL) was evacuated with argon 4 times. The resulting clear yellow solution was stirred at rt under argon for 10 min. 6-Chloro-3-fluoro-N-methylpyridin-2-amine (160 mg, 1.0 mmol) and tBuONa (191.5 mg, 1.99 mmol) were added to the mixture and vessel was evacuated with argon 4 times. The resulting yellow reaction was stirred at room temperature for 5 min before treatment with hydrazine (99.8 mg, 1.99 mmol) via syringe and the reaction vessel was evacuated with argon 4 times. The mixture was stirred at 50° C. under argon for 2 h. Upon filtration, the solvent was concentrated under reduced pressure to give the crude product as a brown solid, which was used directly for the next step.

C. Ethyl-(5-fluoro-6-(methylamino)pyridin-2-yl)-5-(trifluoromethyl)-1H-pyrazole-4-carboxylate, Cpd 150c

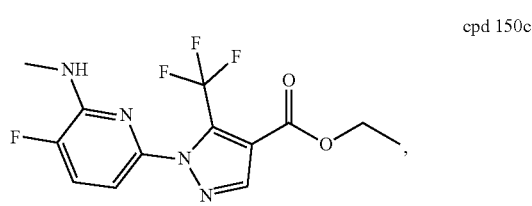 [SMILES: CCOC(=O)c1cnn(-c2ccc(F)c(NC)n2)c1C(F)(F)F]

3-Fluoro-6-hydrazinyl-N-methylpyridin-2-amine (160 mg, 1.03 mmol) was added to a solution of ethyl 2-(ethoxymethylene)-4,4,4-trifluoro-3-oxobutanoate, INT1 (369.1 mg, 1.54 mmol) in EtOH (5 mL) and the mixture was stirred at 80° C. for 1 h. The mixture was concentrated under reduced pressure, then was purified by FFS (petroleum ether/ethyl acetate=100:0 to petroleum ether/ethyl acetate=80:20). The desired fractions were collected and the solvent was concentrated under reduced pressure to give the product as a brown oil (180 mg, 49.0%). LCMS (ESI) m/z M-55: 331.0.

D. 1-(5-fluoro-6-(methylamino)pyridin-2-yl)-5-(trifluoromethyl)-1H-pyrazole-4-carboxylic Acid, Cpd 150d

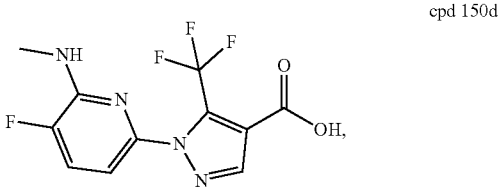 [SMILES: CNc1nc(-n2ncc(C(=O)O)c2C(F)(F)F)ccc1F]

LiOH (50.109 mg, 2.092 mmol) was added to a solution of ethyl-(5-fluoro-6-(methylamino)pyridin-2-yl)-5-(trifluoromethyl)-1H-pyrazole-4-carboxylate (150 mg, 0.418 mmol) in THF/H₂O (2:1, 9 mL) and the mixture was reacted at 23° C. for 2 h. The solvent was concentrated under reduced pressure. 1M HCl solution was added to the mixture to adjust the mixture to pH 5. A solid formed and was collected by filtration to afford the product (130 mg, 88.1%). LCMS (ESI) m/z M+1: 305.0.

E. N-(5-cyano-6-(2H-1,2,3-triazol-2-yl)pyridin-3-yl)-1-(5-fluoro-6-(methylamino)pyridin-2-yl)-5-(trifluoromethyl)-1H-pyrazole-4-carboxamide, Cpd 150

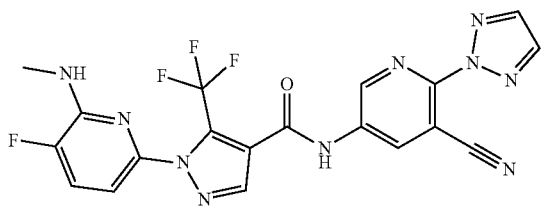 [SMILES: CNc1nc(-n2ncc(C(=O)Nc3cnc(-n4nccn4)c(C#N)c3)c2C(F)(F)F)ccc1F]

1-(5-Fluoro-6-(methylamino)pyridin-2-yl)-5-(trifluoromethyl)-1H-pyrazole-4-carboxylic acid (130 mg, 0.37 mmol), 5-amino-2-[1,2,3]triazol-2-yl-nicotinonitrile, INT3 (72.1 mg, 0.39 mmol), and POCl₃ (67.8 mg, 0.44 mmol) were dissolved in CH₂Cl₂ (8 mL), and pyridine (87.5 mg, 1.11 mmol) was added. The mixture was stirred at 25° C. for 1 h. Sat. NaHCO₃(10 mL) was added and the mixture extracted with CH₂Cl₂ (15 mL×2). The combined organic layers were dried with Na₂SO₄, filtered and the filtrates were concentrated under reduced pressure to afford a crude brown oil, which was purified by preparative HPLC (67% to 37% (v/v) CH₃CN and H₂O with 0.05% HCl) and lyophilized to dryness to afford the title compound (39 mg, 21.8%). LCMS (ESI) m/z M+1: 473.0. ¹H NMR (400 MHz, DMSO-d₆) δ ppm 2.81 (d, J=3.75 Hz, 3H), 6.83 (dd, J=8.16, 2.43 Hz, 1 H), 7.18 (br s, 1H), 7.58 (dd, J=10.58, 8.16 Hz, 1H), 8.28 (s, 2H), 8.32 (s, 1H), 8.81 (d, J=2.43 Hz, 1H), 9.03 (d, J=2.43 Hz, 1H), 11.30 (s, 1H).

Example 151

N-(5-chloro-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide, Cpd 151

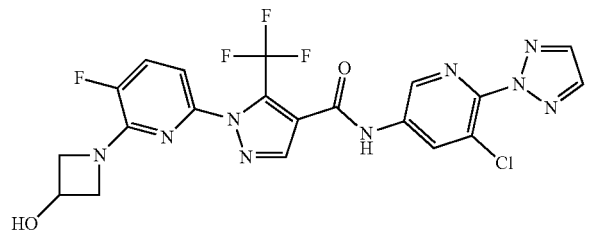 [SMILES: O=C(Nc1cnc(-n2nccn2)c(Cl)c1)c1cnn(-c2ccc(F)c(N3CC(O)C3)n2)c1C(F)(F)F]

A. 3,6-difluoro-2-hydrazinylpyridine, Cpd 151a

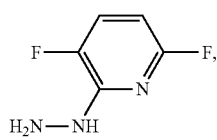

2,3,6-Trifluoropyridine (7 g, 52.60 mmol) was dissolved in hydrazine hydrate (5.374 g, 105.21 mmol) and EtOH (70 mL). The reaction mixture was stirred at reflux for 2 h. The solvent was removed and the mixture diluted with water (300 mL) and extracted with CH₂Cl₂ (200 mL×2). The combined organic layers were dried with Na₂SO₄, filtered and the filtrates were concentrated under reduced pressure to afford the crude product. The residue was recrystallized from EtOH to obtain the product (7 g, 91.7%) as a light yellow solid.

B. 2-bromo-3,6-difluoropyridine, Cpd 151b

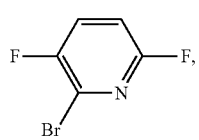

3,6-Difluoro-2-hydrazinylpyridine (2.5 g, 17.23 mmol) was dissolved in CHCl₃ (100 mL), and bromine was added dropwise. The reaction mixture was stirred at 60° C. for 1 h. Sat. NaHCO₃(40 mL) was added dropwise and the mixture was extracted with CH₂Cl₂ (100 mL×2). The combined organic layers were dried with Na₂SO₄, filtered and the filtrates were concentrated under reduced pressure to afford the crude product, which was purified by FCC (eluent: petroleum ether/ethyl acetate from 100/0 to 85/15) to afford the title compound (1.8 g, 53.9%) as a yellow oil.

C. 2-bromo-3-fluoro-6-hydrazinylpyridine, Cpd 151c

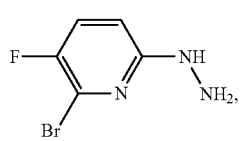

2-Bromo-3,6-difluoropyridine (1.8 g, 9.28 mmol) was dissolved in hydrazine hydrate (1.394 g, 27.84 mmol) and MeCN (50 mL). The reaction mixture was stirred at 80° C. for 36 h. The solvent was concentrated under reduced pressure to afford a brown solid. The solid was co-evaporated with toluene three times to remove water and afford the title compound (1.9 g, 99.4%) as a brown solid.

D. Ethyl 1-(6-bromo-5-fluoropyridin-2-yl)-5-(trifluoromethyl)-1H-pyrazole-4-carboxylate, Cpd 151d

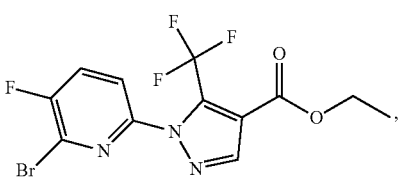

2-Bromo-3-fluoro-6-hydrazinylpyridine (1.9 g, 9.22 mmol) was dissolved in ethanol (15 mL), ethyl 2-(ethoxymethylene)-4,4,4-trifluoro-3-oxobutanoate, INT1 (3.323 g, 13.83 mmol) was added. The reaction mixture was stirred at 80° C. for 2 h. The reaction mixture was concentrated under reduced pressure to afford the crude product as a yellow oil, which was purified by FCC (eluent: petroleum ether/ethyl acetate from 100/0 to 90/10) to afford the title compound (2 g, 33.6%) as a yellow oil. LCMS (ESI) m/z M+1: 381.9.

E. 1-(6-bromo-5-fluoropyridin-2-yl)-5-(trifluoromethyl)-1H-pyrazole-4-carboxylic Acid, Cpd 151e

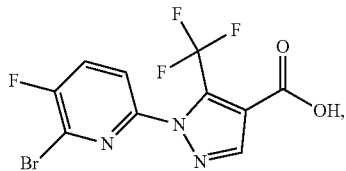

cpd 151e

Ethyl 1-(6-bromo-5-fluoropyridin-2-yl)-5-(trifluoromethyl)-1H-pyrazole-4-carboxylate (500 mg, 0.77 mmol) was dissolved in THF (5 mL) and water (5 mL). Lithium hydroxide (185.4 mg, 7.74 mmol) was added. The reaction mixture was stirred at 25° C. for 12 h. The reaction mixture was adjusted to pH 5 using HCl (5-6 N), extracted with EtOAc (30 mL×3). The combined organic layers were dried with $Na_2SO_4$, filtered and the filtrates were concentrated under reduced pressure to afford a crude title compound (350 mg, 93.5%) as a yellow solid. LCMS (ESI) m/z M+1: 356.0.

F. 1-(6-bromo-5-fluoropyridin-2-yl)-N-(5-chloro-6-(2H-1,2,3-triazol-2-yl)pyridin-3-yl)-5-(trifluoromethyl)-1H-pyrazole-4-carboxamide, Cpd 151f

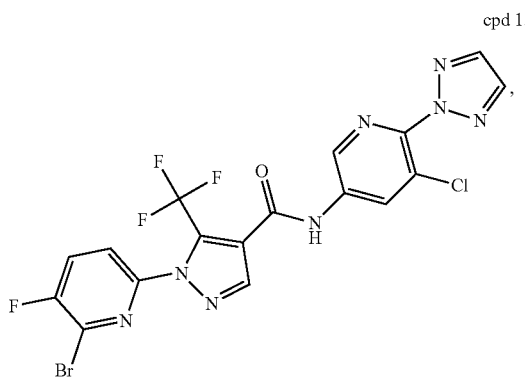

cpd 151f 1-(6-Bromo-5-fluoropyridin-2-yl)-5-(trifluoromethyl)-1H-pyrazole-4-carboxylic acid, (350 mg, 0.72 mmol), 5-chloro-6-(2H-1,2,3-triazol-2-yl)pyridin-3-amine, INT2 (141.6 mg, 0.72 mmol), pyridine (443.9 mg, 2.90 mmol) were dissolved in $CH_2Cl_2$ (10 mL), and phosphorus oxychloride (149.2 mg, 0.97 mmol) was added. The mixture was stirred at 25° C. for 2 h. Sat.$NaHCO_3$(30 mL) was added and extracted with $CH_2Cl_2$ (30 mL×2). The combined organic layers were dried with $Na_2SO_4$, filtered and the filtrates were concentrated under reduced pressure to afford the crude product as a yellow oil, which was purified by FCC (eluent: petroleum ether/ethyl acetate from 100/0 to 0/100) to afford the title compound (350 mg, 69.3%) as a yellow solid. LCMS (ESI) m/z M+1: 533.0.

G. N-(5-chloro-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide, Cpd 151

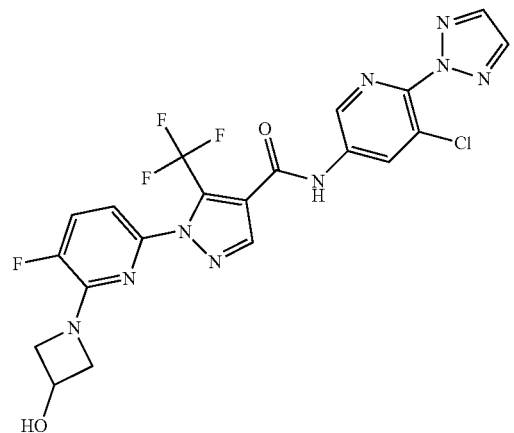 [SMILES: O=C(Nc1cnc(-n2nccn2)c(Cl)c1)c1cnn(-c2ccc(F)c(N3CC(O)C3)n2)c1C(F)(F)F]

1-(6-Bromo-5-fluoropyridin-2-yl)-N-(5-chloro-6-(2H-1,2,3-triazol-2-yl)pyridin-3-yl)-5-(trifluoromethyl)-1H-pyrazole-4-carboxamide (300 mg, 0.56 mmol), azetidin-3-ol (123.64 mg, 1.13 mmol), cesium carbonate (551.6 mg, 1.69 mmol) was dissolved in dioxane (10 mL) under $N_2$ atmosphere. Tris(dibenzylideneacetone)dipalladium(0) (51.7 mg, 0.056 mmol) and 9,9-dimethyl-9H-xanthene-4,5-diyl)bis(diphenylphosphine) (65.3 mg, 0.11 mmol) was added and stirred at 100° C. for 16 h. The combined mixture was filtered and the filtrates were concentrated under reduced pressure to afford the crude product as a yellow solid, which was purified by preparative HPLC (40% to 70% (v/v) $CH_3CN$ and $H_2O$ with 0.05% ammonia hydroxide) and lyophilized to dryness to afford the title compound (23 mg, 7.7%). LCMS (ESI) m/z M+1: 524.1. $^1$H NMR (400 MHz, DMSO-$d_6$) δ ppm 3.84 (br dd, J=8.56, 4.40 Hz, 2H), 4.29 (br t, J=7.21 Hz, 2H), 4.50-4.65 (m, 1H), 5.72 (d, J=6.36 Hz, 1H), 6.99 (dd, J=8.07, 1.96 Hz, 1H), 7.67 (dd, J=11.25, 8.31 Hz, 1H), 8.16 (s, 2H) 8.32 (s, 1H), 8.60 (d, J=1.96 Hz, 1H), 8.77 (d, J=1.96 Hz, 1H), 11.25 (br s, 1H).

Example 152

N-(5-cyano-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide, Cpd 152

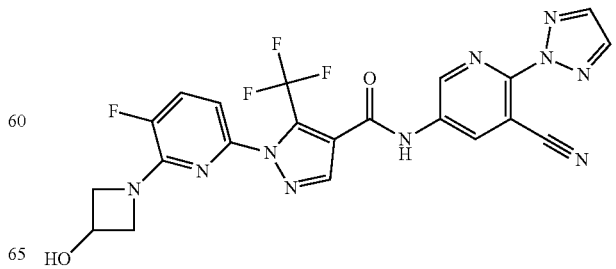

347

A. 1-(6-bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide, Cpd 152a

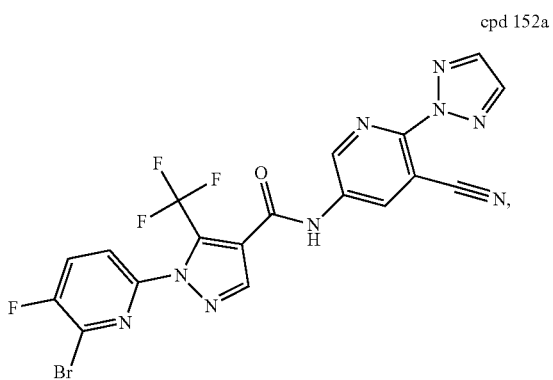 [SMILES: N#Cc1cc(NC(=O)c2cnn(-c3ccc(F)c(Br)n3)c2C(F)(F)F)cnc1-n1nccn1]

cpd 152a 1-(6-Bromo-5-fluoropyridin-2-yl)-5-(trifluoromethyl)-1H-pyrazole-4-carboxylic acid, (350 mg, 0.76 mmol), 5-amino-2-[1,2,3]triazol-2-yl-nicotinonitrile, INT3 (141.7 mg, 0.76 mmol), pyridine (466.9 mg, 3.05 mmol) were dissolved in $CH_2Cl_2$ (10 mL), and phosphorus oxychloride (361.3, 4.57 mmol) was added. The mixture was stirred at 25° C. for 2 h. Sat.$NaHCO_3$(30 mL) was added and the mixture was extracted with $CH_2Cl_2$ (30 mL×2). The combined organic layers were dried with $Na_2SO_4$, filtered and the filtrates were concentrated under reduced pressure to afford the crude product as a yellow oil, which was purified by FCC (eluent: petroleum ether/ethyl acetate from 100/0 to 0/100) to afford the title compound (250 mg, 62.9%) as a yellow solid. LCMS (ESI) m/z M+1: 524.0.

B. N-(5-cyano-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide, Cpd 152

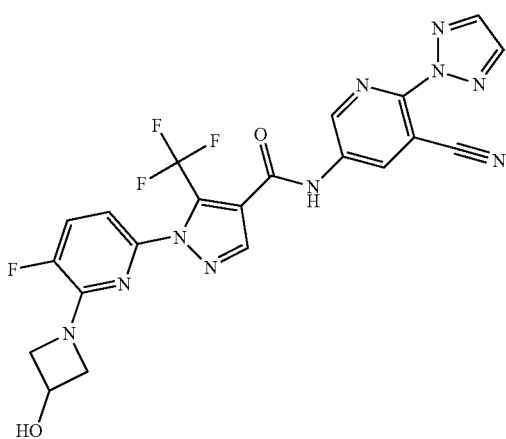 [SMILES: N#Cc1cc(NC(=O)c2cnn(-c3ccc(F)c(N4CC(O)C4)n3)c2C(F)(F)F)cnc1-n1nccn1]

348

1-(6-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide (250 mg, 0.48 mmol), azetidin-3-ol (104.9 mg, 0.96 mmol), cesium carbonate (467.9 mg, 1.44 mmol) was dissolved in dioxane (10 mL) under $N_2$ atmosphere. Tris(dibenzylideneacetone) dipalladium(0) (43.8 mg, 0.048 mmol) and 9,9-dimethyl-9H-xanthene-4,5-diyl)bis(diphenylphosphine(55.4 mg, 0.096 mmol) was added and the mixture was stirred at 100° C. for 16 h. The combined mixture was filtered and the filtrates were concentrated under reduced pressure to afford the crude product as a yellow solid which was purified by preparative HPLC (35% to 65% (v/v) $CH_3CN$ and $H_2O$ with 0.05% ammonia hydroxide) and lyophilized to dryness to afford the title compound (38 mg, 14.7%). LCMS (ESI) m/z M+1: 515.2. $^1$H NMR (400 MHz, DMSO-$d_6$) δ ppm 3.88 (br dd, J=8.53, 4.77 Hz, 2H), 4.32 (br t, J=7.28 Hz, 2H), 4.56-4.67 (m, 1H), 5.75 (d, J=6.53 Hz, 1H), 7.03 (dd, J=8.03, 2.26 Hz, 1H), 7.71 (dd, J=11.29, 8.28 Hz, 1H), 8.27-8.39 (m, 3H), 8.83 (d, J=2.51 Hz, 1H), 9.05 (d, J=2.51 Hz, 1H), 11.33 (br s, 1H).

Example 153

4-(4-((5-chloro-6-(2H-1,2,3-triazol-2-yl)pyridin-3-yl)carbamoyl)-5-(trifluoromethyl)-1H-pyrazol-1-yl)-3-methylpyridine 1-oxide, Cpd 153

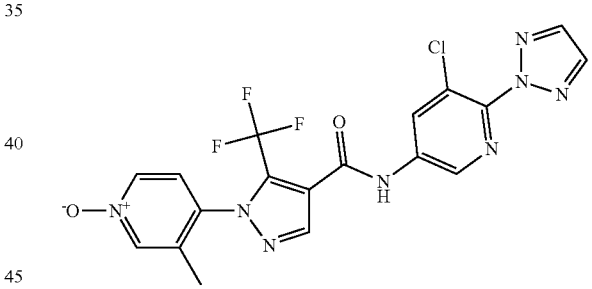

N-(5-Chloro-6-(2H-1,2,3-triazol-2-yl)pyridin-3-yl)-1-(3-methylpyridin-4-yl)-5-(trifluoromethyl)-1H-pyrazole-4-carboxamide (898 mg, 2 mmol) was stirred in DCM (50 mL). mCPBA (518 mg, 3 mmol) was added portionwise. The reaction mixture was stirred for 4 h. Additional mCPBA (518 mg, 3 mmol) was added portionwise. Stirring was continued for 4 h. Additional mCPBA (518 mg, 3 mmol) was added portionwise. Stirring was continued for 16 h. The reaction mixture was poured into water (50 mL) and was treated with a solution of sodium sulfite (1260 mg, 10 mmol) and stirring was continued for 15 min. The reaction mixture was treated with a solution of $NaHCO_3$(840 mg, 10 mmol) and stirred for 5 min. The layers were separated and the aqueous layer was extracted with DCM-MeOH (90/10). The combined organic layers were concentrated under reduced pressure to afford the title compound (992 mg, 101%). LCMS (ESI): mass calcd. for $C_{18}H_{12}ClF_3N_8O_2$ 464.1, m/z found 465.1 [M+H]$^+$.

Example 154 and Example 155

1-(2-chloro-5-methyl-4-pyridyl)-N-[5-chloro-6-(triazol-2-yl)-3-pyridyl]-5-(trifluoromethyl)pyrazole-4-carboxamide, Cpd 154

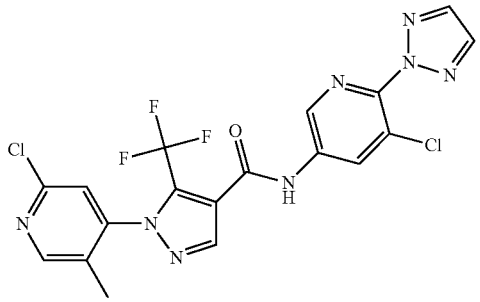 [SMILES: Cc1cnc(Cl)cc1-n1ncc(C(=O)Nc2cnc(-n3nccn3)c(Cl)c2)c1C(F)(F)F]

1-(2-chloro-3-methylpyridin-4-yl)-N-(5-chloro-6-(2H-1,2,3-triazol-2-yl)pyridin-3-yl)-5-(trifluoromethyl)-1H-pyrazole-4-carboxamide, Cpd 155

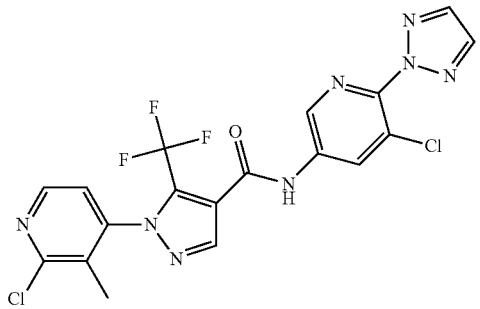 [SMILES: Cc1c(-n2ncc(C(=O)Nc3cnc(-n4nccn4)c(Cl)c3)c2C(F)(F)F)ccnc1Cl]

N-[5-Chloro-6-(triazol-2-yl)-3-pyridyl]-1-(3-methyl-1-oxido-pyridin-1-ium-4-yl)-5-(trifluoromethyl)pyrazole-4-carboxamide (930 mg, 2 mmol) was stirred in POCl$_3$ (30 mL) at 80° C. for 24 h. The reaction mixture was concentrated under reduced pressure. The residue was dissolved in DCM and was slowly added to an aqueous Na$_2$CO$_3$ solution. The layers were separated and the organic layer was extracted two times with DCM. The combined organic layers were dried and concentrated. The residue was purified via Prep HPLC (Stationary phase: RP XBridge Prep C18 OBD-10 µm, 50×150 mm, Mobile phase: 0.25% NH$_4$HCO$_3$ solution in water, CH$_3$CN). The fractions containing compound were collected and evaporated. The residue was purified via Prep SFC (Stationary phase: Chiralpak Diacel AD 20×250 mm, Mobile phase: CO$_2$, MeOH+0.4 iPrNH$_2$) yielding title compounds, cpd 154 (117 mg, 12%): LCMS (ESI): mass calcd. for C$_{18}$H$_{11}$Cl$_2$F$_3$N$_8$O 482, m/z found 483 [M+H]$^+$. $^1$H NMR (400 MHz, CHLOROFORM-d) δ ppm 2.08 (s, 3H), 7.30 (s, 1H), 7.94 (s, 2H), 8.16 (s, 1H), 8.47 (s, 1H), 8.49 (d, J=2.4 Hz, 1H), 8.52 (br s, 1H), 8.70 (d, J=1.0 Hz, 1H) and cpd 155 (123 mg, 13%): LCMS (ESI): mass calcd. for C$_{18}$H$_{11}$Cl$_2$F$_3$N$_8$O 482, m/z found 483 [M+H]$^+$. $^1$H NMR (400 MHz, CHLOROFORM-d) δ ppm 2.10 (s, 3H), 7.20 (d, J=5.3 Hz, 1H), 7.93 (s, 2H), 8.19 (s, 1H), 8.44 (d, J=5.3 Hz, 1H), 8.52 (d, J=2.4 Hz, 1H), 8.67-8.76 (m, 2H).

Example 156

N-(5-chloro-6-(2H-1,2,3-triazol-2-yl)pyridin-3-yl)-1-(2-(3-hydroxyazetidin-1-yl)-5-methylpyridin-4-yl)-5-(trifluoromethyl)-1H-pyrazole-4-carboxamide, Cpd 156

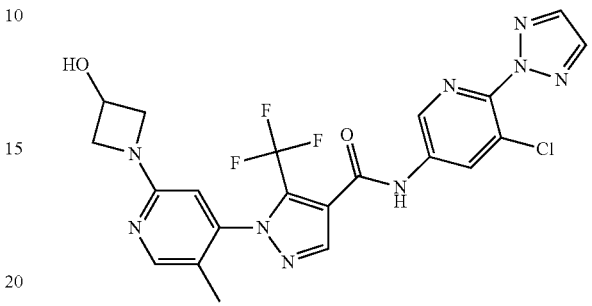

A mixture of 1-(2-chloro-5-methyl-4-pyridyl)-N-[5-chloro-6-(triazol-2-yl)-3-pyridyl]-5-(trifluoromethyl)pyrazole-4-carboxamide (50 mg, 0.1 mmol), 3-hydroxy azetidine (14 mg, 0.2 mmol) and Cs$_2$CO$_3$ (63 mg, 0.2 mmol) in DMA (3 mL) were stirred at 100° C. for 104 h. The reaction mixture was poured into water and extracted with ethyl acetate. The organic layer was washed with water, dried, filtered, and the filtrate concentrated under reduced pressure. The residue was purified via Prep SFC (Stationary phase: Chiralpak Diacel AD 20×250 mm, Mobile phase: CO$_2$, EtOH+0.4 iPrNH$_2$) yielding title compound (20 mg, 40%). LCMS (ESI): mass calcd. for C$_{21}$H$_{17}$ClF$_3$N$_9$O$_2$ 519, m/z found 520 [M+H]$^+$. $^1$H NMR (400 MHz, CHLOROFORM-d) δ ppm 1.91 (s, 3H), 3.84-3.91 (m, 2H), 4.25-4.33 (m, 2H), 4.75-4.84 (m, 1H), 6.21 (s, 1H), 7.93 (s, 2H), 8.11 (s, 1H), 8.14 (s, 1H), 8.50 (d, J=2.4 Hz, 1H), 8.62 (br s, 1H), 8.73 (d, J=2.4 Hz, 1H).

Example 157

N-(5-chloro-6-(2H-1,2,3-triazol-2-yl)pyridin-3-yl)-1-(2-(3-hydroxyazetidin-1-yl)-3-methylpyridin-4-yl)-5-(trifluoromethyl)-1H-pyrazole-4-carboxamide, Cpd 157

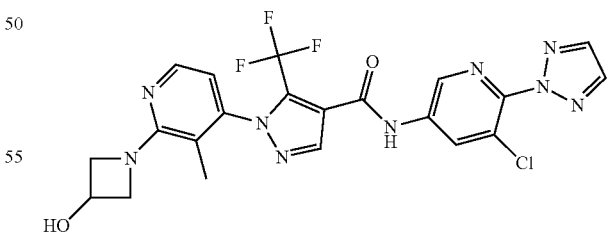

1-(2-Chloro-3-methylpyridin-4-yl)-N-(5-chloro-6-(2H-1,2,3-triazol-2-yl)pyridin-3-yl)-5-(trifluoromethyl)-1H-pyrazole-4-carboxamide (50 mg, 0.1 mmol), 3-hydroxy azetidine (14 mg, 0.2 mmol) and Cs$_2$CO$_3$ (63 mg, 0.2 mmol) in DMA (3 mL) were stirred at 100° C. for 32 h. The reaction mixture was poured into water and extracted with ethyl acetate. The organic layer was washed with water, dried, filtered, and the filtrate concentrated under reduced pressure. The residue was purified via Prep SFC (Stationary phase: Chiralpak Diacel AD 20×250 mm, Mobile phase: CO$_2$, EtOH+0.4 iPrNH$_2$) yielding title compound (18 mg, 36%). LCMS (ESI): mass calcd. for C$_{21}$H$_{17}$ClF$_3$N$_9$O$_2$ 519, m/z found 520 [M+H]$^+$. $^1$H NMR (400 MHz, CHLOROFORM-d) δ ppm 1.82 (s, 3H), 3.99-4.07 (m, 2H), 4.37-4.48 (m, 2H), 4.71-4.80 (m, 1H), 6.65 (d, J=5.3 Hz, 1H), 7.93 (s, 2H), 8.12 (s, 1H), 8.17 (d, J=5.3 Hz, 1H), 8.50 (d, J=2.2 Hz, 1H), 8.53 (br s, 1H), 8.73 (d, J=1.0 Hz, 1H).

Following the procedure described in Example 156, above, selecting and substituting the appropriate reagents, starting materials, and purification methods, and adjusting reaction temperatures, times and other variables or parameters, as needed or desirable, as would be readily recognized by those skilled in the art, the following compounds (Examples 158-165) were prepared.

Example 158

N-(5-chloro-6-(2H-1,2,3-triazol-2-yl)pyridin-3-yl)-1-(3-methylpyridin-4-yl)-5-(trifluoromethyl)-1H-pyrazole-4-carboxamide, Cpd 158

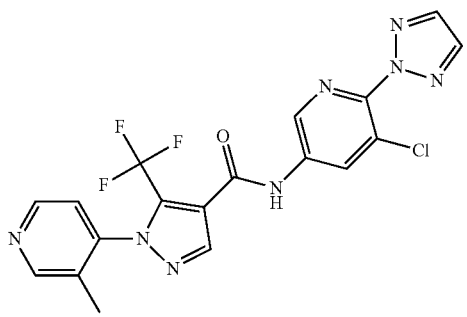 [SMILES: Cc1cnccc1-n1ncc(C(=O)Nc2cnc(-n3nccn3)c(Cl)c2)c1C(F)(F)F]

$^1$H NMR (400 MHz, DMSO-d$_6$) δ ppm 2.06 (s, 3H), 7.57 (d, J=5.07 Hz, 1H), 8.17 (s, 2H), 8.63 (d, J=2.20 Hz, 1H), 8.66 (d, J=5.07 Hz, 1H), 8.76 (s, 1H), 8.81 (d, J=2.21 Hz, 1H), 11.21 (s, 1H). LC-MS: (ES, m/z): [M+1]$^+$ 449.0

Example 159

N-(5-chloro-6-(2H-1,2,3-triazol-2-yl)pyridin-3-yl)-1-(4-methylpyridazin-3-yl)-5-(trifluoromethyl)-1H-pyrazole-4-carboxamide, Cpd 159

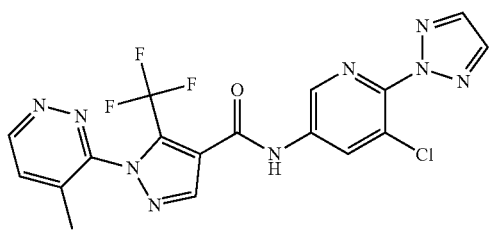

$^1$H NMR (400 MHz, DMSO-d$_6$) δ ppm 2.24 (s, 3H), 8.00 (d, J=4.63 Hz, 1H), 8.16 (s, 2H), 8.58 (s, 1H), 8.63 (d, J=2.21 Hz, 1H), 8.81 (d, J=2.21 Hz, 1H), 9.35 (d, J=5.29 Hz, 1H). LC-MS: (ES, m/z): [M+1]$^+$ 449.9

Example 160

N-(5-cyano-6-(2H-1,2,3-triazol-2-yl)pyridin-3-yl)-1-(5-fluoro-6-methylpyridin-2-yl)-5-(trifluoromethyl)-1H-pyrazole-4-carboxamide, Cpd 160

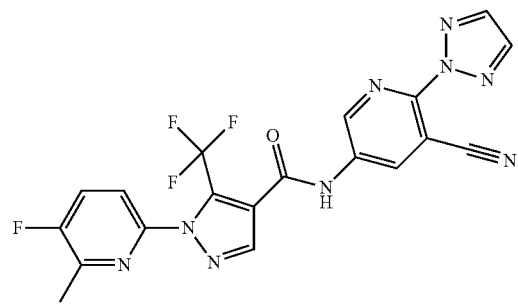 [SMILES: Cc1nc(-n2ncc(C(=O)Nc3cnc(-n4nccn4)c(C#N)c3)c2C(F)(F)F)ccc1F]

$^1$H NMR (400 MHz, DMSO-d$_6$) δ ppm 11.32 (s, 1H), 9.03 (d, J=2.43 Hz, 1H), 8.82 (d, J=2.43 Hz, 1H), 8.41 (s, 1H), 8.29 (s, 2H), 7.99 (t, J=8.71 Hz, 1H), 7.74 (dd, J=8.60, 2.87 Hz, 1H), 2.50 (br d, J=1.76 Hz, 3H). LC-MS: (ES, m/z): [M+1]$^+$ 458.0

Example 161

N-(5-chloro-6-(2H-1,2,3-triazol-2-yl)pyridin-3-yl)-1-(5-fluoro-6-methylpyridin-2-yl)-5-(trifluoromethyl)-1H-pyrazole-4-carboxamide, Cpd 161

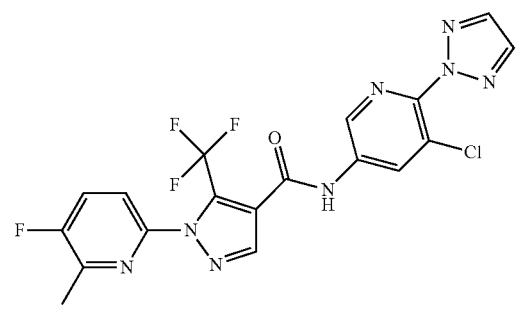 [SMILES: Cc1nc(-n2ncc(C(=O)Nc3cnc(-n4nccn4)c(Cl)c3)c2C(F)(F)F)ccc1F]

$^1$H NMR (400 MHz, CHLOROFORM-d) δ ppm 8.73 (d, J=2.43 Hz, 1H), 8.47 (d, J=2.21 Hz, 1H), 7.99-8.14 (m, 2H), 7.93 (s, 2H), 7.46-7.60 (m, 2H), 2.56 (d, J=3.09 Hz, 3H). LC-MS: (ES, m/z): [M+1]$^+$ 466.9

Example 162

N-(5-cyano-6-(2H-1,2,3-triazol-2-yl)pyridin-3-yl)-1-(3,6-dichloropyridin-2-yl)-5-(trifluoromethyl)-1H-pyrazole-4-carboxamide, Cpd 162

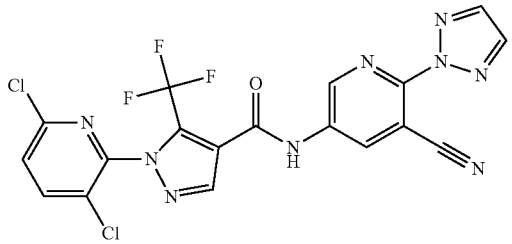 [SMILES: N#Cc1cc(NC(=O)c2cnn(-c3nc(Cl)ccc3Cl)c2C(F)(F)F)cnc1-n1nccn1]

$^1$H NMR (400 MHz, DMSO-d$_6$) δ ppm 11.27-11.34 (m, 1H), 8.99-9.07 (m, 1H), 8.78-8.86 (m, 1H), 8.54-8.59 (m, 1H), 8.43-8.50 (m, 1H), 8.24-8.30 (m, 2H), 7.93-8.01 (m, 1H). LC-MS: (ES, m/z): [M+1]$^+$ 494.0

Example 163

N-(5-chloro-6-(2H-1,2,3-triazol-2-yl)pyridin-3-yl)-1-(3,6-dichloropyridin-2-yl)-5-(trifluoromethyl)-1H-pyrazole-4-carboxamide, Cpd 163

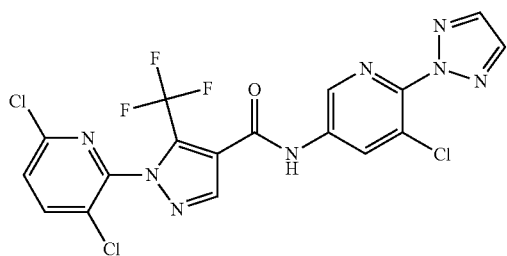 [SMILES: O=C(Nc1cnc(-n2nccn2)c(Cl)c1)c1cnn(-c2nc(Cl)ccc2Cl)c1C(F)(F)F]

$^1$H NMR (400 MHz, DMSO-d$_6$) δ ppm 11.32 (s, 1H), 8.83 (d, J=1.98 Hz, 1H), 8.58-8.66 (m, 2H), 8.46 (d, J=8.60 Hz, 1H), 8.12-8.18 (m, 2H), 7.97 (d, J=8.38 Hz, 1H). LC-MS: (ES, m/z): [M+1]$^+$ 502.9

Example 164

1-(6-chloro-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide, Cpd 164

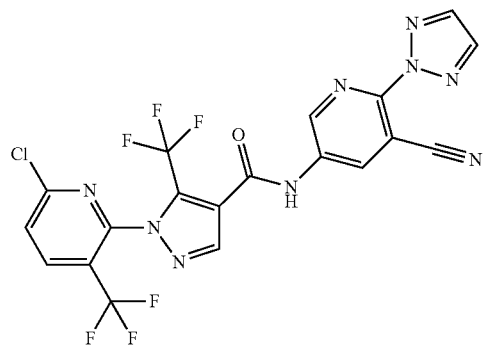 [SMILES: N#Cc1cc(NC(=O)c2cnn(-c3nc(Cl)ccc3C(F)(F)F)c2C(F)(F)F)cnc1-n1nccn1]

$^1$H NMR (400 MHz, DMSO-d$_6$) δ ppm 11.34 (1H, s), 9.04 (1H, d, J=2.43 Hz), 8.83 (1H, d, J=2.43 Hz), 8.70 (1H, d, J=8.38 Hz), 8.59 (1H, s), 8.28 (2H, s), 8.17 (1H, d, J=8.38 Hz). LC-MS: (ES, m/z): [M+1]$^+$ 527.9

Example 165

1-(6-chloro-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide, Cpd 165

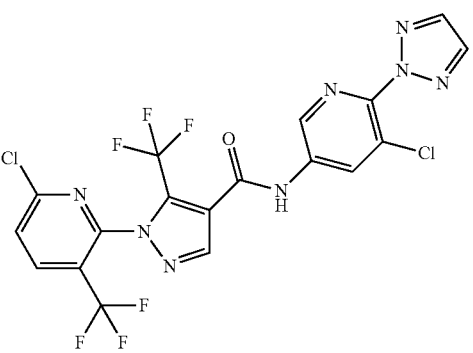 [SMILES: O=C(Nc1cnc(-n2nccn2)c(Cl)c1)c1cnn(-c2nc(Cl)ccc2C(F)(F)F)c1C(F)(F)F]

$^1$H NMR (400 MHz, DMSO-d$_6$) δ ppm 11.30 (1H, s), 8.82 (1H, d, J=2.21 Hz), 8.70 (1H, d, J=8.38 Hz), 8.63 (1H, d, J=2.21 Hz), 8.60 (1H, s), 8.18 (1H, s), 8.16 (2H, s). LC-MS: (ES, m/z): [M+1]$^+$ 536.8

Following the procedure described in Example 50, above, selecting and substituting the appropriate reagents, starting materials, and purification methods, and adjusting reaction temperatures, times and other variables or parameters, as needed or desirable, as would be readily recognized by those skilled in the art, the following compounds (examples 166-174) were prepared

Example 166

1-(4-chloro-2-methylphenyl)-N-(5-cyano-6-(2H-1,2,3-triazol-2-yl)pyridin-3-yl)-5-(trifluoromethyl)-1H-pyrazole-4-carboxamide, Cpd 166

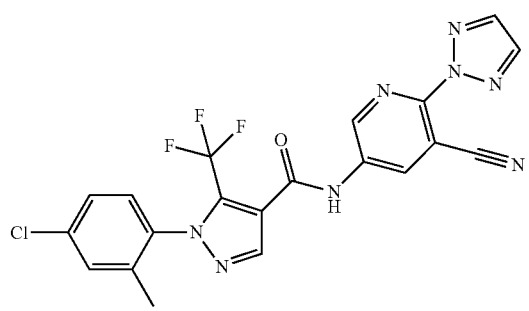 [SMILES: Cc1cc(Cl)ccc1-n1ncc(C(=O)Nc2cnc(-n3nccn3)c(C#N)c2)c1C(F)(F)F]

$^1$H NMR (400 MHz, DMSO-d$_6$) δ ppm 2.01 (s, 3H), 7.48-7.52 (m, 2H), 7.63 (s, 1H), 8.30 (s, 2H), 8.47 (s, 1H), 8.82-8.86 (m, 1H), 9.04-9.08 (m, 1H), 11.26 (s, 1H). LC-MS: (ES, m/z): [M+1]$^+$ 472.9

Example 167

N-(5-cyano-6-(2H-1,2,3-triazol-2-yl)pyridin-3-yl)-1-(3-fluoro-2-methylphenyl)-5-(trifluoromethyl)-1H-pyrazole-4-carboxamide, Cpd 167

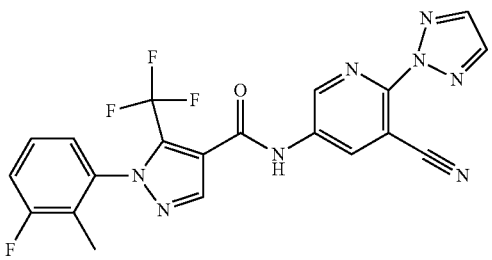 [SMILES: Cc1c(F)cccc1-n1ncc(C(=O)Nc2cnc(-n3nccn3)c(C#N)c2)c1C(F)(F)F]

¹H NMR (400 MHz, DMSO-d₆) δ ppm 1.90 (d, J=1.76 Hz, 3H), 7.31-7.40 (m, 1H), 7.41-7.54 (m, 2H), 8.29 (s, 2H), 8.47 (s, 1H), 8.83 (d, J=2.65 Hz, 1H), 9.05 (d, J=2.43 Hz, 1H), 11.26 (s, 1H). LC-MS: (ES, m/z): [M+1]⁺ 457.0

Example 168

N-(5-cyano-6-(2H-1,2,3-triazol-2-yl)pyridin-3-yl)-1-(3,4-difluoro-2-methylphenyl)-5-(trifluoromethyl)-1H-pyrazole-4-carboxamide, Cpd 168

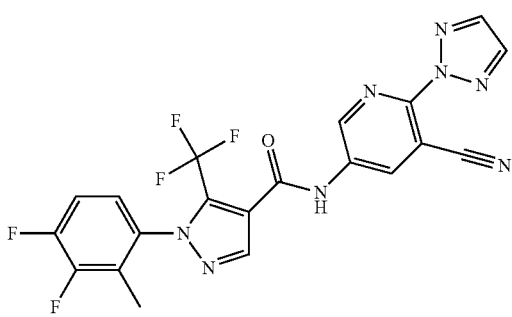 [SMILES: Cc1c(-n2ncc(C(=O)Nc3cnc(-n4nccn4)c(C#N)c3)c2C(F)(F)F)ccc(F)c1F]

¹H NMR (400 MHz, DMSO-d₆) δ ppm 1.97 (d, J=1.98 Hz, 3H), 7.44-7.50 (m, 1H), 7.55 (q, J=8.89 Hz, 1H), 8.31 (s, 2H), 8.49 (s, 1H), 8.85 (br d, J=2.43 Hz, 1H), 9.06 (d, J=2.43 Hz, 1H), 11.29 (s, 1H). LC-MS: (ES, m/z): [M+1]⁺ 474.9

Example 169

N-(5-cyano-6-(2H-1,2,3-triazol-2-yl)pyridin-3-yl)-1-(4-cyanophenyl)-5-(trifluoromethyl)-1H-pyrazole-4-carboxamide, Cpd 169

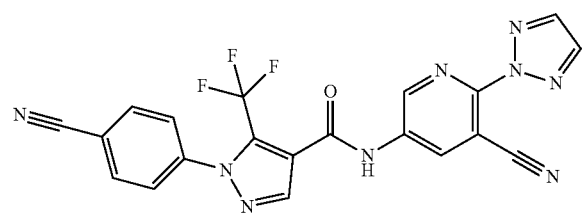 [SMILES: N#Cc1ccc(-n2ncc(C(=O)Nc3cnc(-n4nccn4)c(C#N)c3)c2C(F)(F)F)cc1]

¹H NMR (400 MHz, DMSO-d₆) δ ppm 11.31 (1H, s), 9.07 (1H, d, J=2.51 Hz), 8.85 (1H, d, J=2.51 Hz), 8.51 (1H, s), 8.32 (2H, s), 8.15 (1H, s), 8.13 (1H, s), 7.85 (1H, s), 7.83 (1H, s). LC-MS: (ES, m/z): [M+1]⁺ 450.0

Example 170

N-(5-cyano-2-methyl-6-(2H-1,2,3-triazol-2-yl)pyridin-3-yl)-1-(4-fluoro-2-methylphenyl)-5-(trifluoromethyl)-1H-pyrazole-4-carboxamide, Cpd 170

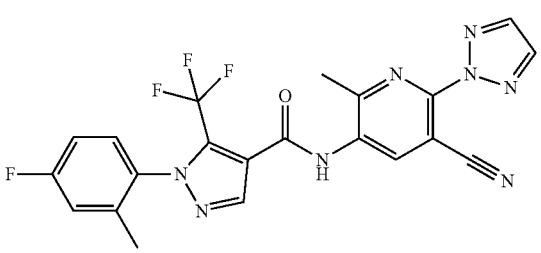 [SMILES: Cc1cc(F)ccc1-n1ncc(C(=O)Nc2cc(C#N)c(-n3nccn3)nc2C)c1C(F)(F)F]

¹H NMR (400 MHz, DMSO-d₆) δ ppm 2.03 (s, 3H), 2.65 (s, 3H), 7.27 (td, J=8.43, 2.76 Hz, 1H), 7.40 (dd, J=9.48, 2.87 Hz, 1H), 7.54 (dd, J=8.71, 5.18 Hz, 1H), 8.31 (s, 2H), 8.46 (s, 1H), 8.66 (s, 1H), 10.62 (s, 1H), LC-MS: (ES, m z): [M+1]⁺ 471.0

Example 171

N-(5-chloro-6-(2H-1,2,3-triazol-2-yl)pyridin-3-yl)-1-(3-fluoro-2-methylphenyl)-5-(trifluoromethyl)-1H-pyrazole-4-carboxamide, Cpd 171

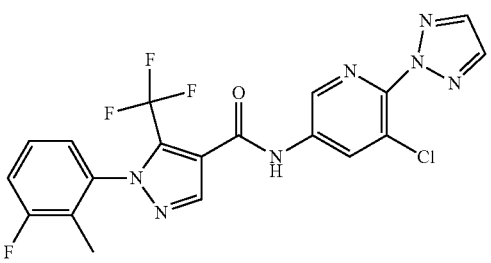 [SMILES: Cc1c(F)cccc1-n1ncc(C(=O)Nc2cnc(-n3nccn3)c(Cl)c2)c1C(F)(F)F]

¹H NMR (400 MHz, DMSO-d₆) δ ppm 0.85-1.26 (m, 1H), 1.90 (d, J=1.76 Hz, 4H), 7.34-7.38 (m, 1H), 7.44-7.51 (m, 2H), 8.17 (s, 2H), 8.47 (s, 1H), 8.63 (d, J=2.21 Hz, 1H), 8.81 (d, J=2.43 Hz, 1H), 11.21 (s, 1H). LC-MS: (ES, m z): [M+1]⁺ 466.1

Example 172

N-(5-chloro-2-methyl-6-(2H-1,2,3-triazol-2-yl)pyridin-3-yl)-1-(4-fluoro-2-methylphenyl)-5-(trifluoromethyl)-1H-pyrazole-4-carboxamide, Cpd 172

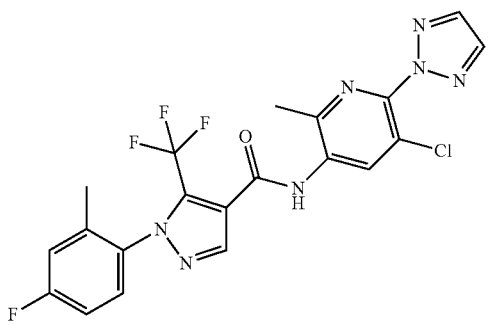 [SMILES: Cc1cc(F)ccc1-n1ncc(C(=O)Nc2cc(Cl)c(-n3nccn3)nc2C)c1C(F)(F)F]

$^1$H NMR (400 MHz, DMSO-d$_6$) δ ppm 2.00 (s, 3H), 2.52 (s, 3H), 7.25 (td, J=8.54, 2.98 Hz, 1H), 7.38 (dd, J=9.59, 2.54 Hz, 1H), 7.51 (dd, J=8.49, 5.40 Hz, 1H), 8.16 (s, 2H) 8.41 (d, J=13.67 Hz, 2H), 10.55 (s, 1H). LC-MS: (ES, m/z): [M+1]$^+$ 479.9

Example 173

N-(5-cyano-6-(2H-1,2,3-triazol-2-yl)pyridin-3-yl)-5-(trifluoromethyl)-1-(2,4,6-trifluorophenyl)-1H-pyrazole-4-carboxamide, Cpd 173

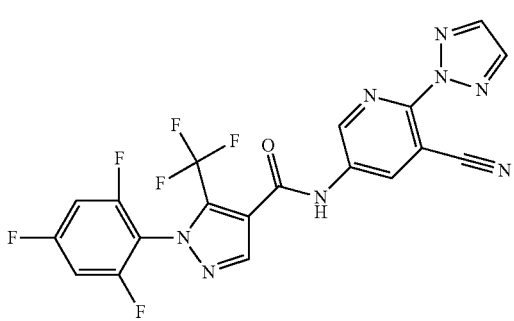 [SMILES: N#Cc1cc(NC(=O)c2cnn(-c3c(F)cc(F)cc3F)c2C(F)(F)F)cnc1-n1nccn1]

$^1$H NMR (400 MHz, DMSO-d$_6$) δ ppm 11.40 (br s, 1H), 9.03 (d, J=2.43 Hz, 1H), 8.81 (d, J=2.43 Hz, 1H), 8.58 (s, 1H), 8.28 (s, 2H), 7.67 (t, J=8.93 Hz, 2H). LC-MS: (ES, m/z): [M+1]$^+$ 479.0

Example 174

N-(5-chloro-6-(2H-1,2,3-triazol-2-yl)pyridin-3-yl)-1-(3,4-difluoro-2-methylphenyl)-5-(trifluoromethyl)-1H-pyrazole-4-carboxamide, Cpd 174

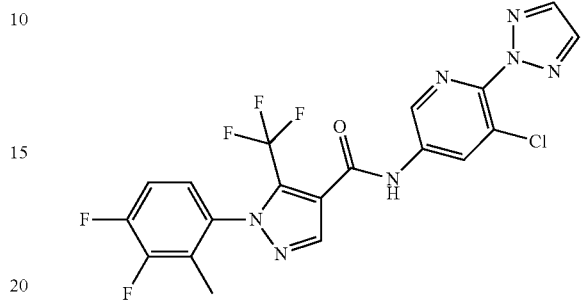

$^1$H NMR (400 MHz, DMSO-d$_6$) δ ppm 1.96 (d, J=2.21 Hz, 3H), 7.43-7.49 (m, 1H), 7.54 (q, J=9.11 Hz, 1H), 8.18 (s, 2H), 8.49 (s, 1H), 8.64 (d, J=2.21 Hz, 1H), 8.82 (d, J=2.43 Hz, 1H), 11.24 (br s, 1H). LC-MS: (ES, m/z): [M+1]$^+$ 483.9

Following the procedure described in Example 56, 139 or 141, above, selecting and substituting the appropriate reagents, starting materials, and purification methods, and adjusting reaction temperatures, times and other variables or parameters, as needed or desirable, as would be readily recognized by those skilled in the art, the following compounds (175-201) were prepared.

Example 175

1-(6-amino-3-chloropyridin-2-yl)-N-(5-cyano-6-(2H-1,2,3-triazol-2-yl)pyridin-3-yl)-5-(trifluoromethyl)-1H-pyrazole-4-carboxamide, Cpd 175

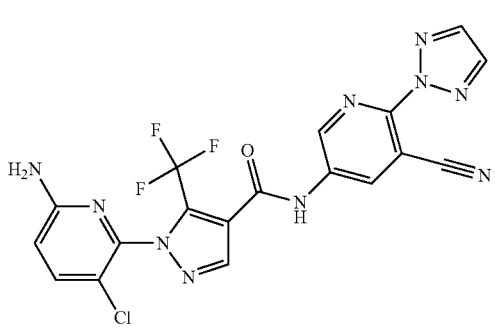 [SMILES: N#Cc1cc(NC(=O)c2cnn(-c3nc(N)ccc3Cl)c2C(F)(F)F)cnc1-n1nccn1]

$^1$H NMR (400 MHz, DMSO-d$_6$) δ ppm 11.25 (s, 1H), 9.06 (d, J=2.65 Hz, 1H), 8.84 (d, J=2.65 Hz, 1H), 8.49 (s, 1H), 8.25-8.30 (m, 2H), 7.72 (d, J=8.82 Hz, 1H), 6.72 (br s, 2H), 6.67-6.70 (m, 1H). LC-MS: (ES, m/z): [M+1]$^+$ 474.9

Example 176

1-(6-amino-4-methylpyridin-2-yl)-N-(5-cyano-6-(2H-1,2,3-triazol-2-yl)pyridin-3-yl)-5-(trifluoromethyl)-1H-pyrazole-4-carboxamide, Cpd 176

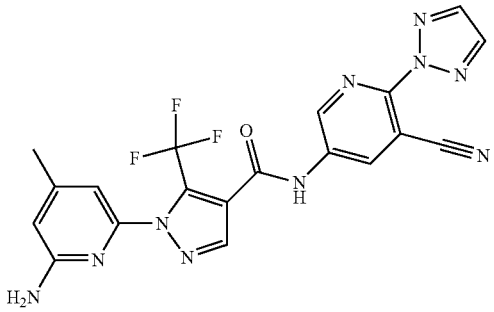 [SMILES: Cc1cc(N)nc(-n2ncc(C(=O)Nc3cnc(-n4nccn4)c(C#N)c3)c2C(F)(F)F)c1]

$^1$H NMR (400 MHz, DMSO-d$_6$) δ ppm 11.35 (s, 1H), 9.08-9.11 (m, 1H), 8.85-8.88 (m, 1H), 8.38 (s, 1H), 8.31 (s, 2H), 6.64 (s, 1H), 6.42 (s, 1H), 2.26 (s, 3H). LC-MS: (ES, m/z): [M+1]$^+$ 455.0

Example 177

1-(6-amino-5-cyanopyridin-2-yl)-N-(5-cyano-2-methyl-6-(2H-1,2,3-triazol-2-yl)pyridin-3-yl)-5-(trifluoromethyl)-1H-pyrazole-4-carboxamide, Cpd 177

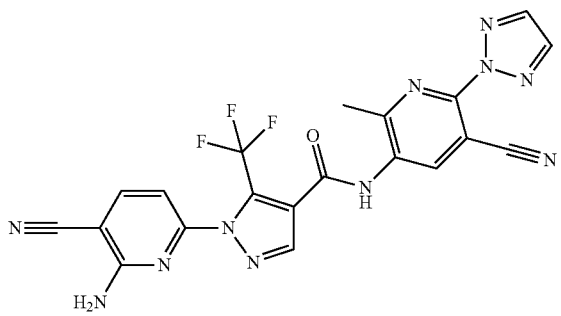 [SMILES: Cc1nc(-n2nccn2)c(C#N)cc1NC(=O)c1cnn(-c2ccc(C#N)c(N)n2)c1C(F)(F)F]

$^1$H NMR (400 MHz, DMSO-d$_6$) δ ppm 2.59 (s, 3H), 7.00 (d, J=8.16 Hz, 1H), 7.32 (s, 2H), 8.15 (d, J=7.94 Hz, 1H), 8.27 (s, 2H), 8.36 (s, 1H), 8.65 (s, 1H), 10.65 (br s, 1H). LC-MS: (ES, m/z): [M+1]$^+$ 480.0

Example 178

1-(6-amino-5-cyanopyridin-2-yl)-N-(5-chloro-2-methyl-6-(2H-1,2,3-triazol-2-yl)pyridin-3-yl)-5-(trifluoromethyl)-1H-pyrazole-4-carboxamide, Cpd 178

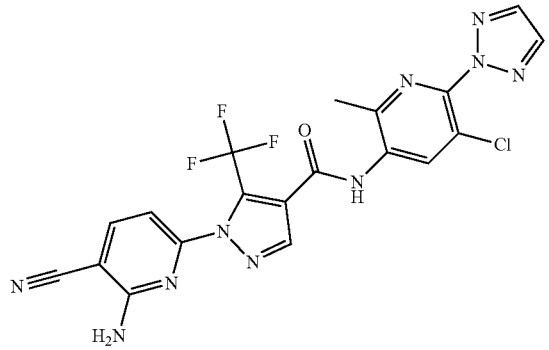 [SMILES: Cc1nc(-n2nccn2)c(Cl)cc1NC(=O)c1cnn(-c2ccc(C#N)c(N)n2)c1C(F)(F)F]

$^1$H NMR (400 MHz, DMSO-d$_6$) δ ppm 2.50 (s, 3H), 7.01 (d, J=8.16 Hz, 1H), 7.31 (s, 2H), 8.12-8.19 (m, 3H), 8.37 (s, 1H), 8.42 (s, 1H), 10.61 (br s, 1H). LC-MS: (ES, m/z): [M+1]$^+$ 488.9

Example 179

1-(6-amino-5-fluoropyridin-2-yl)-N-(5-chloro-2-methyl-6-(2H-1,2,3-triazol-2-yl)pyridin-3-yl)-5-(trifluoromethyl)-1H-pyrazole-4-carboxamide, Cpd 179

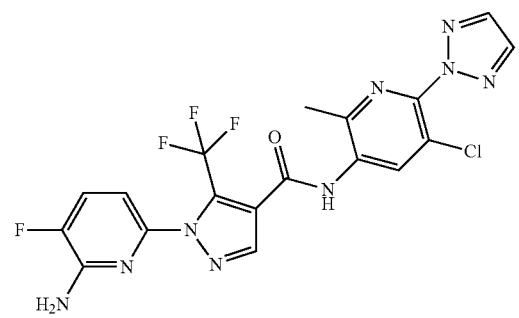 [SMILES: Cc1nc(-n2nccn2)c(Cl)cc1NC(=O)c1cnn(-c2ccc(F)c(N)n2)c1C(F)(F)F]

$^1$H NMR (400 MHz, DMSO-d$_6$) δ ppm 2.53 (s, 3H), 6.72 (s, 2H), 6.81 (dd, J=8.05, 2.54 Hz, 1H), 7.62 (dd, J=10.47, 8.27 Hz, 1H), 8.18 (s, 2H), 8.33 (s, 1H), 8.43 (s, 1H), 10.57 (s, 1H). LC-MS: (ES, m/z): [M+1]$^+$ 481.9

Example 180

1-(6-aminopyridin-2-yl)-N-(5-chloro-6-(2H-1,2,3-triazol-2-yl)pyridin-3-yl)-5-(trifluoromethyl)-1H-pyrazole-4-carboxamide, Cpd 180

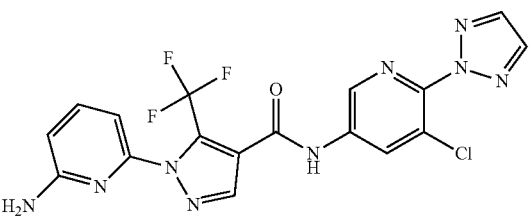 [SMILES: Nc1cccc(-n2ncc(C(=O)Nc3cnc(-n4nccn4)c(Cl)c3)c2C(F)(F)F)n1]

$^1$H NMR (400 MHz, CHLOROFORM-d) δ ppm 8.682 (d, J=2.43 Hz, 1H), 8.421 (d, J=2.21 Hz, 1H), 7.977 (s, 1H), 7.874 (s, 2H), 7.807 (s, 1H), 7.572 (t, J=8.05 Hz, 1H), 6.904 (d, J=7.72 Hz, 1H), 6.540 (d, J=8.16 Hz, 1H), 4.573 (br s, 2H). LC-MS: (ES, m/z): [M+1]$^+$ 449.9

Example 181

1-(6-amino-5-fluoropyridin-2-yl)-N-(5-bromo-2-methyl-6-(2H-1,2,3-triazol-2-yl)pyridin-3-yl)-5-(trifluoromethyl)-1H-pyrazole-4-carboxamide, Cpd 181

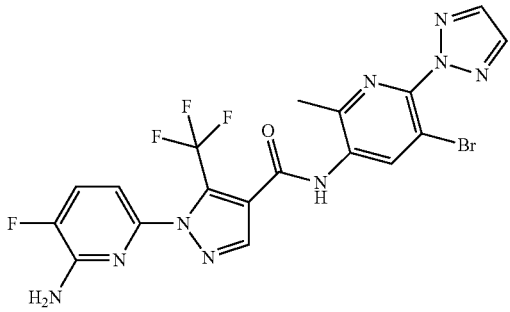

¹H NMR (400 MHz, DMSO-d₆) δ ppm 2.50 (br s, 3H), 6.71 (s, 2H), 6.79 (dd, J=8.05, 2.54 Hz, 1H), 7.60 (dd, J=10.36, 8.16 Hz, 1H), 8.15 (s, 2H), 8.33 (s, 1H), 8.52 (s, 1H), 10.55 (br s, 1H). LC-MS: (ES, m/z): [M+1]⁺ 527.8

Example 182

1-(6-amino-5-fluoropyridin-2-yl)-N-(5-cyano-2-methyl-6-(2H-1,2,3-triazol-2-yl)pyridin-3-yl)-5-(trifluoromethyl)-1H-pyrazole-4-carboxamide, Cpd 182

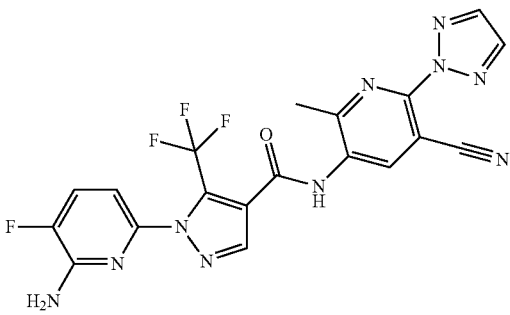 [SMILES: Cc1nc(-n2nccn2)c(C#N)cc1NC(=O)c1cnn(-c2ccc(F)c(N)n2)c1C(F)(F)F]

¹H NMR (400 MHz, DMSO-d₆) δ ppm 2.63 (s, 3H), 6.73 (s, 2H), 6.81 (dd, J=8.05, 2.54 Hz, 1H), 7.62 (dd, J=10.47, 8.05 Hz, 1H), 8.31 (s, 2H), 8.35 (s, 1H), 8.67 (s, 1H), 10.63 (s, 1H). LC-MS: (ES, m/z): [M+1]⁺ 472.9

Example 183

1-(6-amino-3-chloropyridin-2-yl)-N-(5-chloro-6-(2H-1,2,3-triazol-2-yl)pyridin-3-yl)-5-(trifluoromethyl)-1H-pyrazole-4-carboxamide, Cpd 183

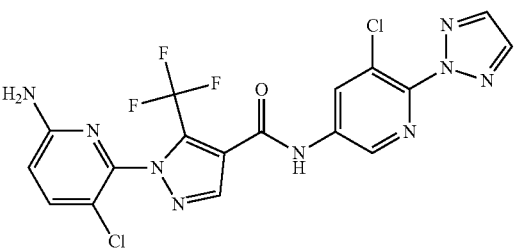 [SMILES: Nc1ccc(Cl)c(-n2ncc(C(=O)Nc3cnc(-n4nccn4)c(Cl)c3)c2C(F)(F)F)n1]

¹H NMR (400 MHz, DMSO-d₆) δ ppm 10.84-11.22 (m, 1H), 8.78-8.85 (m, 1H), 8.59-8.66 (m, 1H), 8.44-8.52 (m, 1H), 8.15 (s, 2H), 7.67-7.75 (m, 1H), 6.70-6.76 (m, 2H), 6.66-6.70 (m, 1H). LC-MS: (ES, m/z): [M+1]⁺ 483.9

Example 184

1-(6-amino-5-methylpyridin-2-yl)-N-(5-chloro-6-(2H-1,2,3-triazol-2-yl)pyridin-3-yl)-5-(trifluoromethyl)-1H-pyrazole-4-carboxamide, Cpd 184

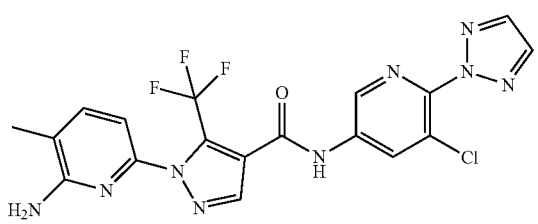 [SMILES: Cc1ccc(-n2ncc(C(=O)Nc3cnc(-n4nccn4)c(Cl)c3)c2C(F)(F)F)nc1N]

¹H NMR (400 MHz, DMSO-d₆) δ ppm 2.10 (s, 3H), 6.15 (s, 2H), 6.71 (d, J=7.72 Hz, 1H), 7.47 (d, J=7.72 Hz, 1H), 8.16 (s, 2H), 8.31 (s, 1H), 8.61 (d, J=2.21 Hz, 1H), 8.79 (s, 1H), 11.17 (s, 1H). LC-MS: (ES, m/z): [M+1]⁺ 463.9

Example 185

1-(6-amino-3-methylpyridin-2-yl)-N-(5-chloro-6-(2H-1,2,3-triazol-2-yl)pyridin-3-yl)-5-(trifluoromethyl)-1H-pyrazole-4-carboxamide, Cpd 185

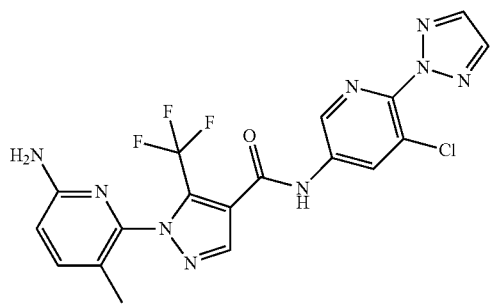 [SMILES: Cc1ccc(N)nc1-n1ncc(C(=O)Nc2cnc(-n3nccn3)c(Cl)c2)c1C(F)(F)F]

¹H NMR (400 MHz, DMSO-d₆) δ ppm 1.88 (s, 3H), 6.63 (d, J=8.28 Hz, 1H), 7.52 (d, J=8.53 Hz, 1H), 8.19 (s, 2H), 8.46 (s, 1H), 8.67 (d, J=2.01 Hz, 1H), 8.87 (d, J=2.01 Hz, 1H), 11.21 (s, 1H). LC-MS: (ES, m/z): [M+1]⁺ 463.9

Example 186

1-(6-amino-5-fluoro-3-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide, Cpd 186

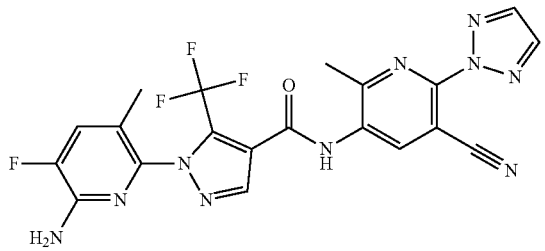 [SMILES: Cc1cc(F)c(N)nc1-n1ncc(C(=O)Nc2cc(C#N)c(-n3nccn3)nc2C)c1C(F)(F)F]

$^1$H NMR (400 MHz, DMSO-d$_6$) δ ppm 8.63 (s, 1H), 8.40 (s, 1H), 8.28 (s, 2H), 7.55 (d, J=11.03 Hz, 1H), 6.50 (s, 2H), 2.61 (s, 3H), 1.87 (s, 3H). LC-MS: (ES, m/z): [M+1]+486.9

Example 187

1-(6-amino-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide, Cpd 187

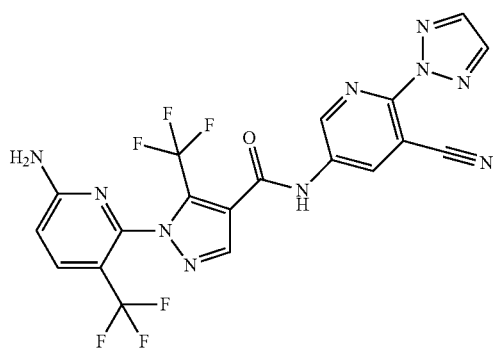 [SMILES: N#Cc1cc(NC(=O)c2cnn(-c3nc(N)ccc3C(F)(F)F)c2C(F)(F)F)cnc1-n1nccn1]

$^1$H NMR (400 MHz, DMSO-d$_6$) δ ppm 11.22 (1H, s), 9.06 (1H, d, J=2.43 Hz), 8.84 (1H, d, J=2.43 Hz), 8.47 (1H, s), 8.29 (2H, s), 7.92 (1H, d, J=8.82 Hz), 7.31 (2H, br s), 6.75 (1H, d, J=8.60 Hz). LC-MS: (ES, m/z): [M+1]$^+$ 508.9

Example 188

1-(6-amino-5-fluoro-3-methylpyridin-2-yl)-N-(5-chloro-2-methyl-6-(2H-1,2,3-triazol-2-yl)pyridin-3-yl)-5-(trifluoromethyl)-1H-pyrazole-4-carboxamide, Cpd 188

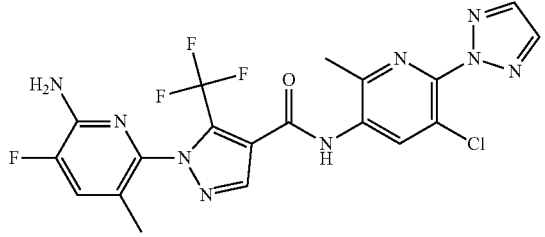 [SMILES: Cc1cc(F)c(N)nc1-n1ncc(C(=O)Nc2cc(Cl)c(-n3nccn3)nc2C)c1C(F)(F)F]

$^1$H NMR (400 MHz, DMSO-d$_6$) δ ppm 10.71 (s, 1H), 8.48 (s, 1H), 8.37 (s, 1H), 8.15 (s, 2H), 7.55 (d, J=11.03 Hz, 1H), 6.50 (s, 2H), 2.51 (s, 3H), 1.87 (s, 3H). LC-MS: (ES, m/z): [M+1]$^+$ 495.9

Example 189

N-(5-cyano-6-(2H-1,2,3-triazol-2-yl)pyridin-3-yl)-1-(6-(methylamino)pyridin-2-yl)-5-(trifluoromethyl)-1H-pyrazole-4-carboxamide, Cpd 189

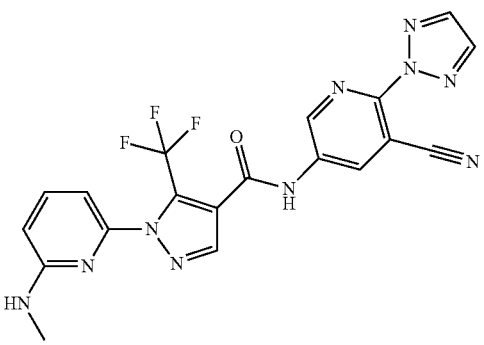 [SMILES: CNc1cccc(-n2ncc(C(=O)Nc3cnc(-n4nccn4)c(C#N)c3)c2C(F)(F)F)n1]

$^1$H NMR (400 MHz, DMSO-d$_6$) δ ppm 2.78 (s, 3H), 6.61 (d, J=8.25 Hz, 1H), 6.82 (d, J=7.47 Hz, 1H), 7.62 (t, J=7.79 Hz, 1H), 8.31 (s, 2H), 8.34 (s, 1H), 8.84 (d, J=2.18 Hz, 1H), 9.06 (d, J=2.34 Hz, 1H), 11.33 (s, 1H). LC-MS: (ES, m/z): [M+1]$^+$ 455.0

Example 190

1-(6-amino-4-methylpyridin-3-yl)-N-(5-cyano-6-(2H-1,2,3-triazol-2-yl)pyridin-3-yl)-5-(trifluoromethyl)-1H-pyrazole-4-carboxamide, Cpd 190

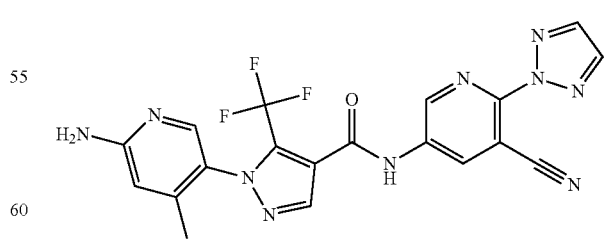

$^1$H NMR (400 MHz, DMSO-d$_6$) δ ppm 11.48 (1H, s), 9.12 (1H, d, J=2.43 Hz), 8.88 (1H, d, J=2.65 Hz), 8.58 (1H, s), 8.35 (1H, s), 8.26-8.30 (2H, m), 6.86 (1H, s), 1.97 (3H, s). LC-MS: (ES, m/z): [M+1]$^+$ 455.0

Example 191

1-(6-amino-4-methylpyridin-3-yl)-N-(5-chloro-6-(2H-1,2,3-triazol-2-yl)pyridin-3-yl)-5-(trifluoromethyl)-1H-pyrazole-4-carboxamide, Cpd 191

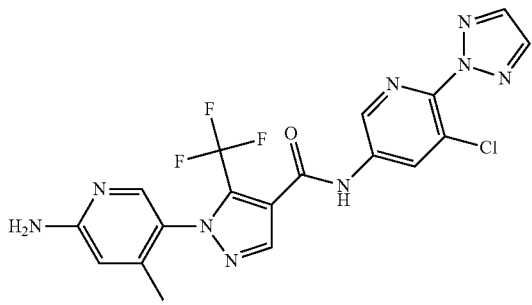 [SMILES: Cc1cc(N)ncc1-n1ncc(C(=O)Nc2cnc(-n3nccn3)c(Cl)c2)c1C(F)(F)F]

$^1$H NMR (400 MHz, DMSO-$d_6$) δ ppm 11.19 (br s, 1H), 8.82 (d, J=2.0 Hz, 1H), 8.64 (d, J=2.0 Hz, 1H), 8.40 (s, 1H), 8.18 (s, 1H), 7.88 (s, 1H), 6.44 (br d, J=9.9 Hz, 1H), 1.87 (s, 1H). LC-MS: (ES, m/z): [M+1]$^+$ 464.0

Example 192

1-(6-amino-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide, Cpd 192

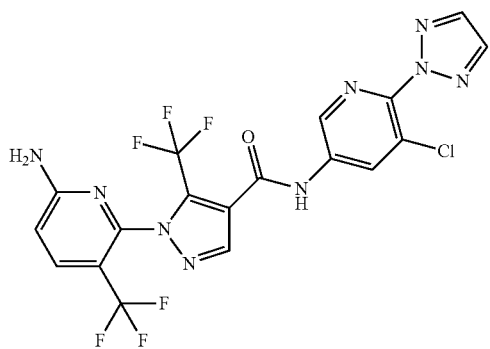 [SMILES: Nc1ccc(C(F)(F)F)c(-n2ncc(C(=O)Nc3cnc(-n4nccn4)c(Cl)c3)c2C(F)(F)F)n1]

$^1$H NMR (400 MHz, DMSO-$d_6$) δ ppm 11.15 (1H, s), 8.82 (1H, d, J=2.43 Hz), 8.63 (1H, d, J=2.20 Hz), 8.46 (1H, s), 8.16 (2H, s), 7.92 (1H, d, J=8.82 Hz), 7.31 (2H, br s), 6.74 (1H, d, J=8.38 Hz). LC-MS: (ES, m/z): [M+1]$^+$ 517.9

Example 193

1-(6-amino-5-fluoropyridin-2-yl)-N-(5-chloro-2-methyl-4-(2H-1,2,3-triazol-2-yl)phenyl)-5-(trifluoromethyl)-1H-pyrazole-4-carboxamide, Cpd 193

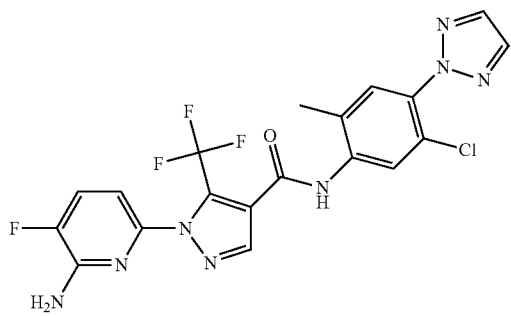 [SMILES: Cc1cc(-n2nccn2)c(Cl)cc1NC(=O)c1cnn(-c2ccc(F)c(N)n2)c1C(F)(F)F]

$^1$H NMR (400 MHz, DMSO-$d_6$) δ ppm 2.29 (s, 3H), 6.68 (s, 2H), 6.77 (dd, J=8.05, 2.54 Hz, 1H), 7.55-7.62 (m, 2H), 7.84 (s, 1H), 8.12 (s, 2H), 8.27 (s, 1H), 10.26 (s, 1H). LC-MS: (ES, m/z): [M+1]$^+$ 481.1

Example 194

1-(6-aminopyridin-3-yl)-N-(5-cyano-6-(2H-1,2,3-triazol-2-yl)pyridin-3-yl)-5-(trifluoromethyl)-1H-pyrazole-4-carboxamide, Cpd 194

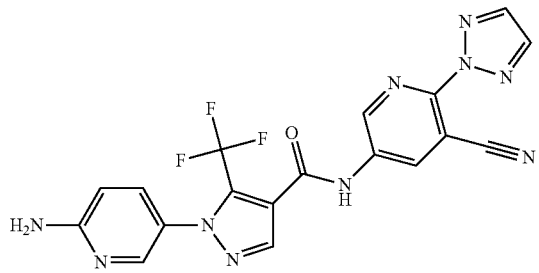 [SMILES: N#Cc1cc(NC(=O)c2cnn(-c3ccc(N)nc3)c2C(F)(F)F)cnc1-n1nccn1]

$^1$H NMR (400 MHz, DMSO-$d_6$) δ ppm 6.79-6.90 (m, 1H), 7.83 (br d, J=9.26 Hz, 1H), 8.25 (br s, 1H), 8.28 (s, 2H), 8.45 (s, 1H), 8.85 (d, J=2.65 Hz, 1H), 9.08 (d, J=2.43 Hz, 1H), 11.34 (s, 1H). LC-MS: (ES, m/z): [M+1]$^+$ 441.0

Example 195

1-(6-amino-5-fluoropyridin-2-yl)-N-(5-cyano-2-methyl-4-(2H-1,2,3-triazol-2-yl)phenyl)-5-(trifluoromethyl)-1H-pyrazole-4-carboxamide, Cpd 195

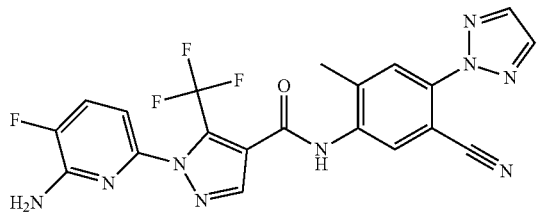 [SMILES: Cc1cc(-n2nccn2)c(C#N)cc1NC(=O)c1cnn(-c2ccc(F)c(N)n2)c1C(F)(F)F]

$^1$H NMR (400 MHz, DMSO-$d_6$) δ ppm 2.42 (s, 3H), 6.68 (br s, 2H), 6.78 (dd, J=8.05, 2.54 Hz, 1H), 7.59 (dd, J=10.58, 8.16 Hz, 1H), 8.01 (s, 1H), 8.13 (s, 1H), 8.24 (s, 2H), 8.28 (s, 1H), 10.35 (s, 1H). LC-MS: (ES, m/z): [M+1]$^+$ 471.9

Example 196

1-(6-amino-2-methylpyridin-3-yl)-N-(5-cyano-6-(2H-1,2,3-triazol-2-yl)pyridin-3-yl)-5-(trifluoromethyl)-1H-pyrazole-4-carboxamide, Cpd 196

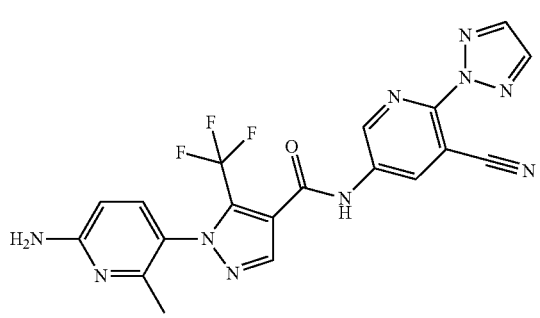 [SMILES: Cc1nc(N)ccc1-n1ncc(C(=O)Nc2cnc(-n3nccn3)c(C#N)c2)c1C(F)(F)F]

¹H NMR (400 MHz, METHANOL-d₄) δ ppm 9.04 (br s, 1H), 8.87 (br s, 1H), 8.28 (s, 1H), 8.12 (s, 2H), 7.55 (br d, J=9.04 Hz, 1H), 6.65 (br d, J=8.60 Hz, 1H), 2.09 (s, 3H).
LC-MS: (ES, m/z): [M+1]⁺ 455.0

Example 197

1-(6-amino-5-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide, Cpd 197

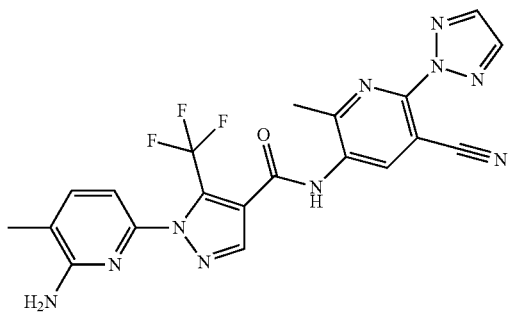 [SMILES: Cc1ccc(-n2ncc(C(=O)Nc3cc(C#N)c(-n4nccn4)nc3C)c2C(F)(F)F)nc1N]

¹H NMR (400 MHz, DMSO-d₆) δ ppm 2.10 (s, 3H), 2.61 (s, 3H), 6.12 (br s, 2H), 6.72 (d, J=7.28 Hz, 1H), 7.47 (d, J=7.50 Hz, 1H), 8.29 (s, 3H), 8.65 (s, 1H), 10.56 (s, 1H).
LC-MS: (ES, m/z): [M+1]⁺ 469.0

Example 198

2-amino-6-(4-((5-chloro-2-methyl-6-(2H-1,2,3-triazol-2-yl)pyridin-3-yl)carbamoyl)-5-(trifluoromethyl)-1H-pyrazol-1-yl)nicotinamide, Cpd 198

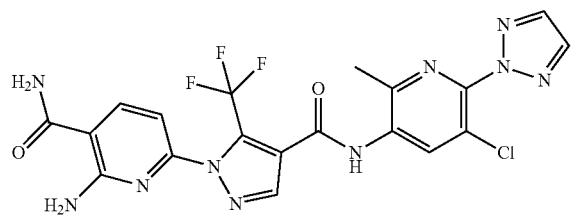 [SMILES: Cc1nc(-n2nccn2)c(Cl)cc1NC(=O)c1cnn(-c2ccc(C(N)=O)c(N)n2)c1C(F)(F)F]

¹H NMR (400 MHz, DMSO-d₆) δ ppm 2.51-2.52 (m, 3H), 6.92 (d, J=7.94 Hz, 1H), 7.49 (br s, 3H), 8.07 (br s, 1H), 8.16 (s, 2H), 8.19 (d, J=8.16 Hz, 1H), 8.35 (s, 1H), 8.43 (s, 1H), 10.59 (s, 1H). LC-MS: (ES, m/z): [M+1]⁺ 506.9

Example 199

1-(2-amino-3-methylpyridin-4-yl)-N-(5-chloro-6-(2H-1,2,3-triazol-2-yl)pyridin-3-yl)-5-(trifluoromethyl)-1H-pyrazole-4-carboxamide, Cpd 199

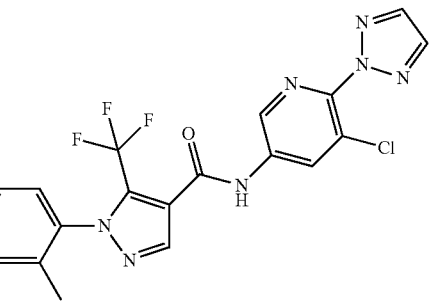

¹H NMR (400 MHz, DMSO-d₆) δ ppm 1.70 (s, 3H), 6.31 (s, 2H), 6.61 (d, J=5.29 Hz, 1H), 7.98 (d, J=5.29 Hz, 1H), 8.19 (s, 2H), 8.46 (s, 1H), 8.65 (d, J=2.43 Hz, 1H), 8.82 (d, J=2.20 Hz, 1H), 11.20 (br s, 1H). LC-MS: (ES, m/z): [M+1]⁺ 463.9

Example 200

1-(6-amino-5-chloropyridin-2-yl)-N-(5-cyano-2-methyl-6-(2H-1,2,3-triazol-2-yl)pyridin-3-yl)-5-(trifluoromethyl)-1H-pyrazole-4-carboxamide, Cpd 200

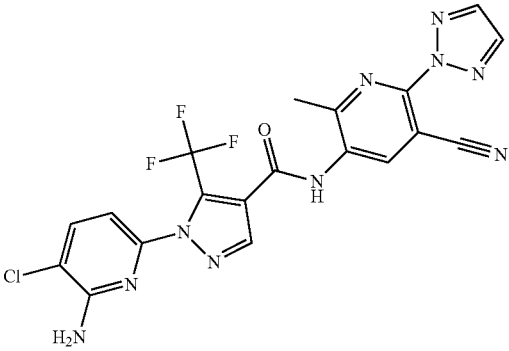 [SMILES: Cc1nc(-n2nccn2)c(C#N)cc1NC(=O)c1cnn(-c2ccc(Cl)c(N)n2)c1C(F)(F)F]

¹H NMR (400 MHz, DMSO-d₆) δ ppm 10.62 (br s, 1H), 8.68 (s, 1H), 8.37 (s, 1H), 8.31 (s, 2H), 7.87 (d, J=8.16 Hz, 1H), 6.88 (d, J=8.16 Hz, 1H), 6.79 (s, 2H), 2.64 (s, 3H).
LC-MS: (ES, m/z): [M+1]⁺ 488.9

Example 201

N-(5-chloro-6-(2H-1,2,3-triazol-2-yl)pyridin-3-yl)-1-(6-cyano-2-methylpyridin-3-yl)-5-(trifluoromethyl)-1H-pyrazole-4-carboxamide, Cpd 201

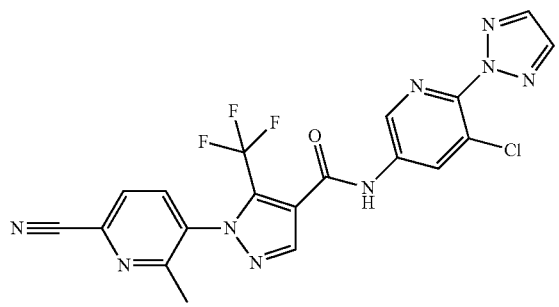 [SMILES: Cc1nc(C#N)ccc1-n1ncc(C(=O)Nc2cnc(-n3nccn3)c(Cl)c2)c1C(F)(F)F]

$^1$H NMR (400 MHz, DMSO-d$_6$) δ ppm 2.27 (3H, s), 8.16 (2H, s), 8.19 (1H, d, J=8.07 Hz), 8.36 (1H, d, J=8.07 Hz), 8.56 (1H, s), 8.63 (1H, d, J=1.96 Hz), 8.80 (1H, d, J=2.20 Hz), 11.21 (1H, br s). LC-MS: (ES, m/z): [M+1]$^+$ 474.1

Example 202

1-(6-bromopyridin-2-yl)-N-(5-chloro-6-(2H-1,2,3-triazol-2-yl)pyridin-3-yl)-5-(trifluoromethyl)-1H-pyrazole-4-carboxamide, Cpd 202

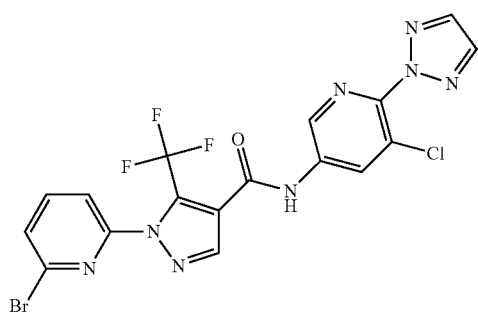 [SMILES: O=C(Nc1cnc(-n2nccn2)c(Cl)c1)c1cnn(-c2cccc(Br)n2)c1C(F)(F)F]

A. Ethyl 1-(6-bromopyridin-2-yl)-5-(trifluoromethyl)-1H-pyrazole-4-carboxylate, Cpd 202a

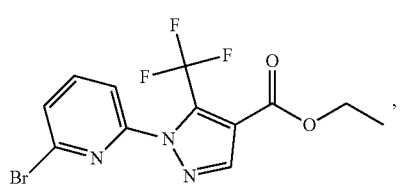

A solution of 2-bromo-6-hydrazinopyridine (10 g, 53 mmol) and ethyl 2-(ethoxymethylene)-4,4,4-trifluoro-3-oxobutyrate (16.6 g, 69 mmol) in ethanol (150 mL) was stirred at 80° C. for 16 h. The reaction mixture was cooled to room temperature and concentrated to dryness under reduced pressure. The crude product was purified by column chromatography over silica gel (petroleum ether/ethyl acetate ratio 80/20 to 50/50). The solvent was evaporated under reduced pressure to yield the title compound (21.6 g, 100%).

B. 1-(6-Bromopyridin-2-yl)-5-(trifluoromethyl)-1H-pyrazole-4-carboxylic Acid, Cpd 202b

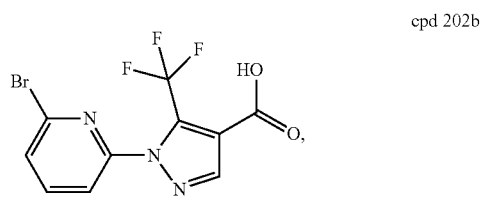 [SMILES: O=C(O)c1cnn(-c2cccc(Br)n2)c1C(F)(F)F]

Ethyl 1-(6-bromopyridin-2-yl)-5-(trifluoromethyl)-1H-pyrazole-4-carboxylate (10 g, 27.5 mmol) and ethanol (20 mL) were stirred at room temperature. A solution of NaOH (3.3 g, 82.5 mmol) in water (10 mL) was added slowly. The reaction mixture was stirred for 3 h. The reaction mixture was concentrated and adjusted to pH 3 with HCl 1N. The reaction mixture was extracted with DCM. The organic layer was washed with water, dried with MgSO$_4$, filtered, and the filtrate concentrated under reduced pressure to yield the title compound (9.1 g, 98.5%)

C. 1-(6-Bromopyridin-2-yl)-N-(5-chloro-6-(2H-1,2,3-triazol-2-yl)pyridin-3-yl)-5-(trifluoromethyl)-1H-pyrazole-4-carboxamide, Cpd 202

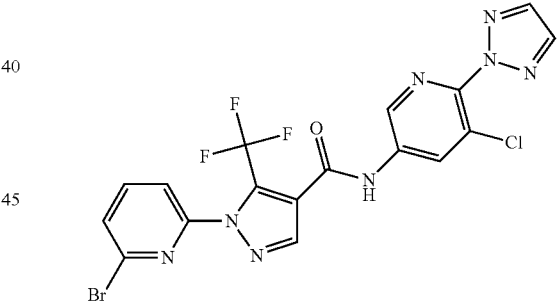

1-(6-Bromopyridin-2-yl)-5-(trifluoromethyl)-1H-pyrazole-4-carboxylic acid (0.92 g, 2.75 mmol), 5-chloro-6-(triazol-2-yl)pyridin-3-amine (0.65 g, 3.3 mmol) and pyridine (1.2 g, 13.75 mmol) in DCM (4 mL) were stirred at room temperature. POCl$_3$ (1 g, 8.25 mmol) was added dropwise to the mixture. The reaction mixture was stirred at room temperature for 2 h. The reaction mixture was poured slowly into a NaHCO$_3$ solution and extracted with DCM. The combined organic layers were washed with water, dried with MgSO$_4$, filtered and the filtrate concentrated under reduced pressure. The residue was purified via Prep HPLC (Stationary phase: RP XBridge Prep C18 OBD-10 μm, 50×150 mm, Mobile phase: 0.25% NH$_4$HCO$_3$ solution in water, CH$_3$CN). The pure fractions were collected, evaporated and the residue was stirred in diisopropylethe, collected by filtration, and dried to yield the title compound (443 mg, 31.5%). LCMS (ESI): mass calcd. for $C_{17}H_9BrClF_3N_8O$ 512, m/z found 515 [M+H]$^+$. $^1$H NMR (400 MHz, CHLOROFORM-d) δ ppm 7.61-7.67 (m, 1H), 7.70-7.75 (m, 1H), 7.77-7.84 (m, 1H), 7.93 (s, 2H), 8.06 (s, 1H), 8.16 (s, 1H), 8.48 (d, J=2.4 Hz, 1H), 8.69 (d, J=2.4 Hz, 1H).

Example 203

(*R)—N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide, Cpd 203

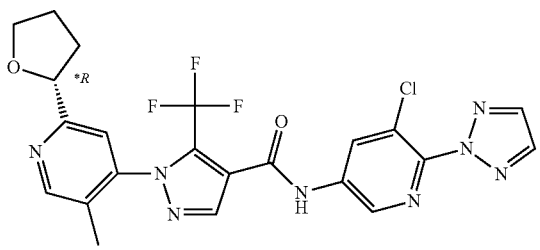 [SMILES: Cc1cnc([C@H]2CCCO2)cc1-n1ncc(C(=O)Nc2cnc(-n3nccn3)c(Cl)c2)c1C(F)(F)F]

(*S)—N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide, Cpd 204

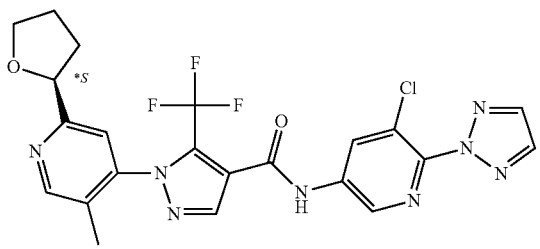 [SMILES: Cc1cnc([C@@H]2CCCO2)cc1-n1ncc(C(=O)Nc2cnc(-n3nccn3)c(Cl)c2)c1C(F)(F)F]

A mixture of THF (1422 mg, 20 mmol), CH$_3$CN (10 mL), water (5 mL), 4-(4-((5-chloro-6-(2H-1,2,3-triazol-2-yl)pyridin-3-yl)carbamoyl)-5-(trifluoromethyl)-1H-pyrazol-1-yl)-3-methylpyridine 1-oxide (448 mg, 1 mmol), TFA (0.076 mL, 1 mmol) and ammonium persulfate (1140 mg, 5 mmol) was weighted in a 20 mL vial. (IR[DF(CF$_3$)PPY]$_2$(DTBPY))PF$_6$ (56 mg, 0.05 mmol) was successively added. The reaction mixture was degassed for 15 min and sealed. The reaction was stirred under blue LED irradiation at room temperature for 3 h. The reaction mixture was poured into water and extracted with DCM. The combined organic layers were dried with MgSO$_4$, filtered and the filtrate was concentrated to dryness. A purification was performed via Prep SFC (Stationary phase: Chiralcel Diacel OJ 20×250 mm, Mobile phase: CO$_2$, EtOH+0.4 iPrNH$_2$) yielding cpd 203 (53 mg, 10.2%): LCMS (ESI): mass calcd. for $C_{22}H_{18}ClF_3N_8O_2$ 518.1, m/z found 519 [M+H]$^+$. $^1$H NMR (400 MHz, CHLOROFORM-d) δ ppm 1.90-2.12 (m, 6H), 2.47 (td, J=6.8, 4.3 Hz, 1H), 3.94-4.01 (m, 1H), 4.03-4.11 (m, 1H), 5.08 (dd, J=7.3, 6.1 Hz, 1H), 7.39 (s, 1H), 7.94 (s, 2H), 8.14 (s, 1H), 8.49 (br s, 1H), 8.53 (d, J=1.0 Hz, 1H), 8.60 (s, 1H), 8.73 (d, J=2.4 Hz, 1H) and cpd 204 (54 mg, 10.4%): LCMS (ESI): mass calcd. for $C_{22}H_{18}ClF_3N_8O_2$ 518.1, m/z found 519 [M+H]$^+$. $^1$H NMR (400 MHz, CHLOROFORM-d) δ ppm 1.91-2.06 (m, 3H), 2.10 (s, 3H), 2.43-2.52 (m, 1H), 3.93-4.01 (m, 1H), 4.03-4.10 (m, 1H), 5.08 (dd, J=7.3, 5.7 Hz, 1H), 7.39 (s, 1H), 7.94 (s, 2H), 8.13 (s, 1H), 8.48-8.51 (m, 2H), 8.60 (s, 1H), 8.73 (d, J=2.4 Hz, 1H).

Following the procedure described in Example 203, above, selecting and substituting the appropriate reagents, starting materials, and purification methods, and adjusting reaction temperatures, times and other variables or parameters, as needed or desirable, as would be readily recognized by those skilled in the art, the following compounds (205-206) were prepared.

Example 204

(*S)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide, Cpd 205

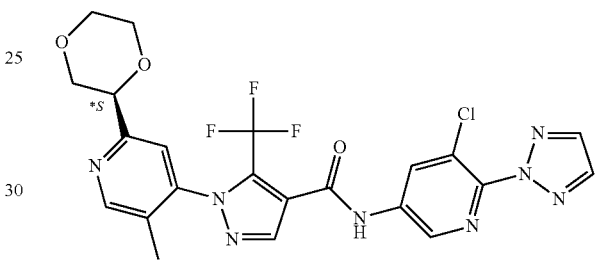

LCMS (ESI): mass calcd. for $C_{22}H_{18}ClF_3N_8O_3$ 534.1, m/z found 535 [M+H]$^+$. $^1$H NMR (400 MHz, CHLOROFORM-d) δ ppm 2.10 (s, 3H), 3.48 (dd, J=11.6, 10.0 Hz, 1H), 3.64-3.76 (m, 1H), 3.78-3.86 (m, 1H), 3.90-3.99 (m, 2H), 4.22 (dd, J=11.4, 2.8 Hz, 1H), 4.80 (dd, J=10.0, 2.6 Hz, 1H), 7.43 (s, 1H), 7.94 (s, 2H), 8.15 (s, 1H), 8.48-8.56 (m, 2H), 8.59 (s, 1H), 8.73 (d, J=2.0 Hz, 1H).

Example 205

(*R)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide, Cpd 206

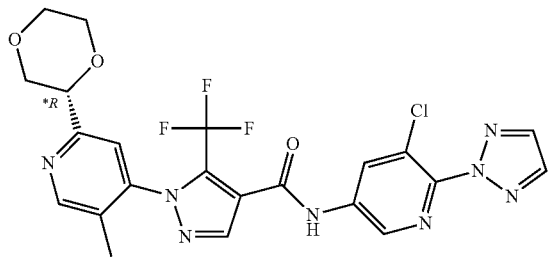 [SMILES: Cc1cnc([C@@H]2COCCO2)cc1-n1ncc(C(=O)Nc2cnc(-n3nccn3)c(Cl)c2)c1C(F)(F)F]

LCMS (ESI): mass calcd. for $C_{22}H_{18}ClF_3N_8O_3$ 534.1, m/z found 535 [M+H]$^+$. $^1$H NMR (400 MHz, CHLOROFORM-d) δ ppm 2.10 (s, 3H), 3.48 (dd, J=11.4, 10.2 Hz, 1H), 3.66-3.75 (m, 1H), 3.78-3.86 (m, 1H), 3.91-3.99 (m, 2H), 4.22 (dd, J=11.4, 2.8 Hz, 1H), 4.80 (dd, J=9.8, 2.8 Hz, 1H), 7.43 (s, 1H), 7.94 (s, 2H), 8.15 (s, 1H), 8.46-8.53 (m, 2H), 8.59 (s, 1H), 8.73 (d, J=2.0 Hz, 1H).

Example 206

N-(5-chloro-6-(2H-1,2,3-triazol-2-yl)pyridin-3-yl)-1-(6-(furan-2-yl)pyridin-2-yl)-5-(trifluoromethyl)-1H-pyrazole-4-carboxamide, Cpd 207

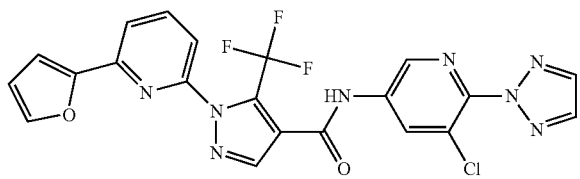 [SMILES: O=C(Nc1cnc(-n2nccn2)c(Cl)c1)c1cnn(-c2cccc(-c3ccco3)n2)c1C(F)(F)F]

1-(6-Bromopyridin-2-yl)-N-(5-chloro-6-(2H-1,2,3-triazol-2-yl)pyridin-3-yl)-5-(trifluoromethyl)-1H-pyrazole-4-carboxamide (103 mg, 0.2 mmol), 2-furanboronic acid pinacol ester (58 mg, 0.3 mmol) and $K_3PO_4$ (85 mg, 0.4 mmol) were suspended in dioxane (20 mL) and water (3 mL). $PdCl_2(dppf) \cdot CH_2Cl_2$ (16.5 mg, 0.02 mmol) was added and the mixture heated at 100° C. overnight. The mixture was poured into 20 mL of water. The mixture was extracted with ethyl acetate (3×) and the organic layer was washed with water (10 mL), dried with $MgSO_4$, filtered, and the filtrate concentrated under reduced pressure. The residue was purified via Prep HPLC (Stationary phase: RP XBridge Prep C18 OBD-m, 50×150 mm, Mobile phase: 0.25% $NH_4HCO_3$ solution in water, $CH_3CN$. A second purification was performed via Prep SFC (Stationary phase: Chiralpak Diacel AD 20×250 mm, Mobile phase: $CO_2$, EtOH+0.4 $iPrNH_2$) yielding the title compound (52 mg, 52%). LCMS (ESI): mass calcd. for $C_{21}H_{12}ClF_3N_8O_2$ 500, m/z found 501.2 $[M+H]^+$. $^1$H NMR (400 MHz, CHLOROFORM-d) δ ppm 6.55-6.60 (m, 1H), 7.12-7.17 (m, 1H), 7.56 (dd, J=1.6, 0.8 Hz, 1H), 7.61 (dd, J=8.1, 0.8 Hz, 1H), 7.79 (dd, J=7.7, 0.8 Hz, 1H), 7.91-7.99 (m, 3H), 8.04 (s, 1H), 8.18 (s, 1H), 8.48 (d, J=2.0 Hz, 1H), 8.72 (d, J=2.0 Hz, 1H).

Example 207

N-(5-chloro-6-(2H-1,2,3-triazol-2-yl)pyridin-3-yl)-1-(6-(5,6-dihydro-1,4-dioxin-2-yl)pyridin-2-yl)-5-(trifluoromethyl)-1H-pyrazole-4-carboxamide, Cpd 208

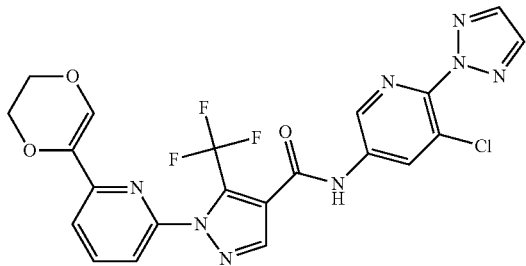 [SMILES: O=C(Nc1cnc(-n2nccn2)c(Cl)c1)c1cnn(-c2cccc(C3=COCCO3)n2)c1C(F)(F)F]

1-(6-Bromopyridin-2-yl)-N-(5-chloro-6-(2H-1,2,3-triazol-2-yl)pyridin-3-yl)-5-(trifluoromethyl)-1H-pyrazole-4-carboxamide (103 mg, 0.2 mmol), 5-(4,4,5,5-tetramethyl-1,3,2-dioxaborolan-2-yl)-2,3-dihydro-1,4-dioxine (63.5 mg, 0.3 mmol) and $K_3PO_4$ (85 mg, 0.4 mmol) were suspended in dioxane (20 mL) and water (3 mL). $PdCl_2(dppf) \cdot CH_2Cl_2$ (16.5 mg, 0.02 mmol) was added and the mixture heated at 100° C. overnight. The mixture was poured into 20 mL of water. The mixture was extracted with ethyl acetate (3×) and the organic layer was washed with water (10 mL), dried over $MgSO_4$, filtered, and the filtrated concentrated to dryness. The residue was purified via Prep HPLC (Stationary phase: RP XBridge Prep C18 OBD-10 μm, 50×150 mm, Mobile phase: 0.25% $NH_4HCO_3$ solution in water, $CH_3CN$) yielding the title compound (52 mg, 50%). LCMS (ESI): mass calcd. for $C_{21}H_{14}ClF_3N_8O_3$ 518.1, m/z found 519.2 $[M+H]^+$. $^1$H NMR (400 MHz, CHLOROFORM-d) δ ppm 4.18-4.23 (m, 2H), 4.25-4.32 (m, 2H), 7.33 (s, 1H), 7.48 (dd, J=10.8, 7.9 Hz, 2H), 7.85 (t, J=7.9 Hz, 1H), 7.92 (s, 2H), 8.01 (s, 1H), 8.41 (s, 1H), 8.49 (d, J=2.4 Hz, 1H), 8.70 (d, J=2.0 Hz, 1H).

Biological Examples

In vitro assays include assays that determine cell morphology, protein expression, and/or the cytotoxicity, enzyme inhibitory activity, and/or the subsequent functional consequences of treatment of cells with compounds of the invention. Alternate or additional in vitro assays may be used to quantitate the ability of the inhibitor to bind to protein or nucleic acid molecules within the cell.

Inhibitor binding may be measured by radiolabelling the inhibitor prior to binding, isolating the inhibitor/target molecule complex and determining the amount of radiolabel bound. Alternatively or additionally, inhibitor binding may be determined by running a competition experiment where new inhibitors are incubated with purified proteins or nucleic acids bound to known radioligands. Detailed conditions of exemplary systems for assaying a compound of Formula (I) of the present invention as MALT1 inhibitors are set forth in the Biological Examples below.

Such assays are exemplary and not intended to limit the scope of the invention. The skilled practitioner can appreciate that modifications can be made to conventional assays to develop equivalent or other assays that can be employed to comparably assess activity or otherwise characterize compounds and/or compositions as described herein.

In Vitro Assays

Biological Example 1

MALT1 Biochemical Protease Assay

MALT1 protease activity was assessed in an in vitro assay using a tetrapeptide as substrate and full-length MALT1 protein (Strep-MALT1(1-824)-His) purified from baculovirus-infected insect cells. The tetrapeptide LRSR is coupled to AMC (7-amino-4-methylcoumarin) and provides a quenched, fluorescent substrate for the MALT1 protease (SM Biochemicals). Cleavage of AMC from the Arginine residue results in an increase in coumarin fluorescence measured at 460 nm (excitation 355 nm). The final assay buffer consisted of 10 nM FL MALT1 protein, 200 μM Ac-LRSR-AMC, 50 mM Tris pH 7.5, 0.6 M Citrate, 1 mM DTT, 1 mM EDTA, 0.05% BSA and 1.5% DMSO. Test compounds were spotted at 50 nL in 100% DMSO per well of a black 384-Proxiplate (Perkin Elmer). Test compound concentrations ranged from 30 μM to 0.5 nM using 11 dilution steps (1:3). Background signal was measured from control wells containing assay buffer without enzyme which functions as low control (LC). High control (HC) values were generated using the reaction with enzyme but no compound treatment. Compounds were pre-incubated with MALT1 enzyme for 50 minutes at RT. Substrate was added subsequently and fluorescence was measured in Labsystems fluoroskan at excitation 355 nm and emission 460 nm to determine time 0. The reaction was subsequently incubated for 4 h at RT and fluorescence was measured. For $IC_{50}$ calculations, timepoint 0 was subtracted from the 4 h timepoint to correct for any potential autofluorescence of the compounds. The enzyme reaction was linear during the 4 h incubation period. Characterization of the substrate Ac-LRSR-AMC determined the Michaelis constant KM at 200 M.

$IC_{50}$ values were calculated using the following formula (Z prime should be >0.5):

$LC$ = Median of the low control values
= Low control: Reaction without enzyme $HC$ = Median of the High control values
= High Control: Reaction without enzyme % Effect = 100 − [(sample − $LC$)/($HC$ − $LC$) × 100]

% Control = (sample/$HC$) × 100

% Controlmin = (sample/$HC$)/($HC$ − $LC$) × 100

A best-fit curve was fitted by a minimum sum of squares method to the plot of % Controlmin vs. compound concentration. From this an $IC_{50}$ value (inhibitory concentration causing 50% inhibition) can be obtained. An estimate of the slope of the plot in terms of the Hill coefficient was also obtained.

$IC_{50}$ Calculation:

$$y = LB + \frac{UB - LB}{1 + 10^{(h(pConc - pIC50))}}$$

With y=estimated response
UB=upper bound
LB=lower bound
h=hill

Used in "Lexis Dose Response Curve Fitting" Version 1.0. Resultant data are shown in Table 2.

TABLE 2

| Cpd | MALT1_Biochemical activity (Ac-LRSR-amc) IC50 (uM) |
|---|---|
| 1 | 0.117 |
| 2 | 0.132 |
| 3 | 0.282 |
| 4 | 0.282 |
| 5 | 0.295 |
| 6 | 0.832 |
| 7 | 0.912 |
| 8 | 1.230 |
| 9 | 2.570 |
| 10 | 4.365 |
| 11 | 4.571 |
| 12 | 1.349 |
| 13 | 1.698 |
| 14 | 0.148 |

TABLE 2-continued

| Cpd | MALT1_Biochemical activity (Ac-LRSR-amc) IC50 (uM) |
|---|---|
| 15 | 3.467 |
| 16 | 1.698 |
| 17 | 2.089 |
| 18 | 0.151 |
| 19 | 0.132 |
| 20 | 0.562 |
| 21 | 1.122 |
| 22 | 0.724 |
| 23 | 0.933 |
| 24 | 2.089 |
| 25 | 2.951 |
| 26 | 7.079 |
| 27 | 0.851 |
| 28 | 2.455 |
| 29 | 0.151 |
| 30 | 0.708 |
| 31 | 6.607 |
| 32 | 0.589 |
| 33 | 0.513 |
| 34 | 0.145 |
| 35 | 2.239 |
| 36 | 0.214 |
| 37 | 0.063 |
| 38 | 0.324 |
| 39 | 0.457 |
| 40 | 1.905 |
| 41 | 2.042 |
| 42 | 0.182 |
| 43 | 0.170 |
| 44 | 0.389 |
| 45 | 0.087 |
| 46 | 0.479 |
| 47 | 0.537 |
| 48 | 0.204 |
| 49 | 0.148 |
| 50 | 0.054 |
| 51 | 0.054 |
| 52 | 0.055 |
| 53 | 0.074 |
| 54 | 0.089 |
| 55 | 0.062 |
| 56 | 0.078 |
| 57 | 0.107 |
| 58 | 0.145 |
| 59 | 0.041 |
| 60 | 0.071 |
| 61 | 0.078 |
| 62 | 0.045 |
| 63 | 0.024 |
| 64 | 0.054 |
| 65 | 5.754 |
| 66 | 3.981 |
| 67 | 0.525 |
| 68 | 0.427 |
| 69 | 0.257 |
| 70 | 0.204 |
| 71 | 0.832 |
| 72 | 0.603 |
| 73 | 0.234 |
| 74 | 2.884 |
| 75 | 1.072 |
| 76 | 0.676 |
| 77 | 0.891 |
| 78 | 0.646 |
| 79 | 0.380 |
| 80 | 0.209 |
| 81 | 0.162 |
| 82 | 0.162 |
| 83 | 0.129 |
| 84 | 0.309 |
| 85 | 2.630 |
| 86 | 1.549 |
| 87 | 0.724 |
| 88 | 0.794 |
| 89 | 0.646 |

TABLE 2-continued

| Cpd | MALT1_Biochemical activity (Ac-LRSR-amc) IC50 (uM) |
|---|---|
| 90 | 0.575 |
| 91 | 0.513 |
| 92 | 0.501 |
| 93 | 0.457 |
| 94 | 0.447 |
| 95 | 0.316 |
| 96 | 0.316 |
| 97 | 0.263 |
| 98 | 0.263 |
| 99 | 0.170 |
| 100 | 0.170 |
| 101 | 0.151 |
| 102 | 0.151 |
| 103 | 0.148 |
| 104 | 0.245 |
| 105 | 0.537 |
| 106 | 0.251 |
| 107 | 0.141 |
| 108 | 0.776 |
| 109 | 0.427 |
| 110 | 0.123 |
| 111 | 0.112 |
| 112 | 0.457 |
| 113 | 0.158 |
| 114 | 1.000 |
| 115 | 0.363 |
| 116 | 0.117 |
| 117 | 0.288 |
| 118 | 2.951 |
| 119 | 0.209 |
| 120 | 0.126 |
| 121 | 1.175 |
| 122 | 1.318 |
| 123 | 0.794 |
| 124 | 1.202 |
| 125 | 1.905 |
| 126 | 0.038 |
| 127 | 0.372 |
| 128 | 0.229 |
| 129 | 2.399 |
| 130 | 0.234 |
| 131 | 0.776 |
| 132 | 0.191 |
| 133 | 0.155 |
| 134 | 0.263 |
| 135 | 0.525 |
| 136 | 0.759 |
| 137 | 0.151 |
| 138 | 5.495 |
| 139 | 0.026 |
| 140 | 0.058 |
| 141 | 0.100 |
| 142 | 0.022 |
| 143 | 0.110 |
| 144 | 0.035 |
| 145 | 0.032 |
| 146 | 0.107 |
| 147 | 0.069 |
| 148 | 0.039 |
| 149 | 0.085 |
| 150 | 0.100 |
| 151 | 2.399 |
| 152 | 0.832 |
| 153 | 4.898 |
| 154 | 0.955 |
| 155 | 0.257 |
| 156 | 1.288 |
| 157 | 8.128 |
| 158 | 0.209 |
| 159 | 3.162 |
| 160 | 0.288 |
| 161 | 0.741 |
| 162 | 0.302 |
| 163 | 0.794 |
| 164 | 1.413 |
| 165 | 2.291 |
| 166 | 0.050 |
| 167 | 0.069 |
| 168 | 0.074 |
| 169 | 0.091 |
| 170 | 0.102 |
| 171 | 0.145 |
| 172 | 0.151 |
| 173 | 0.151 |
| 174 | 0.170 |
| 175 | 0.141 |
| 176 | 0.170 |
| 177 | 0.195 |
| 178 | 0.200 |
| 179 | 0.204 |
| 180 | 0.219 |
| 181 | 0.234 |
| 182 | 0.234 |
| 183 | 0.282 |
| 184 | 0.331 |
| 185 | 0.331 |
| 186 | 0.339 |
| 187 | 0.380 |
| 188 | 0.380 |
| 189 | 0.437 |
| 190 | 0.447 |
| 191 | 0.724 |
| 192 | 1.122 |
| 193 | 1.175 |
| 194 | 1.175 |
| 195 | 1.202 |
| 196 | 1.318 |
| 197 | 2.512 |
| 198 | 3.715 |
| 199 | 0.174 |
| 200 | 0.275 |
| 201 | 0.138 |
| 202 | 0.741 |
| 203 | 0.158 |
| 204 | 0.525 |
| 205 | 1.905 |
| 206 | 2.042 |
| 207 | 5.623 |
| 208 | 5.129 |

Biological Example 2

PMA Induced IL2 Production in Jurkat Cells

Jurkat cells were maintained in complete RPMI 1640 media containing 10% fetal bovine serum, 10 mM HEPES, 100 units/mL of penicillin and 100 μg/mL of streptomycin. Prior to the assay, compounds were made 2- to 4-fold serial dilutions in DMSO. A volume of 10 uL of DMSO-diluted compound in each well were further diluted into 240 uL RPMI1640 complete media. Jurkat cells were harvested by centrifuge at 1200 RPM for 5 min, washed one time with RPMI 1640 media, and suspended in fresh complete RPMI 1640 media at concentration of $1.25 \times 10^6$ cell/mL. A volume of 160 uL of Jurkat cells ($2 \times 10^5$ cells) were seeded in each well of 96 well plate-bottom plates. A volume of 20 uL of diluted compound in RMPI 1640 complete media were added to each well and incubated with Jurkat cells for 30 min at 37° C. in a 5% $CO_2$ incubator. A volume 20 uL of diluted PMA/Ionomycin (81 nM/1.3 uM respectively, ebioscience, catalog number 00-4970-93) in RMPI 1640 complete media were added to each well. After incubation at 37° C. in 5% $CO_2$ incubator for 20 h, supernatants were harvested. IL-2 concentration were assessed by ELISA (IL2 Duoset, R&D Systems, catalog number DY202). Colorimetric intensity at 450 nm was read by Spectramax plate reader and analyzed with Softmax Pro software. Cell viability was assessed by Cell Titer Glo kit (Promega, catalog number G7571) using Victor Luminescence reader (Victor 3V 4202938 by Perkin Elmer).

Resultant data are shown in Table 3.

Biological Example 3

Human IL6/IL10 Mesoscale Assay $NF_KB$ signaling regulates the secretion of multiple cytokines, including IL6 and IL10. Secretion of the cytokines IL6 and IL10 by TMD8 or OCI-LY3 ABC-DLBCL cells was measured using a mesoscale assay. Inhibition of $NF_KB$ signaling by MALT1 or BTK inhibitors results in a decrease of IL6/10 secretion.

TMD8 or OCI-LY3 cells were propagated in RPMI-1640 (Sigma Aldrich) supplemented with 10% fetal bovine serum (HyClone), 1 mM sodium pyruvate (Invitrogen), 2 mM L-glutamine (Sigma Aldrich) and 1% PenStrep (Sigma Aldrich). Cell passage number should not exceed 30. Cells should be kept between 0.5-2.5 million cells per mL during culturing and cells should be supplemented every 2-3 days with fresh 50 M beta-mercaptoenthanol. No beta-mercaptoethanol was used during the mesoscale assay.

For the Mesoscale assay, 100,000 TMD8 or OCI-LY3 cells were seeded per well into black-colored 96-well plates with clear bottom (Corning #3904) and test compounds were added in 9 dilution steps (1:2) ranging from 15 μM to 58.6 nM (final DMSO concentration 0.3%). DMSO control wells were used to determine the maximum signal (High Control (HC)). Treatment with the BTK inhibitor RN486 in a dose range from 30 nM to 131 pM (9 dilutions of 1:2) served as a positive control for $NF_KB$ pathway inhibition and was used to determine the maximum inhibition (Low Control (LC)). Compounds and cells were incubated for 24 h at 37° C. and 5% $CO_2$ (assay volume is 150 μL). After 24 h of incubation 50 μL of the supernatant was transferred to a MSD plate (V-Plex Proinflammation Panel 1 (human) kit, Mesoscale (MSD)) and incubated for 2 h with vigorous shaking (600 rpm) at room temperature. Following incubation, plates were washed 3× with PBS+0.05% Tween-20 and 25 μL detection antibody solution (IL6 & IL10 antibodies in diluent 3 (MSD)) was added per well followed by 2 h of incubation with vigorous shaking (600 rpm) at room temperature. After 3× washes with PBS+0.05% Tween-20, plates were incubated with 150 μL 2× Read Buffer T and read on SECTOR imager. Resultant data are shown in Table 3.

TABLE 3

| Cpd | Human IL10 Mesoscale assay (OCI-LY3) | Human IL6 Mesoscale assay (OCI-LY3) | Human IL6 Mesoscale assay (TMD-8) | Human IL10 Mesoscale assay (TMD-8) |
|---|---|---|---|---|
| 1 | 0.058 | 0.083 | 0.079 | 0.085 |
| 2 | | | 0.148 | 0.065 |
| 3 | | | | 0.832 |
| 4 | | | | 0.933 |
| 5 | | | 0.263 | 0.741 |
| 7 | | | 0.407 | 0.417 |
| 14 | | | 0.316 | 0.282 |
| 18 | | | | 0.115 |
| 19 | | | | 0.117 |
| 20 | | | | 1.000 |
| 21 | | | 0.912 | 1.259 |
| 22 | | | 0.437 | 0.724 |
| 23 | | | 0.891 | 1.072 |
| 27 | | | 1.202 | 1.380 |
| 29 | | | 0.135 | 0.132 |
| 32 | | | 1.122 | 0.646 |
| 34 | | | 0.407 | 0.631 |
| 36 | | | 1.549 | 1.148 |
| 37 | 0.063 | 0.095 | | |
| 43 | | | 4.786 | 2.239 |
| 44 | | | 0.490 | 1.230 |
| 45 | | | 0.162 | 0.339 |
| 48 | | | 1.622 | 0.513 |
| 49 | | | 0.145 | 0.151 |
| 51 | 0.071 | 0.098 | | |
| 52 | 0.056 | 0.120 | | |
| 53 | 0.145 | 0.166 | 0.089 | 0.209 |
| 56 | 0.363 | 0.389 | | |
| 57 | 0.117 | 0.162 | | |
| 58 | 0.195 | 0.407 | | |
| 59 | | | 0.035 | 0.048 |
| 60 | 0.151 | 0.178 | | |
| 62 | 0.427 | 0.380 | | |
| 63 | 0.049 | 0.069 | | |
| 68 | | | 5.495 | 7.079 |
| 69 | | | 2.291 | 3.236 |
| 70 | | | 4.467 | 3.548 |
| 73 | 0.110 | 0.138 | | |
| 81 | 0.138 | 0.138 | | |
| 97 | 0.095 | 0.151 | | |
| 98 | 0.166 | 0.191 | | |
| 99 | 0.174 | 0.148 | | |
| 100 | 0.093 | 0.129 | | |
| 101 | 0.120 | 0.166 | | |
| 102 | 0.158 | 0.158 | | |
| 103 | 0.141 | 0.129 | | |
| 106 | | | 2.291 | 2.042 |
| 107 | 0.112 | 0.158 | | |
| 111 | 0.063 | 0.071 | | |
| 113 | 0.324 | 0.372 | | |
| 116 | 0.105 | 0.107 | | |
| 119 | 0.148 | 0.282 | | |
| 120 | 0.794 | 0.741 | 1.096 | 1.349 |
| 126 | 0.068 | 0.076 | | |
| 128 | | | 1.023 | 2.239 |
| 130 | | | 0.437 | 0.245 |
| 132 | | | 0.550 | 1.349 |
| 137 | 0.100 | 0.123 | | |
| 139 | 0.076 | 0.074 | | |
| 140 | 0.123 | 0.132 | | |
| 141 | 0.407 | 0.427 | | |
| 142 | 0.355 | 0.676 | | |
| 143 | 0.617 | 1.047 | | |
| 144 | 0.026 | 0.046 | | |
| 145 | 0.018 | 0.017 | | |
| 146 | 0.158 | 0.195 | | |
| 147 | 0.040 | 0.052 | | |
| 148 | 0.263 | 0.398 | | |
| 149 | 0.155 | 0.166 | | |
| 150 | 0.204 | 0.269 | | |
| 158 | 0.302 | 0.275 | | |
| 160 | 0.457 | 0.646 | | |
| 162 | 0.182 | 0.251 | | |
| 166 | 0.078 | 0.066 | | |
| 167 | 0.041 | 0.054 | | |
| 168 | 0.046 | 0.078 | | |
| 169 | 0.076 | 0.105 | | |
| 170 | 0.380 | 0.417 | | |
| 171 | 0.076 | 0.098 | | |
| 172 | 0.178 | 0.200 | | |
| 173 | 0.095 | 0.129 | | |
| 174 | 0.083 | | | |
| 175 | 0.229 | 0.331 | | |

TABLE 3-continued

| Cpd | Human IL10 Mesoscale assay (OCI-LY3) | Human IL6 Mesoscale assay (OCI-LY3) | Human IL6 Mesoscale assay (TMD-8) | Human IL10 Mesoscale assay (TMD-8) |
|---|---|---|---|---|
| 176 | 0.813 | 0.813 | | |
| 177 | 2.754 | 7.413 | | |
| 179 | 0.324 | 0.676 | | |
| 180 | 0.170 | 0.257 | | |
| 181 | 0.240 | 0.363 | | |
| 182 | 0.389 | 0.490 | | |
| 183 | 0.195 | 0.269 | | |
| 185 | 0.355 | 0.490 | | |
| 193 | 0.741 | 0.871 | | |
| 195 | 1.862 | 5.370 | | |
| 200 | 0.245 | 0.794 | | |

Biological Example 4

Proliferation Assays

To assess anti-proliferative effects, MALT1 inhibitor test compounds were tested in 4-day proliferation assays using three different DLBCL cell lines. Two ABC-DLBCL cell lines with activating mutations in the classical $NF_KB$ pathway were evaluated (OCI-Ly3 (CARD11, MYD88 & A20 mutations), TMD8 (CD79B & MYD88 mutations), which are generally sensitive to $NF_KB$ pathway inhibition. A GCB-DLBCL cell line (OCI-Ly7), which has not been shown to have active $NF_KB$ signaling, served as a negative control to exclude compounds with general cytotoxic effects.

OCI-Ly3 cells were propagated in RPMI-1640 (Sigma Aldrich) supplemented with 10% fetal bovine serum (HyClone), 2 mM L-glutamine (Sigma Aldrich) and 1% PenStrep (Sigma Aldrich). TMD8 cells were propagated in RPMI-1640 (Sigma Aldrich) supplemented with 10% fetal bovine serum (HyClone), 1 mM sodium pyruvate (Invitrogen), 2 mM L-glutamine (Sigma Aldrich) and 1% PenStrep (Sigma Aldrich). Cells should be kept between 0.5-2.5 million cells per mL during culturing and cells should be supplemented every 2-3 days with fresh 50 µM beta-mercaptoenthanol. No beta-mercaptoethanol is used during the proliferation assay. OCI-Ly7 cells were propagated in IMDM (ThermoFisher) supplemented with 10% fetal bovine serum (HyClone), 2 mM L-glutamine (Sigma Aldrich) and 50 µg/mL Gentamycin. Cell passage numbers should not exceed 30.

To assess anti-proliferative effects, 400 nL of test compounds were spotted per well of 96-well plates (Costar, catalogue number 3904). 10,000 TMD8, 10,000 OCI-Ly3 or 2,000 OCI-Ly7 cells were seeded in 100 µL media per well and incubated for 4 days at 37° C. and 5% $CO_2$. Cell plating numbers were chosen based on growth curves to ensure linear cell growth. After 4 days of incubation 50 µl CellTiterGLO reagent (Promega) were added to each well and luminescence was measured on the Envision after 10 min of incubation at room temperature.

$IC_{50}$ values were calculated using the following formula (Z prime should be >0.5):

$LC$ = median of the low control values
= Low control: Reaction without cells $HC$ = Median of the High control values
= High control: Reaction with cells without compound % Effect = 100-(sample-$LC$)/($HC$-$LC$)×100

% Control = (sample/$HC$)×100

% Controlmin = (sample-$LC$)/($HC$-$LC$)×100

A best-fit curve was fitted by a minimum sum of squares method to the plot of % Control vs. compound concentration. From this an IC50 value (inhibitory concentration causing 50% cytotoxicity) can be obtained. An estimate of the slope of the plot in terms of the Hill coefficient was also obtained.

Resultant data are shown in Table 4.

TABLE 4

| Cpd | Anti-proliferation: OCI-LY-3 IC50 (uM) |
|---|---|
| 1 | 1.349 |
| 2 | 0.741 |
| 3 | 2.455 |
| 4 | 1.047 |
| 5 | 0.380 |
| 7 | 1.549 |
| 14 | 2.138 |
| 18 | 6.457 |
| 19 | 7.943 |
| 20 | 12.589 |
| 21 | 0.741 |
| 22 | 0.490 |
| 23 | 0.479 |
| 27 | 3.890 |
| 29 | 1.230 |
| 32 | 0.575 |
| 34 | 0.457 |
| 36 | 4.266 |
| 43 | 6.310 |
| 44 | 10.965 |
| 45 | 4.786 |
| 48 | 3.631 |
| 49 | 0.437 |
| 50 | 1.072 |
| 51 | 0.851 |
| 52 | 2.399 |
| 53 | 1.862 |
| 54 | 1.622 |
| 55 | 3.388 |
| 56 | 5.012 |
| 57 | 1.202 |
| 58 | 7.244 |
| 59 | 0.468 |
| 60 | 0.741 |
| 61 | 1.862 |
| 62 | 0.912 |
| 63 | 2.512 |
| 64 | 1.549 |
| 68 | 7.079 |
| 69 | 2.089 |
| 70 | 6.607 |
| 81 | 1.259 |
| 82 | 3.388 |
| 83 | 2.239 |
| 98 | 0.437 |
| 99 | 0.324 |
| 100 | 0.269 |
| 101 | 0.479 |
| 103 | 0.275 |
| 106 | 2.884 |
| 111 | 1.820 |
| 112 | 0.724 |
| 117 | 0.407 |

TABLE 4-continued

| Cpd | Anti-proliferation: OCI-LY-3 IC50 (uM) |
|---|---|
| 129 | 1.413 |
| 131 | 19.055 |
| 132 | 1.096 |
| 133 | 5.495 |
| 160 | 0.490 |

Biological Example 5

Tumor Efficacy Studies

The OCI-Ly3 (DSMZ, catalog number ACC 761) human diffuse large B-cell lymphoma tumor cells may be maintained in vitro in RPMI medium supplemented with heat inactivated fetal bovine serum (10% v/v) and 2 mM L-Glutamine 200 mM at 37° C. in an atmosphere of 5% $CO_2$ in air. The cells may be routinely subcultured once weekly. The cells growing in an exponential growth phase may be harvested and counted, and cell suspension diluted 1:1 in Matrigel™ (Corning Matrigel™ Matrix Basement Membrane Growth Factor Reduced) for tumor cell inoculation.

Male NSG (NOD.Cg-Prkdc$^{scid}$ Il2rg$^{tm1Wjl}$/SzJ) mice may be subcutaneously inoculated with OCI-Ly3 cells ($10 \times 10^6$ cells in 1:1 medium:Matrigel™ in a volume of 200 µL) in the inguinal region of each animal. The day of tumor cell inoculation may be denoted as day 0. Tumor measurements may be monitored twice weekly beginning seven days post-implantation, until the mean tumor volume is 169±42 mm$^3$, at which point mice may be randomized by tumor volume into treatment groups. Compound or vehicle may be orally administered according to body weight (5 mL/kg) once or twice daily until study termination. Tumor measurements and body weights may be recorded twice weekly.

The endpoints of the studies are tumor growth inhibition, maximal tumor burden (individual tumor size equaling 10% of body weight), and body weight loss greater than 20% treatment initiation body weight. Percent body weight change may be calculated using the formula: Body weight change=[(C−I)/I]*100 where C is the current body weight and I is the body weight at the initiation of treatment. Tumor size may be measured twice weekly in two dimensions using a caliper and the volume may be expressed in mm$^3$ using the formula: $V=0.5 \times a \times b^2$ where and b are the long and short diameters of the tumor, respectively. Complete tumor regression (CR) is defined as tumors that are reduced to below the limit of palpation (20 mm$^3$). Partial tumor regression (PR) is defined as tumors that are reduced by at least half from initial tumor volume. A minimum duration of CR or PR in three or more successive tumor measurements is required for a CR or PR to be considered durable.

Summary statistics, including mean and the standard error of the mean (SEM), are provided for the tumor volume of difference in tumor volume among each group at each time-point are shown in corresponding study tables. Statistical analysis of difference in tumor volume among the groups may be evaluated using a two-way ANOVA repeated measures test, followed by Tukey post-test, using GraphPad Prism version 6.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound selected from the group consisting of
N-(5-Chloro-6-(2H-1,2,3-triazol-2-yl)pyridin-3-yl)-1-(4-fluoro-2-methylphenyl)-5-(trifluoromethyl)-1H-pyrazole-4-carboxamide;
1-(4-Chloro-2-methylphenyl)-N-(5-chloro-6-(2H-1,2,3-triazol-2-yl)pyridin-3-yl)-5-(trifluoromethyl)-1H-pyrazole-4-carboxamide;
N-(5-Chloro-6-(2H-1,2,3-triazol-2-yl)pyridin-3-yl)-1-(3-methylpyridin-2-yl)-5-(trifluoromethyl)-1H-pyrazole-4-carboxamide;
N-(5-Chloro-6-(2H-1,2,3-triazol-2-yl)pyridin-3-yl)-1-(pyridin-4-yl)-5-(trifluoromethyl)-1H-pyrazole-4-carboxamide;
N-(5-Chloro-6-(2H-1,2,3-triazol-2-yl)pyridin-3-yl)-1-phenyl-5-(trifluoromethyl)-1H-pyrazole-4-carboxamide;
N-(5-Chloro-6-(2H-1,2,3-triazol-2-yl)pyridin-3-yl)-1-(3-fluoropyridin-4-yl)-5-(trifluoromethyl)-1H-pyrazole-4-carboxamide;
N-(5-Chloro-6-(2H-1,2,3-triazol-2-yl)pyridin-3-yl)-1-(5-fluoropyridin-2-yl)-5-(trifluoromethyl)-1H-pyrazole-4-carboxamide;
N-(5-Chloro-6-(2H-1,2,3-triazol-2-yl)pyridin-3-yl)-1-(pyridin-2-yl)-5-(trifluoromethyl)-1H-pyrazole-4-carboxamide;
N-(5-Chloro-6-(2H-1,2,3-triazol-2-yl)pyridin-3-yl)-1-(pyrazin-2-yl)-5-(trifluoromethyl)-1H-pyrazole-4-carboxamide;
N-(5-Chloro-6-(2H-1,2,3-triazol-2-yl)pyridin-3-yl)-1-(pyrimidin-2-yl)-5-(trifluoromethyl)-1H-pyrazole-4-carboxamide;
N-(5-Chloro-6-(2H-1,2,3-triazol-2-yl)pyridin-3-yl)-1-(5-cyanopyridin-2-yl)-5-(trifluoromethyl)-1H-pyrazole-4-carboxamide;
N-(5-Chloro-6-(2H-1,2,3-triazol-2-yl)pyridin-3-yl)-1-(pyridin-3-yl)-5-(trifluoromethyl)-1H-pyrazole-4-carboxamide;
N-(5-Chloro-6-(2H-1,2,3-triazol-2-yl)pyridin-3-yl)-1-(6-methoxypyridin-3-yl)-5-(trifluoromethyl)-1H-pyrazole-4-carboxamide;
N-(5-Chloro-6-(2H-1,2,3-triazol-2-yl)pyridin-3-yl)-1-(2-methoxypyridin-3-yl)-5-(trifluoromethyl)-1H-pyrazole-4-carboxamide;
N-(5-Chloro-6-(2H-1,2,3-triazol-2-yl)pyridin-3-yl)-1-(pyrimidin-5-yl)-5-(trifluoromethyl)-1H-pyrazole-4-carboxamide;
N-(5-Chloro-6-(2H-1,2,3-triazol-2-yl)pyridin-3-yl)-1-(5-methylpyridin-3-yl)-5-(trifluoromethyl)-1H-pyrazole-4-carboxamide;
N-(5-Chloro-6-(2H-1,2,3-triazol-2-yl)pyridin-3-yl)-1-(5-cyanopyridin-3-yl)-5-(trifluoromethyl)-1H-pyrazole-4-carboxamide;
N-(5-chloro-6-(2H-1,2,3-triazol-2-yl)pyridin-3-yl)-1-(4-fluorophenyl)-5-(trifluoromethyl)-1H-pyrazole-4-carboxamide;
N-(5-chloro-6-(2H-1,2,3-triazol-2-yl)pyridin-3-yl)-1-(4-cyanophenyl)-5-(trifluoromethyl)-1H-pyrazole-4-carboxamide;
N-(5-chloro-6-(2H-1,2,3-triazol-2-yl)pyridin-3-yl)-1-(3-fluorophenyl)-5-(trifluoromethyl)-1H-pyrazole-4-carboxamide;

N-(5-chloro-6-(2H-1,2,3-triazol-2-yl)pyridin-3-yl)-1-(3-cyanophenyl)-5-(trifluoromethyl)-1H-pyrazole-4-carboxamide;
N-(5-chloro-6-(2H-1,2,3-triazol-2-yl)pyridin-3-yl)-1-(4-methylpyridin-2-yl)-5-(trifluoromethyl)-1H-pyrazole-4-carboxamide;
N-(5-chloro-6-(2H-1,2,3-triazol-2-yl)pyridin-3-yl)-1-(5-methylpyridin-2-yl)-5-(trifluoromethyl)-1H-pyrazole-4-carboxamide;
N-(5-chloro-6-(2H-1,2,3-triazol-2-yl)pyridin-3-yl)-1-(6-methylpyridin-2-yl)-5-(trifluoromethyl)-1H-pyrazole-4-carboxamide;
N-(5-chloro-6-(2H-1,2,3-triazol-2-yl)pyridin-3-yl)-5-(difluoromethyl)-1-(pyridin-4-yl)-1H-pyrazole-4-carboxamide;
N-(5-chloro-6-(2H-1,2,3-triazol-2-yl)pyridin-3-yl)-5-fluoro-1-phenyl-1H-pyrazole-4-carboxamide;
N-(5-chloro-6-(2H-1,2,3-triazol-2-yl)pyridin-3-yl)-1-(p-tolyl)-5-(trifluoromethyl)-1H-pyrazole-4-carboxamide;
N-(5-chloro-6-(2H-1,2,3-triazol-2-yl)pyridin-3-yl)-1-(m-tolyl)-5-(trifluoromethyl)-1H-pyrazole-4-carboxamide;
N-(5-chloro-6-(2H-1,2,3-triazol-2-yl)pyridin-3-yl)-1-(o-tolyl)-5-(trifluoromethyl)-1H-pyrazole-4-carboxamide;
1-(5-bromo-3-chloropyridin-2-yl)-N-(5-cyano-6-(2H-1,2,3-triazol-2-yl)pyridin-3-yl)-5-(trifluoromethyl)-1H-pyrazole-4-carboxamide;
1-(3-chloro-5-cyanopyridin-2-yl)-N-(5-cyano-6-(2H-1,2,3-triazol-2-yl)pyridin-3-yl)-5-(trifluoromethyl)-1H-pyrazole-4-carboxamide;
1-(3-Chloro-2-methoxypyridin-4-yl)-N-(5-cyano-6-(2H-1,2,3-triazol-2-yl)pyridin-3-yl)-5-(trifluoromethyl)-1H-pyrazole-4-carboxamide;
1-(3-Cyano-2-methylpyridin-4-yl)-N-(5-cyano-6-(2H-1,2,3-triazol-2-yl)pyridin-3-yl)-5-(trifluoromethyl)-1H-pyrazole-4-carboxamide;
1-(3-Bromo-5-fluoropyridin-2-yl)-N-(5-cyano-6-(2H-1,2,3-triazol-2-yl)pyridin-3-yl)-5-(trifluoromethyl)-1H-pyrazole-4-carboxamide;
1-(3-cyano-5-fluoropyridin-2-yl)-N-(5-cyano-6-(2H-1,2,3-triazol-2-yl)pyridin-3-yl)-5-(trifluoromethyl)-1H-pyrazole-4-carboxamide;
N-(5-Cyano-6-(2H-1,2,3-triazol-2-yl)pyridin-3-yl)-1-(3,4-dichloropyridin-2-yl)-5-(trifluoromethyl)-1H-pyrazole-4-carboxamide;
N-(5-chloro-6-(2H-1,2,3-triazol-2-yl)pyridin-3-yl)-1-(4-cyano-2-methylphenyl)-5-(trifluoromethyl)-1H-pyrazole-4-carboxamide;
N-(5-cyano-6-(2H-1,2,3-triazol-2-yl)pyridin-3-yl)-1-(2-methoxy-3-methylpyridin-4-yl)-5-(trifluoromethyl)-1H-pyrazole-4-carboxamide;
1-(2-chloropyridin-4-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(2-cyanopyridin-4-yl)-5-(trifluoromethyl)-1H-pyrazole-4-carboxamide;
N-(5-Cyano-6-(2H-1,2,3-triazol-2-yl)pyridin-3-yl)-1-(2-methoxypyridin-4-yl)-5-(trifluoromethyl)-1H-pyrazole-4-carboxamide;
N-(5-cyano-6-(2H-1,2,3-triazol-2-yl)pyridin-3-yl)-1-(2,3-dimethylpyridin-4-yl)-5-(trifluoromethyl)-1H-pyrazole-4-carboxamide;
1-(3-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide;
1-(3-Chloropyridin-2-yl)-N-(5-cyano-6-(2H-1,2,3-triazol-2-yl)pyridin-3-yl)-5-(trifluoromethyl)-1H-pyrazole-4-carboxamide;
1-(3-chloropyridin-4-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(3-cyanopyridin-4-yl)-5-(trifluoromethyl)-1H-pyrazole-4-carboxamide;
1-(3-chloro-4-methylpyridin-2-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(3,5-dichloropyridin-4-yl)-5-(trifluoromethyl)-1H-pyrazole-4-carboxamide;
N-(5-cyano-6-(2H-1,2,3-triazol-2-yl)pyridin-3-yl)-1-(2,3-dihydrobenzo[b][1,4]dioxin-5-yl)-5-(trifluoromethyl)-1H-pyrazole-4-carboxamide;
1-(2-bromo-4-fluorophenyl)-N-(5-cyano-6-(2H-1,2,3-triazol-2-yl)pyridin-3-yl)-5-(trifluoromethyl)-1H-pyrazole-4-carboxamide;
1-(2-chloro-4-fluorophenyl)-N-(5-cyano-6-(2H-1,2,3-triazol-2-yl)pyridin-3-yl)-5-(trifluoromethyl)-1H-pyrazole-4-carboxamide;
1-([1,3]dioxolo[4,5-b]pyridin-7-yl)-N-(5-chloro-6-(2H-1,2,3-triazol-2-yl)pyridin-3-yl)-5-(trifluoromethyl)-1H-pyrazole-4-carboxamide;
1-([1,3]dioxolo[4,5-b]pyridin-7-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(o-tolyl)-5-(trifluoromethyl)-1H-pyrazole-4-carboxamide;
1-(2-amino-3-chloropyridin-4-yl)-N-(5-cyano-6-(2H-1,2,3-triazol-2-yl)pyridin-3-yl)-5-(trifluoromethyl)-1H-pyrazole-4-carboxamide;
1-(2-amino-3-chloropyridin-4-yl)-N-(5-chloro-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-1-(2,2-difluorobenzo[d][1,3]dioxol-4-yl)-5-(trifluoromethyl)-1H-pyrazole-4-carboxamide;
1-(benzo[d][1,3]dioxol-4-yl)-N-(5-cyano-6-(2H-1,2,3-triazol-2-yl)pyridin-3-yl)-5-(trifluoromethyl)-1H-pyrazole-4-carboxamide;
1-(2-chloro-3,4-difluorophenyl)-N-(5-cyano-6-(2H-1,2,3-triazol-2-yl)pyridin-3-yl)-5-(trifluoromethyl)-1H-pyrazole-4-carboxamide;
1-(2-chloro-3-fluorophenyl)-N-(5-cyano-6-(2H-1,2,3-triazol-2-yl)pyridin-3-yl)-5-(trifluoromethyl)-1H-pyrazole-4-carboxamide;
1-(6-amino-5-fluoropyridin-2-yl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(4-fluoro-2-methylphenyl)-5-(trifluoromethyl)-1H-pyrazole-4-carboxamide;
1-(3-chloro-4-methoxypyridin-2-yl)-N-(5-chloro-6-(2H-1,2,3-triazol-2-yl)pyridin-3-yl)-5-(trifluoromethyl)-1H-pyrazole-4-carboxamide;
1-(3-chloro-4-methoxypyridin-2-yl)-N-(5-cyano-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-1-(3,5-dichloropyridin-4-yl)-5-(trifluoromethyl)-1H-pyrazole-4-carboxamide;

1-(5-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide;
1-(3-chloro-2-methylpyridin-4-yl)-N-(5-chloro-6-(2H-1,2,3-triazol-2-yl)pyridin-3-yl)-5-(trifluoromethyl)-1H-pyrazole-4-carboxamide;
1-(5-chloro-2-methylpyridin-4-yl)-N-(5-cyano-6-(2H-1,2,3-triazol-2-yl)pyridin-3-yl)-5-(trifluoromethyl)-1H-pyrazole-4-carboxamide;
1-(2-chloro-4-fluoro-3-methylphenyl)-N-(5-chloro-6-(2H-1,2,3-triazol-2-yl)pyridin-3-yl)-5-(trifluoromethyl)-1H-pyrazole-4-carboxamide;
1-(2-chloro-4-fluoro-3-methylphenyl)-N-(5-cyano-6-(2H-1,2,3-triazol-2-yl)pyridin-3-yl)-5-(trifluoromethyl)-1H-pyrazole-4-carboxamide;
1-(2-chloro-3,4-difluorophenyl)-N-(5-chloro-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-1-(3-(methylsulfonyl)phenyl)-5-(trifluoromethyl)-1H-pyrazole-4-carboxamide;
N-(5-chloro-6-(2H-1,2,3-triazol-2-yl)pyridin-3-yl)-1-(2-methyl-4-(methylsulfonyl)phenyl)-5-(trifluoromethyl)-1H-pyrazole-4-carboxamide;
N-(5-chloro-6-(2H-1,2,3-triazol-2-yl)pyridin-3-yl)-1-(2-isopropylphenyl)-5-(trifluoromethyl)-1H-pyrazole-4-carboxamide;
N-(5-chloro-6-(2H-1,2,3-triazol-2-yl)pyridin-3-yl)-1-(4-fluoro-2,3-dimethylphenyl)-5-(trifluoromethyl)-1H-pyrazole-4-carboxamide;
N-(5-chloro-6-(2H-1,2,3-triazol-2-yl)pyridin-3-yl)-1-(3,4-difluorophenyl)-5-(trifluoromethyl)-1H-pyrazole-4-carboxamide;
1-(2-chloro-5-fluorophenyl)-N-(5-chloro-6-(2H-1,2,3-triazol-2-yl)pyridin-3-yl)-5-(trifluoromethyl)-1H-pyrazole-4-carboxamide;
1-(2-chloro-5-fluorophenyl)-N-(5-cyano-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-1-(4-fluoro-2-methoxyphenyl)-5-(trifluoromethyl)-1H-pyrazole-4-carboxamide;
1-(2-chloro-3-fluorophenyl)-N-(5-chloro-6-(2H-1,2,3-triazol-2-yl)pyridin-3-yl)-5-(trifluoromethyl)-1H-pyrazole-4-carboxamide;
1-(2-bromo-4-fluorophenyl)-N-(5-chloro-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(4-fluoro-2,3-dimethylphenyl)-5-(trifluoromethyl)-1H-pyrazole-4-carboxamide;
N-(5-chloro-6-(2H-1,2,3-triazol-2-yl)pyridin-3-yl)-1-(3-cyano-4-fluorophenyl)-5-(trifluoromethyl)-1H-pyrazole-4-carboxamide;
1-(3-cyano-4-fluorophenyl)-N-(5-cyano-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-1-(6-fluoro-4-methylpyridin-3-yl)-5-(trifluoromethyl)-1H-pyrazole-4-carboxamide;
N-(5-cyano-6-(2H-1,2,3-triazol-2-yl)pyridin-3-yl)-1-(2-methylpyridin-3-yl)-5-(trifluoromethyl)-1H-pyrazole-4-carboxamide;
N-(5-chloro-6-(2H-1,2,3-triazol-2-yl)pyridin-3-yl)-5-(trifluoromethyl)-1-(2,3,4-trifluorophenyl)-1H-pyrazole-4-carboxamide;
N-(5-chloro-6-(2H-1,2,3-triazol-2-yl)pyridin-3-yl)-1-(2-chloro-6-fluorophenyl)-5-(trifluoromethyl)-1H-pyrazole-4-carboxamide;
N-(5-cyano-6-(2H-1,2,3-triazol-2-yl)pyridin-3-yl)-1-(4-methylpyridin-3-yl)-5-(trifluoromethyl)-1H-pyrazole-4-carboxamide;
N-(5-chloro-6-(2H-1,2,3-triazol-2-yl)pyridin-3-yl)-1-(2-fluoro-6-methylphenyl)-5-(trifluoromethyl)-1H-pyrazole-4-carboxamide;
N-(5-chloro-6-(2H-1,2,3-triazol-2-yl)pyridin-3-yl)-1-(2,6-dichloro-4-fluorophenyl)-5-(trifluoromethyl)-1H-pyrazole-4-carboxamide;
1-(2-chloro-4,6-difluorophenyl)-N-(5-chloro-6-(2H-1,2,3-triazol-2-yl)pyridin-3-yl)-5-(trifluoromethyl)-1H-pyrazole-4-carboxamide;
1-(6-chloro-2-methylpyridin-3-yl)-N-(5-cyano-6-(2H-1,2,3-triazol-2-yl)pyridin-3-yl)-5-(trifluoromethyl)-1H-pyrazole-4-carboxamide;
N-(5-chloro-6-(2H-1,2,3-triazol-2-yl)pyridin-3-yl)-1-(5-fluoro-2-methylphenyl)-5-(trifluoromethyl)-1H-pyrazole-4-carboxamide;
N-(5-cyano-6-(2H-1,2,3-triazol-2-yl)pyridin-3-yl)-5-(trifluoromethyl)-1-(2,3,4-trifluorophenyl)-1H-pyrazole-4-carboxamide;
1-(2-chloro-6-fluorophenyl)-N-(5-cyano-6-(2H-1,2,3-triazol-2-yl)pyridin-3-yl)-5-(trifluoromethyl)-1H-pyrazole-4-carboxamide;
1-(2-chloro-4,6-difluorophenyl)-N-(5-cyano-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(2-cyclopropylphenyl)-5-(trifluoromethyl)-1H-pyrazole-4-carboxamide;
N-(5-cyano-6-(2H-1,2,3-triazol-2-yl)pyridin-3-yl)-1-(2-fluoro-6-methylphenyl)-5-(trifluoromethyl)-1H-pyrazole-4-carboxamide;
N-(5-cyano-6-(2H-1,2,3-triazol-2-yl)pyridin-3-yl)-1-(2,6-dichloro-4-fluorophenyl)-5-(trifluoromethyl)-1H-pyrazole-4-carboxamide;
N-(5-cyano-6-(2H-1,2,3-triazol-2-yl)pyridin-3-yl)-1-(5-fluoro-2-methylphenyl)-5-(trifluoromethyl)-1H-pyrazole-4-carboxamide;
N-(5-cyano-6-(2H-1,2,3-triazol-2-yl)pyridin-3-yl)-1-(3,4-difluorophenyl)-5-(trifluoromethyl)-1H-pyrazole-4-carboxamide;
1-(3-chloro-5-fluoropyridin-2-yl)-N-(5-chloro-6-(2H-1,2,3-triazol-2-yl)pyridin-3-yl)-5-(trifluoromethyl)-1H-pyrazole-4-carboxamide;
1-(3-chloro-5-fluoropyridin-2-yl)-N-(5-cyano-6-(2H-1,2,3-triazol-2-yl)pyridin-3-yl)-5-(trifluoromethyl)-1H-pyrazole-4-carboxamide;
1-(2-chloro-4-fluorophenyl)-N-(5-chloro-6-(2H-1,2,3-triazol-2-yl)pyridin-3-yl)-5-(trifluoromethyl)-1H-pyrazole-4-carboxamide;
1-(3-chloro-4-fluorophenyl)-N-(5-chloro-6-(2H-1,2,3-triazol-2-yl)pyridin-3-yl)-5-(trifluoromethyl)-1H-pyrazole-4-carboxamide;
1-(3-chloro-4-fluorophenyl)-N-(5-cyano-6-(2H-1,2,3-triazol-2-yl)pyridin-3-yl)-5-(trifluoromethyl)-1H-pyrazole-4-carboxamide;
1-(2-chloro-4-cyanophenyl)-N-(5-chloro-6-(2H-1,2,3-triazol-2-yl)pyridin-3-yl)-5-(trifluoromethyl)-1H-pyrazole-4-carboxamide;
N-(5-cyano-6-(2H-1,2,3-triazol-2-yl)pyridin-3-yl)-1-(2,4-difluorophenyl)-5-(trifluoromethyl)-1H-pyrazole-4-carboxamide;

N-(5-chloro-6-(2H-1,2,3-triazol-2-yl)pyridin-3-yl)-1-(5-fluoro-3-methylpyridin-2-yl)-5-(trifluoromethyl)-1H-pyrazole-4-carboxamide;

N-(5-cyano-6-(2H-1,2,3-triazol-2-yl)pyridin-3-yl)-1-(5-fluoro-3-methylpyridin-2-yl)-5-(trifluoromethyl)-1H-pyrazole-4-carboxamide;

N-(5-chloro-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide;

N-(5-cyano-6-(2H-1,2,3-triazol-2-yl)pyridin-3-yl)-1-(4-fluoro-2-(trifluoromethyl)phenyl)-5-(trifluoromethyl)-1H-pyrazole-4-carboxamide;

1-(2-chlorophenyl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2,4-difluorophenyl)-5-(trifluoromethyl)-1H-pyrazole-4-carboxamide;

N-(5-chloro-6-(2H-1,2,3-triazol-2-yl)pyridin-3-yl)-1-(2-(1-methoxyethyl)phenyl)-5-(trifluoromethyl)-1H-pyrazole-4-carboxamide;

1-(4-amino-3-chloropyridin-2-yl)-N-(5-chloro-6-(2H-1,2,3-triazol-2-yl)pyridin-3-yl)-5-(trifluoromethyl)-1H-pyrazole-4-carboxamide;

1-(4-amino-3-chloropyridin-2-yl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-fluoropyridin-3-yl)-5-(trifluoromethyl)-1H-pyrazole-4-carboxamide;

N-(5-chloro-6-(2H-1,2,3-triazol-2-yl)pyridin-3-yl)-1-(6-(methylamino)pyridin-3-yl)-5-(trifluoromethyl)-1H-pyrazole-4-carboxamide;

N-(5-cyano-6-(2H-1,2,3-triazol-2-yl)pyridin-3-yl)-1-(6-(fluoro)pyridin-3-yl)-5-(trifluoromethyl)-1H-pyrazole-4-carboxamide;

N-(5-cyano-6-(2H-1,2,3-triazol-2-yl)pyridin-3-yl)-1-(6-(methylamino)pyridin-3-yl)-5-(trifluoromethyl)-1H-pyrazole-4-carboxamide;

1-(6-aminopyridin-3-yl)-N-(5-chloro-6-(2H-1,2,3-triazol-2-yl)pyridin-3-yl)-5-(trifluoromethyl)-1H-pyrazole-4-carboxamide;

1-(4-cyano-2-methylphenyl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(1-methyl-1,2,3,4-tetrahydroquinolin-5-yl)-5-(trifluoromethyl)-1H-pyrazole-4-carboxamide;

N-(5-cyano-6-(2H-1,2,3-triazol-2-yl)pyridin-3-yl)-1-(1-methylindolin-4-yl)-5-(trifluoromethyl)-1H-pyrazole-4-carboxamide;

N-(5-cyano-6-(2H-1,2,3-triazol-2-yl)pyridin-3-yl)-1-(1,2,3,4-tetrahydroisoquinolin-5-yl)-5-(trifluoromethyl)-1H-pyrazole-4-carboxamide;

N-(5-cyano-6-(2H-1,2,3-triazol-2-yl)pyridin-3-yl)-1-(indolin-4-yl)-5-(trifluoromethyl)-1H-pyrazole-4-carboxamide;

N-(5-cyano-6-(2H-1,2,3-triazol-2-yl)pyridin-3-yl)-1-(1-methyl-1,2,3,4-tetrahydroquinolin-8-yl)-5-(trifluoromethyl)-1H-pyrazole-4-carboxamide;

N-(5-cyano-6-(2H-1,2,3-triazol-2-yl)pyridin-3-yl)-1-(4-methyl-3,4-dihydro-2H-benzo[b][1,4]oxazin-8-yl)-5-(trifluoromethyl)-1H-pyrazole-4-carboxamide;

N-(5-chloro-6-(2H-1,2,3-triazol-2-yl)pyridin-3-yl)-1-(1-oxoisoindolin-4-yl)-5-(trifluoromethyl)-1H-pyrazole-4-carboxamide;

1-(6-aminopyridin-2-yl)-N-(5-cyano-6-(2H-1,2,3-triazol-2-yl)pyridin-3-yl)-5-(trifluoromethyl)-1H-pyrazole-4-carboxamide;

1-(2-cyano-4-fluorophenyl)-N-(5-cyano-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2-cyano-4-fluorophenyl)-5-(trifluoromethyl)-1H-pyrazole-4-carboxamide;

N-(5-chloro-6-(2H-1,2,3-triazol-2-yl)pyridin-3-yl)-1-(2-(methylthio)phenyl)-5-(trifluoromethyl)-1H-pyrazole-4-carboxamide;

N-(5-chloro-6-(2H-1,2,3-triazol-2-yl)pyridin-3-yl)-1-(2-(methylsulfonyl)phenyl)-5-(trifluoromethyl)-1H-pyrazole-4-carboxamide;

1-(6-amino-5-cyanopyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-cyanopyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-3-methylpyridin-2-yl)-N-(5-cyano-6-(2H-1,2,3-triazol-2-yl)pyridin-3-yl)-5-(trifluoromethyl)-1H-pyrazole-4-carboxamide;

1-(2-amino-5-methylpyridin-4-yl)-N-(5-cyano-6-(2H-1,2,3-triazol-2-yl)pyridin-3-yl)-5-(trifluoromethyl)-1H-pyrazole-4-carboxamide;

1-(2-amino-3-methylpyridin-4-yl)-N-(5-cyano-6-(2H-1,2,3-triazol-2-yl)pyridin-3-yl)-5-(trifluoromethyl)-1H-pyrazole-4-carboxamide;

1-(6-amino-5-chloropyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-chloro-6-(2H-1,2,3-triazol-2-yl)pyridin-3-yl)-5-(trifluoromethyl)-1H-pyrazole-4-carboxamide;

N-(6-(2H-1,2,3-triazol-2-yl)-5-(trifluoromethyl)pyridin-3-yl)-1-(6-amino-5-fluoropyridin-2-yl)-5-(trifluoromethyl)-1H-pyrazole-4-carboxamide;

1-(2-amino-5-chloropyridin-4-yl)-N-(5-cyano-6-(2H-1,2,3-triazol-2-yl)pyridin-3-yl)-5-(trifluoromethyl)-1H-pyrazole-4-carboxamide;

1-(2-amino-5-chloropyridin-4-yl)-N-(5-chloro-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(5-fluoro-6-(methylamino)pyridin-2-yl)-5-(trifluoromethyl)-1H-pyrazole-4-carboxamide;

N-(5-chloro-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide;

N-(5-cyano-6-(2H-1,2,3-triazol-2-yl)pyridin-3-yl)-1-(5-fluoro-6-(3-hydroxyazetidin-1-yl)pyridin-2-yl)-5-(trifluoromethyl)-1H-pyrazole-4-carboxamide;

4-(4-((5-chloro-6-(2H-1,2,3-triazol-2-yl)pyridin-3-yl)carbamoyl)-5-(trifluoromethyl)-1H-pyrazol-1-yl)-3-methylpyridine 1-oxide;

1-(2-chloro-5-methyl-4-pyridyl)-N-[5-chloro-6-(triazol-2-yl)-3-pyridyl]-5-(trifluoromethyl)pyrazole-4-carboxamide;

1-(2-chloro-3-methylpyridin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(2-(3-hydroxyazetidin-1-yl)-5-methylpyridin-4-yl)-5-(trifluoromethyl)-1H-pyrazole-4-carboxamide;

N-(5-chloro-6-(2H-1,2,3-triazol-2-yl)pyridin-3-yl)-1-(2-(3-hydroxyazetidin-1-yl)-3-methylpyridin-4-yl)-5-(trifluoromethyl)-1H-pyrazole-4-carboxamide;

N-(5-chloro-6-(2H-1,2,3-triazol-2-yl)pyridin-3-yl)-1-(3-methylpyridin-4-yl)-5-(trifluoromethyl)-1H-pyrazole-4-carboxamide;

N-(5-chloro-6-(2H-1,2,3-triazol-2-yl)pyridin-3-yl)-1-(4-methylpyridazin-3-yl)-5-(trifluoromethyl)-1H-pyrazole-4-carboxamide;

N-(5-cyano-6-(2H-1,2,3-triazol-2-yl)pyridin-3-yl)-1-(5-fluoro-6-methylpyridin-2-yl)-5-(trifluoromethyl)-1H-pyrazole-4-carboxamide;

N-(5-chloro-6-(2H-1,2,3-triazol-2-yl)pyridin-3-yl)-1-(5-fluoro-6-methylpyridin-2-yl)-5-(trifluoromethyl)-1H-pyrazole-4-carboxamide;

N-(5-cyano-6-(2H-1,2,3-triazol-2-yl)pyridin-3-yl)-1-(3,6-dichloropyridin-2-yl)-5-(trifluoromethyl)-1H-pyrazole-4-carboxamide;

N-(5-chloro-6-(2H-1,2,3-triazol-2-yl)pyridin-3-yl)-1-(3,6-dichloropyridin-2-yl)-5-(trifluoromethyl)-1H-pyrazole-4-carboxamide;

1-(6-chloro-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide;

1-(6-chloro-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide;

1-(4-chloro-2-methylphenyl)-N-(5-cyano-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(3-fluoro-2-methylphenyl)-5-(trifluoromethyl)-1H-pyrazole-4-carboxamide;

N-(5-cyano-6-(2H-1,2,3-triazol-2-yl)pyridin-3-yl)-1-(3,4-difluoro-2-methylphenyl)-5-(trifluoromethyl)-1H-pyrazole-4-carboxamide;

N-(5-cyano-6-(2H-1,2,3-triazol-2-yl)pyridin-3-yl)-1-(4-cyanophenyl)-5-(trifluoromethyl)-1H-pyrazole-4-carboxamide;

N-(5-cyano-2-methyl-6-(2H-1,2,3-triazol-2-yl)pyridin-3-yl)-1-(4-fluoro-2-methylphenyl)-5-(trifluoromethyl)-1H-pyrazole-4-carboxamide;

N-(5-chloro-6-(2H-1,2,3-triazol-2-yl)pyridin-3-yl)-1-(3-fluoro-2-methylphenyl)-5-(trifluoromethyl)-1H-pyrazole-4-carboxamide;

N-(5-chloro-2-methyl-6-(2H-1,2,3-triazol-2-yl)pyridin-3-yl)-1-(4-fluoro-2-methylphenyl)-5-(trifluoromethyl)-1H-pyrazole-4-carboxamide;

N-(5-cyano-6-(2H-1,2,3-triazol-2-yl)pyridin-3-yl)-5-(trifluoromethyl)-1-(2,4,6-trifluorophenyl)-1H-pyrazole-4-carboxamide;

N-(5-chloro-6-(2H-1,2,3-triazol-2-yl)pyridin-3-yl)-1-(3,4-difluoro-2-methylphenyl)-5-(trifluoromethyl)-1H-pyrazole-4-carboxamide;

1-(6-amino-3-chloropyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-4-methylpyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-cyanopyridin-2-yl)-N-(5-cyano-2-methyl-6-(2H-1,2,3-triazol-2-yl)pyridin-3-yl)-5-(trifluoromethyl)-1H-pyrazole-4-carboxamide;

1-(6-amino-5-cyanopyridin-2-yl)-N-(5-chloro-2-methyl-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-bromo-2-methyl-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-cyano-2-methyl-6-(2H-1,2,3-triazol-2-yl)pyridin-3-yl)-5-(trifluoromethyl)-1H-pyrazole-4-carboxamide;

1-(6-amino-3-chloropyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-methylpyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-3-methylpyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide;

1-(6-amino-3-(trifluoromethyl)pyridin-2-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoro-3-methylpyridin-2-yl)-N-(5-chloro-2-methyl-6-(2H-1,2,3-triazol-2-yl)pyridin-3-yl)-5-(trifluoromethyl)-1H-pyrazole-4-carboxamide;

N-(5-cyano-6-(2H-1,2,3-triazol-2-yl)pyridin-3-yl)-1-(6-(methylamino)pyridin-2-yl)-5-(trifluoromethyl)-1H-pyrazole-4-carboxamide;

1-(6-amino-4-methylpyridin-3-yl)-N-(5-cyano-6-(2H-1,2,3-triazol-2-yl)pyridin-3-yl)-5-(trifluoromethyl)-1H-pyrazole-4-carboxamide;

1-(6-amino-4-methylpyridin-3-yl)-N-(5-chloro-6-(2H-1,2,3-triazol-2-yl)pyridin-3-yl)-5-(trifluoromethyl)-1H-pyrazole-4-carboxamide;

1-(6-amino-3-(trifluoromethyl)pyridin-2-yl)-N-(5-chloro-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-chloro-2-methyl-4-(2H-1,2,3-triazol-2-yl)phenyl)-5-(trifluoromethyl)-1H-pyrazole-4-carboxamide;

1-(6-aminopyridin-3-yl)-N-(5-cyano-6-(2H-1,2,3-triazol-2-yl)pyridin-3-yl)-5-(trifluoromethyl)-1H-pyrazole-4-carboxamide;

1-(6-amino-5-fluoropyridin-2-yl)-N-(5-cyano-2-methyl-4-(2H-1,2,3-triazol-2-yl)phenyl)-5-(trifluoromethyl)-1H-pyrazole-4-carboxamide;

1-(6-amino-2-methylpyridin-3-yl)-N-(5-cyano-6-(2H-1,2,3-triazol-2-yl)pyridin-3-yl)-5-(trifluoromethyl)-1H-pyrazole-4-carboxamide;

1-(6-amino-5-methylpyridin-2-yl)-N-(5-cyano-2-methyl-6-(2H-1,2,3-triazol-2-yl)pyridin-3-yl)-5-(trifluoromethyl)-1H-pyrazole-4-carboxamide;

2-amino-6-(4-((5-chloro-2-methyl-6-(2H-1,2,3-triazol-2-yl)pyridin-3-yl)carbamoyl)-5-(trifluoromethyl)-1H-pyrazol-1-yl)nicotinamide;

1-(2-amino-3-methylpyridin-4-yl)-N-(5-chloro-6-(2H-1,2,3-triazol-2-yl)pyridin-3-yl)-5-(trifluoromethyl)-1H-pyrazole-4-carboxamide;

1-(6-amino-5-chloropyridin-2-yl)-N-(5-cyano-2-methyl-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-cyano-2-methylpyridin-3-yl)-5-(trifluoromethyl)-1H-pyrazole-4-carboxamide;

1-(6-bromopyridin-2-yl)-N-(5-chloro-6-(2H-1,2,3-triazol-2-yl)pyridin-3-yl)-5-(trifluoromethyl)-1H-pyrazole-4-carboxamide;

(*R)—N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide;

(*S)—N-(5-chloro-6-(2H-1,2,3-triazol-2-yl)pyridin-3-yl)-1-(5-methyl-2-(tetrahydrofuran-2-yl)pyridin-4-yl)-5-(trifluoromethyl)-1H-pyrazole-4-carboxamide;

(*S)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide;

(*R)-1-(2-(1,4-dioxan-2-yl)-5-methylpyridin-4-yl)-N-(5-chloro-6-(2H-1,2,3-triazol-2-yl)pyridin-3-yl)-5-(trifluoromethyl)-1H-pyrazole-4-carboxamide;

N-(5-chloro-6-(2H-1,2,3-triazol-2-yl)pyridin-3-yl)-1-(6-(furan-2-yl)pyridin-2-yl)-5-(trifluoromethyl)-1H-pyrazole-4-carboxamide; and N-(5-chloro-6-(2H-1,2,3-triazol-2-yl)pyridin-3-yl)-1-(6-(5,6-dihydro-1,4-dioxin-2-yl)pyridin-2-yl)-5-(trifluoromethyl)-1H-pyrazole-4-carboxamide;

or a pharmaceutically acceptable salt form thereof.

2. A pharmaceutical composition comprising a compound of claim 1 and at least one of a pharmaceutically acceptable carrier, a pharmaceutically acceptable excipient, and a pharmaceutically acceptable diluent.

3. The pharmaceutical composition of claim 2, wherein the composition is a solid oral dosage form.

4. The pharmaceutical composition of claim 2, wherein the composition is a syrup, an elixir or a suspension.

5. A method of treating a disease, syndrome, condition, or disorder, wherein said disease, syndrome, condition, or disorder is affected by the inhibition of MALT1, comprising administering to a subject in need thereof a therapeutically effective amount of the compound of claim 1.

6. The method of claim 5 wherein said disease, syndrome, condition, or disorder is selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoritic arthritis (PsA), psorisis (Pso), ulcerative colitis (UC), Crohn's disease, systemic lupus erythematosus (SLE), asthma, and chronic obstructive pulmonary disease (COPD).

7. The method of claim 5 additionally comprising the administration of a therapeutically effective amount of ibrutinib.

8. The method of claim 5 additionally comprising the administration of a therapeutically effective amount of rituximab.

9. The method of claim 5 additionally comprising the administration of a therapeutically effective amount of daratumumab.

* * * * *